(12) United States Patent
Iavarone et al.

(10) Patent No.: US 11,505,788 B2
(45) Date of Patent: Nov. 22, 2022

(54) FUSION PROTEINS AND METHODS THEREOF

(71) Applicant: The Trustees of Columbia University in the City of New York, New York, NY (US)

(72) Inventors: Antonio Iavarone, New York, NY (US); Anna Lasorella, New York, NY (US); Raul Rabadan, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 668 days.

(21) Appl. No.: 16/246,167

(22) Filed: Jan. 11, 2019

(65) Prior Publication Data
US 2019/0203188 A1 Jul. 4, 2019

Related U.S. Application Data

(60) Division of application No. 14/853,568, filed on Sep. 14, 2015, now Pat. No. 10,208,296, which is a continuation of application No. PCT/US2014/026351, filed on Mar. 13, 2014.

(60) Provisional application No. 61/793,086, filed on Mar. 15, 2013.

(51) Int. Cl.
| | |
|---|---|
| *C07K 14/705* | (2006.01) |
| *C12N 9/12* | (2006.01) |
| *C07K 14/71* | (2006.01) |
| *C07K 14/47* | (2006.01) |
| *C12N 9/16* | (2006.01) |
| *A61K 38/17* | (2006.01) |
| *A61K 31/404* | (2006.01) |
| *A61K 31/4439* | (2006.01) |
| *A61K 31/47* | (2006.01) |
| *A61K 31/496* | (2006.01) |
| *A61K 31/506* | (2006.01) |
| *A61K 31/519* | (2006.01) |
| *A61K 31/53* | (2006.01) |
| *G01N 33/574* | (2006.01) |
| *A61K 31/517* | (2006.01) |
| *C07K 14/435* | (2006.01) |
| *C07K 16/40* | (2006.01) |
| *C12Q 1/6886* | (2018.01) |
| *G01N 33/573* | (2006.01) |

(52) U.S. Cl.
CPC ............. *C12N 9/12* (2013.01); *A61K 31/404* (2013.01); *A61K 31/4439* (2013.01); *A61K 31/47* (2013.01); *A61K 31/496* (2013.01); *A61K 31/506* (2013.01); *A61K 31/517* (2013.01); *A61K 31/519* (2013.01); *A61K 31/53* (2013.01); *A61K 38/179* (2013.01); *C07K 14/435* (2013.01); *C07K 14/47* (2013.01); *C07K 14/4738* (2013.01); *C07K 14/71* (2013.01); *C07K 16/40* (2013.01); *C12N 9/16* (2013.01); *C12Q 1/6886* (2013.01); *C12Y 301/03003* (2013.01); *G01N 33/573* (2013.01); *G01N 33/57484* (2013.01); *C07K 2317/76* (2013.01); *C07K 2319/00* (2013.01); *C12Y 207/10001* (2013.01); *G01N 2333/71* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,921,475 A | 5/1990 | Sibalis |
| 5,008,110 A | 4/1991 | Benecke et al. |
| 5,087,240 A | 2/1992 | Sibalis |
| 5,088,977 A | 2/1992 | Sibalis |
| 5,163,899 A | 11/1992 | Sibalis |
| 5,164,189 A | 11/1992 | Farhadieh et al. |
| 5,252,479 A | 10/1993 | Srivastava |
| 5,254,346 A | 10/1993 | Tucker et al. |
| 5,290,561 A | 3/1994 | Farhadieh et al. |
| 5,328,470 A | 7/1994 | Nabel et al. |
| 5,332,213 A | 7/1994 | Klose |
| 5,336,168 A | 8/1994 | Sibalis |
| 5,352,456 A | 10/1994 | Fallon et al. |
| 5,407,713 A | 4/1995 | Wilfong et al. |
| 5,747,469 A | 5/1998 | Roth et al. |
| 5,780,597 A | 7/1998 | Gately et al. |
| 5,811,523 A | 9/1998 | Trinchieri et al. |
| 6,017,524 A | 1/2000 | Roth et al. |
| 6,143,290 A | 11/2000 | Zhang et al. |

(Continued)

FOREIGN PATENT DOCUMENTS

| | | |
|---|---|---|
| JP | 2010-533205 A | 10/2010 |
| WO | WO-99/032619 | 7/1999 |

(Continued)

OTHER PUBLICATIONS

Abu-Elneel et al., "A delta-catenin signaling pathway leading to dendritic protrusions," J. Biol. Chem., 283, pp. 32781-32791 (2008).

(Continued)

*Primary Examiner* — Michael D Pak
(74) *Attorney, Agent, or Firm* — Wilmer Cutler Pickering Hale and Dorr LLP

(57) ABSTRACT

The invention discloses oncogenic fusion proteins. The invention provides methods for treating gene-fusion based cancers.

9 Claims, 215 Drawing Sheets
Specification includes a Sequence Listing.

(56) References Cited

U.S. PATENT DOCUMENTS

| | | | |
|---|---|---|---|
| 6,410,010 | B1 | 6/2002 | Zhang et al. |
| 6,509,154 | B1 | 1/2003 | de Paillette |
| 6,511,847 | B1 | 1/2003 | Zhang et al. |
| 6,914,128 | B1 | 7/2005 | Salfeld et al. |
| 7,148,342 | B2 | 12/2006 | Tolentino et al. |
| 7,294,504 | B1 | 11/2007 | Wang |
| 7,419,661 | B2 | 9/2008 | Jahoda et al. |
| 7,422,896 | B1 | 9/2008 | Wang |
| 8,071,559 | B2 | 12/2011 | Hannon et al. |
| 2002/0077313 | A1 | 6/2002 | Clayman |
| 2002/0173478 | A1 | 11/2002 | Gewirtz |
| 2003/0027783 | A1 | 2/2003 | Zernicka-Goetz et al. |
| 2008/0312248 | A1 | 12/2008 | Bold et al. |
| 2009/0318480 | A1 | 12/2009 | Solca |
| 2010/0120678 | A1* | 5/2010 | Kuriyan ............... G01N 33/74 514/7.6 |
| 2011/0023143 | A1 | 1/2011 | Weinstein et al. |
| 2015/0203589 | A1 | 7/2015 | Iavarone et al. |
| 2018/0030152 | A1 | 2/2018 | Iavarone et al. |

FOREIGN PATENT DOCUMENTS

| | | |
|---|---|---|
| WO | WO-1999/35159 | 7/1999 |
| WO | WO-00/01846 | 1/2000 |
| WO | WO-00/044895 | 8/2000 |
| WO | WO-00/044914 | 8/2000 |
| WO | WO-01/029058 | 4/2001 |
| WO | WO-01/32840 | 5/2001 |
| WO | WO-2008/75068 | 6/2008 |
| WO | WO-2009/009778 | 1/2009 |
| WO | WO-2010/129509 | 11/2010 |
| WO | WO-2014/018673 | 1/2014 |
| WO | WO-2014/151734 | 9/2014 |
| WO | WO-2016/105517 | 6/2016 |

OTHER PUBLICATIONS

Altaras et al., "Production and formulation of adenovirus vectors," Adv. Biochem. Eng. Biotechnol., 99, pp. 193-260 (2005).

Anderson, "Human gene therapy," Nature, 392(6679 suppl.), pp. 25-30 (1998).

Anderson, "Human gene therapy," Science, 256, pp. 808-813 (1992).

Arikkath et al., "Delta-catenin regulates spine and synapse morphogenesis and function in hippocampal neurons during development," J. Neurosci., 29, pp. 5435-5442 (2009).

Bandyopadhyay and Temin, "Expression of complete chicken thymidine kinase gene inserted in a retrovirus vector," Mol. Cell Biol., 4(4) pp. 749-754 (1984).

Barringer, "Blunt-end and single-strand ligations by *Escherichia coli* ligase: influence on an in vitro amplification scheme," Gene, 89, pp. 117-122 (1990).

Bass et al., "Genomic sequencing of colorectal adenocarcinomas identifies a recurrent VTI1A-TCF7L2 fusion," Nat. Genet., 43, pp. 964-968 (2011).

Bass, "RNA interference. The short answer," Nature, 411, pp. 428-429 (2001).

Bekker-Jensen et al., "HERC2 coordinates ubiquitin-dependent assembly of DNA repair factors on damaged chromosomes," Nat. Cell Biol., 12, pp. 80-86, sup. pp. 1-12 (2010).

Berkner, "Development of adenovirus vectors for the expression of heterologous genes," Biotechniques, 6(7), pp. 616-629 (1988).

Berkner, "Expression of heterologous sequences in adenoviral vectors," Curr. Top. Microbiol. Immunol., 158, pp. 39-66 (1992).

Beroukhim et al., "The landscape of somatic copy-number aheration across human cancers," Nature, 463, pp. 899-905 (2010).

Boyden et al., "Mutations in kelch-like 3 and cullin 3 cause hypertension and electrolyte abnormalities," Nature, 482, pp. 98-102 (2012).

Breakefield and Geller, "Gene transfer into the nervous system," Mol. Neurobiol., 1 (4), pp. 339-371 (1987).

Brower, "Naked DNA vaccines come of age," Nature Biotechnology, 16, pp. 1304-1305 (1998).

Buchschacher Jr. and Panganiban, "Human immunodeficiency virus vectors for inducible expression of foreign genes," J. Virol., 66(5), pp. 2731-2739 (1992).

Buchwald et al., "Long-term, continuous intravenous heparin administration by an implantable infusion pump in ambulatory patients with recurrent venous thrombosis," Surgery, 88, pp. 507-516 (1980).

Burg et al., "Single molecule detection of RNA reporter probes by amplification with Qβ replicase," Mol. Cell. Probes, 10, pp. 257-271 (1996).

Canning et al., "Structural basis for Cul3 assembly with the BTB-Kelch family of E3 ubiquitin ligases," J. Biol. Chem., 288, pp. 7803-7814 (2013).

Carro et al., "The transcriptional network for mesenchymal transformation of brain tumours," Nature, 463, pp. 318-325 (2010).

Chen et al., "Gene therapy for brain tumors: regression of experimental gliomas by adenovirus-mediated gene transfer in vivo," Proc. Natl. Acad. Sci. USA, 91, pp. 3054-3057 (1994).

Chinnaiyan and Palanisamy, "Chromosomal aberrations in solid tumors," Prog. Mol. Biol. Transl. Sci., 95, pp. 55-94 (2010).

Christ et al., "LRP2 is an auxiliary SHH receptor required to condition the forebrain ventral midline for inductive signals," Dev. Cell, 22, pp. 268-278 (2012).

Cleveland et al., "Routine large-scale production of monoclonal antibodies in a protein-free culture medium," J. Immunol. Methods, 56(2), pp. 221-234 (1983).

Cowin et al., "LRP 1B deletion in high-grade serous ovarian cancers is associated with acquired chemotherapy resistance to liposomal doxorubicin," Cancer Res., 72, pp. 4060-4073 (2012).

Dallas et al., "RNAi: a novel antisense technology and its therapeutic potential," Med. Sci. Monit., 12(4), pp. RA67-RA74 (2006).

Dunn et al., "Emerging insights into the molecular and cellular basis of glioblastoma," Genes Dev., 26, pp. 756-784 (2012).

During et al., "Controlled release of dopamine from a polymeric brain implant: in vivo characterization," Ann. Neurol., 25, 351-356 (1989).

Dzau et al., "Gene therapy for cardiovascular disease," Trends in Biotechnology, 11, pp. 205-210 (1993).

Elbashir et al., "Duplexes of 21-nucleotide RNAs mediate RNA interference in cultured mammalian cells," Nature, 411, pp. 494-498 (2001).

Eliyahu et al., "Polymers for DNA delivery," Molecules, 10(1), pp. 34-64 (2005).

Emanuele et al., "Global identification of modular cullin-RING ligase substrates," Cell, 147, pp. 459-474 (2011).

Errington et al., "Adaptor protein self-assembly drives the control of a cullin-RING ubiquitin ligase," Structure, 20, pp. 1141-1153 (2012).

Extended European Search Report dated Jul. 25, 2016 for European Patent Application No. 14769771.8 (8 pages).

Fan et al., "BCOR regulates mesenchymal stem cell function by epigenetic mechanisms," Nat. Cell Biol., 11, pp. 1002-1009 (2009) incl. 6 pages of Supplemental Information.

Fink et al., "In vivo expression of beta-galactosidase in hippocampal neurons by HSV-mediated gene transfer," Hum. Gene Ther. 3(1), pp. 11-19 (1992).

Forbes et al., "COSMIC (the Catalogue of Somatic Mutations in Cancer): a resource to investigate acquired mutations in human cancer," Nucleic Acids Res., 38, pp. D652-D657 (2010).

Frattini et al., "The integrated landscape of driver genomic alterations in glioblastoma," Nature Genetics, 45(10), pp. 1141-1149 (Aug. 2013).

Freese et al., "HSV-1 vector mediated neuronal gene delivery. Strategies for molecular neuroscience and neurology," Biochem. Pharmacol., 40(10), pp. 2189-2199 (1990).

Friedman et al., "Experimental Chemotherapy of Human Medulloblastoma Cell Lines and Transplantable Xenografts with Bifunctional Alkylating Agents," Cancer Res., 48, pp. 4189-4195 (1988).

Friedmann, "Progress toward human gene therapy," Science, 244, pp. 1275-1281 (1989).

(56) References Cited

OTHER PUBLICATIONS

Fülö p and Jones, "Beta propellers: structural rigidity and functional diversity," Curr. Opin. Struct. Biol., 9, pp. 715-721 (1999).
Galan and Peter, "Ubiquitin-dependent degradation of multiple F-box proteins by an autocatalytic mechanism," Proc. Natl. Acad. Sci. USA, 96, pp. 9124-9129 (1999).
Gavine et al., "AZD4547: an orally bioavailable, potent, and selective inhibitor of the fibroblast growth factor receptor tyrosine kinase family," Cancer Res., 72(8), pp. 2045-2056 (2012).
Gorziglia and Kapikian, "Expression of the OSU rotavirus outer capsid protein VP4 by an adenovirus recombinant," J. Virol., 66(7), pp. 4407-4412 (1992).
Guagnano et al., "Discovery of 3-(2,6-dichloro-3,5-dimethoxy-phenyl)-1-{6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase," J. Med. Chem., 54, pp. 7066-7083 (2011).
Guatelli et al., "Isothermal, in vitro amplification of nucleic acids by a multienzyme reaction modeled after retroviral replication," PNAS, 87, pp. 1874-1878 (1990).
Gunther et al., "Glioblastoma-derived stem cell-enriched cultures form distinct subgroups according to molecular and phenotypic criteria," Oncogene, 27, pp. 2897-2909 (2008).
Harlalka et al., "Mutation of HERC2 causes developmental delay with Angelman-like features," J. Med. Genet., 50, pp. 65-73 (2013).
Helseth et al., "Changes in the transmembrane region of the human immunodeficiency virus type 1 gp41 envelope glycoprotein affect membrane fusion," J. Virol., 64(12), pp. 6314-6318 (1990).
Herweijer et al., "Gene therapy progress and prospects: hydrodynamic gene delivery," Gene Ther., 14(2), pp. 99-107 (2007).
Hicks et al., "Prediction of missense mutation functionality depends on both the algorithm and sequence alignment employed," Hum. Mutat., 32, pp. 661-668 (2011).
Hoffman, "Hydrogels for biomedical applications," Adv. Drug Deliv. Rev., 43, pp. 3-12 (2002).
Hoffman, "Hydrogels for biomedical applications," Ann. NY Acad. Sci., 944, pp. 62-73 (2001).
Howard III et al., "Intracerebral drug delivery in rats with lesion-induced memory deficits," J. Neurosurg., 71, pp. 105 (1989).
Hudson, "Recombinant antibody fragments," Curr. Opin. Biotechnol., 9, pp. 395-402 (1998).
International Search Report and Written Opinion dated Aug. 29, 2014 for International Patent Application No. PCT/US2014/026351 (23 pages).
Isaka et al., "Electroporation-mediated gene therapy," Expert Opin. Drug Deliv., 4(5), pp. 561-571 (2007).
Israely et al., "Deletion of the neuron-specific protein delta-catenin leads to severe cognitive and synaptic dysfunction," Curr. Biol., 14, pp. 1657-1663 (2004).
Iyer et al., "ChimeraScan: a tool for identifying chimeric transcription in sequencing data," Bioinformatics, 27, pp. 2903-2904 (2011).
Jager et al., "Emerging adenoviral vectors for stable correction of genetic disorders," Curr. Gene Ther., 7(4), pp. 272-283 (2007).
Jensen, "Cutaneous gene therapy," Ann. Med., 39(2), pp. 108-115 (2007).
Jhoti, "Fragment-based drug discovery using rational design," Ernst Schering Found Symp. Proc., (3), pp. 169-185 (2007).
Ji and Prive, "Crystal structure of KLHL3 in complex with Cullin3," PLoS One, 8(4), e60445, pp. 1-10 (2013).
Johnson et al., "Effects of gene transfer into cultured CNS neurons with a replication-defective herpes simplex virus type 1 vector," Mol. Brain Res., 12(1-3), pp. 95-102 (1992).
Jones et al., "Application and evaluation of denaturing HPLC for molecular genetic analysis in tuberous sclerosis," Hum. Genet., 106(6), pp. 663-668 (2000).
Jun et al., "δ-Catenin is genetically and biologically associated with cortical cataract and future Alzheimer-related structural and functional brain changes," PLoS One 7(9), e43728, pp. 1-11 (2012).
Kalota et al., "Progress in the development of nucleic acid therapeutics ," Handb. Exp. Pharmacol., 173, pp. 173-196 (2006).

Kantarci et al., "Mutations in LRP2, which encodes the multiligand receptor megalin, cause Donnai-Barrow and facio-oculo-acoustico-renal syndromes," Nat. Genet., 39, pp. 957-959 (2007).
Kikuchi et al., "Cutaneous gene delivery," J. Dermatol. Sci., 50(2), pp. 87-98 (2008).
Kimmel and Berger, "Preparation of cDNA and the generation of cDNA libraries: overview," Methods Enzymol., 152, pp. 307-316 (1987).
Kosik et al., "δ-catenin at the synaptic-adherens junction," Trends Cell Biol., 15, pp. 172-178 (2005).
Krejci et al., "NF449 is a novel inhibitor of fibroblast growth factor receptor 3 (FGFR3) signaling active in chondrocytes and multiple myeloma cells," The Journal of Biological Chemistry, 285(27), pp. 20644-20653 (2010).
Kwoh et al., "Transcription-based amplification system and detection of amplified human immunodeficiency virus type 1 with a bead-based sandwich hybridization format," Proc. Natl. Acad. Sci. USA, 86, pp. 1173-1177 (1989).
Landegren et al., "A ligase-mediated gene detection technique," Science, 241, pp. 1077-1080 (1988).
Langer, "New methods of drug delivery," Science, 249, pp. 1527-1533 (1990).
Lee et al., "Controlled degradation of hydrogels using multifunctional cross-linking molecules," Biomaterials, 25, pp. 2461-2466 (2004).
Levy et al., "Inhibition of calcification of bioprosthetic heart valves by local controlled-release diphosphonate," Science, 228, pp. 190-192 (1985).
Lima et al., "Glioblastoma: therapeutic challenges, what lies ahead. Biochim," Biophys Acta, 1826, pp. 338-349 (2012).
Liu al., "NEDD8 Modification of CUL1 Dissociates p120(CAND1), An Inhibitor of CUL1-SKP1 Binding and SCF Ligases," Molecular Cell., 10, pp. 1511-1518 (Dec. 2002).
Liu et al., "Chemokine receptor CXCR3 promotes growth of glioma," Carcinogenesis, 32, pp. 129-137 (2011).
Lo et al., "Structure of the Keapl:Nrf2 interface provides mechanistic insight into Nrf2 signaling," EMBO J., 25, pp. 3605-3617 (2006).
Louis-Dit-Picard et al., "KLHL3 mutations cause familial hyperkalemic hypertension by impairing ion transport in the distal nephron," Nat. Genet., 44, pp. 456-460 (2012).
Lützelburger et al., "Strategies to identify potential therapeutic target sites in RNA," Handb. Exp. Pharmacol., 173, pp. 243-259 (2006).
Madzak et al., "Efficient in vivo encapsidation of a shuttle vector into pseudo-simian virus 40 virions using a shuttle virus as helper," J. Gen. Virol., 73(Pt 6), pp. 1533-1536 (1992).
Mann and Bahimore, "Varying the position of a retrovirus packaging sequence results in the encapsidation of both unspliced and spliced RNAs," J. Virol. 54(2), pp. 401-407 (1985).
Margolskee, "Epstein-Barr virus based expression vectors," Curr. Top. Microbiol. Immunol., 158, 67-95 (1992).
Maynard and Georgiou, "Antibody engineering," Ann. Rev. Biomed. Eng., 2, pp. 339-376 (2000).
McMnaus and Sharp, "Gene silencing in mammals by small interfering RNAs," Nat. Rev. Genetics, 3, pp. 737-747 (2002).
Mensch et al., "In vivo, in vitro and in silico methods for small molecule transfer across the BBB," J. Pharm. Sci., 98(12), pp. 4429-4468 (2009).
Miller et al., "An activation-dependent, T-lymphocyte-specific transcriptional activator in the mouse mammary tumor virus env gene," Mol. Cell Biol., 12(7), pp. 3262-3272 (1992).
Miller et al., "Deletion of the gag Region from FBR Murine Osteosarcoma Virus Does Not Affect Its Enhanced Transforming Activity," J. Virol. 55(3), pp. 521-526 (1985).
Miller et al., "Design of retrovirus vectors for transfer and expression of the human β-globin gene," J. Virol., 62(11), pp. 4337-4345 (1988).
Miller, "Human gene therapy comes of age," Nature, 357, pp. 455-460 (1992).
Mohammadi et al., "Crystal structure of an angiogenesis inhibitor bound to the FGF receptor tyrosine kinase domain," EMBO J., 17, pp. 5896-5904 (1998).

(56) References Cited

OTHER PUBLICATIONS

Moss, "Vaccinia and other poxvirus expression vectors," Curr. Opin. Biotechnol., 3(5), pp. 518-522 (1992).
Muzyczka, "Use of adeno-associated virus as a general transduction vector for mammalian cells," Curr. Top. Microbiol. Immunol., 158, pp. 97-129 (1992).
Nacak et al., "The BTB-kelch protein LZTR-1 is a novel Golgi protein that is degraded upon induction of apoptosis," J. Biol. Chem., 281, pp. 5065-5071 (2006).
Niola et al., "Mesenchymal high-grade glioma is maintained by the ID-RAPI axis," J. Clin. Invest., 123, pp. 405-417 (2013).
Northcott et al., "Subgroup-specific structural variation across 1,000 medulloblastoma genomes," Nature, 488, pp. 49-56 (2012).
Noushmehr et al., "Identification of a CpG island methylator phenotype that defines a distinct subgroup of glioma," Cancer Cell, 17, pp. 510-522 (2010).
Ohi et al., "Construction and replication of an adeno-associated virus expression vector that contains human beta-globin cDNA," Gene, 89(2), pp. 279-282 (1990).
Page et al., "Construction and use of a human immunodeficiency virus vector for analysis of virus infectivity," J. Virol., 64(11), pp. 5270-5276 (1990).
Parsons et al., "An integrated genomic analysis of human glioblastoma muhiforme," Science, 321, pp. 1807-1812 (2008).
Peppas et al., "Hydrogels in Biology and Medicine: From Molecular Principles to Bionanotechnology," Adv Mater., 18, pp. 1345-1360 (2006).
Peterson et al., "Characterization of a SEPT9 interacting protein, SEPT14, a novel testis-specific septin," Mamm. Genome., 18, pp. 796-807 (Jun. 2007).
Petropoulos et al., "Using Avian Retroviral Vectors for Gene Transfer," J. Virol., 66(6), pp. 3391-3397 (1992).
Phillips et al., "Molecular subclasses of high-grade glioma predict prognosis, delineate a pattern of disease progression, and resemble stages in neurogenesis," Cancer Cell, 9, pp. 157-173 (2006).
Pierotti and Greco, "Oncogenic rearrangements of the NTRKI/NGF receptor," Cancer Lett., 232, pp. 90-98 (2006).
Porter et al., "Prevalence estimates for primary brain tumors in the United States by age, gender, behavior, and histology," Neuro-oncology, 12, pp. 520-527, (2010).
Potyrailo et al., "Combinatorial and high-throughput screening of materials libraries: review of state of the art," ACS Comb. Sci., 13(6), pp. 579-633 (2011).
Pugh et al., "Medulloblastoma exome sequencing uncovers subtype-specific somatic mutations," Nature, 488, pp. 106-110 (2012).
Quantin et al., "Adenovirus as an expression vector in muscle cells in vivo," Proc. Natl. Acad. Sci. USA, 89(7), pp. 2581-2584 (1992).
Langer and Peppas, "Chemical and Physical Structure of Polymers as Carriers for Controlled Release of Bioactive Agents: A Review," J. Macromol. Sci., Part C. Polymer Reviews, 23, pp. 61-126 (1983).
Rosenfeld et al., "In vivo transfer of the human cystic fibrosis transmembrane conductance regulator gene to the airway epithelium," Cell, 68(1), pp. 143-155 (1992).
Roy et al., "I-TASSER: a unified platform for automated protein structure and function prediction," Nat, Protoc., 5, pp. 725-738 (2010).
Rubin and Green "Mutation patterns in cancer genomes," Proc. Natl. Acad. Sci. USA, 106 (2009).
Saudek et al., "A preliminary trial of the programmable implantable medication system for insulin delivery," N. Engl. J. Med., 321, pp. 574-579 (1989).
Schnur, "Recent trends in library design: 'rational design' revisited," Curr. Opin, Drug Discov., Devel., 11(3), pp. 375-380 (2008).
Seal et al., "genenames.org: the HGNC resources in 2011," Nucleic Acids Res. 39, pp. D514-D519 (2011).
Sebe-Pedros et al., "Ancient origin of the integrin-mediated adhesion and signaling machinery," Proc. Natl. Acad. Sci. USA, 107, pp. 10142-10147 (2010).
Sefton, "Implantable pumps," CRC Critical Reviews in Biomed. Eng. 14, pp. 201-240 (1987).

Sen and Blau, "A brief history of RNAi: the silence of the genes," FASEB J., 20, pp. 1293-1299 (2006).
Shimada et al., "Targeted and highly efficient gene transfer into CD4+ cells by a recombinant human immunodeficiency virus retroviral vector," J. Clin. Invest., 88(3), pp. 1043-1047 (1991).
Shinoda et al., "Septin 14 Is Involved in Cortical Neuronal Migration Via Interaction with Septin 4," Molecular Biology of the Cell, 21, pp. 1324-1334 (Apr. 2010).
Singh et al., "Transforming fusions of FGFR and TACC genes in human glioblastoma," Science, 337, pp. 1231-1235 (2012).
Smith et al., "Detection of *Mycobacterium tuberculosis* directly from sputum by using a prototype automated Q-beta replicase assay," J. Clin. Microbiol., 35, pp. 1477-1491 (1997).
Sooknanan and Malek, "NASBA: A detection and amplification system uniquely suited for RNA," Nature Biotechnology, 13, pp. 563-564 (1995).
Sorge et al., "Amphotropic retrovirus vector system for human cell gene transfer," Mol. Cell. Biol., 4(9), pp. 1730-1737 (1984).
Srivastava et al., "The Amphimedon queenslandica genome and the evolution of animal complexity," Nature, 466, pp. 720-726 (2010).
Stogios et al., "Sequence and structural analysis of BTB domain proteins," Genome Biol., 6(10) pp. R82.1-R82.18 (2005).
Stratford-Perricaudet et al., "Evaluation of the transfer and expression in mice of an enzyme-encoding gene using a human adenovirus vector," Hum. Gene Ther., 1(3), pp. 241-256 (1990).
Stupp et al., "Radiotherapy plus concomitant and adjuvant temozolomide for glioblastoma," The New England Journal of Medicine, 352, pp. 987-996 (2005).
Söding, "Protein homology detection by HMM-HMM comparison," Bioinformatics, 21(7), pp. 951-960 (2005).
The Cancer Genome Atlas Research Network, "Comprehensive genomic characterization defines human glioblastoma genes and core pathways," Nature, 455, pp. 1061-1068 (2008).
Tiacci et al., "BRAF mutations in hairy-cell leukemia," The New England Journal of Medicine, 364, pp. 2305-2315 (2011).
Verhaak et al., "Integrated genomic analysis identifies clinically relevant subtypes of glioblastoma characterized by abnormalities in PDGFRA, IDH1, EGFR, and NF1," Cancer Cell, 17, pp. 98-110 (2010).
Verma, "Gene therapy," Scientific American, 68-72, 81-84 (1990).
Vilella et al., "EnsemblCompara GeneTrees: Complete, duplication-aware phylogenetic trees in vertebrates," Genome Res., 19, pp. 327-335 (2009).
Vivanco et al., "Differential Sensitivity of Glioma-versus Lung Cancer-Specific EGFR Mutations to EGFR Kinase Inhibitors," Cancer Discov., 2, pp. 458-471 (2012).
Waehler et al., "Engineering targeted viral vectors for gene therapy," Nat. Rev. Genet., 8(8), pp. 573-587 (2007).
Wamstad and Bardwell, "Characterization of Bcor expression in mouse development," Gene Expr. Patterns, 7, pp. 550-557, (2007).
Wamstad et al., "Role of the Transcriptional Corepressor Bcor in Embryonic Stem Cell Differentiation and Early Embryonic Development," PLoS One, 3, e2814, 12 pages (2008).
Werner et al., "Joining high-throughput technology with in silico modelling advances genome-wide screening towards targeted discovery," Brief. Funct. Genomics Proteomic., 5(1), pp. 32-36 (2006).
Wilkinson et al., "Constitutive and enhanced expression from the CMV major IE promoter in a defective adenovirus vector," Nucleic Acids Res., 20(9), pp. 2233-2239 (1992).
Willnow et al., "Defective forebrain development in mice lacking gp330/megalin," Proc. Natl. Acad. Sci. USA, 93, pp. 8460-8464 (1996).
Wu and Wallace, "The ligation amplification reaction (LAR)—amplification of specific DNA sequences using sequential rounds of template-dependent ligation," Genomics, 4, 560-569 (1989).
Wurdak et al., "A small molecule accelerates neuronal differentiation in the adult rat," Proc. Natl. Acad. Sci. USA, 107(38), pp. 16542-16547 (2010).
Zhang et al., "A novel retinoblastoma therapy from genomic and epigenetic analyses," Nature, 481, pp. 329-334 (2012).
Zhang et al., "Ubiquitination of Keapl, a BTB-Kelch substrate adaptor protein for Cul3, targets Keapl for degradation by a proteasome-independent pathway," J. Biol. Chem., 280, pp. 30091-30099 (2005).

(56) References Cited

OTHER PUBLICATIONS

Zhao et al., "A novel, selective inhibitor of fibroblast growth factor receptors that shows a potent broad spectrum of antitumor activity in several tumor xenograft models," Mol. Cancer Ther., 10(11), pp. 2200-2210 (2011).
Zhao et al., "The N-Myc-DLL3 cascade is suppressed by the ubiquitin ligase Huwe1 to inhibit proliferation and promote neurogenesis in the developing brain," Dev. Cell, 17, pp. 210-221 (2009).
Office Action for corresponding Japanese Patent Application No. 2016-502111 dated Mar. 27, 2018 with English language summary (6 pages).

\* cited by examiner

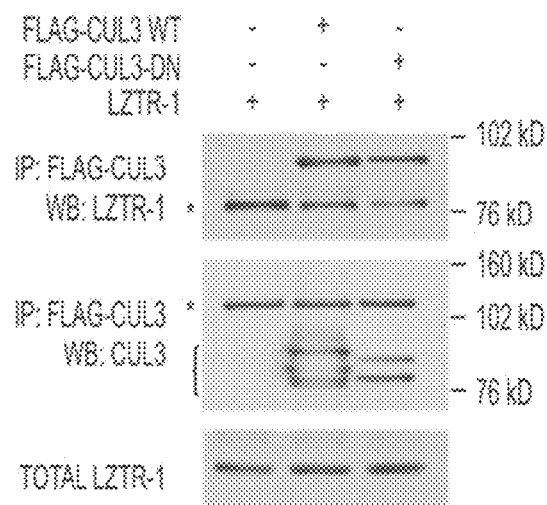
FIG. 2A
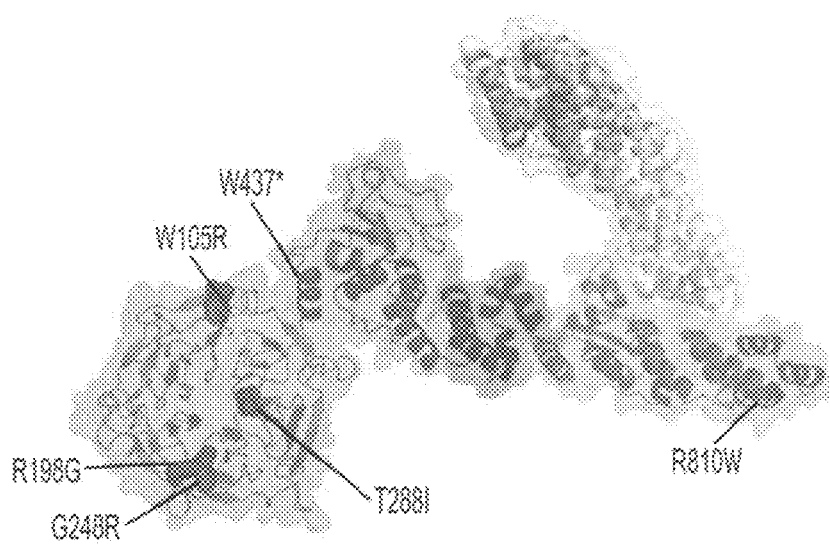
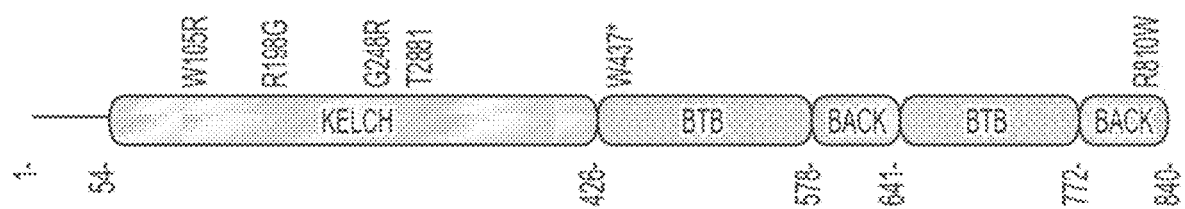
FIG. 2B

MRPSGTAGAALLALLAALCPASRALEEKKVCQGTSNKLTQLGTFEDHFLSLQRMFNNCEVVLG
NLEITYVQRNYDLSFLKTIQEVAGYVLIALNTVERIPLENLQIIRGNMYYENSYALAVLSNYD
ANKTGLKELPMRNLQEILHGAVRFSNNPALCNVESIQWRDIVSSDFLSNMSMDFQNHLGSCQK
CDPSCPNGSCWGAGEENCQKLTKIICAQQCSGRCRGKSPSDCCHNQCAAGCTGPRESDCLVCR
KFRDEATCKDTCPPLMLYNPTTYQMDVNPEGKYSFGATCVKKCPRNYVVTDHGSCVRACGADS
YEMEEDGVRKCKKCEGPCRKVCNGIGIGEFKDSLSINATNIKHFKNCTSISGDLHILPVAFRG
DSFTHTPPLDPQELDILKTVKEITGFLLIQAWPENRTDLHAFENLEIIRGRTKQHGQFSLAVV
SLNITSLGLRSLKEISDGDVIISGNKNLCYANTINWKKLFGTSGQKTKIISNRGENSCKATGQ
VCHALCSPEGCWGPEPRDCVSCRNVSRGRECVDKCNLLEGEPREFVENSECIQCHPECLPQAM
NITCTGRGPDNCIQCAHYIDGPHCVKTCPAGVMGENNTLVWKYADAGHVCHLCHPNCTYGCTG
PGLEGCPTNGPKIPSIATGMVGALLLLLVVALGIGLFMRRRHIVRKRTLRRLLQERELVEPLT
PSGEAPNQALLRILKETEFKKIKVLGSGAFGTVYKGLWIPEGEKVKIPVAIKELREATSPKAN
KEILDEAYVMASVDNPHVCRLLGICLTSTVQLITQLMPFGCLLDYVREHKDNIGSQYLLNWCV
QIAKGMNYLEDRRLVHRDLAARNVLVKTPQHVKITDFGLAKLLGAEEKEYHAEGGKVPIKWMA
LESILHRIYTHQSDVWSYGVTVWELMTFGSKPYDGIPASEISSILEKGERLPQPPICTIDVYM
IMVKCWMIDADSRPKFRELIIEFSKMARDPQRYLVIQLGDNFERLKMIQQENIRELENKKQL
EGEIIDFTKNKAASEALQTQLSTOTKKDKHRKK

EGFR                                              Septin14

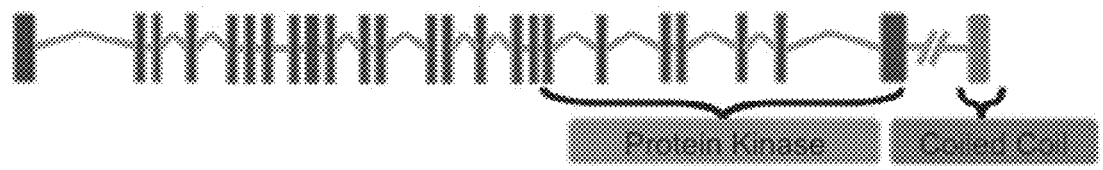

FIG. 4C

| XENOGRAFT | TREATMENT | T-C | P-VALUE | TUMOR REGRESSION | TOXIC DEATHS |
|---|---|---|---|---|---|
| D08-0537 MG EGFR-SEPT14 | ERLOTINIB | 5.63 | 0.037 | 1/10 | 0/10 |
| | LAPATINIB | 7.78 | 0.003 | 1/10 | 0/10 |
| D08-0714 MG EGFR-WT | ERLOTINIB | -1.53 | 0.323 | 0/8 | 0/8 |
| | LAPATINIB | -1.46 | 0.360 | 0/8 | 0/8 |

FIG. 5D

MRPSGTAGAALLALLAALCPASRALEEKKVCQGTSNKLTQLGTFEDHFLSLQRMPNNCEVVLGNLEIT
YVQRNYDLSFLKTIQEVAGYVLIALNTVERIPLENLQIIRGNMYYENSYALAVLSNYDANKTGLKELP
MRNLQEILHGAVRFSNNPALCNVESIQWRDIVSSDFLSNMSDFQNHLGSCQKCDPSCPNGSCWGAGE
ENCQKLTKIICAQQCSGRCRGKSPSDCCHNQCAAGCTGPRESDCLVCRKFRDEATCKDTCPPLMLYNP
TTYQMDVNPEGKYSFGATCVKKCPRNYVVTDHGSCVRACGADSYEMEEDGVRKCKKCEGPCRKVCNGI
GIGEFKDSLSINATNIKHFKNCTSISGDLHILPVAFRGDSFTHTPPLDPQELDILKTVKEITGFLLIQ
AWPENRTDLHAFENLEIIRGRTKQHGQFSLAVVSLNITSLGLRSLKEISDGDVIISGNKNLCYANTIN
WKKLFGTSGQKTKIISNRGENSCKATGQVCHALCSPEGCWGPEPRDCVSCRNVSRGRECVDKCNLLEG
EPREFVENSECIQCHPECLPQAMNITCTGRGPDNCIQCAHYIDGPHCVKTCPAGVMGENNTLVWKYAD
AGHVCHLCHPNCTYGCTGPGLEGCPTNGPKIPSIATGMVGALLLLVVALGIGLFMRRRHIVRKRTLR
RLLQERELVEPLTPSGEAPNQALLRILKETEFKKIKVLGSGAFGTVYKGLWIPEGEKVKIPVAIKELR
EATSPKANKEILDEAYVMASVDNPHVCRLLGICLTSTVQLITQLMPFGCLLDYVREHKDNIGSQYLLN
WCVQIAKGMNYLEDRRLVHRDLAARNVLVKTPQHVKITDFGLARLLGAEEKEYHAEGGKVPIKWMALE
SILHRIYTHQSDVWSYGVTVWELMTFGSKPYDGIPASEISSILEKGERLPQPPICTIDVYMIMVKCWM
IDADSRPKFRELIIEFSKMARDPQRYLVIQGDERMHLPSPTDSNFYRALMDEEDMDDVVDADEYLIPQ

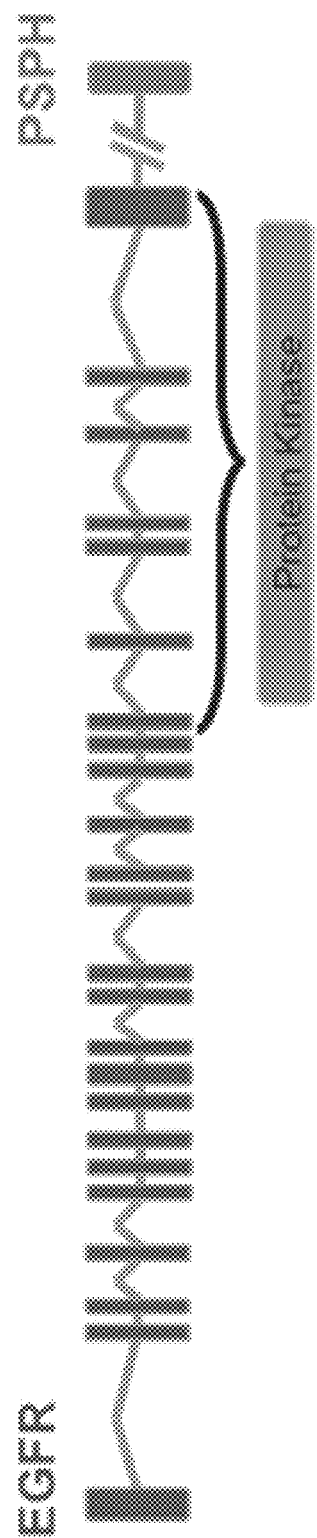

FIG. 11C

MAQPPPPWVRAAFLLCLLSLGGAIEIPMDLTQPPTITQSAKDHIVDPRDNILIECEAK
GNPAPSFEWTRNSRFFNIAKDPRVSMRRRSGTLVIDFRSGGRPEEYEGEYQCFARNKFGT
ALSNRIRLQVSKSPLWPKENLDPVVVQEGAPLTLQCNPPPGLPSPVIFWMSSSMEPITQD
KRVSQGHNGDLYFSNVMLQSMQTDYSCNARFHFTHTIQQKNPFTLKVLTNRPYNDSSLRN
RPDMYSARGVAEDTPSFMYPQGTASSQRVLRGMDLLLECIASGVPTPDIAWYKKGGDLPS
DKAKFENFNKALRITNVSEEDSGEYFCLASNKMGSIRHTISVRVKAAPYWLDEPKNLILA
PGEDGRLVCRANGNPKPTVQWMVNGEPLQSAPPNPNREVAGDTIIFRDTQISSRAVYQCN
TSNEHGYLLANAFVSVLDVPPRMLSPRNQLIRVILYNRTRLDCPFFGSPIPTLRWFKNGQ
GSNLDGGNYHVTENGSLEIRMIRKEDQGIYTCVATNILGKAENQVRLEVKDPTRIYRMPE
DQVARRGTTVQLECRVKHDPSLKLTVSWLKDDEPLYIGHRMRKEDDSLTIFGVAERDQSS
YTCVASTELDQDLAKAYLTVLADQATPTNRLAALPKGRPDRPRDLELTDLAERSVRLTWI
PGDANNSPITDYVVQFEEDQFQPGVWHDHSKYPGSVRSAVLRLSPYVNYQFRVIAINEVG
SSHPSLPSERYRTSGAPPESHPGDVKGEGTRRNNMEITWTPMNATSAFGPNLRYIVKWRR
RETREAWNNVTVWGSRYVVGQTPVYIVPYEIRVQAENDFGRGPEPESVIGYSGEDYTNSTS
GDPVKKDETPPGVSVANGLAVPACLFLSTLLLVLNKCGRRNKFGINRPAVLAPEDGLAM
SLHPMTLGGSSLSPTEGKGSGLQGHIIENPQYFSDACVHHIKRRDIVLKWELGEGAFGKV
FLAECHNLLPEQDKMLVAVKALKEASESARQDFQREAELLTMLQHQHIVRFFGVCTEGRP
LLMVFEYMRHGDLNRFLRSHGPDAKLLAGGEDVAPGPLGLGQLLAVASQVAAGMVYLAGL
HFVHRDLATRNCLVGQGLVVKIGDFGMSRDIYSTDYYRVGGRTMLPIRWMPPESILYRKF
TTESDVWSFGVVLWEIFTYGKQPWYQLSNTEAIDCITQGRELERPRACPPEVYAIMRGCW
QREPQQRHSIKDVHARLQALAQAPPVYLDVLG

MASASYHISNLLEKMTSSDKDFRFMATNDLMTELQKDSIKLD
DDSERKVVKMILKLLEDKNGEVQNLAVKCLGPLVSKVKEYQV
ETIVDTLCTNMLSDKEQLRDISSIGLKTVIGELPPASSGSAL
AANVCKKITGRLTSAIAKQEDVSVQLEALDIMADMLSRCTGP
GLEGCPTNGPKIPSIATGMVGALLLLLVVALGIGLFMRRRHI
VRKRTLRRLLQERELVEPLTPSGEAPNQALLRILKETEFKKI
KVLGSGAFGTVYKGLWIPEGEKVKIPVAIKELREATSPKANK
EILDEAYVMASVDNPHVCRLLGICLTSTVQLITQLMPFGCLL
DYVREHKDNIGSQYLLNWCVQIAKGMNYLEDRRLVHRDLAAR
NVLVKTPQHVKITDFGLAKLLGAEEKEYHAEGGKVPIKWMAL
ESILHRIYTHQSDVWSYGVTVWELMTFGSKPYDGIPASEISS
ILEKGERLPQPPICTIDVYMIMVKCWMIDADSRPKFRELIIE
FSKMARDPQRYLVIQGDERMHLPSPTDSNFYRALMDEEDMDD
VVDADEYLIPQQGFFSSPSTSRTPLLSSLSATSNNSTVACID
RNGLQSCPIKEDSFLQRYSSDPTGALTEDSIDDTFLPVPEYI
NQSVPKRPAGSVQNPVYHNQPLNPAPSRDPHYQDPHSTAVGN
PEYLNTVQPTCVNSTFDSPAHWAQKGSHQISLDNPDYQQDFF
PKEAKPNGIFKGSTAENAEYLRVAPQSSEFIGA*

FIG. 14C

| sample | #chrom 5p | start5p | end5p | Chrom 3p | Start 3p | End 3p |
|---|---|---|---|---|---|---|
| G17807.TCGA-28-5209-01A-01R-1850-01.4 | chr7 | 55086724 | 55268105 | chr7 | 56078745 | 56079561 |
| G17197.TCGA-06-0211-01B-01R-1849-01.2 | chr7 | 55433140 | 55479781 | chr7 | 55861236 | 55886915 |
| G17650.TCGA-28-2513-01A-01R-1850-01.2 | chr7 | 55086724 | 55268105 | chr7 | 55861236 | 55863784 |
| G17506.TCGA-27-1835-01A-01R-1850-01.2 | chr4 | 1795038 | 1808660 | chr4 | 1741428 | 1746894 |
| G17191.TCGA-06-0211-01A-01R-1849-01.2 | chr7 | 55433140 | 55479781 | chr7 | 55861236 | 55886915 |
| G17512.TCGA-27-1837-01A-01R-1850-01.2 | chr7 | 55086724 | 55268105 | chr7 | 55861236 | 55863784 |
| NYU_A | chr4 | 1795038 | 1808660 | chr4 | 1737457 | 1746894 |
| G17814.TCGA-06-5411-01A-01R-1849-01.4 | chr1 | 204797781 | 204951147 | chr1 | 156844362 | 156851641 |
| Fig. G17223.TCGA-06-0750-01A-01R-1849-01.2 | chr7 | 55177539 | 55268105 | chr7 | 55861236 | 55863784 |
| G17798.TCGA-32-5222-01A-01R-1850-01.4 | chr7 | 55086724 | 55268105 | chr7 | 55861236 | 55863784 |
| G17195.TCGA-06-0138-01A-02R-1849-01.2 | chr12 | 69753531 | 69764754 | chr12 | 58339410 | 58351050 |
| G17803.TCGA-76-4925-01A-01R-1850-01.4 | chr4 | 1795038 | 1808660 | chr4 | 1739324 | 1746894 |
| NYU_B | chr17 | 7387849 | 7388175 | chr17 | 7604058 | 7605804 |
| G17507.TCGA-28-1747-01C-01R-1850-01.2 | chr7 | 55086724 | 55268105 | chr7 | 55861236 | 55863784 |
| G17469.TCGA-06-2557-01A-01R-1849-01.2 | chr7 | 73588705 | 73604247 | chr7 | 74173109 | 74175019 |
| G17785.TCGA-06-5413-01A-01R-1849-01.4 | chr14 | 32798478 | 32903022 | chr14 | 34393422 | 34400420 |
| G17467.TCGA-14-0736-02A-01R-2005-01.2 | chr14 | 102606211 | 102606508 | chr19 | 12856190 | 12859137 |
| GBM-CUMC3316_L1 | chr22 | 22160138 | 22221969 | chr12 | 58166799 | 58176322 |
| G17663.TCGA-19-2619-01A-01R-1850-01.2 | chr1 | 156611739 | 156628524 | chr1 | 156844697 | 156851641 |
| G17203.TCGA-06-0211-02A-02R-2005-01.2 | chr7 | 54825187 | 54826938 | chr7 | 55224225 | 55224641 |
| G17784.TCGA-76-4929-01A-01R-1850-01.4 | chr2 | 9675962 | 9695916 | chr2 | 9724106 | 9731643 |
| G17675.TCGA-19-2624-01A-01R-1850-01.2 | chr7 | 55086724 | 55240816 | chr12 | 65107223 | 65110598 |
| G17796.TCGA-41-5651-01A-01R-1850-01.4 | chr12 | 58166382 | 58166910 | chr12 | 58162351 | 58163738 |
| G17666.TCGA-06-5415-01A-01R-1849-01.2 | chr5 | 134209459 | 134210219 | chr2 | 219103386 | 219119069 |
| G17219.TCGA-06-0158-01A-01R-1849-01.2 | chr2 | 42396489 | 42396775 | chrX | 41374190 | 41420896 |

FIG. 27

| sample | #chrom 5p | start5p | end5p | Chrom 3p | Start 3p | End 3p |
|---|---|---|---|---|---|---|
| G17790.TCGA-06-5856-01A-01R-1849-01.4 | chr12 | 122150657 | 122150869 | chr12 | 58191442 | 58193702 |
| NYU_B | chr1 | 19746154 | 19811991 | chr1 | 19401001 | 19433459 |
| G17657.TCGA-19-1787-01B-01R-1850-01.2 | chr3 | 100428159 | 100438901 | chr3 | 100348441 | 100414320 |
| G17643.TCGA-12-5295-01A-01R-1849-01.2 | chr20 | 43976964 | 43977063 | chr3 | 52740659 | 52742194 |
| NYU_G | chr5 | 100191806 | 100238986 | chr5 | 102260660 | 102365415 |
| G17494.TCGA-14-2554-01A-01R-1850-01.2 | chr3 | 48956280 | 48965245 | chr3 | 48265843 | 48266974 |
| G17196.TCGA-06-0178-01A-01R-1849-01.2 | chr12 | 58123421 | 58135939 | chr8 | 94827532 | 94830345 |
| G17782.TCGA-26-5136-01B-01R-1850-01.4 | chr1 | 95392393 | 95392734 | chr1 | 95448278 | 95448861 |
| GBM-CUMC3296_L1 | chr7 | 55639963 | 55640199 | chr12 | 68642024 | 68645357 |
| G17199.TCGA-06-0744-01A-01R-1849-01.2 | chr7 | 55086724 | 55087057 | chr9 | 102741464 | 102784507 |
| G17792.TCGA-28-5204-01A-01R-1850-01.4 | chr4 | 6988888 | 6996028 | chr4 | 8288287 | 8298197 |
| G17476.TCGA-06-2569-01A-01R-1849-01.2 | chr6 | 7310149 | 7313540 | chrX | 31137344 | 32328392 |
| G17195.TCGA-06-0138-01A-02R-1849-01.2 | chr12 | 69139935 | 69145969 | chr12 | 58109542 | 58115337 |
| G17212.TCGA-06-0129-01A-01R-1849-01.2 | chr5 | 140855568 | 140858112 | chr6 | 163956013 | 163991168 |
| G17213.TCGA-06-0157-01A-01R-1849-01.2 | chr4 | 2061586 | 2062888 | chr16 | 90071278 | 90075837 |
| G17200.TCGA-06-0125-01A-01R-1849-01.2 | chr1 | 27022521 | 27094489 | chr14 | 24624365 | 24630546 |
| G17804.TCGA-06-5408-01A-01R-1849-01.4 | chr7 | 55086724 | 55268105 | chr7 | 56078745 | 56079561 |
| G17656.TCGA-28-2514-01A-02R-1850-01.2 | chr1 | 27022521 | 27024030 | chr1 | 49193541 | 49202123 |
| G17654.TCGA-41-4097-01A-01R-1850-01.2 | chr5 | 146017813 | 146461053 | chr1 | 156278751 | 156294879 |
| G17206.TCGA-06-0125-02A-11R-2005-01.2 | chr1 | 27022521 | 27094489 | chr14 | 24624365 | 24630546 |
| G17792.TCGA-28-5204-01A-01R-1850-01.4 | chr9 | 36190891 | 36204175 | chr9 | 33911961 | 33920398 |
| G17663.TCGA-19-2619-01A-01R-1850-01.2 | chr1 | 205719084 | 205719360 | chr1 | 205797153 | 205811016 |
| NYU_E | chr16 | 69221049 | 69333676 | chr16 | 69349910 | 69358944 |
| NYU_G | chr19 | 42759129 | 42759308 | chr19 | 42734337 | 42744293 |
| NYU_B | chr12 | 6457892 | 6473312 | chr12 | 6437923 | 6443409 |
| G17675.TCGA-19-2624-01A-01R-1850-01.2 | chr12 | 69201970 | 69230528 | chr12 | 63037762 | 63195939 |

FIG. 27 Cont.

| sample | #chrom 5p | start5p | end5p | Chrom 3p | Start 3p | End 3p |
|---|---|---|---|---|---|---|
| G17484.TCGA-14-0787-01A-01R-1849-01.2 | chr1 | 155385534 | 155532323 | chr1 | 156374054 | 156384544 |
| G17792.TCGA-28-5204-01A-01R-1850-01.4 | chr7 | 100065174 | 100076901 | chr7 | 100054237 | 100061308 |
| BT299 | chr1 | 23037330 | 23037535 | chr1 | 1246964 | 1256472 |
| G17667.TCGA-26-5134-01A-01R-1850-01.2 | chr4 | 54373483 | 54424435 | chr4 | 53457128 | 53494329 |
| GBM-CUMC3338_L1 | chr19 | 41198855 | 41207363 | chr19 | 41171813 | 41192899 |
| G17815.TCGA-19-5960-01A-11R-1850-01.4 | chr1 | 154918047 | 154928566 | chr1 | 154897208 | 154904890 |
| G17662.TCGA-32-1970-01A-01R-1850-01.2 | chr19 | 58740069 | 58758159 | chr19 | 50285013 | 50310366 |
| NYU_E | chr7 | 65540775 | 65557649 | chr7 | 65592690 | 65619550 |
| G17816.TCGA-28-5215-01A-01R-1850-01.4 | chr7 | 55086724 | 55268105 | chr7 | 56078745 | 56079561 |
| G17650.TCGA-28-2513-01A-01R-1850-01.2 | chr7 | 55433140 | 55433921 | chr7 | 55861236 | 55914329 |
| BT308 | chr20 | 33222418 | 33265088 | chr20 | 33302578 | 33303168 |
| G17656.TCGA-28-2514-01A-02R-1850-01.2 | chr7 | 55086724 | 55268105 | chr7 | 55538306 | 55588822 |
| G17639.TCGA-12-3652-01A-01R-1849-01.2 | chr9 | 33290509 | 33295424 | chr9 | 34379016 | 34382866 |
| G17796.TCGA-41-5651-01A-01R-1850-01.4 | chr12 | 58087885 | 58090155 | chr12 | 57960908 | 57978553 |
| G17468.TCGA-19-0957-02A-11R-2005-01.2 | chr1 | 61547979 | 61554351 | chr10 | 90043860 | 90122481 |
| G17790.TCGA-06-5856-01A-01R-1849-01.4 | chr13 | 20304378 | 20357082 | chr13 | 20977808 | 20987525 |
| GBM-CUMC3338_L1 | chr17 | 7465318 | 7470321 | chr17 | 7215977 | 7217039 |
| G17790.TCGA-06-5856-01A-01R-1849-01.4 | chr12 | 117175594 | 117175842 | chr12 | 69229608 | 69239210 |
| G17802.TCGA-28-5208-01A-01R-1850-01.4 | chr7 | 51203854 | 51258774 | chr7 | 55861236 | 55886915 |
| G17210.TCGA-12-0616-01A-01R-1849-01.2 | chr7 | 101006121 | 101176423 | chr7 | 30536238 | 30536850 |
| NYU_B | chr2 | 233562014 | 233613791 | chr2 | 234862560 | 234928164 |
| G17469.TCGA-06-2557-01A-01R-1849-01.2 | chr7 | 55086724 | 55268105 | chr7 | 55861236 | 55863784 |
| G17480.TCGA-27-1830-01A-01R-1850-01.2 | chr2 | 231921608 | 231945027 | chr2 | 230222345 | 230377651 |
| G17634.TCGA-19-2625-01A-01R-1850-01.2 | chr22 | 36424287 | 36424584 | chr22 | 37966253 | 37967937 |
| G17654.TCGA-41-4097-01A-01R-1850-01.2 | chr3 | 66119284 | 66313802 | chr2 | 86371055 | 86374955 |
| G17485.TCGA-14-1402-02A-01R-2005-01.2 | chr3 | 142166711 | 142166852 | chr1 | 245912644 | 246093238 |
| G17498.TCGA-02-2483-01A-01R-1849-01.2 | chr9 | 119976636 | 120177316 | chr16 | 332024 | 333367 |

FIG. 27 Cont.

| sample | #chrom 5p | start5p | end5p | Chrom 3p | Start 3p | End 3p |
|---|---|---|---|---|---|---|
| G17799.TCGA-06-1804-01A-01R-1849-01.4 | chr13 | 60971426 | 61109366 | chr13 | 47345391 | 47345630 |
| G17660.TCGA-06-5414-01A-01R-1849-01.2 | chr8 | 61591338 | 61655655 | chr8 | 59717976 | 59872566 |
| GBM-CUMC3296_L1 | chr12 | 67663060 | 67688935 | chr7 | 55238867 | 55275029 |
| G17505.TCGA-06-2564-01A-01R-1849-01.2 | chr5 | 216843 | 218296 | chr5 | 1253286 | 1282738 |
| G17798.TCGA-32-5222-01A-01R-1850-01.4 | chr1 | 11313895 | 11322607 | chr1 | 6880240 | 6932096 |
| GBM-CUMC3297_L1 | chr22 | 24640520 | 24641109 | chr22 | 18659538 | 18660159 |
| GBM-CUMC3342_L1 | chr10 | 61083747 | 61122351 | chr10 | 104375024 | 104378415 |
| G17500.TCGA-27-1831-01A-01R-1850-01.2 | chr13 | 39261172 | 39438742 | chr13 | 41790516 | 41808142 |
| G17212.TCGA-06-0129-01A-01R-1849-01.2 | chr6 | 3410421 | 3456792 | chr6 | 47199268 | 47221256 |
| GBM-CUMC3322_L1 | chr7 | 1412251077 | 141255366 | chr7 | 158715067 | 158738881 |
| G17675.TCGA-19-2624-01A-01R-1850-01.2 | chr12 | 54378945 | 54379793 | chr12 | 56295196 | 56297263 |
| G17803.TCGA-76-4925-01A-01R-1850-01.4 | chr17 | 74046508 | 74068577 | chr19 | 10683347 | 10694745 |
| G17796.TCGA-41-5651-01A-01R-1850-01.4 | chr12 | 58176535 | 58186855 | chr12 | 57849876 | 57851788 |
| G17663.TCGA-19-2619-01A-01R-1850-01.2 | chr7 | 70597788 | 70800718 | chr7 | 94827660 | 94925724 |
| G17207.TCGA-06-0156-01A-03R-1849-01.2 | chr11 | 910774 | 910873 | chr16 | 4390252 | 4438631 |
| G17802.TCGA-28-5208-01A-01R-1850-01.4 | chr7 | 55433140 | 55433921 | chr7 | 56078745 | 56079561 |
| G17485.TCGA-14-1402-02A-01R-2005-01.2 | chr7 | 151216545 | 151217009 | chr7 | 151253202 | 151372722 |
| NYU_E | chr11 | 88033697 | 88070940 | chr11 | 87846430 | 87883122 |
| G17212.TCGA-06-0129-01A-01R-1849-01.2 | chr12 | 51079615 | 51128912 | chr6 | 42019094 | 42048642 |
| G17787.TCGA-26-5139-01A-01R-1850-01.4 | chr19 | 13915605 | 13920033 | chr1 | 156005092 | 156012703 |
| G17675.TCGA-19-2624-01A-01R-1850-01.2 | chr12 | 65218409 | 65232630 | chr12 | 63037762 | 63226058 |
| G17800.TCGA-06-5859-01A-01R-1849-01.4 | chr18 | 48556582 | 48586285 | chr18 | 56934268 | 56936732 |
| G17638.TCGA-28-2499-01A-01R-1850-01.2 | chr2 | 234263152 | 234299128 | chr2 | 234967479 | 234978666 |

| sample | Strand 5p | Strand 3p | Genes 5p | Genes 3p | Total frags (split inserts + split reads) | Spanning frags (split reads) |
|---|---|---|---|---|---|---|
| G17807.TCGA-28-5209-01A-01R-1850-01.4 | + | - | EGFR | PSPH | 6849 | 5648 |

FIG. 27 Cont.

| sample | Strand 5p | Strand 3p | Genes 5p | Genes 3p | Total frags (split inserts + split reads) | Spanning frags (split reads) |
|---|---|---|---|---|---|---|
| G17197.TCGA-06-0211-01B-01R-1849-01.2 | + | - | LANCL2 | SEPT14 | 2619 | 2078 |
| G17650.TCGA-28-2513-01A-01R-1850-01.2 | + | - | EGFR | SEPT14 | 1899 | 1464 |
| G17506.TCGA-27-1835-01A-01R-1850-01.2 | + | + | FGFR3 | TACC3 | 1748 | 1604 |
| G17191.TCGA-06-0211-01A-01R-1849-01.2 | + | - | LANCL2 | SEPT14 | 1367 | 1128 |
| G17512.TCGA-27-1837-01A-01R-1850-01.2 | + | - | EGFR | SEPT14 | 989 | 796 |
| NYU_A | + | + | FGFR3 | TACC3 | 973 | 492 |
| G17814.TCGA-06-5411-01A-01R-1849-01.4 | + | + | KIAA0756, NFASC | NTRK1 | 841 | 751 |
| G17223.TCGA-06-0750-01A-01R-1849-01.2 | + | - | EGFR | SEPT14 | 534 | 414 |
| G17798.TCGA-32-5222-01A-01R-1850-01.4 | + | - | EGFR | SEPT14 | 528 | 495 |
| G17195.TCGA-06-0138-01A-02R-1849-01.2 | + | + | YEATS4 | XRCC6BP1 | 328 | 306 |
| G17803.TCGA-76-4925-01A-01R-1850-01.4 | + | + | FGFR3 | TACC3 | 303 | 203 |
| NYU_B | + | + | POLR2A | WRAP53 | 263 | 240 |
| G17507.TCGA-28-1747-01C-01R-1850-01.2 | + | - | EGFR | SEPT14 | 181 | 142 |
| G17469.TCGA-06-2557-01A-01R-1849-01.2 | + | + | EIF4H | GTF2I | 180 | 142 |
| G17785.TCGA-06-5413-01A-01R-1849-01.4 | + | - | AKAP6 | EGLN3 | 171 | 129 |
| G17467.TCGA-14-0736-02A-01R-2005-01.2 | + | + | WDR20 | ASNA1 | 151 | 75 |
| GBM-CUMC3316_L1 | - | + | MAPK1 | FAM119B, DKFZp586D0919 | 145 | 96 |
| G17663.TCGA-19-2619-01A-01R-1850-01.2 | + | + | BCAN | NTRK1 | 130 | 17 |
| G17203.TCGA-06-0211-02A-02R-2005-01.2 | + | + | SEC61G | EGFR | 129 | 103 |
| G17784.TCGA-76-4929-01A-01R-1850-01.4 | + | - | ADAM17 | YWHAQ | 106 | 95 |
| G17675.TCGA-19-2624-01A-01R-1850-01.2 | + | - | EGFR | GNS | 92 | 59 |
| G17796.TCGA-41-5651-01A-01R-1850-01.4 | + | - | FAM119B, DKFZp586D0919 | METTL1 | 29 | 18 |
| G17666.TCGA-06-5415-01A-01R-1849-01.2 | + | + | TXNDC15 | ARPC2 | 90 | 36 |
| G17219.TCGA-06-0158-01A-01R-1849-01.2 | + | - | EML4 | CASK | 86 | 63 |

FIG. 27 Cont.

| sample | Strand 5p | Strand 3p | Genes 5p | Genes 3p | Total frags (split inserts + split reads) | Spanning frags (split reads) |
|---|---|---|---|---|---|---|
| G17790.TCGA-06-5856-01A-01R-1849-01.4 | + | - | TMEM120B | AVIL | 75 | 56 |
| NYU_B | - | - | CAPZB | UBR4 | 72 | 48 |
| G17657.TCGA-19-1787-01B-01R-1850-01.2 | + | + | TFG | GPR128 | 23 | 19 |
| G17643.TCGA-12-5295-01A-01R-1849-01.2 | - | + | SDC4 | SPCS1 | 68 | 18 |
| NYU_G | - | + | ST8SIA4 | PAM | 60 | 55 |
| G17494.TCGA-14-2554-01A-01R-1850-01.2 | + | + | Ari2,ARIH2 | CAMP | 59 | 52 |
| G17196.TCGA-06-0178-01A-01R-1849-01.2 | - | + | AGAP2 | TMEM67 | 59 | 21 |
| G17782.TCGA-26-5136-01B-01R-1850-01.4 | - | - | CNN3 | ALG14 | 54 | 49 |
| GBM-CUMC3296_L1 | - | - | VOPP1 | IL22 | 48 | 35 |
| G17199.TCGA-06-0744-01A-01R-1849-01.2 | + | - | EGFR | ERP44,KIAA0573 | 46 | 30 |
| G17792.TCGA-28-5204-01A-01R-1850-01.4 | + | + | TBC1D14 | HTRA3 | 45 | 33 |
| G17476.TCGA-06-2569-01A-01R-1849-01.2 | - | - | SSR1 | DMD | 44 | 33 |
| G17195.TCGA-06-0138-01A-02R-1849-01.2 | + | + | SLC35E3 | OS9 | 44 | 38 |
| G17212.TCGA-06-0129-01A-01R-1849-01.2 | + | + | PCDHGC3,PCDHGC4 | QKI | 43 | 24 |
| G17213.TCGA-06-0157-01A-01R-1849-01.2 | + | - | NAT8L | DBNDD1,DKFZp761L2416 | 39 | 24 |
| G17200.TCGA-06-0125-01A-01R-1849-01.2 | + | + | ARID1A | hoip,RNF31 | 39 | 26 |
| G17804.TCGA-06-5408-01A-01R-1849-01.4 | + | - | EGFR | PSPH | 38 | 37 |
| G17656.TCGA-28-2514-01A-02R-1850-01.2 | + | - | ARID1A | BEND5 | 37 | 29 |
| G17654.TCGA-41-4097-01A-01R-1850-01.2 | - | - | PPP2R2B | CCT3,DKFZp667A196 | 37 | 18 |
| G17206.TCGA-06-0125-02A-11R-2005-01.2 | + | + | ARID1A | hoip,RNF31 | 36 | 21 |
| G17792.TCGA-28-5204-01A-01R-1850-01.4 | + | + | CLTA | UBE2R2 | 36 | 31 |
| G17663.TCGA-19-2619-01A-01R-1850-01.2 | - | - | NUCKS1 | PM20D1 | 34 | 31 |
| NYU_E | + | + | SNTB2 | VPS4A | 14 | 13 |
| NYU_G | - | - | ERF | GSK3A | 14 | 3 |
| NYU_B | - | - | SCNN1A | TNFRSF1A | 13 | 9 |

FIG. 27 Cont.

| sample | Strand 5p | Strand 3p | Genes 5p | Genes 3p | Total frags (split inserts + split reads) | Spanning frags (split reads) |
|---|---|---|---|---|---|---|
| G17675.TCGA-19-2624-01A-01R-1850-01.2 | + | - | MDM2 | PPM1H | 34 | 22 |
| G17484.TCGA-14-0787-01A-01R-1849-01.2 | - | - | ASH1L | C1orf61 | 33 | 30 |
| G17792.TCGA-28-5204-01A-01R-1850-01.4 | - | - | TSC22D4 | C7orf61 | 12 | 1 |
| BT299 | + | - | EPHB2 | CPSF3L | 33 | 6 |
| G17667.TCGA-26-5134-01A-01R-1850-01.2 | - | - | LNX1 | USP46 | 33 | 27 |
| GBM-CUMC3338_L1 | - | - | ADCK4 | NUMBL | 11 | 4 |
| G17815.TCGA-19-5960-01A-11R-1850-01.4 | - | - | PBXIP1 | PMVK | 10 | 8 |
| G17662.TCGA-32-1970-01A-01R-1850-01.2 | + | + | ZNF544 | DKFZp586H1320,AP2A1 | 31 | 28 |
| NYU_E | + | + | ASL | CRCP | 10 | 8 |
| G17816.TCGA-28-5215-01A-01R-1850-01.4 | + | - | EGFR | PSPH | 31 | 28 |
| G17650.TCGA-28-2513-01A-01R-1850-01.2 | + | - | LANCL2 | SEPT14 | 31 | 14 |
| BT308 | - | - | PIGU | NCOA6 | 30 | 26 |
| G17656.TCGA-28-2514-01A-02R-1850-01.2 | + | - | EGFR | GASP,VOPP1 | 29 | 23 |
| G17639.TCGA-12-3652-01A-01R-1849-01.2 | + | - | NFX1 | C9orf24 | 28 | 20 |
| G17796.TCGA-41-5651-01A-01R-1850-01.4 | + | + | OS9 | KIF5A | 28 | 23 |
| G17468.TCGA-19-0957-02A-11R-2005-01.2 | + | - | NFIA | RNLS,C10orf59 | 27 | 14 |
| G17790.TCGA-06-5856-01A-01R-1849-01.4 | - | - | PSPC1 | CRYL1 | 26 | 18 |
| GBM-CUMC3338_L1 | + | - | SENP3 | GPS2,KIAA1787 | 26 | 15 |
| G17790.TCGA-06-5856-01A-01R-1849-01.4 | - | + | C12orf49 | MDM2 | 26 | 16 |
| G17802.TCGA-28-5208-01A-01R-1850-01.4 | - | - | COBL | SEPT14 | 23 | 15 |
| G17210.TCGA-12-0616-01A-01R-1849-01.2 | + | - | EMID2 | GGCT | 22 | 16 |
| NYU_B | + | + | KIAA0642,GIGYF2 | TRPM8 | 22 | 20 |
| G17469.TCGA-06-2557-01A-01R-1849-01.2 | + | - | EGFR | SEPT14 | 21 | 13 |
| G17480.TCGA-27-1830-01A-01R-1850-01.2 | + | - | PSMD1 | DNER | 20 | 14 |
| G17634.TCGA-19-2625-01A-01R-1850-01.2 | - | - | RBM9 | LGALS2 | 20 | 16 |

FIG. 27 Cont.

| sample | Strand 5p | Strand 3p | Genes 5p | Genes 3p | Total frags (split inserts + split reads) | Spanning frags (split reads) |
|---|---|---|---|---|---|---|
| G17654.TCGA-41-4097-01A-01R-1850-01.2 | + | - | SLC25A26 | IMMT | 19 | 17 |
| G17485.TCGA-14-1402-02A-01R-2005-01.2 | - | - | XRN1 | SMYD3 | 19 | 11 |
| G17498.TCGA-02-2483-01A-01R-1849-01.2 | - | + | ASTN2 | ARHGDIG, PDIA2 | 18 | 6 |
| G17799.TCGA-06-1804-01A-01R-1849-01.4 | + | - | TDRD3 | ESD | 18 | 13 |
| G17660.TCGA-06-5414-01A-01R-1849-01.2 | + | - | CHD7 | TOX | 18 | 16 |
| GBM-CUMC3296_L1 | + | + | CAND1 | EGFR | 17 | 14 |
| G17505.TCGA-06-2564-01A-01R-1849-01.2 | - | - | CCDC127 | hTERT,TERT | 17 | 12 |
| G17798.TCGA-32-5222-01A-01R-1850-01.4 | - | + | MTOR | KIAA0833, CAMTA1 | 17 | 13 |
| GBM-CUMC3297_L1 | - | + | DKFZp566O011,GGT5 | USP18 | 16 | 6 |
| GBM-CUMC3342_L1 | - | + | FAM13C | DKFZp434E2022,SUFU | 15 | 11 |
| G17500.TCGA-27-1831-01A-01R-1850-01.2 | + | - | FREM2 | MTRF1 | 15 | 14 |
| G17212.TCGA-06-0129-01A-01R-1849-01.2 | - | - | SLC22A23, DKFZp434F011 | TNFRSF21 | 15 | 11 |
| GBM-CUMC3322_L1 | + | + | AGK | WDR60 | 15 | 12 |
| G17675.TCGA-19-2624-01A-01R-1850-01.2 | + | - | HOXC10 | WIBG | 15 | 10 |
| G17803.TCGA-76-4925-01A-01R-1850-01.4 | - | - | SRP68 | AP1M2 | 14 | 8 |
| G17796.TCGA-41-5651-01A-01R-1850-01.4 | + | + | TSFM | INHBE | 14 | 9 |
| G17663.TCGA-19-2619-01A-01R-1850-01.2 | + | + | WBSCR17 | PPP1R9A | 14 | 10 |
| G17207.TCGA-06-0156-01A-03R-1849-01.2 | - | - | CHID1 | Magmas,hCG_1787779,CORO7 | 13 | 13 |
| G17802.TCGA-28-5208-01A-01R-1850-01.4 | + | - | LANCL2 | PSPH | 13 | 2 |
| G17485.TCGA-14-1402-02A-01R-2005-01.2 | - | - | RHEB | H91620,PRKAG2 | 12 | 11 |
| NYU_E | - | - | CTSC | RAB38 | 12 | 11 |
| G17212.TCGA-06-0129-01A-01R-1849-01.2 | + | + | DIP2B | TAF8 | 12 | 7 |
| G17787.TCGA-26-5139-01A-01R-1850-01.4 | + | - | ZSWIM4 | UBQLN4 | 11 | 9 |

FIG. 27 Cont.

| sample | Strand 5p | Strand 3p | Genes 5p | Genes 3p | Total frags (split inserts + split reads) | Spanning frags (split reads) |
|---|---|---|---|---|---|---|
| G17675.TCGA-19-2624-01A-01R-1850-01.2 | + | - | TBC1D30, KIAA0984 | PPM1H | 10 | 6 |
| G17800.TCGA-06-5859-01A-01R-1849-01.4 | + | - | SMAD4 | RAX | 10 | 10 |
| G17638.TCGA-28-2499-01A-01R-1850-01.2 | + | + | DGKD | SPP2 | 10 | 10 |

| sample | Gene Breakpoint 5p | Gene Breakpoint 3p | Frame Type | SEQ ID NO: | Fused Sequence |
|---|---|---|---|---|---|
| G17807.TCGA-28-5209-01A-01R-1850-01.4 | 55268106 | 56079562 | InFrame | 8276 | ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCACGAGTAACAAGCTCACGCAGTTGGGCACTTTTGAAGATCATTTTCTCAGCCTCCAGAGGATGTTCAATAACTGTGAGGTGGTCCTTGGGAATTTGGAAATTACCTATGTGCAGAGGAATTATGATCTTTCCTTCTTAAAGACCATCCAGGAGGTGGCTGGTTATGTCCTCATTGCCCTCAACACAGTGGAGCGAATTCCTTTGGAAAACCTGCAGATCATCAGAGGAAATATGTACTACGAAAATTCCTATGCCTTAGCAGTCTTATCTAACTATGATGCAAATAAAACCGGACTGAAGGAGCTGCCCATGAGAAATTTACAGGAAATCCTGCATGGCGCCGTGCGGTTCAGCAACAACCCTGCCCTGTGCAACGTGGAGAGCATCCAGTGGCGGGACATAGTCAGCAGTGACTTTCTCAGCAACATGTCGATGGACTTCCAGAACCACCTGGGCAGCTGCCAAAAGTGTGATCCAAGCTGTCCCAATGGGAGCTGCTGGGGTGCAGGAGAGGAGAACTGCCAGAAACTGACCAAAATCATCTGTGCCCAGCAGTGCTCCGGGCGCTGCCGTGGCAAGTCCCCCAGTGACTGCTGCCACAACCAGTGTGCTGCAGGCTGCACAGGCCCCCGGGAGAGCGACTGCCTGGTCTGCCGCAAATTCCGAGACGAAGCCACGTGCAAGGACACCTGCCCCCCACTCATGCTCTACAACCCCACCACGTACCAGATGGATGTGAACCCCGAGGGCAAATACAGCTTTGGTGCCACCTGCGTGAAGAAGTGTCCCCGTAATTATGTGGTGACAGATCACGGCTCGTGCGTCCGAGCCTGTGGGGCCGACAGCTATGAGATGGAGGAAGACGGCGTCCGCAAGTGTAAGAAGTGCGAAGGGCCTTGCCGCAAAGTGTGTAACGGAATAGGTATTGGTGAATTTAAAGACTCACTCTCCATAAATGCTACGAATATTAAACACTTCAAAAACTGCACCTCCATCAGTGGCGATCTCCACATCCTGCCGGTGGCATTTAGGGGTGACTCCTTCACACATACTCCTCCTCTGGATCCACAGGAACTGGATATTCTGAAAACCGTAAAGGAAATCACAGGGTTTTTGCTGATTCAGGCTTGGCCTGAAAACAGGACGGACCTCCATGCCTTTGAGAACCTAGAAATCATACGCGGCAGGACCAAGCAACATGGTCAGTTTTCTCTTGCAGTCGTCAGCCTGAACATAACATCCTTGGGATTACGCTCCCTCAAGGAGATAAGTGATGGAGATGTGATAATTTCAGGAAACAAAAATTTGTGCTATGCAAATACAATAAACTGGAAAAAACTGTTTGGGACCTCCGGTCAGAAAACCAAAATTATAAGCAACAGAGGTGAAAACAGCTGCAAGGCCACAGGCCAGGTCTGCCATGCCTTGTGCTCCCCCGAGGGCTGCTGGGGCCCGGAGCCCAGGGACTGCGTCTCTTGCCGGAATGTCAGCCGAGGCAGGGAATGCGTGG |

FIG. 27 Cont.

| sample | Gene Break-point 5p | Gene Break-point 3p | Frame Type | SEQ ID NO: | Fused Sequence |
|---|---|---|---|---|---|
| | | | | | ACAAGTGCAACCTTCTGGAGGGTGAGCCAAGGGAGTT TGTGGAGAACTCTGAGTGCATACAGTGCCACCCAGAG TGCCTGCCTCAGGCCATGAACATCACCTGCACAGGACG GGGACCAGACAACTGTATCCAGTGTGCCCACTACATTG ACGGCCCCCACTGCGTCAAGACCTGCCCGGCAGGAGT CATGGGAGAAAACAACACCCTGGTCTGGAAGTACGCA GACGCCGGCCATGTGTGCCACCTGTGCCATCCAAACTG CACCTACGGATGCACTGGGCCAGGTCTTGAAGGCTGT CCAACGAATGGGCCTAAGATCCCGTCCATCGCCACTGG GATGGTGGGGGCCCTCCTCTTGCTGCTGGTGGTGGCC CTGGGGATCGGCCTCTTCATGCGAAGGCGCCACATCG TTCGGAAGCGCACGCTGCGGAGGCTGCTGCAGGAGA GGGAGCTTGTGGAGCCTCTTACACCCAGTGGAGAAGC TCCCAACCAAGCTCTCTTGAGGATCTTGAAGGAAACTG AATTCAAAAAGATCAAAGTGCTGGGCTCCGGTGCGTT CGGCACGGTGTATAAGGGACTCTGGATCCCAGAAGGT GAGAAAGTTAAAATTCCCGTCGCTATCAAGGAATTAA GAGAAGCAACATCTCCGAAAGCCAACAAGGAAATCCT CGATGAAGCCTACGTGATGGCCAGCGTGGACAACCCC CACGTGTGCCGCCTGCTGGGCATCTGCCTCACCTCCAC CGTGCAGCTCATCACGCAGCTCATGCCCTTCGGCTGCC TCCTGGACTATGTCCGGGAACACAAAGACAATATTGG CTCCCAGTACCTGCTCAACTGGTGTGTGCAGATCGCAA AGGGCATGAACTACTTGGAGGACCGTCGCTTGGTGCA CCGCGACCTGGCAGCCAGGAACGTACTGGTGAAAACA CCGCAGCATGTCAAGATCACAGATTTTGGGCTGGCCA AACTGCTGGGTGCGGAAGAGAAAGAATACCATGCAG AAGGAGGCAAAGTGCCTATCAAGTGGATGGCATTGGA ATCAATTTTACACAGAATCTATACCCACCAGAGTGATG TCTGGAGCTACGGGGTGACTGTTTGGGAGTTGATGAC CTTTGGATCCAAGCCATATGACGGAATCCCTGCCAGCG AGATCTCCTCCATCCTGGAGAAAGGAGAACGCCTCCCT CAGCCACCCATATGTACCATCGATGTCTACATGATCAT GGTCAAGTGCTGGATGATAGACGCAGATAGTCGCCCA AAGTTCCGTGAGTTGATCATCGAATTCTCCAAAATGGC CCGAGACCCCCAGCGCTACCTTGTCATTCAG\|GATGCT TTCATTGGATTTGGAGGAAATGTGATCAGGCAACAAG TCAAGGATAACGCCAAATGGTATATCACTGATTTTGTA GAGCTGCTGGGAGAACTGGAAGAA |
| G17197. TCGA-06-0211-01B-01R-1849-01.2 | 55479782 | 55886916 | InFrame | 8277 | ATGGGCGAGACCATGTCAAAGAGGCTGAAGCTCCACC TGGGAGGGGAGGCAGAAATGGAGGAACGGGCGTTCG TCAACCCCTTCCCGGACTACGAGGCCGCCGCCGGGGC GCTGCTCGCCTCCGGAGCGGCCGAAGAGACAGGCTGT GTTCGTCCCCGGCGACCACGGATGAGCCCGGCCTCCC TTTTCATCAGGACGGGAAGATCATTCATAATTTCATAA GACGGATCCAGACCAAAATTAAAGATCTTCTGCAGCA AATGGAAGAAGGGCTGAAGACAGCTGATCCCCATGAC TGCTCTGCTTATACTGGCTGGACAGGCATAGCCCTTTT GTACCTGCAGTTGTACCGGGTCACATGTGACCAAACCT ACCTGCTCCGATCCCTGGATTACGTAAAAAGAACACTT CGGAATCTGAATGGCCGCAGGGTCACCTTCCTCTGTGG GGATGCTGGCCCCCTGGCTGTTGGAGCTGTGATTTATC ACAAACTCAGAAGTGACTGTGAGTCCCAGGAATGTGT CACAAAACTTTTGCAGCTCCAGAGATCGGTTGTCTGCC AAGAATCAGACCTTCCTGATGAGCTGCTTTATGGACGG |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GCAGGTTATCTGTATGCCTTACTGTACCTGAACACAGA GATAGGTCCAGGCACCGTGTGTGAGTCAGCTATTAAA GAGGTAGTCAATGCTATTATTGAATCGGGTAAGACTTT GTCAAGGGAAGAAAGAAAAACGGAGCGCTGCCCGCT GTTGTACCAGTGGCACCGGAAGCAGTACGTTGGAGCA GCCCATGGCATGGCTGGAATTTACTATATGTTAATGCA GCCGGCAGCAAAAGTGGACCAAGAAACCTTGACAGAA ATGGTGAAACCCAGTATTGATTATGTGCGCCACAAAAA ATTCCGATCTGGGAATTACCCATCATCATTAAGCAATG AAACAGACCGGCTGGTGCACTGGTGCCACGGCGCCCC GGGGGTCATCCACATGCTCATGCAGGCGTACAAG\|GG GCTGTTACCCTTTGCTGTGGTAGGGAGTACAGATGAA GTGAAAGTTGGAAAAAGGATGGTCAGAGGCCGTCACT ACCCTTGGGGAGTTTTGCAAGTGGAAAATGAAAATCA CTGTGACTTCGTTAAGCTCCGAGATATGCTTCTTTGTAC CAATATGGAAAATCTAAAAGAAAAAACCCACACTCAG CACTATGAATGTTATAGGTACCAAAAACTGCAGAAAAT GGGCTTTACAGATGTGGGTCCAAACAACCAGCCAGTT AGTTTTCAAGAAATCTTTGAAGCCAAAAGACAAGAGTT CTATGATCAATGTCAGAGGGAAGAAGAAGAGTTGAAA CAGAGATTTATGCAGCGAGTCAAGGAGAAAGAAGCAA CATTTAAAGAAGCTGAAAAAGAGCTGCAGGACAAGTT CGAGCATCTTAAAATGATTCAACAGGAGGAGATAAGG AAGCTCGAGGAAGAGAAAAAACAACTGGAAGGAGAA ATCATAGATTTTTATAAAATGAAAGCTGCCTCCGAAGC ACTGCAGACTCAGCTGAGCACCGATACAAAGAAAGAC AAACATCGTAAGAAA |
| G17650. TCGA-28-2513-01A-01R-1850-01.2 | 55268106 | 55863785 | InFrame | 8278 | ATGCGACCCTCCGGGACGGCCGGGGCAGCGCTCCTGG CGCTGCTGGCTGCGCTCTGCCCGGCGAGTCGGGCTCT GGAGGAAAAGAAAGTTTGCCAAGGCACGAGTAACAA GCTCACGCAGTTGGGCACTTTTGAAGATCATTTTCTCA GCCTCCAGAGGATGTTCAATAACTGTGAGGTGGTCCTT GGGAATTTGGAAATTACCTATGTGCAGAGGAATTATG ATCTTTCCTTCTTAAAGACCATCCAGGAGGTGGCTGGT TATGTCCTCATTGCCCTCAACACAGTGGAGCGAATTCC TTTGGAAAACCTGCAGATCATCAGAGGAAATATGTACT ACGAAAATTCCTATGCCTTAGCAGTCTTATCTAACTATG ATGCAAATAAAACCGGACTGAAGGAGCTGCCCATGAG AAATTTACAGGAAATCCTGCATGGCGCCGTGCGGTTCA GCAACAACCCTGCCCTGTGCAACGTGGAGAGCATCCA GTGGCGGGACATAGTCAGCAGTGACTTTCTCAGCAAC ATGTCGATGGACTTCCAGAACCACTGGGCAGCTGCC AAAAGTGTGATCCAAGCTGTCCCAATGGGAGCTGCTG GGGTGCAGGAGAGGAGAACTGCCAGAAACTGACCAA AATCATCTGTGCCCAGCAGTGCTCCGGGCGCTGCCGTG GCAAGTCCCCAGTGACTGCTGCCACAACCAGTGTGCT GCAGGCTGCACAGGCCCCGGGAGCGACTGCCTG GTCTGCCGCAAATTCCGAGACGAAGCCACGTGCAAGG ACACCTGCCCCCCACTCATGCTCTACAACCCCACCACGT ACCAGATGGATGTGAACCCCGAGGGCAAATACAGCTT TGGTGCCACCTGCGTGAAGAAGTGTCCCCGTAATTATG TGGTGACAGATCACGGCTCGTGCGTCCGAGCCTGTGG GGCCGACAGCTATGAGATGGAGGAAGACGGCGTCCG CAAGTGTAAGAAGTGCGAAGGGCCTTGCCGCAAAGTG TGTAACGGAATAGGTATTGGTGAATTTAAAGACTCACT |

FIG. 27 Cont.

| sample | Gene Break- point 5p | Gene Break- point 3p | Frame Type | SEQ ID NO: | Fused Sequence |
|---|---|---|---|---|---|
| | | | | | CTCCATAAATGCTACGAATATTAAACACTTCAAAAACT GCACCTCCATCAGTGGCGATCTCCACATCCTGCCGGTG GCATTTAGGGGTGACTCCTTCACACATACTCCTCCTCTG GATCCACAGGAACTGGATATTCTGAAAACCGTAAAGG AAATCACAGGGTTTTTGCTGATTCAGGCTTGGCCTGAA AACAGGACGGACCTCCATGCCTTTGAGAACCTAGAAA TCATACGCGGCAGGACCAAGCAACATGGTCAGTTTTCT CTTGCAGTCGTCAGCCTGAACATAACATCCTTGGGATT ACGCTCCCTCAAGGAGATAAGTGATGGAGATGTGATA ATTTCAGGAAACAAAAATTTGTGCTATGCAAATACAAT AAACTGGAAAAAACTGTTTGGGACCTCCGGTCAGAAA ACCAAAATTATAAGCAACAGAGGTGAAAACAGCTGCA AGGCCACAGGCCAGGTCTGCCATGCCTTGTGCTCCCCC GAGGGCTGCTGGGGCCCGGAGCCCAGGGACTGCGTC TCTTGCCGGAATGTCAGCCGAGGCAGGGAATGCGTGG ACAAGTGCAACCTTCTGGAGGGTGAGCCAAGGGAGTT TGTGGAGAACTCTGAGTGCATACAGTGCCACCCAGAG TGCCTGCCTCAGGCCATGAACATCACCTGCACAGGACG GGGACCAGACAACTGTATCCAGTGTGCCCACTACATTG ACGGCCCCCACTGCGTCAAGACCTGCCCGGCAGGAGT CATGGGAGAAAACAACACCCTGGTCTGGAAGTACGCA GACGCCGGCCATGTGTGCCACCTGTGCCATCCAAACTG CACCTACGGATGCACTGGGCCAGGTCTTGAAGGCTGT CCAACGAATGGGCCTAAGATCCCGTCCATCGCCACTGG GATGGTGGGGGCCCTCCTCTTGCTGCTGGTGGTGGCC CTGGGGATCGGCCTCTTCATGCGAAGGCGCCACATCG TTCGGAAGCGCACGCTGCGGAGGCTGCTGCAGGAGA GGGAGCTTGTGGAGCCTCTTACACCCAGTGGAGAAGC TCCCAACCAAGCTCTCTTGAGGATCTTGAAGGAAACTG AATTCAAAAAGATCAAAGTGCTGGGCTCCGGTGCGTT CGGCACGGTGTATAAGGGACTCTGGATCCCAGAAGGT GAGAAAGTTAAAATTCCCGTCGCTATCAAGGAATTAA GAGAAGCAACATCTCCGAAAGCCAACAAGGAAATCCT CGATGAAGCCTACGTGATGGCCAGCGTGGACAACCCC CACGTGTGCCGCCTGCTGGGCATCTGCCTCACCTCCAC CGTGCAGCTCATCACGCAGCTCATGCCCTTCGGCTGCC TCCTGGACTATGTCCGGGAACACAAAGACAATATTGG CTCCCAGTACCTGCTCAACTGGTGTGTGCAGATCGCAA AGGGCATGAACTACTTGGAGGACCGTCGCTTGGTGCA CCGCGACCTGGCAGCCAGGAACGTACTGGTGAAAACA CCGCAGCATGTCAAGATCACAGATTTTGGGCTGGCCA AACTGCTGGGTGCGGAAGAGAAAGAATACCATGCAG AAGGAGGCAAAGTGCCTATCAAGTGGATGGCATTGGA ATCAATTTTACACAGAATCTATACCCACCAGAGTGATG TCTGGAGCTACGGGGTGACTGTTTGGGAGTTGATGAC CTTTGGATCCAAGCCATATGACGGAATCCCTGCCAGCG AGATCTCCTCCATCCTGGAGAAAGGAGAACGCCTCCCT CAGCCACCCATATGTACCATCGATGTCTACATGATCAT GGTCAAGTGCTGGATGATAGACGCAGATAGTCGCCCA AAGTTCCGTGAGTTGATCATCGAATTCTCCAAAATGGC CCGAGACCCCCAGCGCTACCTTGTCATTCAG│CTGCAG GACAAGTTCGAGCATCTTAAAATGATTCAACAGGAGG AGATAAGGAAGCTCGAGGAAGAGAAAAAACAACTGG AAGGAGAAATCATAGATTTTTATAAAATGAAAGCTGCC |

| sample | Gene Breakpoint 5p | Gene Breakpoint 3p | Frame Type | SEQ ID NO: | Fused Sequence |
|---|---|---|---|---|---|
| | | | | | TCCGAAGCACTGCAGACTCAGCTGAGCACCGATACAA AGAAAGACAAACATCGTAAGAAA |
| G17506. TCGA-27-1835-01A-01R-1850-01.2 | 1808661 | 1741429 | InFrame | 8279 | ATGGGCGCCCCTGCCTGCGCCCTCGCGCTCTGCGTGGCC CGTGGCCATCGTGGCCGGCGCCTCCTCGGAGTCCTTG GGGACGGAGCAGCGCGTCGTGGGGCGAGCGGCAGAA GTCCCGGGCCCAGAGCCCGGCCAGCAGGAGCAGTTG GTCTTCGGCAGCGGGGATGCTGTGGAGCTGAGCTGTC CCCCGCCCGGGGGTGGTCCCATGGGGCCCACTGTCTG GGTCAAGGATGGCACAGGGCTGGTGCCCTCGGAGCGT GTCCTGGTGGGGCCCCAGCGGCTGCAGGTGCTGAATG CCTCCCACGAGGACTCCGGGGCCTACAGCTGCCGGCA GCGGCTCACGCAGCGCGTACTGTGCCACTTCAGTGTGC GGGTGACAGACGCTCCATCCTCGGGAGATGACGAAGA CGGGGAGGACGAGGCTGAGGACACAGGTGTGGACAC AGGGGCCCCTTACTGGACACGGCCCGAGCGGATGGAC AAGAAGCTGCTGGCCGTGCCGGCCGCCAACACCGTCC GCTTCCGCTGCCCAGCCGCTGGCAACCCCACTCCCTCC ATCTCCTGGCTGAAGAACGGCAGGGAGTTCCGCGGCG AGCACCGCATTGGAGGCATCAAGCTGCGGCATCAGCA GTGGAGCCTGGTCATGGAAAGCGTGGTGCCCTCGGAC CGCGGCAACTACACCTGCGTCGTGGAGAACAAGTTTG GCAGCATCCGGCAGACGTACACGCTGGACGTGCTGGA GCGCTCCCCGCACCGGCCCATCCTGCAGGCGGGGCTG CCGGCCAACCAGACGGCGGTGCTGGGCAGCGACGTG GAGTTCCACTGCAAGGTGTACAGTGACGCACAGCCCC ACATCCAGTGGCTCAAGCACGTGGAGGTGAATGGCAG CAAGGTGGGCCCGGACGGCACACCCTACGTTACCGTG CTCAAGTCCTGGATCAGTGAGAGTGTGGAGGCCGACG TGCGCCTCCGCCTGGCCAATGTGTCGGAGCGGGACGG GGGCGAGTACCTCTGTCGAGCCACCAATTTCATAGGC GTGGCCGAGAAGGCCTTTTGGCTGAGCGTTCACGGGC CCCGAGCAGCCGAGGAGGAGCTGGTGGAGGCTGACG AGGCGGGCAGTGTGTATGCAGGCATCCTCAGCTACGG GGTGGGCTTCTTCCTGTTCATCCTGGTGGTGGCGGCTG TGACGCTCTGCCGCCTGCGCAGCCCCCCCAAGAAAGG CCTGGGCTCCCCCACCGTGCACAAGATCTCCCGCTTCC CGCTCAAGCGACAGGTGTCCCTGGAGTCCAACGCGTC CATGAGCTCCAACACACCACTGGTGCGCATCGCAAGG CTGTCCTCAGGGGAGGGCCCCACGCTGGCCAATGTCT CCGAGCTCGAGCTGCCTGCCGACCCCAAATGGGAGCT GTCTCGGGCCCGGCTGACCCTGGGCAAGCCCCTTGGG GAGGGCTGCTTCGGCCAGGTGGTCATGGCGGAGGCC ATCGGCATTGACAAGGACCGGGCCGCCAAGCCTGTCA CCGTAGCCGTGAAGATGCTGAAAGACGATGCCACTGA CAAGGACCTGTCGGACCTGGTGTCTGAGATGGAGATG ATGAAGATGATCGGGAAACACAAAAACATCATCAACC TGCTGGGCGCCTGCACGCAGGGCGGGCCCCTGTACGT GCTGGTGGAGTACGCGGCCAAGGGTAACCTGCGGGA GTTTCTgcgggcgcggcggccccgggccTGGACTACTCCTTC GACACCTGCAAGCCGCCCGAGGAGCAGCTCACCTTCA AGGACCTGGTGTCCTGTGCCTACCAGGTGGCCCGGGG CATGGAGTACTTGGCCTCCCAGAAGTGCATCCACAGG GACCTGGCTGCCCGCAATGTGCTGGTGACCGAGGACA ACGTGATGAAGATCGCAGACTTCGGGCTGGCCCGGGA CGTGCACAACCTCGACTACTACAAGAAGACGACCAAC |

FIG. 27 Cont.

| sample | Gene Break- point 5p | Gene Break- point 3p | Frame Type | SEQ ID NO: | Fused Sequence |
|---|---|---|---|---|---|
| | | | | | GGCCGGCTGCCCGTGAAGTGGATGGCGCCTGAGGCCT TGTTTGACCGAGTCTACACTCACCAGAGTGACGTCTGG TCCTTTGGGGTCCTGCTCTGGGAGATCTTCACGCTGGG GGGCTCCCCGTACCCCGGCATCCCTGTGGAGGAGCTCT TCAAGCTGCTGAAGGAGGGCCACCGCATGGACAAGCC CGCCAACTGCACACACGACCTGTACATGATCATGCGG GAGTGCTGGCATGCCGCGCCCTCCCAGAGGCCCACCTT CAAGCAGCTGGTGGAGGACCTGGACCGTGTCCTTACC GTGACGTCCACCGAC\|GTAAAGGCGACACAGGAGGAG AACCGGGAGCTGAGGAGCAGGTGTGAGGAGCTCCAC GGGAAGAACCTGGAACTGGGGAAGATCATGGACAGG TTCGAAGAGGTTGTGTACCAGGCCATGGAGGAAGTTC AGAAGCAGAAGGAACTTTCCAAAGCTGAAATCCAGAA AGTTCTAAAAGAAAAAGACCAACTTACCACAGATCTGA ACTCCATGGAGAAGTCCTTCTCCGACCTCTTCAAGCGT TTTGAGAAACAGAAAGAGGTGATCGAGGGCTACCGCA AGAACGAAGAGTCACTGAAGAAGTGCGTGGAGGATT ACCTGGCAAGGATCACCCAGGAGGGCCAGAGGTACCA AGCCCTGAAGGCCCACGCGGAGGAGAAGCTGCAGCT GGCAAACGAGGAGATCGCCCAGGTCCGGAGCAAGGC CCAGGCGGAAGCGTTGGCCCTCCAGGCCAGCCTGAGG AAGGAGCAGATGCGCATCCAGTCGCTGGAGAAGACA GTGGAGCAGAAGACTAAAGAGAACGAGGAGCTGACC AGGATCTGCGACGACCTCATCTCCAAGATGGAGAAGA TC |
| G17191. TCGA-06- 0211- 01A-01R- 1849- 01.2 | 55479782 | 55886916 | InFrame | 8280 | ATGGGCGAGACCATGTCAAAGAGGCTGAAGCTCCACC TGGAGGGGAGGCAGAAATGGAGGAACGGGCGTTCG TCAACCCCTTCCCGGACTACGAGGCCGCCGCCGGGGC GCTGCTCGCCTCCGGAGCGGCCGAAGAGACAGGCTGT GTTCGTCCCCGGCGACCACGGATGAGCCCGGCCTCCC TTTTCATCAGGACGGGAAGATCATTCATAATTTCATAA GACGGATCCAGACCAAAATTAAAGATCTTCTGCAGCA AATGGAAGAAGGGCTGAAGACAGCTGATCCCCATGAC TGCTCTGCTTATACTGGCTGGACAGGCATAGCCCTTTT GTACCTGCAGTTGTACCGGGTCACATGTGACCAAACCT ACCTGCTCCGATCCCTGGATTACGTAAAAAAGAACACTT CGGAATCTGAATGGCCGCAGGGTCACCTTCCTCTGTGG GGATGCTGGCCCCCTGGCTGTTGGAGCTGTGATTTATC ACAAACTCAGAAGTGACTGTGAGTCCCAGGAATGTGT CACAAAACTTTTGCAGCTCCAGAGATCGGTTGTCTGCC AAGAATCAGACCTTCCTGATGAGCTGCTTTATGGACGG GCAGGTTATCTGTATGCCTTACTGTACCTGAACACAGA GATAGGTCCAGGCACCGTGTGTGAGTCAGCTATTAAA GAGGTAGTCAATGCTATTATTGAATCGGGTAAGACTTT GTCAAGGGAAGAAAGAAAAACGGAGCGCTGCCCGCT GTTGTACCAGTGGCACCGGAAGCAGTACGTTGGAGCA GCCCATGGCATGGCTGGAATTTACTATATGTTAATGCA GCCGGCAGCAAAAGTGGACCAAGAAACCTTGACAGAA ATGGTGAAACCCAGTATTGATTATGTGCGCCACAAAAA ATTCCGATCTGGGAATTACCCATCATCATTAAGCAATG AAACAGACCGGCTGGTGCACTGGTGCCACGGCGCCCC GGGGGTCATCCACATGCTCATGCAGGCGTACAAG\|GG GCTGTTACCCTTTGCTGTGGTAGGGAGTACAGATGAA GTGAAAGTTGGAAAAAGGATGGTCAGAGGCCGTCACT ACCCTTGGGGAGTTTTGCAAGTGGAAAATGAAAATCA |

FIG. 27 Cont.

| sample | Gene Break-point 5p | Gene Break-point 3p | Frame Type | SEQ ID NO: | Fused Sequence |
|---|---|---|---|---|---|
| | | | | | CTGTGACTTCGTTAAGCTCCGAGATATGCTTCTTTGTAC CAATATGGAAAATCTAAAAGAAAAAACCCACACTCAG CACTATGAATGTTATAGGTACCAAAAACTGCAGAAAAT GGGCTTTACAGATGTGGGTCCAAACAACCAGCCAGTT AGTTTTCAAGAAATCTTTGAAGCCAAAAGACAAGAGTT CTATGATCAATGTCAGAGGGAAGAAGAAGAGTTGAAA CAGAGATTTATGCAGCGAGTCAAGGAGAAAGAAGCAA CATTTAAAGAAGCTGAAAAAGAGCTGCAGGACAAGTT CGAGCATCTTAAAATGATTCAACAGGAGGAGATAAGG AAGCTCGAGGAAGAGAAAAAACAACTGGAAGGAGAA ATCATAGATTTTTATAAAATGAAAGCTGCCTCCGAAGC ACTGCAGACTCAGCTGAGCACCGATACAAAGAAAGAC AAACATCGTAAGAAA |
| G17512. TCGA-27-1837-01A-01R-1850-01.2 | 55268106 | 55863785 | InFrame | 8281 | ATGCGACCCTCCGGGACGGCCGGGGCAGCGCTCCTGG CGCTGCTGGCTGCGCTCTGCCCGGCGAGTCGGGCTCT GGAGGAAAGAAAGTTTGCCAAGGCACGAGTAACAA GCTCACGCAGTTGGGCACTTTTGAAGATCATTTTCTCA GCCTCCAGAGGATGTTCAATAACTGTGAGGTGGTCCTT GGGAATTTGGAAATTACCTATGTGCAGAGGAATTATG ATCTTTCCTTCTTAAAGACCATCCAGGAGGTGGCTGGT TATGTCCTCATTGCCCTCAACACAGTGGAGCGAATTCC TTTGGAAAACCTGCAGATCATCAGAGGAAATATGTACT ACGAAAATTCCTATGCCTTAGCAGTCTTATCTAACTATG ATGCAAATAAAACCGGACTGAAGGAGCTGCCCATGAG AAATTTACAGGAAATCCTGCATGGCGCCGTGCGGTTCA GCAACAACCCTGCCCTGTGCAACGTGGAGAGCATCCA GTGGCGGGACATAGTCAGCAGTGACTTTCTCAGCAAC ATGTCGATGGACTTCCAGAACCACCTGGGCAGCTGCC AAAAGTGTGATCCAAGCTGTCCCAATGGGAGCTGCTG GGGTGCAGGAGAGGAGAACTGCCAGAAACTGACCAA AATCATCTGTGCCCAGCAGTGCTCCGGGCGCTGCCGTG GCAAGTCCCCCAGTGACTGCTGCCACAACCAGTGTGCT GCAGGCTGCACAGGCCCCGGGAGAGCGACTGCCTG GTCTGCCGCAAATTCCGAGACGAAGCCACGTGCAAGG ACACCTGCCCCCCACTCATGCTCTACAACCCCACCACGT ACCAGATGGATGTGAACCCCGAGGGCAAATACAGCTT TGGTGCCACCTGCGTGAAGAAGTGTCCCCGTAATTATG TGGTGACAGATCACGGCTCGTGCGTCCGAGCCTGTGG GGCCGACAGCTATGAGATGGAGGAAGACGGCGTCCG CAAGTGTAAGAAGTGCGAAGGGCCTTGCCGCAAAGTG TGTAACGGAATAGGTATTGGTGAATTTAAAGACTCACT CTCCATAAATGCTACGAATATTAAACACTTCAAAAACT GCACCTCCATCAGTGGCGATCTCCACATCCTGCCGGTG GCATTTAGGGGTGACTCCTTCACACATACTCCTCCTCTG GATCCACAGGAACTGGATATTCTGAAAACCGTAAAGG AAATCACAGGGTTTTTGCTGATTCAGGCTTGGCCTGAA AACAGGACGGACCTCCATGCCTTTGAGAACCTAGAAA TCATACGCGGCAGGACCAAGCAACATGGTCAGTTTTCT CTTGCAGTCGTCAGCCTGAACATAACATCCTTGGGATT ACGCTCCCTCAAGGAGATAAGTGATGGAGATGTGATA ATTTCAGGAAACAAAAATTTGTGCTATGCAAATACAAT AAACTGGAAAAAACTGTTTGGGACCTCCGGTCAGAAA ACCAAAATTATAAGCAACAGAGGTGAAAACAGCTGCA AGGCCACAGGCCAGGTCTGCCATGCCTTGTGCTCCCCC GAGGGCTGCTGGGGCCCGGAGCCCAGGGACTGCGTC |

FIG. 27 Cont.

| sample | Gene Break-point 5p | Gene Break-point 3p | Frame Type | SEQ ID NO: | Fused Sequence |
|---|---|---|---|---|---|
| | | | | | TCTTGCCGGAATGTCAGCCGAGGCAGGGAATGCGTGG ACAAGTGCAACCTTCTGGAGGGTGAGCCAAGGGAGTT TGTGGAGAACTCTGAGTGCATACAGTGCCACCCAGAG TGCCTGCCTCAGGCCATGAACATCACCTGCACAGGACG GGGACCAGACAACTGTATCCAGTGTGCCCACTACATTG ACGGCCCCCACTGCGTCAAGACCTGCCCGGCAGGAGT CATGGGAGAAAACAACACCCTGGTCTGGAAGTACGCA GACGCCGGCCATGTGTGCCACCTGTGCCATCCAAACTG CACCTACGGATGCACTGGGCCAGGTCTTGAAGGCTGT CCAACGAATGGGCCTAAGATCCCGTCCATCGCCACTGG GATGGTGGGGGCCCTCCTCTTGCTGCTGGTGGTGGCC CTGGGGATCGGCCTCTTCATGCGAAGGCGCCACATCG TTCGGAAGCGCACGCTGCGGAGGCTGCTGCAGGAGA GGGAGCTTGTGGAGCCTCTTACACCCAGTGGAGAAGC TCCCAACCAAGCTCTCTTGAGGATCTTGAAGGAAACTG AATTCAAAAAGATCAAAGTGCTGGGCTCCGGTGCGTT CGGCACGGTGTATAAGGGACTCTGGATCCCAGAAGGT GAGAAAGTTAAAATTCCCGTCGCTATCAAGGAATTAA GAGAAGCAACATCTCCGAAAGCCAACAAGGAAATCCT CGATGAAGCCTACGTGATGGCCAGCGTGGACAACCCC CACGTGTGCCGCCTGCTGGGCATCTGCCTCACCTCCAC CGTGCAGCTCATCACGCAGCTCATGCCCTTCGGCTGCC TCCTGGACTATGTCCGGGAACACAAAGACAATATTGG CTCCCAGTACCTGCTCAACTGGTGTGTGCAGATCGCAA AGGGCATGAACTACTTGGAGGACCGTCGCTTGGTGCA CCGCGACCTGGCAGCCAGGAACGTACTGGTGAAAACA CCGCAGCATGTCAAGATCACAGATTTTGGGCTGGCCA AACTGCTGGGTGCGGAAGAGAAAGAATACCATGCAG AAGGAGGCAAAGTGCCTATCAAGTGGATGGCATTGGA ATCAATTTTACACAGAATCTATACCCACCAGAGTGATG TCTGGAGCTACGGGGTGACTGTTTGGGAGTTGATGAC CTTTGGATCCAAGCCATATGACGGAATCCCTGCCAGCG AGATCTCCTCCATCCTGGAGAAAGGAGAACGCCTCCCT CAGCCACCCATATGTACCATCGATGTCTACATGATCAT GGTCAAGTGCTGGATGATAGACGCAGATAGTCGCCCA AAGTTCCGTGAGTTGATCATCGAATTCTCCAAAATGGC CCGAGACCCCCAGCGCTACCTTGTCATTCAG\|CTGCAG GACAAGTTCGAGCATCTTAAAATGATTCAACAGGAGG AGATAAGGAAGCTCGAGGAAGAGAAAAAACAACTGG AAGGAGAAATCATAGATTTTTATAAAAATGAAAGCTGCC TCCGAAGCACTGCAGACTCAGCTGAGCACCGATACAA AGAAAGACAAACATCGTAAGAAA |
| NYU_A | 1808661 | 1737458 | InFrame | 8282 | ATGGGCGCCCCTGCCTGCGCCCTCGCGCTCTGCGTGGC CGTGGCCATCGTGGCCGGCGCCTCCTCGGAGTCCTTG GGGACGGAGCAGCGCGTCGTGGGGCGAGCGGCAGAA GTCCCGGGCCCAGAGCCCGGCCAGCAGGAGCAGTTG GTCTTCGGCAGCGGGGATGCTGTGGAGCTGAGCTGTC CCCCGCCCGGGGGTGGTCCCATGGGGCCCACTGTCTG GGTCAAGGATGGCACAGGGCTGGTGCCCTCGGAGCGT GTCCTGGTGGGGCCCCAGCGGCTGCAGGTGCTGAATG CCTCCCACGAGGACTCCGGGGCCTACAGCTGCCGGCA GCGGCTCACGCAGCGCGTACTGTGCCACTTCAGTGTGC GGGTGACAGACGCTCCATCCTCGGGAGATGACGAAGA CGGGGAGGACGAGGCTGAGGACACAGGTGTGGACAC AGGGGCCCCTTACTGGACACGGCCCGAGCGGATGGAC |

FIG. 27 Cont.

| sample | Gene Break-point 5p | Gene Break-point 3p | Frame Type | SEQ ID NO: | Fused Sequence |
|---|---|---|---|---|---|
| | | | | | AAGAAGCTGCTGGCCGTGCCGGCCGCCAACACCGTCC GCTTCCGCTGCCCAGCCGCTGGCAACCCCACTCCCTCC ATCTCCTGGCTGAAGAACGGCAGGGAGTTCCGCGGCG AGCACCGCATTGGAGGCATCAAGCTGCGGCATCAGCA GTGGAGCCTGGTCATGGAAAGCGTGGTGCCCTCGGAC CGCGGCAACTACACCTGCGTCGTGGAGAACAAGTTTG GCAGCATCCGGCAGACGTACACGCTGGACGTGCTGGA GCGCTCCCCGCACCGGCCCATCCTGCAGGCGGGGCTG CCGGCCAACCAGACGGCGGTGCTGGGCAGCGACGTG GAGTTCCACTGCAAGGTGTACAGTGACGCACAGCCCC ACATCCAGTGGCTCAAGCACGTGGAGGTGAATGGCAG CAAGGTGGGCCCGGACGGCACACCCTACGTTACCGTG CTCAAGTCCTGGATCAGTGAGAGTGTGGAGGCCGACG TGCGCCTCCGCCTGGCCAATGTGTCGGAGCGGGACGG GGGCGAGTACCTCTGTCGAGCCACCAATTTCATAGGC GTGGCCGAGAAGGCCTTTTGGCTGAGCGTTCACGGGC CCCGAGCAGCCGAGGAGGAGCTGGTGGAGGCTGACG AGGCGGGCAGTGTGTATGCAGGCATCCTCAGCTACGG GGTGGGCTTCTTCCTGTTCATCCTGGTGGTGGCGGCTG TGACGCTCTGCCGCCTGCGCAGCCCCCCCAAGAAAGG CCTGGGCTCCCCCACCGTGCACAAGATCTCCCGCTTCC CGCTCAAGCGACAGGTGTCCCTGGAGTCCAACGCGTC CATGAGCTCCAACACACCACTGGTGCGCATCGCAAGG CTGTCCTCAGGGGAGGGCCCCACGCTGGCCAATGTCT CCGAGCTCGAGCTGCCTGCCGACCCCAAATGGGAGCT GTCTCGGGCCCGGCTGACCCTGGGCAAGCCCCTTGGG GAGGGCTGCTTCGGCCAGGTGGTCATGGCGGAGGCC ATCGGCATTGACAAGGACCGGGCCGCCAAGCCTGTCA CCGTAGCCGTGAAGATGCTGAAAGACGATGCCACTGA CAAGGACCTGTCGGACCTGGTGTCTGAGATGGAGATG ATGAAGATGATCGGGAAACACAAAAACATCATCAACC TGCTGGGCGCCTGCACGCAGGGCGGGCCCCTGTACGT GCTGGTGGAGTACGCGGCCAAGGGTAACCTGCGGGA GTTTCTgcgggcgcggcggccccgggccTGGACTACTCCTTC GACACCTGCAAGCCGCCCGAGGAGCAGCTCACCTTCA AGGACCTGGTGTCCTGTGCCTACCAGGTGGCCCGGGG CATGGAGTACTTGGCCTCCCAGAAGTGCATCCACAGG GACCTGGCTGCCCGCAATGTGCTGGTGACCGAGGACA ACGTGATGAAGATCGCAGACTTCGGGCTGGCCCGGGA CGTGCACAACCTCGACTACTACAAGAAGACGACCAAC GGCCGGCTGCCCGTGAAGTGGATGGCGCCTGAGGCCT TGTTTGACCGAGTCTACACTCACCAGAGTGACGTCTGG TCCTTTGGGGTCCTGCTCTGGGAGATCTTCACGCTGGG GGGCTCCCCGTACCCCGGCATCCCTGTGGAGGAGCTCT TCAAGCTGCTGAAGGAGGGCCACCGCATGGACAAGCC CGCCAACTGCACACACGACCTGTACATGATCATGCGG GAGTGCTGGCATGCCGCGCCCTCCCAGAGGCCCACCTT CAAGCAGCTGGTGGAGGACCTGGACCGTGTCCTTACC GTGACGTCCACCGAC\|TTTAAGGAGTCGGCCTTGAGG AAGCAGTCCTTATACCTCAAGTTCGACCCCCTCCTGAG GGACAGTCCTGGTAGACCAGTGCCCGTGGCCACCGAG ACCAGCAGCATGCACGGTGCAAATGAGACTCCCTCAG GACGTCCGCGGGAAGCCAAGCTTGTGGAGTTCGATTT CTTGGGAGCACTGGACATTCCTGTGCCAGGCCCACCCC CAGGTGTTCCCGCGCCTGGGGGCCCACCCCTGTCCACC |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GGACCTATAGTGGACCTGCTCCAGTACAGCCAGAAGG ACCTGGATGCAGTGGTAAAGGCGACACAGGAGGAGA ACCGGGAGCTGAGGAGCAGGTGTGAGGAGCTCCACG GGAAGAACCTGGAACTGGGGAAGATCATGGACAGGT TCGAAGAGGTTGTGTACCAGGCCATGGAGGAAGTTCA GAAGCAGAAGGAACTTTCCAAAGCTGAAATCCAGAAA GTTCTAAAAGAAAAAGACCAACTTACCACAGATCTGAA CTCCATGGAGAAGTCCTTCTCCGACCTCTTCAAGCGTTT TGAGAAACAGAAAGAGGTGATCGAGGGCTACCGCAA GAACGAAGAGTCACTGAAGAAGTGCGTGGAGGATTA CCTGGCAAGGATCACCCAGGAGGGCCAGAGGTACCAA GCCCTGAAGGCCCACGCGGAGGAGAAGCTGCAGCTG GCAAACGAGGAGATCGCCCAGGTCCGGAGCAAGGCC CAGGCGGAAGCGTTGGCCCTCCAGGCCAGCCTGAGGA AGGAGCAGATGCGCATCCAGTCGCTGGAGAAGACAGT GGAGCAGAAGACTAAAGAGAACGAGGAGCTGACCAG GATCTGCGACGACCTCATCTCCAAGATGGAGAAGATC |
| G17814. TCGA-06- 5411- 01A-01R- 1849- 01.4 | 204951148 | 156844363 | InFrame | 8283 | ATGGCCAGGCAGCCACCGCCGCCCTGGGTCCATGCAG CCTTCCTCCTCTGCCTCCTCAGTCTTGGCGGAGCCATCG AAATTCCTATGGATCTGACGCAGCCGCCAACCATCACC AAGCAGTCAGCGAAGGATCACATCGTGGACCCCCGTG ATAACATCCTGATTGAGTGTGAAGCAAAAGGGAACCC TGCCCCAGCTTCCACTGGACACGAAACAGCAGATTCT TCAACATCGCCAAGGACCCCCGGGTGTCCATGAGGAG GAGGTCTGGGACCCTGGTGATTGACTTCCGCAGTGGC GGGCGGCCGGAGGAATATGAGGGGGAATATCAGTGC TTCGCCCGCAACAAATTTGGCACGGCCCTGTCCAATAG GATCCGCCTGCAGGTGTCTAAATCTCCTCGTGGCCCA AGGAAAAACCTAGACCCTGTCGTGGTCCAAGAGGGCGC TCCTTTGACGCTCCAGTGCAACCCCCCGCCTGGACTTCC ATCCCCGGTCATCTTCTGGATGAGCAGCTCCATGGAGC CCATCACCCAAGACAAACGTGTCTCTCAGGGCCATAAC GGAGACCTATACTTCTCCAACGTGATGCTGCAGGACAT GCAGACCGACTACAGTTGTAACGCCCGCTTCCACTTCA CCCACACCATCCAGCAGAAGAACCCTTTCACCCTCAAG GTCCTCACCAACCACCCTTATAATGACTCGTCCTTAAGA AACCACCCTGACATGTACAGTGCCCGAGGAGTTGCAG AAAGAACACCAAGCTTCATGTATCCCCAGGGCACCGC GAGCAGCCAGATGGTGCTTCGTGGCATGGACCTCCTG CTGGAATGCATCGCCTCCGGGGTCCCAACACCAGACAT CGCATGGTACAAGAAAGGTGGGGACCTCCCATCTGAT AAGGCCAAGTTTGAGAACTTTAATAAGGCCCTGCGTAT CACAAATGTCTCTGAGGAAGACTCCGGGGAGTATTTCT GCCTGGCCTCCAACAAGATGGGCAGCATCCGGCACAC GATCTCGGTGAGAGTAAAGGCTGCTCCCTACTGGCTG GACGAACCCAAGAACCTTATTCTGGCTCCTGGCGAGG ATGGGAGACTGGTGTGTCGAGCAATGGAAACCCCAA ACCCACTGTCCAGTGGATGGTGAATGGGGAACCTTTG CAATCGGCACCACCTAACCCAAACCGTGAGGTGGCCG GAGACACCATCATCTTCCGGGACACCCAGATCAGCAG CAGGGCTGTGTACCAGTGCAACACCTCCAACGAGCAT GGCTACCTGCTGGCCAACGCCTTTGTCAGTGTGCTGGA TGTGCCGCCTCGGATGCTGTCGCCCCGGAACCAGCTCA TTCGAGTGATTCTTTACAACCGGACGCGGCTGGACTGC CCTTTCTTTGGGTCTCCCATCCCCACACTGCGATGGTTT |

FIG. 27 Cont.

| sample | Gene Break-point 5p | Gene Break-point 3p | Frame Type | SEQ ID NO: | Fused Sequence |
|---|---|---|---|---|---|
| | | | | | AAGAATGGGCAAGGAAGCAACCTGGATGGTGGCAAC<br>TACCATGTTTATGAGAACGGCAGTCTGGAAATTAAGAT<br>GATCCGCAAAGAGGACCAGGGCATCTACACCTGTGTC<br>GCCACCAACATCCTGGGCAAAGCTGAAAACCAAGTCC<br>GCCTGGAGGTCAAAGACCCCACCAGGATCTACCGGAT<br>GCCCGAGGACCAGGTGGCCAGAAGGGGCACCACGGT<br>GCAGCTGGAGTGTCGGGTGAAGCACGACCCCTCCCTG<br>AAACTCACCGTCTCCTGGCTGAAGGATGACGAGCCGC<br>TCTATATTGGAAACAGGATGAAGAAGGAAGACGACTC<br>CCTGACCATCTTTGGGGTGGCAGAGCGGGACCAGGGC<br>AGTTACACGTGTGTCGCCAGCACCGAGCTAGACCAAG<br>ACCTGGCCAAGGCCTACCTCACCGTGCTAGCTGATCAG<br>GCCACTCCAACTAACCGTTTGGCTGCCCTGCCCAAAGG<br>ACGGCCAGACCGGCCCCGGGACCTGGAGCTGACCGAC<br>CTGGCCGAGAGGAGCGTGCGGCTGACCTGGATCCCCG<br>GGGATGCTAACAACAGCCCCATCACAGACTACGTCGTC<br>CAGTTTGAAGAAGACCAGTTCCAACCTGGGGTCTGGC<br>ATGACCATTCCAAGTACCCCGGCAGCGTTAACTCAGCC<br>GTCCTCCGGCTGTCCCCGTATGTCAACTACCAGTTCCGT<br>GTCATTGCCATCAACGAGGTTGGGAGCAGCCACCCCA<br>GCCTCCCATCCGAGCGCTACCGAACCAGTGGAGCACC<br>CCCCGAGTCCAATCCTGGTGACGTGAAGGGAGAGGG<br>GACCAGAAAGAACAACATGGAGATCACGTGGACGCCC<br>ATGAATGCCACCTCGGCCTTTGGCCCCAACCTGCGCTA<br>CATTGTCAAGTGGAGGCGGAGAGAGACTCGAGAGGC<br>CTGGAACAACGTCACAGTGTGGGGCTCTCGCTACGTG<br>GTGGGGCAGACCCCAGTCTACGTGCCCTATGAGATCC<br>GAGTCCAGGCTGAAAATGACTTCGGGAAGGGCCCTGA<br>GCCAGAGTCCGTCATCGGTTACTCCGGAGAAGATT\|AC<br>ACTAACAGCACATCTGGAGACCCGGTGGAGAAGAAG<br>GACGAAACACCTTTTGGGGTCTCGGTGGCTGTGGGCC<br>TGGCCGTCTTTGCCTGCCTCTTCCTTTCTACGCTGCTCC<br>TTGTGCTCAACAAATGTGGACGGAGAAACAAGTTTGG<br>GATCAACCGCCCGGCTGTGCTGGCTCCAGAGGATGGG<br>CTGGCCATGTCCCTGCATTTCATGACATTGGGTGGCAG<br>CTCCCTGTCCCCCACCGAGGGCAAAGGCTCTGGGCTCC<br>AAGGCCACATCATCGAGAACCCACAATACTTCAGTGAT<br>GCCTGTGTTCACCACATCAAGCGCCGGGACATCGTGCT<br>CAAGTGGGAGCTGGGGGAGGGCGCCTTTGGGAAGGT<br>CTTCCTTGCTGAGTGCCACAACCTCCTGCCTGAGCAGG<br>ACAAGATGCTGGTGGCTGTCAAGGCACTGAAGGAGGC<br>GTCCGAGAGTGCTCGGCAGGACTTCCAGCGTGAGGCT<br>GAGCTGCTCACCATGCTGCAGCACCAGCACATCGTGC<br>GCTTCTTCGGCGTCTGCACCGAGGGCCGCCCCCTGCTC<br>ATGGTCTTTGAGTATATGCGGCACGGGGACCTCAACC<br>GCTTCCTCCGATCCCATGGACCTGATGCCAAGCTGCTG<br>GCTGGTGGGAGGATGTGGCTCCAGGCCCCTGGGTC<br>TGGGGCAGCTGCTGGCCGTGGCTAGCCAGGTCGCTGC<br>GGGGATGGTGTACCTGGCGGGTCTGCATTTTGTGCAC<br>CGGGACCTGGCCACACGCAACTGTCTAGTGGGCCAGG<br>GACTGGTGGTCAAGATTGGTGATTTTGGCATGAGCAG<br>GGATATCTACAGCACCGACTATTACCGTGTGGGAGGC<br>CGCACCATGCTGCCCATTCGCTGGATGCCGCCCGAGA<br>GCATCCTGTACCGTAAGTTCACCACCGAGAGCGACGT<br>GTGGAGCTTCGGCGTGGTGCTCTGGGAGATCTTCACC |

| sample | Gene Break-point 5p | Gene Break-point 3p | Frame Type | SEQ ID NO: | Fused Sequence |
|---|---|---|---|---|---|
| | | | | | TACGGCAAGCAGCCCTGGTACCAGCTCTCCAACACGG AGGCAATCGACTGCATCACGCAGGGACGTGAGTTGGA GCGGCCACGTGCCTGCCCACCAGAGGTCTACGCCATC ATGCGGGGCTGCTGGCAGCGGGAGCCCCAGCAACGC CACAGCATCAAGGATGTGCACGCCCGGCTGCAAGCCC TGGCCCAGGCACCTCCTGTCTACCTGGATGTCCTGGGC |
| G17223. TCGA-06-0750-01A-01R-1849-01.2 | 55268106 | 55863785 | InFrame | 8284 | ATGCGACCCTCCGGGACGGCCGGGGCAGCGCTCCTGG CGCTGCTGGCTGCGCTCTGCCCGGCGAGTCGGGCTCT GGAGGAAAAGAAAGTTTGCCAAGGCACGAGTAACAA GCTCACGCAGTTGGGCACTTTTGAAGATCATTTTCTCA GCCTCCAGAGGATGTTCAATAACTGTGAGGTGGTCCTT GGGAATTTGGAAATTACCTATGTGCAGAGGAATTATG ATCTTTCCTTCTTAAAGACCATCCAGGAGGTGGCTGGT TATGTCCTCATTGCCCTCAACACAGTGGAGCGAATTCC TTTGGAAAACCTGCAGATCATCAGAGGAAATATGTACT ACGAAAATTCCTATGCCTTAGCAGTCTTATCTAACTATG ATGCAAATAAAACCGGACTGAAGGAGCTGCCCATGAG AAATTTACAGGAAATCCTGCATGGCGCCGTGCGGTTCA GCAACAACCCTGCCCTGTGCAACGTGGAGAGCATCCA GTGGCGGGACATAGTCAGCAGTGACTTTCTCAGCAAC ATGTCGATGGACTTCCAGAACCACCTGGGCAGCTGCC AAAAGTGTGATCCAAGCTGTCCCAATGGGAGCTGCTG GGGTGCAGGAGAGGAGAACTGCCAGAAACTGACCAA AATCATCTGTGCCCAGCAGTGCTCCGGGCGCTGCCGTG GCAAGTCCCCCAGTGACTGCTGCCACAACCAGTGTGCT GCAGGCTGCACAGGCCCCCGGGAGAGCGACTGCCTG GTCTGCCGCAAATTCCGAGACGAAGCCACGTGCAAGG ACACCTGCCCCCCACTCATGCTCTACAACCCCACCACGT ACCAGATGGATGTGAACCCCGAGGGCAAATACAGCTT TGGTGCCACCTGCGTGAAGAAGTGTCCCCGTAATTATG TGGTGACAGATCACGGCTCGTGCGTCCGAGCCTGTGG GGCCGACAGCTATGAGATGGAGGAAGACGGCGTCCG CAAGTGTAAGAAGTGCGAAGGGCCTTGCCGCAAAGTG TGTAACGGAATAGGTATTGGTGAATTTAAAGACTCACT CTCCATAAATGCTACGAATATTAAACACTTCAAAAACT GCACCTCCATCAGTGGCGATCTCCACATCCTGCCGGTG GCATTTAGGGGTGACTCCTTCACACATACTCCTCCTCTG GATCCACAGGAACTGGATATTCTGAAAACCGTAAAGG AAATCACAGGGTTTTTGCTGATTCAGGCTTGGCCTGAA AACAGGACGGACCTCCATGCCTTTGAGAACCTAGAAA TCATACGCGGCAGGACCAAGCAACATGGTCAGTTTTCT CTTGCAGTCGTCAGCCTGAACATAACATCCTTGGGATT ACGCTCCCTCAAGGAGATAAGTGATGGAGATGTGATA ATTTCAGGAAACAAAAATTTGTGCTATGCAAATACAAT AAACTGGAAAAAACTGTTTGGGACCTCCGGTCAGAAA ACCAAAATTATAAGCAACAGAGGTGAAAACAGCTGCA AGGCCACAGGCCAGGTCTGCCATGCCTTGTGCTCCCCC GAGGGCTGCTGGGGCCCGGAGCCCAGGGACTGCGTC TCTTGCCGGAATGTCAGCCGAGGCAGGGAATGCGTGG ACAAGTGCAACCTTCTGGAGGGTGAGCCAAGGGAGTT TGTGGAGAACTCTGAGTGCATACAGTGCCACCCAGAG TGCCTGCCTCAGGCCATGAACATCACCTGCACAGGACG GGACCAGACAACTGTATCCAGTGTGCCCACTACATTG ACGGCCCCACTGCGTCAAGACCTGCCCGGCAGGAGT CATGGGAGAAAACAACACCCTGGTCTGGAAGTACGCA |

| sample | Gene Break-point 5p | Gene Break-point 3p | Frame Type | SEQ ID NO: | Fused Sequence |
|---|---|---|---|---|---|
| | | | | | GACGCCGGCCATGTGTGCCACCTGTGCCATCCAAACTG CACCTACGGATGCACTGGGCCAGGTCTTGAAGGCTGT CCAACGAATGGGCCTAAGATCCCGTCCATCGCCACTGG GATGGTGGGGGCCCTCCTCTTGCTGCTGGTGGTGGCC CTGGGGATCGGCCTCTTCATGCGAAGGCGCCACATCG TTCGGAAGCGCACGCTGCGGAGGCTGCTGCAGGAGA GGGAGCTTGTGGAGCCTCTTACACCCAGTGGAGAAGC TCCCAACCAAGCTCTCTTGAGGATCTTGAAGGAAACTG AATTCAAAAAGATCAAAGTGCTGGGCTCCGGTGCGTT CGGCACGGTGTATAAGGGACTCTGGATCCCAGAAGGT GAGAAAGTTAAAATTCCCGTCGCTATCAAGGAATTAA GAGAAGCAACATCTCCGAAAGCCAACAAGGAAATCCT CGATGAAGCCTACGTGATGGCCAGCGTGGACAACCCC CACGTGTGCCGCCTGCTGGGCATCTGCCTCACCTCCAC CGTGCAGCTCATCACGCAGCTCATGCCCTTCGGCTGCC TCCTGGACTATGTCCGGGAACACAAAGACAATATTGG CTCCCAGTACCTGCTCAACTGGTGTGTGCAGATCGCAA AGGGCATGAACTACTTGGAGGACCGTCGCTTGGTGCA CCGCGACCTGGCAGCCAGGAACGTACTGGTGAAAACA CCGCAGCATGTCAAGATCACAGATTTTGGGCTGGCCA AACTGCTGGGTGCGGAAGAGAAAGAATACCATGCAG AAGGAGGCAAAGTGCCTATCAAGTGGATGGCATTGGA ATCAATTTTACACAGAATCTATACCCACCAGAGTGATG TCTGGAGCTACGGGGTGACTGTTTGGGAGTTGATGAC CTTTGGATCCAAGCCATATGACGGAATCCCTGCCAGCG AGATCTCCTCCATCCTGGAGAAAGGAGAACGCCTCCCT CAGCCACCCATATGTACCATCGATGTCTACATGATCAT GGTCAAGTGCTGGATGATAGACGCAGATAGTCGCCCA AAGTTCCGTGAGTTGATCATCGAATTCTCCAAAATGGC CCGAGACCCCCAGCGCTACCTTGTCATTCAG\|CTGCAG GACAAGTTCGAGCATCTTAAAATGATTCAACAGGAGG AGATAAGGAAGCTCGAGGAAGAGAAAAAACAACTGG AAGGAGAAATCATAGATTTTTATAAAAATGAAAGCTGCC TCCGAAGCACTGCAGACTCAGCTGAGCACCGATACAA AGAAAGACAAACATCGTAAGAAA |
| G17798. TCGA-32- 5222- 01A-01R- 1850- 01.4 | 55268106 | 55863785 | InFrame | 8285 | ATGCGACCCTCCGGGACGGCCGGGGCAGCGCTCCTGG CGCTGCTGGCTGCGCTCTGCCCGGCGAGTCGGGCTCT GGAGGAAAAGAAAGTTTGCCAAGGCACGAGTAACAA GCTCACGCAGTTGGGCACTTTTGAAGATCATTTTCTCA GCCTCCAGAGGATGTTCAATAACTGTGAGGTGGTCCTT GGGAATTTGGAAATTACCTATGTGCAGAGGAATTATG ATCTTTCCTTCTTAAAGACCATCCAGGAGGTGGCTGGT TATGTCCTCATTGCCCTCAACACAGTGGAGCGAATTCC TTTGGAAAACCTGCAGATCATCAGAGGAAATATGTACT ACGAAAATTCCTATGCCTTAGCAGTCTTATCTAACTATG ATGCAAATAAAACCGGACTGAAGGAGCTGCCCATGAG AAATTTACAGGAAATCCTGCATGGCGCCGTGCGGTTCA GCAACAACCCTGCCCTGTGCAACGTGGAGAGCATCCA GTGGCGGGACATAGTCAGCAGTGACTTTCTCAGCAAC ATGTCGATGGACTTCCAGAACCACCTGGGCAGCTGCC AAAAGTGTGATCCAAGCTGTCCCAATGGGAGCTGCTG GGGTGCAGGAGAGGAGAACTGCCAGAAACTGACCAA AATCATCTGTGCCCAGCAGTGCTCCGGGCGCTGCCGTG GCAAGTCCCCCAGTGACTGCTGCCACAACCAGTGTGCT GCAGGCTGCACAGGCCCCGGGAGAGCGACTGCCTG |

| sample | Gene Break-point 5p | Gene Break-point 3p | Frame Type | SEQ ID NO: | Fused Sequence |
|---|---|---|---|---|---|
| | | | | | GTCTGCCGCAAATTCCGAGACGAAGCCACGTGCAAGG<br>ACACCTGCCCCCCACTCATGCTCTACAACCCCACCACGT<br>ACCAGATGGATGTGAACCCCGAGGGCAAATACAGCTT<br>TGGTGCCACCTGCGTGAAGAAGTGTCCCCGTAATTATG<br>TGGTGACAGATCACGGCTCGTGCGTCCGAGCCTGTGG<br>GGCCGACAGCTATGAGATGGAGGAAGACGGCGTCCG<br>CAAGTGTAAGAAGTGCGAAGGGCCTTGCCGCAAAGTG<br>TGTAACGGAATAGGTATTGGTGAATTTAAAGACTCACT<br>CTCCATAAATGCTACGAATATTAAACACTTCAAAAACT<br>GCACCTCCATCAGTGGCGATCTCCACATCCTGCCGGTG<br>GCATTTAGGGGTGACTCCTTCACACATACTCCTCCTCTG<br>GATCCACAGGAACTGGATATTCTGAAAACCGTAAAGG<br>AAATCACAGGGTTTTTGCTGATTCAGGCTTGGCCTGAA<br>AACAGGACGGACCTCCATGCCTTTGAGAACCTAGAAA<br>TCATACGCGGCAGGACCAAGCAACATGGTCAGTTTTCT<br>CTTGCAGTCGTCAGCCTGAACATAACATCCTTGGGATT<br>ACGCTCCCTCAAGGAGATAAGTGATGGAGATGTGATA<br>ATTTCAGGAAACAAAAATTTGTGCTATGCAAATACAAT<br>AAACTGGAAAAAACTGTTTGGGACCTCCGGTCAGAAA<br>ACCAAAATTATAAGCAACAGAGGTGAAAACAGCTGCA<br>AGGCCACAGGCCAGGTCTGCCATGCCTTGTGCTCCCCC<br>GAGGGCTGCTGGGGCCCGGAGCCCAGGGACTGCGTC<br>TCTTGCCGGAATGTCAGCCGAGGCAGGGAATGCGTGG<br>ACAAGTGCAACCTTCTGGAGGGTGAGCCAAGGGAGTT<br>TGTGGAGAACTCTGAGTGCATACAGTGCCACCCAGAG<br>TGCCTGCCTCAGGCCATGAACATCACCTGCACAGGACG<br>GGGACCAGACAACTGTATCCAGTGTGCCCACTACATTG<br>ACGGCCCCCACTGCGTCAAGACCTGCCCGGCAGGAGT<br>CATGGGAGAAAACAACACCCTGGTCTGGAAGTACGCA<br>GACGCCGGCCATGTGTGCCACCTGTGCCATCCAAACTG<br>CACCTACGGATGCACTGGGCCAGGTCTTGAAGGCTGT<br>CCAACGAATGGGCCTAAGATCCCGTCCATCGCCACTGG<br>GATGGTGGGGGCCCTCCTCTTGCTGCTGGTGGTGGCC<br>CTGGGGATCGGCCTCTTCATGCGAAGGCGCCACATCG<br>TTCGGAAGCGCACGCTGCGGAGGCTGCTGCAGGAGA<br>GGGAGCTTGTGGAGCCTCTTACACCCAGTGGAGAAGC<br>TCCCAACCAAGCTCTCTTGAGGATCTTGAAGGAAACTG<br>AATTCAAAAAGATCAAAGTGCTGGGCTCCGGTGCGTT<br>CGGCACGGTGTATAAGGGACTCTGGATCCCAGAAGGT<br>GAGAAAGTTAAAATTCCCGTCGCTATCAAGGAATTAA<br>GAGAAGCAACATCTCCGAAAGCCAACAAGGAAATCCT<br>CGATGAAGCCTACGTGATGGCCAGCGTGGACAACCCC<br>CACGTGTGCCGCCTGCTGGGCATCTGCCTCACCTCCAC<br>CGTGCAGCTCATCACGCAGCTCATGCCCTTCGGCTGCC<br>TCCTGGACTATGTCCGGGAACACAAAGACAATATTGG<br>CTCCCAGTACCTGCTCAACTGGTGTGTGCAGATCGCAA<br>AGGGCATGAACTACTTGGAGGACCGTCGCTTGGTGCA<br>CCGCGACCTGGCAGCCAGGAACGTACTGGTGAAAACA<br>CCGCAGCATGTCAAGATCACAGATTTTGGGCTGGCCA<br>AACTGCTGGGTGCGGAAGAGAAAGAATACCATGCAG<br>AAGGAGGCAAAGTGCCTATCAAGTGGATGGCATTGGA<br>ATCAATTTTACACAGAATCTATACCCACCAGAGTGATG<br>TCTGGAGCTACGGGGTGACTGTTTGGGAGTTGATGAC<br>CTTTGGATCCAAGCCATATGACGGAATCCCTGCCAGCG<br>AGATCTCCTCCATCCTGGAGAAAGGAGAACGCCTCCCT |

FIG. 27 Cont.

| sample | Gene Breakpoint 5p | Gene Breakpoint 3p | Frame Type | SEQ ID NO: | Fused Sequence |
|---|---|---|---|---|---|
| | | | | | CAGCCACCCATATGTACCATCGATGTCTACATGATCAT GGTCAAGTGCTGGATGATAGACGCAGATAGTCGCCCA AAGTTCCGTGAGTTGATCATCGAATTCTCCAAAATGGC CCGAGACCCCAGCGCTACCTTGTCATTCAG\|CTGCAG GACAAGTTCGAGCATCTTAAAATGATTCAACAGGAGG AGATAAGGAAGCTCGAGGAAGAGAAAAAACAACTGG AAGGAGAAATCATAGATTTTTATAAAATGAAAGCTGCC TCCGAAGCACTGCAGACTCAGCTGAGCACCGATACAA AGAAAGACAAACATCGTAAGAAA |
| G17195. TCGA-06- 0138- 01A-02R- 1849- 01.2 | 69764755 | 58339411 | InFrame | 8286 | ATGTTCAAGAGAATGGCCGAATTTGGGCCTGACTCCG GCGGGAGAGTAAAGGGTGTTACTATCGTTAAACCAAT AGTTTACGGTAATGTTGCTCGGTATTTTGGAAAGAAAA GAGAAGAAGATGGGCACACTCATCAGTGGACAGTATA TGTGAAACCATATAGAAATGAGGATATGTCAGCATAT GTGAAGAAAATCCAGTTTAAATTACATGAAAGCTATG GCAATCCTTTAAGAGTTGTTACTAAACCTCCATATGAA ATTACTGAAACAGGATGGGGTGAATTCGAAATAATCA TCAAAATATTTTTCATTGACCCTAATGAAAGACCTGTAA CCCTGTATCATTTGCTAAAGCTGTTTCAATCAGACACCA ATGCAATGCTGGGGAAAAAGACAGTGGTTTCAGAGTT CTATGATGAAATGATATTTCAAGACCCAACAGCAATGA TGCAACAATTATTGACAACATCTCGTCAGCTAACATTA GGAGCCTATAAGCATGAAACAGAAT\|ATCCATATGTCA AACTTCTGCTTGATGCTATGAAACACTCAGGTTGTGCT GTTAACAAAGATAGACACTTTTCTTGCGAAGACTGTAA TGGAAATGTCAGTGGAGGTTTTGATGCTTCAACATCTC AGATAGTTTTGTGCCAGAATAATATCCATAATCAGGCC CATATGAACAGAGTGGTCACACACGAGCTTATTCATGC ATTTGATCATTGTCGTGCCCATGTCGACTGGTTCACCA ACATCAGACATTTGGCGTGCTCAGAGGTTCGAGCTGCT AACCTTAGTGGAGACTGCTCACTTGTCAATGAAATATT CAGGTTACATTTTGGATTAAAACAACACCACCAGACTT GTGTGCGAGACAGAGCCACTCTTTCTATCCTGGCTGTT AGGAATATCAGCAAAGAAGTAGCTAAAAAGGCTGTTG ATGAAGTTTTTGAATCTTGTTTCAATGACCATGAACCTT TTGGAAGGATCCCACATAACAAGACTTATGCAAGATAT GCTCACAGAGACTTTGAAAACCGTGATCGGTATTATTC AAATATA |
| G17803. TCGA-76- 4925- 01A-01R- 1850- 01.4 | 1808661 | 1739325 | InFrame | 8287 | ATGGGCGCCCCTGCCTGCGCCCTCGCGCTCTGCGTGGC CGTGGCCATCGTGGCCGGCGCCTCCTCGGAGTCCTTG GGGACGGAGCAGCGCGTCGTGGGGCGAGCGGCAGAA GTCCCGGGCCCAGAGCCCGGCCAGCAGGAGCAGTTG GTCTTCGGCAGCGGGGATGCTGTGGAGCTGAGCTGTC CCCCGCCCGGGGGTGGTCCCATGGGGCCCACTGTCTG GGTCAAGGATGGCACAGGGCTGGTGCCCTCGGAGCGT GTCCTGGTGGGGCCCCAGCGGCTGCAGGTGCTGAATG CCTCCCACGAGGACTCCGGGGCCTACAGCTGCCGGCA GCGGCTCACGCAGCGCGTACTGTGCCACTTCAGTGTGC GGGTGACAGACGCTCCATCCTCGGGAGATGACGAAGA CGGGGAGGACGAGGCTGAGGACACAGGTGTGGACAC AGGGGCCCCTTACTGGACACGGCCCGAGCGGATGGAC AAGAAGCTGCTGGCCGTGCCGGCCGCCAACACCGTCC GCTTCCGCTGCCCAGCCGCTGGCAACCCCACTCCCTCC ATCTCCTGGCTGAAGAACGGCAGGGAGTTCCGCGGCG AGCACCGCATTGGAGGCATCAAGCTGCGGCATCAGCA |

FIG. 27 Cont.

| sample | Gene Break-point 5p | Gene Break-point 3p | Frame Type | SEQ ID NO: | Fused Sequence |
|---|---|---|---|---|---|
| | | | | | GTGGAGCCTGGTCATGGAAAGCGTGGTGCCCTCGGAC CGCGGCAACTACACCTGCGTCGTGGAGAACAAGTTTG GCAGCATCCGGCAGACGTACACGCTGGACGTGCTGGA GCGCTCCCCGCACCGGCCCATCCTGCAGGCGGGGCTG CCGGCCAACCAGACGGCGGTGCTGGGCAGCGACGTG GAGTTCCACTGCAAGGTGTACAGTGACGCACAGCCCC ACATCCAGTGGCTCAAGCACGTGGAGGTGAATGGCAG CAAGGTGGGCCCGGACGGCACACCCTACGTTACCGTG CTCAAGTCCTGGATCAGTGAGAGTGTGGAGGCCGACG TGCGCCTCCGCCTGGCCAATGTGTCGGAGCGGGACGG GGGCGAGTACCTCTGTCGAGCCACCAATTTCATAGGC GTGGCCGAGAAGGCCTTTTGGCTGAGCGTTCACGGGC CCCGAGCAGCCGAGGAGGAGCTGGTGGAGGCTGACG AGGCGGGCAGTGTGTATGCAGGCATCCTCAGCTACGG GGTGGGCTTCTTCCTGTTCATCCTGGTGGTGGCGGCTG TGACGCTCTGCCGCCTGCGCAGCCCCCCCAAGAAAGG CCTGGGCTCCCCCACCGTGCACAAGATCTCCCGCTTCC CGCTCAAGCGACAGGTGTCCCTGGAGTCCAACGCGTC CATGAGCTCCAACACACCACTGGTGCGCATCGCAAGG CTGTCCTCAGGGGAGGGCCCCACGCTGGCCAATGTCT CCGAGCTCGAGCTGCCTGCCGACCCCAAATGGGAGCT GTCTCGGGCCCGGCTGACCCTGGGCAAGCCCCTTGGG GAGGGCTGCTTCGGCCAGGTGGTCATGGCGGAGGCC ATCGGCATTGACAAGGACCGGGCCGCCAAGCCTGTCA CCGTAGCCGTGAAGATGCTGAAAGACGATGCCACTGA CAAGGACCTGTCGGACCTGGTGTCTGAGATGGAGATG ATGAAGATGATCGGGAAACACAAAAACATCATCAACC TGCTGGGCGCCTGCACGCAGGGCGGGCCCCTGTACGT GCTGGTGGAGTACGCGGCCAAGGGTAACCTGCGGGA GTTTCTgcgggcgcggcggcccccgggccTGGACTACTCCTTC GACACCTGCAAGCCGCCCGAGGAGCAGCTCACCTTCA AGGACCTGGTGTCCTGTGCCTACCAGGTGGCCCGGGG CATGGAGTACTTGGCCTCCCAGAAGTGCATCCACAGG GACCTGGCTGCCCGCAATGTGCTGGTGACCGAGGACA ACGTGATGAAGATCGCAGACTTCGGGCTGGCCCGGGA CGTGCACAACCTCGACTACTACAAGAAGACGACCAAC GGCCGGCTGCCCGTGAAGTGGATGGCGCCTGAGGCCT TGTTTGACCGAGTCTACACTCACCAGAGTGACGTCTGG TCCTTTGGGGTCCTGCTCTGGGAGATCTTCACGCTGGG GGGCTCCCCGTACCCCGGCATCCCTGTGGAGGAGCTCT TCAAGCTGCTGAAGGAGGGCCACCGCATGGACAAGCC CGCCAACTGCACACACGACCTGTACATGATCATGCGG GAGTGCTGGCATGCCGCGCCCTCCCAGAGGCCCACCTT CAAGCAGCTGGTGGAGGACCTGGACCGTGTCCTTACC GTGACGTCCACCGAC\|GTGCCAGGCCCACCCCCAGGT GTTCCCGCGCCTGGGGGCCCACCCCTGTCCACCGGACC TATAGTGGACCTGCTCCAGTACAGCCAGAAGGACCTG GATGCAGTGGTAAAGGCGACACAGGAGGAGAACCGG GAGCTGAGGAGCAGGTGTGAGGAGCTCCACGGGAAG AACCTGGAACTGGGGAAGATCATGGACAGGTTCGAAG AGGTTGTGTACCAGGCCATGGAGGAAGTTCAGAAGCA GAAGGAACTTTCCAAAGCTGAAATCCAGAAGTTCTA AAAGAAAAAGACCAACTTACCACAGATCTGAACTCCAT GGAGAAGTCCTTCTCCGACCTCTTCAAGCGTTTTGAGA AACAGAAAGAGGTGATCGAGGGCTACCGCAAGAACG |

FIG. 27 Cont.

| sample | Gene Breakpoint 5p | Gene Breakpoint 3p | Frame Type | SEQ ID NO: | Fused Sequence |
|---|---|---|---|---|---|
| | | | | | AAGAGTCACTGAAGAAGTGCGTGGAGGATTACCTGGC AAGGATCACCCAGGAGGGCCAGAGGTACCAAGCCCTG AAGGCCCACGCGGAGGAGAAGCTGCAGCTGGCAAAC GAGGAGATCGCCCAGGTCCGGAGCAAGGCCCAGGCG GAAGCGTTGGCCCTCCAGGCCAGCCTGAGGAAGGAGC AGATGCGCATCCAGTCGCTGGAGAAGACAGTGGAGCA GAAGACTAAAGAGAACGAGGAGCTGACCAGGATCTG CGACGACCTCATCTCCAAGATGGAGAAGATC |
| NYU_B | 7388176 | 7604059 | InFrame | 8288 | ATGCACGGGGGTGGCCCCCCCTCGGGGGACAGCGCAT GCCCGCTGCGCACCATCAAGAGAGTCCAGTTCGGAGT CCTGAGTCCGGATGAACTG\|GTCCCTGTCCTTCGAATG GTGGAAGGTGATACCATCTATGATTACTGCTGGTATTC TCTGATGTCCTCAGCCCAGCCAGACACCTCCTACGTGG CCAGCAGCAGCCGGGAGAACCCGATTCATATCTGGGA CGCATTCACTGGAGAGCTCCGGGCTTCCTTTCGCGCCT ACAACCACCTGGATGAGCTGACGGCAGCCCATTCGCTC TGCTTCTCCCCGGATGGCTCCCAGCTCTTCTGTGGCTTC AACCGGACTGTGCGTGTTTTTTTCCACGGCCCGGCCTGG CCGAGACTGCGAGGTCCGAGCCACATTTGCAAAAAAG CAGGGCCAGAGCGGCATCATCTCCTGCATAGCCTTCAG CCCAGCCCAGCCCCTCTATGCCTGTGGCTCCTACGGCC GCTCCCTGGGTCTGTATGCCTGGGATGATGGCTCCCCT CTCGCCTTGCTGGGAGGGCACCAAGGGGGCATCACCC ACCTCTGCTTTCATCCCGATGGCAACCGCTTCTTCTCAG GAGCCCGCAAGGATGCTGAGCTCCTGTGCTGGGATCT CCGGCAGTCTGGTTACCCACTGTGGTCCCTGGGTCGAG AGGTGACCACCAATCAGCGCATCTACTTCGATCTGGAC CCGACCGGGCAGTTCCTAGTGAGTGGCAGCACGAGCG GGGCTGTCTCTGTGTGGGACACGGACGGGCCTGGCAA TGATGGGAAGCCGGAGCCCGTGTTGAGTTTTCTGCCCC AGAAGGACTGCACCAATGGCGTGAGCCTGCACCCTAG CCTGCCTCTCCTGGCCACTGCCTCCGGTCAGCGTGTGT TTCCTGAGCCCACAGAGAGTGGGGACGAAGGAGAGG AGCTGGGCCTTCCCTTGCTCTCCACGCGCCACGTCCAC CTTGAATGTCGGCTTCAGCTCTGGTGGTGTGGGGGGG CGCCAGACTCCAGCATCCCTGATGATCACCAGGGCGA GAAAGGGCAGGGAGGAACGGAGGGAGGTGTGGGTG AGCTGATA |
| G17507. TCGA-28-1747-01C-01R-1850-01.2 | 55268106 | 55863785 | InFrame | 8289 | ATGCGACCCTCCGGGACGGCCGGGGCAGCGCTCCTGG CGCTGCTGGCTGCGCTCTGCCCGGCGAGTCGGGCTCT GGAGGAAAAGAAAGTTTGCCAAGGCACGAGTAACAA GCTCACGCAGTTGGGCACTTTTGAAGATCATTTTCTCA GCCTCCAGAGGATGTTCAATAACTGTGAGGTGGTCCTT GGGAATTTGGAAATTACCTATGTGCAGAGGAATTATG ATCTTTCCTTCTTAAAGACCATCCAGGAGGTGGCTGGT TATGTCCTCATTGCCCTCAACACAGTGGAGCGAATTCC TTTGGAAAACCTGCAGATCATCAGAGGAAATATGTACT ACGAAAATTCCTATGCCTTAGCAGTCTTATCTAACTATG ATGCAAATAAAACCGGACTGAAGGAGCTGCCCATGAG AAATTTACAGGAAATCCTGCATGGCGCCGTGCGGTTCA GCAACAACCCTGCCCTGTGCAACGTGGAGAGCATCCA GTGGCGGGACATAGTCAGCAGTGACTTTCTCAGCAAC ATGTCGATGGACTTCCAGAACCACCTGGGCAGCTGCC AAAAGTGTGATCCAAGCTGTCCCAATGGGAGCTGCTG GGGTGCAGGAGAGGAGAACTGCCAGAAACTGACCAA |

FIG. 27 Cont.

| sample | Gene Break-point 5p | Gene Break-point 3p | Frame Type | SEQ ID NO: | Fused Sequence |
|---|---|---|---|---|---|
| | | | | | AATCATCTGTGCCCAGCAGTGCTCCGGGCGCTGCCGTG GCAAGTCCCCCAGTGACTGCTGCCACAACCAGTGTGCT GCAGGCTGCACAGGCCCCCGGGAGAGCGACTGCCTG GTCTGCCGCAAATTCCGAGACGAAGCCACGTGCAAGG ACACCTGCCCCCCACTCATGCTCTACAACCCCACCACGT ACCAGATGGATGTGAACCCCGAGGGCAAATACAGCTT TGGTGCCACCTGCGTGAAGAAGTGTCCCCGTAATTATG TGGTGACAGATCACGGCTCGTGCGTCCGAGCCTGTGG GGCCGACAGCTATGAGATGGAGGAAGACGGCGTCCG CAAGTGTAAGAAGTGCGAAGGGCCTTGCCGCAAAGTG TGTAACGGAATAGGTATTGGTGAATTTAAAGACTCACT CTCCATAAATGCTACGAATATTAAACACTTCAAAAACT GCACCTCCATCAGTGGCGATCTCCACATCCTGCCGGTG GCATTTAGGGGTGACTCCTTCACACATACTCCTCCTCTG GATCCACAGGAACTGGATATTCTGAAAACCGTAAAGG AAATCACAGGGTTTTTGCTGATTCAGGCTTGGCCTGAA AACAGGACGGACCTCCATGCCTTTGAGAACCTAGAAA TCATACGCGGCAGGACCAAGCAACATGGTCAGTTTTCT CTTGCAGTCGTCAGCCTGAACATAACATCCTTGGGATT ACGCTCCCTCAAGGAGATAAGTGATGGAGATGTGATA ATTTCAGGAAACAAAAATTTGTGCTATGCAAATACAAT AAACTGGAAAAAACTGTTTGGGACCTCCGGTCAGAAA ACCAAAATTATAAGCAACAGAGGTGAAAACAGCTGCA AGGCCACAGGCCAGGTCTGCCATGCCTTGTGCTCCCCC GAGGGCTGCTGGGGCCCGGAGCCCAGGGACTGCGTC TCTTGCCGGAATGTCAGCCGAGGCAGGGAATGCGTGG ACAAGTGCAACCTTCTGGAGGGTGAGCCAAGGGAGTT TGTGGAGAACTCTGAGTGCATACAGTGCCACCCAGAG TGCCTGCCTCAGGCCATGAACATCACCTGCACAGGACG GGGACCAGACAACTGTATCCAGTGTGCCCACTACATTG ACGGCCCCCACTGCGTCAAGACCTGCCCGGCAGGAGT CATGGGAGAAAACAACACCCTGGTCTGGAAGTACGCA GACGCCGGCCATGTGTGCCACCTGTGCCATCCAAACTG CACCTACGGATGCACTGGGCCAGGTCTTGAAGGCTGT CCAACGAATGGGCCTAAGATCCCGTCCATCGCCACTGG GATGGTGGGGGCCCTCCTCTTGCTGCTGGTGGTGGCC CTGGGGATCGGCCTCTTCATGCGAAGGCGCCACATCG TTCGGAAGCGCACGCTGCGGAGGCTGCTGCAGGAGA GGGAGCTTGTGGAGCCTCTTACACCCAGTGGAGAAGC TCCCAACCAAGCTCTCTTGAGGATCTTGAAGGAAACTG AATTCAAAAAGATCAAAGTGCTGGGCTCCGGTGCGTT CGGCACGGTGTATAAGGGACTCTGGATCCCAGAAGGT GAGAAAGTTAAAATTCCCGTCGCTATCAAGGAATTAA GAGAAGCAACATCTCCGAAAGCCAACAAGGAAATCCT CGATGAAGCCTACGTGATGGCCAGCGTGGACAACCCC CACGTGTGCCGCCTGCTGGGCATCTGCCTCACCTCCAC CGTGCAGCTCATCACGCAGCTCATGCCCTTCGGCTGCC TCCTGGACTATGTCCGGGAACACAAAGACAATATTGG CTCCCAGTACCTGCTCAACTGGTGTGTGCAGATCGCAA AGGGCATGAACTACTTGGAGGACCGTCGCTTGGTGCA CCGCGACCTGGCAGCCAGGAACGTACTGGTGAAAACA CCGCAGCATGTCAAGATCACAGATTTTGGGCTGGCCA AACTGCTGGGTGCGGAAGAGAAAGAATACCATGCAG AAGGAGGCAAAGTGCCTATCAAGTGGATGGCATTGGA ATCAATTTTACACAGAATCTATACCCACCAGAGTGATG |

FIG. 27 Cont.

| sample | Gene Breakpoint 5p | Gene Breakpoint 3p | Frame Type | SEQ ID NO: | Fused Sequence |
|---|---|---|---|---|---|
| | | | | | TCTGGAGCTACGGGGTGACTGTTTGGGAGTTGATGAC CTTTGGATCCAAGCCATATGACGGAATCCCTGCCAGCG AGATCTCCTCCATCCTGGAGAAAGGAGAACGCCTCCCT CAGCCACCCATATGTACCATCGATGTCTACATGATCAT GGTCAAGTGCTGGATGATAGACGCAGATAGTCGCCCA AAGTTCCGTGAGTTGATCATCGAATTCTCCAAAATGGC CCGAGACCCCCAGCGCTACCTTGTCATTCAG\|CTGCAG GACAAGTTCGAGCATCTTAAAATGATTCAACAGGAGG AGATAAGGAAGCTCGAGGAAGAGAAAAAACAACTGG AAGGAGAAATCATAGATTTTTATAAAATGAAAGCTGCC TCCGAAGCACTGCAGACTCAGCTGAGCACCGATACAA AGAAAGACAAACATCGTAAGAAA |
| G17469. TCGA-06-2557-01A-01R-1849-01.2 | 73604248 | 74173110 | InFrame | 8290 | ATGGCGGACTTCGACACCTACGACGATCGGGCCTACA GCAGCTTCGGCGGCGGCAGAGGGTCCCGCGGCAGTG CTGGTGGCCATGGTTCCCGTAGCCAGAAGGAGTTGCC CACAGAGCCCCCTACACAGCATACGTAGGAAATCTAC CTTTCAATACGGTTCAGGGCGACATAGATGCTATCTTT AAGGATCTCAGCATAAGGAGTGTACGGCTAGTCAGAG ACAAAGACACAGATAAATTTAAAGGATTCTGCTATGTA GAATTCGATGAAGTGGATTCCCTTAAGGAAGCCTTGAC ATACGATGGTGCACTGTTGGGCGATCGGTCACTTCGTG TGGACATTGCAGAAGGCAGAAAACAAGATAAAGGTG GCTTTGGATTCAGAAAAGGTGGACCAGATGACAGAG \| AAATAAAAGAGACTGATGGAAGCTCTCAGATCAAGCA AGAACCAGACCCCACGTGG |
| G17785. TCGA-06-5413-01A-01R-1849-01.4 | 32903023 | 34400421 | InFrame | 8291 | ATGTTAACCATGAGCGTGACACTTTCCCCCCTGAGGTC ACAGGACCTGGATCCCATGGCTACTGATGCTTCACCCA TGGCCATCAACATGACACCCACTGTGGAGCAGGGTGA GGGAGAAGAGGCAATGAAGGACATGGACTCTGACCA GCAGTATGAAAAGCCACCCCACTACACACAGGGGCT GACTGGAAGATTGTCCTCCACTTACCTGAAATTGAGAC CTGGCTCCGGATGACCTCAGAGAGGGTCCGAGACCTA ACCTATTCAGTCCAGCAGGATTCGGACAGCAAGCATGT GGATGTACATCTAGTTCAACTAAAG\|GCAATGGTGGCT TGCTATCCGGGAAATGGAACAGGTTATGTTCGCCACGT GGACAACCCCAACGGTGATGGTCGCTGCATCACCTGC ATCTACTATCTGAACAAGAATTGGGATGCCAAGCTACA TGGTGGGATCCTGCGGATATTTCCAGAGGGGAAATCA TTCATAGCAGATGTGGAGCCCATTTTTGACAGACTCCT GTTCTTCTGGTCAGATCGTAGGAACCCACACGAAGTGC AGCCCTCTTACGCAACCAGATATGCTATGACTGTCTGG TACTTTGATGCTGAAGAAGGGCAGAAGCCAAAAAGA AATTCAGGAATTTAACTAGGAAAACTGAATCTGCCCTC ACTGAAGAC |
| G17467. TCGA-14-0736-02A-01R-2005-01.2 | 102606509 | 12856191 | InFrame | 8292 | ATGGCGACGGAGGGAGGAGGGAAGGAGATGAACGA GATTAAGACCCAATTCACCACCCGGGAAGGTCTGTACA AGCTGCTGCCGCACTCGGAGTACAGCCGGCCCAACCG GGTGCCCTTCAACTCGCAGGGATCCAACCCTGTCCGCG TCTCCTTCGTAAACCTCAACGACCAGTCTGGCAACGGC GACCGCCTCTGCTTCAATGTGGGCCGGGAGCTGTACTT CTATATCTACAAGGGGGTCCGCAAG\|GAGATTGACCCC AGCCTGGGCGTGGCGGAGCTGCCTGACGAGTTCTTCG AGGAGGACAACATGCTGAGCATGGGCAAGAAGATGA TGCAGGAGGCCATGAGCGCATTTCCCGGCATCGATGA GGCCATGAGCTATGCCGAGGTCATGAGGCTGGTGAAG |

| sample | Gene Break-point 5p | Gene Break-point 3p | Frame Type | SEQ ID NO: | Fused Sequence |
|---|---|---|---|---|---|
| | | | | | GGCATGAACTTCTCGGTGGTGGTATTTGACACGGCACC CACGGGCCACACCCTGAGGCTGCTCAACTTCCCCACCA TCGTGGAGCGGGGCCTGGGCCGGCTTATGCAGATCAA GAACCAGATCAGCCCTTTCATCTCACAGATGTGCAACA TGCTGGGCCTGGGGGACATGAACGCAGACCAGCTGGC CTCCAAGCTGGAGGAGACGCTGCCCGTCATCCGCTCA GTCAGCGAACAGTTCAAGGACCCTGAGCAGACAACTT TCATCTGCGTATGCATTGCTGAGTTCCTGTCCCTGTATG AGACAGAGAGGCTGATCCAGGAGCTGGCCAAGTGCA AGATTGACACACACAATATAATTGTCAACCAGCTCGTC TTCCCCGACCCCGAGAAGCCCTGCAAGATGTGTGAGG CCCGTCACAAGATCCAGGCCAAGTATCTGGACCAGAT GGAGGACCTGTATGAAGACTTCCACATCGTGAAGCTG CCGCTGTTACCCCATGAGGTGCGGGGGGCAGACAAGG TCAACACCTTCTCGGCCCTCCTCCTGGAGCCCTACAAG CCCCCCAGTGCCCAG |
| GBM-CUMC33 16_L1 | 22160139 | 58166800 | InFrame | 8293 | atggcggcggcggcggcggcggGCGCGGGCCCGGAGATGGT CCGCGGGCAGGTGTTCGACGTGGGGCCGCGCTACACC AACCTCTCGTACATCGGCGAGGGCGCCTACGGCATGG TGTGCTCTGCTTATGATAATGTCAACAAAGTTCGAGTA GCTATCAAGAAAATCAGCCCCTTTGAGCACCAGACCTA CTGCCAGAGAACCCTGAGGGAGATAAAAATCTTACTG CGCTTCAGACATGAGAACATCATTGGAATCAATGACAT TATTCGAGCACCAACCATCGAGCAAATGAAAGATGTAT ATATAGTACAGGACCTCATGGAAACAGATCTTTACAAG CTCTTGAAGACACAACACCTCAGCAATGACCATATCTG CTATTTTCTCTACCAGATCCTCAGAGGGTTAAAATATAT CCATTCAGCTAACGTTCTGCACCGTGACCTCAAGCCTTC CAACCTGCTGCTCAACACCACCTGTGATCTCAAG\|GCC CTGAGCCTGTGCAATTATTTCGAGAGTCAAAATGTGGA TTTCCGAGGCAAGAAGGTGATCGAACTGGGTGCGGG GACAGGCATCGTGGGGATCTTGGCAGCGCTGCAGGG GGGGGATGTTACCATCACTGACCTGCCCCTGGCCCTAG AACAGATCCAGGGCAACGTCCAGGCCAATGTGCCAGC TGGAGGCCAGGCCCAGGTGCGTGCCTTGTCCTGGGGG ATTGACCATCATGTCTTCCCTGCAAACTATGACCTGGT GCTGGGGGCTGATATCGTGTACCTGGAACCCACCTTCC CTCTGCTGCTGGGGACCCTCCAACACCTGTGCAGGCCC CATGGCACCATCTATCTGGCCTCCAAGATGAGAAAGG AGCATGGGACAGAGAGCTTCTTTCAGCACCTCCTGCCC CAGCATTTCCAACTGGAGCTGGCTCAGCGGGATGAGG ATGAAAATGTCAACATCTATAGGGCCAGGCACAGGGA ACCAAGACCTGCT |
| G17663. TCGA-19-2619-01A-01R-1850-01.2 | 156628525 | 156844698 | InFrame | 8294 | ATGGCCCAGCTGTTCCTGCCCCTGCTGGCAGCCCTGGT CCTGGCCCAGGCTCCTGCAGCTTTAGCAGATGTTCTGG AAGGAGACAGCTCAGAGGACCGCGCTTTTCGCGTGCG CATCGCGGGCGACGCGCCACTGCAGGGCGTGCTCGGC GGCGCCCTCACCATCCCTTGCCACGTCCACTACCTGCG GCCACCGCCGAGCCGCCGGGCTGTGCTGGGCTCTCCG CGGGTCAAGTGGACTTTCCTGTCCCGGGGCCGGGAGG CAGAGGTGCTGGTGGCGCGGGGAGTGCGCGTCAAGG TGAACGAGGCCTACCGGTTCCGCGTGGCACTGCCTGC GTACCCAGCGTCGCTCACCGACGTCTCCCTGGCGCTGA GCGAGCTGCGCCCCAACGACTCAGGTATCTATCGCTGT GAGGTCCAGCACGGCATCGATGACAGCAGCGACGCTG |

FIG. 27 Cont.

| sample | Gene Breakpoint 5p | Gene Breakpoint 3p | Frame Type | SEQ ID NO: | Fused Sequence |
|---|---|---|---|---|---|
| | | | | | TGGAGGTCAAGGTCAAAGGGGTCGTCTTTCTCTACCG AGAGGGCTCTGCCCGCTATGCTTTCTCCTTTTCTGGGG CCCAGGAGGCCTGTGCCCGCATTGGAGCCCACATCGC CACCCCGGAGCAGCTCTATGCCGCCTACCTTGGGGGCT ATGAGCAATGTGATGCTGGCTGGCTGTCGGATCAGAC CGTGAGGTATCCCATCCAGACCCCACGAGAGGCCTGTT ACGGAGACATGGATGGCTTCCCCGGGGTCCGGAACTA TGGTGTGGTGGACCCGGATGACCTCTATGATGTGTACT GTTATGCTGAAGACCTAAATGGAGAACTGTTCCTGGGT GACCCTCCAGAGAAGCTGACATTGGAGGAAGCACGG GCGTACTGCCAGGAGCGGGGTGCAGAGATTGCCACCA CGGGCCAACTGTATGCAGCCTGGGATGGTGGCCTGGA CCACTGCAGCCCAGGGTGGCTAGCTGATGGCAGTGTG CGCTACCCCATCGTCACACCCAGCCAGCGCTGTGGTGG GGGCTTGCCTGGTGTCAAGACTCTCTTCCTCTTCCCCAA CCAGACTGGCTTCCCCAATAAGCACAGCCGCTTCAACG TCTACTGCTTCCGAGACTCGGCCCAGCCTTCTGCCATCC CTGAGgcctccaacccagcctccaacccagcctcTGATGGACTA GAGGCTATCGTCACAGTGACAGAGACCCTGGAGGAAC TGCAGCTGCCTCAGGAAGCCACAGAGAGTGAATCCCG TGGGGCCATCTACTCCATCCCCATCATGGAGGACGGA GGAGGTGGAAGCTCCACTCCAGAAGACCCAGCAGAG GCCCCTAGGACGCTCCTAGAATTTGAAACACAATCCAT GGTACCGCCCACGGGGTTCTCAGAAGAGGAAGGTAA GGCATTggaggaagaagagaaatatgaagatgaagaagagaaag aggaggaagaagaagaggaggaggtggaggatgaggCTCTGTGG GCATGGCCCAGCGAGCTCAGCAGCCCGGGCCCTGAGG CCTCTCTCCCCACTGAGCCAGCAGCCCAGGAGGAGTCA CTCTCCCAGGCGCCAGCAAGGGCAGTCCTGCAGCCTG GTGCATCACCACTTCCTGATGGAGAGTCAGAAGCTTCC AGGCCTCCAAGGGTCCATGGACCACCTACTGAGACTCT GCCCACTCCCAGGGAGAGGAACCTAGCATCCCCATCA CCTTCCACTCTGGTTGAGGCAAGAGAGGTGGGGGAGG CAACTGGTGGTCCTGAGCTATCTGGGGTCCCTCGAGG AGAGAGCGAGGAGACAGGAAGCTCCGAGGGTGCCCC TTCCCTGCTTCCAGCCACACGGGCCCCTGAGGGTACCA GGGAGCTGGAGGCCCCCTCTGAAGATAATTCTGGAAG AACTGCCCCAGCAGGGACCTCAGTGCAGGCCCAGCCA GTGCTGCCCACTGACAGCGCCAGCCGAGGTGGAGTGG CCGTGGTCCCCGCATCAGGTGACTGTGTCCCCAGCCCC TGCCACAATGGTGGGACATGCTTGGAGGAGGAGGAA GGGGTCCGCTGCCTATGTCTGCCTGGCTATGGGGGGG ACCTGTGCGATGTTGGCCTCCGCTTCTGCAACCCCGGC TGGGACGCCTTCCAGGGCGCCTGCTACAAGCACTTTTC CACACGAAGGAGCTGGAGGAGGCAGAGACCCAGTG CCGGATGTACGGCGCGCATCTGGCCAGCATCAGCACA CCCGAGGAACAGGACTTCATCAACAACCGGTACCGGG AGTACCAGTGGATCGGACTCAACGACAGGACCATCGA AGGCGACTTCTTGTGGTCGGATGGCGTCCCCCTGCTCT ATGAGAACTGGAACCCTGGGCAGCCTGACAGCTACTT CCTGTCTGGAGAGAACTGCGTGGTCATGGTGTGGCAT GATCAGGGACAATGGAGTGACGTGCCCTGCAACTACC ACCTGTCCTACACCTGCAAGATGGGGCTGGTGTCCTGT GGGCCGCCACCGGAGCTGCCCCTGGCTCAAGTGTTCG GCCGCCCACGGCTGCGCTATGAGGTGGACACTGTGCT |

FIG. 27 Cont.

| sample | Gene Break-point 5p | Gene Break-point 3p | Frame Type | SEQ ID NO: | Fused Sequence |
|---|---|---|---|---|---|
| | | | | | TCGCTACCGGTGCCGGGAAGGACTGGCCCAGCGCAAT CTGCCGCTGATCCGATGCCAAGAGAACGGTCGTTGGG AGGCCCCCCAGATCTCCTGTGTGCCCAGAAGACCT\|GT CTCGGTGGCTGTGGGCCTGGCCGTCTTTGCCTGCCTCT TCCTTTCTACGCTGCTCCTTGTGCTCAACAAATGTGGAC GGAGAAACAAGTTTGGGATCAACCGCCCGGCTGTGCT GGCTCCAGAGGATGGGCTGGCCATGTCCCTGCATTTCA TGACATTGGGTGGCAGCTCCCTGTCCCCACCGAGGG CAAAGGCTCTGGGCTCCAAGGCCACATCATCGAGAAC CCACAATACTTCAGTGATGCCTGTGTTCACCACATCAA GCGCCGGGACATCGTGCTCAAGTGGGAGCTGGGGGA GGGCGCCTTTGGGAAGGTCTTCCTTGCTGAGTGCCACA ACCTCCTGCCTGAGCAGGACAAGATGCTGGTGGCTGT CAAGGCACTGAAGGAGGCGTCCGAGAGTGCTCGGCA GGACTTCCAGCGTGAGGCTGAGCTGCTCACCATGCTG CAGCACCAGCACATCGTGCGCTTCTTCGGCGTCTGCAC CGAGGGCCGCCCCCTGCTCATGGTCTTTGAGTATATGC GGCACGGGGACCTCAACCGCTTCCTCCGATCCCATGGA CCTGATGCCAAGCTGCTGGCTGGTGGGGAGGATGTGG CTCCAGGCCCCCTGGGTCTGGGGCAGCTGCTGGCCGT GGCTAGCCAGGTCGCTGCGGGGATGGTGTACCTGGCG GGTCTGCATTTTGTGCACCGGGACCTGGCCACACGCAA CTGTCTAGTGGGCCAGGGACTGGTGGTCAAGATTGGT GATTTTGGCATGAGCAGGGATATCTACAGCACCGACT ATTACCGTGTGGGAGGCCGCACCATGCTGCCCATTCGC TGGATGCCGCCCGAGAGCATCCTGTACCGTAAGTTCAC CACCGAGAGCGACGTGTGGAGCTTCGGCGTGGTGCTC TGGGAGATCTTCACCTACGGCAAGCAGCCCTGGTACC AGCTCTCCAACACGGAGGCAATCGACTGCATCACGCA GGGACGTGAGTTGGAGCGGCCACGTGCCTGCCCACCA GAGGTCTACGCCATCATGCGGGGCTGCTGGCAGCGGG AGCCCCAGCAACGCCACAGCATCAAGGATGTGCACGC CCGGCTGCAAGCCCTGGCCCAGGCACCTCCTGTCTACC TGGATGTCCTGGGC |
| G17203. TCGA-06-0211-02A-02R-2005-01.2 | 54825188 | 55224226 | InFrame | 8295 | ATGGATCAGGTAATGCAGTTTGTTGAGCCAAGTCGGC AGTTTGTAAAGGACTCCATTCGGCTGGTTAAAAGATGC ACTAAACCTGATAGAAAAG\|TGTGTAACGGAATAGGT ATTGGTGAATTTAAAGACTCACTCTCCATAAATGCTAC GAATATTAAACACTTCAAAAACTGCACCTCCATCAGTG GCGATCTCCACATCCTGCCGGTGGCATTTAGGGGTGAC TCCTTCACACATACTCCTCCTCTGGATCCACAGGAACTG GATATTCTGAAAACCGTAAAGGAAATCACAGGGTTTTT GCTGATTCAGGCTTGGCCTGAAAACAGGACGGACCTC CATGCCTTTGAGAACCTAGAAATCATACGCGGCAGGA CCAAGCAACATGGTCAGTTTTCTCTTGCAGTCGTCAGC CTGAACATAACATCCTTGGGATTACGCTCCCTCAAGGA GATAAGTGATGGAGATGTGATAATTTCAGGAAACAAA AATTTGTGCTATGCAAATACAATAAACTGGAAAAAACT GTTTGGGACCTCCGGTCAGAAAACCAAAATTATAAGC AACAGAGGTGAAAACAGCTGCAAGGCCACAGGCCAG GTCTGCCATGCCTTGTGCTCCCCGAGGGCTGCTGGG GCCCGGAGCCCAGGGACTGCGTCTCTTGCCGGAATGT CAGCCGAGGCAGGGAATGCGTGGACAAGTGCAACCTT CTGGAGGGTGAGCCAAGGGAGTTTGTGGAGAACTCTG AGTGCATACAGTGCCACCCAGAGTGCCTGCCTCAGGC |

FIG. 27 Cont.

| sample | Gene Breakpoint 5p | Gene Breakpoint 3p | Frame Type | SEQ ID NO: | Fused Sequence |
|---|---|---|---|---|---|
| | | | | | CATGAACATCACCTGCACAGGACGGGGACCAGACAAC TGTATCCAGTGTGCCCACTACATTGACGGCCCCCACTG CGTCAAGACCTGCCCGGCAGGAGTCATGGGAGAAAAC AACACCCTGGTCTGGAAGTACGCAGACGCCGGCCATG TGTGCCACCTGTGCCATCCAAACTGCACCTACGGATGC ACTGGGCCAGGTCTTGAAGGCTGTCCAACGAATGGGC CTAAGATCCCGTCCATCGCCACTGGGATGGTGGGGGC CCTCCTCTTGCTGCTGGTGGTGGCCCTGGGGATCGGCC TCTTCATGCGAAGGCGCCACATCGTTCGGAAGCGCAC GCTGCGGAGGCTGCTGCAGGAGAGGGAGCTTGTGGA GCCTCTTACACCCAGTGGAGAAGCTCCCAACCAAGCTC TCTTGAGGATCTTGAAGGAAACTGAATTCAAAAAGATC AAAGTGCTGGGCTCCGGTGCGTTCGGCACGGTGTATA AGGGACTCTGGATCCCAGAAGGTGAGAAAGTTAAAAT TCCCGTCGCTATCAAGGAATTAAGAGAAGCAACATCTC CGAAAGCCAACAAGGAAATCCTCGATGAAGCCTACGT GATGGCCAGCGTGGACAACCCCCACGTGTGCCGCCTG CTGGGCATCTGCCTCACCTCCACCGTGCAGCTCATCAC GCAGCTCATGCCCTTCGGCTGCCTCCTGGACTATGTCC GGGAACACAAAGACAATATTGGCTCCCAGTACCTGCTC AACTGGTGTGTGCAGATCGCAAAGGGCATGAACTACT TGGAGGACCGTCGCTTGGTGCACCGCGACCTGGCAGC CAGGAACGTACTGGTGAAAACACCGCAGCATGTCAAG ATCACAGATTTTGGGCTGGCCAAACTGCTGGGTGCGG AAGAGAAAGAATACCATGCAGAAGGAGGCAAAGTGC CTATCAAGTGGATGGCATTGGAATCAATTTTACACAGA ATCTATACCCACCAGAGTGATGTCTGGAGCTACGGGG TGACTGTTTGGGAGTTGATGACCTTTGGATCCAAGCCA TATGACGGAATCCCTGCCAGCGAGATCTCCTCCATCCT GGAGAAAGGAGAACGCCTCCCTCAGCCACCCATATGT ACCATCGATGTCTACATGATCATGGTCAAGTGCTGGAT GATAGACGCAGATAGTCGCCCAAAGTTCCGTGAGTTG ATCATCGAATTCTCCAAAATGGCCCGAGACCCCCAGCG CTACCTTGTCATTCAGGGGGATGAAAGAATGCATTTGC CAAGTCCTACAGACTCCAACTTCTACCGTGCCCTGATG GATGAAGAAGACATGGACGACGTGGTGGATGCCGAC GAGTACCTCATCCCACAGCAGGGCTTCTTCAGCAGCCC CTCCACGTCACGGACTCCCCTCCTGAGCTCTCTGAGTG CAACCAGCAACAATTCCACCGTGGCTTGCATTGATAGA AATGGGCTGCAAAGCTGTCCCATCAAGGAAGACAGCT TCTTGCAGCGATACAGCTCAGACCCCACAGGCGCCTTG ACTGAGGACAGCATAGACGACACCTTCCTCCCAGTGCC TGaATACATAAACCAGTCCGTTCCCAAAAGGCCCGCTG GCTCTGTGCAGAATCCTGTCTATCACAATCAGCCTCTG AACCCCGCGCCCAGCAGAGACCCACACTACCAGGACC CCCACAGCACTGCAGTGGGCAACCCCGAGTATCTCAAC ACTGTCCAGCCCACCTGTGTCAACAGCACATTCGACAG CCCTGCCCACTGGGCCCAGAAAGGCAGCCACCAAATT AGCCTGGACAACCCTGACTACCAGCAGGACTTCTTTCC CAAGGAAGCCAAGCCAAATGGCATCTTTAAGGGCTCC ACAGCTGAAAATGCAGAATACCTAAGGGTCGCGCCAC AAAGCAGTGAATTTATTGGAGCA |
| G17784. TCGA-76- 4929- | 9675963 | 9731644 | InFrame | 8296 | ATGAGGCAGTCTCTCCTATTCCTGACCAGCGTGGTTCC TTTCGTGCTGGCGCCGCGACCTCCGGATGACCCGGGC TTCGGCCCCCACCAGAGACTCGAGAAGCTTGATTCTTT |

FIG. 27 Cont.

| sample | Gene Breakpoint 5p | Gene Breakpoint 3p | Frame Type | SEQ ID NO: | Fused Sequence |
|---|---|---|---|---|---|
| 01A-01R-1850-01.4 | | | | | GCTCTCAGACTACGATATTCTCTCTTTATCTAATATCCA GCAGCATTCGGTAAGAAAAAGAGATCTACAGACTTCA ACACATGTAGAAACACTACTAACTTTTTCAGCTTTGAA AAGGCATTTTAAATTATACCTGACATCAAGTACTGAAC GTTTTTCACAAAATTTCAAGGTCGTGGTGGTGGATGGT AAAAACGAAAGCGAGTACACTGTAAAATGGCAGGACT TCTTCACTGGACACGTGGTTGGTGAGCCTGACTCTAGG GTTCTAGCCCACATAAGAGATGATGATGTTATAATCAG AATCAACACAGATGGGGCCGAATATAACATAGAG\|GA ATTGTTGGATAAATATTTAATAGCCAATGCAACTAATC CAGAGAGTAAGGTCTTCTATCTGAAAATGAAGGGTGA TTACTTCCGGTACCTTGCTGAAGTTGCGTGTGGTGATG ATCGAAAACAAACGATAGATAATTCCCAAGGAGCTTAC CAAGAGGCATTTGATATAAGCAAGAAAGAGATGCAAC CCACACACCCAATCCGCCTGGGGCTTGCTCTTAACTTTT CTGTATTTTACTATGAGATTCTTAATAACCCAGAGCTTG CCTGCACGCTGGCTAAAACGGCTTTTGATGAGGCCATT GCTGAACTTGATACACTGAATGAAGACTCATACAAAG ACAGCACCCTCATCATGCAGTTGCTTAGAGACAACCTA ACACTTTGGACATCAGACAGTGCAGGAGAAGAATGTG ATGCGGCAGAAGGGGCTGAAAAC |
| G17675. TCGA-19-2624-01A-01R-1850-01.2 | 55240817 | 65110599 | InFrame | 8297 | ATGGAGGAAGACGGCGTCCGCAAGTGTAAGAAGTGC GAAGGGCCTTGCCGCAAAGTGTGTAACGGAATAGGTA TTGGTGAATTTAAAGACTCACTCTCCATAAATGCTACG AATATTAAACACTTCAAAAACTGCACCTCCATCAGTGG CGATCTCCACATCCTGCCGGTGGCATTTAGGGGTGACT CCTTCACACATACTCCTCCTCTGGATCCACAGGAACTG GATATTCTGAAAACCGTAAAGGAAATCACAGGGTTTTT GCTGATTCAGGCTTGGCCTGAAAACAGGACGGACCTC CATGCCTTTGAGAACCTAGAAATCATACGCGGCAGGA CCAAGCAACAGGACCAGACAACTGTATCCAGTGTGCC CACTACATTGACGGCCCCCACTGCGTCAAGACCTGCCC GGCAGGAGTCATGGGAGAAAACAACACCCTGGTCTGG AAGTACGCAGACGCCGGCCATGTGTGCCACCTGTGCC ATCCAAACTGCACCTACGGATGCACTGGGCCAGGTCTT GAAGGCTGTCCAACGAATGGGCCTAAGATCCCGTCCA TCGCCACTGGGATGGTGGGGGCCCTCCTCTTGCTGCTG GTGGTGGCCCTGGGGATCGGCCTCTTCATGCGAAGGC GCCACATCGTTCGGAAGCGCACGCTGCGGAGGCTGCT GCAGGAGAGGGAG\|ATACAGGTTTGACCCCCGTCTCA TGTTCAGCAATCGCGGCAGTGTCAGGACTCGAAGATTT TCCAAACATCTTCTG |
| G17796. TCGA-41-5651-01A-01R-1850-01.4 | 58166911 | 58163739 | InFrame | 8298 | ATGGCGGACCCCGGCCCAGATCCCGAATCTGAGTCGG AATCGGTGTTCCCGCGGGAGGTCGGGCTCTTTGCAGA CTCTTACTCGGAGAAGAGCCAGTTCTGTTTCTGTGGGC ATGTGCTGACCATCACGCAGAACTTTGGGTCCCGCCTC GGGGTGGCGGCGCGCGTGTGGGACGCGGCCCTGAGC CTGTGCAATTATTTCGAGAGTCAAAATGTGGATTTCCG AGGCAAGAAGGTGATCGAACTGGGTGCGGGGACAGG CATCGTGGGGATCTTGGCAGCGCTGCAGG\|TGGAACT GTCACCGCTGTTCCCAGACACACTTATTCTGGGTCTGG AGATCCGGGTGAAGGTCTCAGACTATGTACAAGACCG GATTCGGGCCCTACGCGCAGCTCCTGCAGGTGGCTTCC AGAACATCGCCTGTCTCCGTAGCAATGCCATGAAGCAC CTTCCTAACTTCTTCTACAAGGGGCCAGCTGACAAAGAT |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GTTCTTCCTCTTCCCCGACCCACATTTCAAGCGGACAAA GCACAAGTGGCGAATCATCAGTCCCACCCTGCTAGCA GAATATGCCTACGTGCTAAGAGTTGGGGGGCTGGTGT ATACCATAACCGATGTGCTGGAGCTACACGACTGGAT GTGCACTCATTTCGAAGAGCACCCACTGTTTGAGCGTG TGCCTCTGGAGGACCTGAGTGAAGACCCCGTTGTGGG ACATCTAGGCACCTCAACTGAGGAGGGGAAGAAAGTT CTACGTAATGGAGGGAAGAATTTCCCAGCCATCTTCCG AAGAATACAAGATCCCGTCCTCCAGGCAGTGACCTCCC AAACCAGCCTGCCTGGTCAC |
| G17666. TCGA-06-5415-01A-01R-1849-01.2 | 134210220 | 219103387 | InFrame | 8299 | ATGGTCCCGGCTGCCGGTCGACGACCGCCCCGCGTCA TGCGGCTCCTCGGCTGGTGGCAAGTATTGCTGTGGGT GCTGGGACTTCCCGTCCGCGGCGTGGAGG\|GATACAA TGTCTCTTTGCTATATGACCTTGAAAATCTTCCGGCATC CAAGGATTCCATTGTGCATCAAGCTGGCATGTTGAAGC GAAATTGTTTTGCCTCTGTCTTTGAAAAATACTTCCAAT TCCAAGAAGAGGGCAAGGAAGGAGAGAACAGGGCAG TTATCCATTATAGGGATGATGAGACCATGTATGTTGAG TCTAAAAAGGACAGAGTCACAGTAGTCTTCAGCACAG TGTTTAAGGATGACGACGATGTGGTCATTGGAAAGGT GTTCATGCAGGAGTTCAAAGAAGGACGCAGAGCCAGC CACACAGCCCCACAGGTCCTCTTTAGCCACAGGGAACC TCCTCTGGAGCTGAAAGACACAGACGCCGCTGTGGGT GACAACATTGGCTACATTACCTTTGTGCTGTTCCCTCGT CACACCAATGCCAGTGCTCGAGACAACACCATCAACCT GATCCACACGTTCCGGGACTACCTGCACTACCACATCA AGTGCTCTAAGGCCTATATTCACACACGTATGCGGGCG AAAACGTCTGACTTCCTCAAGGTGCTGAACCGCGCACG CCCAGATGCCGAGAAAAAGAAATGAAAACAATCACG GGGAAGACGTTTTCATCCCGC |
| G17219. TCGA-06-0158-01A-01R-1849-01.2 | 42396776 | 41420897 | InFrame | 8300 | ATGGACGGTTTCGCCGGCAGTCTCG\|GTACACTTCATG TTGGTGATGAAATTCGAGAAATCAATGGCATCAGTGT GGCTAACCAAACAGTGGAACAACTGCAAAAAATGCTT AGGGAAATGCGGGGGAGTATTACCTTCAAGATTGTGC CAAGTTACCGCACTCAGTCTTCGTCCTGTGAGAGAGAT TCCCCTTCCACTTCCAGACAGTCCCCAGCTAATGGTCAT AGCAGCACTAACAATTCTGTTTCGGACTTGCCATCAAC TACCCAACCAAAAGGACGACAGATCTATGTAAGAGCA CAATTTGAATATGATCCAGCCAAGGATGACCTCATCCC CTGTAAAGAAGCTGGCATTCGATTCAGAGTTGGTGAC ATCATCCAGATTATTAGTAAGGATGATCATAATTGGTG GCAGGGTAAACTGGAAAACTCCAAAAATGGAACTGCA GGTCTCATTCCTTCTCCTGAACTTCAGGAATGGCGAGT AGCTTGCATTGCCATGGAGAAGACCAAACAGGAGCAG CAGGCCAGCTGTACTTGGTTTGGCAAGAAAAAGAAGC AGTACAAAGATAAATATTTGGCAAAGCACAATGCAGT GTTTGATCAATTAGATCTTGTCACATATGAAGAAGTAG TAAAACTGCCAGCATTCAAGAGGAAAACACTAGTCTTA TTAGGCGCACATGGTGTTGGGAGAAGACACATAAAAA ACACTCTCATCACAAAGCACCCAGACCGGTTTGCGTAC CCTATTCCACATACAACCAGACCTCCAAAGAAAGACGA AGAAAATGGAAAGAATTATTACTTTGTATCTCATGACC AAATGATGCAAGACATCTCTAATAACGAGTACTTGGA GTACGGCAGCCACGAGGATGCGATGTATGGGACAAA ACTGGAGACCATCCGGAAGATCCACGAGCAGGGGCTG |

| sample | Gene Breakpoint 5p | Gene Breakpoint 3p | Frame Type | SEQ ID NO: | Fused Sequence |
|---|---|---|---|---|---|
| | | | | | ATTGCAATACTGGACGTGGAGCCTCAGGCACTGAAGG TCCTGAGAACTGCAGAGTTTGCTCCTTTTGTTGTTTTCA TTGCTGCACCAACTATTACTCCAGGTTTAAATGAGGAT GAATCTCTTCAGCGTCTGCAGAAGGAGTCTGACATCTT ACAGAGAACATATGCACACTACTTCGATCTCACAATTA TCAACAATGAAATTGATGAGACAATCAGACATCTGGA GGAAGCTGTTGAGCTCGTGTGCACAGCCCCACAGTGG GTCCCTGTCTCCTGGGTCTAT |
| G17790. TCGA-06-5856-01A-01R-1849-01.4 | 122150870 | 581933703 | InFrame | 8301 | ATGTCCGGGCAGCTGGAGCGTTGCGAGCGCGAATGGC ACGAGCTGGAGGGAGAATTTCAAGAACTGCAG\|GACA TGAAGAATGCAACCCTCTCCCTGAATTCTAATGACAGT GAGCCAAAATATTACCCTATAGCAGTTCTGTTGAAAAA CCAGAATCAGGAGCTGCCTGAGGATGTAAACCCTGCC AAAAAGGAGAATTACCTCTCTGAACAGGACTTTGTGTC TGTGTTTGGCATCACAAGAGGGCAATTTGCAGCTCTGC CTGGCTGGAAACAGCTCCAAATGAAGAAAGAAAAGG GGCTTTTC |
| NYU_B | 19746155 | 19433460 | InFrame | 8302 | ATGGGTGGCCCACAGGACAAGGATGAACGCACAATCG CCCTTGTGAGGCCGTGGCCTTGGGGGCACCAGGCCCT GGATCCAGCATATGGCCTGGACACGATGCACCCAAGC AGGCGCAGCCTCCCCTTCCCTCTGAACTGTCAGCTTGC AAGGGTTGGAACTGCTGATTATGGAAGTCCCTCGGAT CAGAGTGATCAGCAGCTGGACTGTGCCTTGGACCTAA TGAGGCGCCTGCCTCCCCAGCAAATCGAGAAAAACCT CAGCGACCTGATCGACCTG\|GATGTCCCCGTTGAGGCC CTCACCACGGTGAAGCCATACTGCAATGAGATCCATGC CCAGGCTCAACTGTGGCTCAAGAGAGACCCCAAGGCA TCCTATGATGCCTGGAAGAAGTGTCTTCCTATCAGAGG GATAGATGGCAATGGGAAAGCCCCCAGCAAATCAGAG CTCCGCCATCTCTATTTGACTGAGAAGTATGTGTGGAG GTGGAAACAGTTCCTGAGTCGTCGGGGGAAGAGGAC CTCCCCCTTGGATCTCAAACTGGGGCATAACAACTGGC TGCGACAAGTGCTTTTCACTCCAGCAACGCAGGCCGCA CGGCAGGCAGCCTGTACCATTGTGGAAGCTCTAGCCA CCATTCCCAGCCGCAAGCAGCAGGTCCTGGACCTGCTT ACCAGTTACCTGGATGAGCTGAGCATAGCTGGGGAGT GTGCAGCTGAGTACCTGGCTCTCTACCAGAAGCTCATC ACTTCTGCGCACTGGAAAGTCTACTTGGCAGCTCGGG GAGTCCTACCCTATGTGGGCAACCTCATCACCAAGGAA ATAGCTCGTCTGCTGGCCCTGGAGGAGGCTACCCTGA GTACCGATCTGCAGCAGGGTTATGCCCTTAAAAGTCTC ACAGGCCTTCTCTCCTCCTTTGTTGAGGTGGAATCCATC AAAAGACATTTTAAAAGTCGCTTGGTGGGTACTGTGCT GAATGGATACCTGTGCTTGCGGAAGCTGGTGGTGCAG AGGACCAAGCTGATCGATGAGACGCAGGACATGCTGC TGGAGATGCTGGAGGACATGACCACAGGTACAGAATC AGAAACCAAGGCCTTCATGGCTGTGTGCATTGAGACA GCCAAGCGCTACAATCTGGATGACTACCGGACCCCGG TGTTCATCTTCGAGAGGCTCTGCAGCATCATTTATCCTG AGGAGAATGAAGTCACTGAGTTCTTTGTGACCCTGGA GAAGGATCCCCAACAAGAAGACTTCTTACAGGGCAGG ATGCCTGGGAACCCGTATAGCAGCAATGAGCCAGGCA TCGGGCCGCTGATGAGGGATATAAAGAACAAGATTTG CCAGGACTGTGACTTAGTGGCCCTCCTGGAAGATGAC AGTGGCATGGAGCTTCTAGTGAACAATAAAATCATTA |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GTTTGGACCTTCCTGTGGCTGAAGTTTACAAGAAAGTC
TGGTGTACCACGAATGAGGGAGAGCCCATGAGGATTG
TTTATCGTATGCGGGGGCTGCTGGGCGATGCCACAGA
GGAGTTCATTGAGTCCCTGGACTCTACTACAGatgaaga
agaagatgaagaagaagTGTATAAAATGGCTGGTGTGATG
GCCCAGTGTGGGGGCCTGGAATGCATGCTTAACAGAC
TCGCAGGGATCAGAGATTTCAAGCAGGGACGCCACCT
TCTAACAGTGCTACTGAAATTGTTCAGTTACTGCGTGA
AGGTGAAAGTCAACCGGCAGCAACTGGTCAAACTGGA
AATGAACACCTTGAACGTCATGCTGGGGACCCTAAACC
TGGCCCTTGTAGCTGAACAAGAAAGCAAGGACAGTGG
GGGTGCAGCTGTGGCTGAGCAGGTGCTTAGCATCATG
GAGATCATTCTAGATGAGTCCAATGCTGAGCCCCTGAG
TGAGGACAAGGGCAACCTCCTCCTGACAGGTGACAAG
GATCAACTGGTGATGCTCTTGGACCAGATCAACAGCAC
CTTTGTTCGCTCCAACCCCAGTGTGCTCCAGGGCCTGC
TTCGCATCATCCCGTACCTTTCCTTTGGAGAGGTGGAG
AAAAATGCAGATCTTGGTGGAGCGATTCAAACCATACT
GCAACTTTGATAAATATGATGAAGATCACAGTGGTGAT
GATAAAGTCTTCCTGGACTGCTTCTGTAAAATAGCTGC
TGGCATCAAGAACAACAGCAATGGGCACCAGCTGAAG
GATCTGATTCTCCAGAAGGGGATCACCCAGAATGCACT
TGACTACATGAAAAAGCACATCCCTAGCGCCAAGAATT
TGGATGCCGACATCTGGAAAAAGTTTTTGTCTCGCCCA
GCCTTGCCATTTATCCTAAGGCTGCTTCGGGGCCTGGC
CATCCAGCACCCTGGCACCCAGGTTCTGATTGGAACTG
ATTCCATCCCGAACCTGCATAAGCTGGAGCAGGTGTCC
AGTGATGAGGGCATTGGGACCTTGGCAGAGAACCTGC
TGGAAGCCCTGCGGGAACACCCTGACGTAAACAAGAA
GATTGACGCAGCCCGCAGGGAGACCCGGGCAGAGAA
GAAGCGCATGGCCATGGCAATGAGGCAGAAGGCCCT
GGGCACCCTGGGCATGACGACAAATGAAAAGGGCCA
GGTCGTGACCAAGACAGCACTCCTGAAGCAGATGGAA
GAGCTGATCGAGGAGCCTGGCCTCACGTGCTGCATCT
GCAGGGAGGGATACAAGTTCCAGCCCACAAAGGTCCT
GGGCATTTATACCTTCACGAAGCGGGTAGCCTTGGAG
GAGATGGAGAATAAGCCCCGGAAACAGCAGGGCTAC
AGCACCGTGTCCCACTTCAACATTGTGCACTACGACTG
CCATCTGGCTGCCGTCAGGTTGGCTCGAGGCCGGGAA
GAGTGGGAGAGTGCCGCCCTGCAGAATGCCAACACCA
AGTGCAACGGGCTCCTTCCGGTCTGGGGACCTCATGTC
CCTGAATCAGCTTTTGCCACTTGCTTGGCAAGACACAA
CACTTACCTCCAGGAATGTACAGGCCAGCGGGAGCCC
ACGTATCAGCTCAACATCCATGACATCAAACTGCTCTTC
CTGCGCTTCGCCATGGAGCAGTCGTTCAGCGCAGACA
CTGGCGGGGCGGCCGGGAGAGCAACATCCACCTGA
TCCCGTACATCATTCACACTGTGCTTTACGTCCTGAACA
CAACCCGAGCAACTTCCCGAGAAGAGAAGAACCTCCA
AGGCTTTCTGGAACAGCCCAAGGAGAAGTGGGTGGA
GAGTGCCTTTGAAGTGGACGGGCCCTACTATTTCACAG
TCTTGGCCCTTCACATCCTGCCCCCTGAGCAGTGGAGA
GCCACACGTGTGGAAATCTTGCGGAGGCTGTTGGTGA
CCTCGCAGGCTCGGGCAGTGGCTCCAGGTGGAGCCAC
CAGGCTGACAGATAAGGCAGTGAAGGACTATTCCGCT
TACCGTTCTTCCCTTCTCTTTTGGGCCCTCGTCGATCTC |

FIG. 27 Cont.

| sample | Gene Break-point 5p | Gene Break-point 3p | Frame Type | SEQ ID NO: | Fused Sequence |
|---|---|---|---|---|---|
| | | | | | ATTTACAACATGTTTAAGAAACAAACAACCCCAACTGT GGGAGGGATTGACACTGGCAGCCTGGAGCCTTGTGTC TGTGAGAAGGTGCCTACCAGTAACACAGAGGGAGGCT GGTCCTGCTCTCTCGCTGAGTACATCCGCCACAACGAC ATGCCCATCTACGAAGCTGCCGACAAAGCCCTGAAAA CCTTCCAGGAGGAGTTCATGCCAGTGGAGACCTTCTCA GAGTTCCTCGATGTGGCCGGTCTTTTATCAGAAATCAC CGATCCAGAGAGCTTCCTGAAGGACCTGTTGAACTCA GTCCCC |
| G17657. TCGA-19-1787-01B-01R-1850-01.2 | 100438902 | 100348442 | InFrame | 8303 | ATGAACGGACAGTTGGATCTAAGTGGGAAGCTAATCA TCAAAGCTCAACTTGGGGAGGATATTCGGCGAATTCCT ATTCATAATGAAGATATTACTTATGATGAATTAGTGCT AATGATGCAACGAGTTTTCAGAGGAAAACTTCTGAGT AATGATGAAGTAACAATAAAGTATAAAGATGAAGATG GAGATCTTATAACAATTTTTGATAGTTCTGACCTTTCCT TTGCAATTCAGTGCAGTAGGATACTGAAACTGACATTA TTTG|GAAAATCTACTTCCTCATCAAGCACCCCTACAGA GTTCTGCAGGAATGGTGGAACCTGGGAAAATGGCAGA TGTATTTGTACAGAAGAGTGGAAAGGACTGAGATGTA CAATTGCTAATTTTTGTGAAAATAGTACCTATATGGGTT TTACTTTTGCCAGAATCCCAGTGGGCAGATATGGACCA TCCTTGCAAACATGTGGCAAGGATACTCCAAATGCGG GCAATCCAATGGCAGTCCGGTTGTGCAGTCTCTCTCTA TATGGAGAGATAGAATTACAAAAAGTGACAATAGGAA ATTGCAATGAAAATCTGGAAACCCTGGAAAAGCAGGT AAAGGATGTCACAGCACCACTTAATAACATTTCTTCTG AAGTCCAGATTTTAACATCTGATGCCAATAAATTAACT GCTGAGAACATCACTAGTGCTACGCGAGTGGTTGGAC AGATATTCAACACTTCCAGAAATGCTTCACCTGAGGCA AAGAAAGTTGCCATAGTAACAGTGAGTCAACTCCTAG ATGCCAGTGAAGATGCTTTTCAAAGAGTTGCTGCTACT GCTAATGATGATGCCCTTACAACGCTTATTGAGCAAAT GGAGACTTATTCCTTGTCTTTGGGTAATCAATCAGTGG TGGAACCTAACATAGCAATACAGTCAGCAAATTTCTCT TCAGAAAATGCGGTGGGGCCTTCAAATGTTCGCTTCTC TGTGCAGAAAGGAGCTAGCAGTTCTCTAGTTTCTAGTT CAACATTTATACATACAAATGTGGATGGCCTTAACCCA GATGCACAGACTGAGCTTCAGGTCTTGCTTAATATGAC GAAAAATTACACCAAGACATGCGGCTTTGTAGTTTATC AAAATGACAAGCTTTTCCAATCAAAAACTTTTACAGCT AAATCGGATTTTAGTCAAAAAATTATCTCAAGCAAAAC TGATGAAAATGAGCAAGATCAGAGTGCTTCTGTTGAC ATGGTCTTTAGTCCAAAGTACAACCAAAAAGAATTTCA ACTCTATTCCTATGCCTGTGTCTATTGGAATTTGTCAGC GAAGGACTGGGACACATATGGCTGTCAAAAAGACAAG GGCACTGATGGATTCCTGCGCTGCCGCTGCAACCATAC TACTAATTTTGCTGTATTAATGACTTTCAAAAAGGATTA TCAATATCCCAAATCACTTGACATATTATCCAACGTTGG ATGTGCACTGTCTGTTACTGGTCTGGCTCTCACAGTTAT ATTTCAGATTGTCACCAGGAAAGTCAGAAAAACCTCAG TAACCTGGGTTTTGGTCAATCTGTGCATATCAATGTTG ATTTTCAACCTCCTCTTTGTGTTTGGAATTGAAAACTCC AATAAGAACTTGCAGACAAGTGATGGTGACATCAATA ATATTGACTTTGACAATAATGACATACCCAGGACAGAC ACCATTAACATCCCGAATCCCATGTGCACTGCGATTGC |

| sample | Gene Breakpoint 5p | Gene Breakpoint 3p | Frame Type | SEQ ID NO: | Fused Sequence |
|---|---|---|---|---|---|
| | | | | | CGCCTTACTGCACTATTTTCTGTTAGTGACATTTACCTG GAACGCACTCAGCGCTGCACAGCTCTATTACCTTCTAA TAAGGACCATGAAGCCTCTTCCTCGGCATTTCATTCTTT TCATCTCATTAATTGGATGGGGAGTCCCAGCTATAGTA GTGGCTATAACAGTGGGAGTTATTTATTCTCAGAATGG AAATAATCCACAGTGGGAATTAGACTACCGGCAAGAG AAAATCTGCTGGCTGGCAATTCCAGAACCCAATGGTGT TATAAAAAGTCCGCTGTTGTGGTCATTCATCGTACCTG TAACCATTATCCTCATCAGCAATGTTGTTATGTTTATTA CAATCTCGATCAAAGTGCTGTGGAAGAATAACCAGAA CCTGACAAGCACAAAAAAAGTTTCATCCATGAAGAAG ATTGTTAGCACATTATCTGTTGCAGTTGTTTTTGGAATT ACCTGGATTCTAGCATACCTGATGCTAGTTAATGATGA TAGCATCAGGATCGTCTTCAGCTACATATTCTGCCTTTT CAACACTACACAGGGATTGCAAATTTTTATCCTGTACA CTGTTAGAACAAAAGTCTTCCAGAGTGAAGCTTCCAAA GTGTTGATGTTGCTATCGTCTATTGGGAGAAGGAAGTC ATTGCCTTCAGTGACGCGGCCGAGGCTGCGTGTAAAG ATGTATAATTTCCTCAGGTCATTGCCAACCTTACATGAA CGCTTTAGGCTACTGGAAACCTCTCCGAGTACTGAGGA AATCACACTCTCTGAAAGTGACAATGCAAAGGAAAGC ATC |
| G17643. TCGA-12- 5295- 01A-01R- 1849- 01.2 | 43976965 | 52740660 | InFrame | 8304 | ATGGCCCCGCCCGTCTGTTCGCGCTGCTGCTGTTCTTC GTAGGCGGAGTCGCCGAGTCG\|GATTACAAGGGCCAG AAGCTAGCTGAACAGATGTTTCAGGGAATTATTCTTTT TTCTGCAATAGTTGGATTTATCTACGGGTACGTGGCTG AACAGTTCGGGTGGACTGTCTATATAGTTATGGCCGG ATTTGCTTTTTCATGTTTGCTGACACTTCCTCCATGGCC CATCTATCGCCGGCATCCTCTCAAGTGGTTACCTGTTCA AGAATCAAGCACAGACGACAAGAAACCAGGGGAAAG AAAAATTAAGAGGCATGCTAAAAATAAT |
| NYU_G | 100191807 | 102260661 | InFrame | 8305 | ATGCGCTCCATTAGGAAGAGGTGGACGATCTGCACAA TAAGTCTGCTCCTGATCTTTTATAAGACAAAAGAAATA GCAAGAACTGAGGAGCACCAGGAGACGCAACTCATCG GAGATGGTGAATTGTCTTTGAGTCGGTCACTTGTCAAT AGCTCTGATAAAATCATTCGAAAGGCTGGCTCTTCAAT CTTCCAGCACAATGTAGAAGGTTGGAAAATCAATTCCT CTTTGGTCCTAGAGATAAGGAAGAACATACTTCGTTTC TTAGATGCAGAACGAGATGTGTCAGTGGTCAAGAGCA GTTTTAAGCCTGGTGATGTCATACACTATGTGCTTGAC AGGCGCCGGACACTAAACATTTCTCATGATCTACATAG CCTCCTACCTGAAGTTTCACCAATGAAGAATCGCAGGT TAAGACCTGTGCAGTTGTTGGAAATTCTGGCATTCTG TTAGACAGTGAATGTGGAAAGGAGATTGACAGTCACA ATTTTGTAATAAGGTGTAATCTAGCTCCTGTGGTGGAG TTTGCTGCAGATGTGGGAACTAAATCAGATTTTATTAC CATGAATCCATCAGTTGTACAAAGAGCATTTGGAGGCT TTCGAAATGAGAGTGACAGAGAAAATTTGTGCATAG ACTTTCCATGCTGAATGACAGTGTCCTTTGGATTCCTGC TTTCATGGTCAAAGGAGGAGAGAAGCACGTGGAGTG GGTTAATGCATTAATCCTTAAGAATAAACTGAAAGTGC GAACTGCCTATCCGTCATTGAGACTTATTCATGCTGTCA GAGG\|GTTTTGTGATGAAGGAACCTGTACAGATAAAG CCAATATTCTGTATGCCTGGGCGAGAAATGCTCCCCCT ACCCGGCTCCCCAAAGGTGTTGGATTCAGAGTTGGAG |

FIG. 27 Cont.

| sample | Gene Break-point 5p | Gene Break-point 3p | Frame Type | SEQ ID NO: | Fused Sequence |
|---|---|---|---|---|---|
| | | | | | GAGAGACTGGAAGTAAATACTTTGTACTACAGGTACA |
| | | | | | CTATGGGGATATTAGTGCTTTTAGAGATAATAACAAGG |
| | | | | | ACTGTTCTGGTGTGTCCTTACACCTCACACGTCTGCCAC |
| | | | | | AGCCTTTAATTGCTGGCATGTACCTTATGATGTCTGTTG |
| | | | | | ACACTGTTATCCCAGCAGGAGAAAAAGTGGTGAATTC |
| | | | | | TGACATTTCATGCCATTATAAAAATTATCCAATGCATGT |
| | | | | | CTTTGCCTATAGAGTTCACACTCACCATTTAGGTAAGG |
| | | | | | TAGTAAGTGGATACAGAGTAAGAAATGGACAGTGGAC |
| | | | | | ACTGATTGGACGGCAGAGCCCTCAGCTGCCACAGGCT |
| | | | | | TTCTACCCTGTGGGGCATCCAGTTGATGTAAGTTTTGG |
| | | | | | TGACCTACTGGCTGCAAGATGTGTATTCACTGGTGAAG |
| | | | | | GAAGGACAGAAGCCACACACATTGGTGGCACGTCTAG |
| | | | | | TGATGAAATGTGCAACTTATACATTATGTATTACATGG |
| | | | | | AAGCCAAGCATGCAGTTTCTTTCATGACCTGTACCCAG |
| | | | | | AATGTAGCTCCAGATATGTTCAGAACCATACCACCAGA |
| | | | | | GGCCAACATTCCAATTCCCGTGAAGTCTGATATGGTTA |
| | | | | | TGATGCATGAACATCATAAAGAAACAGAATATAAAGA |
| | | | | | TAAGATTCCTTTACTACAGCAGCCAAAAACGAGAAGAA |
| | | | | | GAAGAAGTGTTAGACCAGGGTGATTTCTATTCACTACT |
| | | | | | TTCCAAGCTGCTAGGAGAAAGGGAAGATGTTGTTCAT |
| | | | | | GTGCACAAATATAATCCTACAGAAAAGGCAGAATCAG |
| | | | | | AGTCAGACCTGGTAGCTGAGATTGCAAATGTAGTCCA |
| | | | | | AAAAAAGGATCTTGGTCGATCTGATGCCAGAGAGGGT |
| | | | | | GCAGAACATGAGAGGGGTAATGCTATTCTTGTCAGAG |
| | | | | | ACAGAATTCACAAATTCCACAGACTAGTATCTACCTTG |
| | | | | | AGGCCACCAGAGAGCAGAGTTTTCTCATTACAGCAGC |
| | | | | | CCCCACCTGGTGAAGGCACCTGGGAACCAGAACACAC |
| | | | | | AGGAGATTTCCACATGGAAGAGGCACTGGATTGGCCT |
| | | | | | GGAGTATACTTGTTACCAGGCCAGGTTTCTGGGGTGG |
| | | | | | CTCTAGACCCTAAGAATAACCTGGTGATTTTCCACAGA |
| | | | | | GGTGACCATGTCTGGGATGGAAACTCGTTTGACAGCA |
| | | | | | AGTTTGTTTACCAGCAAATAGGACTCGGACCAATTGAA |
| | | | | | GAAGACACTATTCTTGTCATAGATCCAAATAATGCTGC |
| | | | | | AGTACTCCAGTCCAGTGGAAAAAATCTGTTTTACTTGC |
| | | | | | CACATGGCTTGAGTATAGATAAAGATGGGAATTATTG |
| | | | | | GGTCACAGACGTGGCTCTCCATCAGGTGTTCAAACTGG |
| | | | | | ATCCAAACAATAAAGAAGGCCCTGTATTAATCCTGGGA |
| | | | | | AGGAGCATGCAACCAGGCAGTGACCAGAATCACTTCT |
| | | | | | GTCAACCCACTGATGTGGCTGTGGATCCAGGCACTGG |
| | | | | | AGCCATTTATGTATCAGATGGTTACTGCAACAGCAGGA |
| | | | | | TTGTGCAGTTTTCACCAAGTGGAAAGTTCATCACACAG |
| | | | | | TGGGGAGAAGAGTCTTCAGGGAGCAGTCCTCTGCCAG |
| | | | | | GCCAGTTCACTGTTCCTCACAGCTTGGCTCTTGTGCCTC |
| | | | | | TTTTGGGCCAATTATGTGTGGCAGACCGGGAAAATGG |
| | | | | | TCGGATCCAGTGTTTTAAAACTGACACCAAAGAATTTG |
| | | | | | TGAGAGAGATTAAGCATTCATCATTTGGAAGAAATGT |
| | | | | | ATTTGCAATTTCATATATACCAGGCTTGCTCTTTGCAGT |
| | | | | | GAATGGGAAGCCTCATTTTGGGGACCAAGAACCTGTA |
| | | | | | CAAGGATTTGTGATGAACTTTTCCAATGGGGAAATTAT |
| | | | | | AGACATCTTCAAGCCAGTGCGCAAGCACTTTGATATGC |
| | | | | | CTCATGATATTGTTGCATCTGAAGATGGGACTGTGTAC |
| | | | | | ATTGGAGATGCTCATACCAACACCGTGTGGAAGTTCAC |
| | | | | | CTTGACTGAGAAATTGGAACATCGATCAGTTAAAAAG |
| | | | | | GCTGGCATTGAGGTCCAGGAAATCAAAGAAGCCGAG |
| | | | | | GCAGTTGTTGAAACCAAAATGGAGAACAAACCCACCT |

FIG. 27 Cont.

| sample | Gene Break-point 5p | Gene Break-point 3p | Frame Type | SEQ ID NO: | Fused Sequence |
|---|---|---|---|---|---|
| | | | | | CCTCAGAATTGCAGAAGATGCAAGAGAAACAGAAACT GATCAAAGAGCCAGGCTCGGGAGTGCCTGTTGTTCTC ATTACAACCCTTCTGGTTATTCCGGTGGTTGTCCTGCTG GCCATTGCCATATTTATTCGGTGGAAAAAATCAAGGGC CTTTGGAGCAGATTCTGAACACAAACTCGAGACGAGTT CAGGAAGAGTACTGGGAAGATTTAGAGGAAAGGGAA GTGGAGGCTTAAACCTTGGTAATTTCTTTGCAAGCCGT AAGGGCTACAGTCGAAAAGGGTTTGACCGGCTTAGCA CTGAGGGCAGTGACCAAGAGAAAGAGGATGATGGAA GTGAATCAGAAGAGGAGTATTCAGCACCTCTGCCTGC GCTCGCACCTTCCTCCTCC |
| G17494. TCGA-14-2554-01A-01R-1850-01.2 | 48965246 | 48265844 | InFrame | 8306 | ATGTCAGTGGACATGAATAGCCAGGGGTCTGACAGCA ATGAAGAGGACTATGACCCAAATTGTgaggaagaggaaga agaagaagaagaCGACCCTGGGGACATAGAGGACTATTA CGTGGGAGTAGCCAGCGATGTGGAGCAGCAGGGGGC TGATGCCTTTGATCCCGAGGAGTACCAGTTCACTTGCT TGACCTACAAGGAATCTGAGGGTGCCCTCAATGAGCA CATGACCAGCTTAGCTTCTGTCCTAAAG\|GATGGGGAC CCAGACACGCCAAAGCCTGTGAGCTTCACAGTGAAGG AGACAGTGTGCCCCAGGACGACACAGCAGTCACCAGA GGATTGTGACTTCAAGAAGGACGGGCTGGTGAAGCG GTGTATGGGGACAGTGACCCTCAACCAGGCCAGGGGC TCCTTTGACATCAGTTGTGATAAGGATAACAAGAGATT TGCCCTGCTGGGTGATTTCTTCCGGAAATCTAAAGAGA AGATTGGCAAAGAGTTTAAAAGAATTGTCCAGAGAAT CAAGGATTTTTTGCGGAATCTTGTACCCAGGACAGAGT CC |
| G17196. TCGA-06-0178-01A-01R-1849-01.2 | 58123422 | 94827533 | InFrame | 8307 | ATGAGCCGGGGCGCGGGCGCGCTTCAGCGCCGGACA ACGACCTACCTCATCTCGCTGACCCTGGTTAAGCTCGA gtcggtgcctccgccgccgccttctccgtctgcggccgcggccggcgc gccggtgccAGAGGCTCCGAGACTGGGGATCCTGGCAGC CCCCGAGGCGCGGAGGAGCCGGGCAAGAAGCGGCAC GAACGTCTCTTCCACCGGCAGGATGCGCTGTGGATCA GCACGAGCAGCGCGGGCACCGGGGGCGCGGAGCCCC CAGCCCTGTCCCCGGCTCCGGCCAGTCCGGCCCGCCCA GTCTCCCCCGCTCCCGGCCGCCGCCTCTCCCTCTGGGC CGTCCCTCCGGGACCCCCGCTCTCCGGGGGACTGAGC CCCGACCCCAAGCCTGGGGGCGCCCCCACCTCCTCCCG GCGCCCCTGCTCAGCAGCCCGAGCTGGGGCGGCCCG GAGCCCGAAGGCCGGGCGGGCGGCGGCATCCCTGGC TCATCCTCTCCGCACCCTGGCACCGGCAGCCGGAGGCT CAAGGTGGCGCCTCCTCCGCCGGCTCCCAAGCCTTGCA AGACCGTGACCACGAGTGGAGCCAAAGCCGGCGGGG GCAAGGGCGCGGGTAGCCGCCTGTCATGGCCCGAAA GCGAGGGCAAGCCCAGGGTCAAGGGGTCAAAGAGCA GCGCCGGGACTGGAGCTTCGGTCTCTgccgccgccaccgcc gccgccgccGGGGAGGGGGCTCTACAGCTTCGACCTCT GGTGGGGTCGGGGCTGGGGCTGGAGCCCGAGGGAA GTTGTCCCCTCGGAAAGGCAAGAGTAAGACCTTGGAC AACAGTGACTTGCATCCGGGACCGCCTGCCGGCTCTCC TCCTCCGCTAACCCTCCCACCAACTCCGAGTCCAGCCAC TGCTGTCACCGCTGCTTCCGCGCAGCCCCCCGGGCCTG CACCTCCAATCACTCTGGAGCCTCCAGCTCCGGGCTG AAACGGGGCCGGGAGGGGGGCCGAGCATCCACTCGT GACCGCAAGATGCTCAAGTTTATCAGCGGCATCTTCAC |

FIG. 27 Cont.

| sample | Gene Break-point 5p | Gene Break-point 3p | Frame Type | SEQ ID NO: | Fused Sequence |
|---|---|---|---|---|---|
| | | | | | CAAGAGCACAGGAGGGCCTCCTGGCTCCGGGCCCCTT CCCGGACCCCCCAGCCTGTCTTCTGGCAGCGGGTCCAG GGAGCTGCTGGGCGCCGAGCTCCGCGCTTCCCCTAAG GCTGTGATCAATAGCCAGGAATGGACTTTGAGCCGCT CCATTCCTGAACTGCGCCTGGGTGTGCTGGGCGATGCC AGGAGTGGGAAGTCATCGCTCATCCACCGATTCCTGAC TGGCTCATACCAGGTGCTGGAGAAGACAGAGAGTGA GCAGTACAAGAAAGAAATGTTGGTGGATGGACAGAC ACATCTGGTGCTAATCCGAGAGGAAGCTGGGGCACCT GATGCCAAGTTCTCAGGCTGGGCAGATGCTGTGATCTT CGTCTTCAGCCTGGAGGATGAGAACAGTTTCCAGGCT GTGAGCCGTCTCCATGGGCAGCTGAGTTCCCTTCGCGG GGAGGGACGAGGAGGCCTGGCCTTGGCACTGGTGGG GACACAAGACAGGATCAGTGCTTCCTCCCCTCGGGTG GTGGGAGATGCTCGTGCCAGAGCTCTGTGCGCGGACA TGAAACGCTGCAGCTACTATGAGACTTGTGCAACCTAT GGGCTCAATGTGGATCGGGTCTTCCAGGAGGTGGCCC AGAAGGTGGTGACCTTGCGCAAGCAGCAACAGCTTCT GGCTGCCTGCAAGTCCCTGCCCAGCTCCCAAGCCACT CAGCTGCATCCACTCCGGTAGCTGGCCAGGCTAGTAAC GGGGGCCACACTAGCGACTACTCTTCTTCCCTCCCGTC CTCACCGAATGTTGGTCACCGGGAGCTCCGAGCCGAG GCAGCTGCAGTGGCTGGATTGAGCACCCCAGGGTCCC TGCACCGGGCAGCCAAGCGCAGGACCAGCCTTTTTGC GAATCGTCGGGGTAGTGACTCCGAGAAACGAAGCTTG GATAGTCGGGGAGAGACAACAGGGAGTGGGCGAGCC ATCCCCATCAAACAGAGCTTCCTACTAAAACGAAGTGG CAATTCCTTGAACAAAGAATGGAAGAAGAAATATGTA ACCCTGTCCAGTAATGGCTTTCTACTCTACCACCCCAGT ATTAACGATTACATCCACAGTACCCACGGCAAGGAGAT GGACTTGCTGCGAACAACAGTCAAAGTCCCGGGCAAG CGGCCCCCGAGGGCCATCTCTGCCTTTGGCCCCTCAGC CAGCATTAACGGGCTCGTCAAGGACATGAGCACTGTC CAGATGGGTGAAGGCCTGGAAGCCACTACTCCCATGC CAAGCCCTAGCCCCAGCCCCAGTTCCTGCAGCCACCA CCAGATCAGACATCCAAACACCTGCTGAAGCCAGACC GGAATTTGGCCCGAGCCCTCAGCACGGACTGTACCCC ATCTGGAGACCTGAGCCCCCTGAGTCGGGAACCCCCTC CTTCTCCCATGGTGAAGAAGCAGAGGAGGAAAAAATT GACAACACCATCCAAGACTGAAGGCTCGGCTGGGCAG GCTGAAG\|ATGAAGGTTATTCTTTCAGCAGTGTCCTGT ATTATGGAAATGAAGCTACTCTTCTTATTTTTGATCTGC TGTTCTTCTGTGTTGTGGATTTGGCTTGCCAAAATTTTA TTTTAGCATCCTTCCTTACATATCTACAACAAGAGATTT TTAGATATATCCGTAATACAGTAGGACAAAAGAATTTG GCATCCAAAACATTGGTGGATCAAAGATTTTTGATT |
| G17782. TCGA-26-5136-01B-01R-1850-01.4 | 95392394 | 95448862 | InFrame | 8308 | ATGACCCACTTCAACAAGGGCCCTTCCTATGGGCTCTC GGCCGAAGTCAAGAACAAG\|GTGTTGTGTAACGGACC AGGAACATGTGTTCCTATCTGTGTATCTGCCCTTCTCCT TGGGATACTAGGAATAAAGAAAGTGATCATTGTCTAC GTTGAAAGCATCTGCCGTGTAGAAACGTTATCCATGTC CGGAAAGATTCTGTTTCATCTCTCAGATTACTTCATTGT TCAGTGGCCGGCTCTGAAAGAAAAGTATCCCAAATCG GTGTACCTTGGGCGAATTGTT |

FIG. 27 Cont.

| sample | Gene Break- point 5p | Gene Break- point 3p | Frame Type | SEQ ID NO: | Fused Sequence |
|---|---|---|---|---|---|
| GBM-CUMC32 96_L1 | 55639964 | 68645358 | InFrame | 8309 | ATGAGGCGCCAGCCTGCGAAGGTGGCGGCGCTGCTGC TCGGGCTGCTCTTGGAG\|CATATTGAAGGTGATGACCT GCATATCCAGAGGAATGTGCAAAAGCTGAAGGACACA GTGAAAAAGCTTGGAGAGAGTGGAGAGATCAAAGCA ATTGGAGAACTGGATTTGCTGTTTATGTCTCTGAGAAA TGCCTGCATT |
| G17199. TCGA-06-0744-01A-01R-1849-01.2 | 55087058 | 102784508 | InFrame | 8310 | ATGCGACCCTCCGGGACGGCCGGGGCAGCGCTCCTGG CGCTGCTGGCTGCGCTCTGCCCGGCGAGTCGGGCTCT GGAGGAAAAGAAAG\|CTGACATAGCCCAGAGATACA GGATAAGCAAATACCCAACCCTCAAATTGTTTCGTAAT GGGATGATGATGAAGAGAGAATACAGGGGTCAGCGA TCAGTGAAAGCATTGGCAGATTACATCAGGCAACAAA AAAGTGACCCCATTCAAGAAATTCGGGACTTAGCAGA AATCACCACTCTTGATCGCAGCAAAAGAAATATCATTG GATATTTTGAGCAAAAGGACTCGGACAACTATAGAGT TTTTGAACGAGTAGCGAATATTTTGCATGATGACTGTG CCTTTCTTTCTGCATTTGGGGATGTTTCAAAACCGGAA AGATATAGTGGCGACAACATAATCTACAAACCACCAG GGCATTCTGCTCCGGATATGGTGTACTTGGGAGCTATG ACAAATTTTGATGTGACTTACAATTGGATTCAAGATAA ATGTGTTCCTCTTGTCCGAGAAATAACATTTGAAAATG GAGAGGAATTGACAGAAGAAGGACTGCCTTTTCTCAT ACTCTTTCACATGAAAGAAGATACAGAAAGTTTAGAAA TATTCCAGAATGAAGTAGCTCGGCAATTAATAAGTGAA AAAGGTACAATAAAACTTTTTACATGCCGATTGTGACAA ATTTAGACATCCTCTTCTGCACATACAGAAAACTCCAG CAGATTGTCCTGTAATCGCTATTGACAGCTTTAGGCAT ATGTATGTGTTTGGAGACTTCAAAGATGTATTAATTCC TGGAAAACTCAAGCAATTCGTATTTGACTTACATTCTG GAAAACTGCACAGAGAATTCCATCATGGACCTGACCC AACTGATACAGCCCCAGGAGAGCAAGCCCAAGATGTA GCAAGCAGTCCACCTGAGAGCTCCTTCCAGAAACTAGC ACCCAGTGAATATAGGTATACTCTATTGAGGGATCGA GATGAGCTT |
| G17792. TCGA-28-5204-01A-01R-1850-01.4 | 6996029 | 8288288 | InFrame | 8311 | ATGACTGATGGAAAACTCTCCACCTCTACAAATGGCGT AGCCTTCATGGGTATTCTGGATGGTCGACCAGGAAAC CCCCTTCAGAACCTGCAACACGTCAATCTCAAGGCGCC CCGACTCCTCTCCGCGCCTGAGTACGGGCCCAAGCTGA AACTCAGGGCTTTAGAAGACCGGCACAGCCTCCAGTC CGTGGACTCGGGGATTCCTACCCTGGAGATCGGGAAC CCGGAGCCTGTACCCTGCAGCGCGGTCCACGTGAGGA GGAAGCAGTCCGACTCCGACCTCATCCCCGAGCGGGC CTTCCAGAGCGCCTGCGCGCTGCCATCCTGTGCGCCAC CAGCTCCTAGCAGCACCGAGCGGGAACAGAGCGTGCG CAAATCCTCCACGTTTCCCAGGACAGGCTATGACTCGG TAAAGCTCTATAGCCCCGACCTCCAAAGCCCTGACCCGC AGCGATGATGTCTCCGTCTGCAGCGTGTCCAGTCTTGG GACAGAGCTGTCCACCACGCTGTCCGTCAGCAATGAG GACATCTTGGACCTTGTGGTCACGAGCAGCTCCAGTGC CATTGTGACCCTGGAGAATGACGATGACCCACAGTTTA CCAACGTCACCTTGAGCTCTATCAAGGAAACCCGTGGC TTACACCAGCAGGACTGTGTTCATGAAGCTGAGGAGG GGAGTAAATTGAAAATATTGGGGCCATTTAGTAACTTC TTTGCAAGGAACTTGCTTGCTAGAAAACAAAGTGCAA GGCTTGACAAACACAATGACTTGGGATGGAAGTTATTT |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GGGAAAGCGCCACTCCGAGAGAATGCCCAGAAGGATT<br>CAAAGAGAATACAGAAGgaatatgaagacaaggctggaagac<br>ctagCAAGCCACCCTCTCCAAAGCAGAATGTGAGGAAG<br>AATCTTGACTTTGAACCACTTTCCACCACCGCACTCATC<br>CTCGAGGACAGACCAGC\|ACACCCGCTGTTTGGCCGCA<br>ACGTGCCCCTGTCCAGCGGTTCTGGCTTCATCATGTCA<br>GAGGCCGGCCTGATCATCACCAATGCCCACGTGGTGT<br>CCAGCAACAGTGCTGCCCCGGGCAGGCAGCAGCTCAA<br>GGTGCAGCTACAGAATGGGGACTCCTATGAGGCCACC<br>ATCAAAGACATCGACAAGAAGTCGGACATTGCCACCA<br>TCAAGATCCATCCCAAGAAAAAGCTCCCTGTGTTGTTG<br>CTGGGTCACTCGGCCGACCTGCGGCCTGGGGAGTTTG<br>TGGTGGCCATCGGCAGTCCCTTCGCCCTACAGAACACA<br>GTGACAACGGGCATCGTCAGCACTGCCCAGCGGGAGG<br>GCAGGGAGCTGGGCCTCCGGGACTCCGACATGGACTA<br>CATCCAGACGGATGCCATCATCAACTACGGGAACTCCG<br>GGGGACCACTGGTGAACCTGGATGGCGAGGTCATTGG<br>CATCAACACGCTCAAGGTCACGGCTGGCATCTCCTTTG<br>CCATCCCCTCAGACCGCATCACACGGTTCCTCACAGAG<br>TTCCAAGACAAGCAGATCAAAGACTGGAAGAAGCGCT<br>TCATCGGCATACGGATGCGGACGATCACACCAAGCCT<br>GGTGGATGAGCTGAAGGCCAGCAACCCGGACTTCCCA<br>GAGGTCAGCAGTGGAATTTATGTGCAAGAGGTTGCGC<br>CGAATTCACCTTCTCAGAGAGGCGGCATCCAAGATGG<br>TGACATCATCGTCAAGGTCAACGGGCGTCCTCTAGTGG<br>ACTCGAGTGAGCTGCAGGAGGCCGTGCTGACCGAGTC<br>TCCTCTCCTACTGGAGGTGCGGCGGGGAACGACGAC<br>CTCCTCTTCAGCATCGCACCTGAGGTGGTCATG |
| G17476.<br>TCGA-06-<br>2569-<br>01A-01R-<br>1849-<br>01.2 | 7310150 | 32328393 | InFrame | 8312 | ATGAGACTCCTCCCCCGCTTGCTGCTGCTTCTCTTACTC<br>GTGTTCCCTGCCACTGTCTTGTTCCGAGGCGGCCCCAG<br>AGGCTTGTTAGCAGTGGCACAAGATCTTACAGAGGAT<br>GAAGAAACAGTAGAAGATTCCATAATTGAGGATGAAG<br>ATGATGAAGCCGAGGTAGAAGAAGATGAACCCACAG<br>ATTTG\|CACACTGTCCGTGAAGAAACGATGATGGTGAT<br>GACTGAAGACATGCCTTTGGAAATTTCTTATGTGCCTT<br>CTACTTATTTGACTGAAATCACTCATGTCTCACAAGCCC<br>TATTAGAAGTGGAACAACTTCTCAATGCTCCTGACCTC<br>TGTGCTAAGGACTTTGAAGATCTCTTTAAGCAAGAGGA<br>GTCTCTGAAGAATATAAAAGATAGTCTACAACAAAGCT<br>CAGGTCGGATTGACATTATTCATAGCAAGAAGACAGC<br>AGCATTGCAAAGTGCAACGCCTGTGGAAAGGGTGAAG<br>CTACAGGAAGCTCTCTCCCAGCTTGATTTCCAATGGGA<br>AAAAGTTAACAAAATGTACAAGGACCGACAAGGGCGA<br>TTTGACAGATCTGTTGAGAAATGGCGGCGTTTTCATTA<br>TGATATAAAGATATTTAATCAGTGGCTAACAGAAGCTG<br>AACAGTTTCTCAGAAAGACACAAATTCCTGAGAATTGG<br>GAACATGCTAAATACAAATGGTATCTTAAGGAACTCCA<br>GGATGGCATTGGGCAGCGGCAAACTGTTGTCAGAACA<br>TTGAATGCAACTGGGGAAGAAATAATTCAGCAATCCTC<br>AAAAACAGATGCCAGTATTCTACAGGAAAAATTGGGA<br>AGCCTGAATCTGCGGTGGCAGGAGGTCTGCAAACAGC<br>TGTCAGACAGAAAAAGAGGCTAGAAGAACAAAAGA<br>ATATCTTGTCAGAATTTCAAAGAGATTTAAATGAATTT<br>GTTTTATGGTTGGAGGAAGCAGATAACATTGCTAGTAT<br>CCCACTTGAACCTGGAAAAGAGCAGCAACTAAAAGAA |

FIG. 27 Cont.

| sample | Gene Break-point 5p | Gene Break-point 3p | Frame Type | SEQ ID NO: | Fused Sequence |
|---|---|---|---|---|---|
| | | | | | AAGCTTGAGCAAGTCAAGTTACTGGTGGAAGAGTTGC
CCCTGCGCCAGGGAATTCTCAAACAATTAAATGAAACT
GGAGGACCCGTGCTTGTAAGTGCTCCCATAAGCCCAG
AAGAGCAAGATAAACTTGAAAATAAGCTCAAGCAGAC
AAATCTCCAGTGGATAAAGGTTTCCAGAGCTTTACCTG
AGAAACAAGGAGAAATTGAAGCTCAAATAAAAGACCT
TGGGCAGCTTGAAAAAAAGCTTGAAGACCTTGAAGAG
CAGTTAAATCATCTGCTGCTGTGGTTATCTCCTATTAGG
AATCAGTTGGAAATTTATAACCAACCAAACCAAGAAG
GACCATTTGACGTTAAGGAAACTGAAATAGCAGTTCA
AGCTAAACAACCGGATGTGGAAGAGATTTTGTCTAAA
GGGCAGCATTTGTACAAGGAAAAACCAGCCACTCAGC
CAGTGAAGAGGAAGTTAGAAGATCTGAGCTCTGAGTG
GAAGGCGGTAAACCGTTTACTTCAAGAGCTGAGGGCA
AAGCAGCCTGACCTAGCTCCTGGACTGACCACTATTGG
AGCCTCTCCTACTCAGACTGTTACTCTGGTGACACAAC
CTGTGGTTACTAAGGAAACTGCCATCTCCAAACTAGAA
ATGCCATCTTCCTTGATGTTGGAGGTACCTGCTCTGGC
AGATTTCAACCGGGCTTGGACAGAACTTACCGACTGG
CTTTCTCTGCTTGATCAAGTTATAAAATCACAGAGGGT
GATGGTGGGTGACCTTGAGGATATCAACGAGATGATC
ATCAAGCAGAAGGCAACAATGCAGGATTTGGAACAGA
GGCGTCCCCAGTTGGAAGAACTCATTACCGCTGCCCAA
AATTTGAAAAACAAGACCAGCAATCAAGAGGCTAGAA
CAATCATTACGGATCGAATTGAAAGAATTCAGAATCAG
TGGGATGAAGTACAAGAACACCTTCAGAACCGGAGGC
AACAGTTGAATGAAATGTTAAAGGATTCAACACAATG
GCTGGAAGCTAAGGAAGAAGCTGAGCAGGTCTTAGG
ACAGGCCAGAGCCAAGCTTGAGTCATGGAAGGAGGG
TCCCTATACAGTAGATGCAATCCAAAAGAAAATCACAG
AAACCAAGCAGTTGGCCAAAGACCTCCGCCAGTGGCA
GACAAATGTAGATGTGGCAAATGACTTGGCCCTGAAA
CTTCTCCGGGATTATTCTGCAGATGATACCAGAAAAGT
CCACATGATAACAGAGAATATCAATGCCTCTTGGAGAA
GCATTCATAAAAGGGTGAGTGAGCGAGAGGCTGCTTT
GGAAGAAACTCATAGATTACTGCAACAGTTCCCCCTGG
ACCTGGAAAAGTTTCTTGCCTGGCTTACAGAAGCTGAA
ACAACTGCCAATGTCCTACAGGATGCTACCCGTAAGGA
AAGGCTCCTAGAAGACTCCAAGGGAGTAAAAGAGCTG
ATGAAACAATGGCAAGACCTCCAAGGTGAAATTGAAG
CTCACACAGATGTTTATCACAACCTGGATGAAAACAGC
CAAAAAATCCTGAGATCCCTGGAAGGTTCCGATGATG
CAGTCCTGTTACAAAGACGTTTGGATAACATGAACTTC
AAGTGGAGTGAACTTCGGAAAAAGTCTCTCAACATTA
GGTCCCATTTGGAAGCCAGTTCTGACCAGTGGAAGCG
TCTGCACCTTTCTCTGCAGGAACTTCTGGTGTGGCTAC
AGCTGAAAGATGATGAATTAAGCCGGCAGGCACCTAT
TGGAGGCGACTTTCCAGCAGTTCAGAAGCAGAACGAT
GTACATAGGGCCTTCAAGAGGGAATTGAAAACTAAAG
AACCTGTAATCATGAGTACTCTTGAGACTGTACGAATA
TTTCTGACAGAGCAGCCTTTGGAAGGACTAGAGAAAC
TCTACCAGGAGCCCAGAGAGCTGCCTCCTGAGGAGAG
AGCCCAGAATGTCACTCGGCTTCTACGAAAGCAGGCT
GAGGAGGTCAATACTGAGTGGGAAAAATTGAACCTGC
ACTCCGCTGACTGGCAGAGAAAAATAGATGAGACCCT |

FIG. 27 Cont.

| sample | Gene Breakpoint 5p | Gene Breakpoint 3p | Frame Type | SEQ ID NO: | Fused Sequence |
|---|---|---|---|---|---|
| | | | | | TGAAAGACTCCGGGAACTTCAAGAGGCCACGGATGAG
CTGGACCTCAAGCTGCGCCAAGCTGAGGTGATCAAGG
GATCCTGGCAGCCCGTGGGCGATCTCCTCATTGACTCT
CTCCAAGATCACCTCGAGAAAGTCAAGGCACTTCGAG
GAGAAATTGCGCCTCTGAAAGAGAACGTGAGCCACGT
CAATGACCTTGCTCGCCAGCTTACCACTTTGGGCATTC
AGCTCTCACCGTATAACCTCAGCACTCTGGAAGACCTG
AACACCAGATGGAAGCTTCTGCAGGTGGCCGTCGAGG
ACCGAGTCAGGCAGCTGCATGAAGCCCACAGGGACTT
TGGTCCAGCATCTCAGCACTTTCTTTCCACGTCTGTCCA
GGGTCCCTGGGAGAGAGCCATCTCGCCAAACAAAGTG
CCCTACTATATCAACCACGAGACTCAAACAACTTGCTG
GGACCATCCCAAAATGACAGAGCTCTACCAGTCTTTAG
CTGACCTGAATAATGTCAGATTCTCAGCTTATAGGACT
GCCATGAAACTCCGAAGACTGCAGAAGGCCCTTTGCTT
GGATCTCTTGAGCCTGTCAGCTGCATGTGATGCCTTGG
ACCAGCACAACCTCAAGCAAAATGACCAGCCCATGGA
TATCCTGCAGATTATTAATTGTTTGACCACTATTTATGA
CCGCCTGGAGCAAGAGCACAACAATTTGGTCAACGTC
CCTCTCTGCGTGGATATGTGTCTGAACTGGCTGCTGAA
TGTTTATGATACGGGACGAACAGGGAGGATCCGTGTC
CTGTCTTTTAAAACTGGCATCATTTCCCTGTGTAAAGCA
CATTTGGAAGACAAGTACAGATACCTTTTCAAGCAAGT
GGCAAGTTCAACAGGATTTTGTGACCAGCGCAGGCTG
GGCCTCCTTCTGCATGATTCTATCCAAATTCCAAGACA
GTTGGGTGAAGTTGCATCCTTTGGGGGCAGTAACATT
GAGCCAAGTGTCCGGAGCTGCTTCCAATTTGCTAATAA
TAAGCCAGAGATCGAAGCGGCCCTCTTCCTAGACTGG
ATGAGACTGGAACCCCAGTCCATGGTGTGGCTGCCCG
TCCTGCACAGAGTGGCTGCTGCAGAAACTGCCAAGCA
TCAGGCCAAATGTAACATCTGCAAAGAGTGTCCAATCA
TTGGATTCAGGTACAGGAGTCTAAAGCACTTTAATTAT
GACATCTGCCAAAGCTGCTTTTTTTCTGGTCGAGTTGC
AAAAGGCCATAAAATGCACTATCCCATGGTGGAATATT
GCACTCCGACTACATCAGGAGAAGATGTTCGAGACTTT
GCCAAGGTACTAAAAAACAAATTTCGAACCAAAAGGT
ATTTTGCGAAGCATCCCCGAATGGGCTACCTGCCAGTG
CAGACTGTCTTAGAGGGGGACAACATGGAAACTCCCG
TTACTCTGATCAACTTCTGGCCAGTAGATTCTGCGCCTG
CCTCGTCCCCTCAGCTTTCACACGATGATACTCATTCAC
GCATTGAACATTATGCTAGCAGGCTAGCAGAAATGGA
AAACAGCAATGGATCTTATCTAAATGATAGCATCTCTC
CTAATGAGAGCATAGATGATGAACATTTGTTAATCCAG
CATTACTGCCAAAGTTTGAACCAGGACTCCCCCCTGAG
CCAGCCTCGTAGTCCTGCCCAGATCTTGATTTCCTTAGA
GAGTGAGGAAAGAGGGGAGCTAGAGAGAATCCTAGC
AGATCTTGAGGAAGAAAACAGGAATCTGCAAGCAGAA
TATGACCGTCTAAAGCAGCAGCACGAACATAAAGGCC
TGTCCCCACTGCCGTCCCTCCTGAAATGATGCCCACCT
CTCCCCAGAGTCCCCGGGATGCTGAGCTCATTGCTGAG
GCCAAGCTACTGCGTCAACACAAAGGCCGCCTGGAAG
CCAGGATGCAAATCCTGGAAGACCACAATAAACAGCT
GGAGTCACAGTTACACAGGCTAAGGCAGCTGCTGGAG
CAACCCCAGGCAGAGGCCAAAGTGAATGGCACAACG
GTGTCCTCTCCTTCTACCTCTCTACAGAGGTCCGACAGC |

FIG. 27 Cont.

| sample | Gene Break-point 5p | Gene Break-point 3p | Frame Type | SEQ ID NO: | Fused Sequence |
|---|---|---|---|---|---|
| | | | | | AGTCAGCCTATGCTGCTCCGAGTGGTTGGCAGTCAAAC TTCGGACTCCATGGGTGAGGAAGATCTTCTCAGTCCTC CCCAGGACACAAGCACAGGGTTAGAGGAGGTGATGG AGCAACTCAACAACTCCTTCCCTAGTTCAAGAGGAAGA AATACCCCTGGAAAGCCAATGAGAGAGGACACAATG |
| G17195. TCGA-06-0138-01A-02R-1849-01.2 | 69145970 | 58109543 | InFrame | 8313 | ATGCCACTCCTGGGTCAGACGGTGAGGTCGGCGTCTG CGAGGACGCGGCGGTGGAGTAGAAGGGCAGCCGGA GACAGGCCCGGCGCCCCTTCCGAGGCTAGACGGCCCC AGCTTCGCGGGGATCATGGCATTGTGGACCGAGTGCG GGGCCACTGGCGAATCGCCGGCTCCTGTTCAACCTGCT GGTGTCCATCTGCATTGTGTTCCTCAACAAATGGATTT ATGTGTACCTTCCCCAACATGAGCCTGACCCTGGTGCA CTTCGTGGTCACCTGGCTGGGCTTGTATATCTGCCAGA AGCTGGACATCTTTGCCCCCAAAAGTCTGCCGCCCTCC AGGCTCCTCCTCCTGGCCCTCAGCTTCTGTGGCTTTGTG GTCTTCACTAACCTTTCTCTGCAGAACAACACCATAGG CACCTATCAGCTGGCCAAGGCCATGACCACGCCGGTG ATCATAGCCATCCAGACCTTCTGCTACCAGAAAACCTT CTCCACCAGAATCCAGCTCACGCTGATTCCTATAACTTT AGGTGTAATCCTAAATTCTTATTACGATGTGAAGTTTA ATTTCCTTGGAATGGTGTTTGCTGCTCTTGGTGTTTTAG TTACATCCCTTTATCAAGTGTGGGTAGGAGCCAAACAG CATGAATTACAAGTGAACTCAATGCAGCTGCTGTACTA CCAGGCTCCGATGTCATCTGCCATGTTGCTGGTTGCTG TGCCCTTCTTTGAGCCAGTGTTTGGAGAAGGAGGAAT ATTTGGTCCCTGGTCAGTTTCTGCTTTG\|TTCCTCTGTG ACGAGGGTGCAGGTATCTCTGGGGACTACATCGATCG CGTGGACGAGCCCTTGTCCTGCTCTTATGTGCTGACCA TTCGCACTCCTCGGCTCTGCCCCACCCTCTCCTCCGGC CCCCACCCAGTGCTGCACCGCAGGCCATCCTCTGTCAC CCTTCCCTACAGCCTGAGGAGTACATGGCCTACGTTCA GAGGCAAGCCGACTCAAAGCAGTATGGAGATAAAATC ATAGAGGAGCTGCAAGATCTAGGCCCCCAAGTGTGGA GTGAGACCAAGTCTGGGGTGGCACCCCAAAAGATGGC AGGTGCGAGCCCGACCAAGGATGACAGTAAGGACTCA GATTTCTGGAAGATGCTTAATGAGCCAGAGGACCAGG CCCCAGGAGGGAGGAGGTGCCGGCTGAGGAGCAGG ACCCAAGCCCTGAGGCAGCAGATTCAGCTTCTGGTGCT CCCAATGATTTTCAGAACAACGTGCAGGTCAAAGTCAT TCGAAGCCCTGCGGATTTGATTCGATTCATAGAGGAGC TGAAAGGTGGAACAAAAAGGGGAAGCCAAATATAG GCCAAGAGCAGCCTGTGGATGATGCTGCAGAAGTCCC TCAGAGGGAACCAGAGAAGGAAAGGGGTGATCCAGA ACGGCagagagagatggaagaagaggaggatgaggatgaggatg aggatgaagatgaggatgaACGGCAGTTACTGGGAGAATTT GAGAAGGAACTGGAAGGGATCCTGCTTCCGTCAGACC GAGACCGGCTCCGTTCGGAGGTGAAGGCTGGCATGG AGCGGGAACTGGAAAACATCATCCAGGAGACAGAGA AAGAGCTGGACCCAGATGGGCTGAAGAAGGAGTCAG AGCGGGATCGGGCAATGCTGGCTCTCACATCCACTCTC AACAAACTCATCAAAAGACTGGAGGAAAAACAGAGTC CAGAGCTGGTGAAGAAGCACAAGAAAAGAGGGTTG TCCCCAAAAAGCCTCCCCCATCACCCCAACCTACAGAG GAGGATCCTGAGCACAGAGTCCGGGTCCGGGTCACCA AGCTCCGTCTCGGAGGCCCTAATCAGGATCTGACTGTC |

FIG. 27 Cont.

| sample | Gene Break-point 5p | Gene Break-point 3p | Frame Type | SEQ ID NO: | Fused Sequence |
|---|---|---|---|---|---|
|  |  |  |  |  | CTCGAGATGAAACGGGAAAACCCACAGCTGAAACAAA TCGAGGGGCTGGTGAAGGAGCTGCTGGAGAGGGAGG GACTCACAGCTGCAGGGAAAATTGAGATCAAAATTGT CCGCCCATGGGCTGAAGGGACTGAAGAGGGTGCACG TTGGCTGACTGATGAGGACACGAGAAACCTCAAGGAG ATCTTCTTCAATATCTTGGTGCCGGGAGCTGAAGAGGC CCAGAAGGAACGCCAGCGGCAGAAAGAGCTGGAGAG CAATTACCGCCGGGTGTGGGGCTCTCCAGGTGGGGAG GGCACAGGGGACCTGGACGAATTTGACTTC |
| G17212. TCGA-06- 0129- 01A-01R- 1849- 01.2 | 140858113 | 163956014 | InFrame | 8314 | ATGGTCCCAGAGGCCTGGAGGAGCGGACTGGTAAGC ACCGGGAGGGTAGTGGGAGTTTTGCTTCTGCTTGGTG CCTTGAACAAGGCTTCCACGGTCATTCACTATGAGATC CCGGAGGAAAGAGAGAAGGGTTTCGCTGTGGGCAAC GTGGTCGCGAACCTTGGTTTGGATCTCGGTAGCCTCTC AGCCCGCAGGTTCCGGGTGGTGTCTGGAGCTAGCCGA AGATTCTTTGAGGTGAACCGGGAGACCGGAGAGATGT TTGTGAACGACCGTCTGGATCGAGAGGAGCTGTGTGG GACACTGCCCTCTTGCACTGTAACTCTGGAGTTGGTAG TGGAGAACCCGCTGGAGCTGTTCAGCGTGGAAGTGGT GATCCAGGACATCAACGACAACAATCCTGCTTTCCCTA CCCAGGAAATGAAATTGGAGATTAGCGAGGCCGTGGC TCCGGGGACGCGCTTTCCGCTCGAGAGCGCGCACGAT CCCGATGTGGGAAGCAACTCTTTACAAACCTATGAGCT GAGCCGAAATGAATACTTTGCGCTTCGCGTGCAGACG CGGGAGGACAGCACCAAGTACGCGGAGCTGGTGTTG GAGCGCGCCCTGGACCGAGAACGGGAGCCTAGTCTCC AGTTAGTGCTGACGGCGTTGGACGGAGGGACCCCAGC TCTCTCCGCCAGCCTGCCTATTCACATCAAGGTGCTGG ACGCGAATGACAATGCGCCTGTCTTCAACCAGTCCTTG TACCGGGCGCGCGTCCTGGAGGATGCACCCTCCGGCA CGCGCGTGGTACAAGTCCTTGCAACGGATCTGGATGA AGGCCCCAACGGTGAAATTATTTACTCCTTCGGCAGCC ACAACCGCGCCGGCGTGCGGCAACTATTCGCCTTAGA CCTTGTAACCGGGATGCTGACAATCAAGGGTCGGCTG GACTTCGAGGACACCAAACTCCATGAGATTTACATCCA GGCCAAAGACAAGGGCGCCAATCCCGAAGGAGCACA TTGCAAAGTGTTGGTGGAGGTTGTGGATGTGAATGAC AACGCCCCGGAGATCACAGTCACCTCCGTGTACAGCCC AGTACCCGAGGATGCCCCTCTGGGGACTGTCATCGCTT TGCTCAGTGTGACTGACCTGGATGCTGGCGAGAACGG GCTGGTGACCTGCGAAGTTCCACCGGGTCTCCCTTTCA GCCTTACTTCTTCCCTCAAGAATTACTTCACTTTGAAAA CCAGTGCAGACCTGGATCGGGAGACTGTGCCAGAATA CAACCTCAGCATCACCGCCCGAGACGCCGGAACCCCTT CCCTCTCAGCCCTTACAATAGTGCGTGTTCAAGTGTCC GACATCAATGACAACCCTCCACAATCTTCTCAATCTTCC TACGACGTTTACATTGAAGAAAACAACCTCCCCGGGGC TCCAATACTAAACCTAAGTGTCTGGGACCCCGACGCCC CGCAGAATGCTCGGCTTTCTTTCTTTCTTGGAGCAA GGAGCTGAAACCGGGCTAGTGGGTCGCTATTTCACAA TAAATCGTGACAATGGCATAGTGTCATCCTTAGTGCCC CTAGACTATGAGGATCGGCGGGAATTTGAATTAACAG CTCATATCAGCGATGGGGGCACCCCGGTCCTAGCCACC AACATCAGCGTGAACATATTTGTCACTGATCGCAATGA CAATGCCCCCCAGGTCCTATATCCTCGGCCAGGTGGGA |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GCTCGGTGGAGATGCTGCCTCGAGGTACCTCAGCTGG CCACCTAGTGTCACGGGTGGTAGGCTGGGACGCGGAT GCAGGGCACAATGCCTGGCTCTCCTACAGTCTCTTGGG ATCCCCTAACCAGAGCCTTTTTGCCATAGGGCTGCACA CTGGTCAAATCAGTACTGCCCGTCCAGTCCAAGACACA GATTCACCCAGGCAGACTCTCACGGTCTTGATCAAAGA CAATGGGGAGCCTTCGCTCTCCACCACTGCTACCCTCA CTGTGTCAGTAACCGAGGACTCTCCTGAAGCCCGAGCC GAGTTCCCCTCTGGCTCTGCCCCCGGGAGCAGAAAA AAAATCTCACCTTTTATCTACTTCTTTCTCTAATCCTGGT TTCTGTGGGGTTTGTGGTCACAGTGTTCGGAGTAATCA TATTCAAAGTTTACAAGTGGAAGCAGTCTAGAGACCTA TACCGAGCCCGGTGAGCTCACTGTACCGAACACCAG GGCCCTCCTTGCACGCGGACGCCGTGCGGGGAGGCCT GATGTCGCCGCACCTTTACCATCAGGTGTATCTCACCA CGGACTCCCGCCGCAGCGACCCGCTGCTGAAGAAACC TGGTGCAGCCAGTCCACTGGCCAGCCGCCAGAACACG CTGCGGAGCTGTGATCCGGTGTTCTATAGGCAGGTGT TGGGTGCAGAGAGCGCCCCTCCCGGACAG\|GAGGAG CAAAATAGAGGCAAGCCCAATTGGGAGCATCTAAATG AAGATTTACATGTACTAATCACTGTGGAAGATGCTCAG AACAGAGCAGAAATCAAATTGAAGAGAGCAGTTGAAG AAGTGAAGAAATTATTGGTACCTGCAGCAGAAGGAGA AGACAGCCTGAAGAAGATGCAGCTGATGGAGCTTGCG ATTCTGAATGGCACCTACAGAGATGCCAACATTAAATC ACCAGCCCTTGCCTTTTCTCTTGCAGCAACAGCCCAGG CTGCTCCAAGGATCATTACTGGGCCTGCGCCGGTTCTC CCACCAGCTGCCCTGCGTACTCCTACGCCAGCTGGCCC TACCATAATGCCTTTGATCAGACAAATACAGACCGCTG TCATGCCAAACGGAACTCCTCACCCAACTGCTGCAATA GTTCCTCCAGGGCCCGAAGCTGGTTTAATCTATACACC CTATGAGTACCCCTACACATTGGCACCAGCTACATCAA TCCTTGAGTATCCTATTGAACCTAGTGGTGTATTAGGT GCGGTGGCTACTAAAGTTCGAAGGCACGATATGCGTG TCCATCCTTACCAAAGGATTGTGACCGCAGACCGAGCC GCCACCGGCAAC |
| G17213. TCGA-06-0157-01A-01R-1849-01.2 | 20062889 | 90075838 | InFrame | 8315 | ATGGCGGACATCGAGCAGTACTACATGAAGCCGCCCG \|AGATCGTTAAGGAGGCTGAGGTGCCGCAGGCTGCGC TGGGCGTCCCAGCCCAGGGGACAGGGGACAATGGCC ACACGCCTGTGGAGGAGGAGGTCGGGGGCATCCCAG TACCAGCACCGGGGCTCCTGCAGGTCACGGAGAGGAG GCAGCCTCTGAGCAGCGTCTCCTCTCTGGAGGTCCACT TCGACCTCCTGGACCTCACTGAGCTCACCGACATGTCG GACCAGGAGCTGGCCGAGGTCTTTGCTGACTCGGACG ACGAGAACCTCAACACCGAGTCCCCAGCAGGTCTGCA CCCGCTGCCCCGGGCCGGCTACCTGCGCTCCCCTTCCT GGACGAGGACAAGGGCTGAGCAGAGCCACGAGAAGC AGCCCCTAGGCGACCCCGAGCGGCAGGCCACAGTCCT GGACACGTTTCTCACTGTGGAGAGGCCCCAGGAGGAC |
| G17200. TCGA-06-0125-01A-01R-1849-01.2 | 27094490 | 24624366 | InFrame | 8316 | ATGGCCGCGCAGGTCGCCCCCGCCGCCGCCAGCAGCC TGGGCAACCCGCCGCCGCCGCCGCCCTCGGAGCTGAA GAAAGCCGAgcagcagcagcggggaggaggcgggggggcgaggcg gcggcggcgcagcggcCGAGCGCGGGGAAATGAAGGCA GCCGCCGGGCAGGAAAGCGAGGGCCCCGCCGTGGGG CCGCCGCAGCCGCTGGGAAAGGAGCTGCAGGACGGG |

| sample | Gene Breakpoint 5p | Gene Breakpoint 3p | Frame Type | SEQ ID NO: | Fused Sequence |
|---|---|---|---|---|---|
| | | | | | GCCGAGAGCAATGGGggtggcggcggcggcggagccggcagc ggcggcggGCCCGGCGCGGAGCCGGACCTGAAGAACTC GAACGGGAACGCGGGCCCTAGGCCCGCCCTGAACAAT AACCTCACGGAGCCGCCcggcggcggcggtggcggcagcagc gatggggtgggggcgCCTCCTCACTCAGCCGCGGCCGCCTT GCCGCCCCAGCCTACGGCTTCGGGCAACCCTACGGCC GGAGCCCGTCTGCCGTCGCCGCCGCCGCGGCCGCCGT CTTCCACCAACAACATGGCGGACAACAAAGCCCTGGC CTGGCAGCGCTGCAGAGCGGCGGCGGCGGGGGCCTG GAGCCCTACGCGGGGCCCAGCAGAACTCTCACGACC ACGGCTTCCCCAACCACCAGTACAACTCCTACTACCCC AACCGCAGCGCCTACCCCCCGCCCGCCCCGGCCTACGC GCTGAGCTCCCCGAGAGGTGGCACTCCGGGCTCCGGC GCGGCGGCGGCTGCCGGCTCCAAGCCGCCTCCCTCCTC CAGCGCCTCCGCCTCCTCGTCGTCTTCGTCCTTCGCTCA GCAGCGCTTCGGGGCCATGGGGGGAGGCGGCCCCTC CGCGGCCGGCGGGGGAACTCCCCAGCCCACCGCCACC CCCACCCCTCAACCAACTGCTCACGTCGCCCAGCTCGGC CCGGGGCTACCAGGGCTACCCCGGGGGCGACTACAGT GGCGGGCCCCAGGACGGGGGCGCCGGCAAGGGCCCG GCGGACATGGCCTCGCAGTGTTGGGGggctgcggcggcgg cagctgcggcggcggcCGCCTCGGGAGGGGCCCAACAAAG GAGCCACCACGCGCCCATGAGCCCCGGGAGCAGCGGC GGCGGGGGGCAGCCGCTCGCCCGGACCCCTCAGCCAT CCAGTCCAATGGATCAGATGGGCAAGATGAGACCTCA GCCATATGGCGGGACTAACCCATACTCGCAGCAACAG GGACCTCCGTCAGGACCGCAGCAAGGACATGGGTACC CAGGGCAGCCATACGGGTCCCAGACCCCGCAGCGGTA CCCGATGACCATGCAGGGCCGGGCGCAGAGTGCCATG GGCGGCCTCTCTTATACACAGCAGATTCCTCCTTATGG ACAACAAGGCCCCAGCGGGTATGGTCAACAGGGCCAG ACTCCATATTACAACCAGCAAAGTCCTCACCCTCAGCA GCAGCAGCCACCCTACTCCCAGCAACCACCGTCCCAGA CCCCTCATGCCCAACCTTCGTATCAGCAGCAGCCACAG TCTCAACCACCACAGCTCCAGTCCTCTCAGCCTCCATAC TCCCAGCAGCCATCCCAGCCTCCACATCAGCAGTCCCC GGCTCCATACCCCTCCCAGCAGTCGACGACACAGCAGC ACCCCAGAGCCAGCCCCCCTACTCACAGCCACAGGCT CAGTCTCCTTACCAGCAGCAGCAACCTCAGCAGCCAGC ACCCTCGACGCTCTCCCAGCAGGCTGCGTATCCTCAGC CCCAGTCTCAGCAGTCCCAGCAAACTGCCTATTCCCAG CAGCGCTTCCCTCCACCGCAGGAGCTATCTCAAGATTC ATTTGGGTCTCAGGCATCCTCAGCCCCCTCAATGACCT CCAGTAAGGGAGGGCAAGAAGATATGAACCTGAGCCT TCAGTCAAGACCCTCCAGCTTGCCTGATCTATCTGGTTC AATAGATGACCTCCCCATGGGGACAGAAGGAGCTCTG AGTCCTGGAGTGAGCACATCAGGGATTTCCAGCAGCC AAGGAGAGCAGAGTAATCCAGCTCAGTCTCCTTTCTCT CCTCATACCTCCCCTCACCTGCCTGGCATCCGAGGCCCT TCCCCGTCCCTGTTGGCTCTCCCGCCAGTGTTGCTCAG TCTCGCTCAGGACCACTCTCGCCTGCTGCAGTGCCAGG CAACCAGATGCCACCTCGGCCACCCAGTGGCCAGTCG GACAGCATCATGCATCCTTCCATGAACCAATCAAGCAT TGCCCAAGATCGAGGTTATATGCAGAGGAACCCCCAG ATGCCCCAGTACAGTTCCCCCCAGCCCGGCTCAGCCTT |

FIG. 27 Cont.

| sample | Gene Break-point 5p | Gene Break-point 3p | Frame Type | SEQ ID NO: | Fused Sequence |
|---|---|---|---|---|---|
| | | | | | ATCTCCGCGTCAGCCTTCCGGAGGACAGATACACACA GGCATGGGCTCCTACCAGCAGAACTCCATGGGGAGCT ATGGTCCCCAGGGGGGTCAGTATGGCCCACAAGGTGG CTACCCCAGGCAGCCAAACTATAATGCCTTGCCCAATG CCAACTACCCCAGTGCAGGCATGGCTGGAGGCATAAA CCCCATGGGTGCCGGAGGTCAAATGCATGGACAGCCT GGCATCCCACCTTATGGCACACTCCCTCCAGGGAGGAT GAGTCACGCCTCCATGGGCAACCGGCCTTATGGCCCTA ACATGGCCAATATGCCACCTCAGGTTGGGTCAGGGAT GTGTCCCCCACCAGGGGGCATGAACCGGAAAACCCAA GAAACTGCTGTCGCCATGCATGTTGCTGCCAACTCTAT CCAAAACAGGCCGCCAGGCTACCCCAATATGAATCAA GGGGGCATGATGGGAACTGGACCTCCTTATGGACAAG GGATTAATAGTATGGCTGGCATGATCAACCCTCAGGG ACCCCCATATTCCATGGGTGGAACCATGGCCAACAATT CTGCAGGGATGGCAGCCAGCCCAGAGATGATGGGCCT TGGGGATGTAAAGTTAACTCCAGCCACCAAAATGAAC AACAAGGCAGATGGGACACCCAAGACAGAATCCAAAT CCAAGAAATCCAGTTCTTCTACTACAACCAATGAGAAG ATCACCAAGTTGTATGAGCTGGGTGGTGAGCCTGAGA GGAAGATGTGGGTGGACCGTTATCTGGCCTTCACTGA GGAGAAGGCCATGGGCATGACAAATCTGCCTGCTGTG GGTAGGAAACCTCTGGACCTCTATCGCCTCTATGTGTC TGTGAAGGAGATTGGTGGATTGACTCAG\|ATGCAGGC CCTGACTTCCTGTGAGTGCACCATCTGTCCTGACTGCTT CCGCCAGCACTTCACCATCGCCTTGAAGGAGAAGCAC ATCACAGACATGGTGTGCCCTGCCTGTGGCCGCCCCGA CCTCACCGATGACACACAGTTGCTCAGCTACTTCTCTAC CCTTGACATCCAGCTTCGCGAGAGCCTAGAGCCAGAT GCCTATGCGTTGTTCCATAAGAAGCTGACCGAGGGTG TGCTGATGCGGGACCCCAAGTTCTTGTGGTGTGCCCAG TGCTCCTTTGGCTTCATATATGAGCGTGAGCAGCTGGA GGCAACTTGTCCCCAGTGTCACCAGACCTTCTGTGTGC GCTGCAAGCGCCAGTGGGAGGAGCAGCACCGAGGTC GGAGCTGTGAGGACTTCCAGAACTGGAAACGCATGAA CGACCCAGAATACCAGGCCCAGGGCCTAGCAATGTAT CTTCAGGAAAACGGCATTGACTGCCCCAAATGCAAGTT CTCGTACGCCCTGGCCCGAGGAGGCTGCATGCACTTTC ACTGTACCCAGTGCCGCCACCAGTTCTGCAGCGGCTGC TACAATGCCTTTTACGCCAAGAATAAATGTCCAGAGCC TAACTGCAGGGTGAAAAAGTCCCTGCACGGCCACCAC CCTCGAGACTGCCTCTTCTACCTGCGGGACTGGACTGC TCTCCGGCTTCAGAAGCTGCTACAGGACAATAACGTCA TGTTTAATACAGAGCCTCCAGCTGGGGCCGGGCAGT CCCTGGAGGCGGCTGCCGAGTGATAGAGCAGAAGGA GGTTCCCAATGGGCTCAGGGACGAAGCTTGTGGCAAG GAAACTCCAGCTGGCTATGCCGGCCTGTGCCAGGCAC ACTACAAAGAGTATCTTGTGAGCCTCATCAATGCCCAC TCGCTGGACCCAGCCACCTTGTATGAGGTGGAAGAGC TGGAGACGGCCACTGAGCGCTACCTGCACGTACGCCC CCAGCCTTTGGCTGGAGAGGATCCCCCTGCTTACCAGG CCCGCTTGTTACAGAAGCTGACAGAAGAGGTACCCTT GGGACAGAGTATCCCCCGCAGGCGGAAG |
| G17804. TCGA-06- | 55268106 | 56079562 | InFrame | 8317 | ATGCGACCCTCCGGGACGGCCGGGGCAGCGCTCCTGG CGCTGCTGGCTGCGCTCTGCCCGGCGAGTCGGGCTCT |

FIG. 27 Cont.

| sample | Gene Break-point 5p | Gene Break-point 3p | Frame Type | SEQ ID NO: | Fused Sequence |
|---|---|---|---|---|---|
| 5408-01A-01R-1849-01.4 | | | | | GGAGGAAAAGAAAGTTTGCCAAGGCACGAGTAACAA
GCTCACGCAGTTGGGCACTTTTGAAGATCATTTTCTCA
GCCTCCAGAGGATGTTCAATAACTGTGAGGTGGTCCTT
GGGAATTTGGAAATTACCTATGTGCAGAGGAATTATG
ATCTTTCCTTCTTAAAGACCATCCAGGAGGTGGCTGGT
TATGTCCTCATTGCCCTCAACACAGTGGAGCGAATTCC
TTTGGAAAACCTGCAGATCATCAGAGGAAATATGTACT
ACGAAAATTCCTATGCCTTAGCAGTCTTATCTAACTATG
ATGCAAATAAAACCGGACTGAAGGAGCTGCCCATGAG
AAATTTACAGGAAATCCTGCATGGCGCCGTGCGGTTCA
GCAACAACCCTGCCCTGTGCAACGTGGAGAGCATCCA
GTGGCGGGACATAGTCAGCAGTGACTTTCTCAGCAAC
ATGTCGATGGACTTCCAGAACCACCTGGGCAGCTGCC
AAAAGTGTGATCCAAGCTGTCCCAATGGGAGCTGCTG
GGGTGCAGGAGAGGAGAACTGCCAGAAACTGACCAA
AATCATCTGTGCCCAGCAGTGCTCCGGGCGCTGCCGTG
GCAAGTCCCCCAGTGACTGCTGCCACAACCAGTGTGCT
GCAGGCTGCACAGGCCCCGGGAGAGCGACTGCCTG
GTCTGCCGCAAATTCCGAGACGAAGCCACGTGCAAGG
ACACCTGCCCCCCACTCATGCTCTACAACCCCACCACGT
ACCAGATGGATGTGAACCCCGAGGGCAAATACAGCTT
TGGTGCCACCTGCGTGAAGAAGTGTCCCCGTAATTATG
TGGTGACAGATCACGGCTCGTGCGTCCGAGCCTGTGG
GGCCGACAGCTATGAGATGGAGGAAGACGGCGTCCG
CAAGTGTAAGAAGTGCGAAGGGCCTTGCCGCAAAGTG
TGTAACGGAATAGGTATTGGTGAATTTAAAGACTCACT
CTCCATAAATGCTACGAATATTAAACACTTCAAAAACT
GCACCTCCATCAGTGGCGATCTCCACATCCTGCCGGTG
GCATTTAGGGGTGACTCCTTCACACATACTCCTCCTCTG
GATCCACAGGAACTGGATATTCTGAAAACCGTAAAGG
AAATCACAGGGTTTTTGCTGATTCAGGCTTGGCCTGAA
AACAGGACGGACCTCCATGCCTTTGAGAACCTAGAAA
TCATACGCGGCAGGACCAAGCAACATGGTCAGTTTTCT
CTTGCAGTCGTCAGCCTGAACATAACATCCTTGGGATT
ACGCTCCCTCAAGGAGATAAGTGATGGAGATGTGATA
ATTTCAGGAAACAAAAATTTGTGCTATGCAAATACAAT
AAACTGGAAAAAACTGTTTGGGACCTCCGGTCAGAAA
ACCAAAATTATAAGCAACAGAGGTGAAAACAGCTGCA
AGGCCACAGGCCAGGTCTGCCATGCCTTGTGCTCCCCC
GAGGGCTGCTGGGGCCCGGAGCCCAGGGACTGCGTC
TCTTGCCGGAATGTCAGCCGAGGCAGGGAATGCGTGG
ACAAGTGCAACCTTCTGGAGGGTGAGCCAAGGGAGTT
TGTGGAGAACTCTGAGTGCATACAGTGCCACCCAGAG
TGCCTGCCTCAGGCCATGAACATCACCTGCACAGGACG
GGACCAGACAACTGTATCCAGTGTGCCCACTACATTG
ACGGCCCCACTGCGTCAAGACCTGCCCGGCAGGAGT
CATGGGAGAAAACAACACCCTGGTCTGGAAGTACGCA
GACGCCGGCCATGTGTGCCACCTGTGCCATCCAAACTG
CACCTACGGATGCACTGGGCCAGGTCTTGAAGGCTGT
CCAACGAATGGGCCTAAGATCCCGTCCATCGCCACTGG
GATGGTGGGGGCCCTCCTCTTGCTGCTGGTGGTGGCC
CTGGGGATCGGCCTCTTCATGCGAAGGCGCCACATCG
TTCGGAAGCGCACGCTGCGGAGGCTGCTGCAGGAGA
GGGAGCTTGTGGAGCCTCTTACACCCAGTGGAGAAGC
TCCCAACCAAGCTCTCTTGAGGATCTTGAAGGAAACTG |

FIG. 27 Cont.

| sample | Gene Break-point 5p | Gene Break-point 3p | Frame Type | SEQ ID NO: | Fused Sequence |
|---|---|---|---|---|---|
| | | | | | AATTCAAAAAGATCAAAGTGCTGGGCTCCGGTGCGTT CGGCACGGTGTATAAGGGACTCTGGATCCCAGAAGGT GAGAAAGTTAAAATTCCCGTCGCTATCAAGGAATTAA GAGAAGCAACATCTCCGAAAGCCAACAAGGAAATCCT CGATGAAGCCTACGTGATGGCCAGCGTGGACAACCCC CACGTGTGCCGCCTGCTGGGCATCTGCCTCACCTCCAC CGTGCAGCTCATCACGCAGCTCATGCCCTTCGGCTGCC TCCTGGACTATGTCCGGGAACACAAAGACAATATTGG CTCCCAGTACCTGCTCAACTGGTGTGTGCAGATCGCAA AGGGCATGAACTACTTGGAGGACCGTCGCTTGGTGCA CCGCGACCTGGCAGCCAGGAACGTACTGGTGAAAACA CCGCAGCATGTCAAGATCACAGATTTTGGGCTGGCCA AACTGCTGGGTGCGGAAGAGAAAGAATACCATGCAG AAGGAGGCAAAGTGCCTATCAAGTGGATGGCATTGGA ATCAATTTTACACAGAATCTATACCCACCAGAGTGATG TCTGGAGCTACGGGGTGACTGTTTGGGAGTTGATGAC CTTTGGATCCAAGCCATATGACGGAATCCCTGCCAGCG AGATCTCCTCCATCCTGGAGAAAGGAGAACGCCTCCCT CAGCCACCCATATGTACCATCGATGTCTACATGATCAT GGTCAAGTGCTGGATGATAGACGCAGATAGTCGCCCA AAGTTCCGTGAGTTGATCATCGAATTCTCCAAAATGGC CCGAGACCCCAGCGCTACCTTGTCATTCAG\|GATGCT TTCATTGGATTTGGAGGAAATGTGATCAGGCAACAAG TCAAGGATAACGCCAAATGGTATATCACTGATTTTGTA GAGCTGCTGGGAGAACTGGAAGAA |
| G17656. TCGA-28-2514-01A-02R-1850-01.2 | 27024031 | 49202124 | InFrame | 8318 | ATGGCCGCGCAGGTCGCCCCCGCCGCCGCCAGCAGCC TGGGCAACCCGCCGCCGCCGCCGCCCTCGGAGCTGAA GAAAGCCGAgcagcagcagcggggaggaggcggggggcgaggcg gcggcggcggcagcgggCGAGCGCGGGGAAATGAAGGCA GCCGCCGGGCAGGAAAGCGAGGGCCCCGCCGTGGGG CCGCCGCAGCCGCTGGGAAAGGAGCTGCAGGACGGG GCCGAGAGCAATGGGgtggcggcggcggcggagccggcagc ggcggcggGCCCGGCGCGGAGCCGGACCTGAAGAACTC GAACGGGAACGCGGGCCCTAGGCCCGCCCTGAACAAT AACCTCACGGAGCCGCCCggcggcggcggtggcggcagcagc gatgggtggggcgCCTCCTCACTCAGCCGCGGCCGCCTT GCCGCCCCAGCCTACGGCTTCGGGCAACCCTACGGCC GGAGCCCGTCTGCCGTCGCCGCCGCCGCCGGCCGCCGT CTTCCACCAACAACATGGCGGACAACAAAGCCCTGGC CTGGCAGCGCTGCAGAGCGGCGGCGGCGGGGGCCTG GAGCCCTACGCGGGGCCCCAGCAGAACTCTCACGACC ACGGCTTCCCCAACCACCAGTACAACTCCTACTACCCC AACCGCAGCGCCTACCCCCCGCCCGCCCCGGCCTACGC GCTGAGCTCCCCGAGAGGTGGCACTCCGGGCTCCGGC GCGGCGGCGGCTGCCGGCTCCAAGCCGCCTCCCTCCTC CAGCGCCTCCGCCTCCTCGTCGTCTTCGTCCTTCGCTCA GCAGCGCTTCGGGGCCATGGGGGGAGGCGGCCCCTC CGCGGCCGGCGGGGGAACTCCCAGCCCACCGCCACC CCCACCCTCAACCAACTGCTCACGTCGCCCAGCTCGGC CCGGGGCTACCAGGGCTACCCCGGGGGCGACTACAGT GGCGGGCCCAGGACGGGGGCGCCGGCAAGGGCCCG GCGGACATGGCCTCGCAGTGTTGGGGggctgcggcggcgg cagctgcggcggcggcCGCCTCGGGAGGGGCCCAACAAAG GAGCCACCACGCGCCCATGAGCCCCGGGAGCAGCGGC GGCGGGGGGCAGCCGCTCGCCCGGACCCCTCAG\|GTC |

FIG. 27 Cont.

| sample | Gene Breakpoint 5p | Gene Breakpoint 3p | Frame Type | SEQ ID NO: | Fused Sequence |
|---|---|---|---|---|---|
| | | | | | CATCTGGGAAGCGGGATTTGGGTTGATGAGGAGAAAT GGCACCAGCTACAAGTAACCCAAGGAGATTCCAAGTA CACGAAGAACTTGGCAGTTATGATTTGGGGAACAGAT GTTCTGAAAAACAGAAGCGTCACAGGCGTCGCCACAA AAAAAAAGAAAGATGCAGTCCCTAAACCACCCCTCTCG CCTCACAAACTAAGCATCGTCAGAGAGTGTTTGTATGA CAGAATAGCACAAGAAACTGTGGATGAAACTGAAATT GCACAGAGACTCTCCAAAGTCAACAAGTACATCTGTGA AAAAATCATGGATATCAATAAATCCTGTAAAAATGAAG AACGAAGGGAAGCAAAATACAATTTGCAA |
| G17654. TCGA-41- 4097- 01A-01R- 1850- 01.2 | 146017814 | 156294880 | InFrame | 8319 | ATGCTTCTCTCGTTACCTGCCTTACATCTTCAGACCTCC GAACACCATCCTTTCTTCCAGCTGCCACACAGAAGGCT CGGACCATGGTGCAGTCCCACTGGCTCCCTGCCCCCC TCTCCTGTGAGACTGGCTGCGGGGAGGGATCATGGAT ACTTGTCTGCCGGCTTCTGGTTCCCACGCAAGTAAGCC TGCTGTCAATGGAGGAGGACATTGATACCCGCAAAAT CAACAACAGTTTCCTGCGCGACCACAGCTATGCGACCG AAGCTGACATTATCTCTACGGTAGAATTCAACCACACG GGAGAATTACTAGCGACAGGGGACAAGGGGGGTCGG GTTGTAATATTTCAACGAGAGCAGGAGAGTAAAAATC AGGTTCATCGTAGGGGTGAATACAATGTTTACAGCAC ATTCCAGAGCCATGAACCCGAGTTCGATTACCTGAAGA GTTTAGAAATAGAAGAAAAATCAATAAAATAAGATG GCTCCCCCAGCAGAATGCAGCTTACTTTCTTCTGTCTAC TAATGATAAAACTGTGAAGCTGTGGAAAGTCAGCGAG CGTGATAAGAGGCCAGAAGGCTACAATCTGAAAGATG AGGAGGGCCGGCTCCGGGATCCTGCCACCATCACAAC CCTGCGGGTGCCTGTCCTGAGACCCATGGACCTGATG GTGGAGGCCACCCCACGAAGAGTATTTGCCAACGCAC ACACATATCACATCAACTCCATATCTGTCAACAGCGAC TATGAAACCTACATGTCCGCTGATGACCTGAGGATTAA CCTATGGAACTTTGAAATAACCAATCAAAGTTTTAATA TTGTGGACATTAAGCCAGCCAACATGGAGGAGCTCAC GGAGGTGATCACAGCAGCCGAGTTCCACCCCCATCATT GCAACACCTTCGTGTACAGCAGCAGCAAAGGGACAAT CCGGCTGTGTGACATGCGGGCATCTGCCCTGTGTGAC AGGCACACCAAAT\|CAGGGGAAATGCTGTCTGTAGCT GAGCACTTCCTGGAGCAGCAGATGCACCCAACAGTGG TGATCAGTGCTTACCGCAAGGCATTGGATGATATGATC AGCACCCTAAAGAAAATAAGTATCCCAGTCGACATCAG TGACAGTGATATGATGCTGAACATCATCAACAGCTCTA TTACTACCAAAGCCATCAGTCGGTGGTCATCTTTGGCT TGCAACATTGCCCTGGATGCTGTCAAGATGGTACAGTT TGAGGAGAATGGTCGGAAAGAGATTGACATAAAAAA ATATGCAAGAGTGGAAAAGATACCTGGAGGCATCATT GAAGACTCCTGTGTCTTGCGTGGAGTCATGATTAACAA GGATGTGACCCATCCACGTATGCGGCGCTATATCAAG AACCCTCGCATTGTGCTGCTGGATTCTTCTCTGGAATAC AAGAAAGGAGAAAGCCAGACTGACATTGAGATTACAC GAGAGGAGGACTTCACCCGAATTCTCCAGATGGAGGA AGAGTACATCCAGCAGCTCTGTGAGGACATTATCCAAC TGAAGCCCGATGTGGTCATCACTGAAAAGGGCATCTC AGATTTAGCTCAGCACTACCTTATGCGGGCCAATATCA CAGCCATCCGCAGAGTCCGGAAGACAGACAATAATCG CATTGCTAGAGCCTGTGGGGCCCGGATAGTCAGCCGA |

FIG. 27 Cont.

| sample | Gene Breakpoint 5p | Gene Breakpoint 3p | Frame Type | SEQ ID NO: | Fused Sequence |
|---|---|---|---|---|---|
| | | | | | CCAGAGGAACTGAGAGAAGATGATGTTGGAACAGGA GCAGGCCTGTTGGAAATCAAGAAAATTGGAGATGAAT ACTTTACTTTCATCACTGACTGCAAAGACCCCAAGGCC TGCACCATTCTCCTCCGGGGGGCTAGCAAAGAGATTCT CTCGGAAGTAGAACGCAACCTCCAGGATGCCATGCAA GTGTGTCGCAATGTTCTCCTGGACCCTCAGCTGGTGCC AGGGGGTGGGGCCTCCGAGATGGCTGTGGCCCATGCC TTGACAGAAAAATCCAAGGCCATGACTGGTGTGGAAC AATGGCCATACAGGGCTGTTGCCCAGGCCCTAGAGGT CATTCCTCGTACCCTGATCCAGAACTGTGGGGCCAGCA CCATCCGTCTACTTACCTCCCTTCGGGCCAAGCACACCC AGGAGAACTGTGAGACCTGGGGTGTAAATGGTGAGA CGGGTACTTTGGTGGACATGAAGGAACTGGGCATATG GGAGCCATTGGCTGTGAAGCTGCAGACTTATAAGACA GCAGTGGAGACGGCAGTTCTGCTACTGCGAATTGATG ACATCGTTTCAGGCCACAAAAAGAAAGGCGATGACCA GAGCCGGCAAGGCGGGGCTCCTGATGCTGGCCAGGA G |
| G17206. TCGA-06- 0125- 02A-11R- 2005- 01.2 | 27094490 | 24624366 | InFrame | 8320 | ATGGCCGCGCAGGTCGCCCCCGCCGCCGCCAGCAGCC TGGGCAACCCGCCGCCGCCGCCGCCCTCGGAGCTGAA GAAAGCCGAgcagcagcagcggggaggaggcggggggcgaggcg gcggcggcggcagcggcCGAGCGCGGGGAAATGAAGGCA GCCGCCGGGCAGGAAAGCGAGGGCCCCGCCGTGGGG CCGCCGCAGCCGCTGGGAAAGGAGCTGCAGGACGGG GCCGAGAGCAATGGGggtggcggcggcggcggagccggcagc ggcggcggGCCCGGCGCGGAGCCGGACCTGAAGAACTC GAACGGGAACGCGGGCCCTAGGCCCGCCCTGAACAAT AACCTCACGGAGCCGCCcggcggcggcggtggcggcagcagc gatggggtggggggcgCCTCCTCACTCAGCCGCGGCCGCCTT GCCGCCCCAGCCTACGGCTTCGGGCAACCCTACGGCC GGAGCCCGTCTGCCGTCGCCGCCGCCGCGGCCGCCGT CTTCCACCAACAACATGGCGGACAACAAAGCCCTGGC CTGGCAGCGCTGCAGAGCGGCGGCGGCGGGGGCCTG GAGCCCTACGCGGGGCCCCAGCAGAACTCTCACGACC ACGGCTTCCCCAACCACCAGTACAACTCCTACTACCCC AACCGCAGCGCCTACCCCCCGCCCGCCCCGGCCTACGC GCTGAGCTCCCCGAGAGGTGGCACTCCGGGCTCCGGC GCGGCGGCGGCTGCCGGCTCCAAGCCGCCTCCCTCCTC CAGCGCCTCCGCCTCCTCGTCGTCTTCGTCCTTCGCTCA GCAGCGCTTCGGGGCCATGGGGGGAGGCGGCCCCTC CGCGGCCGGCGGGGGAACTCCCCAGCCCACCGCCACC CCCACCCTCAACCAACTGCTCACGTCGCCCAGCTCGGC CCGGGGCTACCAGGGCTACCCCGGGGGCGACTACAGT GGCGGGCCCAGGACGGGGGCGCCGGCAAGGGCCCG GCGGACATGGCCTCGCAGTGTTGGGGggctgcggcggcgg cagctgcggcggcggCGCCTCGGGAGGGGCCCAACAAAG GAGCCACCACGCGCCCATGAGCCCCGGGAGCAGCGGC GGCGGGGGGCAGCCGCTCGCCCGGACCCCTCAGCCAT CCAGTCCAATGGATCAGATGGGCAAGATGAGACCTCA GCCATATGGCGGGACTAACCCATACTCGCAGCAACAG GGACCTCCGTCAGGACCGCAGCAAGGACATGGGTACC CAGGGCAGCCATACGGGTCCCAGACCCCGCAGCGGTA CCCGATGACCATGCAGGGCCGGGCGCAGAGTGCCATG GGCGGCCTCTCTTATACACAGCAGATTCCTCCTTATGG ACAACAAGGCCCCAGCGGGTATGGTCAACAGGGCCAG |

FIG. 27 Cont.

| sample | Gene Break-point 5p | Gene Break-point 3p | Frame Type | SEQ ID NO: | Fused Sequence |
|---|---|---|---|---|---|
| | | | | | ACTCCATATTACAACCAGCAAAGTCCTCACCCTCAGCA GCAGCAGCCACCCTACTCCCAGCAACCACCGTCCCAGA CCCCTCATGCCCAACCTTCGTATCAGCAGCAGCCACAG TCTCAACCACCACAGCTCCAGTCCTCTCAGCCTCCATAC TCCCAGCAGCCATCCCAGCCTCCACATCAGCAGTCCCC GGCTCCATACCCCTCCCAGCAGTCGACGACACAGCAGC ACCCCAGAGCCAGCCCCCCTACTCACAGCCACAGGCT CAGTCTCCTTACCAGCAGCAGCAACCTCAGCAGCCAGC ACCCTCGACGCTCTCCCAGCAGGCTGCGTATCCTCAGC CCCAGTCTCAGCAGTCCCAGCAAACTGCCTATTCCCAG CAGCGCTTCCCTCCACCGCAGGAGCTATCTCAAGATTC ATTTGGGTCTCAGGCATCCTCAGCCCCCTCAATGACCT CCAGTAAGGGAGGGCAAGAAGATATGAACCTGAGCCT TCAGTCAAGACCCTCCAGCTTGCCTGATCTATCTGGTTC AATAGATGACCTCCCCATGGGGACAGAAGGAGCTCTG AGTCCTGGAGTGAGCACATCAGGGATTTCCAGCAGCC AAGGAGAGCAGAGTAATCCAGCTCAGTCTCCTTTCTCT CCTCATACCTCCCCTCACCTGCCTGGCATCCGAGGCCCT TCCCCGTCCCCTGTTGGCTCTCCCGCCAGTGTTGCTCAG TCTCGCTCAGGACCACTCTCGCCTGCTGCAGTGCCAGG CAACCAGATGCCACCTCGGCCACCCAGTGGCCAGTCG GACAGCATCATGCATCCTTCCATGAACCAATCAAGCAT TGCCCAAGATCGAGGTTATATGCAGAGGAACCCCCAG ATGCCCCAGTACAGTTCCCCCCAGCCCGGCTCAGCCTT ATCTCCGCGTCAGCCTTCCGGAGGACAGATACACACA GGCATGGGCTCCTACCAGCAGAACTCCATGGGGAGCT ATGGTCCCCAGGGGGGTCAGTATGGCCCACAAGGTGG CTACCCCAGGCAGCCAAACTATAATGCCTTGCCCAATG CCAACTACCCCAGTGCAGGCATGGCTGGAGGCATAAA CCCCATGGGTGCCGGAGGTCAAATGCATGGACAGCCT GGCATCCCACCTTATGGCACACTCCCTCCAGGGAGGAT GAGTCACGCCTCCATGGGCAACCGGCCTTATGGCCCTA ACATGGCCAATATGCCACCTCAGGTTGGGTCAGGGAT GTGTCCCCCACCAGGGGGCATGAACCGGAAAACCCAA GAAACTGCTGTCGCCATGCATGTTGCTGCCAACTCTAT CCAAAACAGGCCGCCAGGCTACCCCAATATGAATCAA GGGGGCATGATGGGAACTGGACCTCCTTATGGACAAG GGATTAATAGTATGGCTGGCATGATCAACCCTCAGGG ACCCCATATTCCATGGGTGGAACCATGGCCAACAATT CTGCAGGGATGGCAGCCAGCCCAGAGATGATGGGCCT TGGGGATGTAAAGTTAACTCCAGCCACCAAAATGAAC AACAAGGCAGATGGGACACCCAAGACAGAATCCAAAT CCAAGAAATCCAGTTCTTCTACTACAACCAATGAGAAG ATCACCAAGTTGTATGAGCTGGGTGGTGAGCCTGAGA GGAAGATGTGGGTGGACCGTTATCTGGCCTTCACTGA GGAGAAGGCCATGGGCATGACAAATCTGCCTGCTGTG GGTAGGAAACCTCTGGACCTCTATCGCCTCTATGTGTC TGTGAAGGAGATTGGTGGATTGACTCAG\|ATGCAGGC CCTGACTTCCTGTGAGTGCACCATCTGTCCTGACTGCTT CCGCCAGCACTTCACCATCGCCTTGAAGGAGAAGCAC ATCACAGACATGGTGTGCCCTGCCTGTGGCCGCCCCGA CCTCACCGATGACACACAGTTGCTCAGCTACTTCTCTAC CCTTGACATCCAGCTTCGCGAGAGCCTAGAGCCAGAT GCCTATGCGTTGTTCCATAAGAAGCTGACCGAGGGTG TGCTGATGCGGGACCCCAAGTTCTTGTGGTGTGCCCAG |

FIG. 27 Cont.

| sample | Gene Break-point 5p | Gene Break-point 3p | Frame Type | SEQ ID NO: | Fused Sequence |
|---|---|---|---|---|---|
| | | | | | TGCTCCTTTGGCTTCATATATGAGCGTGAGCAGCTGGA GGCAACTTGTCCCCAGTGTCACCAGACCTTCTGTGTGC GCTGCAAGCGCCAGTGGGAGGAGCAGCACCGAGGTC GGAGCTGTGAGGACTTCCAGAACTGGAAACGCATGAA CGACCCAGAATACCAGGCCCAGGGCCTAGCAATGTAT CTTCAGGAAAACGGCATTGACTGCCCCAAATGCAAGTT CTCGTACGCCCTGGCCCGAGGAGGCTGCATGCACTTTC ACTGTACCCAGTGCCGCCACCAGTTCTGCAGCGGCTGC TACAATGCCTTTTACGCCAAGAATAAATGTCCAGAGCC TAACTGCAGGGTGAAAAAGTCCCTGCACGGCCACCAC CCTCGAGACTGCCTCTTCTACCTGCGGGACTGGACTGC TCTCCGGCTTCAGAAGCTGCTACAGGACAATAACGTCA TGTTTAATACAGAGCCTCCAGCTGGGGCCCGGGCAGT CCCTGGAGGCGGCTGCCGAGTGATAGAGCAGAAGGA GGTTCCCAATGGGCTCAGGGACGAAGCTTGTGGCAAG GAAACTCCAGCTGGCTATGCCGGCCTGTGCCAGGCAC ACTACAAAGAGTATCTTGTGAGCCTCATCAATGCCCAC TCGCTGGACCCAGCCACCTTGTATGAGGTGGAAGAGC TGGAGACGGCCACTGAGCGCTACCTGCACGTACGCCC CCAGCCTTTGGCTGGAGAGGATCCCCCTGCTTACCAGG CCCGCTTGTTACAGAAGCTGACAGAAGAGGTACCCTT GGGACAGAGTATCCCCGCAGGCGGAAG |
| G17792. TCGA-28- 5204- 01A-01R- 1850- 01.4 | 36204176 | 33911962 | InFrame | 8321 | ATGGCTGAGCTGGATCCGTTCGGCGCCCCTGCCGGCG CCCCTGGCGGTCCCGCGCTGGGGAACGGAGTGGCCG GCGCCGGCGAAGAAGACCCGGCTGCGGCCTTCTTGGC GCAGCAAGAGAGCGAGATTGCGGGCATCGAGAACGA CGAGGCCTTCGCCATCCTGGACggcggcgccccgggccca gccgcacggcgagccgccgggggggTCCGGATGCTGTTGATGG AGTAATGAATGGTGAATACTACCAGGAAAGTAATGGT CCAACAGACAGTTATGCAGCTATTTCACAAGTGGATCG ATTGCAGTCAGAGCCTGAAAGTATCCGTAAATGGAGA GAAGAACAAATGGAACGCTTGGAAGCCCTTGATGCCA ATTCTCGGAAGCAAGAAGCAGAGTGGAAAGAAAAGG CAATAAAGGAGCTAGAAGAATGGTATGCAAGACAGG ACGAGCAGCTACAGAAAACAAAAGCAAACAACAG\|GA CTATCCTATTAAGTGTAATCTCACTGCTTAATGAGCCCA ACACCTTCTCCCCAGCCAATGTCGATGCTTCAGTTATGT TCAGGAAATGGAGAGACAGTAAAGGAAAAGACAAAG AATATGCTGAAATTATTAGGAAACAAGTTTCAGCCACT AAGGCCGAAGCAGAAAAGGATGGAGTGAAGGTCCCC ACAACCCTGGCGGAATACTGCATCAAAACTAAAGTGC CTTCCAATGACAACAGCTCAGATTTGCTTTACGACGAC TTGTatgatgacgacattgatgatgaagatgaggaggaggaagatgc cgactgttatgatgatgatgatTCTGGGAATGAGGAGTCG |
| G17663. TCGA-19- 2619- 01A-01R- 1850- 01.2 | 205719085 | 205811017 | InFrame | 8322 | ATGTCGCGGCCTGTCAG\|GTTTATGGAGAGAAATCCCT TAACCAATGCAATAATCAGGACCACCACGGCACTCACC ATATTCAAAGCAGGGGTCAAGTTCAATGTCATCCCCCC AGTGGCCCAGGCCACAGTCAACTTCCGGATTCACCCTG GACAGACAGTCCAAGAGGTCCTAGAACTCACGAAGAA CATTGTGGCTGATAACAGAGTCCAGTTCCATGTGTTGA GTGCCTTTGACCCCCTCCCCGTCAGCCCTTCTGATGACA AGGCCTTGGGCTACCAGCTGCTCCGCCAGACCGTACA GTCCGTCTTCCCGGAAGTCAATATTACTGCCCCAGTTA CTTCTATTGGCAACACAGACAGCCGATTCTTTACAAAC CTCACCACTGGCATCTACAGGTTCTACCCCATCTACATA |

FIG. 27 Cont.

| sample | Gene Break-point 5p | Gene Break-point 3p | Frame Type | SEQ ID NO: | Fused Sequence |
|---|---|---|---|---|---|
| | | | | | CAGCCTGAAGACTTCAAACGCATCCATGGAGTCAACG AGAAAATCTCAGTCCAAGCCTATGAGACCCAAGTGAA ATTCATCTTTGAGTTGATTCAGAATGCTGACACAGACC AGGAGCCAGTTTCTCACCTGCACAAACTG |
| NYU_E | 69333677 | 69349911 | InFrame | 8323 | ATGAGGGTAGCTGCGGCGACTGCGGCGGCTGGAGCG GGGCCGGCCATGGCGGTGTGGACGCGGGCCACCAAA GCGGGGCTGGTGGAGCTGCTCCTGAGGGAGCGCTGG GTCCGAGTGGTGGCCGAGCTGAGCGGGGAGAGCCTG AGCCTGACGGGCGACGCCGCCGCGGCCGAGCTGGAG CCCGCTCTGGGACCCGCGGCCGCCGCCTTCAACGGCCT CCCAAACGGCGGCGGCGCGGGCGACTCGCTGCCCGG GAGCCCAAgccgcggcctggggccccgagcccgccggcgccgcct cggggccccgcgggtgaggcgggcgcgtcgccgcccgtgcgccgggT GCGGGTGGTGAAGCAAGAGGCGGGCGGCCTGGGCAT CAGCATCAAGGGCGGCCGCGAGAACCGGATGCCGATC CTCATCTCCAAGATCTTCCCCGGGCTGGCTGCCGACCA GAGCCGGGCGCTGCGGCTGGGCGACGCCATCCTGTCG GTGAACGGCACCGACCTGCGCCAGGCCACCCACGACC AGGCCGTGCAGGCGCTGAAGCGCGCGGGCAAGGAGG TGCTGCTGGAGGTCAAGTTCATCCGAGAAGTAACACC ATATATCAAGAAGCCATCATTAGTATCAGATCTGCCGT GGGAAGGTGCAGCCCCCCAGTCACCAAGCTTTAGTGG CAGTGAGGACTCTGGTTCGCCAAAACACCAGAACAGC ACCAAGGACAGGAAGATCATCCCTCTCAAAATGTGCTT TGCTGCTAGAAACCTAAGCATGCCGGATCTGGAAAAC AGATTGATAGAGCTACATTCTCCTGATAGCAGGAACAC GTTGATCCTACGCTGCAAAGATACAGCCACAGCACACT CCTGGTTCGTAGCTATCCACACCAACATAATGGCTCTC CTCCCACAGGTGTTGGCTGAACTCAACGCCATGCTTGG GGCAACCAGTACAGCAGGAGGCAGTAAAGAGGTGAA GCATATTGCCTGGCTGGCAGAACAGGCAAAACTAGAT GGTGGAAGACAGCAATGGAGACCTGTCCTCATGGCTG TGACTGAGAAGGATTTGCTGCTCTATGACTGTATGCCG TGGACAAGAGATGCCTGGGCGTCACCATGCCACAGCT ACCCACTTGTTGCCACCAGGTTGGTTCATTCTGGCTCC GGATGTCGATCCCCCTCCCTTGGATCTGACCTTACATTT GCTACCAGGACAGGCTCTCGACAGGGCATTGAGATGC ATCTCTTCAGGGTGGAGACACATCGGGATCTGTCATCC TGGACCAGGATACTTGTTCAGGGTTGCCATGCTGCTGC TGAGCTGATCAAGGAAGTCTCTAGGCTGCATGTTAA ATGGCCAAGAGGTGAGGCTTACTATTCACTATGAAAAT GGGTTCACCATCTCAAGGGAAAATGGAGGCTCCAGCA GCATATTGTACCGCTACCCCTTTGAAAGGCTGAAGATG TCTGCTGATGATGGCATCCGAAATCTATACTTGGATTTT GGTGGTCCCGAGGGAGAACTG\|AAAGCCATTGATCTG GTGACGAAAGCCACAGAGGAGGACAAAGCCAAGAAC TACGAGGAGGCGCTGCGGCTGTACCAGCATGCGGTGG AGTACTTCCTCCACGCTATCAAGTATGAGGCCCACAGC GACAAGGCCAAGGAGAGCATTCGAGCCAAGTGCGTG CAGTACCTAGACCGGGCCGAGAAGCTGAAGGATTATT TACGAAGCAAAGAGAAACACGGCAAGAAGCCAGTCA AAGAGAACCAGAGTGAGGGCAAGGGCAGTGACAGTG ACAGTGAAGGGGATAATCCGGAGAAAAAGAAACTGC AAGAACAGCTGATGGGTGCCGTCGTGATGGAGAAGCC CAACATACGGTGGAACGACGTGGCCGGGCTGGAGGG |

FIG. 27 Cont.

| sample | Gene Break- point 5p | Gene Break- point 3p | Frame Type | SEQ ID NO: | Fused Sequence |
|---|---|---|---|---|---|
| | | | | | GGCCAAGGAGGCCCTCAAAGAAGCTGTCATTTTGCCA ATCAAATTCCCACACTTGTTCACAGGCAAGCGCACCCC CTGGCGGGGGATTCTGCTGTTCGGACCCCCTGGCACA GGGAAATCCTACCTGGCCAAAGCCGTGGCAACAGAGG CCAACAACTCCACCTTCTTCTCTGTGTCCTCCTCAGATC TGATGTCCAAGTGGCTGGGGGAGAGTGAAAAGCTGG TCAAGAACCTGTTTGAGCTGGCCAGGCAGCACAAGCC CTCCATCATCTTCATCGATGAGGTGGATTCCCTCTGCG GGTCCCGAAATGAAATGAGAGTGAGGCCGCCCGGA GGATCAAAACGGAGTTCTTGGTCCAGATGCAGGGGGT GGGGAATAACAATGATGGGACTCTGGTTCTTGGAGCC ACAAACATCCCATGGGTGTTGGATTCGGCCATCAGGA GGAGGTTTGAAAAACGAATTTATATCCCCTTGCCGGAG GAAGCTGCCCGCGCCCAGATGTTCCGGTTGCATCTCGG GAGCACTCCCCACAACCTCACGGATGCAAACATCCACG AGCTGGCCCGGAAGACGGAAGGCTACTCGGGCGCGG ACATCAGCATCATCGTGCGGGACTCTCTCATGCAGCCC GTGAGGAAGGTGCAGTCGGCCACACACTTCAAAAAGG TCTGTGGCCCCTCTCGCACCAACCCCAGCATGATGATT GATGACCTCCTGACTCCATGCTCACCAGGGGACCCAG GAGCCATGGAGATGACTTGGATGGATGTCCCTGGGGA CAAACTCTTAGAGCCTGTGGTTTGCATGTCGGACATGC TGCGGTCTCTGGCCACCACCCGGCCCACGGTGAATGC AGACGACCTCCTGAAAGTGAAGAAATTCTCAGAGGAC TTTGGGCAAGAGAGT |
| NYU_G | 42759130 | 42744294 | InFrame | 8324 | ATGAAGACCCCGGCGGACACAG\|GTGACAGCGGGAA GGTGACCACAGTCGTAGCCACTCTAGGCCAAGGCCCA GAGCGCTCCCAAGAAGTGGCTTACACGGACATCAAAG TGATTGGCAATGGCTCATTTGGGGTCGTGTACCAGGC ACGGCTGGCAGAGACCAGGGAACTAGTCGCCATCAAG AAGGTTCTCCAGGACAAGAGGTTCAAGAACCGAGAGC TGCAGATCATGCGTAAGCTGGACCACTGCAATATTGTG AGGCTGAGATACTTTTTCTACTCCAGTGGCGAGAAGAA AGACGAGCTTTACCTAAATCTGGTGCTGGAATATGTGC CCGAGACAGTGTACCGGGTGGCCCGCCACTTCACCAA GGCCAAGTTGACCATCCCTATCCTCTATGTCAAGGTGT ACATGTACCAGCTCTTCCGCAGCTTGGCCTACATCCACT CCCAGGGCGTGTGTCACCGCGACATCAAGCCCCAGAA CCTGCTGGTGGACCCTGACACTGCTGTCCTCAAGCTCT GCGATTTTGGCAGTGCAAAGCAGTTGGTCCGAGGGGA GCCCAATGTCTCCTACATCTGTTCTCGCTACTACCGGGC CCCAGAGCTCATCTTTGGAGCCACTGATTACACCTCAT CCATCGATGTTTGGTCAGCTGGCTGTGTACTGGCAGAG CTCCTCTTGGGCCAGCCCATCTTCCCTGGGGACAGTGG GGTGGACCAGCTGGTGGAGATCATCAAGGTGCTGGG AACACCAACCCGGGAACAAATCCGAGAGATGAACCCC AACTACACGGAGTTCAAGTTCCCTCAGATTAAAGCTCA CCCCTGGACAAAGGTGTTCAAATCTCGAACGCCGCCA GAGGCCATCGCGCTCTGCTCTAGCCTGCTGGAGTACAC CCCATCCTCAAGGCTCTCCCCACTAGAGGCCTGTGCGC ACAGCTTCTTTGATGAACTGCGATGTCTGGGAACCCAG CTGCCTAACAACCGCCCACTTCCCCCTCTCTTCAACTTC AGTGCTGGTGAACTCTCCATCCAACCGTCTCTCAACGC CATTCTTATCCCTCCTCACTTGAGGTCCCCAGCGGGCAC TACCACCCTCACCCCGTCCTCACAAGCTTTAACTGAGAC |

FIG. 27 Cont.

| sample | Gene Break-point 5p | Gene Break-point 3p | Frame Type | SEQ ID NO: | Fused Sequence |
|---|---|---|---|---|---|
| | | | | | TCCGACCAGCTCAGACTGGCAGTCGACCGATGCCACA CCTACCCTCACTAACTCCTCC |
| NYU_B | 6457893 | 6443410 | InFrame | 8325 | ATGGGCATGGCCAGGGGCAGCCTCACTCGGGTTCCAG GGGTGATGGGAGAGGGCACTCAGGGCCCAGAGCTCA GCCTTGACCCTGACCCTTGCTCTCCCCAATCCACTCCGG GGCTCATGAAGGGGAACAAGCTGGAGGAGCAGGACC CTAGACCTCTGCAGCCCATACCAGGTCTCATGGAGGG GAACAAGCTGGAGGAGCAGGACTCTAGCCCTCCACAG TCCACTCCAGGGCTCATGAAGGGGAACAAGCGTGAGG AGCAGGGGCTGGGCCCCGAACCTGCGGCGCCCCAGCA GCCCACGGCGGAGGAGGAGGCCCTGATCGAGTTCCAC CGCTCCTACCGAGAGCTCTTCGAGTTCTTCTGCAACAA CACCACCATCCACGGCGCCATCCGCCTGGTGTGCTCCC AGCACAACCGCATGAAGACGGCCTTCTGGGCAGTGCT GTGGCTCTGCACCTTTGGCATGATGTACTGGCAATTCG GCCTGCTTTTCGGAGAGTACTTCAGCTACCCCGTCAGC CTCAACATCAACCTCAACTCGGACAAGCTCGTCTTCCCC GCAGTGACCATCTGCACCCTCAATCCCTACAGGTACCC GGAAATTAAAGAGGAGCTGGAGGAGCTGGACCGCAT CACAGAGCAGACGCTCTTTGACCTGTACAAATACAGCT CCTTCACCACTCTCGTGGCCGGCTCCCGCAGCCGTCGC GACCTGCGGGGACTCTGCCGCACCCCTTGCAGCGCC TGAGGGTCCCGCCCCCGCCTCACGGGGCCCGTCGAGC CCGTAGCGTGGCCTCCAGCTTGCGGGACAACAACCCC CAGGTGGACTGGAAGGACTGGAAGATCGGCTTCCAGC TGTGCAACCAGAACAAATCGGACTGCTTCTACCAGACA TACTCATCAGGGGTGGATGCGGTGAGGGAGTGGTACC GCTTCCACTACATCAACATCCTGTCGAGGCTGCCAGAG ACTCTGCCATCCCTGGAGGAGGACACGCTGGGCAACT TCATCTTCGCCTGCCGCTTCAACCAGGTCTCCTGCAACC AGGCGAATTACTCTCACTTCCACCACCCGATGTATGGA AACTGCTATACTTTCAATGACAAGAACAACTCCAACCT CTGGATGTCTTCCATGCCTGGAATCAACAACGGTCTGT CCCTGATGCTGCGCGCAGAGCAGAATGACTTCATTCCC CTGCTGTCCACAGTGACTGGGGCCGGGTAATGGTGC ACGGGCAGGATGAACCTGCCTTTATGGATGATGGTGG CTTTAACTTGCGGCCTGGCGTGGAGACCTCCATCAGCA TGAGGAAGGAAACCCTGGACAGACTTGGGGGCGATT ATGGCGACTGCACCAAGAATGGCAGTGATGTTCCTGTT GAGAACCTTTACCCTTCAAAGTACACACAGCAGGTGTG TATTCACTCCTGCTTCCAGGAGAGCATGATCAAGGAGT GTGGCTGTGCCTACATCTTCTATCCGCGGCCCCAGAAC GTGGAGTACTGTGACTACAGAAAGCACAGTTCCTGGG GGTACTGCTACTATAAGCTCCAGGTTGACTTCTCCTCA GACCACCTGGGCTGTTTCACCAAGTGCCGGAAGCCAT GCAGCGTGACCAGCTACCAGCTCTCTGCTGGTTACTCA CGATGGCCCTCGGTGACATCCCAGGAATGGGTCTTCCA GATGCTATCGCGACAGAACAATTACACCGTCAACAACA AGAGAAATGGAGTGGCCAAAGTCAACATCTTCTTCAA GGAGCTGAACTACAAAACCAATTCTGAGTCTCCCTCTG TCACG\|GTGCTCCTGGAGCTGTTGGTGGGAATATACCC CTCAGGGGTTATTGGACTGGTCCCTCACCTAGGGGAC AGGGAGAAGAGAGATAGTGTGTGTCCCCAAGGAAAA TATATCCACCCTCAAAATAATTCGATTTGCTGTACCAAG TGCCACAAAGGAACCTACTTGTACAATGACTGTCCAGG |

FIG. 27 Cont.

| sample | Gene Breakpoint 5p | Gene Breakpoint 3p | Frame Type | SEQ ID NO: | Fused Sequence |
|---|---|---|---|---|---|
| | | | | | CCCGGGGCAGGATACGGACTGCAGGGAGTGTGAGAG<br>CGGCTCCTTCACCGCTTCAGAAAACCACCTCAGACACT<br>GCCTCAGCTGCTCCAAATGCCGAAAGGAAATGGGTCA<br>GGTGGAGATCTCTTCTTGCACAGTGGACCGGGACACC<br>GTGTGTGGCTGCAGGAAGAACCAGTACCGGCATTATT<br>GGAGTGAAAACCTTTTCCAGTGCTTCAATTGCAGCCTC<br>TGCCTCAATGGGACCGTGCACCTCTCCTGCCAGGAGAA<br>ACAGAACACCGTGTGCACCTGCCATGCAGGTTTCTTTC<br>TAAGAGAAAACGAGTGTGTCTCCTGTAGTAACTGTAA<br>GAAAAGCCTGGAGTGCACGAAGTTGTGCCTACCCCAG<br>ATTGAGAATGTTAAGGGCACTGAGGACTCAGGCACCA<br>CAGTGCTGTTGCCCCTGGTCATTTTCTTTGGTCTTTGCC<br>TTTTATCCCTCCTCTTCATTGGTTTAATGTATCGCTACCA<br>ACGGTGGAAGTCCAAGCTCTACTCCATTGTTTGTGGGA<br>AATCGACACCTGAAAAAGAGGGGGAGCTTGAAGGAA<br>CTACTACTAAGCccctggccccaaacccaagcttcagtcccactcc<br>aggcttcaccccaccctgggcttcagtcccgtgcccagttccaccttca<br>cctccagctccaCCTATACCCCCGGTGACTGTCCCAACTTT<br>GCGGCTCCCCGCAGAGAGGTGGCACCACCCTATCAGG<br>GGGCTGACCCCATCCTTGCGACAGCCCTCGCCTCCGAC<br>CCCATCCCCAACCCCCTTCAGAAGTGGGAGGACAGCG<br>CCCACAAGCCACAGAGCCTAGACACTGATGACCCCGC<br>GACGCTGTACGCCGTGGTGGAGAACGTGCCCCCGTTG<br>CGCTGGAAGGAATTCGTGCGGCGCCTAGGGCTGAGCG<br>ACCACGAGATCGATCGGCTGGAGCTGCAGAACGGGC<br>GCTGCCTGCGCGAGGCGCAATACAGCATGCTGGCGAC<br>CTGGAGGCGGCGCACGCCGCGGCGCGAGGCCACGCT<br>GGAGCTGCTGGGACGCGTGCTCCGCGACATGGACCTG<br>CTGGGCTGCCTGGAGGACATCGAGGAGGCGCTTTgcgg<br>ccccgccgccctcccgcccgcgcccAGTCTTCTCAGA |
| G17675.<br>TCGA-19-<br>2624-<br>01A-01R-<br>1850-<br>01.2 | 69230529 | 63195940 | InFrame | 8326 | ATGGTGAGGAGCAGGCAAATGTGCAATACCAACATGT<br>CTGTACCTACTGATGGTGCTGTAACCACCTCACAGATT<br>CCAGCTTCGGAACAAGAGACCCTGGTTAGACCAAAGC<br>CATTGCTTTTGAAGTTATTAAAGTCTGTTGGTGCACAA<br>AAAGACACTTATACTATGAAAGAGGTTCTTTTTTATCTT<br>GGCCAGTATATTATGACTAAACGATTATATGATGAGAA<br>GCAACAACATATTGTATATTGTTCAAATGATCTTCTAG<br>GAGATTTGTTTGGCGTGCCAAGCTTCTCTGTGAAAGAG<br>CACAGGAAAATATATACCATGATCTACAGGAACTTGGT<br>AGTAGTCAATCAGCAGGAATCATCGGACTCAGGTACA<br>TCTGTGAGTGAGAACAGGTGTCACCTTGAAGGTGGGA<br>GTGATCAAAAGGACCTTGTACAAGAGCTTCAGGAAGA<br>GAAACCTTCATCTTCACATTTGGTTTCTAGACCATCTAC<br>CTCATCTAGAAGGAGAGCAATTAGTGAGACAGAAGAA<br>AATTCAGATGAATTATCTGGTGAACGACAAAGAAAAC<br>GCCACAAATCTGATAGTATTTCCCTTTCCTTTGATGAAA<br>GCCTGGCTCTGTGTGTAATAAGGGAGATATGTTGTGA<br>AAGAAGCAGTAGCAGTGAATCTACAGGGACGCCATCG<br>AATCCGGATCTTGATGCTGGTGTAAGTGAACATTCAGG<br>TGATTGGTTGGATCAGGATTCAGTTTCAGATCAGTTTA<br>GTGTAGAATTTGAAGTTGAATCTCTCGACTCAGAAGAT<br>TATAGCCTTAGTGAAGAAGGACAAGAACTCTCAGATG<br>AAGATGATGAGGTATATCAAGTTACTGTGTATCAGGC<br>AGGGGAGAGTGATACAGATTCATTTGAAGAAGATCCT<br>GAAATTTCCTTAGCT\|GAATCCGAGGGTGTTTCCTGCC |

FIG. 27 Cont.

| sample | Gene Break-point 5p | Gene Break-point 3p | Frame Type | SEQ ID NO: | Fused Sequence |
|---|---|---|---|---|---|
| | | | | | ACTATTGGTCGCTGTTTGACGGGCACGCGGGGTCCGG GGCCGCGGTGGTGGCGTCACGCCTGCTGCAGCACCAC ATCACGGAGCAGCTGCAGGACATCGTGGACATCCTGA AGAACTCCGCCGTCCTGCCCCCTACCTGCCTGGGGGAG GAGCCTGAGAACACGCCCGCCAACAGCCGGACTCTGA CCCGGGCAGCCTCCCTGCGCGGAGGGGTGGGGGCCC CGGGCTCCCCAGCACGCCCCCCACACGCTTCTTTACC GAGAAGAAGATTCCCCATGAGTGCCTGGTCATCGGAG CGCTTGAAAGTGCATTCAAGGAAATGGACCTACAGAT AGAACGAGAGAGGAGTTCATATAATATATCTGGTGGC TGCACGGCCCTCATTGTGATTTGCCTTTTGGGGAAGCT GTATGTTGCAAATGCTGGGGATAGCAGGGCCATAATC ATCAGAAATGGAGAAATTATCCCCATGTCTTCAGAATT TACCCCCGAGACGGAGCGCCAGCGACTTCAGTACCTG GCATTCATGCAGCCTCACTTGCTGGGAAATGAGTTCAC ACATTTGGAGTTTCCAAGGAGAGTACAGAGAAAGGAG CTTGGAAAGAAGATGCTCTACAGGGACTTTAATATGAC AGGCTGGGCATACAAAACCATTGAGGATGAGGACTTG AAGTTCCCCCTTATATATGGAGAAGGCAAGAAGGCCC GGGTAATGGCAACTATTGGAGTGACCAGGGGACTTGG GGACCATGACCTGAAGGTGCATGACTCCAACATCTACA TTAAACCATTCCTGTCTTCAGCTCCAGAGGTAAGAATC TACGATCTTTCAAAATATGATCATGGATCAGATGATGT GCTGATCTTGGCCACTGATGGACTCTGGGACGTTTTAT CAAATGAAGAAGTAGCAGAAGCAATCACTCAGTTTCTT CCTAACTGTGATCCAGATGATCCTCACAGGTACACACT GGCAGCTCAGGACCTGGTGATGCGTGCCCGGGGTGTG CTGAAGGACAGAGGATGGCGGATATCTAATGACCGAC TGGGCTCAGGAGACGACATTTCTGTATATGTCATTCCT TTAATACATGGAAACAAGCTGTCA |
| G17484. TCGA-14-0787-01A-01R-1849-01.2 | 155385535 | 156384545 | InFrame | 8327 | ATGGACCCTAGAAATACTGCTATGTTAGGATTGGGTTC TGATTCCGAAGGTTTTTCAAGAAAGAGTCCTTCTGCCA TCAGTACTGGCACATTGGTCAGTAAGAGAGAAGTAGA GCTAGAAAAAAACACAAAGGAGGAAGAGGACCTTCG CAAACGGAATCGAGAAAGAAACATCGAAGCTGGGAA AGATGATGGTTTGACTGATGCACAGCAACAGTTTTCAG TGAAAGAAACAAACTTTTCAGAGGGAAATTTAAAATT GAAAATTGGCCTCCAGGCTAAGAGAACTAAAAAACCT CCAAAGAACTTGGAGAACTATGTATGTCGACCTGCCAT AAAAACAACTATTAAGCACCCAAGGAAAGCACTTAAA AGTGGAAAGATGACGGATGAAAAGAATGAACACTGTC CTTCAAAACGAGACCCTTCAAAGTTGTACAAGAAAGCA GATGATGTTGCAGCCATTGAATGCCAGTCTGAAGAAG TCATCCGTCTTCATTCACAGGGAGAAAACAATCCTTTG TCTAAGAAGCTGTCTCCAGTACACTCAGAAATGGCAGA TTATATTAATGCAACGCCATCTACTCTTCTTGGTAGCCG GGATCCTGATTTAAAGGACAGAGCATTACTTAATGGA GGAACTAGTGTAACAGAAAAGTTGGCACAGCTGATTG CTACCTGTCCTCCTTCCAAGTCTTCCAAGACAAAACCGA AGAAGTTAGGAACTGGCACTACAGCAGGATTGGTTAG CAAGGATTTGATCAGGAAAGCAGGTGTTGGCTCTGTA GCTGGAATAATACATAAGGACTTAATAAAAAAGCCAA CCATCAGCACAGCAGTTGGATTGGTAACTAAAGATCCT GGGAAAAAGCCAGTGTTTAATGCAGCAGTAGGATTGG TCAATAAGGACTCTGTGAAAAAACTGGGAACTGGCAC |

FIG. 27 Cont.

| sample | Gene Breakpoint 5p | Gene Breakpoint 3p | Frame Type | SEQ ID NO: | Fused Sequence |
|---|---|---|---|---|---|
| | | | | | TACAGCGGTATTCATTAATAAAAACTTAGGCAAAAAGC CAGGAACTATCACTACAGTAGGACTGCTAAGCAAAGA TTCAGGAAAGAAGCTAGGAATTGGTATTGTTCCAGGTT TAGTGCATAAAGAGTCTGGCAAGAAGTTAGGACTTGG CACTGTGGTTGGACTGGTTAATAAAGATTTGGGAAAG AAATTGGGTTCTACTGTTGGCCTAGTGGCCAAGGACTG TGCAAAGAAGATTGTAGCAAGTTCAGCAATGGGATTG GTTAATAAGGACATTGGAAAGAAACTAATGAGTTGTC CTTTGGCAGGTCTGATCAGTAAAGATGCCATAAACCTT AAAGCCGAAGCACTGCTCCCCACTCAGGAACCGCTTAA GGCTTCTTGTAGTACAAACATCAATAATCAGGAAAGTC AGGAACTTTCTGAATCCCTGAAAGATAGTGCCACCAGC AAAACTTTTGAAAAGAATGTTGTACGGCAGAATAAAG AAAGCATATTGGAAAAGTTCTCAGTACGAAAAGAAAT CATTAATTTGGAGAAAGAAATGTTTAATGAAGGAACA TGCATTCAGCAAGACAGTTTCTCATCCAGTGAAAAGGG ATCTTATGAAACCTCAAAGCATGAAAAGCAGCCTCCTG TATATTGCACTTCTCCGGACTTTAAAATGGGAGGTGCT TCTGATGTATCTACCGCTAAATCCCCATTCAGTGCAGTA GGAGAAAGCAATCTCCCTTCCCCATCACCTACTGTATCT GTTAATCCTTTAACCAGAAGTCCCCCTGAAACTTCTTCA CAGTTGGCTCCTAATCCATTACTTTTAAGTTCTACTACA GAACTAATCGAAGAAATTTCTGAATCTGTTGGAAAGA ACCAGTTTACTTCTGAAAGTACCCACTTGAACGTTGGT CATAGGTCAGTTGGTCATAGTATAAGTATTGAATGTAA AGGGATTGATAAAGAGGTAAATGATTCAAAAACTACC CATATAGATATTCCAAGAATAAGCTCTTCCCTTGGAAA AAAGCCAAGTTTGACTTCTGAATCCAGCATTCATACTA TTACTCCTTCAGTTGTTAACTTCACTAGTTTATTTAGTA ATAAGCCTTTTTTAAAACTGGGTGCAGTATCTGCATCA GACAAACACTGCCAAGTTGCTGAAAGCCTAAGTACTA GTTTGCAGTCCAAACCATTAAAAAAAAGAAAAGGAAG AAAACCTCGGTGGACTAAAGTGGTGGCAAGAAGCACA TGCCGGTCTCCAAAAGGGCTAGAATTAGAAAGATCAG AGCTTTTTAAAAACGTTTCATGTAGCTCACTATCAAATA GTAATTCTGAGCCAGCCAAGTTTATGAAAAACATTGGA CCCCCTTCATTTGTAGATCATGACTTCCTTAAACGCCGA TTGCCAAAGTTGAGCAAATCCACAGCTCCATCTCTTGC TCTCTTAGCTGATAGTGAAAAACCATCTCATAAGTCTTT TGCTACTCACAAACTATCCTCCAGTATGTGTGTCTCTAG TGACCTTTTGTCTGATATTTATAAGCCCAAAAGAGGAA GGCCTAAATCTAAGGAGATGCCTCAACTGGAAGGGCC ACCTAAAAGGACTTTAAAAATCCCTGCTTCTAAAGTGT TTTCTTTACAGTCTAAGGAAGAACAAGAACCCCCAATT TTACAGCCAGAAATTGAAATCCCTTCCTTCAAACAAGG TCTGTCTGTGTCTCCTTTTCCAAAAAAGAGAGGCAGGC CTAAGAGGCAAATGAGGTCACCAGTCAAGATGAAGCC ACCTGTACTGTCAGTGGCTCCATTTGTTGCCACTGAAA GTCCAAGCAAGCTAGAATCTGAAAGTGACAACCATAG AAGTAGCAGTGATTTCTTTGAGAGCGAGGATCAACTTC AGGATCCAGATGACCTAGATGACAGTCATAGGCCAAG TGTCTGTAGTATGAGTGACCTTGAGATGGAACCAGAT AAAAAAATTACCAAGAGAAACAATGGACAATTAATGA AAACAATTATCCGCAAAATAAATAAAATGAAGACTTTA AAGAGAAAGAAACTGTTGAATCAGATTCTTTCAAGTTC |

FIG. 27 Cont.

| sample | Gene Breakpoint 5p | Gene Breakpoint 3p | Frame Type | SEQ ID NO: | Fused Sequence |
|---|---|---|---|---|---|
| | | | | | TGTAGAATCAAGTAATAAAGGGAAAGTGCAATCCAAA
CTCCATAATACGGTATCAAGTCTTGCTGCCACATTTGG
CTCTAAATTGGGCCAACAGATAAATGTCAGCAAGAAA
GGAACCATTTATATAGGAAAGAGAAGAGGTCGCAAAC
CAAAAACTGTCTTAAATGGTATTCTTTCTGGTAGTCCTA
CTAGCCTTGCTGTTCTTGAGCAAACAGCTCAACAGGCA
GCTGGGTCAGCATTAGGACAGATTCTTCCCCCATTACT
GCCTTCATCTGCTAGTAGTTCTGAGATTCTTCCATCACC
TATTTGCTCTCAGTCTTCTGGGACTAGTGGAGGTCAGA
GCCCTGTAAGTAGTGATGCAGGTTTTGTTGAACCCAGT
TCAGTGCCATATTTGCATTTACACTCCAGACAGGGCAG
TATGATTCAGACTCTTGCAATGAAGAAGGCCTCAAAG
GGGAGGAGGCGGTTATCTCCTCCTACTTTGTTGCCAAA
TTCTCCTTCGCACTTGAGTGAACTCACATCTCTAAAAGA
AGCTACTCCTTCCCCAATCAGTGAGTCTCATAGTGATG
AGACCATTCCCAGTGATAGTGGAATTGGAACAGATAA
TAACAGCACATCAGACAGGGCAGAGAAATTTTGTGGG
CAAAAAAAGAGGAGGCATTCTTTTGAGCATGTTTCTCT
GATTCCCCCTGAAACCTCTACAGTGCTAAGCAGTCTTA
AAGAAAAACATAAACACAAATGTAAGCGCAGGAATCA
TGATTACCTCAGCTATGACAAGATGAAAAGGCAGAAA
CGAAAACGGAAAAAGAAATATCCCCAGCTTCGAAATA
GACAGGATCCAGACTTTATTGCAGAGCTGGAGGAACT
AATAAGTCGCCTAAGTGAAATTCGGATCACTCATCGAA
GTCATCATTTTATCCCCGAGATCTTCTGCCAACTATCT
TTCGAATCAACTTTAATAGTTTCTATACACATCCTTCTTT
CCCCTTAGACCCCTTTGCACTACATTCGAAAACCTGACTT
AAAAAAGAAAAGAGGGAGACCCCCTAAGATGAGGGA
GGCAATGGCTGAAATGCCTTTTATGCACAGCCTTAGTT
TTCCTCTTTCTAGTACTGGATTCTATCCATCTTATGGTAT
GCCTTACTCTCCTTCACCCCTTACAGCTGCTCCCATAGG
ATTAGGTTACTATGGAAGGTATCCTCCCACTCTTTATCC
ACCTCCTCCATCTCCTTCTTTCACCACGCCACTTCCACCT
CCTTCCTATATGCATGCTGGTCATTTACTTCTCAATCCT
GCCAAATACCATAAGAAAAAGCATAAGCTACTTCGACA
GGAGGCCTTTCTTACAACCAGCAGGACTCCCCTCCTTT
CCATGAGTACCTACCCCAGTGTTCCTCCTGAGATGGCC
TATGGTTGGATGGTTGAGCACAAACACAGGCACCGTC
ACAAACACAGAGAACACCGTTCTTCTGAACAACCCCAG
GTTTCTATGGACACTGGCTCTTCCCGATCTGTCCTGGA
ATCTTTGAAGCGCTATAGATTTGGAAAGGATGCTGTTG
GAGAGCGATATAAGCATAAGGAAAAGCACCGTTGTCA
CATGTCCTGCCCTCATCTCTCTCCTTCAAAAAGCTTAAT
AAACAGAGAGGAACAGTGGGTCCACCGAGAGCCTTCA
GAATCTAGTCCATTGGCCTTGGGATTGCAGACACCTTT
ACAGATTGACTGTTCAGAAAGTTCTCCAAGCTTATCCC
TTGGAGGATTCACTCCCAACTCTGAGCCAGCCAGCAGT
GATGAACATACAAACCTTTTCACAAGTGCAATAGGCAG
CTGCAGAGTTTCAAACCCTAACTCCAGTGGCCGGAAG
AAATTAACTGACAGCCCTGGACTCTTTTCTGCACAGGA
CACTTCACTAAATCGGCTTCACAGAAAGGAGTCACTGC
CTTCTAACGAAAGGGCAGTACAGACTTTGGCAGGCTC
CCAGCCAACCTCTGATAAACCCTCCCAGCGGCCATCAG
AGAGCACAAATTGTAGCCCTACCCGGAAAAGGTCTTC
ATCTGAGAGTACTTCTTCAACAGTAAACGGAGTTCCCT |

FIG. 27 Cont.

| sample | Gene Break-point 5p | Gene Break-point 3p | Frame Type | SEQ ID NO: | Fused Sequence |
|---|---|---|---|---|---|
| | | | | | CTCGAAGTCCAAGATTAGTTGCTTCTGGGGATGACTCT GTGGATAGTCTGCTGCAGCGGATGGTACAAAATGAGG ACCAAGAGCCCATGGAGAAAAGTATTGATGCTGTGAT TGCAACTGCCTCTGCACCACCTTCTTCCAGTCCAGGCC GTAGCCACAGCAAGGACCGAACCCTGGGAAAACCAGA CAGCCTTTTAGTGCCTGCAGTCACAAGTGACTCTTGCA ATAATAGCATCTCACTCCTATCTGAAAAGTTGACAAGC AGCTGTTCCCCCCATCATATCAAGAGAAGTGTAGTGGA AGCTATGCAACGCCAAGCTCGGAAAATGTGCAATTAC GACAAAATCTTGGCCACAAAGAAAAACCTAGACCATG TCAATAAAATCTTAAAAGCCAAAAAACTTCAAAGGCAG GCCAGGACAGGGAATAACTTTGTGAAACGTAGGCCAG GTCGACCTCGGAAATGTCCCCTTCAGGCTGTCGTATCA ATGCAAGCATTCCAGGCTGCTCAGTTTGTCAACCCAGA ATTGAACAGAGACGAGGAAGGAGCAGCACTGCACCTC AGTCCTGACACAGTTACAGATGTAATTGAGGCTGTTGT TCAGAGTGTAAATCTGAACCCAGAACATAAAAAGGGG TTGAAGAGAAAAGGTTGGCTATTGGAAGAACAGACCA GAAAAAAGCAGAAGCCATTACCAGAGGAAGAAGAGC AAGAGAATAATAAAAGCTTTAATGAAGCACCAGTTGA GATTCCCAGTCCTTCTGAAACCCCAGCTAAACCTTCTGA ACCTGAAAGTACCTTGCAGCCTGTGCTTTCTCTCATCCC AAGGGAAAAGAAGCCCCCACGTCCCCCAAAGAAGAAG TATCAGAAAGCAGGGCTGTATTCTGACGTTTACAAAAC TACAGA\|CTTCTCACCTGGGGCGGGTGGGTTCTGCACC ACCCTCCCACCCTCCTTCCTCCGTGTGGACGATAGAGC CACATCCAGCACCACGGACAGCTCCCGGGCGCCTTCAT CTCCTCGTCCTCCAGGCAGCACAAGCCATTGTGGAATC TCCACCAGGTGTACAGAACGGTGCCTCTGCGTCCTGCC ACTCAGGACCTCTCAAGTCCCCGATGTGATGGCTCCTC AGCATGATCAGGAgaaattccatgatcttgcttattcctgtcttggg aagtccttctccatgtctaaccaagatctatatggctatagcaccagctc tttggctcttggcttggcatggctaagttggggagACCAAAAAGAAG AATGTACTTCATCTGGTTGGGCTGGATTCCCTC |
| G17792. TCGA-28- 5204- 01A-01R- 1850- 01.4 | 100065175 | 100061309 | InFrame | 8328 | ATGAGCGGGGGCAAGAAGAAGAGTAGTTTCCAAATCA CCAGCGTCACCACGGACTATGAGGGCCCTGGGAGCCC AGGGGCTTCGGATCCCCCTACCCCACAGCCCCCAACCG GGCCCCCGCCCCGCCTGCCCAATGGGGAGCCCAGCCC CGATCCGGGGGGCAAGGGCACCCCCCGGAATGGCTCC CCACCACCTGGGGCCCCTTCCTCCCGTTTCCGGGTGGT GAAGCTGCCCCACGGCCTGGGAGAGCCTTATCGCCGC GGTCGCTGGACGTGTGTGGATGTTTATGAGCGAGACC TGGAGCCCCACAGCTTCGGCGGACTCCTGGAGGGAAT TCGAGGGGCCTCAGGGGGCGCCGGGGGCAGATCTTT GGATTCCAGGTTGGAGCTGGCCAGCCTCGGCCTGGGC GCCCCCACCCCACCGTCAGGCCTGTCTCAGGGCCCCAC CTCCTGGCTCCGTCCACCCCCCACCTCTCCTGGACCTCA GGCCCGCTCCTTCACTGGGGGACTGGGCCAGCTGGTG GTGCCCAGCAAAGCCAAGGCAGAGAAACCCCCACTGT CGGCCTCCTCACCCCAGCAGCGCCCCCCAGAGCCTGAG ACCGGTGAGAGTGCGGGCACATCCCGGGCTGCCACGC CCCTGCCCTCTCTGAGGGTGGAAGCGGAGGCTGGGGG CTCAGGGGCCAGGACCCCTCCACTGTCCCGGAGGAAA GCTGTAGACATGCGGCTGCGGATGGAGTTGGGTGCTC CAGAAGAGATGGGGCAGGTGCCCCACTTGACTCTCG |

FIG. 27 Cont.

| sample | Gene Breakpoint 5p | Gene Breakpoint 3p | Frame Type | SEQ ID NO: | Fused Sequence |
|---|---|---|---|---|---|
| | | | | | CCCCAGCTCCCCAGCCCTCTACTTCACCCACGATGCCA GCCTGGTTCACAAATCTCCAGACCCCTTCGGAGCAGTA GCAGCTCAGAAGTTCAGCCTGGCCCACTCCATGTTGGC CATCAGTGGTCACCTAGACAGCGACGATGATAGTGGC TCCGGAAGCCTGGTTGGCATTGACAACAAAATCGAGC AAGCCATG\|GTTTTCTTCTGGAGGCAAAAAATTAAACC AACCATCTCAGGACACCCTGACTCCAAGAAACACTCAT TGAAGAAGATGGAGAAGACTCTCCAGGTGGTTGAGAC TTTGAGGTTGGTCGAGCTCCCAAAAGAGGCTAAGCCC AAGTTGGGTGAGTCCCCCGAGCTGGCAGATCCCTGCG TGTTGGCCAAGACTACAGAGGAGACCGAGGTGGAGCT GGGCCAACAGGGCCAATCCCTACTGCAGCTGCCGAGG ACGGCCGTCAAGTCTGTCTCCACGCTCATGGTCTCTGC CCTGCAGAGCGGCTGGCAGATGTGCAGCTGGAAGTCA TCAGTGAGTTCTGCCTCAGTCAGCTCCCAAGTGAGGAC GCAGTCACCTTTGAAGACTCCGGAGGCTGAGTTGCTGT GGGAGGTGTACCTGGTGCTGTGGGCCGTTCGGAAACA CCTGCGCCGGCTGTACCGCAGGCAGGAGAGGCACAG ACGGCACCACGTCCGATGCCATGCTGCCCCCCGACCCA ACCCGGCTCAGTCCCTGAAACTGGATGCCCAAAGTCCC CTC |
| BT299 | 23037536 | 1256473 | InFrame | 8329 | ATGGCTCTGCGGAGGCTGGGGGCCGCGCTGCTGCTG TGCCGCTGCTCGCCGCCGTGGAAg\|GGGCCGGCCAGG ACGTGGGCCGAAGCTGCATCCTGGTCTCCATTGCGGG CAAGAATGTCATGCTGGACTGTGGAATGCACATGGGC TTCAATGACGACCGACGCTTCCCTGACTTCTCCTACATC ACCCAGAACGGCCGCCTAACAGACTTCCTGGACTGTGT GATCATTAGCCACTTCCACCTGGACCACTGCGGGGCAC TCCCCTACTTCAGCGAGATGGTGGGCTACGACGGGCC CATCTACATGACTCACCCCACCCAGGCCATCTGCCCCAT CTTGCTGGAGGACTACCGCAAGATCGCCGTAGACAAG AAGGGCGAGGCCAACTTCTTCACCTCCCAGATGATCAA AGACTGCATGAAGAAGGTGGTGGCTGTCCACCTCCAC CAGACGGTCCAGGTAGATGATGAGCTGGAGATCAAG GCCTACTATGCAGGCCACGTGCTGGGGGCAGCCATGT TCCAGATTAAAGTGGGCTCAGAGTCTGTGGTCTACACG GGTGATTATAACATGACCCCAGACCGACACTTAGGAG CTGCCTGGATTGACAAGTGCCGCCCCAACCTGCTCATC ACAGAGTCCACGTACGCCACGACCATCCGTGACTCCAA GCGCTGCCGGGAGCGAGACTTCCTGAAGAAAGTCCAC GAGACCGTGGAGCGTGGTGGGAAGGTGCTGATACCT GTGTTCGCGCTGGGCCGCGCCCAGGAGCTCTGCATCC TCCTGGAGACCTTCTGGGAGCGCATGAACCTGAAGGT GCCCATCTACTTCTCCACGGGGCTGACCGAGAAGGCC AACCACTACTACAAGCTGTTCATCCCTGGACCAACCA GAAGATCCGCAAGACTTTCGTGCAGAGGAACATGTTT GAGTTCAAGCACATCAAGGCCTTCGACCGGGCTTTTGC TGACAACCCAGGACCGATGGTTGTGTTTGCCACGCCA GGAATGCTGCACGCTGGGCAGTCCCTGCAGATCTTCC GGAAATGGGCCGGAAACGAAAAGAACATGGTCATCAT GCCCGGCTACTGCGTGCAGGGCACCGTCGGCCACAAG ATCCTCAGCGGGCAGCGGAAGCTCGAGATGGAGGGG CGGCAGGTGCTGGAGGTCAAGATGCAGGTGGAGTAC ATGTCATTCAGCGCACACGCGGACGCCAAGGGCATCA TGCAGCTGGTGGGCCAGGCAGAGCCGGAGAGCGTGC |

FIG. 27 Cont.

| sample | Gene Break-point 5p | Gene Break-point 3p | Frame Type | SEQ ID NO: | Fused Sequence |
|---|---|---|---|---|---|
| | | | | | TGCTGGTGCATGGCGAGGCCAAGAAGATGGAGTTCCT GAAGCAGAAGATCGAGCAGGAGCTCCGGGTCAACTG CTACATGCCGGCCAATGGCGAGACGGTGACGCTGCCC ACAAGCCCCAGCATCCCCGTAGGCATCTCGCTGGGGCT GCTGAAGCGGGAGATGGCGCAGGGGCTGCTCCCTGA GGCCAAGAAGCCTCGGCTCCTGCACGGCACCCTGATC ATGAAGGACAGCAACTTCCGGCTGGTGTCCTCAGAGC AAGCCCTCAAAGAGCTGGGTCTGGCTGAGCACCAGCT GCGCTTCACCTGCCGCGTGCACCTGCATGACACACGCA AGGAGCAGGAGACGGCATTGCGCGTCTACAGCCACCT CAAGAGCGTCCTGAAGGACCACTGTGTGCAGCACCTC CCAGACGGCTCTGTGACTGTGGAGTCCGTCCTCCTCCA GGCCGCCGCCCCTTCTGAGGACCCAGGCACCAAGGTG CTGCTGGTCTCCTGGACCTACCAGGACGAGGAGCTGG GGAGCTTCCTCACATCTCTGCTGAAGAAGGGCCTCCCC CAGGCCCCCAGC |
| G17667. TCGA-26-5134-01A-01R-1850-01.2 | 54373484 | 53494330 | InFrame | 8330 | ATGAACCAGCCAGAGTCTGCCAACGATCCTGAACCCCT GTGTGCAGTGTGTGGCCAAGCCCACTCCTTGGAGGAA AACCACTTCTACAGCTATCCAGAGGAAGTGGATGATG ACCTCATCTGCCACATCTGCCTGCAGGCTTTGCTGGAC CCCCTGGACACTCCGTGTGGACACACCTACTGCACCCT CTGCCTCACCAACTTCCTGGTGGAGAAGGACTTCTGTC CCATGGACCGCAAGCCTCTGGTTCTGCAGCACTGCAAG AAGTCCAGCATCCTGGTCAACAAACTCCTCAACAAGCT ACTGGTGACCTGCCCCATTCAGGGAGCACTGCACCCAG GTGTTGCAGCGCTGTGACCTCGAGCATCACTTTCAAAC CAGCTGTAAAGGTGCCTCCCACTACGGCCTGACCAAA GATAGGAAGAGGCGCTCACAAGATGGCTGTCCAGACG GCTGTGCGAGCCTCACAGCCACGGCTCCCTCCCCAGAG GTTTCTGCAGCTGCCACCATCTCCTTAATGACAGACGA GCCTGGCCTAGACAACCCTGCCTACGTGTCCTCGGCAG AGGACGGGCAGCCAGCAATCAGCCCAGTGGACTCTGG CCGGAGCAACCGAACTAGGGCACGGCCCTTTGAGAGA TCCACTATTAGAAGCAGATCATTTAAAAAAATAAATCG AGCTTTGAGTGTTCTTCGAAGGACAAAGAGCGGGAGT GCAGTTGCCAACCATGCCGACCAGGGCAGGGAAAATT CTGAAAACACCACTGCCCCTGAAG\|TTTGGAAACACAT GCTACTG |
| GBM-CUMC33 38_L1 | 41198856 | 41192900 | InFrame | 8331 | ATGTGGCTGAAGGTGGGGGGCCTACTTCGGGGGACC GGTGGACAGCTGGGCCAGACTGTTGGTTGGCCTTGTG GGGCCCTGGGGCCTGGGCCCCACCGCTGGGGACCATG TGGAGGTTCTTGGGCCCAAAAGTTTTACCAGGATGGG CCTGGGAGAGGCCTGGGTGAGGAGGACATTCGCAGG GCACGGGAGGCCCGTCCCAGGAAGACACCCCGGCCCC AGCTGAGTGACCGCTCTCGAGAACGCAAGGTGCCTGC CTCCCGCATCAGCCGCTTGGCCAACTTTGGGGGACTGG CTGTGGGCTTGGGGCTAGGAGTACTGGCCGAGATGGC TAAGAAGTCCATGCCAGGAGGTCGTCTGCAGTCAGAG GGTGGTTCTGGGCTGGACTCCAGCCCCTTCCTGTCGGA GGCCAATGCCGAGCGGATTGTGCAGACCTTATGTACA GTTCGAGGGGCCGCCCTCAAGGTTGGCCAGATGCTCA GCATCCAGGACAACAGCTTCATCAGCCCTCAGCTGCAG CACATCTTTGAGCGGGTCCGCCAGAGCGCCGACTTCAT GCCCCGCTGGCAGATGCTGagagttcttgaagaggagctcggc agggactggcaggccaaggtggcctccttggaggaggtgccctttgCC |

FIG. 27 Cont.

| sample | Gene Break-point 5p | Gene Break-point 3p | Frame Type | SEQ ID NO: | Fused Sequence |
|---|---|---|---|---|---|
| | | | | | GCTGCCTCAATTGGGCAGGTGCACCAGGGCCTGCTGA GGGACGGGACGGAGGTGGCCGTGAAGATCCAGTACC CCGGCATAGCCCAGAGCATTCAGAGCGATGTCCAGAA CCTGCTGGCGGTACTCAAGATGAGCGCGGCCCTGCCC GCGGGCCTGTTTGCCGAGCAGAGCCTGCAGGCCTTGC AGCAGGAGCTGGCTTGGGAGTGTGACTACCGTCGTGA GGCGGCTTGTGCCCAGAATTTCAGGCAGCTGCTGGCA AATGACCCCTTCTTCCGGGTCCCAGCCGTGGTTAAGGA GCTGTGCACGACACGGGTGCTGGGCATGGAGCTGGCT GGAGGGGTCCCCCTGGACCAGTGCCAGGGCCTAAGCC AGGACCTGCGGAACCAGATTTGCTTCCAGCTCCTGACG CTGTGTCTGCGGGAGCTGTTTGAGTTCCGATTCATGCA GACTGACCCCAACTGGGCCAACTTCCTGTATGATGCCT CCAGCCACCAGGTGACCCTGCTGGACTTTGGTGCAAG CCGGGAGTTTGGGACAGAGTTCACAGACCATTACATC GAGGTGGTGAAGGCTGCAGCTGATGGAGACAGAGAC TGTGTCCTGCAGAAGTCCAGGGACCTCAAATTCCTCAC AGGCTTTGAAACCAAG\|GGCGGACCCCGGAGGCCTGA GCGGCACCTGCCCCCAGCCCCTGTGGGGCCCCGGGG CCCCCAGAAACCTGCAGGACGGAGCCAGACGGGGCG GGCACCATGAACAAGTTACGGCAGAGCCTGCGGCGGA GGAAGCCAGCCTACGTGCCCGAGGCGTCGCGCCCGCA CCAGTGGCAGGCAGACGAGGACGCGGTGCGGAAGGG CACGTGCAGCTTCCCGGTCAGGTACCTGGGTCACGTG GAGGTAGAGGAGTCCCGGGGAATGCACGTGTGTGAA GATGCGGTGAAGAAGCTGAAGGCGATGGGCCGAAAG TCCGTGAAGTCTGTCCTGTGGGTGTCAGCCGATGGGC TCCGAGTGGTGGACGACAAAACCAAGGATCTTCTGGT CGACCAGACCATCGAAAAGGTCTCCTTTTGTGCTCCTG ACCGCAACCTGGACAAGGCTTTCTCCTATATCTGTCGT GACGGGACTACCCGCCGCTGGATCTGCCACTGTTTTCT GGCACTGAAGGACTCCGGCGAGAGGCTGAGCCACGCT GTGGGCTGTGCTTTTGCCGCCTGCCTGGAGCGAAAAC AGCGACGGGAGAAGGAATGTGGGGTCACGGCCGCCT TCGATGCCAGCCGCACCAGCTTCGCCCGCGAGGGCTC CTTCCGCCTGTCTGGGGGTGGGCGGCCTGCTGAGCGA GAGGCCCCGGACAAGAAGAAAGCAGAGGCAGCAGCT GCCCCCACTGTGGCTCCTGGCCCTGCCCAGCCTGGGCA CGTGTCCCCGACACCAGCCACCACATCCCTGGTGAGA AGGGTGAGGCAGGCACCCCTGTGGCTGCAGGCACCAC TGCGGCCGCCATCCCCCGGCGCCATGCACCCCTGGAG CAGCTGGTTCGCCAGGGCTCCTTCCGTGGGTTCCCAGC ACTCAGCCAGAAGAACTCGCCTTTCAAACGGCAGCTG AGCCTACGGCTGAATGAGCTGCCATCCACGCTGCAGC GCCGCACTGACTTCCAGGTGAAGGGCACAGTGCCTGA GATGGAGCCTCCTGGTGCCGGCGACAGTGACAGCATC AACGCTCTGTGCACACAGATCAGTTCATCTTTTGCCAG TGCTGGAGCGCCAGCACCAGGGCCACCACCTGCCACA ACAGGGACTTCTGCCTGGGGTGAGCCCTCCGTGCCCCC TGCAGCTGCCTTCCAGCCTGGGCACAAGCGGACACCTT CAGAGGCTGAGCGATGGCTGGAGGAGGTGTCACAGG TGGCCAAGGCCcagcagcagcagcagcagcaacagcaacagca gcagcagcagcagcagcaacagcagcaagcagcCTCAGTGGCCC CAGTGCCCACCATGCCTCCTGCCCTGCAGCCTTTCCCCG CCCCCGTGGGGCCCTTTGACGCTGCACCTGCCCAAGTG |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GCCGTGTTCCTGCCACCCCCACACATGCAGCCCCCTTTT<br>GTGCCCGCCTACCCGGGCTTGGGCTACCCACCGATGCC<br>CCGGGTGCCCGTGGTGGGCATCACACCCTCACAGATG<br>GTGGCAAACGCCTTCTGCTCAGCCGCCCAGCTCCAGCC<br>TCAGCCTGCCACTCTGCTTGGGAAAGCTGGGGCCTTCC<br>CGCCCCCTGCCATACCCAGTGCCCCTGGGAGCCAGGCC<br>CGCCCTCGCCCCAATGGGGCCCCCTGGCCCCCTGAGCC<br>AGCGCCTGCCCCAGCTCCAGAGTTGGACCCCTTTGAGG<br>CCCAGTGGGCGGCATTAGAAGGCAAAGCCACTGTAGA<br>GAAACCCTCCAACCCCTTTTCTGGCGACCTGCAAAAGA<br>CATTCGAGATTGAACTG |
| G17815.<br>TCGA-19-<br>5960-<br>01A-11R-<br>1850-<br>01.4 | 154918048 | 154904891 | InFrame | 8332 | ATGGCCTCCTGCCCAGACTCTGATAATAGCTGGGTGCT<br>TGCTGGCTCCGAGAGCCTGCCAGTGGAGACACTGGGC<br>CCGGCATCCAGGATGGACCCAGAATCTGAGAGAGCCC<br>TGCAGGCCCCTCACAGCCCCTCCAAGACAGATGGGAA<br>AGAATTAGCTGGGACCATGGATGGAGAAGGGACGCT<br>CTTCCAGACTGAAAGCCCTCAGTCTGGCAGCATTCTAA<br>CAGAGGAGACTGAGGTCAAGGGCACCCTGGAAGGTG<br>ATGTTTGTGGTGTGGAGCCTCCTGGCCCAGGAGACAC<br>AGTAGTCCAGGGAGACCTGCAGGAGACCACCGTGGTG<br>ACAGGCCTGGGACCAGACACACAGGACCTGGAAGGC<br>CAGAGCCCTCCACAGAGCCTGCCTTCAACCCCCAAAGC<br>AGCTTGGATCAGGGAGGAGGGCCGCTGCTCCAGCAGT<br>GACGATGACACCGACGTGGACATGGAGGGTCTGCGG<br>AGACGGCGGGGCCGGGAGGCCGGCCCACCTCAGCCC<br>ATGGTGCCCCTGGCTGTGGAGAACCAGGCTGGGGGTG<br>AGGGTGCAGGCGGGGAGCTGGGCATCTCCCTCAACAT<br>GTGCCTCCTTGGGGCCCTGGTTCTGCTTGGCCTGGGG<br>GTCCTCCTCTTCTCAGGTGGCCTCTCAGAGTCTGAGAC<br>TGGGCCCATGGAGGAAGTGGAGCGGCAGGTCCTCCCA<br>GACCCCGAGGTGCTGGAAGCTGTGGGGGACAGGCAG<br>GATGGGCTAAGGGAACAGCTGCAGGCCCCAGTGCCTC<br>CTGACAGTGTCCCCAGCCTGCAAAAACATGGGTCTTCTG<br>CTGGACAAGCTGGCCAAGGAGAACCAGGACATCCGGC<br>TGCTGCAGGCCCAGCTGCAGGCCCAAAAGGAAGAGCT<br>TCAGAGCCTGATGCACCAGCCCAAAGGGCTAGAGGAG<br>GAGAATGCCCAGCTCCGGGGGGCTCTGCAGCAGGGC<br>GAAGCCTTCCAGCGGGCTCTGGAGTCAGAGCTGCAGC<br>AGCTGCGGGCCCGGCTCCAGGGGCTGGAGGCCGACT<br>GTGTCCGGGGCCCAGATGGGGTGTGCCTCAGTGGGG<br>GTAGAGGCCCACAGGGTGACAAGGCCATCAGGGAGC<br>AAGGCCCCAGGGAGCAGGAGCCAGAACTCAGCTTCCT<br>GAAGCAGAAGGAACAGCTGGAGGCTGAGGCACAGGC<br>ATTAAGGCAAGAGTTAGAGAGGCAGCGACGGCTGCT<br>GGGGTCTGTACAGCAGGATCTGGAGAGGAGCTTGCA<br>GGATGCCAGCCGCGGGGACCCAGCTCATGCTGGCTTG<br>GCTGAGCTGGGCCACAGATTGGCCCAGAAACTGCAGG<br>GCCTGGAGAACTGGGGCCAGGACCCTGGGGTCTCTGC<br>CAATGCCTCAAAGGCCTGGCACCAGAAGTCCCACTTCC<br>AGAATTCTAGGGAGTGGAGTGGAAAGGAAAAGTGGT<br>GGGATGGGCAGAGAGACCGGAAGGCTGAGCACTGGA<br>AACATAAGAAGGAAGAATCTGGCCGGGAAAGGAAGA<br>AGAACTGGGGAGGTCAGGAGGACAGGGAGCCAGCAG<br>GAAGGTGGAAGGAGGGCAGGCCAAGGGTGGAGGAG<br>TCGGGGAGCAAGAAGGAGGGCAAGCGACAGGGCCCG |

FIG. 27 Cont.

| sample | Gene Break-point 5p | Gene Break-point 3p | Frame Type | SEQ ID NO: | Fused Sequence |
|---|---|---|---|---|---|
| | | | | | AAGGAACCCCCAAGGAAAAGTGGTAGCTTCCACTCCTCTGGAGAAAAGCAGAAGCAACCTCGGTGGAGGGAAGGGACTAAGGACAGCCATGACCCCCTGCCATCCTGGGCAGAGCTGTTGAGGCCCAAGTACCGGGCACCCCAGGGCTGCTCAGGTGTGGACGAGTGTGCCCGGCAGGAGGGCCTGACTTTCTTTGGCACAGAGCTAGCCCCAGTGCGGCAACAGGAGCTGGCCTCTCTGCTAAGAACATACTTGGCACGGCTGCCCTGGGCTGGGCAGCTGACCAAGGAGCTACCCCTCTCACCTGCTTTCTTTGGTGAGGATGGCATCTTCCGTCATGACCGCCTCCGCTTCCGGGATTTTGTGGATGCCCTGGAGGACAGCTTGGAGGAGGTGGCTGTGCAACAGACAGGTGATGATGATGAAGTAGATGACTTTGAGGACTTCATCTTCAGCCACTTCTTTGGAGACAAAGCACTGAAGAAGAG\|ACTTGGAGCTGATGTCTGTGCTGTCCTCCGGCTCTCTGGTCCACTCAAGGAACAGTATGCTCAGGAGCATGGCTTGAACTTCCAGAGACTCCTGGACACCAGCACCTACAAGGAGGCCTTTCGGAAGGACATGATCCGCTGGGGAGAGGAGAAACGCCAGGCTGACCCAGGCTTCTTTTGCAGGAAGATTGTGGAGGGCATCTCCCAGCCCATCTGGCTGGTGAGTGACACACGGAGAGTGTCTGACATCCAGTGGTTTCGGGAGGCCTATGGGGCCGTGACGCAGACGGTCCGCGTTGTAGCGTTGGAGCAGAGCCGACAGCAGCGGGGCTGGGTGTTCACGCCAGGGGTGGACGATGCTGAGTCAGAATGTGGCCTGGACAACTTCGGGGACTTTGACTGGGTCATCGAGAACCATGGAGTTGAACAGCGCCTGGAGGAGCAGTTGGAGAACCTGATAGAATTTATCCGCTCCAGACTT |
| G17662.TCGA-32-1970-01A-01R-1850-01.2 | 58758160 | 50285014 | InFrame | 8333 | ATGGAAGCACGTTCTATGCTGGTTCCACCCCAGGCATCTGTGTGCTTCGAGGATGTGGCTATGGCATTCACACAGGAGGAGTGGGAACAGCTGGACCTGGCCCAGAGGACACTGTACCGAGAGGTGACACTGGAGACCTGGGAGCATATTGTCTCCCTGGGGCTTTTCCTTTCCAAATCTGATGTGATCTCTCAGCTGGAGCAAGAAGAGGACCTGTGCAGGGCAGAGCAGGAGGCCCCCCGAG\|GTAAGAGCAAAGAGGCGGAAATTAAGAGAATCAACAAGGAACTGGCCAACATCCGCTCCAAGTTCAAAGGAGACAAAGCCTTGGATGGCTACAGTAAGAAAAAATATGTGTGTAAACTGCTTTTCATCTTCCTGCTTGGCCATGACATTGACTTTGGGCACATGGAGGCTGTGAATCTGTTGAGTTCCAATAAATACACAGAGAAGCAAATAGGTTACCTGTTCATTTCTGTGCTGGTGAACTCGAACTCGGAGCTGATCCGCCTCATCAACAACGCCATCAAGAATGACCTGGCCAGCCGCAACCCCACCTTCATGTGCCTGGCCCTGCACTGCATCGCCAACGTGGGCAGCCGGGAGATGGGCGAGGCCTTTGCCGCTGACATCCCCCGCATCCTGGTGGCCGGGGACAGCATGGACAGTGTCAAGCAGAGTGCGGCCCTGTGCCTCCTTCGACTGTACAAGGCCTCGCCTGACCTGGTGCCCATGGGCGAGTGGACGGCGCGTGTGGTACACCTGCTCAATGACCAGCACATGGGTGTGGTCACGGCCGCCGTCAGCCTCATCACCTGTCTCTGCAAGAAGAACCCAGATGACTTCAAGACGTGCGTCTCTCTGGCTGTGTCGCGCCTGAGCCGGATCGTCTCCTCTGCCTCCACCGACCTCCAGGACTACACCTACTACTTCGTCCCAGCACCCTGGCTCTCGGTGAAGCTCCTGCGGCTGCTGCAGTGCTACCCGCCTCCAGAGGATGCGGCTGTGAAGGGGCGGCTGGTGGAATGTCTGGAGACTGTGCTCAACAAGGC |

FIG. 27 Cont.

| sample | Gene Break-point 5p | Gene Break-point 3p | Frame Type | SEQ ID NO: | Fused Sequence |
|---|---|---|---|---|---|
| | | | | | CCAGGAGCCCCCCAAATCCAAGAAGGTGCAGCATTCC
AACGCCAAGAACGCCATCCTCTTCGAGACCATCAGCCT
CATCATCCACTATGACAGTGAGCCCAACCTCCTGGTTC
GGGCCTGCAACCAGCTGGGCCAGTTCCTGCAGCACCG
GGAGACCAACCTGCGCTACCTGGCCCTGGAGAGCATG
TGCACGCTGGCCAGCTCCGAGTTCTCCCATGAAGCCGT
CAAGACGCACATTGACACCGTCATCAATGCCCTCAAGA
CGGAGCGGGACGTCAGCGTGCGGCAGCGGGCGGCTG
ACCTCCTCTACGCCATGTGTGACCGGAGCAATGCCAAG
CAGATCGTGTCGGAGATGCTGCGGTACCTGGAGACGG
CAGACTACGCCATCCGCGAGGAGATCGTCCTGAAGGT
GGCCATCCTGGCCGAGAAGTACGCCGTGGACTACAGC
TGGTACGTGGACACCATCCTCAACCTCATCCGCATTGC
GGGCGACTACGTGAGTGAGGAGGTGTGGTACCGTGT
GCTACAGATCGTCACCAACCGTGATGACGTCCAGGGC
TATGCCGCCAAGACCGTCTTTGAGGCGCTCCAGGCCCC
TGCCTGTCACGAGAACATGGTGAAGGTTGGCGGCTAC
ATCCTTGGGGAGTTTGGGAACCTGATTGCTGGGGACC
CCCGCTCCAGCCCCCCAGTGCAGTTCTCCCTGCTCCACT
CCAAGTTCCATCTGTGCAGCGTGGCCACGCGGGCGCT
GCTGCTGTCCACCTACATCAAGTTCATCAACCTCTTCCC
CGAGACCAAGGCCACCATCCAGGGCGTCCTGCGGGCC
GGCTCCCAGCTGCGCAATGCTGACGTGGAGCTGCAGC
AGCGAGCCGTGGAGTACCTCACCCTCAGCTCAGTGGC
CAGCACCGACGTCCTGGCCACGGTGCTGGAGGAGATG
CCGCCCTTCCCCGAGCGCGAGTCGTCCATCCTGGCCAA
GCTGAAACGCAAGAAGGGGCCAGGGGCCGGCAGCGC
CCTGGACGATGGCCGGAGGGACCCCAGCAGCAACGA
CATCAACGGGGCATGGAGCCCACCCCCAGCACTGTG
TCGACGCCCTCGCCCTCCGCCGACCTCCTGGGGCTGCG
GGCAGCCCCTCCCCCGGCAGCACCCCCGGCTTCTGCAG
GAGCAGGGAACCTTCTGGTGGACGTCTTCGATGGCCC
GGCCGCCCAGCCCAGCCTGGGGCCCACCCCCGAGGAG
GCCTTCCTCAGCGAGCTGGAGCCGCCTGCCCCCGAGA
GCCCCATGGCTTTGCTGGCTGACCCAGCTCCAGCTGCT
GACCCAGGTCCTGAGGACATCGGCCCTCCCATTCCGGA
AGCCGATGAGTTGCTGAATAAGTTTGTGTGTAAGAAC
AACGGGGTCCTGTTCGAGAACCAGCTGCTGCAGATCG
GAGTCAAGTCAGAGTTCCGACAGAACCTGGGCCGCAT
GTATCTCTTCTATGGCAACAAGACCTCGGTGCAGTTCC
AGAATTTCTCACCCACTGTGGTTCACCCGGGAGACCTC
CAGACTCATCTGGCTGTGCAGACCAAGCGCGTGGCGG
CGCAGGTGGACGGCGGCGCGCAGGTGCAGCAGGTGC
TCAATATCGAGTGCCTGCGGGACTTCCTGACGCCCCG
CTGCTGTCCGTGCGCTTCCGGTACGGTGGCGCCCCCA
GGCCCTCACCCTGAAGCTCCCAGTGACCATCAACAAGT
TCTTCCAGCCCACCGAGATGGCGGCCCAGGATTTCTTC
CAGCGCTGGAAGCAGCTGAGCCTCCCTCAACAGGAGG
CGCAGAAAATCTTCAAAGCCAACCACCCCATGGACGCA
GAAGTTACTAAGGCCAAGCTTCTGGGGTTGGCTCTGC
TCTCCTGGACAATGTGGACCCCAACCCTGAGAACTTCG
TGGGGCGGGGATCATCCAGACTAAAGCCCTGCAGGT
GGGCTGTCTGCTTCGGCTGGAGCCCAATGCCCAGGCC
CAGATGTACCGGCTGACCCTGCGCACCAGCAAGGAGC |

FIG. 27 Cont.

| sample | Gene Break-point 5p | Gene Break-point 3p | Frame Type | SEQ ID NO: | Fused Sequence |
|---|---|---|---|---|---|
| | | | | | CCGTCTCCCGTCACCTGTGTGAGCTGCTGGCACAGCAGTTC |
| NYU_E | 65557650 | 65592691 | InFrame | 8334 | ATGGCCTCGGAGAGTGGGAAGCTTTGGGGTGGCCGGTTTGTGGGTGCAGTGGACCCCATCATGGAGAAGTTCAACGCGTCCATTGCCTACGACCGGCACCTTTGGGAGGTGGATGTTCAAGGCAGCAAAGCCTACAGCAGGGGCCTGGAGAAGGCAGGGCTCCTCACCAAGGCCGAGATGGACCAGATACTCCATGGCCTAGACAAGGTGGCTGAGGAGTGGGCCCAGGGCACCTTCAAACTGAACTCCAATGATGAGGACATCCACACAGCCAATGAGCGCCGCCTGAAGGAGCTCATTGGTGCAACGGCAGGGAAGCTGCACACGGGACGGAGCCGGAATGACCAGGTGGTCACAGACCTCAGGCTGTGGATGCGGCAGACCTGCTCCACGCTCTCGGGCCTCCTCTGGGAGCTCATTAGGACCATGGTGGATCGGGCAGAGGCGGAACGTGATGTTCTCTTCCCGGGGTACACCCATTTGCAGAGGGCCCAGCCCATCCGCTGGAGCCACTGGATTCTGAGCCACGCCGTGGCACTGACCCGAGACTCTGAGCGGCTGCTGGAGGTGCGGAAGCGGATCAATGTCCTGCCCCTGGGGAGTGGGGCCATTGCAGGCAATCCCCTGGGTGTGGACCGAGAGCTGCTCCGAGCAGAACTCAACTTTGGGGCCATCACTCTCAACAGCATGGATGCCACTAGTGAGCGGGACTTTGTGGCCGAGTTCCTGTTCTGGGCTTCGCTGTGCATGACCCATCTCAGCAGGATGGCCGAGGACCTCATCCTCTACTGCACCAAGGAATTCAGCTTCGTGCAGCTCTCAGATGCCTACAGCACGGGAAGCAGCCTGATGCCCCAGAAGAAAAACCCCGACAGTTTGGAGCTGATCCGGAGCAAGGCTGGGCGTGTGTTTGGGCGGTGTGCCGGGCTCCTGATGACCCTCAAGGGACTTCCCAGCACCTACAACAAAGACTTACAGGAGGACAAGGAAGCTGTGTTTGAAGTGTCAGACACTATGAGTGCCGTGCTCCAGGTGGCCACTGGCGTCATCTCTACGCTGCAGATTCACCAAGAGAACATGGGACAGGCTCTCAGCCCCGACATGCTGGCCACTGACCTTGCCTATTACCTGGTCCGCAAAGGGATGCCATTCCGCCAGGCCCACGAGGCCTCCGGGAAAGCTGTGTTCATGGCCGAGACCAAGGGGGTCGCCCTCAACCAGCTGTCACTGCAGGAGCTGCAGACCATCAG\|GAAGGATGCCAATTCTGCGCTTCTCAGTAACTACGAGGTATTTCAGTTACTAACTGATCTGAAAGAGCAGCGTAAAGAAAGTGGAAAGAATAAACACAGCTCTGGGCAACAGAACTTGAACACTATCACCTATGAAACGTTAAAATACATATCAAAAACACCATGCAGGCACCAGAGTCCTGAAATTGTCAGAGAATTTCTCACAGCATTGAAAAGCCACAAGTTGACCAAAGCTGAGAAGCTCCAGCTGCTGAACCACCGGCCTGTGACTGCTGTGGAGATCCAGCTGATGGTGGAAGAGAGTGAAGAGCGGCTCACGGAGGAGCAGATTGAAGCTCTTCTCCACACCGTCACCAGCATTCTGCCTGCAGAGCCAGAGGCTGAGCAGAAGAAGAATACAAACAGCAATGTGGCAATGGACGAAGAGGACCCAGCA |
| G17816.TCGA-28-5215-01A-01R-1850-01.4 | 55268106 | 56079562 | InFrame | 8335 | ATGCGACCCTCCGGGACGGCCGGGGCAGCGCTCCTGGCGCTGCTGGCTGCGCTCTGCCCGGCGAGTCGGGCTCTGGAGGAAAAGAAAGTTTGCCAAGGCACGAGTAACAAGCTCACGCAGTTGGGCACTTTTGAAGATCATTTTCTCAGCCTCCAGAGGATGTTCAATAACTGTGAGGTGGTCCTTGGGAATTTGGAAATTACCTATGTGCAGAGGAATTATGATCTTTCCTTCTTAAAGACCATCCAGGAGGTGGCTGGT |

| sample | Gene Break-point 5p | Gene Break-point 3p | Frame Type | SEQ ID NO: | Fused Sequence |
|---|---|---|---|---|---|
| | | | | | TATGTCCTCATTGCCCTCAACACAGTGGAGCGAATTCC<br>TTTGGAAAACCTGCAGATCATCAGAGGAAATATGTACT<br>ACGAAAATTCCTATGCCTTAGCAGTCTTATCTAACTATG<br>ATGCAAATAAAACCGGACTGAAGGAGCTGCCCATGAG<br>AAATTTACAGGAAATCCTGCATGGCGCCGTGCGGTTCA<br>GCAACAACCCTGCCCTGTGCAACGTGGAGAGCATCCA<br>GTGGCGGGACATAGTCAGCAGTGACTTTCTCAGCAAC<br>ATGTCGATGGACTTCCAGAACCACCTGGGCAGCTGCC<br>AAAAGTGTGATCCAAGCTGTCCCAATGGGAGCTGCTG<br>GGGTGCAGGAGAGGAGAACTGCCAGAAACTGACCAA<br>AATCATCTGTGCCCAGCAGTGCTCCGGGCGCTGCCGTG<br>GCAAGTCCCCCAGTGACTGCTGCCACAACCAGTGTGCT<br>GCAGGCTGCACAGGCCCCCGGGAGAGCGACTGCCTG<br>GTCTGCCGCAAATTCCGAGACGAAGCCACGTGCAAGG<br>ACACCTGCCCCCCACTCATGCTCTACAACCCCACCACGT<br>ACCAGATGGATGTGAACCCCGAGGGCAAATACAGCTT<br>TGGTGCCACCTGCGTGAAGAAGTGTCCCCGTAATTATG<br>TGGTGACAGATCACGGCTCGTGCGTCCGAGCCTGTGG<br>GGCCGACAGCTATGAGATGGAGGAAGACGGCGTCCG<br>CAAGTGTAAGAAGTGCGAAGGGCCTTGCCGCAAAGTG<br>TGTAACGGAATAGGTATTGGTGAATTTAAAGACTCACT<br>CTCCATAAATGCTACGAATATTAAACACTTCAAAAACT<br>GCACCTCCATCAGTGGCGATCTCCACATCCTGCCGGTG<br>GCATTTAGGGGTGACTCCTTCACACATACTCCTCCTCTG<br>GATCCACAGGAACTGGATATTCTGAAAACCGTAAAGG<br>AAATCACAGGGTTTTTGCTGATTCAGGCTTGGCCTGAA<br>AACAGGACGGACCTCCATGCCTTTGAGAACCTAGAAA<br>TCATACGCGGCAGGACCAAGCAACATGGTCAGTTTTCT<br>CTTGCAGTCGTCAGCCTGAACATAACATCCTTGGGATT<br>ACGCTCCCTCAAGGAGATAAGTGATGGAGATGTGATA<br>ATTTCAGGAAACAAAAATTTGTGCTATGCAAATACAAT<br>AAACTGGAAAAAACTGTTTGGGACCTCCGGTCAGAAA<br>ACCAAAATTATAAGCAACAGAGGTGAAAACAGCTGCA<br>AGGCCACAGGCCAGGTCTGCCATGCCTTGTGCTCCCCC<br>GAGGGCTGCTGGGGCCCGGAGCCCAGGGACTGCGTC<br>TCTTGCCGGAATGTCAGCCGAGGCAGGGAATGCGTGG<br>ACAAGTGCAACCTTCTGGAGGGTGAGCCAAGGGAGTT<br>TGTGGAGAACTCTGAGTGCATACAGTGCCACCCAGAG<br>TGCCTGCCTCAGGCCATGAACATCACCTGCACAGGACG<br>GGGACCAGACAACTGTATCCAGTGTGCCCACTACATTG<br>ACGGCCCCCACTGCGTCAAGACCTGCCCGGCAGGAGT<br>CATGGGAGAAAACAACACCCTGGTCTGGAAGTACGCA<br>GACGCCGGCCATGTGTGCCACCTGTGCCATCCAAACTG<br>CACCTACGGATGCACTGGGCCAGGTCTTGAAGGCTGT<br>CCAACGAATGGGCCTAAGATCCCGTCCATCGCCACTGG<br>GATGGTGGGGCCCTCCTCTTGCTGCTGGTGGTGGCC<br>CTGGGGATCGGCCTCTTCATGCGAAGGCGCCACATCG<br>TTCGGAAGCGCACGCTGCGGAGGCTGCTGCAGGAGA<br>GGGAGCTTGTGGAGCCTCTTACACCCAGTGGAGAAGC<br>TCCCAACCAAGCTCTCTTGAGGATCTTGAAGGAAACTG<br>AATTCAAAAAGATCAAAGTGCTGGGCTCCGGTGCGTT<br>CGGCACGGTGTATAAGGGACTCTGGATCCCAGAAGGT<br>GAGAAAGTTAAAATTCCCGTCGCTATCAAGGAATTAA<br>GAGAAGCAACATCTCCGAAAGCCAACAAGGAAATCCT<br>CGATGAAGCCTACGTGATGGCCAGCGTGGACAACCCC |

FIG. 27 Cont.

| sample | Gene Breakpoint 5p | Gene Breakpoint 3p | Frame Type | SEQ ID NO: | Fused Sequence |
|---|---|---|---|---|---|
| | | | | | CACGTGTGCCGCCTGCTGGGCATCTGCCTCACCTCCAC CGTGCAGCTCATCACGCAGCTCATGCCCTTCGGCTGCC TCCTGGACTATGTCCGGGAACACAAAGACAATATTGG CTCCCAGTACCTGCTCAACTGGTGTGTGCAGATCGCAA AGGGCATGAACTACTTGGAGGACCGTCGCTTGGTGCA CCGCGACCTGGCAGCCAGGAACGTACTGGTGAAAACA CCGCAGCATGTCAAGATCACAGATTTTGGGCTGGCCA AACTGCTGGGTGCGGAAGAGAAAGAATACCATGCAG AAGGAGGCAAAGTGCCTATCAAGTGGATGGCATTGGA ATCAATTTTACACAGAATCTATACCCACCAGAGTGATG TCTGGAGCTACGGGGTGACTGTTTGGGAGTTGATGAC CTTTGGATCCAAGCCATATGACGGAATCCCTGCCAGCG AGATCCTCCATCCTGGAGAAAGGAGAACGCCTCCCT CAGCCACCCATATGTACCATCGATGTCTACATGATCAT GGTCAAGTGCTGGATGATAGACGCAGATAGTCGCCCA AAGTTCCGTGAGTTGATCATCGAATTCTCCAAAATGGC CCGAGACCCCCAGCGCTACCTTGTCATTCAG\|GATGCT TCATTGGATTTGGAGGAAATGTGATCAGGCAACAAG TCAAGGATAACGCCAAATGGTATATCACTGATTTTGTA GAGCTGCTGGGAGAACTGGAAGAA |
| G17650. TCGA-28-2513-01A-01R-1850-01.2 | 55433922 | 55914330 | Inframe | 8336 | ATGGGCGAGACCATGTCAAAGAGGCTGAAGCTCCACC TGGGAGGGGAGGCAGAAATGGAGGAACGGGCGTTCG TCAACCCCTTCCCGGACTACGAGGCCGCCGCCGGGGC GCTGCTCGCCTCCGGAGCGGCCGAAGAGACAGGCTGT GTTCGTCCCCCGGCGACCACGGATGAGCCCGGCCTCCC TTTTCATCAGGACGGGAAG\|CAAAAAGAAAATAATATT CGTTGTTTAACTACGATTGGACATTTTGGTTTTGAATGT TTGCCCAATCAGTTGGTGAGCAGATCTATCCGACAAGG ATTCACTTTTAATATTCTCTGTGTGGGGGAGACTGGAA TTGGAAAATCGACACTGATAGACACATTGTTAATACT AACTTGAAAGATAACAAATCCTCACATTTTTACTCAAAT GTTGGACTTCAAATTCAGACATATGAACTTCAGGAAAG CAATGTTCAGTTGAAATTGACTGTTGTGGAGACAGTAG GGTATGGTGATCAAATAGACAAAGAAGCCAGCTACCA ACCAATAGTTGACTACATAGATGCCCAATTTGAGGCCT ATCTTCAAGAAGAACTGAAGATTAAACGTTCCTTGTTT GAGTACCATGATTCTCGCGTCCACGTGTGTCTTTACTTC ATTTCACCTACAGGACATTCCCTGAAGTCTCTTGATCTA TTAACAATGAAGAACCTTGACAGTAAGGTGAATATTAT ACCACTGATTGCCAAAGCAGACACTATTTCTAAAAATG ATTTACAGACGTTTAAGAATAAGATAATGAGTGAATTG ATTAGCAATGGCATCCAGATATATCAGCTCCCAACAGA TGAAGAAACTGCTGCTCAAGCGAACTCCTCAGTTAGTG GGCTGTTACCCTTTGCTGTGGTAGGGAGTACAGATGA AGTGAAAGTTGGAAAAAGGATGGTCAGAGGCCGTCA CTACCCTTGGGGAGTTTTGCAAGTGGAAAATGAAAAT CACTGTGACTTCGTTAAGCTCCGAGATATGCTTCTTTGT ACCAATATGGAAAATCTAAAAGAAAAAACCCACACTCA GCACTATGAATGTTATAGGTACCAAAAACTGCAGAAAA ATGGGCTTTACAGATGTGGGTCCAAACAACCAGCCAG TTAGTTTTCAAGAAATCTTTGAAGCCAAAAGACAAGAG TTCTATGATCAATGTCAGAGGGAAGAAGAAGAGTTGA AACAGAGATTTATGCAGCGAGTCAAGGAGAAAGAAGC AACATTTAAAGAAGCTGAAAAAGAGCTGCAGGACAAG TTCGAGCATCTTAAAAATGATTCAACAGGAGGAGATAA |

| sample | Gene Break-point 5p | Gene Break-point 3p | Frame Type | SEQ ID NO: | Fused Sequence |
|---|---|---|---|---|---|
| | | | | | GGAAGCTCGAGGAAGAGAAAAAACAACTGGAAGGAG AAATCATAGATTTTTATAAAATGAAAGCTGCCTCCGAA GCACTGCAGACTCAGCTGAGCACCGATACAAAGAAAG ACAAACATCGTAAGAAA |
| BT308 | 33222419 | 33303169 | InFrame | 8337 | ATGGCGGCTCCCTTGGTCCTGGTGCTGGTGGTGGCTG TGACAGTGCGGGCGGCCTTGTTCCGCTCCAGTCTGGCC GAGTTCATTTCCGAGCGGGTGGAGGTGGTGTCCCCAC TGAGCTCTTGGAAGAGAGTGGTTGAAGGCCTTTCACT GTTGGACTTGGGAGTATCTCCGTATTCTGGAGCAGTAT TTCATGAAACTCCATTAATAATATACCTCTTTCATTTCCT AATTGACTATGCTGAATTGGTGTTTATGATAACTGATG CACTCACTGCTATTGCCCTGTATTTTGCAATCCAGGACT TCAATAAAGTTGTGTTTAAAAAGCAGAAACTCCTCCTA GAACTGGACCAGTATGCCCCAGATGTGGCCGAACTCA TCCGGACCCCTATGGAAATGCGTTACATCCCTTTGAAA GTGGCCCTGTTCTATCTCTTAAATCCTTACACGATTTTG TCTTGTGTTGCCAAGTCTACCTGTGCCATCAACAACACC CTCATTGCTTTCTTCATTTTGACTACGATAAAAG\|ACAT AACCAGTGCGGTGCAATCCAAGCGAAGAAAATCCAAG |
| G17656. TCGA-28- 2514- 01A-02R- 1850- 01.2 | 55268106 | 55588823 | InFrame | 8338 | ATGCGACCCTCCGGGACGGCCGGGGCAGCGCTCCTGG CGCTGCTGGCTGCGCTCTGCCCGGCGAGTCGGGCTCT GGAGGAAAAGAAAGTTTGCCAAGGCACGAGTAACAA GCTCACGCAGTTGGGCACTTTTGAAGATCATTTTCTCA GCCTCCAGAGGATGTTCAATAACTGTGAGGTGGTCCTT GGGAATTTGGAAATTACCTATGTGCAGAGGAATTATG ATCTTTCCTTCTTAAAGACCATCCAGGAGGTGGCTGGT TATGTCCTCATTGCCCTCAACACAGTGGAGCGAATTCC TTTGGAAAACCTGCAGATCATCAGAGGAAATATGTACT ACGAAAATTCCTATGCCTTAGCAGTCTTATCTAACTATG ATGCAAATAAAACCGGACTGAAGGAGCTGCCCATGAG AAATTTACAGGAAATCCTGCATGGCGCCGTGCGGTTCA GCAACAACCCTGCCCTGTGCAACGTGGAGAGCATCCA GTGGCGGGACATAGTCAGCAGTGACTTTCTCAGCAAC ATGTCGATGGACTTCCAGAACCACCTGGGCAGCTGCC AAAAGTGTGATCCAAGCTGTCCCAATGGGAGCTGCTG GGGTGCAGGAGAGGAGAACTGCCAGAAACTGACCAA AATCATCTGTGCCCAGCAGTGCTCCGGGCGCTGCCGTG GCAAGTCCCCCAGTGACTGCTGCCACAACCAGTGTGCT GCAGGCTGCACAGGCCCCCGGGAGAGCGACTGCCTG GTCTGCCGCAAATTCCGAGACGAAGCCACGTGCAAGG ACACCTGCCCCCCACTCATGCTCTACAACCCCACCACGT ACCAGATGGATGTGAACCCCGAGGGCAAATACAGCTT TGGTGCCACCTGCGTGAAGAAGTGTCCCCGTAATTATG TGGTGACAGATCACGGCTCGTGCGTCCGAGCCTGTGG GGCCGACAGCTATGAGATGGAGGAAGACGGCGTCCG CAAGTGTAAGAAGTGCGAAGGGCCTTGCCGCAAAGTG TGTAACGGAATAGGTATTGGTGAATTTAAAGACTCACT CTCCATAAATGCTACGAATATTAAACACTTCAAAAACT GCACCTCCATCAGTGGCGATCTCCACATCCTGCCGGTG GCATTTAGGGGTGACTCCTTCACACATACTCCTCCTCTG GATCCACAGGAACTGGATATTCTGAAAACCGTAAAGG AAATCACAGGGTTTTTGCTGATTCAGGCTTGGCCTGAA AACAGGACGGACCTCCATGCCTTTGAGAACCTAGAAA TCATACGCGGCAGGACCAAGCAACATGGTCAGTTTTCT CTTGCAGTCGTCAGCCTGAACATAACATCCTTGGGATT |

| sample | Gene Break-point 5p | Gene Break-point 3p | Frame Type | SEQ ID NO: | Fused Sequence |
|---|---|---|---|---|---|
| | | | | | ACGCTCCCTCAAGGAGATAAGTGATGGAGATGTGATA<br>ATTTCAGGAAACAAAAATTTGTGCTATGCAAATACAAT<br>AAACTGGAAAAAACTGTTTGGGACCTCCGGTCAGAAA<br>ACCAAAATTATAAGCAACAGAGGTGAAAACAGCTGCA<br>AGGCCACAGGCCAGGTCTGCCATGCCTTGTGCTCCCCC<br>GAGGGCTGCTGGGGCCCGGAGCCCAGGGACTGCGTC<br>TCTTGCCGGAATGTCAGCCGAGGCAGGGAATGCGTGG<br>ACAAGTGCAACCTTCTGGAGGGTGAGCCAAGGGAGTT<br>TGTGGAGAACTCTGAGTGCATACAGTGCCACCCAGAG<br>TGCCTGCCTCAGGCCATGAACATCACCTGCACAGGACG<br>GGGACCAGACAACTGTATCCAGTGTGCCCACTACATTG<br>ACGGCCCCACTGCGTCAAGACCTGCCCGGCAGGAGT<br>CATGGGAGAAAACAACACCCTGGTCTGGAAGTACGCA<br>GACGCCGGCCATGTGTGCCACCTGTGCCATCCAAACTG<br>CACCTACGGATGCACTGGGCCAGGTCTTGAAGGCTGT<br>CCAACGAATGGGCCTAAGATCCCGTCCATCGCCACTGG<br>GATGGTGGGGGCCCTCCTCTTGCTGCTGGTGGTGGCC<br>CTGGGGATCGGCCTCTTCATGCGAAGGCGCCACATCG<br>TTCGGAAGCGCACGCTGCGGAGGCTGCTGCAGGAGA<br>GGGAGCTTGTGGAGCCTCTTACACCCAGTGGAGAAGC<br>TCCCAACCAAGCTCTCTTGAGGATCTTGAAGGAAACTG<br>AATTCAAAAAGATCAAAGTGCTGGGCTCCGGTGCGTT<br>CGGCACGGTGTATAAGGGACTCTGGATCCCAGAAGGT<br>GAGAAAGTTAAAATTCCCGTCGCTATCAAGGAATTAA<br>GAGAAGCAACATCTCCGAAAGCCAACAAGGAAATCCT<br>CGATGAAGCCTACGTGATGGCCAGCGTGGACAACCCC<br>CACGTGTGCCGCCTGCTGGGCATCTGCCTCACCTCCAC<br>CGTGCAGCTCATCACGCAGCTCATGCCCTTCGGCTGCC<br>TCCTGGACTATGTCCGGGAACACAAAGACAATATTGG<br>CTCCCAGTACCTGCTCAACTGGTGTGTGCAGATCGCAA<br>AGGGCATGAACTACTTGGAGGACCGTCGCTTGGTGCA<br>CCGCGACCTGGCAGCCAGGAACGTACTGGTGAAAACA<br>CCGCAGCATGTCAAGATCACAGATTTTGGGCTGGCCA<br>AACTGCTGGGTGCGGAAGAGAAAGAATACCATGCAG<br>AAGGAGGCAAAGTGCCTATCAAGTGGATGGCATTGGA<br>ATCAATTTTACACAGAATCTATACCCACCAGAGTGATG<br>TCTGGAGCTACGGGGTGACTGTTTGGGAGTTGATGAC<br>CTTTGGATCCAAGCCATATGACGGAATCCCTGCCAGCG<br>AGATCTCCTCCATCCTGGAGAAAGGAGAACGCCTCCCT<br>CAGCCACCCATATGTACCATCGATGTCTACATGATCAT<br>GGTCAAGTGCTGGATGATAGACGCAGATAGTCGCCCA<br>AAGTTCCGTGAGTTGATCATCGAATTCTCCAAAATGGC<br>CCGAGACCCCAGCGCTACCTTGTCATTCAG\|TGCACA<br>GAAGCCAAAAAGCATTGCTGGTATTTCGAAGGACTCT<br>ATCCAACCTATTATATATGCCGCTCCTACGAGGACTGC<br>TGTGGCTCCAGGTGCTGTGTGCGGGCCCTCTCCATACA<br>GAGGCTGTGGTACTTCTGGTTCCTTCTGATGATGGGCG<br>TGCTTTTCTGCTGCGGAGCCGGCTTCTTCATCCGGAGG<br>CGCATGTACCCCCGCCGCTGATCGAGGAGCCAGCCTT<br>CAATGTGTCCTACACCAGGCAGCCCCCAAATCCCGGCC<br>CAGGAGCCCAGCAGCCGGGGCCGCCCTATTACACCGA<br>CCCAGGAGGACCGGGGATGAACCCTGTCGGGAATTCC<br>ATGGCAATGGCTTTCCAGGTCCCACCCAACTCACCCCA<br>GGGGAGTGTGGCCTGCCCGCCCCCTCCAGCCTACTGC |

FIG. 27 Cont.

| sample | Gene Breakpoint 5p | Gene Breakpoint 3p | Frame Type | SEQ ID NO: | Fused Sequence |
|---|---|---|---|---|---|
| | | | | | AACACGCCTCCGCCCCCGTACGAACAGGTAGTGAAGGCCAAG |
| G17639. TCGA-12-3652-01A-01R-1849-01.2 | 33295425 | 34382867 | InFrame | 8339 | ATGGCGGAGGCGCCTCCTGTCTCAGGTACTTTTAAATTCAATACAGATGCTGCTGAATTCATTCCTCAGGAGAAAAAAAATTCTGGTCTAAATTGTGGGACTCAAAGGAGACTAGACTCTAATAGGATTGGTAGAAGAAATTACAGTTCACCACCTCCCTGTCACCTTTCCAGGCAGGTCCCTTATGATGAAATCTCTGCTGTTCATCAGCATAGTTATCATCCGTCAGGAAGCAAACCTAAGAGTCAGCAGACGTCTTTCCAGTCCTCTCCTTGTAATAAATCGCCCAAGAGCCATGGCCTTCAGAATCAACCTTGGCAGAAATTGAGGAATGAGAAGCACCATATCAGAGTCAAGAAAGCACAGAGTCTTGCTGAGCAGACCTCAGATACAGCTGGATTAGAGAGCTCGACCAGATCAGAGAGTGGGACAGACCTCAGAGAGCATAGTCCTTCTGAGAGTGAGAAGGAAGTTGTGGGTGCAGATCCCAGGGGAGCAAAACCCAAAAAAGCAACACAGTTTGTATACAGCTATGGTAGAGGACCAAAAGTCAAGGGGAAACTCAAATGTGAATGGAGTAACCGAACAACTCCAAAACCGGAGGATGCTGGACCCGAAAGTACCAAACCTGTGGGGGTTTTCCACCCTGACTCTTCAGAGGCATCCTCTAGAAAAGGAGTATTGGATGGGTATGGAGCCAGACGAAATGAGCAGAGAAGATACCCACAGAAAAGGCCTCCCTGGGAAGTGGAGGGGGCCAGGCCACGACCAGGCAGAAATCCACCAAAACAGGAGGGCCACCGACATACAAACGCAGGACACAGAAACAACATGGGCCCCATTCAAAGGATGACCTCAATGAAAGACCAGCAAAATCTACCTGTGACAGTGAGAACTTGGCAGTCATCAACAAGTCTTCCAGGAGGGTTGACCAAGAGAAATGCACTGTACGGAGGCAGGATCCTCAAGTAGTATCTCCTTTCTCCCGAGGCAAACAGAACCATGTGCTAAAGAATGTGGAAACGCACACAG\|CAGACAAATGCAGCCCAAACTACCTGGGCAGTGACTGGTACAACACATGGAGGATGGAACCTTACAACAGCAGCTGCTGCAACAAGTATACCACCTACCTTCCTCGGCTGCCTAAGGAGGCCAGGATGGAGACAGCAGTTCGAGGAATGCCCTTGGAATGCCCTCCTAGGCCGGAGCGGCTCAATGCCTACGAGCGCGAAGTGATGGTGAACATGCTGAACTCACTGTCGCGGAACCAGCAGCTGCCGCGGATCACGCCCCGATGCGGGTGCGTGGACCCGCTGCCCGGCCGCCTGCCCTTCCATGGTTACGAAAGTGCTTGCTCGGGCCGCCACTACTGTCTGCGCGGGATGGACTACTACGCCAGCGGGGCGCCCTGCACCGACCGCCGCCTGCGGCCTTGGTGCCGGGAGCAACCGACTATGTGTACCTCCCTACGAGCACCGGCCCGGAATGCAGTGTGCTGTTACAACTCCCCCGCCGTCATACTACCCATATCCGAACCCT |
| G17796. TCGA-41-5651-01A-01R-1850-01.4 | 58090156 | 57960909 | InFrame | 8340 | ATGGCGGCGGAAACGCTGCTGTCCAGTTTGTTAGGACTGCTGCTTCTGGGACTCCTGTTACCCGCAAGTCTGACCGGCGGTGTCGGGAGCCTGAACCTGGAGGAGCTGAGTGAGATGCGTTATGGGATCGAGATCCTGCCGTTGCCTGTCATGGGAGGGCAGAGCCAATCTTCGGACGTGGTGATTGTCTCCTCTAAGTACAAACAGCGCTATGAGTGTCGCCTGCCAGCTGGAGCTATTCACTTCCAGCGTGAAAGGGAGGAGGAAACACCTGCTTACCAAGGGCCTGGGATCCCTGAGTTGTTGAGCCCAATGAGAGATGCTCCCTGCTTGCTGAAGACAAAGGACTGGTGGACATATGAATTCTGTTATGGACGCCACATCCAGCAATACCACATGGAAGATTCAGA |

| sample | Gene Break-point 5p | Gene Break-point 3p | Frame Type | SEQ ID NO: | Fused Sequence |
|---|---|---|---|---|---|
| | | | | | GATCAAAGGTGAAGTCCTCTATCTCGGCTACTACCAAT CAGCCTTCGACTGGGATGATGAAACAGCCAAGGCCTC CAAGCAGCATCGTCTTAAACGCTACCACAGCCAGACCT ATGGCAATGGGTCCAAGTGCGACCTTAATGGGAGGCC CCGGGAGGCCGAGGTTCGG\|GGTTGTACTGAACGCTT TGTGTCCAGCCCGGAGGAGATTCTGGATGTGATTGAT GAAGGGAAATCAAATCGTCATGTGGCTGTCACCAACA TGAATGAACACAGCTCTCGGAGCCACAGCATCTTCCTC ATCAACATCAAGCAGGAGAACATGGAAACGGAGCAG AAGCTCAGTGGGAAGCTGTATCTGGTGGACCTGGCAG GGAGTGAGAAGGTCAGCAAGACTGGAGCAGAGGGAG CCGTGCTGGACGAGGCAAAGAATATCAACAAGTCACT GTCAGCTCTGGGCAATGTGATCTCCGCACTGGCTGAG GGCACTAAAAGCTATGTTCCATATCGTGACAGCAAAAT GACAAGGATTCTCCAGGACTCTCTCGGGGGAAACTGC CGGACGACTATGTTCATCTGTTGCTCACCATCCAGTTAT AATGATGCAGAGACCAAGTCCACCCTGATGTTTGGGC AGCGGGCAAAGACCATTAAGAACACTGCCTCAGTAAA TTTGGAGTTGACTGCTGAGCAGTGgaagaagaaatatgag aaggagaaggagaagacaaaggcccagaaggagaCGATTGCGA AGCTGGAGGCTGAGCTGAGCCGGTGGCGCAATGGAG AGAATGTGCCTGAGACAGAGCGCCTGGCTGGGGAGG AGGCAGCCCTGGGAGCCGAGCTCTGTGAGGAGACCCC TGTGAATGACAACTCATCCATCGTGGTGCGCATCGCGC CCGAGGAGCGGCAGAAATACGAGGAGGAGATCCGCC GTCTCTATAAGCAGCTTGACGACAAGGATGATGAAAT CAACCAACAAAGCCAACTCATAGAGAAGCTCAAGCAG CAAATGCTGGACCAGGAAGAGCTGCTGGTGTCCACCC GAGGAGACAACGAGAAGGTCCAGCGGGAGCTGAGCC ACCTGCAATCAGAGAACGATGCCGCTAAGGATGAGGT GAAGGAAGTGCTGCAGGCCCTGGAGGAGCTGGCTGT GAACTATGACCAGAAGTCCCAGGAGGTGGAGGAGAA GAGCCAGCAGAACCAGCTTCTGGTGGATGAGCTGTCT CAGAAGGTGGCCACCATGCTGTCCCTGGAGTCTGAGT TGCAGCGGCTACAGGAGGTCAGTGGACACCAGCGAA AACGAATTGCTGAGGTGCTGAACGGGCTGATGAAGGA TCTGAGCGAGTTCAGTGTCATTGTGGGCAACGGGGAG ATTAAGCTGCCAGTGGAGATCAGTGGGGCCATCGAGG AGGAGTTCACTGTGGCCCGACTCTACATCAGCAAAATC AAATCAGAAGTCAAGTCTGTGGTCAAGCGGTGCCGGC AGCTGGAGAACCTCCAGGTGGAGTGTCACCGCAAGAT GGAAGTGACCGGGCGGGAGCTCTCATCCTGCCAGCTC CTCATCTCTCAGCATGAGGCCAAGATCCGCTCGCTTAC GGAATACATGCAGAGCGTGGAGCTAAAGAAGCGGCA CCTGGAAGAGTCCTATGACTCCTTGAGCGATGAGCTG GCCAAGCTCCAGGCCCAGGAAACTGTGCATGAAGTGG CCCTGAAGGACAAGGAGCCTGACACTCAGGATGCAGA TGAAGTGAAGAAGGCTCTGGAGCTGCAGATGGAGAG TCACCGGGAGGCCCATCACCGGCAGCTGGCCCGGCTC CGGGACGAGATCAACGAGAAGCAGAAGACCATTGAT GAGCTCAAAGACCTAAATCAGAAGCTCCAGTTAGAGC TAGAGAAGCTTCAGGCTGACTACGAAGCTGAAGAG CGAAGAACACGAGAAGAGCACCAAGCTGCAGGAGCT GACATTTCTGTACGAGCGACATGAGCAGTCCAAGCAG GACCTCAAGGGTCTGGAGGAGACAGTTGCCCGGGAAC |

FIG. 27 Cont.

| sample | Gene Break-point 5p | Gene Break-point 3p | Frame Type | SEQ ID NO: | Fused Sequence |
|---|---|---|---|---|---|
| | | | | | TCCAGACCCTCCACAACCTTCGCAAGCTGTTCGTTCAA GACGTCACGACTCGAGTCAAGAAAAGTGCAGAAATGG AGCCCGAAGACAGTGGGGGGATTCACTCCCAAAAGCA GAAGATTTCCTTTCTTGAGAACAACCTGGAACAGCTTA CAAAGGTTCACAAACAGCTGGTACGTGACAATGCAGA TCTGCGTTGTGAGCTTCCTAAATTGGAAAAACGACTTA GGGCTACGGCTGAGAGAGTTAAGGCCCTGGAGGGTG CACTGAAGGAGGCCAAGGAGGGCGCCATGAAGGACA AGCGCCGGTACCAGCAGGAGGTGGACCGCATCAAGG AGGCCGTTCGCTACAAGAGCTCGGGCAAACGGGGCCA TTCTGCCCAGATTGCCAAACCCGTCCGGCCTGGCCACT ACCCAGCATCCTCACCCACCAACCCCTATGGCACCCGG AGCCCTGAGTGCATCAGTTACACCAACAGCCTCTTCCA GAACTACCAGAATCTCTACCTGCAGGCCACACCCAGCT CCACCTCAGATATGTACTTTGCAAACTCCTGTACCAGC AGTGGAGCCACATCTTCTGGCGGCCCCTTGGCTTCCTA CCAGAAGGCCAACATGGACAATGGAAATGCCACAGAT ATCAATGACAATAGGAGTGACCTGCCGTGTGGCTATG AGGCTGAGGACCAGGCCAAGCTTTTCCCTCTCCACCAA GAGACAGCAGCCAGC |
| G17468. TCGA-19-0957-02A-11R-2005-01.2 | 61554352 | 90122482 | InFrame | 8341 | ATGAAGCTTGCTGACAGCGTAATGGCAGGGAAAGCTT CCGACGGCTCCATCAAATGGCAGCTCTGCTACGACATC TCGGCCAGAACTTGGTGGATGGATGAATTTCATCCTTT CATCGAAGCACTTCTGCCCCACGTCCGAGCCTTTGCCT ACACATGGTTCAACCTGCAGGCCCGAAAACGAAAATA CTTCAAAAAACATGAAAAGCGTATGTCAAAAGAAGAA GAGAGAGCCGTGAAGGATGAATTGCTAAGTGAAAAA CCAGAGGTCAAGCAGAAGTGGGCATCTCGACTTCTGG CAAAGTTGCGGAAAGATATCCGACCCGAATATCGAGA GGATTTTGTTCTTACAGTTACAGGGAAAAAACCTCCAT GTTGTGTTCTTTCCAACCCAGACCAGAAAGGCAAGATG CGAAGAATTGACTGCCTCCGCCAGGCAGATAAAGTCT GGAGGTTGGACCTTGTTATGGTGATTTTGTTTAAAGGT ATTCCGCTGGAAAGTACTGATGGCGAGCGCCTTGTAA AGTCCCCACAATGCTCTAATCCAGGGCTCTGTGTCCAA CCCCATCACATAGGGGTTTCTGTTAAGGAACTCGATTT ATATTTGGCATACTTTGTGCATGCAGCAG|TAATTAGT GAATGCCAAAGGCAGCAACTGGAGGCTGTGAGCTACT CCTCTCGATATGCTCTGGGCCTCTTTTATGAAGCTGGT ACGAAGATTGATGTCCCTTGGGCTGGGCAGTACATCA CCAGTAATCCCTGCATACGCTTCGTCTCCATTGATAATA AGAAGCGCAATATAGAGTCATCAGAAATTGGGCCTTC CCTCGTGATTCACACCACTGTCCCATTTGGAGTTACATA CTTGGAACACAGCATTGAGGATGTGCAAGAGTTAGTC TTCCAGCAGCTGGAAAACATTTTGCCGGGTTTGCCTCA GCCAATTGCTACCAAATGCCAAAAATGGAGACATTCAC AGGTTACAAATGCTGCTGCCAACTGTCCTGGCCAAATG ACTCTGCATCACAAACCTTTCCTTGCATGTGGAGGGGA TGGATTTACTCAGTCCAACTTTGATGGCTGCATCACTTC TGCCCTATGTGTTCTGGAAGCTTTAAAGAATTATATT |
| G17790. TCGA-06-5856-01A-01R- | 20304379 | 20987526 | InFrame | 8342 | ATGATGTTAAGAGGAAACCTGAAGCAAGTGCGCATTG AGAAAAACCCGGCCCGCCTTCGCGCCCTGGAGTCCGC GGTGGGCGAGAGCGAGCCGGCGGCCGCGGCAGCCAT GGCGCTCGCTCTTGCCGGGGAGCCGGCACCGCCCGCG CCCGCGCCCTCCAGAGGACCACCCGGACGAGGAGATGG |

FIG. 27 Cont.

| sample | Gene Break- point 5p | Gene Break- point 3p | Frame Type | SEQ ID NO: | Fused Sequence |
|---|---|---|---|---|---|
| 1849-01.4 | | | | | GGTTCACTATCGACATCAAGAGTTTCCTCAAGCCGGGC GAGAAGACGTACACGCAGCGCTGCCGCCTCTTCGTGG GAAATCTGCCCACCGACATCACGGAGGAGGACTTCAA GAGGCTCTTCGAACGCTATGGCGAGCCCAGCGAAGTC TTCATCAACCGGGACCGTGGCTTCGGCTTCATCCGCTT GGAATCCAGAACCCTGGCTGAAATTGCAAAAGCAGAG CTGGACGGCACCATTCTCAAGAGCAGACCTCTACGGAT TCGCTTCGCTACACATGGAGCAGCCTTGACTGTCAAGA ACCTTTCTCCAGTTGTTTCCAATGAGCTGCTAGAGCAA GCATTTTCTCAGTTTGGTCCAGTAGAGAAAGCTGTTGT GGTTGTGGATGATCGCGGTAGAGCTACAGGAAAAGGT TTTGTAGAGTTTGCAGCAAAACCTCCTGCACGAAAGGC TCTGGAAAGATGTGGTGATGGGGCATTCTTGCTAACA ACGACCCTCGTCCAGTCATTGTGGAACCCATGGAGCA GTTTGATGATGAAGATGGCTTGCCAGAGAAGCTGATG CAGAAAACTCAACAATATCATAAGGAAAGAGAACAAC CACCACGTTTTGCTCAACCTGGGACATTTGAATTTGAG TATGCATCTCGATGGAAGGCTCTTGATGAAATGGAAA AGCAGCAGCGTGAGCAGGTTGATAGAAACATCAGAG AAGCCAAAGAGAAACTGGAGGCAGAAATGGAAGCAG CTAGGCATGAACACCAATTAATGCTAATGAGGCAAGA TCTAATGAGGCGTCAAGAAGAACTCAGACGCTTGGAA GAACTCAGAAACCAAGAGTTGCAAAAACGGAAGCAAA TACAACTAAGACATGAAGAGGAGCATCGGCGGCGTGA GGAAGAAATGATCCGACACAGAGAACAGGAGGAACT GAGGCGACAGCAAGAGGGCTTTAAGCCAAACTACATG GAAAAT\|GAAGGAATCGTGTCTCCTAGTGACCTGGACC TTGTCATGTCAGAAGGGTTGGGCATGCGGTATGCATTC ATTGGACCCCTGGAAACCATGCATCTCAATGCAGAAG GTATGTTAAGCTACTGCGACAGATACAGCGAAGGCAT AAAACATGTCCTACAGACTTTTGGACCCCATTCCAGAGT TTTCCAGGGCCACTGCTGAGAAGGTTAACCAGGACAT GTGCATGAAGGTCCCTGATGACCCGGAGCACTTAGCT GCCAGGAGGCAGTGGAGGGACGAGTGCCTCATGAGA CTCGCCAAGTTGAAGAGTCAAGTGCAGCCCCAG |
| GBM-CUMC3338_L1 | 7470322 | 7217040 | InFrame | 8343 | ATGAAAGAGACTATACAAGGGACCGGGTCCTGGGGG CCTGAGCCTCCTGGACCCGGCATACCCCCAGCTTACTC AAGTCCCAGGCGGGAGCGTCTTCGTTGGCCCCCACCTC CCAAACCCCGACTCAAGTCAGGTGGAGGGTTTGGGCC AGATCCTGGGTCAGGGACCACAGTGCCAGCCAGACGC CTCCCTGTCCCCCGACCCTCTTTTGATGCCTCAGCAAGT gaagaggaggaagaagaggaggaggaggaggatgaagatgaagag gaggaAGTGGCAGCTTGGAGGCTGCCCCAAGATGGA GTCAGCTGGGAACCTCCCAGCGGCCCCGCCCTTCCCGC CCCACTCATCGAAAAACCTGCTCACAGCGCCGCCGCCG AGCCATGAGAGCCTTCCGGATGCTGCTCTACTCAAAAA GCACCTCGCTGACATTCCACTGGAAGCTTTggggcgcca ccggggccggcggcggggccTCGCACACCCCAAGAACCATCT TTCACCCCAGCAAGGGGGTGCGACGCCACAGGTGCCA TCCCCCTGTTGTCGTTTTGACTCCCCCGGGGGCCACCT CCACCCCGGCTGGGTCTGCTAGGTGCTCTCATGGCTGA GGATGGGGTGAGAGGGTCTCCACCAGTGCCCTCTGGG CCCCCCATGGAGGAAGATGGACTCAGGTGGACTCCAA AGTCTCCTCTGGACCCTGACTCGGGCCTCCTTTCATGTA CTCTGCCCAACGGTTTTGGGGGACAATCTGGGCCAGA |

FIG. 27 Cont.

| sample | Gene Breakpoint 5p | Gene Breakpoint 3p | Frame Type | SEQ ID NO: | Fused Sequence |
|---|---|---|---|---|---|
| | | | | | AGGGGAGCGCAGCTTGGCACCCCCTGATGCCAGCATC CTCATCAGCAATGTGTGCAGCATCGGGGACCATGTGG CCCAGGAGCTTTTTCAGGGCTCAGATTTGGGCATGGCA GAAGAGGCAGAGAGGCCTGGGGAGAAAGCCGGCCA GCACAGCCCCCTGCGAGAGGAGCATGTGACCTGCGTA CAGAGCATCTTGGACGAATTCCTTCAAACGTATGGCAG CCTCATACCCCTCAGCACTGATGAGGTAGTAGAGAAG CTGGAGGACATTTTCCAGCAGGAGTTTTCCACCCCTTC CAGGAAGGGCCTGGTGTTGCAGCTGATCCAGTCTTAC CAGCGGATGCCAGGCAATGCCATGGTGAGGGGCTTCC GAGTGGCTTATAAGCGGCACGTGCTGACCATGGATGA CTTGGGGACCTTGTATGGACAGAACTGGCTCAATGAC CAGGTGATGAACATGTATGGAGACCTGGTCATGGACA CAGTCCCTGAAAAGGTGCATTTCTTCAATAGTTTCTTCT ATGATAAACTCCGTACCAAGGGGTTATGATGGGGTGAA AAGGTGGACCAAAAAC\|ACCCGGCACTACGTGGGCTC AGCAGCTGCTTTTGCAGGGACACCAGAGCATGGACAA TTCCAAGGCAGTCCTGGTGGTGCCTATGGGACTGCTCA GCCCCCACCTCACTATGGGCCCACACAGCCAGCTTATA GTCCTAGTCAGCAGCTCAGAGCTCCTTCGGCATTCCCT GCAGTGCAGTACCTATCTCAGCCACAGCCACAGCCCTA TGCTGTGCATGGCCACTTTCAGCCCACTCAGACAGGTT TCCTCCAGCCTGGTGGTGCCCTGTCCTTGCAAAAGCAG ATGGAACATGCTAACCAGCAGACTGGCTTCTCCGACTC ATCCTCTCTGCGCCCCATGCACCCCCAGGCTCTGCATCC AGCCCCTGGACTCCTTGCTTCCCCCCAGCTCCCTGTGCA GATGCAGCCAGCAGGAAAGTCGGGCTTTGCAGCTACC AGCCAACCTGGCCCTCGGCTCCCCTTCATCCAACACAG CCAGAACCCGCGATTCTACCACAAG |
| G17790. TCGA-06-5856-01A-01R-1849-01.4 | 117175595 | 69229609 | InFrame | 8344 | ATGGTGAACCTGGCGGCCATGGTGTGGCGCCGGCTTC TGCGGAAGAGGTGGGTGCTCGCCCTGGTCTTCGGGCT GTCGCTCGTCTACTTCCTCAGCAGCACCTTCAAGCAG\| GATCTTGATGCTGGTGTAAGTGAACATTCAGGTGATTG GTTGGATCAGGATTCAGTTTCAGATCAGTTTAGTGTAG AATTTGAAGTTGAATCTCTCGACTCAGAAGATTATAGC CTTAGTGAAGAAGGACAAGAACTCTCAGATGAAGATG ATGAGGTATATCAAGTTACTGTGTATCAGGCAGGGGA GAGTGATACAGATTCATTTGAAGAAGATCCTGAAATTT CCTTAGCTGACTATTGGAAATGCACTTCATGCAATGAA ATGAATCCCCCCCTTCCATCACATTGCAACAGATGTTG GGCCCTTCGTGAGAATTGGCTTCCTGAAGATAAAGGG AAAGATAAAGGGGAAATCTCTGAGAAAGCCAAACTGG AAAACTCAACACAAGCTGAAGAGGGCTTTGATGTTCCT GATTGTAAAAAAACTATAGTGAATGATTCCAGAGAGT CATGTGTTGAGGAAATGATGATAAAATTACACAAGC TTCACAATCACAAGAAAGTGAAGACTATTCTCAGCCAT CAACTTCTAGTAGCATTATTTATAGCAGCCAAGAAGAT GTGAAAGAGTTTGAAAGGGAAGAAACCCAAGACAAA GAAGAGAGTGTGGAATCTAGTTTGCCCCTTAATGCCAT TGAACCTTGTGTGATTTGTCAAGGTCGACCTAAAAATG GTTGCATTGTCCATGGCAAAACAGGACATCTTATGGCC TGCTTTACATGTGCAAAGAAGCTAAAGAAAAGGAATA AGCCCTGCCCAGTATGTAGACAACCAATTCAAATGATT GTGCTAACTTATTTCCCC |

FIG. 27 Cont.

| sample | Gene Breakpoint 5p | Gene Breakpoint 3p | Frame Type | SEQ ID NO: | Fused Sequence |
|---|---|---|---|---|---|
| G17802. TCGA-28-5208-01A-01R-1850-01.4 | 51203855 | 55886916 | InFrame | 8345 | ATGGACGCGCCGCGCGCCTCGGCGGCCAAGCCCCCGA CCGGGAGGAAGATGAAGGCTCGTGCTCCCCCACCTCC TGGAAAGGCTGCCACTCTGCATGTGCACAGTGACCAG AAGCCCCCCCACGATGGGGCCCTCGGGTCGCAGCAGA ACTTGGTTCGCATGAAGGAGGCGCTGAGGGCCAGCAC CATGGACGTCACCGTGGTCCTGCCTAGTGGGCTGGAG AAGAGGAGCGTGCTCAATGGGAGCCATGCGATGATG GACCTACTGGTTGAACTTTGCCTTCAGAACCACCTGAA TCCATCCCACCATGCCCTTGAAATTCGGTCTTCAGAAAC CCAACAACCTTTGAGTTTTAAGCCAAATACTTTGATTG GGACCCTGAATGTGCATACTGTGTTTCTGAAAGAAAAA GTTCCTGAAGAGAAGGTTAAGCCTGGTCCCCCTAAGG TGCCTGAGAAATCTGTGCGTTTGGTCGTGAATTACCTG CGGACACAAAAAGCTGTTGTGCGTGTGAGCCCTGAGG TTCCTCTCCAGAATATTCTCCCAGTCATTTGTGCAAAGT GTGAGGTCAGCCCAGAGCACGTGGTTCTCCTCAGGGA CAACATTGCCGGAGAGGAGCTGGAGCTGTCCAAGTCC CTGAACGAGCTCGGGATAAAGGAGCTCTACGCGTGGG ACAACAGAAGAGAAACCTTTAGGAAATCATCACTTGG CAATGATGAGACAGATAAAGAGAAGAAAAAATTTCTG GGATTTTTCAAAGTTAATAAAAGAAGCAATAGTAAGG CTGAGCAGCTCGTGCTGTCGGGTGCAGACAGCGATGA GGACACCTCCAGGGCTGCCCCAGGAAGGGGTTTGAAC GGCTGTTTAACGACCCCCAACTCCCCATCCATGCACTC ACGTTCTCTTACGCTGGGTCCATCCCTCTCGCTGGGCA GCATCTCAGGGGTGTCCGTGAAGTCGGAGATGAAGAA GCGCCGAGCCCCTCCTCCTCCAGGTTCAGGGCCACCTG TGCAAGACAAGGCATCGGAAAAG\|GGGCTGTTACCCT TTGCTGTGGTAGGGAGTACAGATGAAGTGAAAGTTGG AAAAAGGATGGTCAGAGGCCGTCACTACCCTTGGGGA GTTTTGCAAGTGGAAAATGAAAATCACTGTGACTTCGT TAAGCTCCGAGATATGCTTCTTTGTACCAATATGGAAA ATCTAAAAGAAAAAACCCACACTCAGCACTATGAATGT TATAGGTACCAAAAACTGCAGAAAATGGGCTTTACAG ATGTGGGTCCAAACAACCAGCCAGTTAGTTTTCAAGAA ATCTTTGAAGCCAAAAGACAAGAGTTCTATGATCAATG TCAGAGGGAAGAAGAAGAGTTGAAACAGAGATTTAT GCAGCGAGTCAAGGAGAAAGAAGCAACATTTAAAGA AGCTGAAAAAGAGCTGCAGGACAAGTTCGAGCATCTT AAAATGATTCAACAGGAGGAGATAAGGAAGCTCGAG GAAGAGAAAAAACAACTGGAAGGAGAAATCATAGATT TTTATAAAATGAAAGCTGCCTCCGAAGCACTGCAGACT CAGCTGAGCACCGATACAAAGAAAGACAAACATCGTA AGAAA |
| G17210. TCGA-12-0616-01A-01R-1849-01.2 | 101176424 | 30536851 | InFrame | 8346 | ATGAAGCTGGCCCTGCTCCTGCCCTGGGCGTGTTGCTG CCTCTGCGGGTCGGCGCTGGCCACCGGCTTCCTCTATC CCTTCTCGGCCGCAGCTCTGCAGCAGCACGGCTACCCC GAGCCCGGCGCCGGCTCCCCTGGCAGCGGCTACGCGA GCCGCCGGCACTGGTGCCATCACACAGTGACACGGAC GGTGTCCTGCCAGGTGCAGAATGGCTCGGAGACGGTG GTCCAGCGCGTGTACCAGAGCTGCCGGTGGCCGGGGC CCTGCGCCAACCTCGTAAGTTACAGGACTCTGATCAGA CCCACCTACAGAGTGTCCTACCGCACGGTGACGGTGCT GGAGTGGAGATGCTGCCCTGGCTTCACCGGGAGCAAC TGTGATGAGGAATGCATGAACTGCACCCGGCTCAGTG |

FIG. 27 Cont.

| sample | Gene Break-point 5p | Gene Break-point 3p | Frame Type | SEQ ID NO: | Fused Sequence |
|---|---|---|---|---|---|
| | | | | | ACATGAGTGAGCGACTGACCACACTGGAGGCCAAG\|A TTATTTGCATGGGTGCAAAAGAAAATGGTTTGCCGCTG GAGTATCAAGAGAAGTTAAAAGCAATAGAACCAAATG ACTATACAGGAAAGGTCTCAGAAGAAATTGAAGACAT CATCAAAAAGGGGGAAACACAAACTCTT |
| NYU_B | 233613792 | 234862561 | InFrame | 8347 | ATGGCAGCGGAAACGCAGACACTGAACTTTGGGCCTG AATGGCTCCGAGCTCTGTCCAGTGGTGGGAGTATTAC ATCCCCTCCTCTTTCTCCAGCATTGCCGAAGTATAAATT AGCAGATTATCGTTACGGCAGAGAAGAAATGTTAGCA CTTTTCCTTAAAGACAACAAGATACCTTCAGACCTTCTG GATAAAGAATTTCTGCCTATCCTCCAGGAGGAACCCCT TCCACCATTGGCTCTGGTACCCTTTACAGAAGAAGAAC AG\|CTCAAAGAAATTCTCGAATGTTCTCACCTATTAACA GTTATTAAAATGGAAGAAGCTGGGGATGAAATTGTGA GCAATGCCATCTCCTACGCTCTATACAAAGCCTTCAGC ACCAGTGAGCAAGACAAGGATAACTGGAATGGGCAG CTGAAGCTTCTGCTGGAGTGGAACCAGCTGGACTTAG CCAATGATGAGATTTTCACCAATGACCGCCGATGGGA GTCTGCTGACCTTCAAGAAGTCATGTTTACGGCTCTCA TAAAGGACAGACCCAAGTTTGTCCGCCTCTTTCTGGAG AATGGCTTGAACCTACGGAAGTTTCTCACCCATGATGT CCTCACTGAACTCTTCTCCAACCACTTCAGCACGCTTGT GTACCGGAATCTGCAGATCGCCAAGAATTCCTATAATG ATGCCCTCCTCACGTTTGTCTGGAAACTGGTTGCGAAC TTCCGAAGAGGCTTCCGGAAGGAAGACAGAAATGGCC GGGACGAGATGGACATAGAACTCCACGACGTGTCTCC TATTACTCGGCACCCCCTGCAAGCTCTCTTCATCTGGGC CATTCTTCAGAATAAGAAGGAACTCTCCAAAGTCATTT GGGAGCAGACCAGGGGCTGCACTCTGGCAGCCCTGG GAGCCAGCAAGCTTCTGAAGACTCTGGCCAAAGTGAA GAACGACATCAATGCTGCTGGGGAGTCCGAGGAGCTG GCTAATGAGTACGAGACCCGGGCTGTTGAGCTGTTCA CTGAGTGTTACAGCAGCGATGAAGACTTGGCAGAACA GCTGCTGGTCTATTCCTGTGAAGCTTGGGGTGGAAGC AACTGTCTGGAGCTGGCGGTGGAGGCCACAGACCAGC ATTTCATCGCCCAGCCTGGGGTCCAGAATTTTCTTTCTA AGCAATGGTATGGAGAGATTTCCCGAGACACCAAGAA CTGGAAGATTATCCTGTGTCTGTTTATTATACCCTTGGT GGGCTGTGGCTTTGTATCATTTAGGAAGAAACCTGTCG ACAAGCACAAGAAGCTGCTTTGGTACTATGTGGCGTTC TTCACCTCCCCCTTCGTGGTCTTCTCCTGGAATGTGGTC TTCTACATCGCCTTCCTCCTGCTGTTTGCCTACGTGCTG CTCATGGATTTCCATTCGGTGCCACACCCCCCGAGCT GGTCCTGTACTCGCTGGTCTTTGTCCTCTTCTGTGATGA AGTGAGACAGTGGTACGTAAATGGGGTGAATTATTTT ACTGACCTGTGGAATGTGATGGACACGCTGGGGCTTT TTTACTTCATAGCAGGAATTGTATTTCGGCTCCACTCTT CTAATAAAAGCTCTTTGTATTCTGGACGAGTCATTTTCT GTCTGGACTACATTATTTTCACTCTAAGATTGATCCACA TTTTTACTGTAAGCAGAAACTTAGGACCCAAGATTATA ATGCTGCAGAGGATGCTGATCGATGTGTTCTTCTTCCT GTTCCTCTTTGCGGTGTGGATGGTGGCCTTTGGCGTGG CCAGGCAAGGGATCCTTAGGCAGAATGAGCAGCGCTG GAGGTGGATATTCCGTTCGGTCATCTACGAGCCCTACC TGGCCATGTTCGGCCAGGTGCCCAGTGACGTGGATGG |

FIG. 27 Cont.

| sample | Gene Breakpoint 5p | Gene Breakpoint 3p | Frame Type | SEQ ID NO: | Fused Sequence |
|---|---|---|---|---|---|
| | | | | | TACCACGTATGACTTTGCCCACTGCACCTTCACTGGGA ATGAGTCCAAGCCACTGTGTGTGGAGCTGGATGAGCA CAACCTGCCCCGGTTCCCCGAGTGGATCACCATCCCCC TGGTGTGCATCTACATGTTATCCACCAACATCCTGCTG GTCAACCTGCTGGTCGCCATGTTTGGCTACACGGTGGG CACCGTCCAGGAGAACAATGACCAGGTCTGGAAGTTC CAGAGGTACTTCCTGGTGCAGGAGTACTGCAGCCGCC TCAATATCCCCTTCCCCTTCATCGTCTTCGCTTACTTCTA CATGGTGGTGAAGAAGTGCTTCAAGTGTTGCTGCAAG GAGAAAAACATGGAGTCTTCTGTCTGCTGTTTCAAAAA TGAAGACAATGAGACTCTGGCATGGGAGGGTGTCATG AAGGAAAACTACCTTGTCAAGATCAACACAAAAGCCA ACGACACCTCAGAGGAAATGAGGCATCGATTTAGACA ACTGGATACAAAGCTTAATGATCTCAAGGGTCTTCTGA AAGAGATTGCTAATAAAATCAAA |
| G17469. TCGA-06-2557-01A-01R-1849-01.2 | 55268106 | 55863785 | InFrame | 8348 | ATGCGACCCTCCGGGACGGCCGGGGCAGCGCTCCTGG CGCTGCTGGCTGCGCTCTGCCCGGCGAGTCGGGCTCT GGAGGAAAGAAAGTTTGCCAAGGCACGAGTAACAA GCTCACGCAGTTGGGCACTTTTGAAGATCATTTTCTCA GCCTCCAGAGGATGTTCAATAACTGTGAGGTGGTCCTT GGGAATTTGGAAATTACCTATGTGCAGAGGAATTATG ATCTTTCCTTCTTAAAGACCATCCAGGAGGTGGCTGGT TATGTCCTCATTGCCCTCAACACAGTGGAGCGAATTCC TTTGGAAAACCTGCAGATCATCAGAGGAAATATGTACT ACGAAAATTCCTATGCCTTAGCAGTCTTATCTAACTATG ATGCAAATAAAACCGGACTGAAGGAGCTGCCCATGAG AAATTTACAGGAAATCCTGCATGGCGCCGTGCGGTTCA GCAACAACCCTGCCCTGTGCAACGTGGAGAGCATCCA GTGGCGGGACATAGTCAGCAGTGACTTTCTCAGCAAC ATGTCGATGGACTTCCAGAACCACCTGGGCAGCTGCC AAAAGTGTGATCCAAGCTGTCCCAATGGGAGCTGCTG GGGTGCAGGAGAGGAGAACTGCCAGAAACTGACCAA AATCATCTGTGCCCAGCAGTGCTCCGGGCGCTGCCGTG GCAAGTCCCCCAGTGACTGCTGCCACAACCAGTGTGCT GCAGGCTGCACAGGCCCCGGGAGAGCGACTGCCTG GTCTGCCGCAAATTCCGAGACGAAGCCACGTGCAAGG ACACCTGCCCCCCACTCATGCTCTACAACCCCACCACGT ACCAGATGGATGTGAACCCCGAGGGCAAATACAGCTT TGGTGCCACCTGCGTGAAGAAGTGTCCCCGTAATTATG TGGTGACAGATCACGGCTCGTGCGTCCGAGCCTGTGG GGCCGACAGCTATGAGATGGAGGAAGACGGCGTCCG CAAGTGTAAGAAGTGCGAAGGGCCTTGCCGCAAAGTG TGTAACGGAATAGGTATTGGTGAATTTAAAGACTCACT CTCCATAAATGCTACGAATATTAAACACTTCAAAAACT GCACCTCCATCAGTGGCGATCTCCACATCCTGCCGGTG GCATTTAGGGGTGACTCCTTCACACATACTCCTCCTCTG GATCCACAGGAACTGGATATTCTGAAAACCGTAAAGG AAATCACAGGGTTTTTGCTGATTCAGGCTTGGCCTGAA AACAGGACGGACCTCCATGCCTTTGAGAACCTAGAAA TCATACGCGGCAGGACCAAGCAACATGGTCAGTTTTCT CTTGCAGTCGTCAGCCTGAACATAACATCCTTGGGATT ACGCTCCCTCAAGGAGATAAGTGATGGAGATGTGATA ATTTCAGGAAACAAAAATTTGTGCTATGCAAATACAAT AAACTGGAAAAAACTGTTTGGGACCTCCGGTCAGAAA ACCAAAATTATAAGCAACAGAGGTGAAAACAGCTGCA |

| sample | Gene Breakpoint 5p | Gene Breakpoint 3p | Frame Type | SEQ ID NO: | Fused Sequence |
|---|---|---|---|---|---|
| | | | | | AGGCCACAGGCCAGGTCTGCCATGCCTTGTGCTCCCCC GAGGGCTGCTGGGGCCCGGAGCCCAGGGACTGCGTC TCTTGCCGGAATGTCAGCCGAGGCAGGGAATGCGTGG ACAAGTGCAACCTTCTGGAGGGTGAGCCAAGGGAGTT TGTGGAGAACTCTGAGTGCATACAGTGCCACCCAGAG TGCCTGCCTCAGGCCATGAACATCACCTGCACAGGACG GGGACCAGACAACTGTATCCAGTGTGCCCACTACATTG ACGGCCCCACTGCGTCAAGACCTGCCCGGCAGGAGT CATGGGAGAAAACAACACCCTGGTCTGGAAGTACGCA GACGCCGGCCATGTGTGCCACCTGTGCCATCCAAACTG CACCTACGGATGCACTGGGCCAGGTCTTGAAGGCTGT CCAACGAATGGGCCTAAGATCCCGTCCATCGCCACTGG GATGGTGGGGGCCCTCCTCTTGCTGCTGGTGGTGGCC CTGGGGATCGGCCTCTTCATGCGAAGGCGCCACATCG TTCGGAAGCGCACGCTGCGGAGGCTGCTGCAGGAGA GGGAGCTTGTGGAGCCTCTTACACCCAGTGGAGAAGC TCCCAACCAAGCTCTCTTGAGGATCTTGAAGGAAACTG AATTCAAAAAGATCAAAGTGCTGGGCTCCGGTGCGTT CGGCACGGTGTATAAGGGACTCTGGATCCCAGAAGGT GAGAAAGTTAAAATTCCCGTCGCTATCAAGGAATTAA GAGAAGCAACATCTCCGAAAGCCAACAAGGAAATCCT CGATGAAGCCTACGTGATGGCCAGCGTGGACAACCCC CACGTGTGCCGCCTGCTGGGCATCTGCCTCACCTCCAC CGTGCAGCTCATCACGCAGCTCATGCCCTTCGGCTGCC TCCTGGACTATGTCCGGGAACACAAAGACAATATTGG CTCCCAGTACCTGCTCAACTGGTGTGTGCAGATCGCAA AGGGCATGAACTACTTGGAGGACCGTCGCTTGGTGCA CCGCGACCTGGCAGCCAGGAACGTACTGGTGAAAACA CCGCAGCATGTCAAGATCACAGATTTTGGGCTGGCCA AACTGCTGGGTGCGGAAGAGAAAGAATACCATGCAG AAGGAGGCAAAGTGCCTATCAAGTGGATGGCATTGGA ATCAATTTTACACAGAATCTATACCCACCAGAGTGATG TCTGGAGCTACGGGGTGACTGTTTGGGAGTTGATGAC CTTTGGATCCAAGCCATATGACGGAATCCCTGCCAGCG AGATCTCCTCCATCCTGGAGAAAGGAGAACGCCTCCCT CAGCCACCCATATGTACCATCGATGTCTACATGATCAT GGTCAAGTGCTGGATGATAGACGCAGATAGTCGCCCA AAGTTCCGTGAGTTGATCATCGAATTCTCCAAAATGGC CCGAGACCCCCAGCGCTACCTTGTCATTCAG\|CTGCAG GACAAGTTCGAGCATCTTAAAATGATTCAACAGGAGG AGATAAGGAAGCTCGAGGAAGAGAAAAAACAACTGG AAGGAGAAATCATAGATTTTTATAAAAATGAAAGCTGCC TCCGAAGCACTGCAGACTCAGCTGAGCACCGATACAA AGAAAGACAAACATCGTAAGAAA |
| G17480. TCGA-27- 1830- 01A-01R- 1850- 01.2 | 231945028 | 230377652 | InFrame | 8349 | ATGATCACCTCGGCCGCTGGAATTATTTCTCTTCTGGAT GAAGATGAACCACAGCTTAAGGAATTTGCACTACACA AATTGAATGCAGTTGTTAATGACTTCTGGGCAGAAATT TCCGAGTCCGTAGACAAAATAGAGGTTTTATACGAAG ATGAAGGTTTCCGGAGTCGGCAGTTTGCAGCCTTAGT GGCATCTAAAGTATTTTATCACCTGGGGGCTTTTGAGG AGTCTCTGAATTATGCTCTTGGAGCAGGGGACCTCTTC AATGTCAATGATAACTCTGAATATGTGGAAACTATTAT AGCAAAATGCATTGATCACTACACCAAACAATGTGTGG AAAATGCAGATTTGCCTGAAGGAGAAAAAAAACCAAT TGACCAGAGATTGGAAGGCATCGTAAATAAAATGTTC |

FIG. 27 Cont.

| sample | Gene Break-point 5p | Gene Break-point 3p | Frame Type | SEQ ID NO: | Fused Sequence |
|---|---|---|---|---|---|
| | | | | | CAGCGATGTCTAGATGATCACAAGTATAAACAGGCTAT |
| | | | | | TGGCATTGCTCTGGAGACACGAAGACTGGACGTCTTT |
| | | | | | GAAAAGACCATACTGGAGTCGAATGATGTCCCAGGAA |
| | | | | | TGTTAGCTTATAGCCTTAAGCTCTGCATGTCTTTAATGC |
| | | | | | AGAATAAACAGTTTCGGAATAAAGTACTAAGAGTTCTA |
| | | | | | GTTAAAATCTACATGAACTTGGAGAAACCTGATTTCAT |
| | | | | | CAATGTTTGTCAGTGCTTAATTTTCTTAGATGATCCTCA |
| | | | | | GGCTGTGAGTGATATCTTAGAGAAACTGGTAAAGGAA |
| | | | | | GACAACCTCCTGATGGCATATCAGATTTGTTTTGATTTG |
| | | | | | TATGAAAGTGCTAGCCAGCAGTTTTTGTCATCTGTAAT |
| | | | | | CCAGAATCTTCGAACTGTTGGCACCCCTATTGCTTCTGT |
| | | | | | GCCTGGATCCACTAATACGGGTACTGTTCCGGGATCAG |
| | | | | | AGAAAGACAGTGACTCGATGGAAACAGAAGAAAAGA |
| | | | | | CAAGCAGTGCATTTGTAGGAAAGACACCAGAAGCCAG |
| | | | | | TCCAGAGCCTAAGGACCAGACTTTGAAAATGATTAAA |
| | | | | | ATTTTAAGTGGTGAAATGGCTATTGAGTTACATCTGCA |
| | | | | | GTTCTTAATACGAAACAATAATACAGACCTCATGATTC |
| | | | | | TAAAAAACACAAAGGATGCAGTACGGAATTCTGTATG |
| | | | | | TCATACTGCAACCGTTATAGCAAACTCTTTTATGCACTG |
| | | | | | TGGGACAACCAGTGACCAGTTTCTTAGAGATAATTTGG |
| | | | | | AATGGTTAGCCAGAGCCACTAACTGGGCAAAATTTACT |
| | | | | | GCTACAGCCAGTTTGGGTGTAATTCATAAGGGTCATGA |
| | | | | | AAAAGAAGCATTACAGTTAATGGCAACATACCTTCCCA |
| | | | | | AGGATACTTCTCCAGGATCAGCCTATCAGGAAGGTGG |
| | | | | | AGGTCTCTATGCACTAGGTCTTATTCATGCCAATCATG |
| | | | | | GTGGTGATATAATTGACTATCTGCTTAATCAGCTTAAG |
| | | | | | AACGCCAGCAATGAT\|GCAACTTTTTCCTGTACCTGTG |
| | | | | | AGGAGCAGTACGTGGGTACTTTCTGTGAAGAATACGA |
| | | | | | TGCTTGCCAGAGGAAACCTTGCCAAAACAACGCGAGC |
| | | | | | TGTATTGATGCAAATGAAAAGCAAGATGGGAGCAATT |
| | | | | | TCACCTGTGTTTGCCTTCCTGGTTATACTGGAGAGCTTT |
| | | | | | GCCAGTCCAAGATTGATTACTGCATCCTAGACCCATGC |
| | | | | | AGAAATGGAGCAACATGCATTTCCAGTCTCAGTGGATT |
| | | | | | CACCTGCCAGTGTCCAGAAGGATACTTCGGATCTGCTT |
| | | | | | GTGAAGAAAAGGTGGACCCCTGCGCCTCGTCTCCGTG |
| | | | | | CCAGAACAACGGCACCTGCTATGTGGACGGGGTACAC |
| | | | | | TTTACCTGCAACTGCAGCCCGGGCTTCACAGGGCCGAC |
| | | | | | CTGTGCCCAGCTTATTGACTTCTGTGCCCTCAGCCCCTG |
| | | | | | TGCTCATGGCACGTGCCGCAGCGTGGGCACCAGCTAC |
| | | | | | AAATGCCTCTGTGATCCAGGTTACCATGGCCTCTACTG |
| | | | | | TGAGGAGGAATATAATGAGTGCCTCTCCGCTCCATGCC |
| | | | | | TGAATGCAGCCACCTGCAGGGACCTCGTTAATGGCTAT |
| | | | | | GAGTGTGTGTGCCTGGCAGAATACAAAGGAACACACT |
| | | | | | GTGAATTGTACAAGGATCCCTGCGCTAACGTCAGCTGT |
| | | | | | CTGAACGGAGCCACCTGTGACAGCGACGGCCTGAATG |
| | | | | | GCACGTGCATCTGTGCACCCGGGTTTACAGGTGAAGA |
| | | | | | GTGCGACATTGACATAAATGAATGTGACAGTAACCCCT |
| | | | | | GCCACCATGGTGGGAGCTGCCTGGACCAGCCCAATGG |
| | | | | | TTATAACTGCCACTGCCCGCATGGTTGGGTGGGAGCA |
| | | | | | AACTGTGAGATCCACCTCCAATGGAAGTCCGGGCACA |
| | | | | | TGGCGGAGAGCCTCACCAACATGCCACGGCACTCCCTC |
| | | | | | TACATCATCATTGGAGCCCTCTGCGTGGCCTTCATCCTT |
| | | | | | ATGCTGATCATCCTGATCGTGGGGATTTGCCGCATCAG |
| | | | | | CCGCATTGAATACCAGGGTTCTTCCAGGCCAGCCTATG |
| | | | | | AGGAGTTCTACAACTGCCGCAGCATCGACAGCGAGTT |

FIG. 27 Cont.

| sample | Gene Breakpoint 5p | Gene Breakpoint 3p | Frame Type | SEQ ID NO: | Fused Sequence |
|---|---|---|---|---|---|
| | | | | | CAGCAATGCCATTGCATCCATCCGGCATGCCAGGTTTG GAAAGAAATCCCGGCCTGCAATGTATGATGTGAGCCC CATCGCCTATGAAGATTACAGTCCTGATGACAAACCCT TGGTCACACTGATTAAAACTAAAGATTTG |
| G17634. TCGA-19-2625-01A-01R-1850-01.2 | 36424288 | 37967938 | InFrame | 8350 | ATGGCGGAGGGCGCCCAGCCGCATCAGCCGCCTCAGC Tcgggcccggcgccgccgccgggggc ATGAAGCGGGAGTCGG AGCTGGAGCTGCCGGTGCCCGGAGCGGGAGGAGACG GAGCCGATCCCGGCCTGAGCAAGCGGCCGCGCACTGA GGAGGCGGCGGCCGACGGTGGCGGCGGGATGCAG\|G GGGAACTTGAGGTTAAGAACATGGACATGAAGCCGG GGTCAACCCTGAAGATCACAGGCAGCATCGCCGATGG CACTGATGGCTTTGTAATTAATCTGGGCCAGGGGACA GACAAGCTGAACCTGCATTTCAACCCTCGCTTCAGCGA ATCCACCATTGTCTGCAACTCATTGGACGGCAGCAACT GGGGGCAAGAACAACGGGAAGATCACCTGTGCTTCAG CCCAGGGTCAGAGGTCAAGTTCACAGTGACCTTTGAG AGTGACAAATTCAAGGTGAAGCTGCCAGATGGGCACG AGCTGACTTTTCCCAACAGGCTGGGTCACAGCCACCTG AGCTACCTGAGCGTAAGGGGCGGGTTCAACATGTCCT CTTTCAAGTTAAAAGAA |
| G17654. TCGA-41-4097-01A-01R-1850-01.2 | 66313803 | 86374956 | InFrame | 8351 | ATGGACCGGCCGGGGTTCGTGGCAGCGCTGGTGGCT GGTGGGGTAGCAGGTGTTTCTGTTGACTTGATATTATT TCCTCTGGATACCATTAAAACCAGGCTGCAGAGTCCCC AAGGATTTAGTAAGGCTGGTGGTTTTCATGGAATATAT GCTGGCGTTCCTTCTGCTGCTATTGGATCCTTTCCTAAT GCTGCTGCATTTTTTATCACCTATGAATATGTGAAGTG GTTTTTGCATGCTGATTCATCTTCATATTTGACACCTAT GAAACATATGTTGGCTGCCTCTGCTGGAGAAGTGGTT GCCTGCCTGATTCGAGTTCCATCTGAAGTGGTTAAGCA GAGGGCACAGGTATCTGCTTCTACAAGAACATTTCAGA TTTTCTCTAACATCTTATATGAAGAGGGTATCCAAGGG TTGTATCGAGGCTATAAAAGCACAGTTTTAAGAGAG\|A TAGAAGAAGTCAGAGATGCCATGGAAAATGAAATGAG AACCCAGCTTCGCCGACAGGCAGCTGCCCACACTGATC ACTTGCGAGATGTCCTTAGGGTACAAGAACAGGAATT GAAGTCTGAATTTGAGCAGAACCTGTCTGAGAAACTCT CTGAACAAGAATTACAATTTCGTCGTCTCAGTCAAGAG CAAGTTGACAACTTTACTCTGGATATAAATACTGCCTAT GCCAGACTCAGAGGAATCGAACAGGCTGTTCAGAGCC ATGCAGTTGCTGAAGAGGAAGCCAGAAAAGCCCACCA ACTCTGGCTTTCAGTGGAGGCATTAAAGTACAGCATGA AGACCTCATCTGCAGAAACACCTACTATCCCGCTGGGT AGTGCAGTTGAGGCCATCAAAGCCAACTGTTCTGATAA TGAATTCACCCAAGCTTTAACCGCAGCTATCCCTCCAG AGTCCCTGACCCGTGGGGTGTACAGTGAAGAGACCCT TAGAGCCCGTTTCTATGCTGTTCAAAAACTGGCCCGAA GGGTAGCAATGATTGATGAAACCAGAAATAGCTTGTA CCAGTACTTCCTCTCCTACCTACAGTCCCTGCTCCTATTC CCACCTCAGCAACTGAAGCCGCCCCAGAGCTCTGCCC TGAGGATATAAACACATTTAAATTACTGTCATATGCTTC CTATTGCATTGAGCATGGTGATCTGGAGCTAGCAGCA AAGTTTGTCAATCAGCTGAAGGGGGAATCCAGACGAG TGGCACAGGACTGGCTGAAGGAAGCCCGAATGACCCT AGAAACGAAACAGATAGTGGAAATCCTGACAGCATAT |

FIG. 27 Cont.

| sample | Gene Break-point 5p | Gene Break-point 3p | Frame Type | SEQ ID NO: | Fused Sequence |
|---|---|---|---|---|---|
| | | | | | GCCAGCGCCGTAGGAATAGGAACCACTCAGGTGCAGC CAGAG |
| G17485. TCGA-14-1402-02A-01R-2005-01.2 | 142166712 | 246093239 | InFrame | 8352 | ATGGGAGTCCCCAAGTTTTACAGATGGATCTCAGAGC GGTATCCCTGTCTCAGCGAAGTGGTGAAAGAGCATCA G\|GTGATCTGCAACTCTTTCACCATCTGTAATGCGGAG ATGCAGGAAGTTGGTGTTGGCCTATATCCCAGTATCTC TTTGCTCAATCACAGCTGTGACCCCAACTGTTCGATTGT GTTCAATGGGCCCCACCTCTTACTGCGAGCAGTCCGAG ACATCGAGGTGGGAGAGGAGCTCACCATCTGCTACCT GGATATGCTGATGACCAGTGAGGAGCGCCGGAAGCA GCTGAGGGACCAGTACTGCTTTGAATGTGACTGTTTCC GTTGCCAAACCCAGGACAAGGATGCTGATATGCTAAC TGGTGATGAGCAAGTATGGAAGGAAGTTCAAGAATCC CTGAAAAAAATTGAAGAACTGAAGGCACACTGGAAGT GGGAGCAGGTTCTGGCCATGTGCCAGGCAATCATAAG CAGCAATTCTGAACGGCTTCCCGATATCAACATCTACC AGCTGAAGGTGCTCGACTGCGCCATGGATGCCTGCAT CAACCTCGGCCTGTTGGAGGAAGCCTTGTTCTATGGTA CTCGGACCATGGAGCCATACAGGATTTTTTTCCCAGGA AGCCATCCCGTCAGAGGGGTTCAAGTGATGAAAGTTG GCAAACTGCAGCTACATCAAGGCATGTTTCCCCAAGCA ATGAAGAATCTGAGACTGGCTTTTGATATTATGAGAGT GACACATGGCAGAGAACACAGCCTGATTGAAGATTTG ATTCTACTTTTAGAAGAATGCGACGCCAACATCAGAGC ATCC |
| G17498. TCGA-02-2483-01A-01R-1849-01.2 | 119976637 | 332025 | InFrame | 8353 | atggccgccgccggcgccCGGCTCAgccccggccccggctcggggc tccggggcggccgAGGCTCTGCTTCCACCCGGGgccgccgc cactgctgccgctgctgctgctgttcctgctcctgctgccgccgccgccgc tgctgGCCGGCGCCACCGCCGCTGCCTCGCGGGAGCCC GACAGCCCGTGCCGGCTGAAGACCGTCACGGTGTCCA CACTGCCCGCCCTGCGGGAGAGCGACATCggctggagcg gcgcccgcgccggggccggggctgggaccggggccggagccgCCGC CGCCGCCGCGTCCCCGGGCTCTCCTGGCTCTGCCGGCA CCGCCGCCGAGTCGCGCCTCCTGCTCTTTGTGCGTAAC GAGCTGCCGGGGCGCATCGCGGTGCAGGACGACCTG GACAACACCGAGCTGCCCTTCTTCACCCTGGAGATGTC TGGCACAGCAGCGGACATCTCGCTGGTGCACTGGAGA CAGCAGTGGCTGGAGAATGGCACCTTGTACTTCCACGT CTCCATGAGCAGCTCCGGGCAGCTGGCCCAAGCCACC GCCCCCACTCTCCAGGAGCCCTCGGAGATTGTTGAGG AGCAGATGCACATCCTCCACATTTCTGTGATGGGTGGC CTCATCGCGCTGCTGCTGCTGCTGGTGTTCACCGT GGCGCTGTACGCCCAGCGACGTTGGCAGAAGCGTCGC CGCATCCCCCAGAAGAGCGCAAGCACAGAAGCCACTC ATGAGATCCACTACATCCCATCTGTGCTGCTGGGTCCC CAGGCGCGGGAGAGCTTCCGTTCATCCCGGCTGCAAA CCCACAATTCCGTCATTGGCGTGCCCATCCGGGAGACT CCCATCCTGGATGACTATGACTGTGAGGAGGATGAGG AGCCACCTAGGCGGGCCAACCATGTCTCCCGCGAGGA CGAGTTTGGCAGCCAGGTGACCCACACTCTGGACAGT CTGGGACATCCAGGGGAAGAGAAGGTGGACTTTGAG AAGAAAG\|ACCCAAGCCTGCCCAATGTGCAGGTGACC AGGCTGACACTCCTGTCGGAACAGGCTCCGGGGCCCG TCGTCATGGATCTCACAGGGGACCTGGCTGTTCTGAAG GACCAGGTGTTTGTCCTGAAGGAAGGTGTTGATTACA |

FIG. 27 Cont.

| sample | Gene Break-point 5p | Gene Break-point 3p | Frame Type | SEQ ID NO: | Fused Sequence |
|---|---|---|---|---|---|
| | | | | | GAGTGAAGATCTCCTTCAAGGTCCACAGGGAGATTGT CAGCGGCCTCAAGTGTCTGCACCACACCTACCGCCGG GGCCTGCGCGTGGACAAGACCGTCTACATGGTGGGCA GCTATGGCCCGAGCGCCCAGGAGTATGAGTTTGTGAC TCCGGTGGAGGAAGCGCCGAGGGGTGCGCTGGTGCG GGGCCCCTATCTGGTGGTGTCCCTCTTCACCGACGATG ACAGGACGCACCACCTGTCCTGGGAGTGGGGTCTCTG CATCTGCCAGGACTGGAAGGAC |
| G17799. TCGA-06-1804-01A-01R-1849-01.4 | 61109367 | 47345631 | InFrame | 8354 | ATGCTGCGATTACAGATGACTGATGGTCATATAAGTTG CACAGCAGTAGAATTTAGTTATATGTCAAAAATAAGCC TGAACACACCACCTGGAACTAAAGTTAAGCTCTCAGGC ATTGTTGACATAAAAAATGGATTCCTGCTCTTGAATGA CTCTAACACCACAGTTCTTGGTGGTGAAGTGGAACACC TTATTGAGAAATGGGAGTTACAGAGAAGCTTATCAAA ACACAATAGAAGCAATATTGGAACTGAAGGTGGACCA CCGCCTTTTGTGCCTTTTGGACAGAAGTGTGTATCTCAT GTCCAAGTGGATAGCAGAGAACTTGATCGAAGAAAAA CATTGCAAGTTACAATGCCTGTCAAACCTACAAATGAT AATGATGAATTTGAAAAGCAAAGGACGGCTGCTATTG CTGAAGTTGCAAAGAGCAAGGAAACCAAGACATTTGG AGGAGGTGGTGGTGGTGCTAGAAGTAATCTCAATATG AATGCTGCTGGTAACCGAAATAGGGAAGTTTTACAGA AAGAAAAGTCAACCAAATCAGAGGGAAAACATGAAG GTGTCTATAGAGAACTGGTTGATGAGAAAGCTCTGAA GCACATAACGGAAATGGGCTTCAGTAAGGAAGCATCG AGGCAAGCTCTTATGGATAATGGCAACAACTTAGAAG CAGCACTGAACGTACTTCTTACAAGCAATAAACAGAAA CCTGTTATGGGTCCTCCTCTGAGAGGTAGAGGAAAAG GCAGGGGCGAATAAGATCTGAAGATGAAGAGGACC TGGGAAATGCAAGGCCATCAGCACCAAGCACATTATTT GATTTCTTGGAATCTAAAATGGGAACTTTGAATGTGGA AGAACCTAAATCACAGCCACAGCAGCTTCATCAGGGA CAATACAGATCATCAAATACTGAGCAAAATGGAGTAA AAGATAATAATCATCTGAGACATCCTCCTCGAAATGAT ACCAGGCAGCCAAGAAATGAAAAACCGCCTCGTTTTC AAAAGAGACTCCCAAAATTCAAAGTCAGTTTTAGAAGG CAGTGGATTACCTAGAAATAGAGGTTCTGAAAGACCA AGTACTTCTTCAGTATCTGAAGTATGGGCTGAAGACAG AATCAAATGTGATAGACCGTATTCTAGATATGACAGAA CTAAAGATACTTCATATCCTTTAGGTTCTCAGCATAGTG ATGGTGCTTTTAAAAAAGAGATAACTCTATGCAAAGC AGATCAGGAAAAGGTCCCTCCTTTGCAGAGGCAAAAG AAAATCCACTTCCTCAAGGATCTGTAGATTATAATAAT CAAAAACGTGGAAAAAGAGAAAGCCAAACATCTATTC CTGATTATTTTTATGACAGGAAATCACAAACAATAAAT AATGAAGCTTTCAGTGGTATAAAAATTGAAAACATTT TAATGTAAATACTGATTATCAGAATCCAGTTCGAAGTA ATAGTTTCATTGGTGTTCCAAATGGAGAAGTAGAAATG CCACTGAAAGGAAGACGAATAGGACCTATTAAGCCAG CAGGACCTGTCACAGCTGTACCCTGTGATGATAAAATA TTTTACAATAGTGGGCCCAAACGAAGATCTGGGCCAAT TAAGCCAGAAAAAATACTAGAATCATCTATTCCTATGG AGTATGCAAAAATGTGGAAACCTGGAGATGAATGTTT TGCACTTTATTGGGAAGACAACAAGTTTTACCGGGCAG AAGTTGAAGCCCTCCATTCTTCGGGTATGACAGCAGTT |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GTTAAATTCATTGACTACGGAAACTATGAAGAGGTGCT ACTGAGCAATATCAAGCCCATTCAAACAGAGGCATGG \|GGTTATGATCATAGCTACTACTTCATTGCAACCTTTAT TACTGACCACATCAGACATCATGCTAAATACCTGAATG CA |
| G17660. TCGA-06-5414-01A-01R-1849-01.2 | 61655656 | 59872567 | InFrame | 8355 | ATGGCAGATCCAGGAATGATGAGTCTTTTTGGCGAGG ATGGGAATATTTTCAGTGAAGGTCTTGAAGGCCTCGG AGAATGTGGTTACCCGGAAAATCCAGTAAATCCTATG GGTCAGCAAATGCCAATAGACCAAGGCTTTGCCTCTTT ACAGCCATCCCTTCATCATCCTTCAACTAATCAAAATCA AACAAAGCTGACACATTTTGATCACTATAATCAGTATG AACAACAAAAGATGCATCTGATGGATCAGCCGAACAG AATGATGAGCAACACCCCTGGGAACGGACTCGCGTCT CCGCACTCGCAGTATCACACCCCTCCCGTTCCTCAGGT GCCCCATGGTGGCAGTGGTGGCGGTCAGATGGGTGTC TACCCTGGCATGCAGAATGAGAGGCATGGGCAATCCT TTGTGGACAGCAGCTCCATGTGGGGCCCCAGGGCTGT TCAGGTACCAGACCAGATACGAGCCCCCTACCAGCAG CAGCAGCCACAGCCGCAGCCACCGCAGCCGGCTCCGT CGGGGCCCCCTGCACAGGGCCACCCTCAGCACATGCA GCAGATGGGCAGCTATATGGCACGTGGGGATTTTTCC ATGCAGCAGCATGGTCAGCCACAGCAGAGGATGAGCC AGTTTTCCCAAGGCCAAGAGGGCCTCAATCAGGGAAA TCCTTTTATTGCCACCTCAGGACCTGGCCACTTGTCCCA CGTGCCCCAGCAGAGTCCCAGCATGGCACCTTCCTTGC GTCACTCGGTGCAGCAGTTCCATCACCACCCCTCTACT GCTCTCCATGGAGAATCCGTTGCCCACAGTCCCAGATT CTCCCCGAATCCTCCCCAACAAGGGGCTGTTAGGCCGC AAACCCTTAACTTTAGTTCTCGGAGCCAGACAGTCCCC TCTCCTACTATAAACAACTCAGGGCAGTATTCTCGATAT CCTTACAGTAACCTAAATCAGGGATTAGTTAACAATAC AGGGATGAATCAAAATTTAGGCCTTACAAATAATACTC CAATGAATCAGTCCGTACCAAGATACCCCAATGCTGTA GGATTCCCATCAAACAGTGGTCAAGGACTAATGCACC AGCAGCCCATCCACCCCAGTGGCTCACTTAACCAAATG AACACACAAACTATGCATCCTTCACAGCCTCAGGGAAC TTATGCCTCTCCACCTCCCATGTCACCCATGAAAGCAAT GAGTAATCCAGCAGGCACTCCTCCTCCACAAGTCAGGC CGGGAAGTGCTGGGATACCAATGGAAGTTGGCAGTTA TCCAAATATGCCCCATCCTCAGCCATCTCACCAGCCCCC TGGTGCCATGGGAATCGGACAGAGGAATATGGGCCCC AGAAACATGCAGCAGTCTCGTCCATTTATAGGCATGTC CTCGGCACCAAGGGAATTGACTGGGCACATGAGGCCA AATGGTTGTCCTGGTGTTGGCCTTGGAGACCCACAAGC AATCCAGGAACGACTGATACCTGGCCAACAACATCCTG GTCAACAGCCATCTTTTCAGCAGTTGCCAACCTGTCCTC CACTGCAGCCTCACCCGGGCTTGCACCACCAGTCTTCA CCTCCACACCCTCATCACCAGCCTTGGGCACAGCTCCA CCCATCACCCCAGAACACCCCGCAGAAAGTGCCTGTGC ATCAG\|TTTGACGGTGAGAACATGTATATGAGCATGAC AGAGCCGAGCCAGGACTATGTGCCAGCCAGCCAGTCC TACCCTGGTCCAAGCCTGGAAAGTGAAGACTTCAACAT TCCACCAATTACTCCTCCTTCCCTCCCAGACCACTCGCT GGTGCACCTGAATGAAGTTGAGTCTGGTTACCATTCTC TGTGTCACCCCATGAACCATAATGGCCTGCTACCATTTC |

FIG. 27 Cont.

| sample | Gene Breakpoint 5p | Gene Breakpoint 3p | Frame Type | SEQ ID NO: | Fused Sequence |
|---|---|---|---|---|---|
| | | | | | ATCCACAAAACATGGACCTCCCTGAAATCACAGTCTCC AATATGCTGGGCCAGGATGGAACACTGCTTTCTAATTC CATTTCTGTGATGCCAGATATACGAAACCCAGAAGGA ACTCAGTACAGTTCCCATCCTCAGATGGCAGCCATGAG ACCAAGGGGCCAGCCTGCAGACATCAGGCAGCAGCCA GGAATGATGCCACATGGCCAGCTGACTACCATTAACCA GTCACAGCTAAGTGCTCAACTTGGTTTGAATATGGGAG GAAGCAATGTTCCCCACAACTCACCATCTCCACCTGGA AGCAAGTCTGCAACTCCTTCACCATCCAGTTCAGTGCA TGAAGATGAAGGCGATGATACCTCTAAGATCAATGGT GGAGAGAAGCGGCCTGCCTCTGATATGGGGAAAAAA CCAAAAACTCCCAAAAAGAAGAAGAAGAAGGATCCCA ATGAGCCCCAGAAGCCTGTGTCTGCCTATGCGTTATTC TTTCGTGATACTCAGGCCGCCATCAAGGGCCAAAATCC AAACGCTACCTTTGGCGAAGTCTCTAAAATTGTGGCTT CAATGTGGGACGGTTTAGGAGAAGAGCAAAAACAGG TCTATAAAAAGAAAACCGAGGCTGCGAAGAAGGAGTA CCTGAAGCAACTCGCAGCATACAGAGCCAGCCTTGTAT CCAAGAGCTACAGTGAACCTGTTGACGTGAAGACATC TCAACCTCCTCAGCTGATCAATTCGAAGCCGTCGGTGT TCCATGGGCCCAGCCAGGCCCACTCGGCCCTGTACCTA AGTTCCCACTATCACCAACAACCGGGAATGAATCCTCA CCTAACTGCCATGCATCCTAGTCTCCCCAGGAACATAG CCCCCAAGCCGAATAACCAAATGCCAGTGACTGTCTCT ATAGCAAACATGGCTGTGTCCCCTCCTCCTCCCCTCCAG ATCAGCCCGCCTCTTCACCAGCATCTCAACATGCAGCA GCACCAGCCGCTCACCATGCAGCAGCCCCTTGGGAAC CAGCTCCCCATGCAGGTCCAGTCTGCCTTACACTCACC CACCATGCAGCAAGGATTTACTCTTCAACCCGACTATC AGACTATTATCAATCCTACATCTACAGCTGCACAAGTT GTCACCCAGGCAATGGAGTATGTGCGTTCGGGGTGCA GAAATCCTCCCCCACAACCGGTGGACTGGAATAACGA CTACTGCAGTAGTGGGGGCATGCAGAGGGACAAAGC ACTGTACCTTACT |
| GBM-CUMC3296_L1 | 67688936 | 55238868 | InFrame | 8356 | ATGGCGAGCGCCTCGTACCACATTTCCAATTTGCTGGA AAAAATGACATCCAGCGACAAGGACTTTAGGTTTATG GCTACAAATGATTTGATGACGGAACTGCAGAAAGATT CCATCAAGTTGGATGATGATAGTGAAAGGAAAGTAGT GAAAATGATTTTGAAGTTATTGGAAGATAAAAATGGA GAGGTACAGAATTTAGCTGTCAAATGTCTTGGTCCTTT AGTGAGTAAAGTGAAAGAATACCAAGTAGAGACAATT GTAGATACCCTCTGCACTAACATGCTTTCTGATAAAGA ACAACTTCGAGACATTTCAAGTATTGGTCTTAAAACAG TAATTGGAGAACTTCCTCCAGCTTCCAGTGGCTCTGCA TTAGCTGCTAATGTATGTAAAAAGATTACTGGACGTCT TACAAGTGCAATAGCAAAACAGGAAGATGTCTCTGTTC AGCTAGAAGCCTTGGATATTATGGCTGATATGTTGAGC AG\|ATGCACTGGGCCAGGTCTTGAAGGCTGTCCAACG AATGGGCCTAAGATCCCGTCCATCGCCACTGGGATGG TGGGGGCCCTCCTCTTGCTGCTGGTGGTGGCCCTGGG GATCGGCCTCTTCATGCGAAGGCGCCACATCGTTCGGA AGCGCACGCTGCGGAGGCTGCTGCAGGAGAGGGAGC TTGTGGAGCCTCTTACACCCAGTGGAGAAGCTCCCAAC CAAGCTCTCTTGAGGATCTTGAAGGAAACTGAATTCAA AAAGATCAAAGTGCTGGGCTCCGGTGCGTTCGGCACG |

FIG. 27 Cont.

| sample | Gene Break-point 5p | Gene Break-point 3p | Frame Type | SEQ ID NO: | Fused Sequence |
|---|---|---|---|---|---|
| | | | | | GTGTATAAGGGACTCTGGATCCCAGAAGGTGAGAAAG TTAAAATTCCCGTCGCTATCAAGGAATTAAGAGAAGCA ACATCTCCGAAAGCCAACAAGGAAATCCTCGATGAAG CCTACGTGATGGCCAGCGTGGACAACCCCCACGTGTG CCGCCTGCTGGGCATCTGCCTCACCTCCACCGTGCAGC TCATCACGCAGCTCATGCCCTTCGGCTGCCTCCTGGAC TATGTCCGGGAACACAAAGACAATATTGGCTCCCAGTA CCTGCTCAACTGGTGTGTGCAGATCGCAAAGGGCATG AACTACTTGGAGGACCGTCGCTTGGTGCACCGCGACCT GGCAGCCAGGAACGTACTGGTGAAAACACCGCAGCAT GTCAAGATCACAGATTTTGGGCTGGCCAAACTGCTGG GTGCGGAAGAGAAAGAATACCATGCAGAAGGAGGCA AAGTGCCTATCAAGTGGATGGCATTGGAATCAATTTTA CACAGAATCTATACCCACCAGAGTGATGTCTGGAGCTA CGGGGTGACTGTTTGGGAGTTGATGACCTTTGGATCC AAGCCATATGACGGAATCCCTGCCAGCGAGATCTCCTC CATCCTGGAGAAAGGAGAACGCCTCCCTCAGCCACCC ATATGTACCATCGATGTCTACATGATCATGGTCAAGTG CTGGATGATAGACGCAGATAGTCGCCCAAAGTTCCGT GAGTTGATCATCGAATTCTCCAAAATGGCCCGAGACCC CCAGCGCTACCTTGTCATTCAGGGGATGAAAGAATG CATTTGCCAAGTCCTACAGACTCCAACTTCTACCGTGCC CTGATGGATGAAGAAGACATGGACGACGTGGTGGAT GCCGACGAGTACCTCATCCCACAGCAGGGCTTCTTCAG CAGCCCCTCCACGTCACGGACTCCCCTCCTGAGCTCTCT GAGTGCAACCAGCAACAATTCCACCGTGGCTTGCATTG ATAGAAATGGGCTGCAAAGCTGTCCCATCAAGGAAGA CAGCTTCTTGCAGCGATACAGCTCAGACCCCACAGGCG CCTTGACTGAGGACAGCATAGACGACACCTTCCTCCCA GTGCCTGaATACATAAACCAGTCCGTTCCCAAAAGGCC CGCTGGCTCTGTGCAGAATCCTGTCTATCACAATCAGC CTCTGAACCCCGCGCCCAGCAGAGACCCACACTACCAG GACCCCCACAGCACTGCAGTGGGCAACCCCGAGTATC TCAACACTGTCCAGCCCACCTGTGTCAACAGCACATTC GACAGCCCTGCCCACTGGGCCCAGAAAGGCAGCCACC AAATTAGCCTGGACAACCCTGACTACCAGCAGGACTTC TTTCCCAAGGAAGCCAAGCCAAATGGCATCTTTAAGG GCTCCACAGCTGAAAATGCAGAATACCTAAGGGTCGC GCCACAAAGCAGTGAATTTATTGGAGCA |
| G17505. TCGA-06-2564-01A-01R-1849-01.2 | 216844 | 1282739 | InFrame | 8357 | ATGAATAACCTAAATGATCCCCCAAATTGGAATATCCG GCCTAATTCCAGGGCGGATGGTGGTGATGGAAGCAG GTGGAATTATGCCCTGTTGGTTCAATGCTGGGATTGG CTGCTTTTC\|GGGTTGGCTGTGTTCCGGCCGCAGAGCA CCGTCTGCGTGAGGAGATCCTGGCCAAGTTCCTGCACT GGCTGATGAGTGTGTACGTCGTCGAGCTGCTCAGGTC TTTCTTTTATGTCACGGAGACCACGTTTCAAAAGAACA GGCTCTTTTTCTACCGGAAGAGTGTCTGGAGCAAGTTG CAAAGCATTGGAATCAGACAGCACTTGAAGAGGGTGC AGCTGCGGGAGCTGTCGGAAGCAGAGGTCAGGCAGC ATCGGGAAGCCAGGCCCGCCCTGCTGACGTCCAGACT CCGCTTCATCCCCAAGCCTGACGGGCTGCGGCCGATTG TGAACATGGACTACGTCGTGGGAGCCAGAACGTTCCG CAGAGAAAAGAGGGCCGAGCGTCTCACCTCGAGGGT GAAGGCACTGTTCAGCGTGCTCAACTACGAGCGGGCG CGGCGCCCCGGCCTCCTGGGCGCCTCTGTGCTGGGCC |

FIG. 27 Cont.

| sample | Gene Break-point 5p | Gene Break-point 3p | Frame Type | SEQ ID NO: | Fused Sequence |
|---|---|---|---|---|---|
| | | | | | TGGACGATATCCACAGGGCCTGGCGCACCTTCGTGCT GCGTGTGCGGGCCCAGGACCCGCCGCCTGAGCTGTAC TTTGTCAAGGTGGATGTGACGGGCGCGTACGACACCA TCCCCCAGGACAGGCTCACGGAGGTCATCGCCAGCAT CATCAAACCCCAGAACACGTACTGCGTGCGTCGGTATG CCGTGGTCCAGAAGGCCGCCCATGGGCACGTCCGCAA GGCCTTCAAGAGCCACGTCTCTACCTTGACAGACCTCC AGCCGTACATGCGACAGTTCGTGGCTCACCTGCAGGA GACCAGCCCGCTGAGGGATGCCGTCGTCATCGAGCAG AGCTCCTCCCTGAATGAGGCCAGCAGTGGCCTCTTCGA CGTCTTCCTACGCTTCATGTGCCACCACGCCGTGCGCA TCAGGGGCAAGTCCTACGTCCAGTGCCAGGGGATCCC GCAGGGCTCCATCCTCTCCACGCTGCTCTGCAGCCTGT GCTACGGCGACATGGAGAACAAGCTGTTTGCGGGGAT TCGGCGGGACGGGCTGCTCCTGCGTTTGGTGGATGAT TTCTTGTTGGTGACACCTCACCTCACCCACGCGAAAAC CTTCCTCAGGACCCTGGTCCGAGGTGTCCCTGAGTATG GCTGCGTGGTGAACTTGCGGAAGACAGTGGTGAACTT CCCTGTAGAAGACGAGGCCCTGGGTGGCACGGCTTTT GTTCAGATGCCGGCCCACGGCCTATTCCCCTGGTGCGG CCTGCTGCTGGATACCCGGACCCTGGAGGTGCAGAGC GACTACTCCAGCTATGCCCGGACCTCCATCAGAGCCAG TCTCACCTTCAACCGCGGCTTCAAGGCTGGGAGGAAC ATGCGTCGCAAACTCTTTGGGGTCTTGCGGCTGAAGTG TCACAGCCTGTTTCTGGATTTGCAGGTGAACAGCCTCC AGACGGTGTGCACCAACATCTACAAGATCCTCCTGCTG CAGGCGTACAGGTTTCACGCATGTGTGCTGCAGCTCCC ATTTCATCAGCAAGTTTGGAAGAACCCCACATTTTTCCT GCGCGTCATCTCTGACACGGCCTCCCTCTGCTACTCCAT CCTGAAAGCCAAGAACGCAGGGATGTCGCTGGGGGC CAAGGGCGCCGCCGGCCCTCTGCCCTCCGAGGCCGTG CAGTGGCTGTGCCACCAAGCATTCCTGCTCAAGCTGAC TCGACACCGTGTCACCTACGTGCCACTCCTGGGGTCAC TCAGGACAGCCCAGACGCAGCTGAGTCGGAAGCTCCC GGGGACGACGCTGACTGCCCTGGAGGCCGCAGCCAAC CCGGCACTGCCCTCAGACTTCAAGACCATCCTGGAC |
| G17798. TCGA-32-5222-01A-01R-1850-01.4 | 11313896 | 6880241 | InFrame | 8358 | ATGCTTGGAACCGGACCTGCCGCCGCCACCACCGCTGC CACCCACATCTAGCAATGTGAGCGTCCTGCAGCAGTTTG CCAGTGGCCTAAAGAGCCGGAATGAGGAAACCAGGG CCAAAGCCGCCAAGGAGCTCCAGCACTATGTCACCAT GGAACTCCGAGAGATGAGTCAAGAGGAGTCTACTCGC TTCTATGACCAACTGAACCATCACATTTTTGAATTGGTT TCCAGCTCAGATGCCAATGAGAGGAAAGGTGGCATCT TGGCCATAGCTAGCCTCATAGGAGTGGAAGGTGGGAA TGCCACCCGAATTGGCAGATTTGCCAACTATCTTCGGA ACCTCCTCCCCTCCAATGACCCAGTTGTCATGGAAATG GCATCCAAGGCCATTGGCCGTCTTGCCATGGCAGGGG ACACTTTTACCGCTGAGTACGTGGAATTTGAGGTGAAG CGAGCCCTGGAATGGCTGGGTGCTGACCGCAATGAGG GCCGGAGACATGCAGCTGTCCTGGTTCTCCGTGAGCT GGCCATCAGCGTCCCTACCTTCTTCTTCCAGCAAGTGC AACCCTCTTTGACAACATTTTGTGGCCGTGTGGGAC CCCAAACAGGCCATCCGTGAGGGAGCTGTAGCCGCCC TTCGTGCCTGTCTGATTCTCACAACCCAGCGTGAGCCG AAGGAGATGCAGAAGCCTCAGTGGTACAGGCACACAT |

FIG. 27 Cont.

| sample | Gene Break-point 5p | Gene Break-point 3p | Frame Type | SEQ ID NO: | Fused Sequence |
|---|---|---|---|---|---|
| | | | | | TTGAAGAAGCAGAGAAGGGATTTGATGAGACCTTGGC CAAAGAGAAGGGCATGAATCGGGATGATCGGATCCAT GGAGCCTTGTTGATCCTTAACGAGCTGGTCCGAATCAG CAGCATGGAGGGAGAG\|agcgtttcccaaagtgtattctgcgg aacTAGCACCTACTGTGTTCTCAACACCGTGCCACCTAT AGAAGATGATCATGGGAACAGCAATAGTAGTCATGTA AAAATCTTTTTACCGAAAAAGCTGCTTGAATGTCTGCC GAAATGTTCAAGTTTACCAAAAGAGAGGCACCGCTGG AACACTAATGAGGAAATTGCAGCTTATTTAATAACATT TGAGAAACACGAAGAATGGCTAACCACCTCCCCTAAG ACAAGACCACAGAATGGCTCAATGATACTCTACAACAG GAAGAAAGTGAAATACAGGAAAGATGGGTATTGCTG GAAAAAGAGGAAAGATGGGAAAACGACCAGAGAGGA CCACATGAAACTCAAGGTCCAGGGAGTGGAGTGCTTG TACGGCTGCTATGTCCATTCCTCCATCATCCCCACCTTC CACCGGAGGTGCTACTGGCTCCTTCAGAACCCCGACAT CGTCCTGGTGCACTACCTGAACGTGCCGGCCATCGAG GACTGCGGCAAGCCTTGCGGCCCCATCCTCTGCTCCAT CAACACCGACAAGAAGGAGTGGGCGAAATGGACGAA AGAAGAGCTCATCGGGCAGCTGAAACCCATGTTCCAT GGCATCAAGTGGACCTGCAGCAATGGGAACAGCAGCT CAGGCTTCTCGGTGGAACAGCTGGTGCAGCAGATCCT CGACAGCCACCAGACCAAGCCCCAGCCGCGGACCCAC AACTGCCTCTGCACCGGCAGCCTGGGAGCTGGCGGCA GCGTGCATCACAAGTGTAACAGCGCCAAACACCGCAT CATCTCGCCCAAGGTGGAGCCACGGACAGGGGGGTAC GGGAGCCACTCGGAGGTGCAGCACAATGACGTGTCG GAGGGCAAGCACGAGCACAGCCACAGCAAGGGCTCC AGCCGTGAGAAGAGGAACGGCAAGGTGGCCAAGCCC GTGCTCCTGCACCAGAGCAGCACCGAGGTCTCCTCCAC CAACCAGGTGGAAGTCCCCGACACCACCCAGAGCTCC CCTGTGTCCATCAGCAGCGGGCTCAACAGCGACCCGG ACATGGTGGACAGCCCGGTGGTCACAGGTGTGTCCGG TATGGCGGTGGCCTCTGTGATGGGGAGCTTGTCCCAG AGCGCCACGGTGTTCATGTCAGAGGTCACCAATGAGG CCGTGTACACCATGTCCCCCACCGCTGGCCCCAACCAC CACCTCCTCTCACCTGACGCCTCTCAGGGCCTCGTCCTG GCCGTGAGCTCTGATGGCCACAAGTTCGCCTTTCCCAC CACGGGCAGCTCGGAGAGCCTGTCCATGCTGCCCACC AACGTGTCCGAAGAGCTGGTCCTCTCCACCACCCTCGA CGGTGGCCGGAAGATTCCAGAAACCACCATGAACTTT GACCCCGACTGTTTCCTTAATAACCCAAAGCAGGGCCA GACGTACGGGGGTGGAGGCCTGAAAGCCGAGATGGT CAGCTCCAACATCCGGCACTCGCCACCCGGGGAGCGG AGCTTCAGCTTTACCACCGTCCTCACCAAGGAGATCAA GACCGAGGACACCTCCTTCGAGCAGCAGATGGCCAAA GAAGCGTACTCCTCCTCCGCGGCGGCTGTGGCAGCCA GCTCCCTCACCCTGACCGCCGGCTCCAGCCTCCTGCCG TCGGGCGGCGGCCTGAGTCCAGCACCACCCTGGAGC AGATGGACTTCAGCGCCATCGACTCCAACAAGGACTA CACGTCCAGCTTCAGCCAGACGGGCCACAGCCCCCAC ATCCACCAGACCCCCTCCCCGAGCTTCTTCCTGCAGGA CGCCAGCAAACCCCTCCCCGTCGAGCAGAACACCCACA GCAGCCTGAGTGACTCTGGGGGCACCTTCGTGATGCC CACGGTGAAAACGGAGGCCTCGTCCCAAACCAGCTCC |

FIG. 27 Cont.

| sample | Gene Breakpoint 5p | Gene Breakpoint 3p | Frame Type | SEQ ID NO: | Fused Sequence |
|---|---|---|---|---|---|
| | | | | | TGCAGCGGTCACGTGGAGACGCGGATCGAGTCCACTT CCTCCCTCCACCTCATGCAGTTCCAGGCCAACTTCCAG GCCATGACGGCAGAAGGGGAGGTCACCATGGAGACC TCGCAGGCGGCGGAAGGGAGCGAGGTCCTGCTCAAG TCTGGGGAGCTGCAGGCTTGCAGCTCTGAGCACTACCT GCAGCCGGAGACCAACGGGGTAATCCGAAGCGCCGG CGGCGTCCCCATCCTCCCGGGCAACGTGGTGCAGGGA CTCTACCCCGTGGCCCAGCCCAGCCTCGGCAACGCCTC CAACATGGAGCTCAGCCTGGACCACTTTGACATCTCCT TCAGCAACCAGTTCTCCGACCTGATCAACGACTTCATCT CCGTGGAGGGGGGCAGCAGCACCATCTATGGGCACCA GCTGGTGTCGGGGGACAGCACGGCGCTCTCACAGTCA GAGGACGGGGCGCGGGCCCCCTTCACCCAGGCAGAG ATGTGCCTCCCCTGCTGTAGCCCCCAGCAGGGTAGCCT GCAGCTGAGCAGCTCGGAGGGCGGGGCCAGCACCAT GGCCTACATGCACGTCGCCGAGGTGGTCTCGGCCGCC TCGGCCCAGGGCACCCTAGGCATGCTGCAGCAGAGCG GACGGGTGTTCATGGTGACCGACTACTCCCCAGAGTG GTCTTACCCAGAGGGAGGAGTGAAGGTCCTCATCACA GGCCCGTGGCAAGAAGCCAGCAATAACTACAGCTGCC TGTTTGACCAGATCTCAGTGCCTGCATCCCTGATTCAG CCTGGGGTGCTGCGCTGCTACTGCCCAGCCCATGACAC TGGTCTTGTGACCCTACAAGTTGCCTTCAACAACCAGA TCATCTCCAACTCGGTGGTGTTTGAGTACAAAGCCCGG GCTCTGCCCACGCTCCCTTCCTCCCAGCACGACTGGCT GTCGTTGGACGATAACCAGTTCAGGATGTCCATCCTGG AACGACTGGAGCAGATGGAGAGGAGGATGGCCGAGA TGACGGGGTCCCAGCAGCACAAACAGGCGAGCGGAG GCGGCAGCAGTGGAGGCGGCAGCGGGAGCGGGAAT GGAGGGAGCCAGGCACAGTGTGCTTCTGGGACTGGG GCCTTGGGGAGCTGCTTTGAGAGCCGTGTGGTCGTGG TATGCGAGAAGATGATGAGCCGAGCCTGCTGGGCGAA GTCCAAGCACTTGATCCACTCAAAGACTTTCCGCGGAA TGACCCTACTCCACCTGGCCGCTGCCCAGGGCTATGCC ACCCTAATCCAGACCCTCATCAAATGGCGTACAAAGCA CGCGGATAGCATTGACCTGGAACTGGAAGTTGACCCC TTGAATGTGGACCACTTCTCCTGTACTCCTCTGATGTG GGCGTGTGCCCTAGGGCACTTGGAAGCTGCCGTCGTG CTGTACAAGTGGGACCGTCGGGCCATCTCGATTCCCGA CTCTCTAGGAAGGCTGCCTTTGGGAATTGCCAGGTCAC GGGGTCATGTGAAATTAGCAGAGTGTCTGGAGCACCT GCAGAGAGATGAGCAGGCTCAGCTGGGACAGAACCC CAGAATCCACTGTCCTGCAAGCGAAGAGCCCAGCACA GAGAGCTGGATGGCCCAGTGGCACAGCGAAGCCATCA GCTCTCCAGAAATACCCAAGGGAGTCACTGTTATTGCA AGCACCAACCCAGAGCTGAGAAGACCTCGTTCTGAAC CCTCTAATTACTACAGCAGTGAGAGCCACAAAGATTAT CCGGCTCCCAAAAAGCATAAATTGAACCCTGAGTACTT CCAGACAAGGCAGGAGAAGCTGCTTCCCACTGCACTG AGTCTGGAAGAGCCAAATATCAGGAAGCAAAGCCCTA GTTCTAAGCAGTCTGTCCCCGAGACACTCAGCCCCAGT GAAGGAGTGAGGGACTTCAGCCGGGAACTCTCCCCTC CCACTCCAGAGACTGCAGCATTTCAAGCCTCTGGATCT CAGCCTGTAGGAAAGTGGAATTCCAAAGATCTTTACAT TGGTGTGTCTACAGTACAGGTGACTGGAAATCCGAAG |

FIG. 27 Cont.

| sample | Gene Break-point 5p | Gene Break-point 3p | Frame Type | SEQ ID NO: | Fused Sequence |
|---|---|---|---|---|---|
| | | | | | GGGACCAGTGTAGGAAAGGAGGCAGCACCTTCACAG GTGCGTCCACGGGAACCAATGAGTGTCCTGATGATGG CTAACAGAGAGGTGGTGAATACAGAGCTGGGGTCCTA CCGTGATAGTGCAGAAAATGAAGAATGCGGCCAGCCC ATGGATGACATACAGGTGAACATGATGACCTTGGCAG AACACATTATTGAAGCCACACCTGACCGAATCAAGCAG GAGAATTTTGTGCCCATGGAGTCCTCAGGATTGGAAA GAACAGACCCTGCCACCATTAGCAGTACAATGAGCTG GCTGGCCAGTTATCTAGCGGATGCTGACTGCCTTCCCA GTGCTGCCCAGATCCGAAGTGCATATAACGAGCCTCTA ACCCCTTCTTCTAATACCAGCTTGAGCCCTGTTGGCTCT CCCGTCAGTGAAATCGCTTTCGAGAAACCTAACCTTCC CTCCGCCGCGGATTGGTCAGAATTCCTGAGTGCATCTA CCAGTGAGAAGGTAGAGAATGAGTTTGCTCAGCTCAC TCTGTCTGATCATGAACAGAGAGAACTCTATGAGGCTG CCAGGCTTGTCCAGACAGCTTTCCGGAAATACAAGGG CCGACCCTTGCGGGAACAGCAAGAAGTAGCTGCTGCT GTTATTCAGCGTTGTTACAGAAAATATAAACAGTACGC ACTTTATAAAAAGATGACACAGGCTGCCATCCTTATCC AGAGCAAATTCCGAAGTTACTATGAACAAAAAAATTC CAGCAGAGCCGACGGGCTGCTGTGCTCATCCAAAAGT ACTACCGAAGTTATAAGAAATGTGGCAAAGACGGCA GGCTCGCCGGACGGCTGTGATTGTACAACAGAAACTC AGGAGCAGTTTGCTAACCAAAAAGCAGGATCAAGCTG CTCGAAAAATAATGAGGTTTCTTCGCCGCTGTCGCCAC AGCCCCTGGTGGACCATAGGCTGTACAAAAGGAGTG AAAGAATTGAAAAAGGCCAAGGAACT |
| GBM-CUMC32 97_L1 | 74640521 | 18659539 | InFrame | 8359 | ATGGCCCGGGGCTACGGGGCCACGGTCAGCCTAGTCC TGCTGGGTCTGGGGCTGGCGCTGGCTGTCATTGTGCT GGCTGTGGTCCTCTCTCGACACCAGGCCCCATGTGGCC CCCAGGCCTTTGCCCACGCTGCTGTTGCCGCCGACTCC AAGGTCTGCTCGGATATTGGACG\|GCAGGAAACTGCA TATCTTCTGGTTTACATGAAGATGGAGTGC |
| GBM-CUMC33 42_L1 | 61083748 | 104375025 | InFrame | 8360 | ATGTTTGTGTATGTGCTCACTCCCGGAGAGCAATCAGG GAGACGGCTCCCCGGCCAGACTTGGCTGATGTTTTCTT GTTTCTGTTTCAGCCTTCAGGATAATTCCTTCAGCAGCA CCACTGTAACAGAGTGTGACGAAGATCCAGTCTCTCTA CATGAAGACCAGACTGATTGCTCCAGTCTCAGAGATG AAAACAATAAAGAGAACTACCCCGACGCAGGGGCTCT GGTAGAAGAGCACGCGCCGCCCTCTTGGGAGCCGCAG CAGCAGAATGTAGAGGCGACCGTGCTGGTGGACAGC GTATTGCGACCCAGCATGGGCAACTTCAAGTCCAGGA AGCCCAAGTCCATCTTCAAAGCGGAGAGCGGGAGGA GCCACGGAGAAAGTCAGGAGACAGAGCATGTGGTAT CCAGCCAGTCAGAGTGTCAGGTGAGAGCAGGAACACC AGCTCATGAGAGTCCACAAAACAATGCCTTCAAGTGCC AAGAAACAGTGCGACTTCAACCAAG\|GAGCCGCAAAG ACAGCCTGGAAAGTGACAGCTCCACGGCCATCATTCCC CATGAGCTGATTCGCACGCGGCAGCTTGAGAGCGTAC ATCTGAAATTCAACCAGGAGTCCGGAGCCCTCATTCCT CTCTGCCTAAGGGGCAGGCTCCTGCATGGACGGCACT TTACATATAAAAGTATCACAGGTGACATGGCCATCACG TTTGTCTCCACGGGAGTGGAAGGCGCCTTTGCCACTGA GGAGCATCCTTACGCGGCTCATGGACCCTGGTTACAAA TTCTGTTGACCGAAGAGTTTGTAGAGAAAATGTTGGA |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GGATTTAGAAGATTTGACTTCTCCAGAGGAATTCAAAC TTCCCAAAGAGTACAGCTGGCCTGAAAAGAAGCTGAA GGTCTCCATCCTGCCTGACGTGGTGTTCGACAGTCCGC TACAC |
| G17500. TCGA-27-1831-01A-01R-1850-01.2 | 39438743 | 41808143 | InFrame | 8361 | ATGCACTCAGCCGGGACTCCCGGGTTATCCTCGCGCCG GACAGGCAACTCCACCAGCTTTCAACCAGGACCGCCAC CGCCGCCCCGgctgctgctgctgctgctgctTCTCCTGTCACTG GTAAGCCGCGTCCCGGCACAGCCCGCTGCCTTCGGCA GGGCGTTGCTGTCCCCTGGTCTCGCGGGGCTGCAGG GGTCCCTGCTGAGGAGGCCATAGTGCTGGCGAACCGC GGACTCCGGGTGCCTTTCGGCCGTGAAGTCTGGCTGG ATCCCTGCATGACCTGGTGTTGCAGGTGCAGCCCGG GGACCGCTGCGCGGTTTCGGTACTAGACAACGACGCA CTGGCCCAGCGACCGGGCCGCCTGAGTCCCAAGCGCT TCCCGTGCGACTTTGGCCCTGGCGAGGTGCGCTACTCT CACCTGGGCGCGCGCAGCCCGTCTCGGGACCGCGTCC GGCTGCAGCTGCGCTATGACGCGCCCGGAGGGGCAGT AGTGCTACCACTGGTACTGGAGGTGGAGGTGGTCTTC ACCCAGCTGGAGGTTGTGACTCGGAACTTGCCTCTGGT CGTGGAAGAGCTGCTGGGGACCAGCAATGCCCTGGAC GCGCGGAGCCTGGAGTTCGCCTTCCAGCCCGAGACAG AGGAGTGCCGCGTGGGCATCCTGTCCGGCTTGGGCGC GCTGCCTCGCTATGGAGAACTCCTCCACTACCCGCAGG TCCCTGGAGGAGCCAGAGAGGGAGGCGCCCGGAGA CTCTCCTGATGGACTGCAAAGCTTTCCAGGAACTAGGC GTGCGCTATCGCCACACAGCCGCCAGTCGCTCACCAAA CAGGGACTGGATACCCATGGTGGTGGAGCTGCGTTCA CGAGGGGCTCCTGTGGGCAGCCCTGCTTTGAAACGCG AGCACTTCCAGGTTCTGGTGAGGATCCGAGGAGGGGC CGAGAACACTGCACCCAAGCCCAGTTTCGTGGCCATG ATGATGATGGAGGTGGACCAGTTTGTACTGACGGCCC TGACCCCAGACATGCTGGCAGCCGAGGATGCTGAGTC TCCCTCTGACCTGTTGATCTTCAACCTTACTTCTCCATTC CAGCCTGGCCAGGGCTACTTGGTGAGCACCGATGATC GCAGCCTGCCCCTTTCCTCCTTCACTCAGAGGGATCTG CGGCTCCTGAAGATTGCCTACCAGCCCCCTTCTGAAGA CTCTGACCAGGAGCGCCTCTTTGAACTGGAATTGGAG GTAGTGGATCTAGAAGGAGCAGCTTCAGACCCTTTTGC CTTCATGGTAGTGGTGAAGCCCATGAACACAATGGCTC CGGTGGTCACCCGGAATACCGGTCTTATTCTCTATGAG GGTCAGTCTCGGCCCCTCACAGGCCCTGCAGGCAGTG GTCCGCAAAACTTGGTCATCAGCGATGAGGATGACCT AGAAGCAGTGCGGCTAGAGGTGGTGGCTGGGCTCCG GCATGGTCACCTTGTCATTCTGGGTGCTTCCAGTGGCA GCTCTGCTCCCAAGAGCTTTACAGTGGCTGAGCTGGCA GCCGGCCAGGTGGTCTACCAGCATGATGACAGAGACG GCTCGCTGAGCGACAACCTGGTGCTTCGCATGGTGGA TGGAGGAGGCAGGCACCAGGTACAGTTTCTGTTCCCC ATCACCTTAGTGCCTGTGGATGACCAGCCACCTGTTCT CAATGCCAACACGGGGCTGACACTGGCAGAGGGTGA AACAGTGCCCATCCTGCCCCTTTCCCTGAGTGCAACTG ACATGGATTCAGATGATTCTCTGCTGCTTTTTGTGCTG GAGTCACCCTTCTTAACTACGGGGCATCTGCTTCTCCG CCAAACTCACCCTCCCCATGAGAAGCAGGAACTTCTCA GAGGCCTTTGGAGGAAGGAGGGGGCATTTTATGAGC |

FIG. 27 Cont.

| sample | Gene Break-point 5p | Gene Break-point 3p | Frame Type | SEQ ID NO: | Fused Sequence |
|---|---|---|---|---|---|
| | | | | | GAACAGTGACAGAGTGGCAGCAGCAGGACATAACAG<br>AGGGCAGGCTGTTCTATAGACACTCTGGGCCCCATAGT<br>CCTGGGCCAGTCACAGACCAGTTCACATTTAGAGTCCA<br>GGATAACCATGACCCTCCTAATCAGTCCGGGCTACAGC<br>GGTTTGTGATTCGTATCCATCCTGTGGATCGCCTCCCTC<br>CGGAGCTGGGCAGTGGCTGTCCCCTTCGTATGGTGGT<br>ACAGGAATCCCAGCTCACACCACTGAGGAAGAAGTGG<br>CTGCGCTACACTGACCTGGACACAGATGACCGAGAAC<br>TACGTTACACAGTGACTCAGTCCCCCACAGACACAGAC<br>GAAAATCACCTGCCAGCCCCACTGGGTACCTTGGTCTT<br>GACTGACAACCCCTCAGTCGTGGTGACCCATTTTACCC<br>AAGCCCAGATCAACCATCATAAAATTGCTTACAGACCC<br>CCGGGTCAAGAACTGGGCGTGGCTACTCGAGTGGCCC<br>AGTTCCAGTTCCAGGTGGAAGACCGAGCTGGGAATGT<br>GGCTCCAGGTACCTTTACCCTTTACTTGCATCCCGTGGA<br>CAACCAGCCACCTGAGATCCTCAACACCGGCTTCACTA<br>TTCAGGAGAAGGGTCACCACATCCTGAGTGAGACAGA<br>GTTGCACGTGAATGATGTAGACACTGATGTTGCCCATA<br>TCTCTTTCACTCTCACTCAGGCACCCAAACATGGCCACA<br>TGAGAGTGTCTGGACAGATCCTGCATGTAGGGGGTCT<br>CTTCCACTTGGAGGACATAAAACAGGGCCGAGTTTCCT<br>ATGCCCATAATGGGGACAAGTCCCTGACTGATAGCTG<br>CTCCTTGGAAGTCAGTGACAGACATCATGTGGTGCCCA<br>TCACTCTCAGAGTAAATGTCCGGCCAGTGGATGATGA<br>AGTGCCCATACTGAGCCATCCTACTGGCACTCTGGAGT<br>CCTATCTAGATGTCTTAGAAAATGGGGCTACTGAAATC<br>ACTGCCAATGTTATTAAGGGGACCAATGAGGAAACTG<br>ATGACTTGATGTTGACTTTCCTCTTGGAAGATCCACCTT<br>TGTATGGGGAAATCTTGGTCAATGGCATTCCAGCAGA<br>GCAGTTTACTCAAAGGGACATCTTGGAGGGCTCTGTTG<br>TATATACCCACACCAGTGGTGAGATAGGCCTATTGCCT<br>AAAGCGGATTCTTTTAACCTGAGTCTGTCAGATATGTC<br>TCAAGAATGGAGAATTGGTGGCAATACTATCCAAGGA<br>GTTACTATATGGGTGACCATCCTGCCTGTTGATAGCCA<br>GGCCCCAGAAATCTTTGTAGGTGAACAGTTGATAGTA<br>ATGGAAGGTGATAAAAGTGTTATAACATCAGTGCATA<br>TAAGTGCTGAAGATGTCGACTCCCTGAATGATGACATC<br>TTGTGCACTATAGTTATTCAGCCTACTTCAGGTTATGTT<br>GAAAACATTTCTCCAGCACCAGGCTCTGAGAAATCAAG<br>AGCAGGGATTGCCATAAGTGCTTTCAACTTGAAAGATC<br>TCAGGCAGGGCCACATAAACTATGTCCAGAGTGTCCAT<br>AAAGGGGTGGAACCTGTGGAGGACCGATTTGTATTTC<br>GTTGTTCTGATGGCATTAACTTTTCAGAGAGACAGTTC<br>TTCCCCATTGTAATCATTCCCACCAATGATGAACAGCCA<br>GAGATGTTTATGAGAGAATTTATGGTGATGGAAGGCA<br>TGAGTCTGGTAATTGATACACCCATTCTCAATGCTGCT<br>GATGCTGATGTTCCCCTGGATGATTTAACTTTCACTATT<br>ACCCAATTCCCCACTCATGGTCACATCATGAATCAGCT<br>GATAAATGGCACGGTTTTGGTCGAAAGCTTCACCTTGG<br>ATCAGATCATAGAGAGTTCCAGCATTATTTATGAGCAT<br>GATGACTCCGAGACCCAGGAAGACAGTTTTGTGATTA<br>AACTAACAGATGGGAAGCACTCTGTGGAAAAGACGGT<br>CCTCATTATAGTTATCCCTGTTGATGATGAGACGCCCA<br>GAATGACTATCAATAATGGACTAGAAATAGAAATTGG<br>GGATACCAAGATTATCAACAACAAAATATTAATGGCAA |

FIG. 27 Cont.

| sample | Gene Break-point 5p | Gene Break-point 3p | Frame Type | SEQ ID NO: | Fused Sequence |
|---|---|---|---|---|---|
| | | | | | CAGATTTAGATTCAGAAGACAAATCTTTGGTTTATATT ATTCGTTATGGGCCAGGACATGGCTTATTACAGAGAC GAAAACCTACTGGTGCCTTTGAAAATATCACACTGGGC ATGAATTTTACCCAGGATGAAGTAGACAGAAACTTAAT TCAGTATGTCCATTTGGGGCAAGAGGGCATTCGGGAC CTAATTAAATTTGATGTGACTGATGGAATAAATCCCCT CATAGATCGTTACTTTTATGTGTCCATCGGGAGCATTG ACATTGTCTTCCCTGATGTGATAAGTAAGGGAGTGTCC TTGAAAGAAGGTGGCAAAGTCACTCTTACAACAGACC TACTAAGCACTAGTGACTTGAACAGTCCTGATGAAAAC TTGGTTTTTACCATCACCAGGGCTCCCATGCGAGGTCA CCTGGAATGCACGGATCAGCCTGGTGTGTCCATCACGT CTTTCACTCAGCTGCAACTGGCTGGAAACAAAATCTAC TACATCCACACAGCTGATGATGAAGTGAAAATGGACA GTTTTGAGTTTCAAGTCACCGATGGACGTAACCCTGTC TTTCGGACATTCCGTATCTCCATTAGCGATGTGGACAA TAAAAAGCCAGTGGTCACCATCCACAAGCTGGTTGTCA GTGAAAGTGAAAACAAGCTGATTACTCCTTTTGAGCTC ACTGTCGAAGACAGAGATACTCCTGACAAGCTCCTGA AATTCACTATCACCCAGGTGCCTATTCATGGCCATCTCC TATTCAACAATACCAGACCTGTCATGGTTTTTACCAAGC AAGACTTGAATGAAAACTTAATCAGCTACAAACATGAT GGCACTGAGTCAAGTGAAGATAGCTTCTCCTTCACAGT GACTGATGGCACCCATACAGACTTCTATGTTTTTCCTGA TACGGTGTTTGAAACAAGGAGACCCCAAGTGATGAAG ATCCAGGTCTTGGCTGTTGACAACAGTGTCCCCCAAAT CGCAGTGAATAAGGGGGCCTCTACACTTCGCACTCTAG CCACTGGCCACTTGGGGTTCATGATCACAAGCAAAATA TTGAAAGTGGAGGACAGAGACAGCTTACACATTTCTCT TAGATTTATCGTGACAGAGGCCCCTCAACATGGATATC TTCTCAACCTGGACAAAGGCAACCACAGCATCACTCAG TTCACACAAGCTGACATTGATGACATGAAAATATGCTA TGTCTTAAGAGAAGGGGCTAATGCCACAAGTGATATG TTCTATTTTGCAGTTGAAGATGGTGGTGGAAACAAGTT AACGTACCAGAATTTTCGTCTGAATTGGGCATGGATCT CCTTTGAAAAGGAATATTACCTGGTCAATGAGGACTCC AAATTTCTAGATGTTGTTCTTAAACGTAGAGGTTACTT GGGAGAAACTTCTTTTATAAGTATTGGCACAAGAGAC AGAACTGCAGAAAAAGACAAAGACTTCAAGGGCAAA GCACAGAAACAAGTGCAGTTCAACCCAGGCCAGACCA GGGCCACATGGCGAGTGCGGATCCTGAGTGATGGGG AGCATGAGCAGTCTGAAACCTTTCAGGTGGTACTCTCA GAGCCCGTGCTGGCTGCCTTGGAATTCCCCACAGTCGC CACTGTTGAGATCGTTGATCCAGGAGATGAGCCAACT GTGTTTATTCCCCAGTCCAAATACTCCGTTGAAGAAGA TGTTGGTGAGCTGTTCATTCCCATCAGGAGGAGCGGA GATGTGAGCCAGGAGTTGATGGTGGTCTGTTATACCC AACAAGGAACAGCAACTGGAACTGTGCCGACTTCCGT GTTGTCTTACTCTGATTACATATCCAGGCCTGAGGACC ACACCAGTGTTGTCCGCTTTGACAAAGATGAACGGGA GAAACTGTGTCGGATAGTCATAATTGATGACTCTTTGT ACGAGGAGGAGGAAACCTTCCATGTCCTTCTGAGCAT GCCCATGGGGGGAAGAATCGGATCAGAGTTCCCAGG GGCTCAAGTTACAATCGTTCCTGACAAAGATGATGAAC CCATCTTTTACTTCGGTGATGTGGAATACTCTGTGGAT |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GAGAGTGCTGGCTATGTGGAAGTGCAGGTGTGGAGA ACGGGCACTGACCTGTCCAAGTCTTCTAGTGTCACAGT GAGGTCTCGGAAAACAGATCCTCCCTCTGCAGATGCTG GAACAGACTATGTGGGCATCAGCCGTAATTTAGATTTT GCACCTGGAGTCAACATGCAGCCTGTTCGTGTTGTCAT TCTGGATGACCTTGGACAACCAGCGCTGGAGGGAATT GAGAAATTTGAACTGGTGCTTCGCATGCCTATGAACGC AGCCCTTGGCGAGCCCAGCAAAGCCACAGTGTCCATA AATGACTCTGTCTCCGATTTGCCTAAGATGCAATTCAA AGAACGAATATATACTGGCAGCGAAAGTGATGGGCAG ATAGTTACAATGATCCATAGGACTGGGGATGTCCAGT ACAGATCTTCAGTGAGATGCTACACCCGGCAGGGGTC TGCACAGGTGATGATGGACTTTGAAGAACGCCCAAAC ACTGATACCTCCATCATCACATTCCTCCCTGGTGAGACA GAAAAGCCCTGCATTCTTGAGCTGATGGACGATGTGCT CTATGAGGAGGTAGAGGAGCTCCGCCTGGTACTCGGC ACTCCACAAAGCAACTCTCCCTTTGGGGCTGCAGTTGG TGAACAAAATGAAACTCTCATAAGGATCCGAGATGAT GCTGATAAGACTGTTATTAAATTTGGAGAAACCAAATT TAGTGTCACTGAACCCAAAGAACCTGGAGAGTCGGTG GTTATAAGAATTCCAGTGATTCGCCAAGGAGACACTTC AAAGGTTTCCATTGTGAGAGTCCACACCAAGGATGGC TCGGCCACCTCTGGAGAAGACTACCACCCTGTGTCAGA AGAAATTGAGTTTAAGGAAGGGGAAACCCAGCACGTG GTTGAAATCGAAGTTACCTTTGACGGGGTGAGAGAGA TGAGAGAGGCCTTCACTGTTCACCTAAAACCTGATGAA AATATATGATAGCAGAGATGCAGTTGACGAAAGCCATTG TGTACATAGAAGAAATGAGCAGCATGGCAGATGTCAC TTTTCCTTCTGTCCCTCAAATTGTATCCCTGTTGATGTAT GACGACACTTCCAAAGCTAAGGAGAGTGCTGAACCCA TGTCTGGCTATCCTGTCATCTGTATCACAGCTTGCAACC CCAAATATTCAGACTACGATAAAACAGGCTCTATCTGT GCAAGTGAGAACATCAATGACACTTTGACGCGGTACC GGTGGCTGATTAGTGCACCTGCGGGCCCTGACGGTGT GACCAGCCCTATGAGAGAAGTGGACTTCGACACCTTTT TTACGTCATCCAAGATGGTCACACTGGACTCCATATAC TTTCAGCCTGGCTCCCGGGTACAGTGCGCAGCTCGTGC TGTGAACACCAATGGGGATGAAGGCCTGGAGCTCATG AGCCCTATTGTAACCATCAGCAGAGAAGAAGGTCTTTG TCAGCCCCGTGTACCTGGGGTTGTTGGAGCAGAGCCG TTCTCAGCTAAATTGCGCTACACAGGCCCTGAGGATGC AGACTACACAAACCTTATCAAGCTCACTGTCACAATGC CACACATAGATGGCATGCTCCCCGTGATCTCCACTAGA GAGCTTTCCAACTTTGAGCTCACCCTCAGCCCTGATGG CACAAGAGTTGGAAACCACAAGTGCTCCAACCTCCTG GATTATACTGAAGTGAAGACTCATTATGGTTTCTTGAC TGATGCTACCAAAAATCCAGAAATAATTGGAGAGACA TATCCTTACCAGTACAGCTTGTCCATCAGAGGTTCCACT ACCTTGCGCTTCTACCGGAACCTGAACCTAGAGGCCTG TTTATGGGAGTTCGTTAGCTACTATGACATGTCAGAAC TCCTTGCTGACTGTGGTGGCACCATTGGAACAGATGG ACAG\|GTGGATGTGAAATTGGACCCCAAGGATTTGCG AATAGATACATTTCGAGCCAAAGGAGCAGGAGGGCA GCATGTTAATAAAACTGATAGTGCCGTCAGACTTGTCC ACATCCCCACAGGGCTAGTAGTAGAATGCCAACAAGA |

FIG. 27 Cont.

| sample | Gene Break-point 5p | Gene Break-point 3p | Frame Type | SEQ ID NO: | Fused Sequence |
|---|---|---|---|---|---|
| | | | | | AAGATCACAGATAAAAAATAAAGAAATAGCCTTTCGT GTGTTGAGAGCTAGACTCTACCAGCAGATTATTGAGA AAGACAAGCGTCAGCAACAAAGTGCTAGAAAACTGCA GGTGGGAACAAGAGCCCAGTCAGAGCGAATTCGGAC ATATAATTTCACCCAGGATAGAGTCAGTGACCACAGG ATAGCATATGAAGTTCGTGATATTAAGGCTCAGTCTCA TTCCACGGGTGGTAGTCGTGACCCTGCACATTCCACAT TCCTATCCTTGGATTCTGTGAGATCACCTGGTATTCTCA TTATGACTTCTTCTGTTAGGAATTTTTATGTGGTGGGA AGGGCCTGGATCAGC |
| G17212. TCGA-06-0129-01A-01R-1849-01.2 | 3410422 | 47221257 | InFrame | 8362 | ATGGCCATAGAccggcggcgcgaggcggcgggcggcgggcctgg gcggcagccggccccggccgaggagaacggctccctgccgcccgggg acgcggcggcctcggcgccctcgggggacgcgcgggccccggcggc ggcgcggAGATCCAGCCGCTGCCCCCACTGCATCCTGGA GGCGGCCCGCACCCGAGCTGCTGCTCCGCGGCTGCGG CCCCGAGCCTCTTGTTGCTGGACTATGACGGGTCGGTG CTGCCCTTCCTCGGGGGCCTGGGCGGGGGCTATCAGA AGACCCTCGTGCTGCTCACCTGGATCCCGGCGCTGTTC ATCGGCTTCAGCCAGTTCTCGGACTCGTTCCTCCTGGA CCAGCCCAACTTCTGGTGCCGCGGGGCCGGCAAAGGC ACCGAGCTGGCAGGGGTCACCACCACAGGCCGGGGC GGGGACATGGGCAACTGGACCAGCCTCCCCACCACCC CCTTCGCCACTGCCCCCTGGGAGGCTGCGGGCAACCG GAGCAACAGCAGCGGCGCGGACGGAGGCGACACACC ACCCCTGCCATCCCCTCCGGACAAGGGGGACAACGCC TCCAACTGTGACTGCCGCGCATGGGACTACGGCATCC GCGCCGGCCTCGTCCAGAACGTGGTCAGCAAGTGGGA TCTTGTGTGTGATAATGCCTGGAAGGTCCATATCGCTA AGTTCTCCTTACTGGTTGGATTAATCTTTGGCTACCTAA TAACTGGATGCATTGCTGACTGGGTCGGCCGGCGGCC TGTGCTGCTGTTTTCCATCATCTTCATTCTGATCTTTGG ACTGACTGTGGCACTGTCAGTGAATGTGACAATGTTCA GCACACTCAGGTTCTTTGAAGGATTTTGCCTGGCTGGA ATCATTCTCACCTTGTATGCTTTAC\|GTATCGATATCCT GAAGCTTGTAGCAGCCCAAGTGGGAAGCCAGTGGAA AGATATCTATCAGTTTCTTTGCAATGCCAGTGAGAGGG AGGTTGCTGCTTTCTCCAATGGGTACACAGCCGACCAC GAGCGGGCCTACGCAGCTCTGCAGCACTGGACCATCC GGGGCCCCGAGGCCAGCCTCGCCCAGCTAATTAGCGC CCTGCGCCAGCACCGGAGAAACGATGTTGTGGAGAAG ATTCGTGGGCTGATGGAAGACACCACCCAGCTGGAAA CTGACAAACTAGCTCTCCCGATGagccccagcccgcttagcc cgagcccatcccagccccaacGCGAAACTTGAGAATTCCG CTCTCCTGACGGTGGAGCCTTCCCCACAGGACAAGAAC AAGGGCTTCTTCGTGGATGAGTCGGAGCCCCTTCTCCG CTGTGACTCTACATCCAGCGGCTCCTCCGCGCTGAGCA GGAACGGTTCCTTTATTACCAAAGAAAAGAAGGACAC AGTGTTGCGGCAGGTACGCCTGGACCCTGTGACTTG CAGCCTATCTTTGATGACATGCTCCACTTTCTAAATCCT GAGGAGCTGCGGGTGATTGAAGAGATTCCCCAGGCTG AGGACAAACTAGACCGGCTATTCGAAATTATTGGAGT CAAGAGCCAGGAAGCCAGCCAGACCCTCCTGGACTCT GTTTATAGCCATCTTCCTGACCTGCTG |

FIG. 27 Cont.

| sample | Gene Break- point 5p | Gene Break- point 3p | Frame Type | SEQ ID NO: | Fused Sequence |
|---|---|---|---|---|---|
| GBM-CUMC33 22_L1 | 141255367 | 158715068 | InFrame | 8363 | ATGGAAAACACTG\|ATCGAAAAGTATCCTCCTTGCACA CCTCCCGAGTTCAGAGGCAGATGGTGGTCTCCGTTCAC GACTTACCCGAGAAGAGCTTTGTGCCCCTGCTGGACA GCAAATACGTCCTCTGTGTGTGGGATATTTGGCAGCCT TCAGGGCCACAGAAAGTTCTGATATGTGAGTCCCAGG TCACGTGTTGCTGCTTGAGCCCTTTGAAAGCATTTTTAC TGTTTGCCGGAACAGCGCACGGCTCAGTTGTCGTCTGG GATTTGAGAGAAGACTCAAGGCTGCATTACTCTGTGAC GCTGAGCGATGGCTTCTGGACGTTCCGGACCGCCACG TTTTCCACCGATGGAATCCTTACCTCAGTAAACCACCG AAGCCCTCTTCAAGCAGTAGAACCTATCTCAACGTCCG TCCACAAAAAGCAGAGCTTTGTGCTTTCACCCTTTTCTA CTCAAGAAGAAATGTCAGGTTTGTCCTTCCACATCGCT TCCTTGGATGAGAGTGGGGTTCTCAATGTATGGGTGG TTGTTGAATTACCAAAGGCAGACATCGCAGGTTCAATA AGTGATTTAGGTCTGATGCCTGGAGGGAGGGTCAAGC TGGTACATAGTGCTCTGATCCAGTTGGGTGACAGTCTT TCCCATAAAGGTAATGAATTTTGGGGCACTACACAAAC ACTGAATGTTAAATTTCTGCCTTCAGATCCTAATCACTT TATTATTGGCACAGACATGGGTCTCATAAGCCATGGCA CAAGACAAGATTTGAGAGTGGCTCCCAAACTATTCAAA CCTCAGCAACATGGTATAAGACCAGTGAAAGTTAATGT CATTGATTTTTCACCATTTGGAGAACCAATATTTTTGGC CGGCTGTTCGGACGGAAGCATCAGGCTGCACCAGCTG AGCTCCGCGTTTCCGCTCCTGCAGTGGGACAGCAGCAC GGACAGCCATGCGGTCACCGGCCTGCAGTGGTCCCCA ACCAGGCCTGCCGTGTTCCTGGTGCAGGACGACACAT CCAACATCTACATCTGGGACCTCCTCCAGAGCGATCTG GGTCCTGTCGCCAAACAGCAGGTCTCCCCCAACAGGCT GGTGGCCATGGCTGCGGTGGGTGAGCCTGAGAAGGC TGGTGGCAGCTTCCTGGCCCTGGTGCTGGCCAGGGCG TCTGGCTCCATCGACATCCAGCACCTGAAGAGGCGGT GGGCGGCCCCGGAGGTGGACGAGTGCAACAGGCTGC GTCTGCTTTTGCAGGAAGCCCTGTGGCCAGAGGGAAA ACTGCACAAG |
| G17675. TCGA-19-2624-01A-01R-1850-01.2 | 54379794 | 56297264 | InFrame | 8364 | ATGACATGCCCTCGCAATGTAACTCCGAACTCGTACGC GGAGCCCTTGGCTGCGCCCGGCGGAGGAGAGCGCTAT AGCCGGAGCGCAGGCATGTATATGCAGTCTGGGAGTG ACTTCAATTGCGGGGTGATGAGGGGCTGCGGGCTCGC GCCCTGCTCTCCAAGAGGGACGAGGGCAGCAGCCCC AGCCTCGCCCTCAACACCTATCCGTCCTACCTCTCGCAG CTGGACTCCTGGGGCGACCCCAAAGCCGCCTATCGCCT GGAACAACCTGTTGGCAGGCCGCTGTCCTCCTGCTCCT ACCCACCTAGTGTCAAGGAGGAGAATGTCTGCTGCAT GTACAGCGCAGAGAAGCGGGCGAAAAGTGGCCCCGA GGCAGCTCTCTACTCCCACCCCTTGCCGGAGTCCTGCC TTGGGGAGCACGAGGTACCCGTGCCCAGCTACTACCG CGCCAGCCCGAGCTACTCCGCGCTGGACAAGACGCCC CACTGTTCTGGGGCCAACGACTTCGAAGCCCCTTTCGA GCAGCGGGCCAGTCTCAACCCGCGCGCCGAACATCTG GAATCGCCTCAGCTGGGGGGCAAAGTGAGTTTCCCTG AGACCCCCAAGTCCGACAGCCAGACCCCCAGCCCCAAT GAAATCAAGACGGAGCAGAGCCTGGCGGGCCCTAAA GGGAGCCCCTCGGAGAGCGAAAAGGAGAGGGCCAAA GCTGCCGACTCCAGCCCAGACACCTCGGATAACGAAG |

FIG. 27 Cont.

| sample | Gene Break-point 5p | Gene Break-point 3p | Frame Type | SEQ ID NO: | Fused Sequence |
|---|---|---|---|---|---|
| | | | | | CGAAAG\|GCAAGTATATCGCGTCAACACAGCGACCTG ACGGGACCTGGCGCAAGCAGCGGAGGGTGAAAGAAG GATATGTGCCCCAGGAGGAGGTCCCAGTATATGAAAA CAAGTATGTGAAGTTTTTCAAGAGTAAACCAGAGTTGC CCCCAGGGCTAAGCCCTGAGGCCACTGCTCCTGTCACC CCATCCAGGCCTGAAGGTGGTGAACCAGGCCTCTCCA AGACAGCCAAACGTAACCTGAAGCGAAAGGAGAAGA GGCGGCAGCAGCAAGAGAAAGGAGAGGCAGAGGCCT TGAGCAGGACTCTTGATAAGGTGTCCCTGGAAGAGAC AGCCCAACTCCCCAGTGCTCCACAGGGCTCTCGGGCA GCCCCCACAGCTGCATCTGACCAGCCTGACTCAGCTGC CACCACTGAGAAAGCCAAGAAGATAAAGAACCTAAAG AAGAAACTCCGGCAGGTGGAAGAGCTGCAGCAGCGG ATCCAGGCTGGGGAAGTCAGCCAGCCTAGCAAAGAGC AGCTAGAAAAGCTAGCAAGGAGGAGGGCGCTAGAAG AGGAGTTAGAGGACTTGGAGTTAGGCCTC |
| G17803. TCGA-76- 4925- 01A-01R- 1850- 01.4 | 74046509 | 10694746 | InFrame | 8365 | ATGGCTGCTGAGAAGCAGGTCCCAggcggcggcggcggcg gcggcagtggcggcggcggcggtggcagtggcggcggcggtagcggcggt ggACGTGGTGCCGGAGGGGAAGAAAATAAAGAAAAC GAACGCCCTTCGGCCGGATCGAAGGCAAACAAAGAAT TTGGGGATAGCCTGAGTTTGGAGATTCTTCAGATTATT AAGGAATCCCAGCAGCAGCATGGTTTACGGCATGGAG ATTTTCAGAGGTACAGGGGCTACTGTTCCCGTAGACAA AGACGTCTTCGAAAAACACTCAACTTCAAGATGGGTAA CAGACACAAATTCACAGGGAAGAAAGTGACTGAAGAG CTTCTGACCGATAATAGATACTTGCTTCTGGTTCTGATG GATGCTGAAAGAGCCTGGAGCTACGCCATGCAGCTGA AACAGGAAGCCAACACTGAACCCCGAAAACGGTTTCA CTTGTTATCTCGCCTACGCAAAGCCGTGAAGCATGCAG AGGAATTGGAACGCTTGTGTGAGAGCAATCGCGTGGA TGCCAAGACCAAATTAGAGGCTCAGGCTTACACAGCTT ACCTCTCAGGAATGCTACGTTTTGAACATCAAGAATGG AAAGCTGCCATTGAGGCTTTTAACAAATGCAAAACTAT CTATGAGAAGCTAGCCAGTGCTTTCACAGAGGAGCAG GCTGTGCTGTATAACCAACGTGTGGAAGAGATTTCACC CAACATCCGCTATTGTGCATATAATATTGGGGACCAGT CAGCCATCAATGAACTCATGCAGATGAGATTGAGGTCT GGGGGCACTGAGGGTCTCTTGGCTGAAAAATTGGAGG CTTTGATCACTCAGACTCGAGCCAAACAGGCAGCTACC ATGAGTGAAGTGGAGTGGAGAGGGAGAACGGTTCCA GTGAAGATTGACAAAGTGCGCATTTTCTTATTAGGACT GGCTGATAACGAAGCAGCTATTGTCCAGGCTGAAAGC GAAGAAACTAAGGAGCGCCTGTTTGAATCAATGCTCA GCGAGTGTCGGGACGCCATCCAGGTGGTTCGGGAGG AGCTCAAGCCAGATCAG\|CCATTGATCAGCCGCAACTA CAAGGGCGATGTGGCCATGAGCAAGATTGAGCACTTC ATGCCTTTGCTGGTACAGCGGGAGGAGGAAGGCGCCC TGGCCCCGCTGCTGAGCCACGGCCAGGTCCACTTCCTA TGGATCAAACACAGCAACCTCTACTTGGTGGCCACCAC ATCGAAGAATGCCAATGCCTCCCTGGTGTACTCCTTCC TGTATAAGACAATAGAGGTATTCTGCGAATACTTCAAG GAGCTGGAGGAGGAGAGCATCCGGGACAACTTTGTCA TCGTCTACAGTTGCTGGACGAGCTCATGGACTTTGGC TTCCCGCAGACCACCGACAGCAAGATCCTGCAGGAGT ACATCACTCAGCAGAGCAACAAGCTGGAGACGGGCAA |

FIG. 27 Cont.

| sample | Gene Break-point 5p | Gene Break-point 3p | Frame Type | SEQ ID NO: | Fused Sequence |
|---|---|---|---|---|---|
| | | | | | GTCACGGGTGCCACCCACTGTCACCAACGCTGTGTCCT GGCGCTCCGAGGGTATCAAGTATAAGAAGAACGAGGT CTTCATTGATGTCATAGAGTCTGTCAACCTGCTGGTCA ATGCCAACGGCAGCGTCCTTCTGAGCGAAATCGTCGG TACCATCAAGCTCAAGGTGTTTCTGTCAGGAATGCCAG AGCTGCGGCTGGGCCTCAATGACCGCGTGCTCTTCGA GCTCACTGGCCTTTCAGGCAGCAAGAACAAATCAGTA GAGCTGGAGGATGTAAAATTCCACCAGTGCGTGCGGC TCTCTCGCTTTGACAACGACCGCACCATCTCCTTCATCC CGCCTGATGGTGACTTTGAGCTCATGTCATACCGCCTC AGCACCCAGGTCAAGCCACTGATCTGGATTGAGTCTGT CATTGAGAAGTTCTCCCACAGCCGCGTGGAGATCATG GTCAAGGCCAAGGGGCAGTTTAAGAAACAGTCAGTGG CCAACGGTGTGGAGATATCTGTGCCTGTACCCAGCGAT GCCGACTCCCCCAGATTCAAGACCAGTGTGGGCAGCG CCAAGTATGTGCCGGAGAGAAACGTCGTGATTTGGAG TATTAAGTCTTTCCCGGGGGGCAAGGAGTACTTGATGC GAGCCCACTTTGGCCTCCCCAGTGTGGAAAAGGAAGA GGTGGAGGGCCGGCCCCCCATCGGGGTCAAGTTTGAG ATCCCCTACTTCACCGTCTCTGGGATCCAGGTCCGATA CATGAAGATCATTGAGAAAGTGGTTACCAGGCCCTG CCCTGGGTTCGCTACATCACCCAGAGTGGCGATTACCA ACTTCGTACCAGC |
| G17796. TCGA-41-5651-01A-01R-1850-01.4 | 58186856 | 57849877 | InFrame | 8366 | ATGTCGCTGCTGCGGTCGCTGCGCGTGTTTCTGGTCGC GCGGACCGGGAGCTACCCGGCTGGGTCTCTTCTGCGT CAGTCGCCCCAGCCAAGGCACACATTTTATGCTGGGCC CCGTCTGTCTGCCTCGGCCTCCAGCAAGGAGCTCCTCA TGAAGCTGCGGCGGAAAACAGGCTACTCCTTTGTAAA TTGCAAGAAAGCTCTGGAGACTTGTGGCGGGGACCTC AAACAGGCAGAGATCTGGCTCCACAAGGAGGCCCAGA AGGAGGGCTGGAGCAAAGCTGCCAAGCTCCAAGGGA GGAAGACCAAAGAAGGCCTGATTGGGCTGTTGCAGG AAGGAAACACAACTGTATTAGTAGAGGTAAACTGTGA GACAGATTTTGTTTCTAGAAATTTAAAATTTCAACTGTT GGTCCAGCAAGTAGCCCTTGGAACCATGATGCATTGTC AGACCCTAAAGGATCAACCCTCTGCATACAGTAAAgtgc agtggctcacgcctgtaaacctagcactttgggaggctgaagcaggtgg atcacttgagGGTTTCTTGAATTCCTCTGAGCTTTCTGGAC TTCCAGCTGGGCCTGACAGAGAAGGCTCACTCAAGGA TCAGTTGGCTTTAGCAATTG\|ACTCCACTTCAGCCTACA GCTCCCTGCTCACTTTTCACCTGTCCACTCCTCGGTCCC ACCACCTGTACCATGCCCGCCTGTGGCTGCACGTGCTC CCCACCCTTCCTGGCACTCTTTGCTTGAGGATCTTCCGA TGGGGACCAAGGAGGAGGCGCCAAGGGTCCCGCACT CTCCTGGCTGAGCACCACATCACCAACCTGGGCTGGCA TACCTTAACTCTGCCCTCTAGTGGCTTGAGGGGTGAGA AGTCTGGTGTCCTGAAACTGCAACTAGACTGCAGACCC CTAGAAGGCAACAGCACAGTTACTGGACAACCGAGGC GGCTCTTGGACACAGCAGGACACCAGCAGCCCTTCCTA GAGCTTAAGATCCGAGCCAATGAGCCTGGAGCAGGCC GGGCCAGGAGGAGGACCCCCACCTGTGAGCCTGCGAC CCCCTTATGTTGCAGGCGAGACCATTACGTAGACTTCC AGGAACTGGGATGGCGGGACTGGATACTGCAGCCCG AGGGGTACCAGCTGAATTACTGCAGTGGGCAGTGCCC TCCCCACCTGGCTGGCAGCCCAGGCATTGCTGCCTCTT |

FIG. 27 Cont.

| sample | Gene Breakpoint 5p | Gene Breakpoint 3p | Frame Type | SEQ ID NO: | Fused Sequence |
|---|---|---|---|---|---|
| | | | | | TCCATTCTGCCGTCTTCAGCCTCCTCAAAGCCAACAATC CTTGGCCTGCCAGTACCTCCTGTTGTGTCCCTACTGCCC GAAGGCCCCTCTCTCCTCTACCTGGATCATAATGGC AATGTGGTCAAGACGGATGTGCCAGATATGGTGGTGG AGGCCTGTGGCTGCAGC |
| G17663. TCGA-19-2619-01A-01R-1850-01.2 | 70800719 | 94827661 | InFrame | 8367 | ATGGCTTCACTGAGAAGAGTCAAAGTGCTGTTGGTGTT GAACTTGATCGCGGTAGCCGGCTTCGTGCTCTTCCTGG CCAAGTGCCGGCCCATCGCGGTGCGCAGCGGAGACGC CTTCCACGAGATCCGGCCGCGCGCCGAGGTGGCCAAC CTCAGCGCGCACAGCGCCAGCCCCATCCAGGATGCGG TCCTGAAGCGCCTGTCGCTGCTGGAGGACATCGTGTAC CGGCAGCTGAATGGCTTATCCAAATCCCTTGGGCTCAT TGAAGGTTATGGTGGGCGGGGTAAAGGGGGCCTTCC GGCTACTCTTTCCCCGGCTGAAGAAGAAAGGCTAAG GGACCCCATGAGAAGTATGGCTACAATTCATACCTCAG TGAAAAAATTTCACTGGACCGTTCCATTCCGGATTATC GTCCCACCAA|ATTTGTTATTGGGCGGGAAAAACCAGG ACAAGTGAGCGAGGTTGCCCAGTTGATAAGCCAGACA CTGGAACAGGAGAGGCGCCAGAGAGAGCTGCTGGAA CAGCACTATGCCCAGTATGATGCCGACGATGACGAGA ACACTGTGGCTGAATTGCAAGGAATGTCTGGCAACTG CAATAACAATAACAACTATTTTCTTAAGACAGGAGAAT ATGCCACAGATGAAGAAGAAGATGAGGTAGGACCTGT CCTTCCTGGCAGCGACATGGCCATTGAAGTCTTTGAGC TGCCTGAGAATGAGGACATGTTTTCCCCATCAGAACTG GACACAAGCAAGCTCAGTCACAAGTTCAAAGAGTTGC AAATCAAACATGCAGTTACAGAAGCAGAGATTCAAAA ATTGAAGACCAAGCTGCAGGCAGCAGAAAATGAGAAA GTGAGGTGGGAACTAGAAAAAACCCAACTCCAACAAA ACATAGAAGAGAATAAGGAAAGAATGTTGAAGTTGGA AAGCTACTGGATTGAGGCCCAAACATTATGCCACACA GTGAATGAGCATCTCAAAGAGACTCAAAGCCAGTATC AGGCCTTGGAAAAGAAATACAACAAGGCAAAGAAGTT GATCAAGGATTTTCAACAAAAAGAGCTTGATTTCATCA AAAGACAGGAAGCAGAAAGAAAGAAAATAGAAGATT TGGAAAAAGCTCATCTTGTGGAAGTGCAAGGCCTCCA AGTGCGGATTAGAGATTTGGAAGCTGAGGTATTCAGG CTACTGAAGCAAAATGGGACTCAAGTTAACAATAATAA CAACATCTTTGAGAGAAGAACATCTCTTGGTGAAGTCT CTAAAGGGGATACCATGGAGAACTTGGATGGCAAGCA GACATCTTGCCAAGATGGCCTAAGTCAAGACTTGAATG AAGCAGTCCCAGAGACAGAGCGCCTGGATTCAAAAGC ACTGAAAACTCGAGCCCAGCTCTCTGTGAAGAACAGA CGCCAGAGACCCTCTAGGACAAGACTGTATGATAGTG TTAGTTCCACAGATGGGGAGGACAGTCTAGAGAGAAA GCCATCAAACAGTTTCTATAACCACATGCATATTACCA AATTACTTCCACCTAAGGGTTTGAGAACGTCTTCTCCA GAATCAGATTCTGGTGTTCCACCCCTCACCCCGGTGGA TAGCAATGTGCCCTTCTCGTCTGACCACATAGCTGAAT TTCAAGAAGAACCACTGGACCCAGAAATGGGGCCTCT CTCCTCTATGTGGGGAGACACTTCACTGTTTTCTACTTC AAAGTCTGATCATGATGTGGAAGAATCTCCTTGCCATC ACCAAACCACCAACAAGAAAATATTACGAGAAAAAGA TGATGCCAAAGATCCCAAATCACTAAGGGCATCCAGTT CATTGGCGGTGCAAGGAGGAAAAATTAAGCGGAAGTT |

FIG. 27 Cont.

| sample | Gene Break-point 5p | Gene Break-point 3p | Frame Type | SEQ ID NO: | Fused Sequence |
|---|---|---|---|---|---|
| | | | | | TGTGGATCTGGGGGCGCCTTTGCGAAGGAATTCCAGC AAGGGAAAGAAGTGGAAAGAAAAAGAAAAAGAAGCC AGTAGGTTTTCTGCAGGTAGCAGGATCTTCAGAGGCA GACTGGAAAACTGGACACCCAAGCCATGTTCAACAGC TCAGACCTCCACTCGTTCCCCTTGCATGCCTTTCTCATG GTTTAATGACAGCCGGAAAGGATCCTATTCCTTCAGGA ACCTGCCTGCGCCTACAAGTTCCCTTCAGCCTTCTCCTG AGACTCTAATTTCAGATAAAAAGGGGTCCAAGGTAGA AAACACATGGATTACAAAAGCAAACAAGAGAAACCCA AATCCCTCCTCTTCTTCAATCTTTGGAAGGCATTCTCAA CTTATGTCTGTAGTCTGGATCCAAGAAACCAATAATTTT ACCTTCAATGATGACTTCAGTCCCAGCAGTACCAGTTC AGCAGACCTCAGCGGCTTAGGAGCAGAACCTAAAACA CCAGGGCTCTCTCAGTCCTTAGCACTGTCATCAGATGA GATCCTTGATGATGGACAGTCTCCCAAACACAGTCAGT GTCAGAATCGGGCCGTTCAGGAATGGAGTGTGCAGCA GGTTTCTCACTGGTTAATGAGCCTAAATCTGGAGCAGT ATGTATCTGAATTCAGTGCCCAAAACATCACTGGAGAA CAGCTCCTGCAGTTGGATGGAAATAAACTTAAGGCTCT TGGAATGACAGCATCCCAGGACCGAGCAGTGGTCAAA AAGAAACTCAAGGAAATGAAGATGTCTCTAGAGAAGG CTCGGAAGGCCCAAGAGAAAATGGAAAAACAAAGAG AAAAGCTAAGGAGAAAGGAGCAAGAGCAAATGCAGA GGAAGTCCAAAAAGACAGAAAAGATGACGTCAACTAC AGCCGAGGGTGCTGGTGAGCAG |
| G17207. TCGA-06-0156-01A-03R-1849-01.2 | 910775 | 4438632 | InFrame | 8368 | ATGCAG\|AGCACGCAGGCCCATGAGAACAGCAGGGAT AGCCGGCTGGCATGGATGGGCACCTGGGAGCACCTTG TGTCTACTGGATTCAACCAGATGCGTGAGCGCGAAGT GAAGCTGTGGGACACGCGGTTCTTCTCCAGCGCCCTG GCCTCCCTCACCTTGGACACCTCGCTTGGGTGTCTCGT GCCTCTGCTGGACCCTGACTCTGGGCTCCTGGTCCTGG CAGGAAAGGGCGAGAGGCAGCTGTACTGTTACGAGG TGGTCCCGCAGCAGCCGGCGCTGAGCCCAGTGACCCA GTGTGTCCTGGAGAGCGTGCTGCGTGGGGCTGCCCTT GTGCCCCGGCAGGCGCTGGCCGTCATGAGCTGCGAGG TACTCCGCGTCCTACAGCTGAGCGACACAGCCATCGTG CCCATCGGCTACCATGTGCCCCGCAAGGCTGTGGAGTT CCACGAGGACCTGTTCCCGGACACTGCCGGCTGTGTG CCTGCCACCGACCCCCATAGCTGGTGGGCTGGGGACA ACCAGCAGGTGCAGAAGGTCAGCCTCAACCCCGCCTG CCGGCCCCACCCGAGCTTCACTTCCTGTCTGGTGCCCC CTGCGGAGCCCCTCCCTGACACAGCCCAGCCTGCGGT GATGGAGACACCCGTGGGTGATGCAGACGCAAGCGA GGGTTTCTCTTCCCCTCCCAGTTCGCTGACCTCGCCCTC CACGCCCTCCAGCCTGGGGCCCTCACTCTCCAGCACCA GTGGCATCGGGACCAGCCCCAGTTTGAGGTCGCTGCA GAGCCTGCTGGGCCCCAGTTCCAAGTTCCGCCATGCTC AGGGCACTGTCCTGCACCGAGACAGCCACATCACCAA CCTCAAGGGGCTCAACCTCACCACACCTGGTGAGAGT GACGGCTTCTGTGCCAACAAGCTGCGTGTGGCCGTGC CGCTGCTCAGCAGCGGGGACAGGTGGCTGTGCTTGA GCTACGGAAGCCTGGCCGCCTGCCCGACACGGCACTG CCCACGCTGCAGAATGGGGCAGCTGTGACTGATCTGG CCTGGGACCCCTTTGACCCCCATCGCCTCGCTGTGGCT GGTGAGGACGCCAGGATCCGACTGTGGCGGGTACCC |

FIG. 27 Cont.

| sample | Gene Break-point 5p | Gene Break-point 3p | Frame Type | SEQ ID NO: | Fused Sequence |
|---|---|---|---|---|---|
| | | | | | GCAGAGGGCCTGGAAGAGGTGCTCACCACGCCAGAG ACTGTGCTCACAGGCCACACGGAGAAGATCTGCTCCCT GCGCTTCCACCCACTGGCAGCCAATGTGCTGGCCTCGT CCTCCTATGACCTCACTGTTCGCATCTGGGACCTTCAG GCTGGAGCTGATCGGCTGAAGCTGCAGGGCCACCAAG ACCAGATCTTCAGCCTGGCCTGGAGTCCTGATGGGCA GCAGCTGGCCACTGTCTGCAAGGATGGGCGTGTGCGG GTCTACAGGCCCCGGAGTGGCCCTGAGCCCCTGCAGG AAGGCCCAGGGCCCAAGGGAGGACGCGGAGCTCGCA TTGTCTGGGTATGTGATGGTCGCTGTCTGCTGGTGTCT GGCTTTGACAGCCAAAGTGAGCGCCAGCTGCTCCTATA TGAAGCTGAGGCCCTGGCCGGCGGACCCTTGGCAGTG TTGGGCCTGGACGTGGCTCCCTCAACCCTGCTGCCCAG CTACGACCCAGACACTGGCCTGGTGCTCCTGACCGGCA AGGGCGACACCCGTGTATTCCTGTACGAGCTGCTCCCC GAGTCCCCTTTCTTCCTGGAGTGCAACAGCTTCACGTC GCCTGACCCCACAAGGGCCTCGTCCTCCTGCCTAAGA CGGAGTGCGACGTGCGGGAAGTGGAGCTGATGCGGT GCCTGCGGCTGCGTCAGTCCTCCCTGGAGCCTGTGGCC TTCCGGCTGCCCCGAGTCCGGAAAGAGTTCTTCCAGGA TGACGTGTTCCCAGACACGGCTGTGATCTGGGAGCCT GTGCTCAGTGCCGAGGCCTGGCTGCAAGGCGCTAATG GGCAGCCCTGGCTTCTCAGCCTGCAGCCTCCTGACATG AGCCCAGTGAGCCAAGCCCCCCGAGAGGCCCCTGCTC GTCGGGCCCCATCCTCAGCGCAGTACCTGGAAGAAAA GTCTGACCAGCAAAAGAAGGAGGAGCTGCTGAATGCC ATGGTGGCAAAACTGGGGAACCGGGAGGACCCACTCC CCCAGGACTCCTTTGAAGGCGTGGACGAGGACGAGTG GGAC |
| G17802. TCGA-28-5208-01A-01R-1850-01.4 | 55433922 | 56079562 | InFrame | 8369 | ATGGGCGAGACCATGTCAAAGAGGCTGAAGCTCCACC TGGGAGGGGAGGCAGAAATGGAGGAACGGGCGTTCG TCAACCCCTTCCCGGACTACGAGGCCGCCGCCGGGGC GCTGCTCGCCTCCGGAGCGGCCGAAGAGACAGGCTGT GTTCGTCCCCGGCGACCACGGATGAGCCCGGCCTCCC TTTTCATCAGGACGGGAAG\|GATGCTTTCATTGGATTT GGAGGAAATGTGATCAGGCAACAAGTCAAGGATAAC GCCAAATGGTATATCACTGATTTTGTAGAGCTGCTGGG AGAACTGGAAGAA |
| G17485. TCGA-14-1402-02A-01R-2005-01.2 | 151216546 | 151372723 | InFrame | 8370 | ATGCCGCAGTCCAAGTCCCGGAAGATCGCGATCCTGG GCTACCGGTCTGTGG\|CCTCCGGCCTCTCCTCCTCTCCG TCAACACCCACCCAAGTGACCAAGCAGCACACGTTTCC CCTGGAATCCTATAAGCACGAGCCTGAACGGTTAGAG AATCGCATCTATGCCTCGTCTTCCCCCCCGGACACAGG GCAGAGGTTCTGCCCGTCTTCCTTCCAGAGCCCGACCA GGCCTCCACTGGCATCACCGACACACTATGCTCCCTCC AAAGCCGCGGCGCTGGCGGCGGCCCTGGGACCCGCG GAAGCCGGCATGCTGGAGAAGCTGGAGTTCGAGGAC GAAGCAGTAGAAGACTCAGAAAGTGGTGTTTACATGC GATTCATGAGGTCACACAAGTGTTATGACATCGTTCCA ACCAGTTCAAAGCTTGTTGTCTTTGATACTACATTACAA GTTAAAAAGGCCTTCTTTGCTTTGGTAGCCAACGGTGT CCGAGCAGCGCCACTGTGGGAGAGTAAAAAACAAAGT TTTGTAGGAATGCTAACAATTACAGATTTCATAAATAT ACTACATAGATACTATAAATCACCTATGGTACAGATTT ATGAATTAGAGGAACATAAAATTGAAACATGGAGGGA |

FIG. 27 Cont.

| sample | Gene Break-point 5p | Gene Break-point 3p | Frame Type | SEQ ID NO: | Fused Sequence |
|---|---|---|---|---|---|
| | | | | | GCTTTATTTACAAGAAACATTTAAGCCTTTAGTGAATAT ATCTCCAGATGCAAGCCTCTTCGATGCTGTATACTCCTT GATCAAAAATAAAATCCACAGATTGCCCGTTATTGACC CTATCAGTGGGAATGCACTTTATATACTTACCCACAAA AGAATCCTCAAGTTCCTCCAGCTTTTTATGTCTGATATG CCAAAGCCTGCCTTCATGAAGCAGAACCTGGATGAGC TTGGAATAGGAACGTACCACAACATTGCCTTCATACAT CCAGACACTCCCATCATCAAAGCCTTGAACATATTTGT GGAAAGACGAATATCAGCTCTGCCTGTTGTGGATGAG TCAGGAAAAGTTGTAGATATTTATTCCAAATTTGATGT AATTAATCTTGCTGCTGAGAAAACATACAATAACCTAG ATATCACGGTGACCCAGGCCCTTCAGCACCGTTCACAG TATTTTGAAGGTGTTGTGAAGTGCAATAAGCTGGAAAT ACTGGAGACCATCGTGGACAGAATAGTAAGAGCTGAG GTCCATCGGCTGGTGGTGGTAAATGAAGCAGATAGTA TTGTGGGTATTATTTCCCTGTCGGACATTCTGCAAGCC CTGATCCTCACACCAGCAGGTGCCAAACAAAAGGAGA CAGAAACGGAG |
| NYU_E | 88033698 | 87883123 | InFrame | 8371 | ATGGGTGCTGGGCCCTCCTTGCTGCTCGCCGCCCTCCT GCTGCTTCTCTCCGGCGACGGCGCCGTGCGCTGCGAC ACACCTGCCAACTGCACCTATCTTGACCTGCTGGGCAC CTGGGTCTTCCAGGTGGGCTCCAGCGGTTCCCAGCGC GATGTCAACTGCTCGGTTATGGGACCACAAGAAAAAA AAGTAGTGGTGTACCTTCAGAAGCTGGATACAGCATA TGATGACCTTGGCAATTCTGGCCATTTCACCATCATTTA CAACCAAGGCTTTGAGATTGTGTTGAATGACTACAAGT GGTTTGCCTTTTTTAAGTATAAAGAAGAGGGCAGCAA GGTGACCACTTACTGCAACGAGACAATGACTGGGTGG GTGCATGATGTGTTGGGCCGGAACTGGGCTTGTTTCA CCGGAAAGAAGGTGGGAACTGCCTCTGAGAATGTGTA TGTCAACATAGCACACCTTAAGAATTCTCAGGAAAAGT ATTCTAATAGGCTCTACAAGTATGATCACAACTTTGTG AAAGCTATCAATGCCATTCAGAAGTCTTGGACTGCAAC TACATACATGGAATATGAGACTCTTACCCTGGGAGATA TGATTAGGAGAAGTGGTGGCCACAGTCGAAAAATCCC AAGGCCCAAACCTGCACCACTGACTGCTGAAATACAG CAAAAGATTTTGCATTTGCCAACATCTTGGGACTGGAG AAATGTTCATGGTATCAATTTTGTCAGTCCTGTTCGAAA CCAAG|GTCAAGAAAGATTTGGAAACATGACGAGGGT CTATTACCGAGAAGCTATGGGTGCATTTATTGTCTTCG ATGTCACCAGGCCAGCCACATTTGAAGCAGTGGCAAA GTGGAAAAATGATTTGGACTCCAAGTTAAGTCTCCCTA ATGGCAAACCGGTTTCAGTGGTTTTGTTGGCCAACAAA TGTGACCAGGGGAAGGATGTGCTCATGAACAATGGCC TCAAGATGGACCAGTTCTGCAAGGAGCACGGTTTCGT AGGATGGTTTGAAACATCAGCAAAGGAAAATATAAAC ATTGATGAAGCCTCCAGATGCCTGGTGAAACACATACT TGCAAATGAGTGTGACCTAATGGAGTCTATTGAGCCG GACGTCGTGAAGCCCCATCTCACATCAACCAAGGTTGC CAGCTGCTCTGGCTGTGCCAAATCC |
| G17212. TCGA-06-0129-01A-01R- | 51128913 | 42019095 | InFrame | 8372 | ATGGCGGAACGAGGCCTGGAGCCGTCGCCGGCCGCG GTGGCGGCGCTGCCGCCTGAAGTGCGGGCGCAGCTG GCGGAGCTGGAGCTGGAGCTCTCGGAGGGGGACATC ACCCAGAAGGGCTATGAAAAGAAAAGGTCCAAACTCC TATCTCCTTACAGCCCGCAGACACAAGAAACTGATTCA |

| sample | Gene Break-point 5p | Gene Break-point 3p | Frame Type | SEQ ID NO: | Fused Sequence |
|---|---|---|---|---|---|
| 1849-01.2 | | | | | GCAGTACAGAAAGAACTTAGAAACCAGACACCTGCTC CATCTGCAGCTCAAACTTCTGCTCCCTCTAAGTACCACC GAACTCGATCTGGGGGAGCCAGGGATGAACGATATCG ATCAGATATCCACACAGAAGCAGTTCAGGCTGCACTG GCAAAGCATAAAGAACAGAAGATGGCTTTGCCCATGC CAACCAAAAGGCGATCCACATTTGTTCAGTCTCCTGCA GATGCCTGCACACCTCCTGACACATCTTCGGCCTCTGA GGATGAGGGCTCTCTGAGACGCCAAGCTGCGCTCTCT GCTGCCTTGCAACAGAGCTTACAGAATGCTGAGTCCTG GATCAACCGTTCAATTCAGGGATCGTCCACTTCTTCATC CGCATCTTCTACGCTGTCCCACGGAGAGGTCAAAGGA ACCAGTGGGTCTCTAGCTGATGTATTTGCCAATACTCG AATAGAGAATTTCTCTGCTCCTCCTGATGTCACTACAAC TACCTCTTCCTCCTCATCATCTTCCTCAATTCGCCCAGCA AACATTGACCTGCCCCCCTCGGGGATAGTTAAAGGCAT GCACAAAGGATCCAACAGGTCCAGCCTTATGGATACA GCTGATGGTGTTCCTGTCAGTAGCAGAGTATCTACAAA AATCCAGCAGCTTCTGAACACTCTGAAACGACCCAAAA GGCCTCCCTTAAAGGAATTTTTTGTGGATGACTCTGAA GAAATTGTGGAAGTACCTCAGCCAGACCCCAACCAGC CCAAGCCGGAGGGACGGCAGATGACCCCTGTGAAAG GAGAGCCTTTAGGAGTCATCTGTAACTGGCCTCCTGCT CTTGAATCTGCCCTGCAGCGCTGGGGTACCACTCAAGC AAAATGCTCCTGTCTGACTGCACTGGACATGACAGGG AAACCAGTTTACACTCTTACATATGGAAAGTTGTGGAG CAGAAGTTTAAAGTTGGCCTACACACTTCTTAATAAAC TGGGGACCAAAAATGAACCTGTGTTAAAACCTGGAGA CAGGGTAGCCCTGGTTTACCCCAACAATGATCCAGTCA TGTTTATGGTGGCTTTCTATGGATGCCTCCTGGCAGAA GTGATTCCAGTGCCTATAGAGGTACCTCTTACCAGAAA GGATGCTGGAGGTCAGCAGATTGGCTTCTTGCTAGGA AGCTGTGGTATTGCCTTAGCTCTTACCAGTGAAGTTTG TCTAAAAGGACTGCCAAAAACCCAGAATGGAGAAATT GTACAGTTTAAAGGTTGGCCCCGGCTCAAATGGGTTGT AACAGATTCCAAGTACCTTTCAAAGCCACCGAAAGACT GGCAGCCACACATCTCACCTGCTGGGACAGAACCGGC ATACATTGAGTATAAAACAAGCAAAGAAGGGAGTGTA ATGGGAGTTACAGTATCCCGGCTTGCAATGTTGTCTCA CTGCCAAGCTCTGTCGCAGGCCTGCAATTATTCTGAAG GGGAAACAATAGTAAATGTCTTAGACTTTAAGAAGGA TGCTGGGCTGTGGCACGGCATGTTTGCGAATGTAATG AATAAGATGCACACAATCAGCGTACCCTACTCTGTTAT GAAAACCTGTCCTCTCTCTTGGGTCCAAAGAGTACATG CTCACAAAGCCAAGGTAGCTTTAGTAAAATGTCGGGA CTTGCACTGGGCTATGATGGCACATCGGGACCAAAGA GACGTGAGCTTGAGTTCCCTCCGAATGTTAATTGTGAC TGATGGAGCTAACCCCTGGTCCGTGTCATCCTGTGATG CCTTCCTGAGTCTGTTCCAAAGTCATGGACTGAAGCCT GAGGCCATCTGTCCGTGCGCCACGTCTGCTGAAGCCAT GACTGTAGCAATCCGCAGGCCTGGAGTTCCAGGAGCC CCTTTGCCAGGAAGAGCCATTCTCTCAATGAATGGATT GAGCTATGGGGTAATACGGGTCAATACTGAAGATAAA AATTCAGCACTGACGGTCCAGGATGTAGGGCATGTAA TGCCTGGTGGGATGATGTGCATTGTGAAACCAGATGG ACCTCCCCAGCTCTGCAAAACAGATGAAATTGGAGAA |

FIG. 27 Cont.

| sample | Gene Break-point 5p | Gene Break-point 3p | Frame Type | SEQ ID NO: | Fused Sequence |
|---|---|---|---|---|---|
| | | | | | ATCTGTGTTAGCTCCAGAACTGGAGGCATGATGTACTT TGGGCTTGCTGGTGTGACAAAAAATACATTTGAGGTA ATTCCAGTGAATTCTGCAGGCTCTCCTGTTGGGGATGT GCCATTCATCCGATCAGGATTGCTGGGGTTTGTAGGGC CGGGTAGTTTGGTGTTCGTGGTTGGGAAAATGGATGG CTTACTGATGGTTAGTGGTCGAAGACATAATGCTGATG ACATTGTTGCTACTGGATTGGCTGTAGAATCAATAAAG ACTGTTTATAGAGGAAGAATTGCTGTGTTTTCTGTGTC TGTATTTTATGATGAGCGCATTGTGGTGGTTGCGGAAC AAAGACCTGATGCTTCTGAGGAAGATAGTTTCCAGTG GATGAGCCGCGTGCTGCAGGCGATCGATAGCATTCAT CAAGTGGGGGTTTATTGTCTTGCTCTGGTGCCAGCCAA TACATTGCCAAAAACTCCACTAGGAGGAATCCATATAT CTCAGACGAAACAACTCTTTCTGGAGGGATCACTGCAT CCTTGCAACATCCTCATGTGCCCCCATACATGTGTGAC AAACTTGCCAAAGCCCCGGCAAAAACAACCAGGTGTA GGCCCTGCTTCCGTGATGGTTGGGAATCTGGTTGCTG GAAAACGTATAGCACAAGCTGCTGGAAGGGATCTGGG ACAAATAGAAGAGAATGATTTGGTGAGGAAGCACCAG TTTCTGGCAGAGATCCTACAGTGGCGAGCCCAGGCGA CTCCTGACCATGTACTCTTCATGCTGTTAAATGCCAAG GGAACCACTGTATGCACAGCCAGCTGCCTTCAGCTTCA TAAGCGAGCAGAGAGGATTGCATCTGTTCTTGGTGAT AAGGGACATCTAAATGCAGGAGATAATGTGGTGTTGC TCTATCCACCTGGCATTGAGTTAATCGCCGCCTTCTATG GCTGCCTGTATGCGGGCTGTATACCTGTGACCGTCAGA CCTCCACATGCTCAGAACCTCACGGCCACGCTGCCCAC TGTCCGAATGATTGTTGATGTCAGCAAAGCAGCCTGTA TTCTCACCAGTCAGACCCTAATGAGGCTACTGAGGTCC CGAGAGGCAGCAGCAGCTGTGGATGTGAAAACCTGG CCAACCATCATTGACACAGATGATTTACCCAGGAAAAG GTTACCTCAGCTGTATAAACCGCCCACTCCTGAGATGT TGGCATATCTTGATTTTAGTGTCTCCACAACTGGCATGC TTACAGGAGTGAAGATGTCCCACTCTGCAGTGAACGCT CTGTGTCGAGCCATCAAGCTCCAGTGTGAGTTGTACTC TTCTCGGCAGATCGCCATCTGCCTTGACCCTTACTGTG GACTTGGCTTCGCGCTCTGGTGTCTCTGCAGTGTCTAT TCAGGCCACCAGTCTGTCTTAATTCCTCCTATGGAGTTA GAGAACAACCTTTTCCTCTGGCTCTCCACAGTCAACCA GTACAAAATAAGGGACACTTTCTGCTCCTATTCAGTGA TGGAGCTCTGCACCAAAGGTCTTGGGAACCAAGTGGA AGTGCTAAAGACCAGAGGGATCAACCTCTCCTGCGTCC GGACCTGTGTGGTGGTGGCGGAGGAGAGGCCCCGCG TTGCACTCCAGCAGTCCTTCTCTAAGCTCTTCAAAGACA TCGGGCTGTCCCCGCGGGCTGTCAGCACCACTTTTGGA TCAAGAGTCAATGTAGCAATATGTTTACAGGGAACCTC AGGGCCTGATCCGACTACTGTGTATGTGGATCTGAAAT CACTAAGACATGACAGGGTTCGTCTCGTGGAACGTGG CGCCCCTCAGAGTTTGCTTCTCTCAGAGTCTGGAAAG\| AGATCGGGAAGTAAACAGTCCACTAACCCTGCCGATA ACTATCATCTGGCCCGGAGGAGAACCCTGCAGGTGGT TGTGAGCTCCTTGCTGACAGAGGCAGGGTTTGAGAGT GCCGAGAAAGCATCCGTGGAAACGCTGACAGAGATGC TGCAGAGCTACATTTCAGAAATTGGGAGAAGTGCCAA GTCTTACTGTGAGCACACAGCCAGGACCCAGCCCACAC |

FIG. 27 Cont.

| sample | Gene Break-point 5p | Gene Break-point 3p | Frame Type | SEQ ID NO: | Fused Sequence |
|---|---|---|---|---|---|
| | | | | | TGTCCGATATCGTGGTCACACTTGTTGAGATGGGTTTC AATGTGGACACTCTCCCTGCTTATGCAAAACGGTCTCA GAGGATGGTCATCACTGCTCCTCCGGTGACCAATCAGC CAGTGACCCCCAAGGCCCTCACTGCAGGGCAGAACCG ACCCCACCCGCCGCACATCCCCAGCCATTTTCCTGAGTT CCCTGATCCCCACACCTACATCAAAACTCCGACGTACC GTGAGCCCGTGTCAGACTACCAGGTCCTGCGGGAGAA GGCTGCATCCCAGAGGCGCGATGTGGAGCGGGCACTT ACCCGTTTCATGGCCAAGACAGGCGAGACTCAGAGTC TTTTCAAAGATGACGTCAGCACATTTCCATTGATTGCTG CCAGACCTTTCACCATCCCCTACCTGACAGCTCTTCTTC CGTCTGAACTGGAGATGCAACAAATGGAAGAGACAGA TTCCTCGGAGCAGGATGAACAGACAGACACAGAGAAC CTTGCTCTTCATATCAGCATGatagagtctcgctccgtcaccca ggctggagtgcagtggcaagatcttggctcactgcaacctccgcctcct gggttcaagcgattctccagcctcagcctcctgagtagctggaattaca gGAGGATTCTGGAGCCGAGAAGGAGAACACCTCTGTC CTGCAGCAGAACCCCTCCTTGTCGGGTAGCCGGAATG GGGAGGAGAACATCATCGATAACCCTTATCTGCGGCC GG |
| G17787. TCGA-26-5139-01A-01R-1850-01.4 | 139920034 | 156012704 | Inframe | 8373 | ATGGAACCCCCGCGGCCAAGCGGAGCCGGGGCTGCC CCGCGGGACCCGAGGAGCGCGATgccggggccggggccgc gcgtggccggggccggcccgAGGCGCTGCTGGACCTCAGCG CCAAGCGGGTAGCCGAGAGCTGGGCCTTCGAGCAGGT GGAGGAGCGGTTCTCCCGGGTGCCTGAGCCCGTCCAG AAGCGCATCGTGTTTTGGTCGTTTCCACGCAGTGAACG GGAAATATGTATGTACTCGTCGCTGGGTTACCCGCCCC CAGAGGGCGAGCACGATGCCCGGGTGCCCTTTACCCG CGGGCTGCACCTGCTCCAGAGCGGGGCCGTGGACCGC GTGTTGCAAGTGGGATTCCACCTGAGCGGAAACATCC GCGAGCCAGGGAGTCCTGGAGAGCCCGAGCGCCTCTA CCATGTCTCCATCAGCTTTGATCGCTGCAAGATCACGT CCGTGAGCTGCGGCTGTGACAACCGCGACCTCTTCTAC TGTGCCCACGTGGTGGCCCTGTCCCTGTACCGCATTCG GCACGCCACCAGGTGGAGCTGCGGCTGCCCATCTCC GAGACGCTCTCCCAGATGAACCGGGACCAGCTGCAGA AGTTCGTGCAGTACCTCATCAGCGCCCATCACACTGAG GTGCTGCCCACTGCTCAGCGCTTGGCTGATGAGATCCT CCTGCTGGGCTCCGAGATCAACTTGGTGAATGGTGCCC CAGACCCCACCGCCGGCGCAGGAATCGAGGACGCCAA CTGCTGGCACCTGGACGAGGAGCAGATCCAGGAGCA GGTGAAGCAGCTACTGTCCAATGGCGGCTACTACGGG GCCAGCCAGCAGCTGCGCTCCATGTTCAGCAAGGTGC GGGAGATGCTGCGAATGCGGGACTCCAACGGGGCGC GCATGCTGATTCTCATGACCGAGCAGTTCCTGCAGGAC ACGCGCCTGGCCCTGTGGCGGCAGCAGGGCGCGGGC ATGACGGACAAGTGCCGGCAGCTCTGGGATGAGCTGG \|GGATGTTCAATAGCCCAGAAATGCAAGCCCTCCTCCA GCAGATCTCTGAGAACCCCCAGCTGATGCAGAATGTG ATCTCAGCACCCTACATGCGCAGCATGATGCAGACGCT TGCCCAGAACCCCGACTTTGCTGCTCAGATGATGGTGA ATGTGCCGCTCTTCGCGGGGAACCCCCAACTGCAGGA GCAGCTCCGCCTGCAGCTCCCAGTCTTCCTGCAGCAGA TGCAGAACCCAGAGTCACTCTCCATCCTTACCAATCCCC GAGCCATGCAGGCATTGCTGCAGATCCAGCAGGGACT |

FIG. 27 Cont.

| sample | Gene Break-point 5p | Gene Break-point 3p | Frame Type | SEQ ID NO: | Fused Sequence |
|---|---|---|---|---|---|
| | | | | | ACAGACCTTGCAGACCGAGGCCCCTGGGCTGGTACCC AGCCTTGGCTCCTTTGGGATATCCCGGACCCCAGCACC CTCAGCAGGCAGCAACGCAGGGTCTACGCCCGAGGCC CCCACTTCCTCACCAGCCACGCCAGCCACATCTTCTCCA ACAGGGGCTTCCAGCGCCCAGCAGCAACTCATGCAGC AGATGATCCAGCTTTTGGCTGGAAGTGGAAACTCACA GGTGCAGACGCCAGAAGTGAGATTTCAGCAGCAGCTG GAGCAGCTCAACTCCATGGGCTTCATCAATCGTGAGGC TAACCTGCAGGCCCTGATTGCCACAGGAGGGGACATC AACGCAGCTATCGAGAGACTGCTGGGCTCCCAGCTCTC C |
| G17675. TCGA-19- 2624- 01A-01R- 1850- 01.2 | 65232631 | 63226059 | InFrame | 8374 | ATGGACGTCCTTCCCAccggcggggccgcccggggcTCCGG ACGGAGCTGGAATTCCGCGGCGGCGGTGGCGAGGCG AGGCTGGAGAGTCAGGAGGAAGAAACGATTCCTGCA GCTCCCCCAGCCCCGCGCCTCCGGGGAGCGGCGGAGC GGCCGCGGCGCTCCCGGGACACGTGGGACGGCGATG AGGACACGGAGCCCGGCGAGGCGTGCGGCGGCCGCA CAAGCCGCACGGCGTCCCTGGTGAGCGGGCTGCTCAA CGAGCTGTACAGCTGCACAGAGGAGGAGGAggcggcgg gcggggccgcggggccgagggccgccggcggcgccgcgACAGCC TCGACAGCTCCACCGAGGCCTCGGGCTCCGACGTGGT CCTGGGCGGCCGCAGCGGTGCCGGCGACTCCCGCGTG CTGCAGGAGCTGCAGGAGCGACCGAGCCAGCGGCAT CAGATGCTGTACCTGCGGCAGAAAGACGCTAATGAAC TGAAGACGATCCTTCGAGAGCTAAAGTACAGAATTGG CATCCAGTCGGCCAAGTTACTTCGGCATCTGAAGCAGA AAGATAGGCTTCTGCATAAAGTGCAGAGGAACTGTGA TATTGTGACTGCCTGCTTGCAGGCTGTGTCACAGAAGA GAAGAGTTGATACCAAGTTGAAATTCACTCTTGAGCCA TCTTTAGGTCAAAATGGTTTTCAGCAGTGGTACGATGC TCTCAAGGCAGTTGCCAGGCTATCCACAGGAATACCAA AGGAATGGAGGAGAAAGGTTTGGTTGACCTTGGCAG ATCATTATTTGCACAGTATAGCCATTGACTGGGACAAA ACCATGCGCTTCACTTTCAATGAAAGGAGTAATCCTGA TGATGACTCCATGGGAATTCAGATAGTCAAGGACCTTC ACCGCACAGGCTGTAGTTCTTACTGTGGCCAGGAGGC TGAGCAGGACAGGGTTGTGTTGAAGCGGGTGCTGCTG GCCTATGCCCGATGGAACAAAACTGTTGGGTACTGCC AAGGCTTTAACATCCTGGCTGCACTAATTCTGGAAGTG ATGGAAGGCAATGAAGGGGATGCCCTGAAAATTATGA TTTACCTTATTGATAAGGTACTTCCCGAAAGCTATTTCG TCAATAATCTCCGGGCATTGTCTGTGGATATGGCTGTC TTCAGAGACCTTTTAAGAATGAAGCTGCCGGAATTATC TCAGCACCTGGATACTCTTCAGAGAACTGCAAACAAAG AAAGTGGAGGTGGATATGAGCCCCCACTTACAAATGT CTTCACGATGCAGTGGTTTCTGACTCTCTTTGCCACATG CCTCCCTAATCAGACCGTTTTAAAGATCTGGGATTCAG TCTTCTTTGAAGGTTCAGAAATCATCCTAAGGGTGTCG CTGGCTATCTGGGCAAAATTAGGAGA|GGTTATCAAT GCCGGGAAGAGCACACACAATGAAGACCAAGCCAGCT GTGAGGTGCTCACTGTGAAGAAGAAGGCAGGGGCCG TGACCTCAACCCCAAACAGGAACTCATCCAAGAGACG GTCCTCCCTTCCCAATGGGGAAGGGCTGCAGCTGAAG GAGAACTCGGAATCCGAGGGTGTTTCCTGCCACTATTG GTCGCTGTTTGACGGGCACGCGGGGTCCGGGGCCGC |

FIG. 27 Cont.

| sample | Gene Breakpoint 5p | Gene Breakpoint 3p | Frame Type | SEQ ID NO: | Fused Sequence |
|---|---|---|---|---|---|
| | | | | | GGTGGTGGCGTCACGCCTGCTGCAGCACCACATCACG GAGCAGCTGCAGGACATCGTGGACATCCTGAAGAACT CCGCCGTCCTGCCCCCTACCTGCCTGGGGGAGGAGCCT GAGAACACGCCCGCCAACAGCCGGACTCTGACCCGGG CAGCCTCCCTGCGCGGAGGGGTGGGGGCCCCGGGCTC CCCCAGCACGCCCCCCACACGCTTCTTTACCGAGAAGA AGATTCCCCATGAGTGCCTGGTCATCGGAGCGCTTGAA AGTGCATTCAAGGAAATGGACCTACAGATAGAACGAG AGAGGAGTTCATATAATATCTGGTGGCTGCACGGC CCTCATTGTGATTTGCCTTTTGGGGAAGCTGTATGTTG CAAATGCTGGGGATAGCAGGGCCATAATCATCAGAAA TGGAGAAATTATCCCCATGTCTTCAGAATTTACCCCCG AGACGGAGCGCCAGCGACTTCAGTACCTGGCATTCAT GCAGCCTCACTTGCTGGGAAATGAGTTCACACATTTGG AGTTTCCAAGGAGAGTACAGAGAAAGGAGCTTGGAA AGAAGATGCTCTACAGGGACTTTAATATGACAGGCTG GGCATACAAAACCATTGAGGATGAGGACTTGAAGTTC CCCCTTATATATGGAGAAGGCAAGAAGGCCCGGGTAA TGGCAACTATTGGAGTGACCAGGGGACTTGGGGACCA TGACCTGAAGGTGCATGACTCCAACATCTACATTAAAC CATTCCTGTCTTCAGCTCCAGAGGTAAGAATCTACGAT CTTTCAAAATATGATCATGGATCAGATGATGTGCTGAT CTTGGCCACTGATGGACTCTGGGACGTTTTATCAAATG AAGAAGTAGCAGAAGCAATCACTCAGTTTCTTCCTAAC TGTGATCCAGATGATCCTCACAGGTACACACTGGCAGC TCAGGACCTGGTGATGCGTGCCCGGGGTGTGCTGAAG GACAGAGGATGGCGGATATCTAATGACCGACTGGGCT CAGGAGACGACATTTCTGTATATGTCATTCCTTTAATAC ATGGAAACAAGCTGTCA |
| G17800. TCGA-06-5859-01A-01R-1849-01.4 | 48586286 | 56936733 | InFrame | 8375 | ATGGACAATATGTCTATTACGAATACACCAACAAGTAA TGATGCCTGTCTGAGCATTGTGCATAGTTTGATGTGCC ATAGACAAGGTGGAGAGAGTGAAACATTTGCAAAAAG AGCAATTGAAAGTTTGGTAAAGAAGCTGAAGGAGAAA AAAGATGAATTGGATTCTTTAATAACAGCTATAACTAC AAATGGAGCTCATCCTAGTAAATGTGTTACCATACAGA GAACATTGGATGGGAGGCTTCAGGTGGCTGGTCGGAA AGGATTTCCTCATGTGATCTATGCCCGTCTCTGGAGGT GGCCTGATCTTCACAAAAATGAACTAAAACATGTTAAA TATTGTCAGTATGCGTTTGACTTAAAATGTGATAGTGT CTGTGTGAATCCATATCACTACGAACGAGTTGTATCAC CTGGAATTGATCTCTCAGGATTAACACTGCAGAGTAAT GCTCCATCAAGTATGATGGTGAAGGATGAATATGTGC ATGACTTTGAGGGACAGCCATCGTTGTCCACTGAAGG ACATTCAATTCAAACCATCCAGCATCCACCAAGTAATC GTGCATCGACAGAGACATACAGCACCCAGCTCTGTTA GCCCCATCTGAGTCTAATGCTACCAGCACTGCCAACTT TCCCAACATTCCTGTGGCTTCCACAAGTCAGCCTGCCA GTATACTGGGGGCAGCCATAGTGAAGGACTGTTGCA GATAGCATCAGGGCCTCAGCCAGGACAGCAGCAGAAT GGATTTACTGGTCAGCCAGCTACTTACCATCATAACAG CACTACCACCTGGACTGGAAGTAGGACTGCACCATAC ACACCTAATTTGCCTCACCACCAAAACGGCCATCTTCA GCACCACCCGCCTATGCCGCCCCATCCCGGACATTACT GGCCTGTTCACAATGAGCTTGCATTCCAGCCTCCCATTT CCAATCATCCTG\|GTGTGGTTCCAGAACCGACGGGC |

FIG. 27 Cont.

| sample | Gene Breakpoint 5p | Gene Breakpoint 3p | Frame Type | SEQ ID NO: | Fused Sequence |
|---|---|---|---|---|---|
| G17638. TCGA-28-2499-01A-01R-1850-01.2 | 234299129 | 234967480 | InFrame | 8376 | ATggcggcggcggcgggcgcccctccgccgggtcccccgcaaccgcctccgccgccgccgcccgAGGAGTCGTCCGACAGCGAGCCCGAGGCGGAGCCCGGCTCCCCACAGAAGCTCATCCGCAAGGTGTCCACGTCGGGTCAGATCCGACAGAAGACCATCATCAAAGAGGGGATGCTGACCAAACAGAACAATTCATTCCAGCGATCAAAAAGGAGATACTTTAAGCTTCGAGGGCGAACGCTTTACTATGCCAAAACGGCAAAGTCAATCATATTTGATGAGGTGGATCTGACAGATGCCAGCGTAGCTGAATCCAGTACCAAAAACGTCAACAACAGTTTTACG\|GTTGAGGTCCTAGATGAGAACAACTTGGTCATGAATTTAGAGTTCAGCATCCGGGAGACTACATGCAGGAAGGATTCTGGAGAAGATCCCGCTACATGTGCCTTCCAGAGGGACTACTATGTGTCCACAGCTGTTTGCAGAAGCACCGTGAAGGTATCTGCCCAGCAGGTGCAGGGCGTGCATGCTCGCTGCAGCTGGTCCTCCTCCACGTCTGAGTCTTACAGCAGCGAAGAGATGATTTTTGGGGACATGTTGGGATCTCATAAATGGAGAAACAATTATCTATTTGGTCTCATTTCAGACGAGTCCATAAGTGAACAATTTTATGATCGGTCACTTGGGATCATGAGAAGGGTATTGCCTCCTGGAAACAGAAGGTACCCAAACCACCGGCACAGAGCAAGAATAAATACTGACTTTGAG |

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| G17807.TCGA-28-5209-01A-01R-1850-01.4 | 1 | 982 | 190 | 225 | 8377 | MRPSGTAGAALLALLAALCPASRALEEKKVCQGTSNKLTQLGTFEDHFLSLQRMFNNCEVVLGNLEITYVQRNYDLSFLKTIQEVAGYVLIALNTVERIPLENLQIIRGNMYYENSYALAVLSNYDANKTGLKELPMRNLQEILHGAVRFSNNPALCNVESIQWRDIVSSDFLSNMSMDFQNHLGSCQKCDPSCPNGSCWGAGEENCQKLTKIICAQQCSGRCRGKSPSDCCHNQCAAGCTGPRESDCLVCRKFRDEATCKDTCPPLMLYNPTTYQMDVNPEGKYSFGATCVKKCPRNYVVTDHGSCVRACGADSYEMEEDGVRKCKKCEGPCRKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQVCHALCSPEGCWGPEPRDCVSCRNVSRGRECVDKCNLLEGEPREFVENSECIQCHPECLPQAMNITCTGRGPDNCIQCAHYIDGPHCVKTCPAGVMGENNTLVWKYADAGHVCHLCHPNCTYGCTGPGLEGCPTNGPKIPSIATGMVGALLLLLVVALGIGLFMRRRHIVRKRTLRRLLQERELVEPLTPSGEAPNQALLRILKETEFKKIKVLGSGAFGTVYKGLWIPEGEKVKIPVAIKELREATSPKANKEILDEAYVMASVDNPHVCRLLGICLTSTVQLITQLMPFGCLLDYVREHKDNIGSQYLLNWCVQIAKGMNYLEDRRLVHRDLAARNVLVKTPQHVKITDFGLAKLLGAEEKEYHAEGGKVPIKWMALESILHRIYTHQSDV | 24 | 6 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | WSYGVTVWELMTFGSKPYDGIPASEISSILEK GERLPQPPICTIDVYMIMVKCWMIDADSRPK FRELIIEFSKMARDPQRYLVIQDAFIGFGGNVI RQQVKDNAKWYITDFVELLGELEE | | |
| G17197 .TCGA-06-0211-01B-01R-1849-01.2 | 1 | 336 | 240 | 432 | 8378 | MGETMSKRLKLHLGGEAEMEERAFVNPFPDY EAAAGALLASGAAEETGCVRPPATTDEPGLPF HQDGKIIHNFIRRIQTKIKDLLQQMEEGLKTAD PHDCSAYTGWTGIALLYLQLYRVTCDQTYLLR SLDYVKRTLRNLNGRRVTFLCGDAGPLAVGAV IYHKLRSDCESQECVTKLLQLQRSVVCQESDLP DELLYGRAGYLYALLYLNTEIGPGTVCESAIKEV VNAIIESGKTLSREERKTERCPLLYQWHRKQYV GAAHGMAGIYYMLMQPAAKVDQETLTEMV KPSIDYVRHKKFRSGNYPSSLSNETDRLVHWC HGAPGVIHMLMQAYKGLLPFAVVGSTDEVK VGKRMVRGRHYPWGVLQVENENHCDFVKL RDMLLCTNMENLKEKTHTQHYECYRYQKLQK MGFTDVGPNNQPVSFQEIFEAKRQEFYDQC QREEEELKQRFMQRVKEKEATFKEAEKELQDK FEHLKMIQQEEIRKLEEEKKQLEGEIIDFYKMK AASEALQTQLSTDTKKDKHRKK | 6 | 7 |
| G17650 .TCGA-28-2513-01A-01R-1850-01.2 | 1 | 982 | 373 | 432 | 8379 | MRPSGTAGAALLALLAALCPASRALEEKKVCQ GTSNKLTQLGTFEDHFLSLQRMFNNCEVVLG NLEITYVQRNYDLSFLKTIQEVAGYVLIALNTVE RIPLENLQIIRGNMYYENSYALAVLSNYDANKT GLKELPMRNLQEILHGAVRFSNNPALCNVESI QWRDIVSSDFLSNMSMDFQNHLGSCQKCDP SCPNGSCWGAGEENCQKLTKIICAQQCSGRC RGKSPSDCCHNQCAAGCTGPRESDCLVCRKF RDEATCKDTCPPLMLYNPTTYQMDVNPEGKY SFGATCVKKCPRNYVVTDHGSCVRACGADSY EMEEDGVRKCKKCEGPCRKVCNGIGIGEFKDS LSINATNIKHFKNCTSISGDLHILPVAFRGDSFT HTPPLDPQELDILKTVKEITGFLLIQAWPENRT DLHAFENLEIIRGRTKQHGQFSLAVVSLNITSL GLRSLKEISDGDVIISGNKNLCYANTINWKKLF GTSGQKTKIISNRGENSCKATGQVCHALCSPE GCWGPEPRDCVSCRNVSRGRECVDKCNLLEG EPREFVENSECIQCHPECLPQAMNITCTGRGP DNCIQCAHYIDGPHCVKTCPAGVMGENNTLV WKYADAGHVCHLCHPNCTYGCTGPGLEGCP TNGPKIPSIATGMVGALLLLLVVALGIGLFMRR RHIVRKRTLRRLLQERELVEPLTPSGEAPNQAL LRILKETEFKKIKVLGSGAFGTVYKGLWIPEGEK VKIPVAIKELREATSPKANKEILDEAYVMASVD NPHVCRLLGICLTSTVQLITQLMPFGCLLDYVR EHKDNIGSQYLLNWCVQIAKGMNYLEDRRLV HRDLAARNVLVKTPQHVKITDFGLAKLLGAEE KEYHAEGGKVPIKWMALESILHRIYTHQSDV WSYGVTVWELMTFGSKPYDGIPASEISSILEK GERLPQPPICTIDVYMIMVKCWMIDADSRPK FRELIIEFSKMARDPQRYLVIQLQDKFEHLKMI QQEEIRKLEEEKKQLEGEIIDFYKMKAASEALQ TQLSTDTKKDKHRKK | 24 | 10 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| G17506.TCGA-27-1835-01A-01R-1850-01.2 | 1 | 760 | 647 | 838 | 8380 | MGAPACALALCVAVAIVAGASSESLGTEQRV VGRAAEVPGPEPGQQEQLVFGSGDAVELSCP PPGGGPMGPTVWVKDGTGLVPSERVLVGPQ RLQVLNASHEDSGAYSCRQRLTQRVLCHFSVR VTDAPSSGDDEDGEDEAEDTGVDTGAPYWT RPERMDKKLLAVPAANTVRFRCPAAGNPTPSI SWLKNGREFRGEHRIGGIKLRHQQWSLVMES VVPSDRGNYTCVVENKFGSIRQTYTLDVLERS PHRPILQAGLPANQTAVLGSDVEFHCKVYSDA QPHIQWLKHVEVNGSKVGPDGTPYVTVLKS WISESVEADVRLRLANVSERDGGEYLCRATNF IGVAEKAFWLSVHGPRAAEEELVEADEAGSVY AGILSYGVGFFLFILVVAAVTLCRLRSPPKKGLG SPTVHKISRFPLKRQVSLESNASMSSNTPLVRI ARLSSGEGPTLANVSELELPADPKWELSRARLT LGKPLGEGCFGQVVMAEAIGIDKDRAAKPVT VAVKMLKDDATDKDLSDLVSEMEMMKMIG KHKNIINLLGACTQGGPLYVLVEYAAKGNLREF LRARRPPGLDYSFDTCKPPEEQLTFKDLVSCAY QVARGMEYLASQKCIHRDLAARNVLTEDNV MKIADFGLARDVHNLDYYKKTTNGRLPVKW MAPEALFDRVYTHQSDVWSFGVLLWEIFTLG GSPYPGIPVEELFKLLKEGHRMDKPANCTHDL YMIMRECWHAAPSQRPTFKQLVEDLDRVLTV TSTDVKATQEENRELRSRCEELHGKNLELGKI MDRFEEVVYQAMEEVQKQKELSKAEIQKVLK EKDQLTTDLNSMEKSFSDLFKRFEKQKEVIEGY RKNEESLKKCVEDYLARITQEGQRYQALKAHA EEKLQLANEEIAQVRSKAQAEALALQASLRKE QMRIQSLEKTVEQKTKENEELTRICDDLISKME KI | 17 | 11 |
| G17191.TCGA-06-0211-01A-01R-1849-01.2 | 1 | 336 | 240 | 432 | 8381 | MGETMSKRLKLHLGGEAEMEERAFVNPFPDY EAAAGALLASGAAEETGCVRPPATTDEPGLPF HQDGKIIHNFIRRIQTKIKDLLQQMEEGLKTAD PHDCSAYTGWTGIALLYLQLYRVTCDQTYLLR SLDYVKRTLRNLNGRRVTFLCGDAGPLAVGAV IYHKLRSDCESQECVTKLLQLQRSVVCQESDLP DELLYGRAGYLYALLYLNTEIGPGTVCESAIKEV VNAIIESGKTLSREERKTERCPLLYQWHRKQYV GAAHGMAGIYYMLMQPAAKVDQETLTEMV KPSIDYVRHKKFRSGNYPSSLSNETDRLVHWC HGAPGVIHMLMQAYKGLLPFAVVGSTDEVK VGKRMVRGRHYPWGVLQVENENHCDFVKL RDMLLCTNMENLKEKTHTQHYECYRYQKLQK MGFTDVGPNNQPVSFQEIFEAKRQEFYDQC QREEEELKQRFMQRVKEKEATFKEAEKELQDK FEHLKMIQQEEIRKLEEEKKQLEGEIIDFYKMK AASEALQTQLSTDTKKDKHRKK | 6 | 7 |
| G17512.TCGA-27-1837-01A-01R- | 1 | 982 | 373 | 432 | 8382 | MRPSGTAGAALLALLAALCPASRALEEKKVCQ GTSNKLTQLGTFEDHFLSLQRMFNNCEVVLG NLEITYVQRNYDLSFLKTIQEVAGYVLIALNTVE RIPLENLQIIRGNMYYENSYALAVLSNYDANKT GLKELPMRNLQEILHGAVRFSNNPALCNVESI QWRDIVSSDFLSNMSMDFQNHLGSCQKCDP | 24 | 10 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 1850-01.2 | | | | | | SCPNGSCWGAGEENCQKLTKIICAQQCSGRC RGKSPSDCCHNQCAAGCTGPRESDCLVCRKF RDEATCKDTCPPLMLYNPTTYQMDVNPEGKY SFGATCVKKCPRNYVVTDHGSCVRACGADSY EMEEDGVRKCKKCEGPCRKVCNGIGIGEFKDS LSINATNIKHFKNCTSISGDLHILPVAFRGDSFT HTPPLDPQELDILKTVKEITGFLLIQAWPENRT DLHAFENLEIIRGRTKQHGQFSLAVVSLNITSL GLRSLKEISDGDVIISGNKNLCYANTINWKKLF GTSGQKTKIISNRGENSCKATGQVCHALCSPE GCWGPEPRDCVSCRNVSRGRECVDKCNLLEG EPREFVENSECIQCHPECLPQAMNITCTGRGP DNCIQCAHYIDGPHCVKTCPAGVMGENNTLV WKYADAGHVCHLCHPNCTYGCTGPGLEGCP TNGPKIPSIATGMVGALLLLLVVALGIGLFMRR RHIVRKRTLRRLLQERELVEPLTPSGEAPNQAL LRILKETEFKKIKVLGSGAFGTVYKGLWIPEGEK VKIPVAIKELREATSPKANKEILDEAYVMASVD NPHVCRLLGICLTSTVQLITQLMPFGCLLDYVR EHKDNIGSQYLLNWCVQIAKGMNYLEDRRLV HRDLAARNVLVKTPQHVKITDFGLAKLLGAEE KEYHAEGGKVPIKWMALESILHRIYTHQSDV WSYGVTVWELMTFGSKPYDGIPASEISSILEK GERLPQPPICTIDVYMIMVKCWMIDADSRPK FRELIIEFSKMARDPQRYLVIQLQDKFEHLKMI QQEEIRKLEEEKKQLEGEIIDFYKMKAASEALQ TQLSTDTKKDKHRKK | | |
| NYU_A | 1 | 760 | 548 | 838 | 8383 | MGAPACALALCVAVAIVAGASSESLGTEQRV VGRAAEVPGPEPGQQEQLVFGSGDAVELSCP PPGGGPMGPTVWVKDGTGLVPSERVLVGPQ RLQVLNASHEDSGAYSCRQRLTQRVLCHFSVR VTDAPSSGDDEDGEDEAEDTGVDTGAPYWT RPERMDKKLLAVPAANTVRFRCPAAGNPTPSI SWLKNGREFRGEHRIGGIKLRHQQWSLVMES VVPSDRGNYTCVVENKFGSIRQTYTLDVLERS PHRPILQAGLPANQTAVLGSDVEFHCKVYSDA QPHIQWLKHVEVNGSKVGPDGTPYVTVLKS WISESVEADVRLRLANVSERDGGEYLCRATNF IGVAEKAFWLSVHGPRAAEEELVEADEAGSVY AGILSYGVGFFLFILVVAAVTLCRLRSPPKKGLG SPTVHKISRFPLKRQVSLESNASMSSNTPLVRI ARLSSGEGPTLANVSELELPADPKWELSRARLT LGKPLGEGCFGQVVMAEAIGIDKDRAAKPVT VAVKMLKDDATDKDLSDLVSEMEMMKMIG KHKNIINLLGACTQGGPLYVLVEYAAKGNLREF LRARRPPGLDYSFDTCKPPEEQLTFKDLVSCAY QVARGMEYLASQKCIHRDLAARNVLVTEDNV MKIADFGLARDVHNLDYYKKTTNGRLPVKW MAPEALFDRVYTHQSDVWSFGVLLWEIFTLG GSPYPGIPVEELFKLLKEGHRMDKPANCTHDL YMIMRECWHAAPSQRPTFKQLVEDLDRVLTV TSTDFKESALRKQSLYLKFDPLLRDSPGRPVPV ATETSSMHGANETPSGRPREAKLVEFDFLGAL DIPVPGPPPGVPAPGGPPLSTGPIVDLLQYSQ | 17 | 8 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | KDLDAVVKATQEENRELRSRCEELHGKNLELG KIMDRFEEVVYQAMEEVQKQKELSKAEIQKVL KEKDQLTTDLNSMEKSFSDLFKRFEKQKEVIEG YRKNEESLKKCVEDYLARITQEGQRYQALKAH AEEKLQLANEEIAQVRSKAQAEALALQASLRK EQMRIQSLEKTVEQKTKENEELTRICDDLISKM EKI | | |
| G17814 .TCGA-06-5411-01A-01R-1849-01.4 | 1 | 834 | 399 | 796 | 8384 | MARQPPPPWVHAAFLLCLLSLGGAIEIPMDLT QPPTITKQSAKDHIVDPRDNILIECEAKGNPAP SFHWTRNSRFFNIAKDPRVSMRRRSGTLVIDF RSGGRPEEYEGEYQCFARNKFGTALSNRIRLQ VSKSPLWPKENLDPVVVQEGAPLTLQCNPPP GLPSPVIFWMSSSMEPITQDKRVSQGHNGDL YFSNVMLQDMQTDYSCNARFHFTHTIQQKN PFTLKVLTNHPYNDSSLRNHPDMYSARGVAE RTPSFMYPQGTASSQMVLRGMDLLLECIASG VPTPDIAWYKKGGDLPSDKAKFENFNKALRIT NVSEEDSGEYFCLASNKMGSIRHTISVRVKAA PYWLDEPKNLILAPGEDGRLVCRANGNPKPT VQWMVNGEPLQSAPPNPNREVAGDTIIFRD TQISSRAVYQCNTSNEHGYLLANAFVSVLDVP PRMLSPRNQLIRVILYNRTRLDCPFFGSPIPTLR WFKNGQGSNLDGGNYHVYENGSLEIKMIRKE DQGIYTCVATNILGKAENQVRLEVKDPTRIYR MPEDQVARRGTTVQLECRVKHDPSLKLTVSW LKDDEPLYIGNRMKKEDDSLTIFGVAERDQGS YTCVASTELDQDLAKAYLTVLADQATPTNRLA ALPKGRPDRPRDLELTDLAERSVRLTWIPGDA NNSPITDYVVQFEEDQFQPGVWHDHSKYPG SVNSAVLRLSPYVNYQFRVIAINEVGSSHPSLP SERYRTSGAPPESNPGDVKGEGTRKNNMEIT WTPMNATSAFGPNLRYIVKWRRRETREAWN NVTVWGSRYVVGQTPVYVPYEIRVQAENDFG KGPEPESVIGYSGEDYTNSTSGDPVEKKDETPF GVSVAVGLAVFACLFLSTLLLVLNKCGRRNKF GINRPAVLAPEDGLAMSLHFMTLGGSSLSPTE GKGSGLQGHIIENPQYFSDACVHHIKRRDIVLK WELGEGAFGKVFLAECHNLLPEQDKMLVAVK ALKEASESARQDFQREAELLTMLQHQHIVRFF GVCTEGRPLLMVFEYMRHGDLNRFLRSHGPD AKLLAGGEDVAPGPLGLGQLLAVASQVAAG MVYLAGLHFVHRDLATRNCLVGQGLVVKIGD FGMSRDIYSTDYYRVGGRTMLPIRWMPPESIL YRKFTTESDVWSFGVVLWEIFTYGKQPWYQL SNTEAIDCITQGRELERPRACPPEVYAIMRGC WQREPQQRHSIKDVHARLQALAQAPPVYLD VLG | 21 | 10 |
| G17223 .TCGA-06-0750-01A-01R- | 1 | 982 | 373 | 432 | 8385 | MRPSGTAGAALLALLAALCPASRALEEKKVCQ GTSNKLTQLGTFEDHFLSLQRMFNNCEVVLG NLEITYVQRNYDLSFLKTIQEVAGYVLIALNTVE RIPLENLQIIRGNMYYENSYALAVLSNYDANKT GLKELPMRNLQEILHGAVRFSNNPALCNVESI QWRDIVSSDFLSNMSMDFQNHLGSCQKCDP SCPNGSCWGAGEENCQKLTKIICAQQCSGRC | 24 | 10 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 1849-01.2 | | | | | | RGKSPSDCCHNQCAAGCTGPRESDCLVCRKF RDEATCKDTCPPLMLYNPTTYQMDVNPEGKY SFGATCVKKCPRNYVVTDHGSCVRACGADSY EMEEDGVRKCKKCEGPCRKVCNGIGIGEFKDS LSINATNIKHFKNCTSISGDLHILPVAFRGDSFT HTPPLDPQELDILKTVKEITGFLLIQAWPENRT DLHAFENLEIIRGRTKQHGQFSLAVVSLNITSL GLRSLKEISDGDVIISGNKNLCYANTINWKKLF GTSGQKTKIISNRGENSCKATGQVCHALCSPE GCWGPEPRDCVSCRNVSRGRECVDKCNLLEG EPREFVENSECIQCHPECLPQAMNITCTGRGP DNCIQCAHYIDGPHCVKTCPAGVMGENNTLV WKYADAGHVCHLCHPNCTYGCTGPGLEGCP TNGPKIPSIATGMVGALLLLLVVALGIGLFMRR RHIVRKRTLRRLLQERELVEPLTPSGEAPNQAL LRILKETEFKKIKVLGSGAFGTVYKGLWIPEGEK VKIPVAIKELREATSPKANKEILDEAYVMASVD NPHVCRLLGICLTSTVQLITQLMPFGCLLDYVR EHKDNIGSQYLLNWCVQIAKGMNYLEDRRLV HRDLAARNVLVKTPQHVKITDFGLAKLLGAEE KEYHAEGGKVPIKWMALESILHRIYTHQSDV WSYGVTVWELMTFGSKPYDGIPASEISSILEK GERLPQPPICTIDVYMIMVKCWMIDADSRPK FRELIIEFSKMARDPQRYLVIQLQDKFEHLKMI QQEEIRKLEEEKKQLEGEIIDFYKMKAASEALQ TQLSTDTKKDKHRKK | | |
| G17798 .TCGA-32-5222-01A-01R-1850-01.4 | 1 | 982 | 373 | 432 | 8386 | MRPSGTAGAALLALLAALCPASRALEEKKVCQ GTSNKLTQLGTFEDHFLSLQRMFNNCEVVLG NLEITYVQRNYDLSFLKTIQEVAGYVLIALNTVE RIPLENLQIIRGNMYYENSYALAVLSNYDANKT GLKELPMRNLQEILHGAVRFSNNPALCNVESI QWRDIVSSDFLSNMSMDFQNHLGSCQKCDP SCPNGSCWGAGEENCQKLTKIICAQQCSGRC RGKSPSDCCHNQCAAGCTGPRESDCLVCRKF RDEATCKDTCPPLMLYNPTTYQMDVNPEGKY SFGATCVKKCPRNYVVTDHGSCVRACGADSY EMEEDGVRKCKKCEGPCRKVCNGIGIGEFKDS LSINATNIKHFKNCTSISGDLHILPVAFRGDSFT HTPPLDPQELDILKTVKEITGFLLIQAWPENRT DLHAFENLEIIRGRTKQHGQFSLAVVSLNITSL GLRSLKEISDGDVIISGNKNLCYANTINWKKLF GTSGQKTKIISNRGENSCKATGQVCHALCSPE GCWGPEPRDCVSCRNVSRGRECVDKCNLLEG EPREFVENSECIQCHPECLPQAMNITCTGRGP DNCIQCAHYIDGPHCVKTCPAGVMGENNTLV WKYADAGHVCHLCHPNCTYGCTGPGLEGCP TNGPKIPSIATGMVGALLLLLVVALGIGLFMRR RHIVRKRTLRRLLQERELVEPLTPSGEAPNQAL LRILKETEFKKIKVLGSGAFGTVYKGLWIPEGEK VKIPVAIKELREATSPKANKEILDEAYVMASVD NPHVCRLLGICLTSTVQLITQLMPFGCLLDYVR EHKDNIGSQYLLNWCVQIAKGMNYLEDRRLV HRDLAARNVLVKTPQHVKITDFGLAKLLGAEE KEYHAEGGKVPIKWMALESILHRIYTHQSDV | 24 | 10 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | WSYGVTVWELMTFGSKPYDGIPASEISSILEK GERLPQPPICTIDVYMIMVKCWMIDADSRPK FRELIIEFSKMARDPQRYLVIQLQDKFEHLKMI QQEEIRKLEEEKKQLEGEIIDFYKMKAASEALQ TQLSTDTKKDKHRKK | | |
| G17195 .TCGA-06-0138-01A-02R-1849-01.2 | 1 | 171 | 63 | 246 | 8387 | MFKRMAEFGPDSGGRVKGVTIVKPIVYGNVA RYFGKKREEDGHTHQWTVYVKPYRNEDMSA YVKKIQFKLHESYGNPLRVVTKPPYEITETGWG EFEIIIKIFFIDPNERPVTLYHLLKLFQSDTNAML GKKTVVSEFYDEMIFQDPTAMMQQLLTTSRQ LTLGAYKHETEYPYVKLLLDAMKHSGCAVNKD RHFSCEDCNGNVSGGFDASTSQIVLCQNNIH NQAHMNRVVTHELIHAFDHCRAHVDWFTNI RHLACSEVRAANLSGDCSLVNEIFRLHFGLKQ HHQTCVRDRATLSILAVRNISKEVAKKAVDEV FESCFNDHEPFGRIPHNKTYARYAHRDFENRD RYYSNI | 6 | 2 |
| G17803 .TCGA-76-4925-01A-01R-1850-01.4 | 1 | 760 | 612 | 838 | 8388 | MGAPACALALCVAVAIVAGASSESLGTEQRV VGRAAEVPGPEPGQQEQLVFGSGDAVELSCP PPGGGPMGPTVWVKDGTGLVPSERVLVGPQ RLQVLNASHEDSGAYSCRQRLTQRVLCHFSVR VTDAPSSGDDEDGEDEAEDTGVDTGAPYWT RPERMDKKLLAVPAANTVRFRCPAAGNPTPSI SWLKNGREFRGEHRIGGIKLRHQQWSLVMES VVPSDRGNYTCVVENKFGSIRQTYTLDVLERS PHRPILQAGLPANQTAVLGSDVEFHCKVYSDA QPHIQWLKHVEVNGSKVGPDGTPYVTVLKS WISESVEADVRLRLANVSERDGGEYLCRATNF IGVAEKAFWLSVHGPRAAEEELVEADEAGSVY AGILSYGVGFFLFILVVAAVTLCRLRSPPKKGLG SPTVHKISRFPLKRQVSLESNASMSSNTPLVRI ARLSSGEGPTLANVSELELPADPKWELSRARLT LGKPLGEGCFGQVVMAEAIGIDKDRAAKPVT VAVKMLKDDATDKDLSDLVSEMEMMKMIG KHKNIINLLGACTQGGPLYVLVEYAAKGNLREF LRARRPPGLDYSFDTCKPPEEQLTFKDLVSCAY QVARGMEYLASQKCIHRDLAARNVLVTEDNV MKIADFGLARDVHNLDYYKKTTNGRLPVKW MAPEALFDRVYTHQSDVWSFGVLLWEIFTLG GSPYPGIPVEELFKLLKEGHRMDKPANCTHDL YMIMRECWHAAPSQRPTFKQLVEDLDRVLTV TSTDVPGPPPGVPAPGGPPLSTGPIVDLLQYS QKDLDAVVKATQEENRELRSRCEELHGKNLEL GKIMDRFEEVVYQAMEEVQKQKELSKAEIQK VLKEKDQLTTDLNSMEKSFSDLFKRFEKQKEVI EGYRKNEESLKKCVEDYLARITQEGQRYQALK AHAEEKLQLANEEIAQVRSKAQAEALALQASL RKEQMRIQSLEKTVEQKTKENEELTRICDDLIS KMEKI | 17 | 10 |
| NYU_B | 1 | 31 | 214 | 548 | 8389 | MHGGGPPSGDSACPLRTIKRVQFGVLSPDEL VPVLRMVEGDTIYDYCWYSLMSSAQPDTSYV ASSSRENPIHIWDAFTGELRASFRAYNHLDELT AAHSLCFSPDGSQLFCGFNRTVRVFSTARPGR DCEVRATFAKKQGQSGIISCIAFSPAQPLYACG | 1 | 5 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | SYGRSLGLYAWDDGSPLALLGGHQGGITHLCF HPDGNRFFSGARKDAELLCWDLRQSGYPLWS LGREVTTNQRIYFDLDPTGQFLVSGSTSGAVS VWDTDGPGNDGKPEPVLSFLPQKDCTNGVSL HPSLPLLATASGQRVFPEPTESGDEGEELGLPL LSTRHVHLECRLQLWWCGGAPDSSIPDDHQ GEKGQGGTEGGVGELI | | |
| G17507 .TCGA-28-1747-01C-01R-1850-01.2 | 1 | 982 | 373 | 432 | 8390 | MRPSGTAGAALLALLAALCPASRALEEKKVCQ GTSNKLTQLGTFEDHFLSLQRMFNNCEVVLG NLEITYVQRNYDLSFLKTIQEVAGYVLIALNTVE RIPLENLQIIRGNMYYENSYALAVLSNYDANKT GLKELPMRNLQEILHGAVRFSNNPALCNVESI QWRDIVSSDFLSNMSMDFQNHLGSCQKCDP SCPNGSCWGAGEENCQKLTKIICAQQCSGRC RGKSPSDCCHNQCAAGCTGPRESDCLVCRKF RDEATCKDTCPPLMLYNPTTYQMDVNPEGKY SFGATCVKKCPRNYVVTDHGSCVRACGADSY EMEEDGVRKCKKCEGPCRKVCNGIGIGEFKDS LSINATNIKHFKNCTSISGDLHILPVAFRGDSFT HTPPLDPQELDILKTVKEITGFLLIQAWPENRT DLHAFENLEIIRGRTKQHGQFSLAVVSLNITSL GLRSLKEISDGDVIISGNKNLCYANTINWKKLF GTSGQKTKIISNRGENSCKATGQVCHALCSPE GCWGPEPRDCVSCRNVSRGRECVDKCNLLEG EPREFVENSECIQCHPECLPQAMNITCTGRGP DNCIQCAHYIDGPHCVKTCPAGVMGENNTLV WKYADAGHVCHLCHPNCTYGCTGPGLEGCP TNGPKIPSIATGMVGALLLLLVVALGIGLFMRR RHIVRKRTLRRLLQERELVEPLTPSGEAPNQAL LRILKETEFKKIKVLGSGAFGTVYKGLWIPEGEK VKIPVAIKELREATSPKANKEILDEAYVMASVD NPHVCRLLGICLTSTVQLITQLMPFGCLLDYVR EHKDNIGSQYLLNWCVQIAKGMNYLEDRRLV HRDLAARNVLVKTPQHVKITDFGLAKLLGAEE KEYHAEGGKVPIKWMALESILHRIYTHQSDV WSYGVTVWELMTFGSKPYDGIPASEISSILEK GERLPQPPICTIDVYMIMVKCWMIDADSRPK FRELIIEFSKMARDPQRYLVIQLQDKFEHLKMI QQEEIRKLEEEKKQLEGEIIDFYKMKAASEALQ TQLSTDTKKDKHRKK | 24 | 10 |
| G17469 .TCGA-06-2557-01A-01R-1849-01.2 | 1 | 136 | 980 | 998 | 8391 | MADFDTYDDRAYSSFGGGRGSRGSAGGHGS RSQKELPTEPPYTAYVGNLPFNTVQGDIDAIFK DLSIRSVRLVRDKDTDKFKGFCYVEFDEVDSLK EALTYDGALLGDRSLRVDIAEGRKQDKGGFGF RKGGPDDREIKETDGSSQIKQEPDPTW | 4 | 34 |
| G17785 .TCGA-06-5413-01A-01R- | 1 | 108 | 119 | 239 | 8392 | MLTMSVTLSPLRSQDLDPMATDASPMAINM TPTVEQGEGEEAMKDMDSDQQYEKPPPLHT GADWKIVLHLPEIETWLRMTSERVRDLTYSVQ QDSDSKHVDVHLVQLKAMVACYPGNGTGYV RHVDNPNGDGRCITCIYYLNKNWDAKLHGGI LRIFPEGKSFIADVEPIFDRLLFFWSDRRNPHEV | 2 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 1849-01.4 | | | | | | QPSYATRYAMTVWYFDAEERAEAKKKFRNLTRKTESALTED | | |
| G17467.TCGA-14-0736-02A-01R-2005-01.2 | 1 | 83 | 103 | 348 | 8393 | MATEGGGKEMNEIKTQFTTREGLYKLLPHSEYSRPNRVPFNSQGSNPVRVSFVNLNDQSGNGDRLCFNVGRELYFYIYKGVRKEIDPSLGVAELPDEFFEEDNMLSMGKKMMQEAMSAFPGIDEAMSYAEVMRLVKGMNFSVVVFDTAPTGHTLRLLNFPTIVERGLGRLMQIKNQISPFISQMCNMLGLGDMNADQLASKLEETLPVIRSVSEQFKDPEQTTFICVCIAEFLSLYETERLIQELAKCKIDTHNIIVNQLVFPDPEKPCKMCEARHKIQAKYLDQMEDLYEDFHIVKLPLLPHEVRGADKVNTFSALLLEPYKPPSAQ | 1 | 3 |
| GBM-CUMC3316_L1 | 1 | 164 | 59 | 226 | 8394 | MAAAAAAGAGPEMVRGQVFDVGPRYTNLSYIGEGAYGMVCSAYDNVNKVRVAIKKISPFEHQTYCQRTLREIKILLRFRHENIIGINDIIRAPTIEQMKDVYIVQDLMETDLYKLLKTQHLSNDHICYFLYQILRGLKYIHSANVLHRDLKPSNLLLNTTCDLKALSLCNYFESQNVDFRGKKVIELGAGTGIVGILAALQGGDVTITDLPLALEQIQGNVQANVPAGGQAQVRALSWGIDHHVFPANYDLVLGADIVYLEPTFPLLLGTLQHLCRPHGTIYLASKMRKEHGTESFFQHLLPQHFQLELAQRDEDENVNIYRARHREPRPA | 3 | 2 |
| G17663.TCGA-19-2619-01A-01R-1850-01.2 | 1 | 876 | 417 | 796 | 8395 | MAQLFLPLLAALVLAQAPAALADVLEGDSSEDRAFRVRIAGDAPLQGVLGGALTIPCVHYLRPPPSRRAVLGSPRVKWTFLSRGREAEVLVARGVRVKVNEAYRFRVALPAYPASLTDVSLALSELRPNDSGIYRCEVQHGIDDSSDAVEVKVKGVVFLYREGSARYAFSFSGAQEACARIGAHIATPEQLYAAYLGGYEQCDAGWLSDQTVRYPIQTPREACYGDMDGFPGVRNYGVVDPDDLYDVYCYAEDLNGELFLGDPPEKLTLEEARAYCQERGAEIATTGQLYAAWDGGLDHCSPGWLADGSVRYPIVTPSQRCGGGLPGVKTLFLFPNQTGFPNKHSRFNVYCFRDSAQPSAIPEASNPASNPASDGLEAIVTVTETLEELQLPQEATESESRGAIYSIPIMEDGGGGSSTPEDPAEAPRTLLEFETQSMVPPTGFSEEEGKALEEEEKYEDEEEKEEEEEEEVEDEALWAWPSELSSPGPEASLPTEPAAQEESLSQAPARAVLQPGASPLPDGESEASRPPRVHGPPTETLPTPRERNLASPSPSTLVEAREVGEATGGPELSGVPRGESEETGSSEGAPSLLPATRAPEGTRELEAPSEDNSGRTAPAGTSVQAQPVLPTDSASRGGVAVVPASGDCVPSPCHNGGTCLEEEEGVRCLCLPGYGGDLCDVGLRFCNPGWDAFQGACYKHFSTRRSWEEAETQCRMYGAHLASISTPEEQDFINNRYREYQWIGLNDRTIEGDFLWSDGVPLLYENWNPGQPDSYFLSGENCVVMVWHDQGQWSDVPCNYHLSYTCKMGLVSCGPPPELPLAQVFGRPRLRYEVDTVLRYRCREGLAQRNLPLIRCQENGRWEAPQISCVPRRPVSVAVGLAVFACLFLSTLLLVLNKCGRRNKFGINRPAVLAPEDGLAMSLHFMTLGGSSLSPTEGKGSGLQGHIIEN | 13 | 11 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | PQYFSDACVHHIKRRDIVLKWELGEGAFGKVF LAECHNLLPEQDKMLVAVKALKEASESARQD FQREAELLTMLQHQHIVRFFGVCTEGRPLLM VFEYMRHGDLNRFLRSHGPDAKLLAGGEDVA PGPLGLGQLLAVASQVAAGMVYLAGLHFVHR DLATRNCLVGQGLVVKIGDFGMSRDIYSTDYY RVGGRTMLPIRWMPPESILYRKFTTESDVWS FGVVLWEIFTYGKQPWYQLSNTEAIDCITQGR ELERPRACPPEVYAIMRGCWQREPQQRHSIK DVHARLQALAQAPPVYLDVLG | | |
| G17203 .TCGA- 06- 0211- 02A- 02R- 2005- 01.2 | 1 | 31 | 336 | 1210 | 8396 | MDQVMQFVEPSRQFVKDSIRLVKRCTKPDRK VCNGIGIGEFKDSLSINATNIKHFKNCTSISGDL HILPVAFRGDSFTHTPPLDPQELDILKTVKEITG FLLIQAWPENRTDLHAFENLEIIRGRTKQHGQ FSLAVVSLNITSLGLRSLKEISDGDVIISGNKNLC YANTINWKKLFGTSGQKTKIISNRGENSCKAT GQVCHALCSPEGCWGPEPRDCVSCRNVSRG RECVDKCNLLEGEPREFVENSECIQCHPECLP QAMNITCTGRGPDNCIQCAHYIDGPHCVKTC PAGVMGENNTLVWKYADAGHVCHLCHPNC TYGCTGPGLEGCPTNGPKIPSIATGMVGALLLL LVVALGIGLFMRRRHIVRKRTLRRLLQERELVE PLTPSGEAPNQALLRILKETEFKKIKVLGSGAFG TVYKGLWIPEGEKVKIPVAIKELREATSPKANK EILDEAYVMASVDNPHVCRLLGICLTSTVQLIT QLMPFGCLLDYVREHKDNIGSQYLLNWCVQI AKGMNYLEDRRLVHRDLAARNVLVKTPQHV KITDFGLAKLLGAEEKEYHAEGGKVPIKWMAL ESILHRIYTHQSDVWSYGVTVWELMTFGSKPY DGIPASEISSILEKGERLPQPPICTIDVYMIMVK CWMIDADSRPKFRELIIEFSKMARDPQRYLVI QGDERMHLPSPTDSNFYRALMDEEDMDDV VDADEYLIPQQGFFSSPSTSRTPLLSSLSATSNN STVACIDRNGLQSCPIKEDSFLQRYSSDPTGAL TEDSIDDTFLPVPEYINQSVPKRPAGSVQNPVY HNQPLNPAPSRDPHYQDPHSTAVGNPEYLNT VQPTCVNSTFDSPAHWAQKGSHQISLDNPDY QQDFFPKEAKPNGIFKGSTAENAEYLRVAPQS SEFIGA | 2 | 9 |
| G17784 .TCGA- 76- 4929- 01A- 01R- 1850- 01.4 | 1 | 150 | 98 | 245 | 8397 | MRQSLLFLTSVVPFVLAPRPPDDPGFGPHQRL EKLDSLLSDYDILSLSNIQQHSVRKRDLQTSTH VETLLTFSALKRHFKLYLTSSTERFSQNFKVVVV DGKNESEYTVKWQDFFTGHVVGEPDSRVLA HIRDDDVIIRINTDGAEYNIEELLDKYLIANATN PESKVFYLKMKGDYFRYLAEVACGDDRKQTID NSQGAYQEAFDISKKEMQPTHPIRLGLALNFS VFYYEILNNPELACTLAKTAFDEAIAELDTLNED SYKDSTLIMQLLRDNLTLWTSDSAGEECDAAE GAEN | 4 | 2 |
| G17675 .TCGA- 19- 2624- 01A- | 1 | 228 | 559 | 584 | 8398 | MEEDGVRKCKKCEGPCRKVCNGIGIGEFKDSL SINATNIKHFKNCTSISGDLHILPVAFRGDSFTH TPPLDPQELDILKTVKEITGFLLIQAWPENRTD LHAFENLEIIRGRTKQQDQTTVSSVPTTLTAPT ASRPARQESWEKTTPWSGSTQTPAMCATCAI | 14 | 15 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 01R-1850-01.2 | | | | | | QTAPTDALGQVLKAVQRMGLRSRPSPLGW WGPSSCCWWWPWGSASSCEGATSFGSARC GGCCRRGRYRFDPRLMFSNRGSVRTRRFSKH LL | | |
| G17796 .TCGA-41-5651-01A-01R-1850-01.4 | 1 | 96 | 117 | 301 | 8399 | MADPGPDPESESESVFPREVGLFADSYSEKSQ FCFCGHVLTITQNFGSRLGVAARVWDAALSLC NYFESQNVDFRGKKVIELGAGTGIVGILAALQ VELSPLFPDTLILGLEIRVKVSDYVQDRIRALRA APAGGFQNIACLRSNAMKHLPNFFYKGQLTK MFFLFPDPHFKRTKHKWRIISPTLLAEYAYVLR VGGLVYTITDVLELHDWMCTHFEEHPLFERVP LEDLSEDPVVGHLGTSTEEGKKVLRNGGKNFP AIFRRIQDPVLQAVTSQTSLPGH | 2 | 3 |
| G17666 .TCGA-06-5415-01A-01R-1849-01.2 | 1 | 34 | 90 | 300 | 8400 | MVPAAGRRPPRVMRLLGWWQVLLWVLGLP VRGVEGYNVSLLYDLENLPASKDSIVHQAGML KRNCFASVFEKYFQFQEEGKEGENRAVIHYRD DETMYVESKKDRVTVVFSTVFKDDDDVVIGK VFMQEFKEGRRASHTAPQVLFSHREPPLELKD TDAAVGDNIGYITFVLFPRHTNASARDNTINLI HTFRDYLHYHIKCSKAYIHTRMRAKTSDFLKVL NRARPDAEKKEMKTITGKTFSSR | 1 | 6 |
| G17219 .TCGA-06-0158-01A-01R-1849-01.2 | 1 | 8 | 528 | 926 | 8401 | MDGFAGSLGTLHVGDEIREINGISVANQTVE QLQKMLREMRGSITFKIVPSYRTQSSSCERDS PSTSRQSPANGHSSTNNSVSDLPSTTQPKGR QIYVRAQFEYDPAKDDLIPCKEAGIRFRVGDII QIISKDDHNWWQGKLENSKNGTAGLIPSPEL QEWRVACIAMEKTKQEQQASCTWFGKKKKQ YKDKYLAKHNAVFDQLDLVTYEEVVKLPAFKR KTLVLLGAHGVGRRHIKNTLITKHPDRFAYPIP HTTRPPKKDEENGKNYYFVSHDQMMQDISN NEYLEYGSHEDAMYGTKLETIRKIHEQGLIAIL DVEPQALKVLRTAEFAPFVVFIAAPTITPGLNE DESLQRLQKESDILQRTYAHYFDLTIINNEIDETI RHLEEAVELVCTAPQWVPVSWVY | 1 | 17 |
| G17790 .TCGA-06-5856-01A-01R-1849-01.4 | 1 | 23 | 740 | 819 | 8402 | MSGQLERCEREWHELEGEFQELQDMKNATL SLNSNDSEPKYYPIAVLLKNQNQELPEDVNPA KKENYLSEQDFVSVFGITRGQFAALPGWKQL QMKKEKGLF | 1 | 18 |
| NYU_B | 1 | 93 | 4035 | 5204 | 8403 | MGGPQDKDERTIALVRPWPWGHQALDPAY GLDTMHPSRRSLPFPLNCQLARVGTADYGSP SDQSDQQLDCALDLMRRLPPQQIEKNLSDLID LDVPVEALTTVKPYCNEIHAQAQLWLKRDPK ASYDAWKKCLPIRGIDGNGKAPSKSELRHLYLT EKYVWRWKQFLSRRGKRTSPLDLKLGHNNW LRQVLFTPATQAARQAACTIVEALATIPSRKQ QVLDLLTSYLDELSIAGECAAEYLALYQKLITSA HWKVYLAARGVLPYVGNLITKEIARLLALEEAT LSTDLQQGYALKSLTGLLSSFVEVESIKRHFKSR LVGTVLNGYLCLRKLVVQRTKLIDETQDMLLE MLEDMTTGTESETKAFMAVCIETAKRYNLDD | 3 | 82 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | YRTPVFIFERLCSIIYPEENEVTEFFVTLEKDPQQ EDFLQGRMPGNPYSSNEPGIGPLMRDIKNKIC QDCDLVALLEDDSGMELLVNNKIISLDLPVAE VYKKVWCTTNEGEPMRIVYRMRGLLGDATEE FIESLDSTTDEEEDEEEVYKMAGVMAQCGGL ECMLNRLAGIRDFKQGRHLLTVLLKLFSYCVKV KVNRQQLVKLEMNTLNVMLGTLNLALVAEQ ESKDSGGAAVAEQVLSIMEIILDESNAEPLSED KGNLLLTGDKDQLVMLLDQINSTFVRSNPSVL QGLLRIIPYLSFGEVEKMQILVERFKPYCNFDKY DEDHSGDDKVFLDCFCKIAAGIKNNSNGHQL KDLILQKGITQNALDYMKKHIPSAKNLDADIW KKFLSRPALPFILRLLRGLAIQHPGTQVLIGTDSI PNLHKLEQVSSDEGIGTLAENLLEALREHPDV NKKIDAARRETRAEKKRMAMAMRQKALGTL GMTTNEKGQVVTKTALLKQMEELIEEPGLTCC ICREGYKFQPTKVLGIYTFTKRVALEEMENKPR KQQGYSTVSHFNIVHYDCHLAAVRLARGREE WESAALQNANTKCNGLLPVWGPHVPESAFA TCLARHNTYLQECTGQREPTYQLNIHDIKLLFL RFAMEQSFSADTGGGGRESNIHLIPYIIHTVLY VLNTTRATSREEKNLQGFLEQPKEKWVESAFE VDGPYYFTVLALHILPPEQWRATRVEILRRLLV TSQARAVAPGGATRLTDKAVKDYSAYRSSLLF WALVDLIYNMFKKQTTPTVGGIDTGSLEPCVC EKVPTSNTEGGWSCSLAEYIRHNDMPIYEAAD KALKTFQEEFMPVETFSEFLDVAGLLSEITDPES FLKDLLNSVP | | |
| G17657 .TCGA-19-1787-01B-01R-1850-01.2 | 1 | 89 | 39 | 797 | 8404 | MNGQLDLSGKLIIKAQLGEDIRRIPIHNEDITYD ELVLMMQRVFRGKLLSNDEVTIKYKDEDGDLI TIFDSSDLSFAIQCSRILKLTLFGKSTSSSSTPTEF CRNGGTWENGRCICTEEWKGLRCTIANFCEN STYMGFTFARIPVGRYGPSLQTCGKDTPNAG NPMAVRLCSLSLYGEIELQKVTIGNCNENLETL EKQVKDVTAPLNNISSEVQILTSDANKLTAENI TSATRVVGQIFNTSRNASPEAKKVAIVTVSQLL DASEDAFQRVAATANDDALTTLIEQMETYSLS LGNQSVVEPNIAIQSANFSSENAVGPSNVRFS VQKGASSSLVSSSTFIHTNVDGLNPDAQTELQ VLLNMTKNYTKTCGFVVYQNDKLFQSKTFTA KSDFSQKIISSKTDENEQDQSASVDMVFSPKY NQKEFQLYSYACVYWNLSAKDWDTYGCQKD KGTDGFLRCRCNHTTNFAVLMTFKKDYQYPK SLDILSNVGCALSVTGLALTVIFQIVTRKVRKTS VTWVLVNLCISMLIFNLLFVFGIENSNKNLQTS DGDINNIDFDNNDIPRTDTINIPNPMCTAIAAL LHYFLLVTFTWNALSAAQLYYLLIRTMKPLPRH FILFISLIGWGVPAIVVAITVGVIYSQNGNNPQ WELDYRQEKICWLAIPEPNGVIKSPLLWSFIVP VTIILISNVVMFITISIKVLWKNNQNLTSTKKVS SMKKIVSTLSVAVVFGITWILAYLMLVNDDSIR IVFSYIFCLFNTTQGLQIFILYTVRTKVFQSEASK VLMLLSSIGRRKSLPSVTRPRLRVKMYNFLRSL PTLHERFRLLETSPSTEEITLSESDNAKESI | 3 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| G17643 .TCGA-12-5295-01A-01R-1849-01.2 | 1 | 20 | 79 | 169 | 8405 | MAPARLFALLLFFVGGVAESDYKGQKLAEQM FQGIILFSAIVGFIYGYVAEQFGWTVYIVMAGF AFSCLLTLPPWPIYRRHPLKWLPVQESSTDDK KPGERKIKRHAKNN | 1 | 2 |
| NYU_G | 1 | 265 | 119 | 974 | 8406 | MRSIRKRWTICTISLLLIFYKTKEIARTEEHQET QLIGDGELSLSRSLVNSSDKIIRKAGSSIFQHNV EGWKINSSLVLEIRKNILRFLDAERDVSVVKSSF KPGDVIHYVLDRRRTLNISHDLHSLLPEVSPMK NRRFKTCAVVGNSGILLDSECGKEIDSHNFVIR CNLAPVVEFAADVGTKSDFITMNPSVVQRAF GGFRNESDREKFVHRLSMLNDSVLWIPAFMV KGGEKHVEWVNALILKNKLKVRTAYPSLRLIH AVRGFCDEGTCTDKANILYAWARNAPPTRLP KGVGFRVGGETGSKYFVLQVHYGDISAFRDN NKDCSGVSLHLTRLPQPLIAGMYLMMSVDTV IPAGEKVVNSDISCHYKNYPMHVFAYRVHTH HLGKVVSGYRVRNGQWTLIGRQSPQLPQAFY PVGHPVDVSFGDLLAARCVFTGEGRTEATHIG GTSSDEMCNLYIMYYMEAKHAVSFMTCTQN VAPDMFRTIPPEANIPIPVKSDMVMMHEHH KETEYKDKIPLLQQPKREEEEVLDQGDFYSLLS KLLGEREDVVHVHKYNPTEKAESESDLVAEIA NVVQKKDLGRSDAREGAEHERGNAILVRDRI HKFHRLVSTLRPPESRVFSLQQPPPGEGTWEP EHTGDFHMEEALDWPGVYLLPGQVSGVALD PKNNLVIFHRGDHVWDGNSFDSKFVYQQIGL GPIEEDTILVIDPNNAAVLQSSGKNLFYLPHGL SIDKDGNYWVTDVALHQVFKLDPNNKEGPVL ILGRSMQPGSDQNHFCQPTDVAVDPGTGAIY VSDGYCNSRIVQFSPSGKFITQWGEESSGSSPL PGQFTVPHSLALVPLLGQLCVADRENGRIQCF KTDTKEFVREIKHSSFGRNVFAISYIPGLLFAVN GKPHFGDQEPVQGFVMNFSNGEIIDIFKPVRK HFDMPHDIVASEDGTVYIGDAHTNTVWKFTL TEKLEHRSVKKAGIEVQEIKEAEAVVETKMEN KPTSSELQKMQEKQKLIKEPGSGVPVVLITTLL VIPVVVLLAIAIFIRWKKSRAFGADSEHKLETSS GRVLGRFRGKGSGGLNLGNFFASRKGYSRKG FDRLSTEGSDQEKEDDGSESEEEYSAPLPALAP SSS | 4 | 5 |
| G17494 .TCGA-14-2554-01A-01R-1850-01.2 | 1 | 85 | 67 | 170 | 8407 | MSVDMNSQGSDSNEEDYDPNCEEEEEEEED DPGDIEDYYVGVASDVEQQGADAFDPEEYQF TCLTYKESEGALNEHMTSLASVLKDGDPDTPK PVSFTVKETVCPRTTQQSPEDCDFKKDGLVKR CMGTVTLNQARGSFDISCDKDNKRFALLGDF FRKSKEKIGKEFKRIVQRIKDFLRNLVPRTES | 1 | 2 |
| G17196 .TCGA- | 1 | 852 | 922 | 995 | 8408 | MSRGAGALQRRTTTYLISLTLVKLESVPPPPPS PSAAAAGAAGARGSETGDPGSPRGAEEPGKK | 13 | 27 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 06-0178-01A-01R-1849-01.2 | | | | | | RHERLFHRQDALWISTSSAGTGGAEPPALSPA PASPARPVSPAPGRRLSLWAVPPGPPLSGGLS PDPKPGGAPTSSRRPLLSSPSWGGPEPEGRA GGGIPGSSSPHPGTGSRRLKVAPPPPAPKPCK TVTTSGAKAGGGKGAGSRLSWPESEGKPRVK GSKSSAGTGASVSAAATAAAAGGGGSTASTS GGVGAGAGARGKLSPRKGKSKTLDNSDLHPG PPAGSPPPLTLPPTPSPATAVTAASAQPPGPA PPITLEPPAPGLKRGREGGRASTRDRKMLKFIS GIFTKSTGGPPGSGPLPGPPSLSSGSGSRELLG AELRASPKAVINSQEWTLSRSIPELRLGVLGDA RSGKSSLIHRFLTGSYQVLEKTESEQYKKEMLV DGQTHLVLIREEAGAPDAKFSGWADAVIFVFS LEDENSFQAVSRLHGQLSSLRGEGRGGLALAL VGTQDRISASSPRVVGDARARALCADMKRCS YYETCATYGLNVDRVFQEVAQKVVTLRKQQQ LLAACKSLPSSPSHSAASTPVAGQASNGGHTS DYSSSLPSSPNVGHRELRAEAAAVAGLSTPGSL HRAAKRRTSLFANRRGSDSEKRSLDSRGETTG SGRAIPIKQSFLLKRSGNSLNKEWKKKYVTLSS NGFLLYHPSINDYIHSTHGKEMDLLRTTVKVP GKRPPRAISAFGPSASINGLVKDMSTVQMGE GLEATTPMPSPSPSPSSLQPPPDQTSKHLLKP DRNLARALSTDCTPSGDLSPLSREPPPSPMVK KQRRKKLTTPSKTEGSAGQAEDEGYSFSSVLYY GNEATLLIFDLLFFCVVDLACQNFILASFLTYLQ QEIFRYIRNTVGQKNLASKTLVDQRFLI | | |
| G17782.TCGA-26-5136-01B-01R-1850-01.4 | 1 | 19 | 140 | 216 | 8409 | MTHFNKGPSYGLSAEVKNKVLCNGPGTCVPI CVSALLLGILGIKKVIIVYVESICRVETLSMSGKIL FHLSDYFIVQWPALKEKYPKSVYLGRIV | 1 | 4 |
| GBM-CUMC3296_L1 | 1 | 18 | 132 | 179 | 8410 | MRRQPAKVAALLLGLLLEHIEGDDLHIQRNVQ KLKDTVKKLGESGEIKAIGELDLLFMSLRNACI | 1 | 4 |
| G17199.TCGA-06-0744-01A-01R-1849-01.2 | 1 | 29 | 96 | 406 | 8411 | MRPSGTAGAALLALLAALCPASRALEEKKADI AQRYRISKYPTLKLFRNGMMMKREYRGQRSV KALADYIRQQKSDPIQEIRDLAEITTLDRSKRNII GYFEQKDSDNYRVFERVANILHDDCAFLSAFG DVSKPERYSGDNIIYKPPGHSAPDMVYLGAM TNFDVTYNWIQDKCVPLVREITFENGEELTEE GLPFLILFHMKEDTESLEIFQNEVARQLISEKGT INFLHADCDKFRHPLLHIQKTPADCPVIAIDSFR HMYVFGDFKDVLIPGKLKQFVFDLHSGKLHRE FHHGPDPTDTAPGEQAQDVASSPPESSFQKL APSEYRYTLLRDRDEL | 1 | 5 |
| G17792.TCGA-28-5204-01A- | 1 | 320 | 162 | 453 | 8412 | MTDGKLSTSTNGVAFMGILDGRPGNPLQNL QHVNLKAPRLLSAPEYGPKLKLRALEDRHSLQ SVDSGIPTLEIGNPEPVPCSAVHVRRKQSDSDL IPERAFQSACALPSCAPPAPSSTEREQSVRKSS TFPRTGYDSVKLYSPTSKALTRSDDVSVCSVSS | 4 | 3 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 01R-1850-01.4 | | | | | | LGTELSTTLSVSNEDILDLVVTSSSSAIVTLEND DDPQFTNVTLSSIKETRGLHQQDCVHEAEEGS KLKILGPFSNFFARNLLARKQSARLDKHNDLG WKLFGKAPLRENAQKDSKRIQKEYEDKAGRP SKPPSPKQNVRKNLDFEPLSTTALILEDRPAHP LFGRNVPLSSGSGFIMSEAGLIITNAHVVSSNS AAPGRQQLKVQLQNGDSYEATIKDIDKKSDIA TIKIHPKKKLPVLLLGHSADLRPGEFVVAIGSPF ALQNTVTTGIVSTAQREGRELGLRDSDMDYIQ TDAIINYGNSGGPLVNLDGEVIGINTLKVTAGI SFAIPSDRITRFLTEFQDKQIKDWKKRFIGIRM RTITPSLVDELKASNPDFPEVSSGIYVQEVAPN SPSQRGGIQDGDIIVKVNGRPLVDSSELQEAV LTESPLLLEVRRGNDDLLFSIAPEVVM | | |
| G17476 .TCGA-06-2569-01A-01R-1849-01.2 | 1 | 64 | 1974 | 3685 | 8413 | MRLLPRLLLLLLLVFPATVLFRGGPRGLLAVAQ DLTEDEETVEDSIIEDEDDEAEVEEDEPTDLHT VREETMMVMTEDMPLEISYVPSTYLTEITHVS QALLEVEQLLNAPDLCAKDFEDLFKQEESLKNI KDSLQQSSGRIDIIHSKKTAALQSATPVERVKL QEALSQLDFQWEKVNKMYKDRQGRFDRSVE KWRRFHYDIKIFNQWLTEAEQFLRKTQIPEN WEHAKYKWYLKELQDGIGQRQTVVRTLNAT GEEIIQQSSKTDASILQEKLGSLNLRWQEVCKQ LSDRKKRLEEQKNILSEFQRDLNEFVLWLEEAD NIASIPLEPGKEQQLKEKLEQVKLLVEELPLRQ GILKQLNETGGPVLVSAPISPEEQDKLENKLKQ TNLQWIKVSRALPEKQGEIEAQIKDLGQLEKKL EDLEEQLNHLLLWLSPIRNQLEIYNQPNQEGP FDVKETEIAVQAKQPDVEEILSKGQHLYKEKPA TQPVKRKLEDLSSEWKAVNRLLQELRAKQPDL APGLTTIGASPTQTVTLVTQPVVTKETAISKLE MPSSLMLEVPALADFNRAWTELTDWLSLLDQ VIKSQRVMVGDLEDINEMIIKQKATMQDLEQ RRPQLEELITAAQNLKNKTSNQEARTIITDRIER IQNQWDEVQEHLQNRRQQLNEMLKDSTQW LEAKEEAEQVLGQARAKLESWKEGPYTVDAI QKKITETKQLAKDLRQWQTNVDVANDLALKL LRDYSADDTRKVHMITENINASWRSIHKRVSE REAALEETHRLLQQFPLDLEKFLAWLTEAETTA NVLQDATRKERLLEDSKGVKELMKQWQDLQ GEIEAHTDVYHNLDENSQKILRSLEGSDDAVLL QRRLDNMNFKWSELRKKSLNIRSHLEASSDQ WKRLHLSLQELLVWLQLKDDELSRQAPIGGDF PAVQKQNDVHRAFKRELKTKEPVIMSTLETVR IFLTEQPLEGLEKLYQEPRELPPEERAQNVTRLL RKQAEEVNTEWEKLNLHSADWQRKIDETLER LRELQEATDELDLKLRQAEVIKGSWQPVGDLLI DSLQDHLEKVKALRGEIAPLKENVSHVNDLAR QLTTLGIQLSPYNLSTLEDLNTRWKLLQVAVE DRVRQLHEAHRDFGPASQHFLSTSVQGPWE RAISPNKVPYYINHETQTTCWDHPKMTELYQS LADLNNVRFSAYRTAMKLRRLQKALCLDLLSLS AACDALDQHNLKQNDQPMDILQIINCLTTIYD RLEQEHNNLVNVPLCVDMCLNWLLNVYDTG | 2 | 42 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | RTGRIRVLSFKTGIISLCKAHLEDKYRYLFKQVA SSTGFCDQRRLGLLLHDSIQIPRQLGEVASFGG SNIEPSVRSCFQFANNKPEIEAALFLDWMRLE PQSMVWLPVLHRVAAAETAKHQAKCNICKE CPIIGFRYRSLKHFNYDICQSCFFSGRVAKGHK MHYPMVEYCTPTTSGEDVRDFAKVLKNKFRT KRYFAKHPRMGYLPVQTVLEGDNMETPVTLI NFWPVDSAPASSPQLSHDDTHSRIEHYASRLA EMENSNGSYLNDSISPNESIDDEHLLIQHYCQS LNQDSPLSQPRSPAQILISLESEERGELERILADL EEEENRNLQAEYDRLKQQHEHKGLSPLPSPPE MMPTSPQSPRDAELIAEAKLLRQHKGRLEAR MQILEDHNKQLESQLHRLRQLLEQPQAEAKV NGTTVSSPSTSLQRSDSSQPMLLRVVGSQTSD SMGEEDLLSPPQDTSTGLEEVMEQLNNSFPSS RGRNTPGKPMREDTM | | |
| G17195.TCGA-06-0138-01A-02R-1849-01.2 | 1 | 261 | 193 | 667 | 8414 | MPLLGQTVRSASARTRRWSRRAAGDRPGAP SEARRPQLRGDHGIVDRVRGHWRIAGSCSTC WCPSALCSSTNGFMCTFPNMSLTLVHFVVT WLGLYICQKLDIFAPKSLPPSRLLLLALSFCGFV VFTNLSLQNNTIGTYQLAKAMTTPVIIAIQTFC YQKTFSTRIQLTLIPITLGVILNSYYDVKFNFLG MVFAALGVLVTSLYQVWVGAKQHELQVNS MQLLYYQAPMSSAMLLVAVPFFEPVFGEGGI FGPWSVSALFLCDEGAGISGDYIDRVDEPLSCS YVLTIRTPRLCPHPLLRPPPSAAPQAILCHPSLQ PEEYMAYVQRQADSKQYGDKIIEELQDLGPQ VWSETKSGVAPQKMAGASPTKDDSKDSDFW KMLNEPEDQAPGGEEVPAEEQDPSPEAADSA SGAPNDFQNNVQVKVIRSPADLIRFIEELKGG TKKGKPNIGQEQPVDDAAEVPQREPEKERGD PERQREMEEEEDEDEDEDEDEDERQLLGEFE KELEGILLPSDRDRLRSEVKAGMERELENIIQET EKELDPDGLKKESERDRAMLALTSTLNKLIKRL EEKQSPELVKKHKKKRVVPKKPPPSPQPTEED PEHRVRVRVTKLRLGGPNQDLTVLEMKRENP QLKQIEGLVKELLEREGLTAAGKIEIKIVRPWAE GTEEGARWLTDEDTRNLKEIFFNILVPGAEEA QKERQRQKELESNYRRVWGSPGGEGTGDLD EFDF | 6 | 6 |
| G17212.TCGA-06-0129-01A-01R-1849-01.2 | 1 | 810 | 134 | 341 | 8415 | MVPEAWRSGLVSTGRVVGVLLLLGALNKAST VIHYEIPEEREKGFAVGNVVANLGLDLGSLSAR RFRVVSGASRRFFEVNRETGEMFVNDRLDRE ELCGTLPSCTVTLELVVENPLELFSVEVVIQDIN DNNPAFPTQEMKLEISEAVAPGTRFPLESAHD PDVGSNSLQTYELSRNEYFALRVQTREDSTKY AELVLERALDREREPSLQLVLTALDGGTPALSA SLPIHIKVLDANDNAPVFNQSLYRARVLEDAPS GTRVVQVLATDLDEGPNGEIIYSFGSHNRAGV RQLFALDLVTGMLTIKGRLDFEDTKLHEIYIQA KDKGANPEGAHCKVLVEVVDVNDNAPEITVT SVYSPVPEDAPLGTVIALLSVTDLDAGENGLVT CEVPPGLPFSLTSSLKNYFTLKTSADLDRETVPE YNLSITARDAGTPSLSALTIVRVQVSDINDNPP | 1 | 4 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | QSSQSSYDVYIEENNLPGAPILNLSVWDPDAP QNARLSFFLLEQGAETGLVGRYFTINRDNGIVS SLVPLDYEDRREFELTAHISDGGTPVLATNISV NIFVTDRNDNAPQVLYPRPGGSSVEMLPRGT SAGHLVSRVVGWDADAGHNAWLSYSLLGSP NQSLFAIGLHTGQISTARPVQDTDSPRQTLTV LIKDNGEPSLSTTATLTVSVTEDSPEARAEFPSG SAPREQKKNLTFYLLLSLILVSVGFVVTVFGVIIF KVYKWKQSRDLYRAPVSSLYRTPGPSLHADAV RGGLMSPHLYHQVYLTTDSRRSDPLLKKPGAA SPLASRQNTLRSCDPVFYRQVLGAESAPPGQE EQNRGKPNWEHLNEDLHVLITVEDAQNRAEI KLKRAVEEVKKLLVPAAEGEDSLKKMQLMELA ILNGTYRDANIKSPALAFSLAATAQAAPRIITGP APVLPPAALRTPTPAGPTIMPLIRQIQTAVMP NGTPHPTAAIVPPGPEAGLIYTPYEYPYTLAPA TSILEYPIEPSGVLGAVATKVRRHDMRVHPYQ RIVTADRAATGN | | |
| G17213 .TCGA-06-0157-01A-01R-1849-01.2 | 1 | 12 | 131 | 278 | 8416 | MADIEQYYMKPPEIVKEAEVPQAALGVPAQG TGDNGHTPVEEEVGGIPVPAPGLLQVTERRQ PLSSVSSLEVHFDLLDLTELTDMSDQELAEVFA DSDDENLNTESPAGLHPLPRAGYLRSPSWTRT RAEQSHEKQPLGDPERQATVLDTFLTVERPQE D | 2 | 2 |
| G17200 .TCGA-06-0125-01A-01R-1849-01.2 | 1 | 1066 | 710 | 1072 | 8417 | MAAQVAPAAASSLGNPPPPPPSELKKAEQQQ REEAGGEAAAAAAAERGEMKAAAGQESEGP AVGPPQPLGKELQDGAESNGGGGGGAGSG GGPGAEPDLKNSNGNAGPRPALNNNLTEPP GGGGGGSSDGVGAPPHSAAAALPPPAYGFG QPYGRSPSAVAAAAAAVFHQQHGGQQSPGL AALQSGGGGGLEPYAGPQQNSHDHGFPNH QYNSYYPNRSAYPPPAPAYALSSPRGGTPGSG AAAAAAGSKPPPSSSASASSSSSSFAQQRFGAM GGGGPSAAGGGTPQPTATPTLNQLLTSPSSA RGYQGYPGGDYSGGPQDGGAGKGPADMAS QCWGAAAAAAAAAAASGGAQQRSHHAPM SPGSSGGGGQPLARTPQPSSPMDQMGKMR PQPYGGTNPYSQQQGPPSGPQQGHGYPGQ PYGSQTPQRYPMTMQGRAQSAMGGLSYTQ QIPPYGQQGPSGYGQQGQTPYYNQQSPHPQ QQQPPYSQQPPSQTPHAQPSYQQQPQSQPP QLQSSQPPYSQQPSQPPHQQSPAPYPSQQST TQQHPQSQPPYSQPQAQSPYQQQQPQQPA PSTLSQQAAYPQPQSQQSQQTAYSQQRFPPP QELSQDSFGSQASSAPSMTSSKGGQEDMNLS LQSRPSSLPDLSGSIDDLPMGTEGALSPGVSTS GISSSQGEQSNPAQSPFSPHTSPHLPGIRGPSP SPVGSPASVAQSRSGPLSPAAVPGNQMPPRP PSGQSDSIMHPSMNQSSIAQDRGYMQRNPQ MPQYSSPQPGSALSPRQPSGGQIHTGMGSY QQNSMGSYGPQGGQYGPQGGYPRQPNYN ALPNANYPSAGMAGGINPMGAGGQMHGQ | 11 | 12 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | PGIPPYGTLPPGRMSHASMGNRPYGPNMAN MPPQVGSGMCPPPGGMNRKTQETAVAMH VAANSIQNRPPGYPNMNQGGMMGTGPPY GQGINSMAGMINPQGPPYSMGGTMANNSA GMAASPEMMGLGDVKLTPATKMNNKADGT PKTESKSKKSSSSTTTNEKITKLYELGGEPERKM WVDRYLAFTEEKAMGMTNLPAVGRKPLDLY RLYVSVKEIGGLTQMQALTSCECTICPDCFRQ HFTIALKEKHITDMVCPACGRPDLTDDTQLLS YFSTLDIQLRESLEPDAYALFHKKLTEGVLMRD PKFLWCAQCSFGFIYEREQLEATCPQCHQTFC VRCKRQWEEQHRGRSCEDFQNWKRMNDPE YQAQGLAMYLQENGIDCPKCKFSYALARGGC MHFHCTQCRHQFCSGCYNAFYAKNKCPEPN CRVKKSLHGHHPRDCLFYLRDWTALRLQKLLQ DNNVMFNTEPPAGARAVPGGGCRVIEQKEV PNGLRDEACGKETPAGYAGLCQAHYKEYLVSL INAHSLDPATLYEVEELETATERYLHVRPQPLA GEDPPAYQARLLQKLTEEVPLGQSIPRRRK | | |
| G17804 .TCGA- 06- 5408- 01A- 01R- 1849- 01.4 | 1 | 982 | 190 | 225 | 8418 | MRPSGTAGAALLALLAALCPASRALEEKKVCQ GTSNKLTQLGTFEDHFLSLQRMFNNCEVVLG NLEITYVQRNYDLSFLKTIQEVAGYVLIALNTVE RIPLENLQIIRGNMYYENSYALAVLSNYDANKT GLKELPMRNLQEILHGAVRFSNNPALCNVESI QWRDIVSSDFLSNMSMDFQNHLGSCQKCDP SCPNGSCWGAGEENCQKLTKIICAQQCSGRC RGKSPSDCCHNQCAAGCTGPRESDCLVCRKF RDEATCKDTCPPLMLYNPTTYQMDVNPEGKY SFGATCVKKCPRNYVVTDHGSCVRACGADSY EMEEDGVRKCKKCEGPCRKVCNGIGIGEFKDS LSINATNIKHFKNCTSISGDLHILPVAFRGDSFT HTPPLDPQELDILKTVKEITGFLLIQAWPENRT DLHAFENLEIIRGRTKQHGQFSLAVVSLNITSL GLRSLKEISDGDVIISGNKNLCYANTINWKKLF GTSGQKTKIISNRGENSCKATGQVCHALCSPE GCWGPEPRDCVSCRNVSRGRECVDKCNLLEG EPREFVENSECIQCHPECLPQAMNITCTGRGP DNCIQCAHYIDGPHCVKTCPAGVMGENNTLV WKYADAGHVCHLCHPNCTYGCTGPGLEGCP TNGPKIPSIATGMVGALLLLLVVALGIGLFMRR RHIVRKRTLRRLLQERELVEPLTPSGEAPNQAL LRILKETEFKKIKVLGSGAFGTVYKGLWIPEGEK VKIPVAIKELREATSPKANKEILDEAYVMASVD NPHVCRLLGICLTSTVQLITQLMPFGCLLDYVR EHKDNIGSQYLLNWCVQIAKGMNYLEDRRLV HRDLAARNVLVKTPQHVKITDFGLAKLLGAEE KEYHAEGGKVPIKWMALESILHRIYTHQSDV WSYGVTVWELMTFGSKPYDGIPASEISSILEK GERLPQPPICTIDVYMIMVKCWMIDADSRPK FRELIIEFSKMARDPQRYLVIQDAFIGFGGNVI RQQVKDNAKWYITDFVELLGELEE | 24 | 6 |
| G17656 .TCGA- 28- | 1 | 379 | 298 | 421 | 8419 | MAAQVAPAAASSLGNPPPPPPSELKKAEQQQ REEAGGEAAAAAAAERGEMKAAAGQESEGP AVGPPQPLGKELQDGAESNGGGGGGGAGSG | 1 | 5 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 2514-01A-02R-1850-01.2 | | | | | | GGPGAEPDLKNSNGNAGPRPALNNNLTEPP GGGGGGSSDGVGAPPHSAAAALPPPAYGFG QPYGRSPSAVAAAAAAVFHQQHGGQQSPGL AALQSGGGGGLEPYAGPQQNSHDHGFPNH QYNSYYPNRSAYPPPAPAYALSSPRGGTPGSG AAAAAGSKPPPSSSASASSSSSSFAQQRFGAM GGGGPSAAGGGTPQPTATPTLNQLLTSPSSA RGYQGYPGGDYSGGPQDGGAGKGPADMAS QCWGAAAAAAAAAAASGGAQQRSHHAPM SPGSSGGGGQPLARTPQVHLGSGIWVDEEK WHQLQVTQGDSKYTKNLAVMIWGTDVLKN RSVTGVATKKKKDAVPKPPLSPHKLSIVRECLY DRIAQETVDETEIAQRLSKVNKYICEKIMDINK SCKNEERREAKYNLQ | | |
| G17654.TCGA-41-4097-01A-01R-1850-01.2 | 1 | 329 | 102 | 545 | 8420 | MLLSLPALHLQTSEHHPFFQLPHRRLGPWCSP TGSPAPLSCETGCGEGSWILVCRLLVPTQVSLL SMEEDIDTRKINNSFLRDHSYATEADIISTVEFN HTGELLATGDKGGRVVIFQREQESKNQVHRR GEYNVYSTFQSHEPEFDYLKSLEIEEKINKIRWL PQQNAAYFLLSTNDKTVKLWKVSERDKRPEG YNLKDEEGRLRDPATITTLRVPVLRPMDLMVE ATPRRVFANAHTYHINSISVNSDYETYMSADD LRINLWNFEITNQSFNIVDIKPANMEELTEVIT AAEFHPHHCNTFVYSSSKGTIRLCDMRASALC DRHTKSGEMLSVAEHFLEQQMHPTVVISAYR KALDDMISTLKKISIPVDISDSDMMLNIINSSIT TKAISRWSSLACNIALDAVKMVQFEENGRKEI DIKKYARVEKIPGGIIEDSCVLRGVMINKDVTH PRMRRYIKNPRIVLLDSSLEYKKGESQTDIEITR EEDFTRILQMEEEYIQQLCEDIIQLKPDVVITEK GISDLAQHYLMRANITAIRRVRKTDNNRIARA CGARIVSRPEELREDDVGTGAGLLEIKKIGDEY FTFITDCKDPKACTILLRGASKEILSEVERNLQD AMQVCRNVLLDPQLVPGGGASEMAVAHALT EKSKAMTGVEQWPYRAVAQALEVIPRTLIQN CGASTIRLLTSLRAKHTQENCETWGVNGETGT LVDMKELGIWEPLAVKLQTYKTAVETAVLLLRI DDIVSGHKKKGDDQSRQGGAPDAGQE | 7 | 6 |
| G17206.TCGA-06-0125-02A-11R-2005-01.2 | 1 | 1066 | 710 | 1072 | 8421 | MAAQVAPAAASSLGNPPPPPPSELKKAEQQQ REEAGGEAAAAAAAERGEMKAAAGQESEGP AVGPPQPLGKELQDGAESNGGGGGGGAGSG GGPGAEPDLKNSNGNAGPRPALNNNLTEPP GGGGGGSSDGVGAPPHSAAAALPPPAYGFG QPYGRSPSAVAAAAAAVFHQQHGGQQSPGL AALQSGGGGGLEPYAGPQQNSHDHGFPNH QYNSYYPNRSAYPPPAPAYALSSPRGGTPGSG AAAAAGSKPPPSSSASASSSSSSFAQQRFGAM GGGGPSAAGGGTPQPTATPTLNQLLTSPSSA RGYQGYPGGDYSGGPQDGGAGKGPADMAS QCWGAAAAAAAAAAASGGAQQRSHHAPM SPGSSGGGGQPLARTPQPSSPMDQMGKMR PQPYGGTNPYSQQQGPPSGPQQGHGYPGQ PYGSQTPQRYPMTMQGRAQSAMGGLSYTQ QIPPYGQQGPSGYGQQGQTPYYNQQSPHPQ | 11 | 12 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | QQQPPYSQQPPSQTPHAQPSYQQQPQSQPP QLQSSQPPYSQQPSQPPHQQSPAPYPSQQST TQQHPQSQPPYSQPQAQSPYQQQQPQQPA PSTLSQQAAYPQPQSQQSQQTAYSQQRFPPP QELSQDSFGSQASSAPSMTSSKGGQEDMNLS LQSRPSSLPDLSGSIDDLPMGTEGALSPGVSTS GISSSQGEQSNPAQSPFSPHTSPHLPGIRGPSP SPVGSPASVAQSRSGPLSPAAVPGNQMPPRP PSGQSDSIMHPSMNQSSIAQDRGYMQRNPQ MPQYSSPQPGSALSPRQPSGGQIHTGMGSY QQNSMGSYGPQGGQYGPQGGYPRQPNYN ALPNANYPSAGMAGGINPMGAGGQMHGQ PGIPPYGTLPPGRMSHASMGNRPYGPNMAN MPPQVGSGMCPPPGGMNRKTQETAVAMH VAANSIQNRPPGYPNMNQGGMMGTGPPY GQGINSMAGMINPQGPPYSMGGTMANNSA GMAASPEMMGLGDVKLTPATKMNNKADGT PKTESKSKKSSSSTTTNEKITKLYELGGEPERKM WVDRYLAFTEEKAMGMTNLPAVGRKPLDLY RLYVSVKEIGGLTQMQALTSCECTICPDCFRQ HFTIALKEKHITDMVCPACGRPDLTDDTQLLS YFSTLDIQLRESLEPDAYALFHKKLTEGVLMRD PKFLWCAQCSFGFIYEREQLEATCPQCHQTFC VRCKRQWEEQHRGRSCEDFQNWKRMNDPE YQAQGLAMYLQENGIDCPKCKFSYALARGGC MHFHCTQCRHQFCSGCYNAFYAKNKCPEPN CRVKKSLHGHHPRDCLFYLRDWTALRLQKLLQ DNNVMFNTEPPAGARAVPGGGCRVIEQKEV PNGLRDEACGKETPAGYAGLCQAHYKEYLVSL INAHSLDPATLYEVEELETATERYLHVRPQPLA GEDPPAYQARLLQKLTEEVPLGQSIPRRRK | | |
| G17792 .TCGA-28-5204-01A-01R-1850-01.4 | 1 | 161 | 121 | 238 | 8422 | MAELDPFGAPAGAPGGPALGNGVAGAGEED PAAAFLAQQESEIAGIENDEAFAILDGGAPGP QPHGEPPGGPDAVDGVMNGEYYQESNGPT DSYAAISQVDRLQSEPESIRKWREEQMERLEA LDANSRKQEAEWKEKAIKELEEWYARQDEQL QKTKANNRTILLSVISLLNEPNTFSPANVDASV MFRKWRDSKGKDKEYAEIIRKQVSATKAEAEK DGVKVPTTLAEYCIKTKVPSNDNSSDLLYDDLY DDDIDDEDEEEEDADCYDDDDSGNEES | 4 | 4 |
| G17663 .TCGA-19-2619-01A-01R-1850-01.2 | 1 | 5 | 322 | 502 | 8423 | MSRPVRFMERNPLTNAIIRTTTALTIFKAGVKF NVIPPVAQATVNFRIHPGQTVQEVLELTKNIV ADNRVQFHVLSAFDPLPVSPSDDKALGYQLLR QTVQSVFPEVNITAPVTSIGNTDSRFFTNLTTG IYRFYPIYIQPEDFKRIHGVNEKISVQAYETQVK FIFELIQNADTDQEPVSHLHKL | 1 | 9 |
| NYU_E | 1 | 510 | 7 | 437 | 8424 | MRVAAATAAAGAGPAMAVWTRATKAGLVE LLLRERWVRVVAELSGESLSLTGDAAAAELEP ALGPAAAAFNGLPNGGGAGDSLPGSPSRGLG PPSPPAPPRGPAGEAGASPPVRRVRVVKQEA GGLGISIKGGRENRMPILISKIFPGLAADQSRAL RLGDAILSVNGTDLRQATHDQAVQALKRAGK | 6 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | EVLLEVKFIREVTPYIKKPSLVSDLPWEGAAPQ SPSFSGSEDSGSPKHQNSTKDRKIIPLKMCFAA RNLSMPDLENRLIELHSPDSRNTLILRCKDTAT AHSWFVAIHTNIMALLPQVLAELNAMLGATS TAGGSKEVKHIAWLAEQAKLDGGRQQWRPV LMAVTEKDLLLYDCMPWTRDAWASPCHSYP LVATRLVHSGSGCRSPSLGSDLTFATRTGSRQ GIEMHLFRVETHRDLSSWTRILVQGCHAAAEL IKEVSLGCMLNGQEVRLTIHYENGFTISRENG GSSSILYRYPFERLKMSADDGIRNLYLDFGGPE GELKAIDLVTKATEEDKAKNYEEALRLYQHAVE YFLHAIKYEAHSDKAKESIRAKCVQYLDRAEKL KDYLRSKEKHGKKPVKENQSEGKGSDSDSEG DNPEKKKLQEQLMGAVVMEKPNIRWNDVA GLEGAKEALKEAVILPIKFPHLFTGKRTPWRGIL LFGPPGTGKSYLAKAVATEANNSTFFSVSSSDL MSKWLGESEKLVKNLFELARQHKPSIIFIDEVD SLCGSRNENESEAARRIKTEFLVQMQGVGNN NDGTLVLGATNIPWVLDSAIRRRFEKRIYIPLPE EAARAQMFRLHLGSTPHNLTDANIHELARKTE GYSGADISIIVRDSLMQPVRKVQSATHFKKVC GPSRTNPSMMIDDLLTPCSPGDPGAMEMT WMDVPGDKLLEPVVCMSDMLRSLATTRPTV NADDLLKVKKFSEDFGQES | | |
| NYU_G | 1 | 7 | 95 | 483 | 8425 | MKTPADTGDSGKVTTVVATLGQGPERSQEV AYTDIKVIGNGSFGVVYQARLAETRELVAIKKV LQDKRFKNRELQIMRKLDHCNIVRLRYFFYSSG EKKDELYLNLVLEYVPETVYRVARHFTKAKLTIP ILYVKVYMYQLFRSLAYIHSQGVCHRDIKPQNL LVDPDTAVLKLCDFGSAKQLVRGEPNVSYICS RYYRAPELIFGATDYTSSIDVWSAGCVLAELLL GQPIFPGDSGVDQLVEIIKVLGTPTREQIREM NPNYTEFKFPQIKAHPWTKVFKSRTPPEAIALC SSLLEYTPSSRLSPLEACAHSFFDELRCLGTQLP NNRPLPPLFNFSAGELSIQPSLNAILIPPHLRSP AGTTTLTPSSQALTETPTSSDWQSTDATPTLT NSS | 1 | 2 |
| NYU_B | 1 | 602 | 13 | 455 | 8426 | MGMARGSLTRVPGVMGEGTQGPELSLDPDP CSPQSTPGLMKGNKLEEQDPRPLQPIPGLME GNKLEEQDSSPPQSTPGLMKGNKREEQGLGP EPAAPQQPTAEEEALIEFHRSYRELFEFFCNNT TIHGAIRLVCSQHNRMKTAFWAVLWLCTFG MMYWQFGLLFGEYFSYPVSLNINLNSDKLVFP AVTICTLNPYRYPEIKEELEELDRITEQTLFDLYK YSSFTTLVAGSRSRRDLRGTLPHPLQRLRVPPP PHGARRARSVASSLRDNNPQVDWKDWKIGF QLCNQNKSDCFYQTYSSGVDAVREWYRFHYI NILSRLPETLPSLEEDTLGNFIFACRFNQVSCN QANYSHFHHPMYGNCYTFNDKNNSNLWMS SMPGINNGLSLMLRAEQNDFIPLLSTVTGARV MVHGQDEPAFMDDGGFNLRPGVETSISMRK ETLDRLGGDYGDCTKNGSDVPVENLYPSKYT QQVCIHSCFQESMIKECGCAYIFYPRPQNVEY CDYRKHSSWGYCYYKLQVDFSSDHLGCFTKCR | 11 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | KPCSVTSYQLSAGYSRWPSVTSQEWVFQMLS RQNNYTVNNKRNGVAKVNIFFKELNYKTNSE SPSVTVLLELLVGIYPSGVIGLVPHLGDREKRDS VCPQGKYIHPQNNSICCTKCHKGTYLYNDCPG PGQDTDCRECESGSFTASENHLRHCLSCSKCR KEMGQVEISSCTVDRDTVCGCRKNQYRHYW SENLFQCFNCSLCLNGTVHLSCQEKQNTVCTC HAGFFLRENECVSCSNCKKSLECTKLCLPQIEN VKGTEDSGTTVLLPLVIFFGLCLLSLLFIGLMYR YQRWKSKLYSIVCGKSTPEKEGELEGTTTKPLA PNPSFSPTPGFTPTLGFSPVPSSTFTSSSTYTPG DCPNFAAPRREVAPPYQGADPILATALASDPI PNPLQKWEDSAHKPQSLDTDDPATLYAVVEN VPPLRWKEFVRRLGLSDHEIDRLELQNGRCLR EAQYSMLATWRRRTPRREATLELLGRVLRDM DLLGCLEDIEEALCGPAALPPAPSLLR | | |
| G17675 .TCGA- 19- 2624- 01A- 01R- 1850- 01.2 | 1 | 306 | 137 | 514 | 8427 | MVRSRQMCNTNMSVPTDGAVTTSQIPASEQ ETLVRPKPLLLKLLKSVGAQKDTYTMKEVLFYL GQYIMTKRLYDEKQQHIVYCSNDLLGDLFGVP SFSVKEHRKIYTMIYRNLVVVNQQESSDSGTS VSENRCHLEGGSDQKDLVQELQEEKPSSSHLV SRPSTSSRRRAISETEENSDELSGERQRKRHKS DSISLSFDESLALCVIREICCERSSSSESTGTPSN PDLDAGVSEHSGDWLDQDSVSDQFSVEFEVE SLDSEDYSLSEEGQELSDEDDEVYQVTVYQAG ESDTDSFEEDPEISLAESEGVSCHYWSLFDGH AGSGAAVVASRLLQHHITEQLQDIVDILKNSA VLPPTCLGEEPENTPANSRTLTRAASLRGGVG APGSPSTPPTRFFTEKKIPHECLVIGALESAFKE MDLQIERERSSYNISGGCTALIVICLLGKLYVAN AGDSRAIIIRNGEIIPMSSEFTPETERQRLQYLA FMQPHLLGNEFTHLEFPRRVQRKELGKKMLY RDFNMTGWAYKTIEDEDLKFPLIYGEGKKARV MATIGVTRGLGDHDLKVHDSNIYIKPFLSSAPE VRIYDLSKYDHGSDDVLILATDGLWDVLSNEE VAEAITQFLPNCDPDDPHRYTLAAQDLVMRA RGVLKDRGWRISNDRLGSGDDISVYVIPLIHG NKLS | 10 | 3 |
| G17484 .TCGA- 14- 0787- 01A- 01R- 1849- 01.2 | 1 | 2002 | 24 | 156 | 8428 | MDPRNTAMLGLGSDSEGFSRKSPSAISTGTLV SKREVELEKNTKEEEDLRKRNRERNIEAGKDD GLTDAQQQFSVKETNFSEGNLKLKIGLQAKRT KKPPKNLENYVCRPAIKTTIKHPRKALKSGKMT DEKNEHCPSKRDPSKLYKKADDVAAIECQSEE VIRLHSQGENNPLSKKLSPVHSEMADYINATP STLLGSRDPDLKDRALLNGGTSVTEKLAQLIAT CPPSKSSKTKPKKLGTGTTAGLVSKDLIRKAGV GSVAGIIHKDLIKKPTISTAVGLVTKDPGKKPVF NAAVGLVNKDSVKKLGTGTTAVFINKNLGKKP GTITTVGLLSKDSGKKLGIGIVPGLVHKESGKKL GLGTVVGLVNKDLGKKLGSTVGLVAKDCAKKI VASSAMGLVNKDIGKKLMSCPLAGLISKDAIN LKAEALLPTQEPLKASCSTNINNQESQELSESL KDSATSKTFEKNVVRQNKESILEKFSVRKEIINL EKEMFNEGTCIQQDSFSSSEKGSYETSKHEKQ | 6 | 4 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | PPVYCTSPDFKMGGASDVSTAKSPFSAVGES NLPSPSPTVSVNPLTRSPPETSSQLAPNPLLLSS TTELIEEISESVGKNQFTSESTHLNVGHRSVGH SISIECKGIDKEVNDSKTTHIDIPRISSSLGKKPSL TSESSIHTITPSVVNFTSLFSNKPFLKLGAVSAS DKHCQVAESLSTSLQSKPLKKRKGRKPRWTKV VARSTCRSPKGLELERSELFKNVSCSSLSNSNSE PAKFMKNIGPPSFVDHDFLKRRLPKLSKSTAPS LALLADSEKPSHKSFATHKLSSSMCVSSDLLSDI YKPKRGRPKSKEMPQLEGPPKRTLKIPASKVFS LQSKEEQEPPILQPEIEIPSFKQGLSVSPFPKKR GRPKRQMRSPVKMKPPVLSVAPFVATESPSK LESESDNHRSSSDFFESEDQLQDPDDLDDSHR PSVCSMSDLEMEPDKKITKRNNGQLMKTIIRK INKMKTLKRKKLLNQILSSSVESSNKGKVQSKL HNTVSSLAATFGSKLGQQINVSKKGTIYIGKRR GRKPKTVLNGILSGSPTSLAVLEQTAQQAAGS ALGQILPPLLPSSASSSEILPSPICSQSSGTSGGQ SPVSSDAGFVEPSSVPYLHLHSRQGSMIQTLA MKKASKGRRRLSPPTLLPNSPSHLSELTSLKEA TPSPISESHSDETIPSDSGIGTDNNSTSDRAEKF CGQKKRRHSFEHVSLIPPETSTVLSSLKEKHKH KCKRRNHDYLSYDKMKRQKRKRKKKYPQLRN RQDPDFIAELEELISRLSEIRITHRSHHFIPRDLL PTIFRINFNSFYTHPSFPLDPLHYIRKPDLKKKR GRPPKMREAMAEMPFMHSLSFPLSSTGFYPS YGMPYSPSPLTAAPIGLGYYGRYPPTLYPPPPS PSFTTPLPPPSYMHAGHLLLNPAKYHKKKHKL LRQEAFLTTSRTPLLSMSTYPSVPPEMAYGW MVEHKHRHRHKHREHRSSEQPQVSMDTGSS RSVLESLKRYRFGKDAVGERYKHKEKHRCHMS CPHLSPSKSLINREEQWVHREPSESSPLALGLQ TPLQIDCSESSPSLSLGGFTPNSEPASSDEHTNL FTSAIGSCRVSNPNSSGRKKLTDSPGLFSAQDT SLNRLHRKESLPSNERAVQTLAGSQPTSDKPS QRPSESTNCSPTRKRSSSESTSSTVNGVPSRSP RLVASGDDSVDSLLQRMVQNEDQEPMEKSID AVIATASAPPSSSPGRSHSKDRTLGKPDSLLVP AVTSDSCNNSISLLSEKLTSSCSPHHIKRSVVEA MQRQARKMCNYDKILATKKNLDHVNKILKAK KLQRQARTGNNFVKRRPGRPRKCPLQAVVS MQAFQAAQFVNPELNRDEEGAALHLSPDTV TDVIEAVVQSVNLNPEHKKGLKRKGWLLEEQ TRKKQKPLPEEEEQENNKSFNEAPVEIPSPSET PAKPSEPESTLQPVLSLIPREKKPPRPPKKKYQK AGLYSDVYKTTDFSPGAGGFCTTLPPSFLRVD DRATSSTTDSSRAPSSPRPPGSTSHCGISTRCT ERCLCVLPLRTSQVPDVMAPQHDQEKFHDLA YSCLGKSFSMSNQDLYGYSTSSLALGLAWLSW ETKKKNVLHLVGLDSL | | |
| G17792 .TCGA- 28- 5204- | 1 | 326 | 21 | 206 | 8429 | MSGGKKKSSFQITSVTTDYEGPGSPGASDPPT PQPPTGPPPRLPNGEPSPDPGGKGTPRNGSP PPGAPSSRFRVVKLPHGLGEPYRRGRWTCVD VYERDLEPHSFGGLLEGIRGASGGAGGRSLDS | 4 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 01A-01R-1850-01.4 | | | | | | RLELASLGLGAPTPPSGLSQGPTSWLRPPPTSP GPQARSFTGGLGQLVVPSKAKAEKPPLSASSP QQRPPEPETGESAGTSRAATPLPSLRVEAEAG GSGARTPPLSRRKAVDMRLRMELGAPEEMG QVPPLDSRPSSPALYFTHDASLVHKSPDPFGA VAAQKFSLAHSMLAISGHLDSDDDSGSGSLV GIDNKIEQAMVFFWRQKIKPTISGHPDSKKHS LKKMEKTLQVVETLRLVELPKEAKPKLGESPEL ADPCVLAKTTEETEVELGQQGQSLLQLPRTAV KSVSTLMVSALQSGWQMCSWKSSVSSASVS SQVRTQSPLKTPEAELLWEVYLVLWAVRKHLR RLYRRQERHRRHHVRCHAAPRPNPAQSLKLD AQSPL | | |
| BT299 | 1 | 20 | 10 | 600 | 8430 | MALRRLGAALLLLPLLAAVEGAGQDVGRSCIL VSIAGKNVMLDCGMHMGFNDDRRFPDFSYI TQNGRLTDFLDCVIISHFHLDHCGALPYFSEM VGYDGPIYMTHPTQAICPILLEDYRKIAVDKKG EANFFTSQMIKDCMKKVVAVHLHQTVQVDD ELEIKAYYAGHVLGAAMFQIKVGSESVVYTGD YNMTPDRHLGAAWIDKCRPNLLITESTYATTI RDSKRCRERDFLKKVHETVERGGKVLIPVFALG RAQELCILLETFWERMNLKVPIYFSTGLTEKAN HYYKLFIPWTNQKIRKTFVQRNMFEFKHIKAF DRAFADNPGPMVVFATPGMLHAGQSLQIFR KWAGNEKNMVIMPGYCVQGTVGHKILSGQR KLEMEGRQVLEVKMQVEYMSFSAHADAKGI MQLVGQAEPESVLLVHGEAKKMEFLKQKIEQ ELRVNCYMPANGETVTLPTSPSIPVGISLGLLK REMAQGLLPEAKKPRLLHGTLIMKDSNFRLVS SEQALKELGLAEHQLRFTCRVHLHDTRKEQET ALRVYSHLKSVLKDHCVQHLPDGSVTVESVLL QAAAPSEDPGTKVLLVSWTYQDEELGSFLTSL LKKGLPQAPS | 1 | 2 |
| G17667 .TCGA-26-5134-01A-01R-1850-01.2 | 1 | 258 | 50 | 56 | 8431 | MNQPESANDPEPLCAVCGQAHSLEENHFYSY PEEVDDDLICHICLQALLDPLDTPCGHTYCTLC LTNFLVEKDFCPMDRKPLVLQHCKKSSILVNKL LNKLLVTCPFREHCTQVLQRCDLEHHFQTSCK GASHYGLTKDRKRRSQDGCPDGCASLTATAP SPEVSAAATISLMTDEPGLDNPAYVSSAEDGQ PAISPVDSGRSNRTRARPFERSTIRSRSFKKINR ALSVLRRTKSGSAVANHADQGRENSENTTAP EVWKHMLL | 4 | 4 |
| GBM-CUMC3 338_L1 | 1 | 432 | 8 | 609 | 8432 | MWLKVGGLLRGTGGQLGQTVGWPCGALGP GPHRWGPCGGSWAQKFYQDGPGRGLGEED IRRAREARPRKTPRPQLSDRSRERKVPASRISR LANFGGLAVGLGLGVLAEMAKKSMPGGRLQ SEGGSGLDSSPFLSEANAERIVQTLCTVRGAAL KVGQMLSIQDNSFISPQLQHIFERVRQSADF MPRWQMLRVLEEELGRDWQAKVASLEEVPF AAASIGQVHQGLLRDGTEVAVKIQYPGIAQSI QSDVQNLLAVLKMSAALPAGLFAEQSLQALQ QELAWECDYRREAACAQNFRQLLANDPFFRV PAVVKELCTTRVLGMELAGGVPLDQCQGLSQ DLRNQICFQLLTLCLRELFEFRFMQTDPNWAN | 14 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | FLYDASSHQVTLLDFGASREFGTEFTDHYIEVV KAAADGDRDCVLQKSRDLKFLTGFETKGGPR RPERHLPPAPCGAPGPPETCRTEPDGAGTMN KLRQSLRRRKPAYVPEASRPHQWQADEDAVR KGTCSFPVRYLGHVEVEESRGMHVCEDAVKK LKAMGRKSVKSVLWVSADGLRVVDDKTKDLL VDQTIEKVSFCAPDRNLDKAFSYICRDGTTRR WICHCFLALKDSGERLSHAVGCAFAACLERKQ RREKECGVTAAFDASRTSFAREGSFRLSGGGR PAEREAPDKKKAEAAAAPTVAPGPAQPGHVS PTPATTSPGEKGEAGTPVAAGTTAAAIPRRHA PLEQLVRQGSFRGFPALSQKNSPFKRQLSLRL NELPSTLQRRTDFQVKGTVPEMEPPGAGDSD SINALCTQISSSFASAGAPAPGPPPATTGTSA WGEPSVPPAAAFQPGHKRTPSEAERWLEEVS QVAKAQQQQQQQQQQQQQQQQQQQQQQA ASVAPVPTMPPALQPFPAPVGPFDAAPAQVA VFLPPPHMQPPFVPAYPGLGYPPMPRVPVVG ITPSQMVANAFCSAAQLQPQPATLLGKAGAF PPPAIPSAPGSQARPRPNGAPWPPEPAPAPA PELDPFEAQWAALEGKATVEKPSNPFSGDLQ KTFEIEL | | |
| G17815 .TCGA- 19- 5960- 01A- 11R- 1850- 01.4 | 1 | 700 | 32 | 192 | 8433 | MASCPDSDNSWVLAGSESLPVETLGPASRM DPESERALQAPHSPSKTDGKELAGTMDGEGT LFQTESPQSGSILTEETEVKGTLEGDVCGVEPP GPGDTVVQGDLQETTVVTGLGPDTQDLEGQ SPPQSLPSTPKAAWIREEGRCSSSDDDTDVD MEGLRRRRGREAGPPQPMVPLAVENQAGG EGAGGELGISLNMCLLGALVLLGLGVLLFSGGL SESETGPMEEVERQVLPDPEVLEAVGDRQDG LREQLQAPVPPDSVPSLQNMGLLLDKLAKEN QDIRLLQAQLQAQKEELQSLMHQPKGLEEEN AQLRGALQQGEAFQRALESELQQLRARLQGL EADCVRGPDGVCLSGGRGPQGDKAIREQGP REQEPELSFLKQKEQLEAEAQALRQELERQRR LLGSVQQDLERSLQDASRGDPAHAGLAELGH RLAQKLQGLENWGQDPGVSANASKAWHQK SHFQNSREWSGKEKWWDGQRDRKAEHWK HKKEESGRERKKNWGGQEDREPAGRWKEGR PRVEESGSKKEGKRQGPKEPPRKSGSFHSSGE KQKQPRWREGTKDSHDPLPSWAELLRPKYRA PQGCSGVDECARQEGLTFFGTELAPVRQQEL ASLLRTYLARLPWAGQLTKELPLSPAFFGEDGI FRHDRLRFRDFVDALEDSLEEVAVQQTGDDD EVDDFEDFIFSHFFGDKALKKRLGADVCAVLRL SGPLKEQYAQEHGLNFQRLLDTSTYKEAFRKD MIRWGEEKRQADPGFFCRKIVEGISQPIWLVS DTRRVSDIQWFREAYGAVTQTVRVVALEQSR QQRGWVFTPGVDDAESECGLDNFGDFDWVI ENHGVEQRLEEQLENLIEFIRSRL | 10 | 2 |
| G17662 .TCGA- 32- 1970- | 1 | 81 | 23 | 977 | 8434 | MEARSMLVPPQASVCFEDVAMAFTQEEWE QLDLAQRTLYREVTLETWEHIVSLGLFLSKSDV ISQLEQEEDLCRAEQEAPRGKSKEAEIKRINKEL ANIRSKFKGDKALDGYSKKKYVCKLLFIFLLGH | 3 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 01A-01R-1850-01.2 | | | | | | DIDFGHMEAVNLLSSNKYTEKQIGYLFISVLVN SNSELIRLINNAIKNDLASRNPTFMCLALHCIA NVGSREMGEAFAADIPRILVAGDSMDSVKQS AALCLLRLYKASPDLVPMGEWTARVVHLLND QHMGVVTAAVSLITCLCKKNPDDFKTCVSLAV SRLSRIVSSASTDLQDYTYYFVPAPWLSVKLLRL LQCYPPPEDAAVKGRLVECLETVLNKAQEPPK SKKVQHSNAKNAILFETISLIIHYDSEPNLLVRA CNQLGQFLQHRETNLRYLALESMCTLASSEFS HEAVKTHIDTVINALKTERDVSVRQRAADLLY AMCDRSNAKQIVSEMLRYLETADYAIREEIVLK VAILAEKYAVDYSWYVDTILNLIRIAGDYVSEE VWYRVLQIVTNRDDVQGYAAKTVFEALQAPA CHENMVKVGGYILGEFGNLIAGDPRSSPPVQF SLLHSKFHLCSVATRALLLSTYIKFINLFPETKATI QGVLRAGSQLRNADVELQQRAVEYLTLSSVA STDVLATVLEEMPPFPERESSILAKLKRKKGPG AGSALDDGRRDPSSNDINGGMEPTPSTVSTP SPSADLLGLRAAPPPAAPPASAGAGNLLVDVF DGPAAQPSLGPTPEEAFLSELEPPAPESPMALL ADPAPAADPGPEDIGPPIPEADELLNKFVCKN NGVLFENQLLQIGVKSEFRQNLGRMYLFYGN KTSVQFQNFSPTVVHPGDLQTHLAVQTKRVA AQVDGGAQVQQVLNIECLRDFLTPPLLSVRFR YGGAPQALTLKLPVTINKFFQPTEMAAQDFF QRWKQLSLPQQEAQKIFKANHPMDAEVTKA KLLGFGSALLDNVDPNPENFVGAGIIQTKALQ VGCLLRLEPNAQAQMYRLTLRTSKEPVSRHLC ELLAQQF | | |
| NYU_E | 1 | 416 | 3 | 148 | 8435 | MASESGKLWGGRFVGAVDPIMEKFNASIAYD RHLWEVDVQGSKAYSRGLEKAGLLTKAEMD QILHGLDKVAEEWAQGTFKLNSNDEDIHTAN ERRLKELIGATAGKLHTGRSRNDQVVTDLRLW MRQTCSTLSGLLWELIRTMVDRAEAERDVLF PGYTHLQRAQPIRWSHWILSHAVALTRDSERL LEVRKRINVLPLGSGAIAGNPLGVDRELLRAEL NFGAITLNSMDATSERDFVAEFLFWASLCMT HLSRMAEDLILYCTKEFSFVQLSDAYSTGSSLM PQKKNPDSLELIRSKAGRVFGRCAGLLMTLKG LPSTYNKDLQEDKEAVFEVSDTMSAVLQVAT GVISTLQIHQENMGQALSPDMLATDLAYYLV RKGMPFRQAHEASGKAVFMAETKGVALNQL SLQELQTIRKDANSALLSNYEVFQLLTDLKEQR KESGKNKHSSGQQNLNTITYETLKYISKTPCRH QSPEIVREFLTALKSHKLTKAEKLQLLNHRPVT AVEIQLMVEESEERLTEEQIEALLHTVTSILPAE PEAEQKKNTNSNVAMDEEDPA | 15 | 2 |
| G17816 .TCGA-28-5215-01A-01R- | 1 | 982 | 190 | 225 | 8436 | MRPSGTAGAALLALLAALCPASRALEEKKVCQ GTSNKLTQLGTFEDHFLSLQRMFNNCEVVLG NLEITYVQRNYDLSFLKTIQEVAGYVLIALNTVE RIPLENLQIIRGNMYYENSYALAVLSNYDANKT GLKELPMRNLQEILHGAVRFSNNPALCNVESI QWRDIVSSDFLSNMSMDFQNHLGSCQKCDP SCPNGSCWGAGEENCQKLTKIICAQQCSGRC | 24 | 6 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 1850-01.4 | | | | | | RGKSPSDCCHNQCAAGCTGPRESDCLVCRKF RDEATCKDTCPPLMLYNPTTYQMDVNPEGKY SFGATCVKKCPRNYVVTDHGSCVRACGADSY EMEEDGVRKCKKCEGPCRKVCNGIGIGEFKDS LSINATNIKHFKNCTSISGDLHILPVAFRGDSFT HTPPLDPQELDILKTVKEITGFLLIQAWPENRT DLHAFENLEIIRGRTKQHGQFSLAVVSLNITSL GLRSLKEISDGDVIISGNKNLCYANTINWKKLF GTSGQKTKIISNRGENSCKATGQVCHALCSPE GCWGPEPRDCVSCRNVSRGRECVDKCNLLEG EPREFVENSECIQCHPECLPQAMNITCTGRGP DNCIQCAHYIDGPHCVKTCPAGVMGENNTLV WKYADAGHVCHLCHPNCTYGCTGPGLEGCP TNGPKIPSIATGMVGALLLLLVVALGIGLFMRR RHIVRKRTLRRLLQERELVEPLTPSGEAPNQAL LRILKETEFKKIKVLGSGAFGTVYKGLWIPEGEK VKIPVAIKELREATSPKANKEILDEAYVMASVD NPHVCRLLGICLTSTVQLITQLMPFGCLLDYVR EHKDNIGSQYLLNWCVQIAKGMNYLEDRRLV HRDLAARNVLVKTPQHVKITDFGLAKLLGAEE KEYHAEGGKVPIKWMALESILHRIYTHQSDV WSYGVTVWELMTFGSKPYDGIPASEISSILEK GERLPQPPICTIDVYMIMVKCWMIDADSRPK FRELIIEFSKMARDPQRYLVIQDAFIGFGGNVI RQQVKDNAKWYITDFVELLGELEE | | |
| G17650 .TCGA-28-2513-01A-01R-1850-01.2 | 1 | 68 | 18 | 432 | 8437 | MGETMSKRLKLHLGGEAEMEERAFVNPFPDY EAAAGALLASGAAEETGCVRPPATTDEPGLPF HQDGKQKENNIRCLTTIGHFGFECLPNQLVSR SIRQGFTFNILCVGETGIGKSTLIDTLFNTNLKD NKSSHFYSNVGLQIQTYELQESNVQLKLTVVE TVGYGDQIDKEASYQPIVDYIDAQFEAYLQEEL KIKRSLFEYHDSRVHVCLYFISPTGHSLKSLDLLT MKNLDSKVNIIPLIAKADTISKNDLQTFKNKIM SELISNGIQIYQLPTDEETAAQANSSVSGLLPFA VVGSTDEVKVGKRMVRGRHYPWGVLQVEN ENHCDFVKLRDMLLCTNMENLKEKTHTQHYE CYRYQKLQKMGFTDVGPNNQPVSFQEIFEAK RQEFYDQCQREEEELKQRFMQRVKEKEATFK EAEKELQDKFEHLKMIQQEEIRKLEEEKKQLEG EIIDFYKMKAASEALQTQLSTDTKKDKHRKK | 1 | 3 |
| BT308 | 1 | 176 | 2050 | 2063 | 8438 | MAAPLVLVLVVAVTVRAALFRSSLAEFISERVE VVSPLSSWKRVVEGLSLLDLGVSPYSGAVFHE TPLIIYLFHFLIDYAELVFMITDALTAIALYFAIQD FNKVVFKKQKLLLELDQYAPDVAELIRTPMEM RYIPLKVALFYLLNPYTILSCVAKSTCAINNTLIA FFILTTIKDITSAVQSKRRKSK | 6 | 16 |
| G17656 .TCGA-28-2514-01A-02R-1850-01.2 | 1 | 982 | 18 | 172 | 8439 | MRPSGTAGAALLALLAALCPASRALEEKKVCQ GTSNKLTQLGTFEDHFLSLQRMFNNCEVVLG NLEITYVQRNYDLSFLKTIQEVAGYVLIALNTVE RIPLENLQIIRGNMYYENSYALAVLSNYDANKT GLKELPMRNLQEILHGAVRFSNNPALCNVESI QWRDIVSSDFLSNMSMDFQNHLGSCQKCDP SCPNGSCWGAGEENCQKLTKIICAQQCSGRC RGKSPSDCCHNQCAAGCTGPRESDCLVCRKF | 24 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | RDEATCKDTCPPLMLYNPTTYQMDVNPEGKY SFGATCVKKCPRNYVVTDHGSCVRACGADSY EMEEDGVRKCKKCEGPCRKVCNGIGIGEFKDS LSINATNIKHFKNCTSISGDLHILPVAFRGDSFT HTPPLDPQELDILKTVKEITGFLLIQAWPENRT DLHAFENLEIIRGRTKQHGQFSLAVVSLNITSL GLRSLKEISDGDVIISGNKNLCYANTINWKKLF GTSGQKTKIISNRGENSCKATGQVCHALCSPE GCWGPEPRDCVSCRNVSRGRECVDKCNLLEG EPREFVENSECIQCHPECLPQAMNITCTGRGP DNCIQCAHYIDGPHCVKTCPAGVMGENNTLV WKYADAGHVCHLCHPNCTYGCTGPGLEGCP TNGPKIPSIATGMVGALLLLLVVALGIGLFMRR RHIVRKRTLRRLLQERELVEPLTPSGEAPNQAL LRILKETEFKKIKVLGSGAFGTVYKGLWIPEGEK VKIPVAIKELREATSPKANKEILDEAYVMASVD NPHVCRLLGICLTSTVQLITQLMPFGCLLDYVR EHKDNIGSQYLLNWCVQIAKGMNYLEDRRLV HRDLAARNVLVKTPQHVKITDFGLAKLLGAEE KEYHAEGGKVPIKWMALESILHRIYTHQSDV WSYGVTVWELMTFGSKPYDGIPASEISSILEK GERLPQPPICTIDVYMIMVKCWMIDADSRPK FRELIIEFSKMARDPQRYLVIQCTEAKKHCWYF EGLYPTYYICRSYEDCCGSRCCVRALSIQRLWY FWFLLMMGVLFCCGAGFFIRRRMYPPPLIEEP AFNVSYTRQPPNPGPGAQQPGPPYYTDPGG PGMNPVGNSMAMAFQVPPNSPQGSVACPP PPAYCNTPPPPYEQVVKAK | | |
| G17639 .TCGA- 12- 3652- 01A- 01R- 1849- 01.2 | 1 | 344 | 94 | 262 | 8440 | MAEAPPVSGTFKFNTDAAEFIPQEKKNSGLNC GTQRRLDSNRIGRRNYSSPPPCHLSRQVPYDE ISAVHQHSYHPSGSKPKSQQTSFQSSPCNKSP KSHGLQNQPWQKLRNEKHHIRVKKAQSLAE QTSDTAGLESSTRSESGTDLREHSPSESEKEVV GADPRGAKPKKATQFVYSYGRGPKVKGKLKC EWSNRTTPKPEDAGPESTKPVGVFHPDSSEAS SRKGVLDGYGARRNEQRRYPQKRPPWEVEG ARPRPGRNPPKQEGHRHTNAGHRNNMGPIP KDDLNERPAKSTCDSENLAVINKSSRRVDQEK CTVRRQDPQVVSPFSRGKQNHVLKNVETHTA DKCSPNYLGSDWYNTWRMEPYNSSCCNKYT TYLPRLPKEARMETAVRGMPLECPPRPERLNA YEREVMVNMLNSLSRNQQLPRITPRCGCVDP LPGRLPFHGYESACSGRHYCLRGMDYYASGA PCTDRRLRPWCREQPTMCTSLRAPARNAVCC YNSPAVILPISEP | 2 | 3 |
| G17796 .TCGA- 41- 5651- 01A- 01R- 1850- 01.4 | 1 | 193 | 167 | 1032 | 8441 | MAAETLLSSLLGLLLLGLLLPASLTGGVGSLNLE ELSEMRYGIEILPLPVMGGQSQSSDVVIVSSKY KQRYECRLPAGAIHFQREREEETPAYQGPGIP ELLSPMRDAPCLLKTKDWWTYEFCYGRHIQQ YHMEDSEIKGEVLYLGYYQSAFDWDDETAKA SKQHRLKRYHSQTYGNGSKCDLNGRPREAEV RGCTERFVSSPEEILDVIDEGKSNRHVAVTNM NEHSSRSHSIFLINIKQENMETEQKLSGKLYLV DLAGSEKVSKTGAEGAVLDEAKNINKSLSALG | 5 | 7 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | NVISALAEGTKSYVPYRDSKMTRILQDSLGGN CRTTMFICCSPSSYNDAETKSTLMFGQRAKTIK NTASVNLELTAEQWKKKYEKEKEKTKAQKETI AKLEAELSRWRNGENVPETERLAGEEAALGA ELCEETPVNDNSSIVVRIAPEERQKYEEEIRRLY KQLDDKDDEINQQSQLIEKLKQQMLDQEELL VSTRGDNEKVQRELSHLQSENDAAKDEVKEV LQALEELAVNYDQKSQEVEEKSQQNQLLVDE LSQKVATMLSLESELQRLQEVSGHQRKRIAEV LNGLMKDLSEFSVIVGNGEIKLPVEISGAIEEEF TVARLYISKIKSEVKSVVKRCRQLENLQVECHR KMEVTGRELSSCQLLISQHEAKIRSLTEYMQSV ELKKRHLEESYDSLSDELAKLQAQETVHEVALK DKEPDTQDADEVKKALELQMESHREAHHRQ LARLRDEINEKQKTIDELKDLNQKLQLELEKLQ ADYEKLKSEEHEKSTKLQELTFLYERHEQSKQD LKGLEETVARELQTLHNLRKLFVQDVTTRVKKS AEMEPEDSGGIHSQKQKISFLENNLEQLTKVH KQLVRDNADLRCELPKLEKRLRATAERVKALE GALKEAKEGAMKDKRRYQQEVDRIKEAVRYK SSGKRGHSAQIAKPVRPGHYPASSPTNPYGTR SPECISYTNSLFQNYQNLYLQATPSSTSDMYFA NSCTSSGATSSGGPLASYQKANMDNGNATDI NDNRSDLPCGYEAEDQAKLFPLHQETAAS | | |
| G17468 .TCGA- 19- 0957- 02A- 11R- 2005- 01.2 | 1 | 209 | 176 | 342 | 8442 | MKLADSVMAGKASDGSIKWQLCYDISARTW WMDEFHPFIEALLPHVRAFAYTWFNLQARKR KYFKKHEKRMSKEEERAVKDELLSEKPEVKQK WASRLLAKLRKDIRPEYREDFVLTVTGKKPPCC VLSNPDQKGKMRRIDCLRQADKVWRLDLVM VILFKGIPLESTDGERLVKSPQCSNPGLCVQPH HIGVSVKELDLYLAYFVHAAVISECQRQQLEAV SYSSRYALGLFYEAGTKIDVPWAGQYITSNPCI RFVSIDNKKRNIESSEIGPSLVIHTTVPFGVTYLE HSIEDVQELVFQQLENILPGLPQPIATKCQKW RHSQVTNAAANCPGQMTLHHKPFLACGGDG FTQSNFDGCITSALCVLEALKNYI | 2 | 5 |
| G17790 .TCGA- 06- 5856- 01A- 01R- 1849- 01.4 | 1 | 386 | 211 | 319 | 8443 | MMLRGNLKQVRIEKNPARLRALESAVGESEP AAAAAMALALAGEPAPPAPAPPEDHPDEEM GFTIDIKSFLKPGEKTYTQRCRLFVGNLPTDITE EDFKRLFERYGEPSEVFINRDRGFGFIRLESRTL AEIAKAELDGTILKSRPLRIRFATHGAALTVKNL SPVVSNELLEQAFSQFGPVEKAVVVVDDRGR ATGKGFVEFAAKPPARKALERCGDGAFLLTTT PRPVIVEPMEQFDDEDGLPEKLMQKTQQYHK EREQPPRFAQPGTFEFEYASRWKALDEMEKQ QREQVDRNIREAKEKLEAEMEAARHEHQLML MRQDLMRRQEELRRLEELRNQELQKRKQIQL RHEEEHRRREEEMIRHREQEELRRQQEGFKP NYMENEGIVSPSDLDLVMSEGLGMRYAFIGP LETMHLNAEGMLSYCDRYSEGIKHVLQTFGPI PEFSRATAEKVNQDMCMKVPDDPEHLAARR QWRDECLMRLAKLKSQVQPQ | 6 | 6 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| GBM-CUMC3338_L1 | 1 | 447 | 160 | 327 | 8444 | MKETIQGTSWGPEPPGPGIPPAYSSPRRERL RWPPPPKPRLKSGGGFGPDPGSGTTVPARRL PVPRPSFDASASEEEEEEEEEEDEDEEEEVAA WRLPPRWSQLGTSQRPRPSRPTHRKTCSQRR RRAMRAFRMLLYSKSTSLTFHWKLWGRHRG RRRGLAHPKNHLSPQQGGATPQVPSPCCRFD SPRGPPPPRLGLLGALMAEDGVRGSPPVPSG PPMEEDGLRWTPKSPLDPDSGLLSCTLPNGF GGQSGPEGERSLAPPDASILISNVCSIGDHVA QELFQGSDLGMAEEAERPGEKAGQHSPLREE HVTCVQSILDEFLQTYGSLIPLSTDEVVEKLEDI FQQEFSTPSRKGLVLQLIQSYQRMPGNAMVR GFRVAYKRHVLTMDDLGTLYGQNWLNDQV MNMYGDLVMDTVPEKVHFFNSFFYDKLRTK GYDGVKRWTKNTRHYVGSAAAFAGTPEHGQ FQGSPGGAYGTAQPPPHYGPTQPAYSPSQQL RAPSAFPAVQYLSQPQPQPYAVHGHFQPTQT GFLQPGGALSLQKQMEHANQQTGFSDSSSLR PMHPQALHPAPGLLASPQLPVQMQPAGKSG FAATSQPGPRLPFIQHSQNPRFYHK | 8 | 6 |
| G17790.TCGA-06-5856-01A-01R-1849-01.4 | 1 | 37 | 228 | 497 | 8445 | MVNLAAMVWRRLLRKRWVLALVFGLSLVYFL SSTFKQDLDAGVSEHSGDWLDQDSVSDQFSV EFEVESLDSEDYSLSEEGQELSDEDDEVYQVTV YQAGESDTDSFEEDPEISLADYWKCTSCNEM NPPLPSHCNRCWALRENWLPEDKGKDKGEIS EKAKLENSTQAEEGFDVPDCKKTIVNDSRESC VEENDDKITQASQSQESEDYSQPSTSSSIIYSSQ EDVKEFEREETQDKEESVESSLPLNAIEPCVICQ GRPKNGCIVHGKTGHLMACFTCAKKLKKRNK PCPVCRQPIQMIVLTYFP | 1 | 9 |
| G17802.TCGA-28-5208-01A-01R-1850-01.4 | 1 | 344 | 240 | 432 | 8446 | MDAPRASAAKPPTGRKMKARAPPPPGKAAT LHVHSDQKPPHDGALGSQQNLVRMKEALRA STMDVTVVLPSGLEKRSVLNGSHAMMDLLVE LCLQNHLNPSHHALEIRSSETQQPLSFKPNTLI GTLNVHTVFLKEKVPEEKVKPGPPKVPEKSVRL VVNYLRTQKAVVRVSPEVPLQNILPVICAKCEV SPEHVVLLRDNIAGEELELSKSLNELGIKELYA WDNRRETFRKSSLGNDETDKEKKKFLGFFKVN KRSNSKAEQLVLSGADSDEDTSRAAPGRGLN GCLTTPNSPSMHSRSLTLGPSLSLGSISGVSVK SEMKKRRAPPPPGSGPPVQDKASEKGLLPFA VVGSTDEVKVGKRMVRGRHYPWGVLQVEN ENHCDFVKLRDMLLCTNMENLKEKTHTQHYE CYRYQKLQKMGFTDVGPNNQPVSFQEIFEAK RQEFYDQCQREEEELKQRFMQRVKEKEATFK EAEKELQDKFEHLKMIQQEEIRKLEEEKKQLEG EIIDFYKMKAASEALQTQLSTDTKKDKHRKK | 7 | 7 |
| G17210.TCGA-12-0616-01A-01R- | 1 | 149 | 141 | 188 | 8447 | MKLALLLPWACCCLCGSALATGFLYPFSAAAL QQHGYPEPGAGSPGSGYASRRHWCHHTVTR TVSCQVQNGSETVVQRVYQSCRWPGPCANL VSYRTLIRPTYRVSYRTVTVLEWRCCPGFTGSN CDEECMNCTRLSDMSERLTTLEAKIICMGAKE NGLPLEYQEKLKAIEPNDYTGKVSEEIEDIIKKG ETQTL | 4 | 4 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 1849-01.2 | | | | | | | | |
| NYU_B | 1 | 89 | 380 | 1104 | 8448 | MAAETQTLNFGPEWLRALSSGGSITSPPLSPA LPKYKLADYRYGREEMLALFLKDNKIPSDLLDK EFLPILQEEPLPPLALVPFTEEEQLKEILECSHLLT VIKMEEAGDEIVSNAISYALYKAFSTSEQDKDN WNGQLKLLLEWNQLDLANDEIFTNDRRWES ADLQEVMFTALIKDRPKFVRLFLENGLNLRKFL THDVLTELFSNHFSTLVYRNLQIAKNSYNDALL TFVWKLVANFRRGFRKEDRNGRDEMDIELHD VSPITRHPLQALFIWAILQNKKELSKVIWEQTR GCTLAALGASKLLKTLAKVKNDINAAGESEELA NEYETRAVELFTECYSSDEDLAEQLLVYSCEAW GGSNCLELAVEATDQHFIAQPGVQNFLSKQW YGEISRDTKNWKIILCLFIIPLVGCGFVSFRKKPV DKHKKLLWYYVAFFTSPFVVFSWNVVFYIAFLL LFAYVLLMDFHSVPHPPELVLYSLVFVLFCDEV RQWYVNGVNYFTDLWNVMDTLGLFYFIAGI VFRLHSSNKSSLYSGRVIFCLDYIIFTLRLIHIFTV SRNLGPKIIMLQRMLIDVFFFLFLFAVWMVAF GVARQGILRQNEQRWRWIFRSVIYEPYLAMF GQVPSDVDGTTYDFAHCTFTGNESKPLCVELD EHNLPRFPEWITIPLVCIYMLSTNILLVNLLVA MFGYTVGTVQENNDQVWKFQRYFLVQEYCS RLNIPFPFIVFAYFYMVVKKCFKCCCKEKNMES SVCCFKNEDNETLAWEGVMKENYLVKINTKA NDTSEEMRHRFRQLDTKLNDLKGLLKEIANKI K | 4 | 10 |
| G17469 .TCGA-06-2557-01A-01R-1849-01.2 | 1 | 982 | 373 | 432 | 8449 | MRPSGTAGAALLALLAALCPASRALEEKKVCQ GTSNKLTQLGTFEDHFLSLQRMFNNCEVVLG NLEITYVQRNYDLSFLKTIQEVAGYVLIALNTVE RIPLENLQIIRGNMYYENSYALAVLSNYDANKT GLKELPMRNLQEILHGAVRFSNNPALCNVESI QWRDIVSSDFLSNMSMDFQNHLGSCQKCDP SCPNGSCWGAGEENCQKLTKIICAQQCSGRC RGKSPSDCCHNQCAAGCTGPRESDCLVCRKF RDEATCKDTCPPLMLYNPTTYQMDVNPEGKY SFGATCVKKCPRNYVVTDHGSCVRACGADSY EMEEDGVRKCKKCEGPCRKVCNGIGIGEFKDS LSINATNIKHFKNCTSISGDLHILPVAFRGDSFT HTPPLDPQELDILKTVKEITGFLLIQAWPENRT DLHAFENLEIIRGRTKQHGQFSLAVVSLNITSL GLRSLKEISDGDVIISGNKNLCYANTINWKKLF GTSGQKTKIISNRGENSCKATGQVCHALCSPE GCWGPEPRDCVSCRNVSRGRECVDKCNLLEG EPREFVENSECIQCHPECLPQAMNITCTGRGP DNCIQCAHYIDGPHCVKTCPAGVMGENNTLV WKYADAGHVCHLCHPNCTYGCTGPGLEGCP TNGPKIPSIATGMVGALLLLLVVALGIGLFMRR RHIVRKRTLRRLLQERELVEPLTPSGEAPNQAL LRILKETEFKKIKVLGSGAFGTVYKGLWIPEGEK VKIPVAIKELREATSPKANKEILDEAYVMASVD NPHVCRLLGICLTSTVQLITQLMPFGCLLDYVR EHKDNIGSQYLLNWCVQIAKGMNYLEDRRLV | 24 | 10 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | HRDLAARNVLVKTPQHVKITDFGLAKLLGAEE KEYHAEGGKVPIKWMALESILHRIYTHQSDV WSYGVTVWELMTFGSKPYDGIPASEISSILEK GERLPQPPICTIDVYMIMVKCWMIDADSRPK FRELIIEFSKMARDPQRYLVIQLQDKFEHLKMI QQEEIRKLEEEKKQLEGEIIDFYKMKAASEALQ TQLSTDTKKDKHRKK | | |
| G17480 .TCGA-27-1830-01A-01R-1850-01.2 | 1 | 471 | 331 | 737 | 8450 | MITSAAGIISLLDEDEPQLKEFALHKLNAVVND FWAEISESVDKIEVLYEDEGFRSRQFAALVASK VFYHLGAFEESLNYALGAGDLFNVNDNSEYVE TIIAKCIDHYTKQCVENADLPEGEKKPIDQRLE GIVNKMFQRCLDDHKYKQAIGIALETRRLDVF EKTILESNDVPGMLAYSLKLCMSLMQNKQFR NKVLRVLVKIYMNLEKPDFINVCQCLIFLDDPQ AVSDILEKLVKEDNLLMAYQICFDLYESASQQF LSSVIQNLRTVGTPIASVPGSTNTGTVPGSEKD SDSMETEEKTSSAFVGKTPEASPEPKDQTLKM IKILSGEMAIELHLQFLIRNNNTDLMILKNTKD AVRNSVCHTATVIANSFMHCGTTSDQFLRDN LEWLARATNWAKFTATASLGVIHKGHEKEAL QLMATYLPKDTSPGSAYQEGGGLYALGLIHA NHGGDIIDYLLNQLKNASNDATFSCTCEEQYV GTFCEEYDACQRKPCQNNASCIDANEKQDGS NFTCVCLPGYTGELCQSKIDYCILDPCRNGATC ISSLSGFTCQCPEGYFGSACEEKVDPCASSPCQ NNGTCYVDGVHFTCNCSPGFTGPTCAQLIDF CALSPCAHGTCRSVGTSYKCLCDPGYHGLYCE EEYNECLSAPCLNAATCRDLVNGYECVCLAEY KGTHCELYKDPCANVSCLNGATCDSDGLNGT CICAPGFTGEECDIDINECDSNPCHHGGSCLD QPNGYNCHCPHGWVGANCEIHLQWKSGH MAESLTNMPRHSLYIIIGALCVAFILMLIILIVGI CRISRIEYQGSSRPAYEEFYNCRSIDSEFSNAIAS IRHARFGKKSRPAMYDVSPIAYEDYSPDDKPL VTLIKTKDL | 12 | 6 |
| G17634 .TCGA-19-2625-01A-01R-1850-01.2 | 1 | 62 | 2 | 132 | 8451 | MAEGAQPHQPPQLGPGAAARGMKRESELEL PVPGAGGDGADPGLSKRPRTEEAAADGGGG MQGELEVKNMDMKPGSTLKITGSIADGTDGF VINLGQGTDKLNLHFNPRFSESTIVCNSLDGSN WGQEQREDHLCFSPGSEVKFTVTFESDKFKVK LPDGHELTFPNRLGHSHLSYLSVRGGFNMSSF KLKE | 1 | 2 |
| G17654 .TCGA-41-4097-01A-01R-1850-01.2 | 1 | 151 | 467 | 758 | 8452 | MDRPGFVAALVAGGVAGVSVDLILFPLDTIKT RLQSPQGFSKAGGFHGIYAGVPSAAIGSFPNA AAFFITYEYVKWFLHADSSSYLTPMKHMLAAS AGEVVACLIRVPSEVVKQRAQVSASTRTFQIFS NILYEEGIQGLYRGYKSTVLREIEEVRDAMENE MRTQLRRQAAAHTDHLRDVLRVQEQELKSEF EQNLSEKLSEQELQFRRLSQEQVDNFTLDINT AYARLRGIEQAVQSHAVAEEEARKAHQLWLS VEALKYSMKTSSAETPTIPLGSAVEAIKANCSD NEFTQALTAAIPPESLTRGVYSEETLRARFYAV QKLARRVAMIDETRNSLYQYFLSYLQSLLLFPP | 6 | 13 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | QQLKPPPELCPEDINTFKLLSYASYCIEHGDLEL AAKFVNQLKGESRRVAQDWLKEARMTLETK QIVEILTAYASAVGIGTTQVQPE | | |
| G17485 .TCGA-14-1402-02A-01R-2005-01.2 | 1 | 25 | 118 | 369 | 8453 | MGVPKFYRWISERYPCLSEVVKEHQVICNSFTI CNAEMQEVGVGLYPSISLLNHSCDPNCSIVFN GPHLLLRAVRDIEVGEELTICYLDMLMTSEERR KQLRDQYCFECDCFRCQTQDKDADMLTGDE QVWKEVQESLKKIEELKAHWKWEQVLAMCQ AIISSNSERLPDINIYQLKVLDCAMDACINLGLL EEALFYGTRTMEPYRIFFPGSHPVRGVQVMK VGKLQLHQGMFPQAMKNLRLAFDIMRVTHG REHSLIEDLILLLEECDANIRAS | 1 | 6 |
| G17498 .TCGA-02-2483-01A-01R-1849-01.2 | 1 | 338 | 85 | 225 | 8454 | MAAAGARLSPGPGSGLRGRPRLCFHPGPPPL LPLLLLFLLLLPPPPLLAGATAAASREPDSPCRLK TVTVSTLPALRESDIGWSGARAGAGAGTGAG AAAAAASPGSPGSAGTAAESRLLLFVRNELPG RIAVQDDLDNTELPFFTLEMSGTAADISLVHW RQQWLENGTLYFHVSMSSSGQLAQATAPTL QEPSEIVEEQMHILHISVMGGLIALLLLLLVFTV ALYAQRRWQKRRRIPQKSASTEATHEIHYIPS VLLGPQARESFRSSRLQTHNSVIGVPIRETPILD DYDCEEDEEPPRRANHVSREDEFGSQVTHTL DSLGHPGEEKVDFEKKDPSLPNVQVTRLTLLSE QAPGPVVMDLTGDLAVLKDQVFVLKEGVDY RVKISFKVHREIVSGLKCLHHTYRRGLRVDKTV YMVGSYGPSAQEYEFVTPVEEAPRGALVRGP YLVVSLFTDDDRTHHLSWEWGLCICQDWKD | 3 | 3 |
| G17799 .TCGA-06-1804-01A-01R-1849-01.4 | 1 | 613 | 256 | 282 | 8455 | MLRLQMTDGHISCTAVEFSYMSKISLNTPPGT KVKLSGIVDIKNGFLLLNDSNTTVLGGEVEHLIE KWELQRSLSKHNRSNIGTEGGPPPFVPFGQK CVSHVQVDSRELDRRKTLQVTMPVKPTNDN DEFEKQRTAAIAEVAKSKETKTFGGGGGGARS NLNMNAAGNRNREVLQKEKSTKSEGKHEGV YRELVDEKALKHITEMGFSKEASRQALMDNG NNLEAALNVLLTSNKQKPVMGPPLRGRGKGR GRIRSEDEEDLGNARPSAPSTLFDFLESKMGTL NVEEPKSQPQQLHQGQYRSSNTEQNGVKDN NHLRHPPRNDTRQPRNEKPPRFQRDSQNSKS VLEGSGLPRNRGSERPSTSSVSEVWAEDRIKC DRPYSRYDRTKDTSYPLGSQHSDGAFKKRDNS MQSRSGKGPSFAEAKENPLPQGSVDYNNQK RGKRESQTSIPDYFYDRKSQTINNEAFSGIKIEK HFNVNTDYQNPVRSNSFIGVPNGEVEMPLKG RRIGPIKPAGPVTAVPCDDKIFYNSGPKRRSGP IKPEKILESSIPMEYAKMWKPGDECFALYWED NKFYRAEVEALHSSGMTAVVKFIDYGNYEEVL LSNIKPIQTEAWGYDHSYYFIATFITDHIRHHA KYLNA | 12 | 10 |
| G17660 .TCGA-06-5414-01A-01R- | 1 | 555 | 34 | 526 | 8456 | MADPGMMSLFGEDGNIFSEGLEGLGECGYPE NPVNPMGQQMPIDQGFASLQPSLHHPSTNQ NQTKLTHFDHYNQYEQQKMHLMDQPNRM MSNTPGNGLASPHSQYHTPPVPQVPHGGSG GGQMGVYPGMQNERHGQSFVDSSSMWGP RAVQVPDQIRAPYQQQQPQPQPPQPAPSGP | 2 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| 1849-01.2 | | | | | | PAQGHPQHMQQMGSYMARGDFSMQQHG QPQQRMSQFSQGQEGLNQGNPFIATSGPGH LSHVPQQSPSMAPSLRHSVQQFHHHPSTALH GESVAHSPRFSPNPPQQGAVRPQTLNFSSRS QTVPSPTINNSGQYSRYPYSNLNQGLVNNTG MNQNLGLTNNTPMNQSVPRYPNAVGFPSNS GQGLMHQQPIHPSGSLNQMNTQTMHPSQP QGTYASPPPMSPMKAMSNPAGTPPPQVRP GSAGIPMEVGSYPNMPHPQPSHQPPGAMGI GQRNMGPRNMQQSRPFIGMSSAPRELTGH MRPNGCPGVGLGDPQAIQERLIPGQQHPGQ QPSFQQLPTCPPLQPHPGLHHQSSPPHPHHQ PWAQLHPSPQNTPQKVPVHQFDGENMYMS MTEPSQDYVPASQSYPGPSLESEDFNIPPITPP SLPDHSLVHLNEVESGYHSLCHPMNHNGLLPF HPQNMDLPEITVSNMLGQDGTLLSNSISVMP DIRNPEGTQYSSHPQMAAMRPRGQPADIRQ QPGMMPHGQLTTINQSQLSAQLGLNMGGS NVPHNSPSPPGSKSATPSPSSSVHEDEGDDTS KINGGEKRPASDMGKKPKTPKKKKKKDPNEP QKPVSAYALFFRDTQAAIKGQNPNATFGEVSK IVASMWDGLGEEQKQVYKKKTEAAKKEYLKQ LAAYRASLVSKSYSEPVDVKTSQPPQLINSKPS VFHGPSQAHSALYLSSHYHQQPGMNPHLTA MHPSLPRNIAPKPNNQMPVTVSIANMAVSP PPPLQISPPLHQHLNMQQHQPLTMQQPLGN QLPMQVQSALHSPTMQQGFTLQPDYQTIINP TSTAAQVVTQAMEYVRSGCRNPPPQPVDW NNDYCSSGGMQRDKALYLT | | |
| GBM-CUMC3 296_L1 | 1 | 163 | 627 | 1210 | 8457 | MASASYHISNLLEKMTSSDKDFRFMATNDLM TELQKDSIKLDDDSERKVVKMILKLLEDKNGEV QNLAVKCLGPLVSKVKEYQVETIVDTLCTNML SDKEQLRDISSIGLKTVIGELPPASSGSALAANV CKKITGRLTSAIAKQEDVSVQLEALDIMADML SRCTGPGLEGCPTNGPKIPSIATGMVGALLLLL VVALGIGLFMRRRHIVRKRTLRRLLQERELVEP LTPSGEAPNQALLRILKETEFKKIKVLGSGAFGT VYKGLWIPEGEKVKIPVAIKELREATSPKANKEI LDEAYVMASVDNPHVCRLLGICLTSTVQLITQL MPFGCLLDYVREHKDNIGSQYLLNWCVQIAK GMNYLEDRRLVHRDLAARNVLVKTPQHVKIT DFGLAKLLGAEEKEYHAEGGKVPIKWMALESI LHRIYTHQSDVWSYGVTVWELMTFGSKPYD GIPASEISSILEKGERLPQPPICTIDVYMIMVKC WMIDADSRPKFRELIIEFSKMARDPQRYLVIQ GDERMHLPSPTDSNFYRALMDEEDMDDVVD ADEYLIPQQGFFSSPSTSRTPLLSSLSATSNNST VACIDRNGLQSCPIKEDSFLQRYSSDPTGALTE DSIDDTFLPVPEYINQSVPKRPAGSVQNPVYH NQPLNPAPSRDPHYQDPHSTAVGNPEYLNTV QPTCVNSTFDSPAHWAQKGSHQISLDNPDY QQDFFPKEAKPNGIFKGSTAENAEYLRVAPQS SEFIGA | 4 | 16 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| G17505.TCGA-06-2564-01A-01R-1849-01.2 | 1 | 40 | 525 | 1132 | 8458 | MNNLNDPPNWNIRPNSRADGGDGSRWNYALLVPMLGLAAFRVGCVPAAEHRLREEILAKFLHWLMSVYVVELLRSFFYVTETTFQKNRLFFYRKSVWSKLQSIGIRQHLKRVQLRELSEAEVRQHREARPALLTSRLRFIPKPDGLRPIVNMDYVVGARTFRREKRAERLTSRVKALFSVLNYERARRPGLLGASVLGLDDIHRAWRTFVLRVRAQDPPPELYFVKVDVTGAYDTIPQDRLTEVIASIIKPQNTYCVRRYAVVQKAAHGHVRKAFKSHVSTLTDLQPYMRQFVAHLQETSPLRDAVVIEQSSSLNEASSGLFDVFLRFMCHHAVRIRGKSYVQCQGIPQGSILSTLLCSLCYGDMENKLFAGIRRDGLLLRLVDDFLLVTPHLTHAKTFLRTLVRGVPEYGCVVNLRKTVVNFPVEDEALGGTAFVQMPAHGLFPWCGLLLDTRTLEVQSDYSSYARTSIRASLTFNRGFKAGRNMRRKLFGVLRLKCHSLFLDLQVNSLQTVCTNIYKILLLQAYRFHACVLQLPFHQQVWKNPTFFLRVISDTASLCYSILKAKNAGMSLGAKGAAGPLPSEAVQWLCHQAFLLKLTRHRVTYVPLLGSLRTAQTQLSRKLPGTTLTALEAAANPALPSDFKTILD | 2 | 3 |
| G17798.TCGA-32-5222-01A-01R-1850-01.4 | 1 | 280 | 15 | 1673 | 8459 | MLGTGPAAATTAATTSSNVSVLQQFASGLKSRNEETRAKAAKELQHYVTMELREMSQEESTRFYDQLNHHIFELVSSSDANERKGGILAIASLIGVEGGNATRIGRFANYLRNLLPSNDPVVMEMASKAIGRLAMAGDTFTAEYVEFEVKRALEWLGADRNEGRRHAAVLVLRELAISVPTFFFQQVQPFFDNIFVAVWDPKQAIREGAVAALRACLILTTQREPKEMQKPQWYRHTFEEAEKGFDETLAKEKGMNRDDRIHGALLILNELVRISSMEGESVSQSVFCGTSTYCVLNTVPPIEDDHGNSNSSHVKIFLPKKLLECLPKCSSLPKERHRWNTNEEIAAYLITFEKHEEWLTTSPKTRPQNGSMILYNRKKVKYRKDGYCWKKRKDGKTTREDHMKLKVQGVECLYGCYVHSSIIPTFHRRCYWLLQNPDIVLVHYLNVPAIEDCGKPCGPILCSINTDKKEWAKWTKEELIGQLKPMFHGIKWTCSNGNSSSGFSVEQLVQQILDSHQTKPQPRTHNCLCTGSLGAGGSVHHKCNSAKHRIISPKVEPRTGGYGSHSEVQHNDVSEGKHEHSHSKGSSREKRNGKVAKPVLLHQSSTEVSSTNQVEVPDTTQSSPVSISSGLNSDPDMVDSPVVTGVSGMAVASVMGSLSQSATVFMSEVTNEAVYTMSPTAGPNHHLLSPDASQGLVLAVSSDGHKFAFPTTGSSESLSMLPTNVSEELVLSTTLDGGRKIPETTMNFDPDCFLNNPKQGQTYGGGGLKAEMVSSNIRHSPPGERSFSFTTVLTKEIKTEDTSFEQQMAKEAYSSSAAAVAASSLTLTAGSSLLPSGGGLSPSTTLEQMDFSAIDSNKDYTSSFSQTGHSPHIHQTPSPSFFLQDASKPLPVEQNTHSSLSDSGGTFVMPTVKTEASSQTSSCSGHVETRIESTSSLHLMQFQANFQAMTAEGEVTMETSQAAEGSEVLLKSGELQACSSEHYLQPETNGVIRSAGGVPILPGNVVQGLYPVAQPSLGNASNMELSLDHFDISFSNQFSDLINDFISVEGGS | 6 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | STIYGHQLVSGDSTALSQSEDGARAPFTQAE MCLPCCSPQQGSLQLSSSEGGASTMAYMHV AEVVSAASAQGTLGMLQQSGRVFMVTDYSP EWSYPEGGVKVLITGPWQEASNNYSCLFDQIS VPASLIQPGVLRCYCPAHDTGLVTLQVAFNNQ IISNSVVFEYKARALPTLPSSQHDWLSLDDNQF RMSILERLEQMERRMAEMTGSQQHKQASG GGSSGGGSGSGNGGSQAQCASGTGALGSCF ESRVVVVCEKMMSRACWAKSKHLIHSKTFRG MTLLHLAAAQGYATLIQTLIKWRTKHADSIDL ELEVDPLNVDHFSCTPLMWACALGHLEAAVV LYKWDRRAISIPDSLGRLPLGIARSRGHVKLAE CLEHLQRDEQAQLGQNPRIHCPASEEPSTES WMAQWHSEAISSPEIPKGVTVIASTNPELRRP RSEPSNYYSSESHKDYPAPKKHKLNPEYFQTR QEKLLPTALSLEEPNIRKQSPSSKQSVPETLSPS EGVRDFSRELSPPTPETAAFQASGSQPVGKW NSKDLYIGVSTVQVTGNPKGTSVGKEAAPSQ VRPREPMSVLMMANREVVNTELGSYRDSAE NEECGQPMDDIQVNMMTLAEHIIEATPDRIK QENFVPMESSGLERTDPATISSTMSWLASYLA DADCLPSAAQIRSAYNEPLTPSSNTSLSPVGSP VSEIAFEKPNLPSAADWSEFLSASTSEKVENEF AQLTLSDHEQRELYEAARLVQTAFRKYKGRPL REQQEVAAAVIQRCYRKYKQYALYKKMTQAA ILIQSKFRSYYEQKKFQQSRRAAVLIQKYYRSYK KCGKRRQARRTAVIVQQKLRSSLLTKKQDQA ARKIMRFLRRCRHSPLVDHRLYKRSERIEKGQ GT | | |
| GBM-CUMC3 297_L1 | 1 | 57 | 358 | 372 | 8460 | MARGYGATVSLVLLGLGLALAVIVLAVVLSRH QAPCGPQAFAHAAVAADSKVCSDIGRQETAY LLVYMKMEC | 1 | 10 |
| GBM-CUMC3 342_L1 | 1 | 169 | 341 | 484 | 8461 | MFVYVLTPGEQSGRRLPGQTWLMFSCFCFSL QDNSFSSTTVTECDEDPVSLHEDQTDCSSLRD ENNKENYPDAGALVEEHAPPSWEPQQQNVE ATVLVDSVLRPSMGNFKSRKPKSIFKAESGRS HGESQETEHVVSSQSECQVRAGTPAHESPQN NAFKCQETVRLQPRSRKDSLESDSSTAIIPHELI RTRQLESVHLKFNQESGALIPLCLRGRLLHGRH FTYKSITGDMAITFVSTGVEGAFATEEHPYAA HGPWLQILLTEEFVEKMLEDLEDLTSPEEFKLP KEYSWPEKKLKVSILPDVVFDSPLH | 4 | 9 |
| G17500 .TCGA-27-1831-01A-01R-1850-01.2 | 1 | 2661 | 303 | 468 | 8462 | MHSAGTPGLSSRRTGNSTSFQPGPPPPPRLLL LLLLLLSLVSRVPAQPAAFGRALLSPGLAGAAG VPAEEAIVLANRGLRVPFGREVWLDPLHDLVL QVQPGDRCAVSVLDNDALAQRPGRLSPKRFP CDFGPGEVRYSHLGARSPSRDRVRLQLRYDAP GGAVVLPLVLEVEVVFTQLEVVTRNLPLVVEEL LGTSNALDARSLEFAFQPETEECRVGILSGLGA LPRYGELLHYPQVPGGAREGGAPETLLMDCK AFQELGVRYRHTAASRSPNRDWIPMVVELRS RGAPVGSPALKREHFQVLVRIRGGAENTAPKP SFVAMMMMEVDQFVLTALTPDMLAAEDAE SPSDLLIFNLTSPFQPGQGYLVSTDDRSLPLSSF | 16 | 7 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | TQRDLRLLKIAYQPPSEDSDQERLFELELEVVD LEGAASDPFAFMVVVKPMNTMAPVVTRNTG LILYEGQSRPLTGPAGSGPQNLVISDEDDLEAV RLEVVAGLRHGHLVILGASSGSSAPKSFTVAEL AAGQVVYQHDDRDGSLSDNLVLRMVDGGG RHQVQFLFPITLVPVDDQPPVLNANTGLTLAE GETVPILPLSLSATDMDSDDSLLLFVLESPFLTT GHLLLRQTHPPHEKQELLRGLWRKEGAFYERT VTEWQQQDITEGRLFYRHSGPHSPGPVTDQF TFRVQDNHDPPNQSGLQRFVIRIHPVDRLPPE LGSGCPLRMVVQESQLTPLRKKWLRYTDLDT DDRELRYTVTQSPTDTDENHLPAPLGTLVLTD NPSVVVTHFTQAQINHHKIAYRPPGQELGVA TRVAQFQFQVEDRAGNVAPGTFTLYLHPVDN QPPEILNTGFTIQEKGHHILSETELHVNDVDTD VAHISFTLTQAPKHGHMRVSGQILHVGGLFHL EDIKQGRVSYAHNGDKSLTDSCSLEVSDRHHV VPITLRVNVRPVDDEVPILSHPTGTLESYLDVLE NGATEITANVIKGTNEETDDLMLTFLLEDPPLY GEILVNGIPAEQFTQRDILEGSVVYTHTSGEIGL LPKADSFNLSLSDMSQEWRIGGNTIQGVTIW VTILPVDSQAPEIFVGEQLIVMEGDKSVITSVHI SAEDVDSLNDDILCTIVIQPTSGYVENISPAPGS EKSRAGIAISAFNLKDLRQGHINYVQSVHKGV EPVEDRFVFRCSDGINFSERQFFPIVIIPTNDEQ PEMFMREFMVMEGMSLVIDTPILNAADADV PLDDLTFTITQFPTHGHIMNQLINGTVLVESFT LDQIIESSSIIYEHDDSETQEDSFVIKLTDGKHSV EKTVLIIVIPVDDETPRMTINNGLEIEIGDTKIIN NKILMATDLDSEDKSLVYIIRYGPGHGLLQRRK PTGAFENITLGMNFTQDEVDRNLIQYVHLGQ EGIRDLIKFDVTDGINPLIDRYFYVSIGSIDIVFP DVISKGVSLKEGGKVTLTTDLLSTSDLNSPDEN LVFTITRAPMRGHLECTDQPGVSITSFTQLQLA GNKIYYIHTADDEVKMDSFEFQVTDGRNPVF RTFRISISDVDNKKPVVTIHKLVVSESENKLITPF ELTVEDRDTPDKLLKFTITQVPIHGHLLFNNTR PVMVFTKQDLNENLISYKHDGTESSEDSFSFT VTDGTHTDFYVFPDTVFETRRPQVMKIQVLA VDNSVPQIAVNKGASTLRTLATGHLGFMITSKI LKVEDRDSLHISLRFIVTEAPQHGYLLNLDKGN HSITQFTQADIDDMKICYVLREGANATSDMFY FAVEDGGGNKLTYQNFRLNWAWISFEKEYYL VNEDSKFLDVVLKRRGYLGETSFISIGTRDRTA EKDKDFKGKAQKQVQFNPGQTRATWRVRILS DGEHEQSETFQVVLSEPVLAALEFPTVATVEIV DPGDEPTVFIPQSKYSVEEDVGELFIPIRRSGD VSQELMVVCYTQQGTATGTVPTSVLSYSDYIS RPEDHTSVVRFDKDEREKLCRIVIIDDSLYEEEE TFHVLLSMPMGGRIGSEFPGAQVTIVPDKDD EPIFYFGDVEYSVDESAGYVEVQVWRTGTDLS KSSSVTVRSRKTDPPSADAGTDYVGISRNLDF APGVNMQPVRVVILDDLGQPALEGIEKFELVL RMPMNAALGEPSKATVSINDSVSDLPKMQFK | | |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | ERIYTGSESDGQIVTMIHRTGDVQYRSSVRCY TRQGSAQVMMDFEERPNTDTSIITFLPGETEK PCILELMDDVLYEEVEELRLVLGTPQSNSPFGA AVGEQNETLIRIRDDADKTVIKFGETKFSVTEP KEPGESVVIRIPVIRQGDTSKVSIVRVHTKDGS ATSGEDYHPVSEEIEFKEGETQHVVEIEVTFDG VREMREAFTVHLKPDENMIAEMQLTKAIVYIE EMSSMADVTFPSVPQIVSLLMYDDTSKAKES AEPMSGYPVICITACNPKYSDYDKTGSICASEN INDTLTRYRWLISAPAGPDGVTSPMREVDFDT FFTSSKMVTLDSIYFQPGSRVQCAARAVNTNG DEGLELMSPIVTISREEGLCQPRVPGVVGAEPF SAKLRYTGPEDADYTNLIKLTVTMPHIDGMLP VISTRELSNFELTLSPDGTRVGNHKCSNLLDYT EVKTHYGFLTDATKNPEIIGETYPYQYSLSIRGS TTLRFYRNLNLEACLWEFVSYYDMSELLADCG GTIGTDGQVDVKLDPKDLRIDTFRAKGAGGQ HVNKTDSAVRLVHIPTGLVVECQQERSQIKNK EIAFRVLRARLYQQIIEKDKRQQQSARKLQVG TRAQSERIRTYNFTQDRVSDHRIAYEVRDIKA QSHSTGGSRDPAHSTFLSLDSVRSPGILIMTSS VRNFYVVGRAWIS | | |
| G17212 .TCGA- 06- 0129- 01A- 01R- 1849- 01.2 | 1 | 304 | 415 | 655 | 8463 | MAIDRRREAAGGGPGRQPAPAEENGSLPPG DAAASAPLGGRAGPGGGAEIQPLPPLHPGGG PHPSCCSAAAAPSLLLLDYDGSVLPFLGGLGG GYQKTLVLLTWIPALFIGFSQFSDSFLLDQPNF WCRGAGKGTELAGVTTTGRGGDMGNWTSL PTTPFATAPWEAAGNRSNSSGADGGDTPPLP SPPDKGDNASNCDCRAWDYGIRAGLVQNVV SKWDLVCDNAWKVHIAKFSLLVGLIFGYLITG CIADWVGRRPVLLFSIIFILIFGLTVALSVNVTM FSTLRFFEGFCLAGIILTLYALRIDILKLVAAQVG SQWKDIYQFLCNASEREVAAFSNGYTADHER AYAALQHWTIRGPEASLAQLISALRQHRRND VVEKIRGLMEDTTQLETDKLALPMSPSPLSPSP IPSPNAKLENSALLTVEPSPQDKNKGFFVDESE PLLRCDSTSSGSSALSRNGSFITKEKKDTVLRQ VRLDPCDLQPIFDDMLHFLNPEELRVIEEIPQA EDKLDRLFEIIGVKSQEASQTLLDSVYSHLPDLL | 3 | 4 |
| GBM- CUMC3 322_L1 | 1 | 4 | 641 | 1066 | 8464 | MENTDRKVSSLHTSRVQRQMVVSVHDLPEKS FVPLLDSKYVLCVWDIWQPSGPQKVLICESQV TCCCLSPLKAFLLFAGTAHGSVVVWDLREDSR LHYSVTLSDGFWTFRTATFSTDGILTSVNHRSP LQAVEPISTSVHKKQSFVLSPFSTQEEMSGLSF HIASLDESGVLNVWVVVELPKADIAGSISDLGL MPGGRVKLVHSALIQLGDSLSHKGNEFWGTT QTLNVKFLPSDPNHFIIGTDMGLISHGTRQDL RVAPKLFKPQQHGIRPVKVNVIDFSPFGEPIFL AGCSDGSIRLHQLSSAFPLLQWDSSTDSHAVT GLQWSPTRPAVFLVQDDTSNIYIWDLLQSDL GPVAKQQVSPNRLVAMAAVGEPEKAGGSFL ALVLARASGSIDIQHLKRRWAAPEVDECNRLR LLLQEALWPEGKLHK | 2 | 16 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| G17675.TCGA-19-2624-01A-01R-1850-01.2 | 1 | 250 | 13 | 204 | 8465 | MTCPRNVTPNSYAEPLAAPGGGERYSRSAGMYMQSGSDFNCGVMRGCGLAPSLSKRDEGSSPSLALNTYPSYLSQLDSWGDPKAAYRLEQPVGRPLSSCSYPPSVKEENVCCMYSAEKRAKSGPEAALYSHPLPESCLGEHEVPVPSYYRASPSYSALDKTPHCSGANDFEAPFEQRASLNPRAEHLESPQLGGKVSFPETPKSDSQTPSPNEIKTEQSLAGPKGSPSESEKERAKAADSSPDTSDNEAKGKYIASTQRPDGTWRKQRRVKEGYVPQEEVPVYENKYVKFFKSKPELPPGLSPEATAPVTPSRPEGGEPGLSKTAKRNLKRKEKRRQQQEKGEAEALSRTLDKVSLEETAQLPSAPQGSRAAPTAASDQPDSAATTEKAKKIKNLKKKLRQVEELQQRIQAGEVSQPSKEQLEKLARRRALEEELEDLELGL | 1 | 2 |
| G17803.TCGA-76-4925-01A-01R-1850-01.4 | 1 | 359 | 14 | 425 | 8466 | MAAEKQVPGGGGGGSGGGGGSGGGGSGGGRGAGGEENKENERPSAGSKANKEFGDSLSLEILQIIKESQQQHGLRHGDFQRYRGYCSRRQRRLRKTLNFKMGNRHKFTGKKVTEELLTDNRYLLLVLMDAERAWSYAMQLKQEANTEPRKRFHLLSRLRKAVKHAEELERLCESNRVDAKTKLEAQAYTAYLSGMLRFEHQEWKAAIEAFNKCKTIYEKLASAFTEEQAVLYNQRVEEISPNIRYCAYNIGDQSAINELMQMRLRSGGTEGLLAEKLEALITQTRAKQAATMSEVEWRGRTVPVKIDKVRIFLLGLADNEAAIVQAESEETKERLFESMLSECRDAIQVVREELKPDQPLISRNYKGDVAMSKIEHFMPLLVQREEEGALAPLLSHGQVHFLWIKHSNLYLVATTSKNANASLVYSFLYKTIEVFCEYFKELEEESIRDNFVIVYELLDELMDFGFPQTTDSKILQEYITQQSNKLETGKSRVPPTVTNAVSWRSEGIKYKKNEVFIDVIESVNLLVNANGSVLLSEIVGTIKLKVFLSGMPELRLGLNDRVLFELTGLSGSKNKSVELEDVKFHQCVRLSRFDNDRTISFIPPDGDFELMSYRLSTQVKPLIWIESVIEKFSHSRVEIMVKAKGQFKKQSVANGVEISVPVPSDADSPRFKTSVGSAKYVPERNVVIWSIKSFPGGKEYLMRAHFGLPSVEKEEVEGRPPIGVKFEIPYFTVSGIQVRYMKIIEKSGYQALPWVRYITQSGDYQLRTS | 9 | 2 |
| G17796.TCGA-41-5651-01A-01R-1850-01.4 | 1 | 211 | 100 | 350 | 8467 | MSLLRSLRVFLVARTGSYPAGSLLRQSPQPRHTFYAGPRLSASASSKELLMKLRRKTGYSFVNCKKALETCGGDLKQAEIWLHKEAQKEGWSKAAKLQGRKTKEGLIGLLQEGNTTVLVEVNCETDFVSRNLKFQLLVQQVALGTMMHCQTLKDQPSAYSKVQWLTPVNLALWEAEAGGSLEGFLNSSELSGLPAGPDREGSLKDQLALAIDSTSAYSSLLTFHLSTPRSHHLYHARLWLHVLPTLPGTLCLRIFRWGPRRRQGSRTLLAEHHITNLGWHTLTLPSSGLRGEKSGVLKLQLDCRPLEGNSTVTGQPRRLLDTAGHQQPFLELKIRANEPGAGRARRRTPTCEPATPLCCRRDHYVDFQELGWRDWILQPEGYQLNYCSGQCPPHLAGSPGIAASFHSAVFSLLKANNPWPASTSCCVPTARRPLSLLYLDHNGNVVKTDVPDMVVEACGCS | 6 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| G17663 .TCGA- 19- 2619- 01A- 01R- 1850- 01.2 | 1 | 140 | 585 | 1374 | 8468 | MASLRRVKVLLVLNLIAVAGFVLFLAKCRPIAV RSGDAFHEIRPRAEVANLSAHSASPIQDAVLK RLSLLEDIVYRQLNGLSKSLGLIEGYGGRGKGG LPATLSPAEEEKAKGPHEKYGYNSYLSEKISLDR SIPDYRPTKFVIGREKPGQVSEVAQLISQTLEQ ERRQRELLEQHYAQYDADDDENTVAELQGM SGNCNNNNYFLKTGEYATDEEEDEVGPVLP GSDMAIEVFELPENEDMFSPSELDTSKLSHKF KELQIKHAVTEAEIQKLKTKLQAAENEKVRWE LEKTQLQQNIEENKERMLKLESYWIEAQTLCH TVNEHLKETQSQYQALEKKYNKAKKLIKDFQQ KELDFIKRQEAERKKIEDLEKAHLVEVQGLQVR IRDLEAEVFRLLKQNGTQVNNNNNIFERRTSL GEVSKGDTMENLDGKQTSCQDGLSQDLNEA VPETERLDSKALKTRAQLSVKNRRQRPSRTRLY DSVSSTDGEDSLERKPSNSFYNHMHITKLLPPK GLRTSSPESDSGVPPLTPVDSNVPFSSDHIAEF QEEPLDPEMGPLSSMWGDTSLFSTSKSDHDV EESPCHHQTTNKKILREKDDAKDPKSLRASSSL AVQGGKIKRKFVDLGAPLRRNSSKGKKWKEK EKEASRFSAGSRIFRGRLENWTPKPCSTAQTST RSPCMPFSWFNDSRKGSYSFRNLPAPTSSLQP SPETLISDKKGSKVENTWITKANKRNPNPSSSS IFGRHSQLMSVVWIQETNNFTFNDDFSPSSTS SADLSGLGAEPKTPGLSQSLALSSDEILDDGQS PKHSQCQNRAVQEWSVQQVSHWLMSLNLE QYVSEFSAQNITGEQLLQLDGNKLKALGMTA SQDRAVVKKKLKEMKMSLEKARKAQEKMEK QREKLRRKEQEQMQRKSKKTEKMTSTTAEGA GEQ | 2 | 5 |
| G17207 .TCGA- 06- 0156- 01A- 03R- 1849- 01.2 | 1 | 2 | 205 | 925 | 8469 | MQSTQAHENSRDSRLAWMGTWEHLVSTGF NQMREREVKLWDTRFFSSALASLTLDTSLGCL VPLLDPDSGLLVLAGKGERQLYCYEVVPQQPA LSPVTQCVLESVLRGAALVPRQALAVMSCEVL RVLQLSDTAIVPIGYHVPRKAVEFHEDLFPDTA GCVPATDPHSWWAGDNQQVQKVSLNPACR PHPSFTSCLVPPAEPLPDTAQPAVMETPVGD ADASEGFSSPPSSLTSPSTPSSLGPSLSSTSGIGT SPSLRSLQSLLGPSSKFRHAQGTVLHRDSHITN LKGLNLTTPGESDGFCANKLRVAVPLLSSGGQ VAVLELRKPGRLPDTALPTLQNGAAVTDLAW DPFDPHRLAVAGEDARIRLWRVPAEGLEEVLT TPETVLTGHTEKICSLRFHPLAANVLASSSYDLT VRIWDLQAGADRLKLQGHQDQIFSLAWSPD GQQLATVCKDGRVRVYRPRSGPEPLQEGPGP KGGRGARIVWVCDGRCLLVSGFDSQSERQLL LYEAEALAGGPLAVLGLDVAPSTLLPSYDPDTG LVLLTGKGDTRVFLYELLPESPFFLECNSFTSPD PHKGLVLLPKTECDVREVELMRCLRLRQSSLEP VAFRLPRVRKEFFQDDVFPDTAVIWEPVLSAE AWLQGANGQPWLLSLQPPDMSPVSQAPRE APARRAPSSAQYLEEKSDQQKKEELLNAMVA KLGNREDPLPQDSFEGVDEDEWD | 1 | 8 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| G17802.TCGA-28-5208-01A-01R-1850-01.4 | 1 | 68 | 190 | 225 | 8470 | MGETMSKRLKLHLGGEAEMEERAFVNPFPDYEAAAGALLASGAAEETGCVRPPATTDEPGLPFHQDGKDAFIGFGGNVIRQQVKDNAKWYITDFVELLGELEE | 1 | 6 |
| G17485.TCGA-14-1402-02A-01R-2005-01.2 | 1 | 17 | 156 | 569 | 8471 | MPQSKSRKIAILGYRSVASGLSSSPSTPTQVTKQHTFPLESYKHEPERLENRIYASSSPPDTGQRFCPSSFQSPTRPPLASPTHYAPSKAAALAAALGPAEAGMLEKLEFEDEAVEDSESGVYMRFMRSHKCYDIVPTSSKLVVFDTTLQVKKAFFALVANGVRAAPLWESKKQSFVGMLTITDFINILHRYYKSPMVQIYELEEHKIETWRELYLQETFKPLVNISPDASLFDAVYSLIKNKIHRLPVIDPISGNALYILTHKRILKFLQLFMSDMPKPAFMKQNLDELGIGTYHNIAFIHPDTPIIKALNIFVERRISALPVVDESGKVVDIYSKFDVINLAAEKTYNNLDITVTQALQHRSQYFEGVVKCNKLEILETIVDRIVRAEVHRLVVVNEADSIVGIISLSDILQALILTPAGAKQKETETE | 1 | 4 |
| NYU_E | 1 | 252 | 68 | 211 | 8472 | MGAGPSLLLAALLLLLSGDGAVRCDTPANCTYLDLLGTWVFQVGSSGSQRDVNCSVMGPQEKKVVVYLQKLDTAYDDLGNSGHFTIIYNQGFEIVLNDYKWFAFFKYKEEGSKVTTYCNETMTGWVHDVLGRNWACFTGKKVGTASENVYVNIAHLKNSQEKYSNRLYKYDHNFVKAINAIQKSWTATTYMEYETLTLGDMIRRSGGHSRKIPRPKPAPLTAEIQQKILHLPTSWDWRNVHGINFVSPVRNQGQERFGNMTRVYYREAMGAFIVFDVTRPATFEAVAKWKNDLDSKLSLPNGKPVSVVLLANKCDQGKDVLMNNGLKMDQFCKEHGFVGWFETSAKENINIDEASRCLVKHILANECDLMESIEPDVVKPHLTSTKVASCSGCAKS | 5 | 2 |
| G17212.TCGA-06-0129-01A-01R-1849-01.2 | 1 | 1367 | 15 | 338 | 8473 | MAERGLEPSPAAVAALPPEVRAQLAELELELSEGDITQKGYEKKRSKLLSPYSPQTQETDSAVQKELRNQTPAPSAAQTSAPSKYHRTRSGGARDERYRSDIHTEAVQAALAKHKEQKMALPMPTKRRSTFVQSPADACTPPDTSSASEDEGSLRRQAALSAALQQSLQNAESWINRSIQGSSTSSSASSTLSHGEVKGTSGSLADVFANTRIENFSAPPDVTTTTSSSSSSSSIRPANIDLPPSGIVKGMHKGSNRSSLMDTADGVPVSSRVSTKIQQLLNTLKRPKRPPLKEFFVDDSEEIVEVPQPDPNQPKPEGRQMTPVKGEPLGVICNWPPALESALQRWGTTQAKCSCLTALDMTGKPVYTLTYGKLWSRSLKLAYTLLNKLGTKNEPVLKPGDRVALVYPNNDPVMFMVAFYGCLLAEVIPVPIEVPLTRKDAGGQQIGFLLGSCGIALALTSEVCLKGLPKTQNGEIVQFKGWPRLKWVVTDSKYLSKPPKDWQPHISPAGTEPAYIEYKTSKEGSVMGVTVSRLAMLSHCQALSQACNYSEGETIVNVLDFKKDAGLWHGMFANVMNKMHTISVPYSVMKTCPLSWVQRVHAHKAKVALVKCRDLHWAMMAHRDQRD | 34 | 2 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| | | | | | | VSLSSLRMLIVTDGANPWSVSSCDAFLSLFQS HGLKPEAICPCATSAEAMTVAIRRPGVPGAPL PGRAILSMNGLSYGVIRVNTEDKNSALTVQDV GHVMPGGMMCIVKPDGPPQLCKTDEIGEICV SSRTGGMMYFGLAGVTKNTFEVIPVNSAGSP VGDVPFIRSGLLGFVGPGSLVFVVGKMDGLL MVSGRRHNADDIVATGLAVESIKTVYRGRIAV FSVSVFYDERIVVVAEQRPDASEEDSFQWMS RVLQAIDSIHQVGVYCLALVPANTLPKTPLGGI HISQTKQLFLEGSLHPCNILMCPHTCVTNLPKP RQKQPGVGPASVMVGNLVAGKRIAQAAGRD LGQIEENDLVRKHQFLAEILQWRAQATPDHV LFMLLNAKGTTVCTASCLQLHKRAERIASVLG DKGHLNAGDNVVLLYPPGIELIAAFYGCLYAG CIPVTVRPPHAQNLTATLPTVRMIVDVSKAAC ILTSQTLMRLLRSREAAAAVDVKTWPTIIDTDD LPRKRLPQLYKPPTPEMLAYLDFSVSTTGMLT GVKMSHSAVNALCRAIKLQCELYSSRQIAICLD PYCGLGFALWCLCSVYSGHQSVLIPPMELENN LFLWLSTVNQYKIRDTFCSYSVMELCTKGLGN QVEVLKTRGINLSCVRTCVVVAEERPRVALQQ SFSKLFKDIGLSPRAVSTTFGSRVNVAICLQGTS GPDPTTVYVDLKSLRHDRVRLVERGAPQSLLL SESGKRSGSKQSTNPADNYHLARRRTLQVVVS SLLTEAGFESAEKASVETLTEMLQSYISEIGRSA KSYCEHTARTQPTLSDIVVTLVEMGFNVDTLP AYAKRSQRMVITAPPVTNQPVTPKALTAGQN RPHPPHIPSHFPEFPDPHTYIKTPTYREPVSDY QVLREKAASQRRDVERALTRFMAKTGETQSL FKDDVSTFPLIAARPFTIPYLTALLPSELEMQQ MEETDSSEQDEQTDTENLALHISMIESRSVTQ AGVQWQDLGSLQPPPPGFKRFSSLSLLSSWN YRRILEPRRRTPLSCSRTPPCRVAGMGRRTSSI TLICGR | | |
| G17787 .TCGA- 26- 5139- 01A- 01R- 1850- 01.4 | 1 | 337 | 376 | 601 | 8474 | MEPPAAKRSRGCPAGPEERDAGAGAARGRG RPEALLDLSAKRVAESWAFEQVEERFSRVPEP VQKRIVFWSFPRSEREICMYSSLGYPPPEGEH DARVPFTRGLHLLQSGAVDRVLQVGFHLSGNI REPGSPGEPERLYHVSISFDRCKITSVSCGCDN RDLFYCAHVVALSLYRIRHAHQVELRLPISETLS QMNRDQLQKFVQYLISAHHTEVLPTAQRLAD EILLLGSEINLVNGAPDPTAGAGIEDANCWHL DEEQIQEQVKQLLSNGGYYGASQQLRSMFSK VREMLRMRDSNGARMLILMTEQFLQDTRLA LWRQQGAGMTDKCRQLWDELGMFNSPEM QALLQQISENPQLMQNVISAPYMRSMMQTL AQNPDFAAQMMVNVPLFAGNPQLQEQLRL QLPVFLQQMQNPESLSILTNPRAMQALLQIQ QGLQTLQTEAPGLVPSLGSFGISRTPAPSAGS NAGSTPEAPTSSPATPATSSPTGASSAQQQL MQQMIQLLAGSGNSQVQTPEVRFQQQLEQL NSMGFINREANLQALIATGGDINAAIERLLGS QLS | 5 | 7 |

FIG. 27 Cont.

| sample | Protein Start 5p | Protein Stop 5p | Protein Start 3p | Protein Stop 3p | SEQ ID NO: | Protein Sequence | Exon Break 5p | Exon Break 3p |
|---|---|---|---|---|---|---|---|---|
| G17675 .TCGA-19-2624-01A-01R-1850-01.2 | 1 | 473 | 82 | 514 | 8475 | MDVLPTGGGRPGLRTELEFRGGGGEARLESQ EEETIPAAPPAPRLRGAAERPRRSRDTWDGDE DTEPGEACGGRTSRTASLVSGLLNELYSCTEEE EAAGGGRGAEGRRRRRDSLDSSTEASGSDVV LGGRSGAGDSRVLQELQERPSQRHQMLYLR QKDANELKTILRELKYRIGIQSAKLLRHLKQKDR LLHKVQRNCDIVTACLQAVSQKRRVDTKLKFT LEPSLGQNGFQQWYDALKAVARLSTGIPKEW RRKVWLTLADHYLHSIAIDWDKTMRFTFNER SNPDDDSMGIQIVKDLHRTGCSSYCGQEAEQ DRVVLKRVLLAYARWNKTVGYCQGFNILAALI LEVMEGNEGDALKIMIYLIDKVLPESYFVNNLR ALSVDMAVFRDLLRMKLPELSQHLDTLQRTA NKESGGGYEPPLTNVFTMQWFLTLFATCLPN QTVLKIWDSVFFEGSEIILRVSLAIWAKLGEVIN AGKSTHNEDQASCEVLTVKKKAGAVTSTPNR NSSKRRSSLPNGEGLQLKENSESEGVSCHYWS LFDGHAGSGAAVVASRLLQHHITEQLQDIVDI LKNSAVLPPTCLGEEPENTPANSRTLTRAASLR GGVGAPGSPSTPPTRFFTEKKIPHECLVIGALE SAFKEMDLQIERERSSYNISGGCTALIVICLLGK LYVANAGDSRAIIIRNGEIIPMSSEFTPETERQR LQYLAFMQPHLLGNEFTHLEFPRRVQRKELGK KMLYRDFNMTGWAYKTIEDEDLKFPLIYGEGK KARVMATIGVTRGLGDHDLKVHDSNIYIKPFL SSAPEVRIYDLSKYDHGSDDVLILATDGLWDVL SNEEVAEAITQFLPNCDPDDPHRYTLAAQDLV MRARGVLKDRGWRISNDRLGSGDDISVYVIPL IHGNKLS | 8 | 2 |
| G17800 .TCGA-06-5859-01A-01R-1849-01.4 | 1 | 318 | 97 | 104 | 8476 | MDNMSITNTPTSNDACLSIVHSLMCHRQGG ESETFAKRAIESLVKKLKEKKDELDSLITAITTNG AHPSKCVTIQRTLDGRLQVAGRKGFPHVIYAR LWRWPDLHKNELKHVKYCQYAFDLKCDSVCV NPYHYERVVSPGIDLSGLTLQSNAPSSMMVK DEYVHDFEGQPSLSTEGHSIQTIQHPPSNRAS TETYSTPALLAPSESNATSTANFPNIPVASTSQ PASILGGSHSEGLLQIASGPQPGQQQNGFTG QPATYHHNSTTTWTGSRTAPYTPNLPHHQN GHLQHHPPMPPHPGHYWPVHNELAFQPPIS NHPGVVPEPTG | 7 | 2 |
| G17638 .TCGA-28-2499-01A-01R-1850-01.2 | 1 | 116 | 70 | 211 | 8477 | MAAAAGAPPPGPPQPPPPPPEESSDSEPEA EPGSPQKLIRKVSTSGQIRQKTIIKEGMLTKQN NSFQRSKRRYFKLRGRTLYYAKTAKSIIFDEVDL TDASVAESSTKNVNNSFTVEVLDENNLVMNL EFSIRETTCRKDSGEDPATCAFQRDYYVSTAVC RSTVKVSAQQVQGVHARCSWSSSTSESYSSEE MIFGDMLGSHKWRNNYLFGLISDESISEQFYD RSLGIMRRVLPPGNRRYPNHRHRARINTDFE | 3 | 3 |

FIG. 27 Cont.

| sample | split reads | gene5p | chr5p | Sense 5p | Start 5p | End 5p | Breakpoint 5p | Exon Before Breakpoint 5p |
|---|---|---|---|---|---|---|---|---|
| TCGA-06-0750-01A-01D-1492-08 | 51 | EGFR | chr7 | + | 55054218 | 55268221 | 55268221 | 24 |
| TCGA-27-1837-01A-01D-1494-08 | 648 | EGFR | chr7 | + | 55086724 | 55268937 | 55268937 | 24 |
| TCGA-28-2513-01A-01D-1494-08 | 378 | EGFR | chr7 | + | 55086724 | 55269001 | 55269001 | 24 |
| TCGA-06-5411-01A-01D-1696-08 | 676 | NFASC | chr1 | + | 204797781 | 204951827 | 204951827 | 21 |
| TCGA-32-5222-01A-01D-1486-08 | 0 | EGFR | chr7 | + | 55086724 | N/A | N/A | N/A |
| TCGA-28-5209-01A-01D-1486-08 | 0 | EGFR | chr7 | + | 55086724 | N/A | N/A | N/A |

| sample | split reads | Gene 3p | chr3p | Sense 3p | start3p | end3p | Breakpoint 3p | Exon After Breakpoint 3p |
|---|---|---|---|---|---|---|---|---|
| TCGA-06-0750-01A-01D-1492-08 | 51 | SEPT14 | chr7 | - | 55828730 | 55871487 | 55871487 | 10 |
| TCGA-27-1837-01A-01D-1494-08 | 648 | SEPT14 | chr7 | - | 55861236 | 55870909 | 55870909 | 10 |
| TCGA-28-2513-01A-01D-1494-08 | 378 | SEPT14 | chr7 | - | 55861236 | 55871369 | 55871369 | 10 |
| TCGA-06-5411-01A-01D-1696-08 | 676 | NTRK1 | chr1 | + | 156844170 | 156851642 | 156844170 | 10 |
| TCGA-32-5222-01A-01D-1486-08 | 0 | SEPT14 | chr7 | - | 55861236 | N/A | N/A | N/A |
| TCGA-28-5209-01A-01D-1486-08 | 0 | PSPH | chr7 | - | 56078743 | N/A | N/A | N/A |

Fig. 28

| sample | split inserts | posA5p | posB5p | Read Dir 5p | posA3p | posB3p | readDir 3p |
|---|---|---|---|---|---|---|---|
| TCGA-06-0750-01A-01D-1492-08 | 17 | 55242336 | 55268011 | Fwd | 55871183 | 55871412 | Fwd |
| TCGA-27-1837-01A-01D-1494-08 | 505 | 55268346 | 55268884 | Fwd | 55870367 | 55870871 | Fwd |
| TCGA-28-2513-01A-01D-1494-08 | 251 | 55268377 | 55268962 | Fwd | 55871008 | 55871339 | Fwd |
| TCGA-06-5411-01A-01D-1696-08 | 131 | 204951788 | 204951826 | Fwd | 156844171 | 156844232 | Rev |
| TCGA-32-5222-01A-01D-1486-08 | 1 | 55268015 | 55268015 | Fwd | 55872287 | 55872287 | Fwd |
| TCGA-28-5209-01A-01D-1486-08 | 1 | 55198162 | 55198162 | Rev | 56087184 | 56087184 | Fwd |

| gene | gene | gene | gene |
|---|---|---|---|
| ABCA13 | C21orf29 | CAMKK1 | DNAJC6 |
| ABCC1 | CACNA1C | CAMSAP1 | DYRK3 |
| ABCC12 | CACNA1G | CAMTA1 | EIF2C2 |
| ABCC6 | CNTNAP4 | CAP2 | FAM184B |
| ABL1 | CUL3 | CCDC147 | FREM2 |
| ADAM12 | DMD | CCDC158 | GDPD2 |
| ADCY10 | DUSP27 | CELF2 | GLI3 |
| ADCY2 | ECE1 | CILP | IL1RN |
| ADCY8 | EYS | CMYA5 | ISX |
| AGBL4 | FAM172A | COL14A1 | KIDINS220 |
| AHNAK | FAM184B | CORO7 | LRBA |
| ANXA7 | EGFR4 | CSMD2 | LY75 |
| AP4S1 | ITGAV | CUL3 | MDH2 |
| AQP2 | LRP1 | DDI2 | MMP12 |
| ARMC6 | LY75 | DEPDC5 | N4BP2L2 |
| ATP5B | MAPKAP1 | DEPDC7 | NCF2 |
| ATP6AP1L | MYT1 | DI10L | NCOR1 |
| ATP6V0D2 | NCF2 | DMD | NCRNA00157 |
| ATXN1 | NCOR1 | EDA | NRXN3 |
| BAHD1 | NHSL2 | EFHC1 | PARP16 |
| BBX | NKAIN2 | EFS | PLA2G2F |
| BCA10 | NR3C1 | EIF2C2 | PLEK2 |
| C15orf23 | NUP188 | ENTPD2 | PRKCH |
| C15orf33 | OSBPL10 | EYS | PTPRS |
| C21orf29 | PACSIN1 | FAM160A1 | ROBO1 |
| C2CD3 | PARP16 | MUSK | SASH3 |
| C6orf170 | PDZRN4 | NEUROG1 | SH3BP5 |
| C7orf44 | POLM | NHSL2 | SLC44A2 |
| CACNA1C | PPP1R3A | NR3C1 | SLC5A4 |
| CACNA1G | PSEN1 | ODZ1 | SNX5 |
| FAM168A | PTPRD | PCDH12 | SORCS2 |
| FAM172A | PTPRS | PLCL1 | SRRM1 |
| FAM192A | RALYL | PLEKHM3 | SSX3 |
| FAM19A2 | RERE | PLOD3 | STAG2 |
| FBXL4 | RIMBP2 | PRKCH | STK24 |
| FH | RNF216 | PSEN1 | SURF6 |
| FREM2 | SDAD1 | SEPT5 | SYNPO2 |
| GAPVD1 | SEC14L3 | SLC44A2 | TAF1 |
| GLI3 | SH3RF3 | SNTA1 | TMEM80 |
| GPR182 | SLC9A1 | USP48 | TNFRSF10B |
| GSTA3 | SMOC2 | VSNL1 | TTYH1 |
| IGFBP3 | SNX5 | WDFY1 | UNC93B1 |
| ITGA9 | TACC2 | WISP2 | VSNL1 |
| ITGB2 | SRGAP1 | XRRA1 | XRCC4 |
| JOSD2 | SSX3 | LRRC4B | ZNF410 |
| KIDINS220 | SUMF1 | LRRK2 | TRIOBP |
| LAMA2 | SYNPO2 | MAPKAP1 | TTYH1 |
| LCLAT1 | TNFRSF10B | MST1R | LRBA |
| LIN9 | | | |

| EGFR-SEPT14 | | | | |
|---|---|---|---|---|
| Sample | Fusion Bp | Exon25-26 | Exon26-27 | Exon27-28 |
| TCGA-28-2513 | 1464 | 21 | 12 | 25 |
| TCGA-27-1837 | 796 | 6 | 5 | 6 |
| TCGA-06-0750 | 414 | 69 | 61 | 101 |
| TCGA-32-5222 | 495 | 256 | 190 | 348 |
| TCGA-28-1747 | 142 | 426 | 300 | 502 |
| TCGA-06-2557 | 13 | 1031 | 657 | 1254 |

| EGFR-PSPH | | | | |
|---|---|---|---|---|
| Sample | Fusion Bp | Exon25-26 | Exon26-27 | Exon27-28 |
| TCGA-28-5209 | 5648 | 216 | 122 | 232 |
| TCGA-06-5408 | 37 | 232 | 200 | 292 |
| TCGA-28-5215 | 28 | 29 | 26 | 44 |

Fig. 30

| sample | split reads | Gene 5p | Chr 5p | Sense 5p | Start 5p | End 5p | Break-point 5p | Exon Before Break-point 5p |
|---|---|---|---|---|---|---|---|---|
| TCGA-06-0750-01A-01D-1492-08 | 51 | EGFR | chr7 | + | 55054218 | 55268221 | 55268221 | 24 |
| TCGA-27-1837-01A-01D-1494-08 | 648 | EGFR | chr7 | + | 55086724 | 55268937 | 55268937 | 24 |
| TCGA-28-2513-01A-01D-1494-08 | 378 | EGFR | chr7 | + | 55086724 | 55269001 | 55269001 | 24 |
| TCGA-06-5411-01A-01D-1696-08 | 676 | NFASC | chr1 | + | 204797781 | 204951827 | 204951827 | 21 |
| TCGA-32-5222-01A-01D-1486-08 | 0 | EGFR | chr7 | + | 55086724 | N/A | N/A | N/A |
| TCGA-28-5209-01A-01D-1486-08 | 0 | EGFR | chr7 | + | 55086724 | N/A | N/A | N/A |

Fig. 31

| sample | Gene 3p | Chr 3p | Sense 3p | Start 3p | End 3p | Break-point 3p | Exon After Break-point 3p |
|---|---|---|---|---|---|---|---|
| TCGA-06-0750-01A-01D-1492-08 | SEPT14 | chr7 | - | 55828730 | 55871487 | 55871487 | 10 |
| TCGA-27-1837-01A-01D-1494-08 | SEPT14 | chr7 | - | 55861236 | 55870909 | 55870909 | 10 |
| TCGA-28-2513-01A-01D-1494-08 | SEPT14 | chr7 | - | 55861236 | 55871369 | 55871369 | 10 |
| TCGA-06-5411-01A-01D-1696-08 | NTRK1 | chr1 | + | 156844170 | 156851642 | 156844170 | 10 |
| TCGA-32-5222-01A-01D-1486-08 | SEPT14 | chr7 | - | 55861236 | N/A | N/A | N/A |
| TCGA-28-5209-01A-01D-1486-08 | PSPH | chr7 | - | 56078743 | N/A | N/A | N/A |

| sample | split inserts | posA 5p | posB 5p | Read Dir 5p | posA 3p | posB 3p | Read Dir 3p |
|---|---|---|---|---|---|---|---|
| TCGA-06-0750-01A-01D-1492-08 | 17 | 55242336 | 55268011 | Fwd | 55871183 | 55871412 | Fwd |
| TCGA-27-1837-01A-01D-1494-08 | 505 | 55268346 | 55268884 | Fwd | 55870367 | 55870871 | Fwd |
| TCGA-28-2513-01A-01D-1494-08 | 251 | 55268377 | 55268962 | Fwd | 55871008 | 55871339 | Fwd |
| TCGA-06-5411-01A-01D-1696-08 | 131 | 204951788 | 204951826 | Fwd | 156844171 | 156844232 | Rev |
| TCGA-32-5222-01A-01D-1486-08 | 1 | 55268015 | 55268015 | Fwd | 55872287 | 55872287 | Fwd |
| TCGA-28-5209-01A-01D-1486-08 | 1 | 55198162 | 55198162 | Rev | 56087184 | 56087184 | Fwd |

Fig. 31 Cont.

| Isoform | EGFR-SEPT14 | EGFR-PSPH | Non-Fusion | Total |
|---|---|---|---|---|
| EGFRvIII | 1 | 1 | 14 | 16 |
| No EGFRvIII | 5 | 2 | 64 | 71 |
| Total | 6 | 3 | 78 | 87 |

Fig. 32

| | Classical | Mesenchymal | Proneural | Neural |
|---|---|---|---|---|
| EGFR Fusion | 3 | 5 | 1 | 0 |
| No Fusion | 37 | 47 | 38 | 0 |
| Total | 40 | 52 | 39 | 28 |

Fig. 33

| B-III Tubulin | Mouse | 1:400 | Promega |
|---|---|---|---|
| δ-Catenin | Guinea Pig | 1:500 | Acris |
| Fibronectin | Mouse | 1:1000 | BD-Pharmingen |
| Col5A1 | Rabbit | 1:200 | Santa Cruz Biotech |
| PSD-95 | Rabbit | 1:500 | Invitrogen |
| Smooth muscle actin | Mouse | 1:200 | Sigma |

Fig. 34

| | | | |
|---|---|---|---|
| Anti-Vinculin | Mouse | 1:400 | SIGMA |
| Anti-N-Cadherin | Mouse | 1:200 | BD-Pharmingen |
| Cyclin A | Rabbit | 1:500 | Santa Cruz Biotech |
| p27 | Mouse | 1:250 | BD Transduction |
| B-III Tubulin | Mouse | 1:400 | Promega |
| δ-Catenin | Guinea Pig | 1:500 | Acris |
| Fibronectin | Mouse | 1:1000 | BD-Pharmingen |
| p107 | Rabbit | 1:1000 | Santa Cruz Biotech |
| Nestin | Mouse | 1:500 | BD-Pharmingen |
| CD133 | Rabbit | 1:200 | Abcam |
| Sox2 | Rabbit | 1:500 | Cell Signaling |
| EGFR | Mouse | 1:1000 | Millipore |
| AKT | Rabbit | 1:1000 | Cell Signaling |
| pAKT-S473 | Rabbit | 1:1000 | Cell Signaling |
| ERK1/2 | Rabbit | 1:1000 | Cell Signaling |
| pERK1/2 | Rabbit | 1:1000 | Cell Signaling |
| STAT3 | Rabbit | 1:1000 | Santa Cruz Biotech |
| pSTAT3-Y705 | Rabbit | 1:1000 | Cell Signaling |
| LZTR1 | Rabbit | 1:1000 | Abcam |
| Cul3 | Rabbit | 1:1000 | Bethyl |

Fig. 35

| Primer | SEQ ID NO: | Sequence |
|---|---|---|
| hEGFR-RT-FW1 | 32 | 5'- GGGTGACTGTTTGGGAGTTGATG -3 |
| hSEP14-RT-REV1 | 33 | 5'- TGTTTGTCTTTCTTTGTATCGGTGC-3' |
| hEGFR-RT-FW1 | 87 | 5'-AGAGGTGACCACCAATCAGC-3' |
| hPSPH-RT-REV1 | 88 | 5'-CGTGTCCCACACAGAGACAG-3' |
| hNFASC-RT-FW1 | 36 | 5'- AGTTCCGTGTCATTGCCATCAAC-3' |
| hNTRK1-RT-REV1 | 37 | 5'- TGTTTCGTCCTTCTTCTCCACCG-3' |
| hCAND1-RT-FW1 | 38 | 5'- GGAAAAAATGACATCCAGCGAC-3' |
| hEGFR-RT-REV1 | 39 | 5'- TGGGTGTAAGAGGCTCCACAAG-3' |

Fig. 36

| Primer | SEQ ID NO: | Sequence |
|---|---|---|
| genomic EGFR-FW1 | 40 | 5'- GGATGATAGACGCAGATAGTCGCC-3' |
| genomic SEPT14-REV1 | 41 | 5'- TCCAGTTGTTTTTTCTCTTCCTCG-3' |
| genomic NFASC-FW1 | 12 | 5'- TCCGAGTCCAGGCTGAAAATG-3' |
| genomic NTRK1-REV1 | 89 | 5'- CTACTTCCTATCTCACCCCAAAAGG-3' |
| genomic CAND1-FW1 | 44 | 5'- GCAATAGCAAAACAGGAAGATGTC-3' |
| genomic EGFR-REV1 | 45 | 5'- GAACACTTACCCATTCGTTGG-3' |

Fig. 37

| Primer | SEQ ID NO: | Sequence |
|---|---|---|
| LZTR1 FW | 90 | 5'- TCCCACATCTCAGACAAGCA-3' |
| His-Tag REV | 91 | 5'- TCAATGGTGATGGTGATGATG-3' |
| GAPDH FW | 92 | 5'- GAAGGTGAAGGTCGGAGTCAAC-3' |
| GAPDH REV | 93 | 5'- CAGAGTTAAAAGCAGCCCTGGT-3' |

Fig. 38

FUSION PROTEINS AND METHODS THEREOF

This application is a divisional of U.S. patent application Ser. No. 14/853,568 filed on Sep. 14, 2015, which is a continuation of PCT International Application No. PCT/US2014/026351 filed on Mar. 13, 2014, which claims the benefit of and priority to U.S. Provisional Patent Application No. 61/793,086, filed on Mar. 15, 2013, the content of each of which are hereby incorporated by reference in their entireties.

GOVERNMENT SUPPORT

This invention was made with government support under grant CA101644 awarded by the National Institutes of Health. The Government has certain rights in the invention.

All patents, patent applications and publications cited herein are hereby incorporated by reference in their entirety. The disclosures of these publications in their entireties are hereby incorporated by reference into this application.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted electronically in ASCII format and is hereby incorporated by reference in its entirety. Said ASCII copy, created on Feb. 1, 2019, is named 19240_1034_US3_SL.txt and is 2,207,842 bytes in size.

BACKGROUND OF THE INVENTION

Glioblastoma multiforme (GBM) is the most common form of brain cancer and among the most incurable and lethal of all human cancers. The current standard of care includes surgery, chemotherapy, and radiation therapy. However, the prognosis of GBM remains uniformly poor. There are few available targeted therapies and none that specifically target GBM.

The target population of GBM patients who may carry EGFR gene fusions and would benefit from targeted inhibition of EGFR kinase activity is estimated to correspond to 6,000 patients per year world-wide.

SUMMARY OF THE INVENTION

The invention is based, at least in part, on the discovery of a highly expressed class of gene fusions in GBM, which join the receptor tyrosine kinase (RTK) domain of EGFR genes to the coiled-coil domain of septin proteins, such as Septin-14, or fused to a polypeptide comprising a phosphoserine phosphatase (PSPH) protein or a polypeptide comprising a Cullin-associated and neddylation-dissociated (CAND) protein. The invention is based, at least in part, on the finding that EGFR-SEPT fusions, EGFR-PSPH fusions, and EGFR-CAND fusions identify a subset of GBM patients who will benefit from targeted inhibition of the tyrosine kinase activity of EGFR. Identification of fusions of EGFR genes in glioblastoma patients are useful therapeutic targets.

An aspect of the invention is directed to a purified fusion protein comprising a tyrosine kinase domain of an EGFR protein fused to a polypeptide that constitutively activates the tyrosine kinase domain of the EGFR protein. In one embodiment, the purified fusion protein is essentially free of other human proteins.

An aspect of the invention is directed to a purified fusion protein comprising the tyrosine kinase domain of an EGFR protein fused 5' to a polypeptide comprising the coiled-coil domain of a Septin protein. In one embodiment, the Septin protein is Septin-1, Septin-2, Septin-3, Septin-4, Septin-5, Septin-6, Septin-7, Septin-8, Septin-9, Septin-10, Septin-11, Septin-12, Septin-13, or Septin-14. In another embodiment, the Septin protein is Septin-14 (SEPT14). In another embodiment, the purified fusion protein is essentially free of other human proteins.

An aspect of the invention is directed to a purified fusion protein comprising the tyrosine kinase domain of an EGFR protein fused 5' to a polypeptide comprising a phosphoserine phosphatase (PSPH) protein. In another embodiment, the purified fusion protein is essentially free of other human proteins.

An aspect of the invention is directed to a purified fusion protein comprising the tyrosine kinase domain of an EGFR protein fused 3' to a polypeptide comprising a Cullin-associated and neddylation-dissociated (CAND) protein. In one embodiment, the CAND protein is CAND1, CAND2, or CAND3. In another embodiment, the purified fusion protein is essentially free of other human proteins.

An aspect of the invention is directed to a purified fusion protein encoded by an EGFR-SEPT14 nucleic acid, wherein EGFR-SEPT14 comprises a combination of exons 1-25 of EGFR located on human chromosome 7p11.2 spliced 5' to a combination of exons 7-10 of SEPT14 located on human chromosome 7, wherein a genomic breakpoint occurs in any one of exons 1-25 of EGFR and any one of exons 7-10 of SEPT14. In another embodiment, the purified fusion protein is essentially free of other human proteins.

An aspect of the invention is directed to a purified fusion protein encoded by an EGFR-PSPH nucleic acid, wherein EGFR-PSPH comprises a combination of exons 1-25 of EGFR located on human chromosome 7p12 spliced 5' to a combination of exons 1-10 of PSPH located on human chromosome 7p11.2, wherein a genomic breakpoint occurs in any one of exons 1-25 of EGFR and any one of exons 1-10 of PSPH. In another embodiment, the purified fusion protein is essentially free of other human proteins.

An aspect of the invention is directed to a purified fusion protein encoded by an EGFR-CAND1 nucleic acid, wherein EGFR-CAND1 comprises a combination of exons 1-25 of EGFR located on human chromosome 7p12 spliced 3' to a combination of exons 1-16 of CAND1 located on human chromosome 12q14, wherein a genomic breakpoint occurs in any one of exons 1-25 of EGFR and any one of exons 1-16 of CAND1. In another embodiment, the purified fusion protein is essentially free of other human proteins.

An aspect of the invention is directed to a synthetic nucleic acid encoding the EGFR fusion proteins described above.

An aspect of the invention is directed to a purified EGFR-SEPT14 fusion protein comprising SEQ ID NO: 1 or 5. In one embodiment, the purified fusion protein is essentially free of other human proteins.

An aspect of the invention is directed to a purified EGFR-SEPT14 fusion protein having a genomic breakpoint comprising SEQ ID NO: 4. In another embodiment, the purified fusion protein is essentially free of other human proteins.

An aspect of the invention is directed to a purified EGFR-PSPH fusion protein comprising SEQ ID NO: 7 or 11. In another embodiment, the purified fusion protein is essentially free of other human proteins.

An aspect of the invention is directed to a purified EGFR-PSPH fusion protein having a genomic breakpoint comprising SEQ ID NO: 10. In one embodiment, the purified fusion protein is essentially free of other human proteins.

An aspect of the invention is directed to a purified EGFR-CAND1 fusion protein comprising SEQ ID NO: 13 or 8495. In one embodiment, the purified fusion protein is essentially free of other human proteins.

An aspect of the invention is directed to a purified EGFR-CAND1 fusion protein having a genomic breakpoint comprising SEQ ID NO: 15. In one embodiment, the purified fusion protein is essentially free of other human proteins.

An aspect of the invention is directed to a synthetic nucleic acid encoding an EGFR-SEPT14 fusion protein comprising SEQ ID NO: 2.

An aspect of the invention is directed to a synthetic nucleic acid encoding an EGFR-SEPT14 fusion protein having a genomic breakpoint comprising SEQ ID NO: 4.

An aspect of the invention is directed to a synthetic nucleic acid encoding an EGFR-PSPH fusion protein comprising SEQ ID NO: 8.

An aspect of the invention is directed to a synthetic nucleic acid encoding an EGFR-PSPH fusion protein having a genomic breakpoint comprising SEQ ID NO: 10.

An aspect of the invention is directed to a synthetic nucleic acid encoding an EGFR-CAND1 fusion protein comprising SEQ ID NO: 14.

An aspect of the invention is directed to a synthetic nucleic acid encoding an EGFR-CAND1 fusion protein having a genomic breakpoint comprising SEQ ID NO: 15.

An aspect of the invention is directed to an antibody or antigen-binding fragment thereof that specifically binds to a purified fusion protein comprising a tyrosine kinase domain of an EGFR protein fused to a polypeptide that constitutively activates the tyrosine kinase domain of the EGFR protein. In one embodiment, the fusion protein is an EGFR-SEPT fusion protein, an EGFR-PSPH fusion protein, or an EGFR-CAND fusion protein. In another embodiment, the EGFR-SEPT fusion protein is EGFR-SEPT14. In one embodiment, the EGFR-SEPT fusion protein comprises the amino acid sequence of SEQ ID NO: 1, 3, or 5. In one embodiment, the EGFR-CAND fusion protein is EGFR-CAND1. In one embodiment, the EGFR-CAND fusion protein comprises the amino acid sequence of SEQ ID NO: 13, 16, or 8495.

An aspect of the invention is directed to an antibody or antigen-binding fragment thereof that specifically binds to a purified fusion protein comprising a tyrosine kinase domain of an EGFR protein fused to a polypeptide comprising the coiled-coil domain of a Septin protein. In another embodiment, the EGFR-SEPT fusion protein is EGFR-SEPT14. In one embodiment, the EGFR-SEPT fusion protein comprises the amino acid sequence of SEQ ID NO: 1, 3, or 5.

An aspect of the invention is directed to an antibody or antigen-binding fragment thereof that specifically binds to a purified fusion protein comprising a tyrosine kinase domain of an EGFR protein fused to a polypeptide comprising a phosphoserine phosphatase (PSPH) protein. In one embodiment, the EGFR-PSPH fusion protein comprises the amino acid sequence of SEQ ID NO: 7, 9, or 11.

An aspect of the invention is directed to an antibody or antigen-binding fragment thereof, that specifically binds to a purified fusion protein comprising a tyrosine kinase domain of an EGFR protein fused to a polypeptide comprising a Cullin-associated and neddylation-dissociated (CAND) protein. In one embodiment, the EGFR-CAND fusion protein is EGFR-CAND1. In one embodiment, the EGFR-CAND fusion protein comprises the amino acid sequence of SEQ ID NO: 13, 16, or 8495.

An aspect of the invention is directed to a composition for decreasing the expression level or activity of a fusion protein in a subject comprising the tyrosine kinase domain of an EGFR protein fused to a polypeptide that constitutively activates the tyrosine kinase domain of the EGFR protein, the composition in an admixture of a pharmaceutically acceptable carrier comprising an inhibitor of the fusion protein. In one embodiment, the inhibitor comprises an antibody that specifically binds to an EGFR-SEPT fusion protein, an EGFR-PSPH fusion protein, an EGFR-CAND fusion protein, or a fragment thereof; a small molecule that specifically binds to an EGFR protein; an antisense RNA or antisense DNA that decreases expression of an EGFR-SEPT fusion protein, an EGFR-PSPH fusion protein, an EGFR-CAND fusion; a siRNA that specifically targets an EGFR-SEPT fusion gene, an EGFR-PSPH fusion gene, or an EGFR-CAND; or a combination thereof. In another embodiment, the CAND protein is CAND1. In a further embodiment, the SEPT protein is SEPT14. In some embodiments, the small molecule that specifically binds to an EGFR protein comprises AZD4547, NVP-BGJ398, PD173074, NF449, TK1258, BIBF-1120, BMS-582664, AZD-2171, TSU68, AB1010, AP24534, E-7080, LY2874455, or a combination thereof.

An aspect of the invention is directed to a method for treating a gene-fusion associated cancer in a subject in need thereof, the method comprising administering to the subject an effective amount of an EGFR fusion molecule inhibitor. In one embodiment, the gene-fusion associated cancer comprises glioblastoma multiforme, breast cancer, lung cancer, prostate cancer, or colorectal carcinoma. In one embodiment, the EGFR fusion comprises an EGFR protein fused to a polypeptide that constitutively activates the tyrosine kinase domain of the EGFR protein. In one embodiment, the EGFR fusion protein is an EGFR-SEPT14 fusion protein, an EGFR-PSPH fusion protein, or an EGFR-CAND1 fusion protein. In one embodiment, the inhibitor comprises an antibody that specifically binds to an EGFR-SEPT fusion protein, an EGFR-PSPH fusion protein, an EGFR-CAND fusion protein, or a fragment thereof; a small molecule that specifically binds to an EGFR protein; an antisense RNA or antisense DNA that decreases expression of an EGFR-SEPT fusion protein, an EGFR-PSPH fusion protein, an EGFR-CAND fusion; a siRNA that specifically targets an EGFR-SEPT fusion gene, an EGFR-PSPH fusion gene, or an EGFR-CAND; or a combination thereof. In one embodiment, the small molecule that specifically binds to an EGFR protein comprises AZD4547, NVP-BGJ398, PD173074, NF449, TK1258, BIBF-1120, BMS-582664, AZD-2171, TSU68, AB1010, AP24534, E-7080, LY2874455, or a combination thereof.

An aspect of the invention is directed to a method of decreasing growth of a solid tumor in a subject in need thereof, the method comprising administering to the subject an effective amount of an EGFR fusion molecule inhibitor, wherein the inhibitor decreases the size of the solid tumor. In one embodiment, the subject is afflicted with a gene-fusion associated cancer. In one embodiment, the gene-fusion associated cancer comprises glioblastoma multiforme, breast cancer, lung cancer, prostate cancer, or colorectal carcinoma. In one embodiment, the solid tumor comprises glioblastoma multiforme, breast cancer, lung cancer, prostate cancer, or colorectal carcinoma. In one embodiment, the EGFR fusion comprises an EGFR protein fused to a polypeptide that constitutively activates the tyrosine kinase domain of the EGFR protein. In one embodiment, the EGFR fusion protein is an EGFR-SEPT14 fusion protein, an EGFR-PSPH fusion protein, or an EGFR-CAND1 fusion protein. In one embodiment, the inhibitor comprises an antibody that specifically binds to an EGFR-SEPT fusion protein, an EGFR-PSPH fusion protein, an EGFR-CAND fusion protein, or a fragment thereof a small molecule that specifically binds to an EGFR protein; an antisense RNA or antisense DNA that decreases expression of an EGFR-SEPT fusion protein, an EGFR-PSPH fusion protein, an EGFR-CAND fusion; a siRNA that specifically targets an EGFR-SEPT fusion gene, an EGFR-PSPH fusion gene, or an EGFR-CAND; or a combination thereof. In one embodiment, the small molecule that specifically binds to an EGFR protein comprises AZD4547, NVP-BGJ398, PD173074, NF449, TK1258, BIBF-1120, BMS-582664, AZD-2171, TSU68, AB1010, AP24534, E-7080, LY2874455, or a combination thereof.

An aspect of the invention is directed to a method of reducing cell proliferation in a subject afflicted with a gene-fusion associated cancer, the method comprising administering to the subject an effective amount of an EGFR fusion molecule inhibitor, wherein the inhibitor decreases cell proliferation. In one embodiment, the gene-fusion associated cancer comprises glioblastoma multiforme, breast cancer, lung cancer, prostate cancer, or colorectal carcinoma. In one embodiment, the EGFR fusion comprises an EGFR protein fused to a polypeptide that constitutively activates the tyrosine kinase domain of the EGFR protein. In one embodiment, the EGFR fusion protein is an EGFR-SEPT14 fusion protein, an EGFR-PSPH fusion protein, or an EGFR-CAND1 fusion protein. In one embodiment, the inhibitor comprises an antibody that specifically binds to an EGFR-SEPT fusion protein, an EGFR-PSPH fusion protein, an EGFR-CAND fusion protein, or a fragment thereof a small molecule that specifically binds to an EGFR protein; an antisense RNA or antisense DNA that decreases expression of an EGFR-SEPT fusion protein, an EGFR-PSPH fusion protein, an EGFR-CAND fusion; a siRNA that specifically targets an EGFR-SEPT fusion gene, an EGFR-PSPH fusion gene, or an EGFR-CAND; or a combination thereof. In one embodiment, the small molecule that specifically binds to an EGFR protein comprises AZD4547, NVP-BGJ398, PD173074, NF449, TK1258, BIBF-1120, BMS-582664, AZD-2171, TSU68, AB1010, AP24534, E-7080, LY2874455, or a combination thereof.

An aspect of the invention is directed to a diagnostic kit for determining whether a sample from a subject exhibits a presence of an EGFR fusion, the kit comprising at least one oligonucleotide that specifically hybridizes to an EGFR fusion, or a portion thereof. In one embodiment, the oligonucleotides comprise a set of nucleic acid primers or in situ hybridization probes. In another embodiment, the oligonucleotide comprises SEQ ID NOS 32, 33, 34, 35, 36, 37, 38, 39, 40, 41, 42, 43, 44, 45, 87, 88, 89, or a combination thereof. In a further embodiment, the primers prime a polymerase reaction only when an EGFR fusion is present. In some embodiments, the fusion protein is an EGFR-SEPT14 fusion protein, an EGFR-PSPH fusion protein, or an EGFR-CAND1 fusion protein. In other embodiments, the determining comprises gene sequencing, selective hybridization, selective amplification, gene expression analysis, or a combination thereof.

An aspect of the invention is directed to a diagnostic kit for determining whether a sample from a subject exhibits a presence of an EGFR fusion protein, the kit comprising an antibody that specifically binds to an EGFR fusion protein comprising SEQ ID NO: 1, 3, 5, 7, 9, 11, 13, 16, or 8495, wherein the antibody will recognize the protein only when an EGFR fusion protein is present. In one embodiment, the fusion protein is an EGFR-SEPT14 fusion protein, an EGFR-PSPH fusion protein, or an EGFR-CAND1 fusion protein. In one embodiment, the subject is afflicted with a gene-fusion associated cancer. In one embodiment, the gene-fusion associated cancer comprises glioblastoma multiforme, breast cancer, lung cancer, prostate cancer, or colorectal carcinoma.

An aspect of the invention is directed to a method for detecting the presence of an EGFR fusion in a human subject. The method comprises obtaining a biological sample from the human subject; and detecting whether or not there is an EGFR fusion present in the subject. In one embodiment, the detecting comprises measuring EGFR fusion protein levels by ELISA using an antibody directed to SEQ ID NO: 1, 3, 5, 7, 9, 11, 13, 16, or 8495; western blot using an antibody directed to SEQ ID NO: 1, 3, 5, 7, 9, 11, 13, 16, or 8495; mass spectroscopy, isoelectric focusing, or a combination thereof.

An aspect of the invention is directed to a method for detecting the presence of an EGFR fusion in a human subject. The method comprises obtaining a biological sample from a human subject; and detecting whether or not there is a nucleic acid sequence encoding an EGFR fusion protein in the subject. In one embodiment, the nucleic acid sequence comprises any one of SEQ ID NOS: 2, 4, 8, 10, 14, and 15. In another embodiment, the detecting comprises using hybridization, amplification, or sequencing techniques to detect an EGFR fusion. In a further embodiment, the amplification uses primers comprising SEQ ID NOS 32, 33, 34, 35, 36, 37, 38, 39, 40, 41, 42, 43, 44, 45, 87, 88, or 89. In some embodiments, the fusion protein is an EGFR-SEPT14 fusion protein, an EGFR-PSPH fusion protein, or an EGFR-CAND1 fusion protein.

BRIEF DESCRIPTION OF THE FIGURES

To conform to the requirements for PCT patent applications, many of the figures presented herein are black and white representations of images originally created in color. In the below descriptions and the examples, the colored plots and images are described in terms of its appearance in black and white. The original color versions can be viewed in Frattini et al., (2013) *Nature Genetics*, 45(10):1141-49 (including the accompanying Supplementary Information available in the on-line version of the manuscript available on the Nature Genetics web site). For the purposes of the PCT, the contents of Frattini et al., (2013) *Nature Genetics*, 45(10):1141-49, including the accompanying "Supplementary Information," are herein incorporated by reference.

FIGS. 2A-B shows Localization of altered residues in LZTR-1. FIG. 2A shows lysates from 293T cells transfected with vectors expressing LZTR-1 and the Flag-Cul3 wild type (WT), Flag-Cul3-dominant negative (DN) or the empty vector were immunoprecipitated with Flag antibody and assayed by western blot with the indicated antibodies. *, non specific band; left bracket indicates Cul3 polypeptides. The molecular weight is indicated on the right. FIG. 2B shows homology model of the Kelch (green; grey in black and white image of left hand side of ribbon diagram), BTB (cyan; (light grey in black and white image of center and right of ribbon diagram) and BACK (purple; dark grey in black and white image of center and right of ribbon diagram) domains of LZTR-1 with the Cul3 N-terminal domain (white) docked onto the putative binding site. GBM mutations are indicated in red (dark grey in black and white image; left hand side of ribbon diagram).

FIG. 4C. EGFR-SEPT14 gene fusion identified by whole transcriptome sequencing. EGFR-Septin14 fusion protein sequence (SEQ ID NO: 5) and schematics. Regions corresponding to EGFR and Septin14 are shown in blue (left hand side of diagram; (grey in black and white image; sequence comprising "MRP . . . VIQ" amino acids of SEQ ID NO: 5) and red (right hand side of diagram; light grey in black and white image; sequence comprising "LQD . . . RKK" amino acids of SEQ ID NO: 5), respectively. The fusion joins the tyrosine kinase domain of EGFR and the Coiled-coil domain of Septin14.

FIG. 5D. Expression of EGFR-SEPT14 fusion promotes an aggressive phenotype and inhibition of EGFR kinase delays GBM growth in vivo. In vivo inhibition of tumor growth by EGFR kinase inhibitors in glioma patient derived xenografts carrying EGFR-SEPT14 fusion but not wild type EGFR. T-C indicates the median difference in survival between drug treated and vehicle (control) treated mice.

FIG. 11C. EGFR-PSPH gene fusion identified by whole transcriptome sequencing. EGFR-PSPH fusion protein sequence (SEQ ID NO: 11) and schematics. Regions corresponding to EGFR and PSPH are shown in blue (grey in black and white image; left hand side of schematic; sequence comprising "MRP . . . VIQ" amino acids of SEQ ID NO: 11) and red (light grey in black and white image; right hand side of schematic, encompassing amino acids "DAF . . . LEE" of SEQ ID NO: 11), respectively. The fusion includes the tyrosine kinase domain of EGFR and the last 35 amino acids of PSPH.

FIG. 12C. NFASC-NTRK1 gene fusion identified by whole transcriptome sequencing. NFASC-NTRK1 fusion protein sequence (SEQ ID NO: 8493) and schematics. Regions corresponding to NFASC and NTRK1 are shown in blue (grey in black and white image; sequence comprising "MAR . . . GED" amino acids) and red (light grey in black and white image; sequence comprising "YTN . . . VLG" amino acids), respectively. The fusion includes two of the five fibronectin-type III domain of neurofascin and the protein kinase domain of NTRK1.

FIG. 14A. CAND1-EGFR gene fusion identified by whole transcriptome sequencing. Split reads are shown aligning on the breakpoint. The predicted reading frame at the breakpoint is shown at the top with CAND1 sequences in blue (grey in black and white image; sequence comprising "TSA . . . LSR" amino acids of SEQ ID NO: 13 and "TTA . . . CAG" nucleotides of SEQ ID NO: 14) and EGFR in red (light grey in black and white image; sequence comprising "CTG . . . VGX" amino acids of SEQ ID NO: 13 and "ATC . . . GGC" nucleotides of SEQ ID NO: 14). The amino acid sequence (TOP) is SEQ ID NO: 13; the nucleotide sequence (bottom) is SEQ ID NO: 14.

FIG. 14C. CAND1-EGFR gene fusion identified by whole transcriptome sequencing. CAND1-EGFR fusion protein sequence (SEQ ID NO: 8495). Regions corresponding to CAND1 and EGFR are shown in blue (grey in black and white image; sequence comprising "MAS . . . LSR" amino acids of SEQ ID NO: 8495) and red (grey in black and white image; sequence comprising "CTG . . . IGA*" amino acids of SEQ ID NO: 8495), respectively.

FIG. 18A shows a pattern of expression of δ-catenin in the developing brain, as determined by immunostaining. Double immunofluorescence staining of brain cortex using δ-catenin antibody (red; dark grey in black and white image (center)) and βIII-tubulin (green; light grey in black and white image (right)); Nuclei are counterstained with Dapi (blue; grey in black and white image (Left)). FIG. 18B shows a pattern of expression of δ-catenin in the adult brain, as determined by immunostaining. Upper panels, Double immunofluorescence staining of brain cortex using δ-catenin antibody (red; dark grey in black and white image (center)) and MAP2 (green; light grey in black and white image (right)); Nuclei are counterstained with Dapi (blue; grey in black and white image (Left)). Lower panels, Double immunofluorescence staining of brain cortex using δ-catenin antibody (red; dark grey in black and white image) and GFAP (green; light grey in black and white image); Nuclei are counterstained with Dapi (blue; grey in black and white image).

FIG. 19A is a photographic microscopy image of immunofluorescence for fibronectin, collagen-5α1 (COL5A1) and smooth muscle actin (SMA) in glioma spheres #48 four days after infection with lentiviruses expressing δ-catenin or the empty vector. Nuclei are counterstained with Dapi. FIG. 19B is a bar graph showing the quantification of fluorescence intensity for SMA, COL5A1 and FBN for cultures treated as in a. n=3 independent experiments; data indicate mean±SD.

FIG. 19E shows a linear regression plot of in vitro limiting dilution assay using GBM-derived cells #48 expressing vector or δ-catenin. The frequency of sphere forming cells was 7.42±1.16 and 0.88±0.02 for vector and δ-catenin, respectively (p=0.0098). Error bars are SD. FIG. 19F shows a longitudinal analysis of bioluminescence imaging in mice injected intracranially with GBM-derived line 48 expressing vector or δ-catenin. n=3 mice for vector and 5 for δ-catenin. Data are mean±SEM of photon counts.

FIG. 20A is a graph of a sphere forming assay in the absence of EGF of GBM-derived primary cells (#48) expressing vector, EGFR wild type, EGFR Viii or EGFR-SEP14 fusion. Data are Mean±SD of triplicate samples (p=0.0051 and 0.027 for EGFR-SEP14 fusion and EGFR Viii compared with vector, respectively). FIG. 20B is a western blot analysis of GBM-derived primary cells (#48) expressing vector, EGFR Viii or EGFR-SEP14 fusion cultured in the presence of EGF. FIG. 20C is a photographic image of a blot showing GBM-derived cells (#48) expressing vector, EGFR Viii or EGFR-SEP14 fusion that were cultured in the absence of EGF for 48 h and then stimulated with EGF 20 ng/ml for the indicated time. Cells were assayed by western blot using the indicated antibodies. FIG. 20D is a graph of GSEA showing up-regulation of STAT3 target genes in primary human GBM carrying the EGFR-SEPT14 fusion gene [Enrichment Score (ES)=0.738; P (family-wise error rate, FWER)=0.000 q (false discovery rate, FDR)=0.000]. FIG. 20E is a bar graph showing the survival of GBM-derived cells (#48) expressing vector, EGFR wild type, EGFR Viii or EGFR-SEP14 fusion after treatment with lapatinib for 48 h at the indicated concentrations. Data are Mean±SD of triplicate samples.

FIG. 22A are photographic microscopy images of immunofluorescence staining of human primary GBM included in tissue microarrays (TMA) using δ-catenin antibody (red; dark grey in black and white image); Nuclei are counterstained with Dapi (blue; grey in black and white image). Two representative δ-catenin-positive and two δ-catenin-negative tumors are shown in the upper and lower panels, respectively. FIG. 22B is a Western Blot analysis of the expression of δ-catenin in a panel of GBM-derived glioma sphere cultures. Brain, normal human brain. Arrowhead indicated δ-catenin; Asterisk, non-specific band. Vinculin is shown as control for loading.

FIG. 23A is a western blot using the indicated antibodies in glioma cells expressing δ-catenin or the empty vector. Vinculin is shown as control for loading. FIG. 23B are photographic microscopy images showing U87 glioma cells transduced with a lentivirus expressing wild type δ-catenin, δ-catenin GBM-derived mutants or the empty vector were analyzed by fluorescence microscopy.

FIG. 27 shows gene fusions identified through RNA sequencing.

FIG. 28 shows genomic breakpoints of gene fusions detected through whole-exome DNA sequencing.

FIG. 29 shows that an EGFR fusion molecule can also include a tyrosine kinase domain of an EGFR protein fused to a protein encoded by any one of the genes.

FIG. 30 shows relative expression of EGFR fusion and wild-type transcripts. Expression is estimated using the depth of reads covering the fusion breakpoint or wild-type exon junctions excluded from the fusion transcript. These wild-type exons include exons 25-26, 26-27, and 27-28.

FIG. 31 shows genomic breakpoints of gene fusions detected through whole-exome DNA sequencing.

FIG. 32 shows an analysis of the incidence of EGFR-SEPT14 and EGFR-PSPH gene fusions in GBM harboring or not the EGFRvIII rearrangement.

FIG. 33 shows enrichment of classical/mesenchymal subtype among samples with EGFR-SEPT14 or EGFR-PSPH.

FIG. 34 shows antibodies and concentrations used in immunofluorescence staining.

FIG. 35 shows antibodies and concentrations used for Western blots and immunoprecipitation assays.

FIG. 36 shows primers used for screening gene fusions from cDNA.

FIG. 37 shows primers used for genomic detection of gene fusions.

FIG. 38 shows primers used for semiquantitative RT-PCR to detect exogenous Myc-LZTR1 WT and mutant LZTR1-R801W

DETAILED DESCRIPTION OF THE INVENTION

Figure 1A:
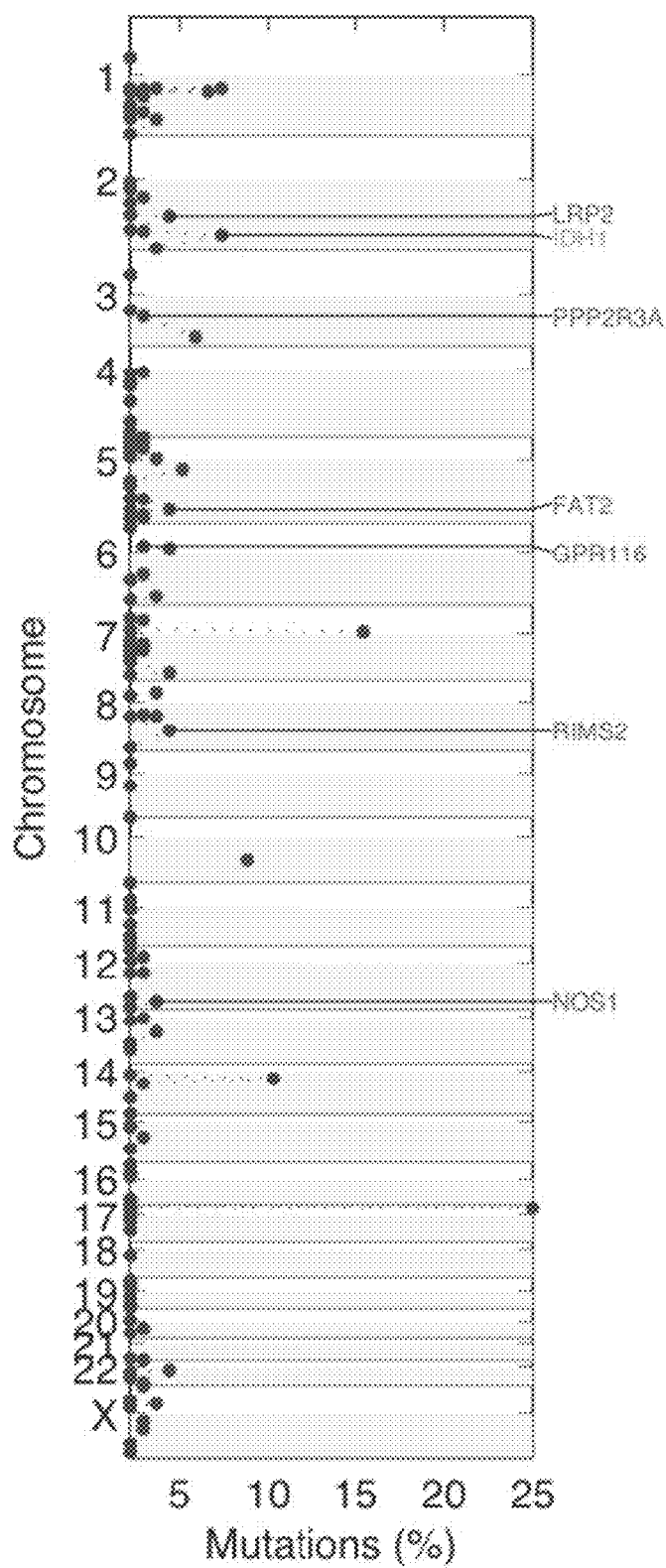
FIG. 1A is a chromosome view of validated GBM genes scoring at the top of each of the three categories by MutComFocal. The plot shows mutated genes without significant copy number alterations (Mut, mutation %, frequency of mutations). Previously known GBM genes are indicated in green (light grey in black and white image), new and independently validated GBM genes are indicated in red (dark grey in black and white image).

Gene fusions retaining the RTK-coding domain of EGFR are the most frequent gene fusion events in GBM. EGFR gene fusions occur in 7.6% of GBM patients and frequently implicate the Sept14 gene as the 3' partner in the fusion, with a consistent breakpoint at the RNA level. This makes the EGFR fusions highly manageable genetic alterations both diagnostically and therapeutically. In one embodiment, EGFR fusions enhance the proliferative and migratory capacity of glioma cells. In another embodiment, the EGFR fusions also confer sensitivity to EGFR inhibition to human GBM grown as mouse xenografts. Gene fusions encompassing RTK-coding genes are thus implicated in the pathogenesis of GBM and provide a strong rationale for the inclusion of GBM patients harboring EGFR fusions in clinical trials based on EGFR inhibitors. The target population of GBM patients who may carry EGFR gene fusions can benefit from targeted inhibition of EGFR kinase activity, and is estimated to correspond to 20,000 patients per year world-wide (~1,000 in USA/year).

Glioblastoma multiformes (GBMs) are the most common form of brain tumors in adults accounting for 12-15% of intracranial tumors and 50-60% of primary brain tumors. GBM is among the most lethal forms of human cancer. The history of successful targeted therapy of cancer largely coincides with the inactivation of recurrent and oncogenic gene fusions in hematological malignancies and recently in some types of epithelial cancer. GBM is among the most lethal and incurable forms of human cancer. Targeted therapies against common genetic alterations in GBM have not changed the dismal clinical outcome of the disease, most likely because they have systematically failed to eradicate the truly addicting oncoprotein activities of GBM. Recurrent chromosomal rearrangements resulting in the creation of oncogenic gene fusions have not been found in GBM.

GBM is among the most difficult forms of cancer to treat in humans (1). So far, the therapeutic approaches that have been tested against potentially important oncogenic targets in GBM have met limited success (2-4). Recurrent chromosomal translocations leading to production of oncogenic fusion proteins are viewed as initiating and addicting events in the pathogenesis of human cancer, thus providing the most desirable molecular targets for cancer therapy (5, 6). Recurrent and oncogenic gene fusions have not been found in GBM. Chromosomal rearrangements are hallmarks of hematological malignancies but recently they have also been uncovered in subsets of solid tumors (breast, prostate, lung and colorectal carcinoma) (7, 8). Important and successful targeted therapeutic interventions for patients whose tumors carry these rearrangements have stemmed from the discovery of functional gene fusions, especially when the translocations involve kinase-coding genes (BCR-ABL, EML4-ALK) (9, 10). GBM, the most common malignant brain tumor, remains one of the most challenging forms of cancer to treat. The abundance of passenger mutations and large regions of copy number alterations has complicated the definition of the landscape of driver mutations in glioblastoma.

A hallmark of GBM is rampant chromosomal instability (CIN), which leads to aneuploidy (11). CIN and aneuploidy are early events in the pathogenesis of cancer (12). Without being bound by theory, genetic alterations targeting mitotic fidelity might be responsible for missegregation of chromosomes during mitosis, resulting in aneuploidy (13, 14).

Epidermal growth factor receptors (EGFR) are transmembrane glycoproteins and members of the protein kinase superfamily. This protein is a receptor for members of the epidermal growth factor family. EGFR is a cell surface protein that binds to epidermal growth factor. Binding of the protein to a ligand induces receptor dimerization and tyrosine autophosphorylation and leads to cell proliferation. Mutations that lead to EGFR overexpression or overactivity have been associated with a number of cancers, including lung cancer, anal cancers and glioblastoma multiforme.

Phosphoserine phosphatase (PSPH) is an enzyme responsible for the third and last step in L-serine formation. It catalyzes magnesium-dependent hydrolysis of L-phosphoserine and is also involved in an exchange reaction between L-serine and L-phosphoserine. Deficiency of this protein is thought to be linked to Williams syndrome.

The singular forms "a," "an," and "the" include plural reference unless the context clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

DNA and Amino Acid Manipulation Methods and Purification Thereof

The practice of aspects of the present invention can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., *Molecular Cloning A Laboratory Manual*, 3$^{rd}$ Ed., ed. by Sambrook (2001), Fritsch and Maniatis (Cold Spring Harbor Laboratory Press: 1989); *DNA Cloning, Volumes I and II* (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription and Translation* (B. D. Hames & S. J. Higgins eds. 1984); *Culture Of Animal Cells* (R. I. Freshney, Alan R. Liss, Inc., 1987); *Immobilized Cells and Enzymes* (IRL Press, 1986); B. Perbal, *A Practical Guide To Molecular Cloning* (1984); the series, *Methods In Enzymology* (Academic Press, Inc., N.Y.), specifically, *Methods In Enzymology*, Vols. 154 and 155 (Wu et al. eds.); *Gene Transfer Vectors For Mammalian Cells* (J. H. Miller and M. P. Calos eds., 1987, Cold Spring Harbor Laboratory); *Immunochemical Methods In Cell And Molecular Biology* (Caner and Walker, eds., Academic Press, London, 1987); *Handbook Of Experimental Immunology*, Volumes I-IV (D. M. Weir and C. C. Black-well, eds., 1986); *Manipulating the Mouse Embryo*, (Cold Spring Harbor Laboratory Press, Cold Spring Harbor, N.Y., 1986). All patents, patent applications and references cited herein are incorporated by reference in their entireties.

One skilled in the art can obtain a protein in several ways, which include, but are not limited to, isolating the protein via biochemical means or expressing a nucleotide sequence encoding the protein of interest by genetic engineering methods.

A protein is encoded by a nucleic acid (including, for example, genomic DNA, complementary DNA (cDNA), synthetic DNA, as well as any form of corresponding RNA). For example, it can be encoded by a recombinant nucleic acid of a gene. The proteins of the invention can be obtained from various sources and can be produced according to various techniques known in the art. For example, a nucleic acid that encodes a protein can be obtained by screening DNA libraries, or by amplification from a natural source. A protein can be a fragment or portion thereof. The nucleic acids encoding a protein can be produced via recombinant DNA technology and such recombinant nucleic acids can be prepared by conventional techniques, including chemical synthesis, genetic engineering, enzymatic techniques, or a combination thereof. For example, a fusion protein of the invention comprises a tyrosine kinase domain of an EGFR protein fused to a polypeptide that constitutively activates the tyrosine kinase domain of the EGFR protein. For example, the fusion protein can be an EGFR-SEPT fusion protein, an EGFR-PSPH fusion protein, or an EGFR-CAND fusion protein. An example of an EGFR-SEPT fusion protein is EGFR-SEPT14. In one embodiment, an EGFR-SEPT14 fusion polypeptide can have the amino acid sequence shown in SEQ ID NO: 1, 3, or 5. An example of an EGFR-PSPH fusion protein is a polypeptide having the amino acid sequence shown in SEQ ID NO: 7, 9, or 11. An example of an EGFR-CAND fusion protein is EGFR-CAND1. In one embodiment, an EGFR-CAND1 fusion polypeptide can have the amino acid sequence shown in SEQ ID NO: 13, 16, or 8495.

The Genbank ID for the EGFR gene is 1956. Four isoforms are listed for EGFR, e.g., having Genebank Accession Nos. NP_005219 (corresponding nucleotide sequence NM_005228); NP_958439 (corresponding nucleotide sequence NM_201282); NP_958440 (corresponding nucleotide sequence NM_201283); NP_958441 (corresponding nucleotide sequence NM_201284). The nucleotide and amino acid sequences can be readily obtained by one of ordinary skill in the art using the listed accession numbers.

The Genbank ID for the SEPT14 gene is 346288. The Genebank Accession No. for SEPT14 is NP_997249 (corresponding nucleotide sequence NM_207366). The nucleotide and amino acid sequences can be readily obtained by one of ordinary skill in the art using the listed accession numbers.

The Genbank ID for the PSPH gene is 5723. The Genebank Accession No. for PSPH is NP_004568 (corresponding nucleotide sequence NM_004577). The nucleotide and amino acid sequences can be readily obtained by one of ordinary skill in the art using the listed accession numbers.

The Genbank ID for the CAND1 gene is 55832. The Genebank Accession No. for CAND1 is NP_060918 (corresponding nucleotide sequence NM_018448). The nucleotide and amino acid sequences can be readily obtained by one of ordinary skill in the art using the listed accession numbers.

As used herein, an "EGFR fusion molecule" can be a nucleic acid which encodes a polypeptide corresponding to a fusion protein comprising a tyrosine kinase domain of an EGFR protein fused to a polypeptide that constitutively activates the tyrosine kinase domain of the EGFR protein. For example, an EGFR fusion molecule can include an EGFR-SEPT fusion (e.g., an EGFR-SEPT14 fusion polypeptide comprising the amino acid sequence shown in SEQ ID NO: 1, 3, or 5, or comprising the nucleic acid sequence shown in SEQ ID NO: 2 or 4); an EGFR-PSPH fusion, (e.g., comprising the amino acid sequence shown in SEQ ID NO: 7, 9, or 11, or comprising the nucleic acid sequence shown in SEQ ID NO: 8 or 10), or an EGFR-CAND fusion (e.g., an EGFR-CAND1 fusion polypeptide comprising the amino acid sequence shown in SEQ ID NO: 13, 16, or 8495, or comprising the nucleic acid sequence shown in SEQ ID NO: 14 or 15). For example, an EGFR fusion molecule can include an EGFR-containing fusion comprising the amino acid sequence corresponding to Genebank Accession no. NP_005219, NP_958439, NP_958440, or NP_958441. AN EGFR fusion molecule can also include a tyrosine kinase domain of an EGFR protein fused to a protein encoded by any one of the genes listed in FIG. 29. AN EGFR fusion molecule can include a variant of the above described examples, such as a fragment thereof.

The nucleic acid can be any type of nucleic acid, including genomic DNA, complementary DNA (cDNA), recombinant DNA, synthetic or semi-synthetic DNA, as well as any form of corresponding RNA. A cDNA is a form of DNA artificially synthesized from a messenger RNA template and is used to produce gene clones. A synthetic DNA is free of modifications that can be found in cellular nucleic acids and include, but are not limited to, histones and methylation. For example, a nucleic acid encoding an EGFR fusion molecule can comprise a recombinant nucleic acid encoding such a protein. The nucleic acid can be a non-naturally occurring nucleic acid created artificially (such as by assembling, cutting, ligating or amplifying sequences). It can be double-stranded or single-stranded.

The invention further provides for nucleic acids that are complementary to an EGFR fusion molecule. Complementary nucleic acids can hybridize to the nucleic acid sequence described above under stringent hybridization conditions. Non-limiting examples of stringent hybridization conditions include temperatures above 30° C., above 35° C., in excess of 42° C., and/or salinity of less than about 500 mM, or less than 200 mM. Hybridization conditions can be adjusted by the skilled artisan via modifying the temperature, salinity and/or the concentration of other reagents such as SDS or SSC.

According to the invention, protein variants can include amino acid sequence modifications. For example, amino acid sequence modifications fall into one or more of three classes: substitutional, insertional or deletional variants. Insertions can include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture.

In one embodiment, an EGFR fusion molecule comprises a protein or polypeptide encoded by a nucleic acid sequence encoding an EGFR fusion molecule, such as the sequences shown in SEQ ID NOS: 2, 4, 8, 10, 14, or 15. In some embodiments, the nucleic acid sequence encoding an EGFR fusion molecule is about 70%, about 75%, about 80%, about 85%, about 90%, about 93%, about 95%, about 97%, about 98%, or about 99% identical to SEQ ID NOS: 2, 4, 8, 10, 14, or 15. In another embodiment, the polypeptide can be modified, such as by glycosylations and/or acetylations and/or chemical reaction or coupling, and can contain one or several non-natural or synthetic amino acids. An example of an EGFR fusion molecule is the polypeptide having the amino acid sequence shown in SEQ ID NOS: 1, 3, 5, 7, 9, 11, 13, 16, or 8495. In some embodiments, the EGFR fusion molecule that is a polypeptide is about 70%, about 75%, about 80%, about 85%, about 90%, about 93%, about 95%, about 97%, about 98%, or about 99% identical to SEQ ID NOS: 1, 3, 5, 7, 9, 11, 13, 16, or 8495. In another embodiment, an EGFR fusion molecule can be a fragment of an EGFR fusion protein. For example, the EGFR fusion molecule can encompass any portion of at least about 8 consecutive amino acids of SEQ ID NOS: 1, 3, 5, 7, 9, 11, 13, 16, or 8495. The fragment can comprise at least about 10 amino acids, a least about 20 amino acids, at least about 30 amino acids, at least about 40 amino acids, at least about 50 amino acids, at least about 60 amino acids, or at least about 75 amino acids of SEQ ID NOS: 1, 3, 5, 7, 9, 11, 13, 16, or 8495. Fragments include all possible amino acid lengths between about 8 and about 100 amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. Fragments include all possible amino acid lengths between about 100 and 800 amino acids, for example, lengths between about 125 and 800 amino acids, between about 150 and 800 amino acids, between about 175 and 800 amino acids, between about 200 and 800 amino acids, between about 225 and 800 amino acids, between about 250 and 800 amino acids, between about 275 and 800 amino acids, between about 300 and 800 amino acids, between about 325 and 800 amino acids, between about 350 and 800 amino acids, between about 375 and 800 amino acids, between about 400 and 800 amino acids, between about 425 and 800 amino acids, between about 450 and 800 amino acids, between about 475 and 800 amino acids, between about 500 and 800 amino acids, between about 525 and 800 amino acids, between about 550 and 800 amino acids, between about 575 and 800 amino acids, between about 600 and 800 amino acids, between about 625 and 800 amino acids, between about 650 and 800 amino acids, between about 675 and 800 amino acids, between about 700 and 800 amino acids, between about 725 and 800 amino acids, between about 750 and 800 amino acids, or between about 775 and 800 amino acids.

Chemical Synthesis.

Nucleic acid sequences encoding an EGFR fusion molecule can be synthesized, in whole or in part, using chemical methods known in the art. Alternatively, a polypeptide can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer).

Optionally, polypeptides fragments can be separately synthesized and combined using chemical methods to produce a full-length molecule. For example, these methods can be utilized to synthesize a fusion protein of the invention. In one embodiment, a fusion protein of the invention comprises a tyrosine kinase domain of an EGFR protein fused to a polypeptide that constitutively activates the tyrosine kinase domain of the EGFR protein. For example, the fusion protein can be an EGFR-SEPT fusion protein, an EGFR-PSPH fusion protein, or an EGFR-CAND fusion protein. An example of an EGFR-SEPT fusion protein is EGFR-SEPT14. In one embodiment, an EGFR-SEPT14 fusion polypeptide can have the amino acid sequence shown in SEQ ID NO: 1, 3, or 5. An example of an EGFR-PSPH fusion protein is a polypeptide having the amino acid sequence shown in SEQ ID NO: 7, 9, or 11. An example of an EGFR-CAND fusion protein is EGFR-CAND1. In one embodiment, an EGFR-CAND1 fusion polypeptide can have the amino acid sequence shown in SEQ ID NO: 13, 16, or 8495.

Obtaining, Purifying and Detecting EGFR Fusion Molecules.

A polypeptide encoded by a nucleic acid, such as a nucleic acid encoding an EGFR fusion molecule, or a variant thereof, can be obtained by purification from human cells expressing a protein or polypeptide encoded by such a nucleic acid. Non-limiting purification methods include size exclusion chromatography, ammonium sulfate fractionation, ion exchange chromatography, affinity chromatography, and preparative gel electrophoresis.

A synthetic polypeptide can be substantially purified via high performance liquid chromatography (HPLC), such as ion exchange chromatography (IEX-HPLC). The composition of a synthetic polypeptide, such as an EGFR fusion molecule, can be confirmed by amino acid analysis or sequencing.

Other constructions can also be used to join a nucleic acid sequence encoding a polypeptide/protein of the claimed invention to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Including cleavable linker sequences (i.e., those specific for Factor Xa or enterokinase (Invitrogen, San Diego, Calif.)) between the purification domain and a polypeptide encoded by a nucleic acid of the invention also can be used to facilitate purification. For example, the skilled artisan can use an expression vector encoding 6 histidine residues that precede a thioredoxin or an enterokinase cleavage site in conjunction with a nucleic acid of interest. The histidine residues facilitate purification by immobilized metal ion affinity chromatography, while the enterokinase cleavage site provides a means for purifying the polypeptide encoded by, for example, an EGFR-SEPT, EGFR-CAND, EGFR-PSPH, or EGFR-containing, nucleic acid.

Host cells which contain a nucleic acid encoding an EGFR fusion molecule, and which subsequently express the same, can be identified by various procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a nucleic acid encoding an EGFR fusion molecule can be detected by DNA-DNA or DNA-RNA hybridization or amplification using probes or fragments of nucleic acids encoding the same. In one embodiment, a nucleic acid fragment of an EGFR fusion molecule can encompass any portion of at least about 8 consecutive nucleotides of SEQ ID NOS: 2, 8, or 14. In another embodiment, the fragment can comprise at least about 10 consecutive nucleotides, at least about 15 consecutive nucleotides, at least about 20 consecutive nucleotides, or at least about 30 consecutive nucleotides of SEQ ID NOS: 2, 8, or 14. Fragments can include all possible nucleotide lengths between about 8 and about 100 nucleotides, for example, lengths between about 15 and about 100 nucleotides, or between about 20 and about 100 nucleotides. Nucleic acid amplification-based assays involve the use of oligonucleotides selected from sequences encoding an EGFR fusion molecule nucleic acid, or EGFR fusion molecule nucleic acid to detect transformants which contain a nucleic acid encoding a protein or polypeptide of the same.

Protocols are known in the art for detecting and measuring the expression of a polypeptide encoded by a nucleic acid, such as a nucleic acid encoding an EGFR fusion molecule, using either polyclonal or monoclonal antibodies specific for the polypeptide. Non-limiting examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a polypeptide encoded by a nucleic acid, such as a nucleic acid encoding an EGFR fusion molecule, can be used, or a competitive binding assay can be employed.

Labeling and conjugation techniques are known by those skilled in the art and can be used in various nucleic acid and amino acid assays. Methods for producing labeled hybridization or PCR probes for detecting sequences related to nucleic acid sequences encoding a protein, such as EGFR fusion molecule, include, but are not limited to, oligolabeling, nick translation, end-labeling, or PCR amplification using a labeled nucleotide. Alternatively, nucleic acid sequences, such as nucleic acids encoding an EGFR fusion molecule, can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, and/or magnetic particles.

A fragment can be a fragment of a protein, such as an EGFR fusion protein. For example, a fragment of an EGFR fusion can encompass any portion of at least about 8 consecutive amino acids of SEQ ID NOS: 1, 3, 5, 7, 9, 11, 13, 16, or 8495. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, at least about 75 consecutive amino acids, at least about 80 consecutive amino acids, at least about 85 consecutive amino acids, at least about 90 consecutive amino acids, at least about 95 consecutive amino acids, at least about 100 consecutive amino acids, at least about 200 consecutive amino acids, at least about 300 consecutive amino acids, at least about 400 consecutive amino acids, at least about 500 consecutive amino acids, at least about 600 consecutive amino acids, at least about 700 consecutive amino acids, or at least about 800 consecutive amino acids of SEQ ID NOS: 1, 3, 5, 7, 9, 11, 13, 16, or 8495. Fragments include all possible amino acid lengths between about 8 and 100 about amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids.

Cell Transfection

Host cells transformed with a nucleic acid sequence of interest can be cultured under conditions suitable for the expression and recovery of the protein from cell culture. The polypeptide produced by a transformed cell can be secreted or contained intracellularly depending on the sequence and/or the vector used. Expression vectors containing a nucleic acid sequence, such as a nucleic acid encoding an EGFR fusion molecule, can be designed to contain signal sequences which direct secretion of soluble polypeptide molecules encoded by the nucleic acid. Cell transfection and culturing methods are described in more detail below.

A eukaryotic expression vector can be used to transfect cells in order to produce proteins encoded by nucleotide sequences of the vector, e.g. those encoding an EGFR fusion molecule. Mammalian cells can contain an expression vector (for example, one that contains a nucleic acid encoding a fusion protein comprising a tyrosine kinase domain of an EGFR protein fused to a polypeptide that constitutively activates the tyrosine kinase domain of the EGFR protein) via introducing the expression vector into an appropriate host cell via methods known in the art.

A host cell strain can be chosen for its ability to modulate the expression of the inserted sequences or to process the expressed polypeptide encoded by a nucleic acid, in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

An exogenous nucleic acid can be introduced into a cell via a variety of techniques known in the art, such as lipofection, microinjection, calcium phosphate or calcium chloride precipitation, DEAE-dextran-mediated transfection, or electroporation. Electroporation is carried out at approximate voltage and capacitance to result in entry of the DNA construct(s) into cells of interest (such as glioma cells (cell line SF188), neuroblastoma cells (cell lines IMR-32, SK-N-SH, SH-F and SH-N), astrocytes and the like). Other transfection methods also include modified calcium phosphate precipitation, polybrene precipitation, liposome fusion, and receptor-mediated gene delivery.

Cells that will be genetically engineered can be primary and secondary cells obtained from various tissues, and include cell types which can be maintained and propagated in culture. Non-limiting examples of primary and secondary cells include epithelial cells, neural cells, endothelial cells, glial cells, fibroblasts, muscle cells (such as myoblasts) keratinocytes, formed elements of the blood (e.g., lymphocytes, bone marrow cells), and precursors of these somatic cell types.

Vertebrate tissue can be obtained by methods known to one skilled in the art, such a punch biopsy or other surgical methods of obtaining a tissue source of the primary cell type of interest. In one embodiment, a punch biopsy or removal (e.g., by aspiration) can be used to obtain a source of cancer cells (for example, glioma cells, neuroblastoma cells, and the like). A mixture of primary cells can be obtained from the tissue, using methods readily practiced in the art, such as explanting or enzymatic digestion (for examples using enzymes such as pronase, trypsin, collagenase, elastase dispase, and chymotrypsin). Biopsy methods have also been described in U.S. Pat. No. 7,419,661 and PCT application publication WO 2001/32840, and each are hereby incorporated by reference.

Primary cells can be acquired from the individual to whom the genetically engineered primary or secondary cells are administered. However, primary cells can also be obtained from a donor, other than the recipient, of the same species. The cells can also be obtained from another species (for example, rabbit, cat, mouse, rat, sheep, goat, dog, horse, cow, bird, or pig). Primary cells can also include cells from an isolated or purified vertebrate tissue source grown attached to a tissue culture substrate (for example, flask or dish) or grown in a suspension; cells present in an explant derived from tissue; both of the aforementioned cell types plated for the first time; and cell culture suspensions derived from these plated cells. Secondary cells can be plated primary cells that are removed from the culture substrate and replated, or passaged, in addition to cells from the subsequent passages. Secondary cells can be passaged one or more times. These primary or secondary cells can contain expression vectors having a gene that encodes an EGFR fusion molecule.

Cell Culturing

Various culturing parameters can be used with respect to the host cell being cultured. Appropriate culture conditions for mammalian cells are well known in the art (Cleveland W L, et al., *J Immunol Methods*, 1983, 56(2): 221-234) or can be determined by the skilled artisan (see, for example, *Animal Cell Culture: A Practical Approach* 2nd Ed., Rickwood, D. and Hames, B. D., eds. (Oxford University Press: New York, 1992)). Cell culturing conditions can vary according to the type of host cell selected. Commercially available medium can be utilized. Non-limiting examples of medium include, for example, Minimal Essential Medium (MEM, Sigma, St. Louis, Mo.); Dulbecco's Modified Eagles Medium (DMEM, Sigma); Ham's F10 Medium (Sigma); HyClone cell culture medium (HyClone, Logan, Utah); RPMI-1640 Medium (Sigma); and chemically-defined (CD) media, which are formulated for various cell types, e.g., CD-CHO Medium (Invitrogen, Carlsbad, Calif.).

The cell culture media can be supplemented as necessary with supplementary components or ingredients, including optional components, in appropriate concentrations or amounts, as necessary or desired. Cell culture medium solutions provide at least one component from one or more of the following categories: (1) an energy source, usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, for example linoleic acid; and (5) trace elements, where trace elements are defined as inorganic compounds or naturally occurring elements that can be required at very low concentrations, usually in the micromolar range.

The medium also can be supplemented electively with one or more components from any of the following categories: (1) salts, for example, magnesium, calcium, and phosphate; (2) hormones and other growth factors such as, serum, insulin, transferrin, and epidermal growth factor; (3) protein and tissue hydrolysates, for example peptone or peptone mixtures which can be obtained from purified gelatin, plant material, or animal byproducts; (4) nucleosides and bases such as, adenosine, thymidine, and hypoxanthine; (5) buffers, such as HEPES; (6) antibiotics, such as gentamycin or ampicillin; (7) cell protective agents, for example pluronic polyol; and (8) galactose. In one embodiment, soluble factors can be added to the culturing medium.

The mammalian cell culture that can be used with the present invention is prepared in a medium suitable for the type of cell being cultured. In one embodiment, the cell culture medium can be any one of those previously discussed (for example, MEM) that is supplemented with serum from a mammalian source (for example, fetal bovine serum (FBS)). In another embodiment, the medium can be a conditioned medium to sustain the growth of host cells.

Three-dimensional cultures can be formed from agar (such as Gey's Agar), hydrogels (such as matrigel, agarose, and the like; Lee et al., (2004) *Biomaterials* 25: 2461-2466) or polymers that are cross-linked. These polymers can comprise natural polymers and their derivatives, synthetic polymers and their derivatives, or a combination thereof. Natural polymers can be anionic polymers, cationic polymers, amphipathic polymers, or neutral polymers. Non-limiting examples of anionic polymers can include hyaluronic acid, alginic acid (alginate), carageenan, chondroitin sulfate, dextran sulfate, and pectin. Some examples of cationic polymers include but are not limited to, chitosan or polylysine. (Peppas et al., (2006) *Adv Mater.* 18: 1345-60; Hoffman, A. S., (2002) *Adv Drug Deliv Rev.* 43: 3-12; Hoffman, A. S., (2001) *Ann NY Acad Sci* 944: 62-73). Examples of amphipathic polymers can include, but are not limited to collagen, gelatin, fibrin, and carboxymethyl chitin. Non-limiting examples of neutral polymers can include dextran, agarose, or pullulan. (Peppas et al., (2006) *Adv Mater.* 18: 1345-60; Hoffman, A. S., (2002) *Adv Drug Deliv Rev.* 43: 3-12; Hoffman, A. S., (2001) *Ann NY Acad Sci* 944: 62-73).

Cells to be cultured can harbor introduced expression vectors, such as plasmids. The expression vector constructs can be introduced via transformation, microinjection, transfection, lipofection, electroporation, or infection. The expression vectors can contain coding sequences, or portions thereof, encoding the proteins for expression and production. Expression vectors containing sequences encoding the produced proteins and polypeptides, as well as the appropriate transcriptional and translational control elements, can be generated using methods well known to and practiced by those skilled in the art. These methods include synthetic techniques, in vitro recombinant DNA techniques, and in vivo genetic recombination which are described in J. Sambrook et al., 2001, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

EGFR Fusion Molecule Inhibitors

The invention provides methods for use of compounds that decrease the expression level or activity of an EGFR fusion molecule in a subject. In addition, the invention provides methods for using compounds for the treatment of a gene-fusion associated cancer. In one embodiment, the gene-fusion associated cancer comprises glioblastoma multiforme, breast cancer, lung cancer, prostate cancer, or colorectal carcinoma.

As used herein, an "EGFR fusion molecule inhibitor" refers to a compound that interacts with an EGFR fusion molecule of the invention and modulates its activity and/or its expression. For example, the compound can decrease the activity or expression of an EGFR fusion molecule. The compound can be an antagonist of an EGFR fusion molecule (e.g., an EGFR fusion molecule inhibitor). Some non-limiting examples of EGFR fusion molecule inhibitors include peptides (such as peptide fragments comprising an EGFR fusion molecule, or antibodies or fragments thereof), small molecules, and nucleic acids (such as siRNA or antisense RNA specific for a nucleic acid comprising an EGFR fusion molecule). Antagonists of an EGFR fusion molecule decrease the amount or the duration of the activity of an EGFR fusion protein. In one embodiment, the fusion protein comprises a tyrosine kinase domain of an EGFR protein fused to a polypeptide that constitutively activates the tyrosine kinase domain of the EGFR protein (e.g., EGFR-SEPT (such as EGFR-SEPT14), EGFR-PSPH, or EGFR-CAND (such as EGFR-CAND1)). Antagonists include proteins, nucleic acids, antibodies, small molecules, or any other molecule which decrease the activity of an EGFR fusion molecule.

The term "modulate," as it appears herein, refers to a change in the activity or expression of an EGFR fusion molecule. For example, modulation can cause a decrease in protein activity, binding characteristics, or any other biological, functional, or immunological properties of an EGFR fusion molecule, such as an EGFR fusion protein.

In one embodiment, an EGFR fusion molecule inhibitor can be a peptide fragment of an EGFR fusion protein that binds to the protein itself.

For example, the EGFR fusion polypeptide can encompass any portion of at least about 8 consecutive amino acids of SEQ ID NOS: 1, 3, 5, 7, 9, 11, 13, 16, or 8495. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, at least about 75 consecutive amino acids, at least about 80 consecutive amino acids, at least about 85 consecutive amino acids, at least about 90 consecutive amino acids, at least about 95 consecutive amino acids, at least about 100 consecutive amino acids, at least about 200 consecutive amino acids, at least about 300 consecutive amino acids, at least about 400 consecutive amino acids, at least about 500 consecutive amino acids, at least about 600 consecutive amino acids, at least about 700 consecutive amino acids, or at least about 800 consecutive amino acids of SEQ ID NOS: 1, 3, 5, 7, 9, 11, 13, 16, or 8495. Fragments include all possible amino acid lengths between about 8 and 100 about amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. These peptide fragments can be obtained commercially or synthesized via liquid phase or solid phase synthesis methods (Atherton et al., (1989) *Solid Phase Peptide Synthesis: a Practical Approach*. IRL Press, Oxford, England). The EGFR fusion peptide fragments can be isolated from a natural source, genetically engineered, or chemically prepared. These methods are well known in the art.

An EGFR fusion molecule inhibitor can be a protein, such as an antibody (monoclonal, polyclonal, humanized, chimeric, or fully human), or a binding fragment thereof, directed against an EGFR fusion molecule. An antibody fragment can be a form of an antibody other than the full-length form and includes portions or components that exist within full-length antibodies, in addition to antibody fragments that have been engineered. Antibody fragments can include, but are not limited to, single chain Fv (scFv), diabodies, Fv, and (Fab')$_2$, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) *Ann. Rev. Biomed. Eng.* 2:339-76; Hudson (1998) *Curr. Opin. Biotechnol.* 9:395-402). Antibodies can be obtained commercially, custom generated, or synthesized against an antigen of interest according to methods established in the art (see U.S. Pat. Nos. 6,914,128, 5,780,597, and 5,811,523; Roland E. Kontermann and Stefan Dübel (editors), *Antibody Engineering, Vol. I & II*, (2010) 2nd ed., Springer; Antony S. Dimitrov (editor), *Therapeutic Antibodies: Methods and Protocols (Methods in Molecular Biology)*, (2009), Humana Press;

Benny Lo (editor) *Antibody Engineering: Methods and Protocols* (*Methods in Molecular Biology*), (2004) Humana Press, each of which are hereby incorporated by reference in their entireties). For example, antibodies directed to an EGFR fusion molecule can be obtained commercially from Abcam, Santa Cruz Biotechnology, Abgent, R&D Systems, Novus Biologicals, etc. Human antibodies directed to an EGFR fusion molecule (such as monoclonal, humanized, fully human, or chimeric antibodies) can be useful antibody therapeutics for use in humans. In one embodiment, an antibody or binding fragment thereof is directed against SEQ ID NOS: 1, 3, 5, 7, 9, 11, 13, 16, or 8495.

Inhibition of RNA encoding an EGFR fusion molecule can effectively modulate the expression of an EGFR fusion molecule. Inhibitors are selected from the group comprising: siRNA; interfering RNA or RNAi; dsRNA; RNA Polymerase III transcribed DNAs; ribozymes; and antisense nucleic acids, which can be RNA, DNA, or an artificial nucleic acid.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the DNA sequence encoding an EGFR fusion molecule can be synthesized, e.g., by conventional phosphodiester techniques (Dallas et al., (2006) *Med. Sci. Monit.* 12(4):RA67-74; Kalota et al., (2006) *Handb. Exp. Pharmacol.* 173:173-96; Lutzelburger et al., (2006) *Handb. Exp. Pharmacol.* 173:243-59). Antisense nucleotide sequences include, but are not limited to: morpholinos, 2'-O-methyl polynucleotides, DNA, RNA and the like.

siRNA comprises a double stranded structure containing from about 15 to about 50 base pairs, for example from about 21 to about 25 base pairs, and having a nucleotide sequence identical or nearly identical to an expressed target gene or RNA within the cell. The siRNA comprise a sense RNA strand and a complementary antisense RNA strand annealed together by standard Watson-Crick base-pairing interactions. The sense strand comprises a nucleic acid sequence which is substantially identical to a nucleic acid sequence contained within the target miRNA molecule. "Substantially identical" to a target sequence contained within the target mRNA refers to a nucleic acid sequence that differs from the target sequence by about 3% or less. The sense and antisense strands of the siRNA can comprise two complementary, single-stranded RNA molecules, or can comprise a single molecule in which two complementary portions are base-paired and are covalently linked by a single-stranded "hairpin" area. See also, McMnaus and Sharp (2002) *Nat Rev Genetics*, 3:737-47, and Sen and Blau (2006) *FASEB J.*, 20:1293-99, the entire disclosures of which are herein incorporated by reference.

The siRNA can be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides. One or both strands of the siRNA can also comprise a 3' overhang. As used herein, a 3' overhang refers to at least one unpaired nucleotide extending from the 3'-end of a duplexed RNA strand. For example, the siRNA can comprise at least one 3' overhang of from 1 to about 6 nucleotides (which includes ribonucleotides or deoxyribonucleotides) in length, or from 1 to about 5 nucleotides in length, or from 1 to about 4 nucleotides in length, or from about 2 to about 4 nucleotides in length. For example, each strand of the siRNA can comprise 3' overhangs of dithymidylic acid ("TT") or diuridylic acid ("uu").

siRNA can be produced chemically or biologically, or can be expressed from a recombinant plasmid or viral vector (for example, see U.S. Pat. Nos. 7,294,504 and 7,422,896, the entire disclosures of which are herein incorporated by reference). Exemplary methods for producing and testing dsRNA or siRNA molecules are described in U.S. Patent Application Publication No. 2002/0173478 to Gewirtz, U.S. Pat. No. 8,071,559 to Hannon et al., and in U.S. Pat. No. 7,148,342 to Tolentino et al., the entire disclosures of which are herein incorporated by reference.

In one embodiment, an siRNA directed to a human nucleic acid sequence comprising an EGFR fusion molecule can be generated against any one of SEQ ID NOS: 2, 4, 8, 10, 14, or 15. In another embodiment, an siRNA directed to a human nucleic acid sequence comprising a breakpoint of an EGFR fusion molecule can be generated against any one of SEQ ID NOS: 4, 10, or 15.

RNA polymerase III transcribed DNAs contain promoters, such as the U6 promoter. These DNAs can be transcribed to produce small hairpin RNAs in the cell that can function as siRNA or linear RNAs, which can function as antisense RNA. The EGFR fusion molecule inhibitor can comprise ribonucleotides, deoxyribonucleotides, synthetic nucleotides, or any suitable combination such that the target RNA and/or gene is inhibited. In addition, these forms of nucleic acid can be single, double, triple, or quadruple stranded. (See for example Bass (2001) *Nature*, 411:428-429; Elbashir et al., (2001) *Nature*, 411:494 498; U.S. Pat. No. 6,509,154; U.S. Patent Application Publication No. 2003/0027783; and PCT Publication Nos. WO 00/044895, WO 99/032619, WO 00/01846, WO 01/029058, WO 00/044914).

EGFR fusion molecule inhibitor can be a small molecule that binds to an EGFR fusion protein described herein and disrupts its function. Small molecules are a diverse group of synthetic and natural substances generally having low molecular weights. They can be isolated from natural sources (for example, plants, fungi, microbes and the like), are obtained commercially and/or available as libraries or collections, or synthesized. Candidate small molecules that inhibit an EGFR fusion protein can be identified via in silico screening or high-through-put (HTP) screening of combinatorial libraries according to methods established in the art (e.g., see Potyrailo et al., (2011) *ACS Comb Sci.* 13(6):579-633; Mensch et al., (2009) *J Pharm Sci.* 98(12):4429-68; Schnur (2008) *Curr Opin Drug Discov Devel.* 11(3):375-80; and Jhoti (2007) *Ernst Schering Found Symp Proc.* (3):169-85, each of which are hereby incorporated by reference in their entireties.) Most conventional pharmaceuticals, such as aspirin, penicillin, and many chemotherapeutics, are small molecules, can be obtained commercially, can be chemically synthesized, or can be obtained from random or combinatorial libraries as described below (see, e.g., Werner et al., (2006) *Brief Funct Genomic Proteomic* 5(1):32-6).

Non-limiting examples of EGFR fusion molecule inhibitors include the EGFR inhibitors AZD4547 (see Gavine et al., (2012) *Cancer Res,* 72(8); 2045-56; see also PCT Application Publication No. WO2008/075068, each of which are hereby incorporated by reference in their entireties); NVP-BGJ398 (see Guagnano et al., (2011) *J. Med. Chem.,* 54:7066-7083; see also U.S. Patent Application Publication No. 2008-0312248 A1, each of which are hereby incorporated by reference in their entireties); PD173074 (see Guagnano et al., (2011) *J. Med. Chem.,* 54:7066-7083; see also Mohammadi et al., (1998) *EMBO J.,* 17:5896-5904, each of which are hereby incorporated by reference in their entireties); NF449 (EMD Millipore (Billerica, Mass.) Cat. No. 480420; see also Krejci, (2010) *the Journal of Biological Chemistry,* 285(27):20644-20653, which is hereby incorporated by reference in its entirety); LY2874455 (Active Biochem; see Zhao et al. (2011) *Mol Cancer Ther.* (11): 2200-10; see also PCT Application Publication No. WO 2010129509, each of which are hereby incorporated by reference in their entireties); TKI258 (Dovitinib); BIBF-1120 (Intedanib-Vargatef); BMS-582664 (Brivanib alaninate); AZD-2171 (Cediranib); TSU-68 (Orantinib); AB-1010 (Masitinib); AP-24534 (Ponatinib); and E-7080 (by Eisai). A non-limiting example of an EGFR fusion molecule inhibitor includes the inhibitor KHS101 (Wurdak et al., (2010) *PNAS,* 107(38): 16542-47, which is hereby incorporated by reference in its entirety).

Structures of EGFR fusion molecule inhibitors useful for the invention include, but are not limited to: the EGFR inhibitor AZD4547,

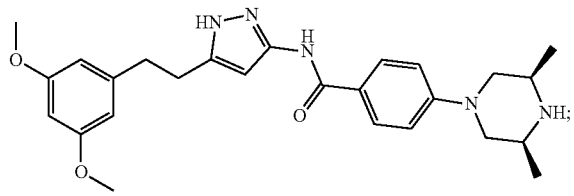 [SMILES: COc1cc(CCc2cc(NC(=O)c3ccc(N4C[C@@H](C)N[C@@H](C)C4)cc3)n[nH]2)cc(OC)c1]

the EGFR inhibitor NVP-BGJ398,

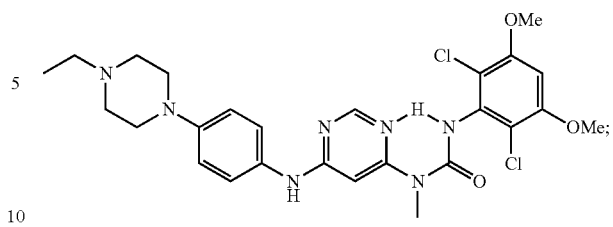

the EGFR inhibitor PD173074,

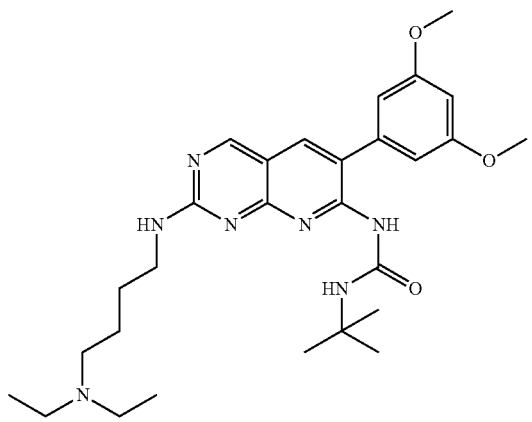 [SMILES: CCN(CC)CCCCNc1ncc2cc(-c3cc(OC)cc(OC)c3)c(NC(=O)NC(C)(C)C)nc2n1]

the EGFR inhibitor LY2874455

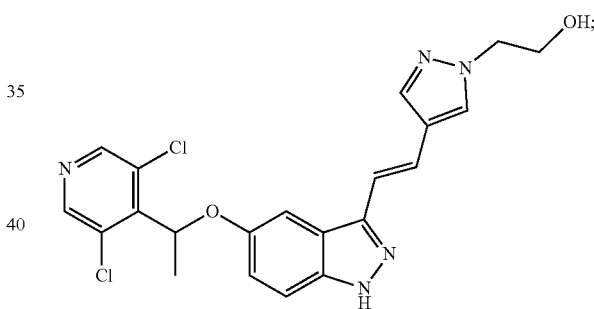

and the EGFR inhibitor NF449 (EMD Millipore (Billerica, Mass.) Cat. No. 480420),

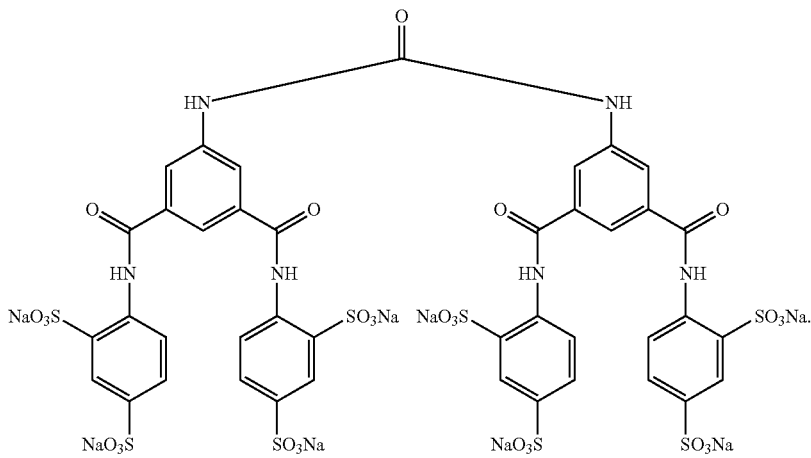

Other EGFR inhibitors include, but are not limited to:

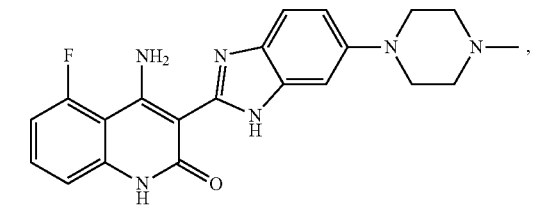

TKI258
Dovitinib
(Novartis)

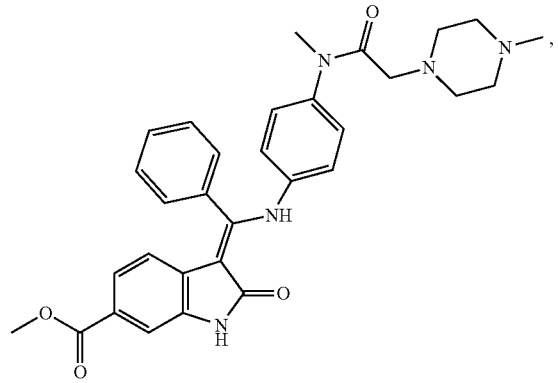

BIBF-1120
Intedanib / Vargatef
(Boehringer Ingelheim)

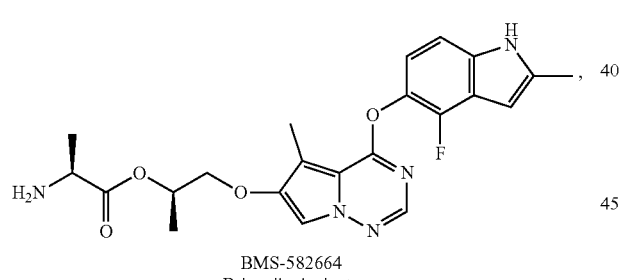

BMS-582664
Brivanib alaninate
(Bristol-Myers Squibb)

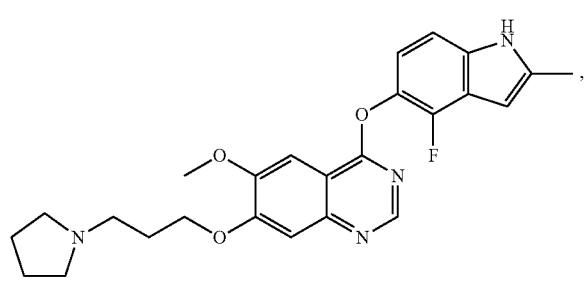

AZD-2171
Cediranib
(AstraZeneca)

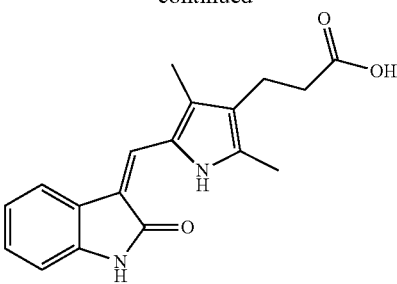

TSU-68
Orantinib
(Taiho Pharmaceutical)

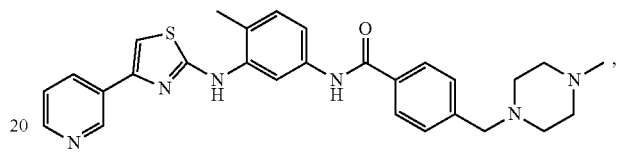

AB-1010
Masitinib
(AB Science)

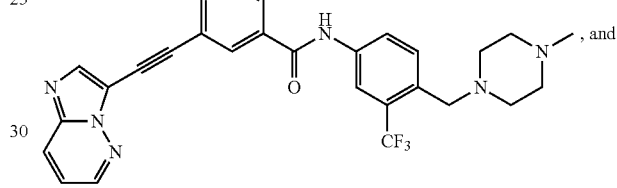

AP-24534
Ponatinib
(Ariad Pharmaceuticals)

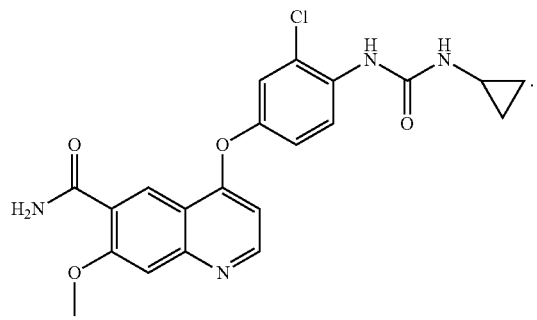

E-7080
(Eisai)

A structure of an EGFR fusion molecule inhibitor useful for the invention includes, but is not limited to the inhibitor KHS101,

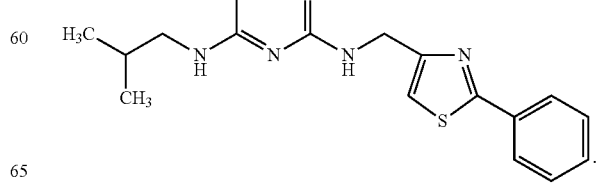

Assessment and Therapeutic Treatment

The invention provides a method of decreasing the growth of a solid tumor in a subject. The tumor is associated with, but not limited to glioblastoma multiforme, breast cancer, lung cancer, prostate cancer, or colorectal carcinoma. In one embodiment, the method comprises detecting the presence of an EGFR fusion molecule in a sample obtained from a subject. In some embodiments, the sample is incubated with an agent that binds to an EGFR fusion molecule, such as an antibody, a probe, a nucleic acid primer, and the like. In further embodiments, the method comprises administering to the subject an effective amount of an EGFR fusion molecule inhibitor, wherein the inhibitor decreases the size of the solid tumor.

The invention also provides a method for treating or preventing a gene-fusion associated cancer in a subject, such as, but not limited to, glioblastoma multiforme, breast cancer, lung cancer, prostate cancer, or colorectal carcinoma. In one embodiment, the method comprises detecting the presence of an EGFR fusion molecule in a sample obtained from a subject, the presence of the fusion being indicative of a gene-fusion associated cancer, and, administering to the subject in need a therapeutic treatment against a gene-fusion associated cancer. In some embodiments, the sample is incubated with an agent that binds to an EGFR fusion molecule, such as an antibody, a probe, a nucleic acid primer, and the like.

The invention also provides a method for decreasing in a subject in need thereof the expression level or activity of a fusion protein comprising the tyrosine kinase domain of an EGFR protein fused to a polypeptide that constitutively activates the tyrosine kinase domain of the EGFR protein. In some embodiments, the method comprises obtaining a biological sample from the subject. In some embodiments, the sample is incubated with an agent that binds to an EGFR fusion molecule, such as an antibody, a probe, a nucleic acid primer, and the like. In some embodiments, the method comprises administering to the subject a therapeutic amount of a composition comprising an admixture of a pharmaceutically acceptable carrier an inhibitor of the fusion protein of the invention. In another embodiment, the method further comprises determining the fusion protein expression level or activity. In another embodiment, the method further comprises detecting whether the fusion protein expression level or activity is decreased as compared to the fusion protein expression level or activity prior to administration of the composition, thereby decreasing the expression level or activity of the fusion protein. In some embodiments, the fusion protein is an EGFR-PSPH fusion protein, an EGFR-CAND fusion protein, or an EGFR-SEPT fusion protein.

The administering step in each of the claimed methods can comprise a drug administration, such as EGFR fusion molecule inhibitor (for example, a pharmaceutical composition comprising an antibody that specifically binds to an EGFR-SEPT fusion protein, an EGFR-PSPH fusion protein, an EGFR-CAND fusion protein, or a fragment thereof; a small molecule that specifically binds to an EGFR protein; an antisense RNA or antisense DNA that decreases expression of an EGFR-SEPT fusion protein, an EGFR-PSPH fusion protein, an EGFR-CAND fusion; a siRNA that specifically targets an EGFR-SEPT fusion gene, an EGFR-PSPH fusion gene, or an EGFR-CAND). In one embodiment, the therapeutic molecule to be administered comprises a polypeptide of an EGFR fusion molecule, comprising at least about 75%, at least about 80%, at least about 85%, at least about 90%, at least about 93%, at least about 95%, at least about 97%, at least about 98%, at least about 99%, or 100% of the amino acid sequence of SEQ ID NOS: 1, 3, 5, 7, 9, 11, 13, 16, or 8495, and exhibits the function of decreasing expression of such a protein, thus treating a gene fusion-associated cancer. In another embodiment, administration of the therapeutic molecule decreases the size of the solid tumor associated with glioblastoma multiforme, breast cancer, lung cancer, prostate cancer, or colorectal carcinoma. In a further embodiment, administration of the therapeutic molecule decreases cell proliferation in a subject afflicted with a gene-fusion associated cancer.

In another embodiment, the therapeutic molecule to be administered comprises an siRNA directed to a human nucleic acid sequence comprising an EGFR fusion molecule. In one embodiment, the siRNA is directed to any one of SEQ ID NOS: 2, 4, 8, 10, 14, or 15. In a further embodiment, the therapeutic molecule to be administered comprises an antibody or binding fragment thereof, that is directed against SEQ ID NOS: 1, 3, 5, 7, 9, 11, 13, 16, or 8495. In some embodiments, the therapeutic molecule to be administered comprises a small molecule that specifically binds to an EGFR protein, such as AZD4547, NVP-BGJ398, PD173074, NF449, TK1258, BIBF-1120, BMS-582664, AZD-2171, TSU68, AB1010, AP24534, E-7080, or LY2874455.

An EGFR fusion molecule, for example, a fusion between EGFR and SEPT, PSPH, or CAND, can be determined at the level of the DNA, RNA, or polypeptide. Optionally, detection can be determined by performing an oligonucleotide ligation assay, a confirmation based assay, a hybridization assay, a sequencing assay, an allele-specific amplification assay, a microsequencing assay, a melting curve analysis, a denaturing high performance liquid chromatography (DHPLC) assay (for example, see Jones et al, (2000) *Hum Genet.*, 106(6):663-8), or a combination thereof. In one embodiment, the detection is performed by sequencing all or part of an EGFR fusion molecule (e.g., EGFR-SEPT fusion (such as an EGFR-SEPT14 fusion), EGFR-CAND fusion (such as an EGFR-CAND1 fusion), EGFR-PSPH), or by selective hybridization or amplification of all or part of an EGFR fusion molecule (e.g., EGFR-SEPT fusion (such as an EGFR-SEPT14 fusion), EGFR-CAND fusion (such as an EGFR-CAND1 fusion), EGFR-PSPH)). AN EGFR fusion molecule specific amplification (e.g., EGFR-SEPT (such as an EGFR-SEPT14), EGFR-CAND (such as an EGFR-CAND1), EGFR-PSPH nucleic acid specific amplification) can be carried out before the fusion identification step.

The invention provides for a method of detecting a chromosomal alteration in a subject afflicted with a gene-fusion associated cancer. In some embodiments, the gene-fusion associated cancer comprises glioblastoma multiforme, breast cancer, lung cancer, prostate cancer, or colorectal carcinoma. In one embodiment, the chromosomal alteration is an in-frame fused transcript described herein, for example an EGFR fusion molecule. An alteration in a chromosome region occupied by an EGFR fusion molecule such as a nucleic acid encoding an EGFR-SEPT fusion (such as an EGFR-SEPT14 fusion), an EGFR-CAND fusion (such as an EGFR-CAND1 fusion), or an EGFR-PSPH, can be any form of mutation(s), deletion(s), rearrangement(s) and/or insertions in the coding and/or non-coding region of the locus, alone or in various combination(s). Mutations can include point mutations. Insertions can encompass the addition of one or several residues in a coding or non-coding portion of the gene locus. Insertions can comprise an addition of between 1 and 50 base pairs in the gene locus. Deletions can encompass any region of one, two or more residues in a coding or non-coding portion of the gene locus, such as from two residues up to the entire gene or locus. Deletions can affect smaller regions, such as domains (introns) or repeated sequences or fragments of less than about 50 consecutive base pairs, although larger deletions can occur as well. Rearrangement includes inversion of sequences. The alteration in a chromosome region occupied by an EGFR fusion molecule, e.g., a nucleic acid encoding a an EGFR-SEPT fusion (such as an EGFR-SEPT14 fusion), an EGFR-CAND fusion (such as an EGFR-CAND1 fusion), or an EGFR-PSPH, can result in amino acid substitutions, RNA splicing or processing, product instability, the creation of stop codons, production of oncogenic fusion proteins, frame-shift mutations, and/or truncated polypeptide production. The alteration can result in the production of an EGFR fusion molecule, for example, a nucleic acid encoding an EGFR-SEPT fusion (such as an EGFR-SEPT14 fusion), an EGFR-CAND fusion (such as an EGFR-CAND1 fusion), or an EGFR-PSPH fusion, with altered function, stability, targeting or structure. The alteration can also cause a reduction, or even an increase in protein expression. In one embodiment, the alteration in the chromosome region occupied by an EGFR fusion molecule can comprise a chromosomal rearrangement resulting in the production of an EGFR fusion molecule, such as an EGFR-SEPT fusion (such as an EGFR-SEPT14 fusion), an EGFR-CAND fusion (such as an EGFR-CAND1 fusion), or an EGFR-PSPH fusion. This alteration can be determined at the level of the DNA, RNA, or polypeptide. In another embodiment, the detection or determination comprises nucleic acid sequencing, selective hybridization, selective amplification, gene expression analysis, or a combination thereof. In another embodiment, the detection or determination comprises protein expression analysis, for example by western blot analysis, ELISA, or other antibody detection methods.

The present invention provides a method for treating a gene-fusion associated cancer in a subject in need thereof. In one embodiment, the method comprises obtaining a sample from the subject to determine the level of expression of an EGFR fusion molecule in the subject. In some embodiments, the sample is incubated with an agent that binds to an EGFR fusion molecule, such as an antibody, a probe, a nucleic acid primer, and the like. In another embodiment, the detection or determination comprises nucleic acid sequencing, selective hybridization, selective amplification, gene expression analysis, or a combination thereof. In another embodiment, the detection or determination comprises protein expression analysis, for example by western blot analysis, ELISA, or other antibody detection methods. In some embodiments, the method further comprises assessing whether to administer an EGFR fusion molecule inhibitor based on the expression pattern of the subject. In further embodiments, the method comprises administering an EGFR fusion molecule inhibitor to the subject. In one embodiment, the gene-fusion associated cancer comprises glioblastoma multiforme, breast cancer, lung cancer, prostate cancer, or colorectal carcinoma.

In one embodiment, the invention provides for a method of detecting the presence of altered RNA expression of an EGFR fusion molecule in a subject, for example, one afflicted with a gene-fusion associated cancer. In another embodiment, the invention provides for a method of detecting the presence of an EGFR fusion molecule in a subject. In some embodiments, the method comprises obtaining a sample from the subject to determine whether the subject expresses an EGFR fusion molecule. In some embodiments, the sample is incubated with an agent that binds to an EGFR fusion molecule, such as an antibody, a probe, a nucleic acid primer, and the like. In other embodiments, the detection or determination comprises nucleic acid sequencing, selective hybridization, selective amplification, gene expression analysis, or a combination thereof. In another embodiment, the detection or determination comprises protein expression analysis, for example by western blot analysis, ELISA, or other antibody detection methods. In some embodiments, the method further comprises assessing whether to administer an EGFR fusion molecule inhibitor based on the expression pattern of the subject. In further embodiments, the method comprises administering an EGFR fusion molecule inhibitor to the subject. Altered RNA expression includes the presence of an altered RNA sequence, the presence of an altered RNA splicing or processing, or the presence of an altered quantity of RNA. These can be detected by various techniques known in the art, including sequencing all or part of the RNA or by selective hybridization or selective amplification of all or part of the RNA.

In a further embodiment, the method can comprise detecting the presence or expression of an EGFR fusion molecule, such as a nucleic acid encoding an EGFR-SEPT fusion (such as an EGFR-SEPT14 fusion), an EGFR-CAND fusion (such as an EGFR-CAND1 fusion), or an EGFR-PSPH fusion. Altered polypeptide expression includes the presence of an altered polypeptide sequence, the presence of an altered quantity of polypeptide, or the presence of an altered tissue distribution. These can be detected by various techniques known in the art, including by sequencing and/or binding to specific ligands (such as antibodies). In one embodiment, the detecting comprises using a northern blot; real time PCR and primers directed to SEQ ID NOS: 2, 4, 8, 10, 14, or 15; a ribonuclease protection assay; a hybridization, amplification, or sequencing technique to detect an EGFR fusion molecule, such as one comprising SEQ ID NOS: 2, 4, 8, 10, 14, or 15; or a combination thereof. In another embodiment, the PCR primers comprise SEQ ID NOS 32, 33, 34, 35, 36, 37, 38, 39, 40, 41, 42, 43, 44, 45, 87, 88, or 89. In a further embodiment, primers used for the screening of EGFR fusion molecules, comprise SEQ ID NOS 32, 33, 34, 35, 36, 37, 38, 39, 40, 41, 42, 43, 44, 45, 87, 88, or 89. In some embodiments, primers used for genomic detection of an EGFR fusion comprise SEQ ID NOS 40, 41, 42, 43, 44, 45, or 89.

Various techniques known in the art can be used to detect or quantify altered gene or RNA expression or nucleic acid sequences, which include, but are not limited to, hybridization, sequencing, amplification, and/or binding to specific ligands (such as antibodies). Other suitable methods include allele-specific oligonucleotide (ASO), oligonucleotide ligation, allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, denaturing HLPC, melting curve analysis, heteroduplex analysis, RNase protection, chemical or enzymatic mismatch cleavage, ELISA, radio-immunoassays (RIA) and immuno-enzymatic assays (IEMA).

Some of these approaches (such as SSCA and constant gradient gel electrophoresis (CGGE)) are based on a change in electrophoretic mobility of the nucleic acids, as a result of the presence of an altered sequence. According to these techniques, the altered sequence is visualized by a shift in mobility on gels. The fragments can then be sequenced to confirm the alteration. Some other approaches are based on specific hybridization between nucleic acids from the subject and a probe specific for wild type or altered gene or RNA. The probe can be in suspension or immobilized on a substrate. The probe can be labeled to facilitate detection of hybrids. Some of these approaches are suited for assessing a polypeptide sequence or expression level, such as Northern blot, ELISA and RIA. These latter require the use of a ligand specific for the polypeptide, for example, the use of a specific antibody.

Hybridization.

Hybridization detection methods are based on the formation of specific hybrids between complementary nucleic acid sequences that serve to detect nucleic acid sequence alteration(s). A detection technique involves the use of a nucleic acid probe specific for a wild type or altered gene or RNA, followed by the detection of the presence of a hybrid. The probe can be in suspension or immobilized on a substrate or support (for example, as in nucleic acid array or chips technologies). The probe can be labeled to facilitate detection of hybrids. In one embodiment, the probe according to the invention can comprise a nucleic acid directed to SEQ ID NOS: 2, 4, 8, 10, 14, or 15. For example, a sample from the subject can be contacted with a nucleic acid probe specific for a gene encoding an EGFR fusion molecule, and the formation of a hybrid can be subsequently assessed. In one embodiment, the method comprises contacting simultaneously the sample with a set of probes that are specific for an EGFR fusion molecule. Also, various samples from various subjects can be investigated in parallel.

According to the invention, a probe can be a polynucleotide sequence which is complementary to and specifically hybridizes with a, or a target portion of a, gene or RNA corresponding to an EGFR fusion molecule. Useful probes are those that are complementary to the gene, RNA, or target portion thereof. Probes can comprise single-stranded nucleic acids of between 8 to 1000 nucleotides in length, for instance between 10 and 800, between 15 and 700, or between 20 and 500. Longer probes can be used as well. A useful probe of the invention is a single stranded nucleic acid molecule of between 8 to 500 nucleotides in length, which can specifically hybridize to a region of a gene or RNA that corresponds to an EGFR fusion molecule.

The sequence of the probes can be derived from the sequences of the EGFR fusion genes provided herein. Nucleotide substitutions can be performed, as well as chemical modifications of the probe. Such chemical modifications can be accomplished to increase the stability of hybrids (e.g., intercalating groups) or to label the probe. Some examples of labels include, without limitation, radioactivity, fluorescence, luminescence, and enzymatic labeling.

A guide to the hybridization of nucleic acids is found in e.g., Sambrook, ed., *Molecular Cloning: A Laboratory Manual* (3$^{rd}$ Ed.), Vols. 1-3, Cold Spring Harbor Laboratory, 1989; *Current Protocols In Molecular Biology*, Ausubel, ed. John Wiley & Sons, Inc., New York, 2001; *Laboratory Techniques In Biochemistry And Molecular Biology: Hybridization With Nucleic Acid Probes, Part I. Theory and Nucleic Acid Preparation*, Tijssen, ed. Elsevier, N.Y., 1993.

Sequencing.

Sequencing can be carried out using techniques well known in the art, using automatic sequencers. The sequencing can be performed on the complete EGFR fusion molecule or on specific domains thereof Amplification.

Amplification is based on the formation of specific hybrids between complementary nucleic acid sequences that serve to initiate nucleic acid reproduction. Amplification can be performed according to various techniques known in the art, such as by polymerase chain reaction (PCR), ligase chain reaction (LCR), strand displacement amplification (SDA) and nucleic acid sequence based amplification (NASBA). These techniques can be performed using commercially available reagents and protocols. Useful techniques in the art encompass real-time PCR, allele-specific PCR, or PCR based single-strand conformational polymorphism (SSCP). Amplification usually requires the use of specific nucleic acid primers, to initiate the reaction. For example, nucleic acid primers useful for amplifying sequences corresponding to an EGFR fusion molecule are able to specifically hybridize with a portion of the gene locus that flanks a target region of the locus. In one embodiment, amplification comprises using forward and reverse PCR primers directed to SEQ ID NOS: 2, 4, 8, 10, 14, or 15. Nucleic acid primers useful for amplifying sequences from an EGFR fusion molecule; the primers specifically hybridize with a portion of an EGFR fusion molecule. In certain subjects, the presence of an EGFR fusion molecule corresponds to a subject with a gene fusion-associated cancer. In one embodiment, amplification can comprise using forward and reverse PCR primers comprising nucleotide sequences of SEQ ID NOS: 32, 33, 34, 35, 36, 37, 38, 39, 40, 41, 42, 43, 44, 45, 87, 88, or 89.

Non-limiting amplification methods include, e.g., polymerase chain reaction, PCR (*PCR Protocols, A Guide To Methods And Applications*, ed. Innis, Academic Press, N.Y., 1990 and *PCR Strategies*, 1995, ed. Innis, Academic Press, Inc., N.Y.); ligase chain reaction (LCR) (Wu (1989) *Genomics* 4:560; Landegren (1988) *Science* 241:1077; Barringer (1990) *Gene* 89:117); transcription amplification (Kwoh (1989) *PNAS* 86:1173); and, self-sustained sequence replication (Guatelli (1990) *PNAS* 87:1874); Q Beta replicase amplification (Smith (1997) *J. Clin. Microbiol.* 35:1477-1491), automated Q-beta replicase amplification assay (Burg (1996) *Mol. Cell. Probes* 10:257-271) and other RNA polymerase mediated techniques (e.g., NASBA, Cangene, Mississauga, Ontario; see also Berger (1987) *Methods Enzymol.* 152:307-316; U.S. Pat. Nos. 4,683,195 and 4,683,202; and Sooknanan (1995) *Biotechnology* 13:563-564). All the references stated above are incorporated by reference in their entireties.

The invention provides for a nucleic acid primer, wherein the primer can be complementary to and hybridize specifically to a portion of an EGFR fusion molecule, such as a nucleic acid (e.g., DNA or RNA), in certain subjects having a gene fusion-associated cancer. In one embodiment, the gene-fusion associated cancer comprises glioblastoma multiforme, breast cancer, lung cancer, prostate cancer, or colorectal carcinoma. Primers of the invention can be specific for fusion sequences in a nucleic acid (DNA or RNA) encoding an EGFR-SEPT fusion (such as an EGFR-SEPT14 fusion), an EGFR-CAND fusion (such as an EGFR-CAND1 fusion), or an EGFR-PSPH fusion. By using such primers, the detection of an amplification product indicates the presence of a fusion of a nucleic acid encoding an EGFR-SEPT fusion (such as an EGFR-SEPT14 fusion), an EGFR-CAND fusion (such as an EGFR-CAND1 fusion), or an EGFR-PSPH fusion. Examples of primers of this invention can be single-stranded nucleic acid molecules of about 5 to 60 nucleotides in length, or about 8 to about 25 nucleotides in length. The sequence can be derived directly from the sequence of an EGFR fusion molecule, e.g. a nucleic acid encoding an EGFR-SEPT fusion (such as an EGFR-SEPT14 fusion), an EGFR-CAND fusion (such as an EGFR-CAND1 fusion), or an EGFR-PSPH fusion. Perfect complementarity is useful to ensure high specificity; however, certain mismatch can be tolerated. For example, a nucleic acid primer or a pair of nucleic acid primers as described above can be used in a method for detecting the presence of a gene fusion-associated cancer in a subject. In one embodiment, primers can be used to detect an EGFR fusion molecule, such as a primer comprising SEQ ID NOS: 32, 33, 34, 35, 36, 37, 38, 39, 40, 41, 42, 43, 44, 45, 87, 88, 89; or a combination thereof Specific Ligand Binding.

As discussed herein, a nucleic acid encoding an EGFR fusion molecule or expression of an EGFR fusion molecule, can also be detected by screening for alteration(s) in a sequence or expression level of a polypeptide encoded by the same. Different types of ligands can be used, such as specific antibodies. In one embodiment, the sample is contacted with an antibody specific for a polypeptide encoded by an EGFR fusion molecule and the formation of an immune complex is subsequently determined. Various methods for detecting an immune complex can be used, such as ELISA, radioimmunoassays (RIA) and immuno-enzymatic assays (IEMA).

For example, an antibody can be a polyclonal antibody, a monoclonal antibody, as well as fragments or derivatives thereof having substantially the same antigen specificity. Fragments include Fab, Fab'2, or CDR regions. Derivatives include single-chain antibodies, humanized antibodies, or poly-functional antibodies. An antibody specific for a polypeptide encoded by an EGFR fusion molecule can be an antibody that selectively binds such a polypeptide. In one embodiment, the antibody is raised against a polypeptide encoded by an EGFR fusion molecule or an epitope-containing fragment thereof. Although non-specific binding towards other antigens can occur, binding to the target polypeptide occurs with a higher affinity and can be reliably discriminated from non-specific binding. In one embodiment, the method can comprise contacting a sample from the subject with an antibody specific for an EGFR fusion molecule, and determining the presence of an immune complex. Optionally, the sample can be contacted to a support coated with antibody specific for an EGFR fusion molecule. In one embodiment, the sample can be contacted simultaneously, or in parallel, or sequentially, with various antibodies specific for different forms of an EGFR fusion molecule, e.g., EGFR-SEPT fusion (such as an EGFR-SEPT14 fusion), an EGFR-CAND fusion (such as an EGFR-CAND1 fusion), or an EGFR-PSPH fusion.

The invention also provides for a diagnostic kit comprising products and reagents for detecting in a sample from a subject the presence of an EGFR fusion molecule. The kit can be useful for determining whether a sample from a subject exhibits reduced expression of an EGFR fusion molecule. For example, the diagnostic kit according to the present invention comprises any primer, any pair of primers, any nucleic acid probe and/or any ligand, or any antibody directed specifically to an EGFR fusion molecule. The diagnostic kit according to the present invention can further comprise reagents and/or protocols for performing a hybridization, amplification, or antigen-antibody immune reaction. In one embodiment, the kit can comprise nucleic acid primers that specifically hybridize to and can prime a polymerase reaction from an EGFR fusion molecule comprising SEQ ID NOS: 32, 33, 34, 35, 36, 37, 38, 39, 40, 41, 42, 43, 44, 45, 87, 88, 89, or a combination thereof. In one embodiment, primers can be used to detect an EGFR fusion molecule, such as a primer comprising SEQ ID NOS: 32, 33, 34, 35, 36, 37, 38, 39, 40, 41, 42, 43, 44, 45, 87, 88, 89; or a combination thereof. In a further embodiment, primers used for the screening of EGFR fusion molecules.

The diagnosis methods can be performed in vitro, ex vivo, or in vivo. These methods utilize a sample from the subject in order to assess the status of an EGFR fusion molecule. The sample can be any biological sample derived from a subject, which contains nucleic acids or polypeptides. Examples of such samples include, but are not limited to, fluids, tissues, cell samples, organs, and tissue biopsies. Non-limiting examples of samples include blood, liver, plasma, serum, saliva, urine, or seminal fluid. The sample can be collected according to conventional techniques and used directly for diagnosis or stored. The sample can be treated prior to performing the method, in order to render or improve availability of nucleic acids or polypeptides for testing. Treatments include, for instance, lysis (e.g., mechanical, physical, or chemical), centrifugation. The nucleic acids and/or polypeptides can be pre-purified or enriched by conventional techniques, and/or reduced in complexity. Nucleic acids and polypeptides can also be treated with enzymes or other chemical or physical treatments to produce fragments thereof. In one embodiment, the sample is contacted with reagents, such as probes, primers, or ligands, in order to assess the presence of an EGFR fusion molecule. Contacting can be performed in any suitable device, such as a plate, tube, well, or glass. In some embodiments, the contacting is performed on a substrate coated with the reagent, such as a nucleic acid array or a specific ligand array. The substrate can be a solid or semi-solid substrate such as any support comprising glass, plastic, nylon, paper, metal, or polymers. The substrate can be of various forms and sizes, such as a slide, a membrane, a bead, a column, or a gel. The contacting can be made under any condition suitable for a complex to be formed between the reagent and the nucleic acids or polypeptides of the sample.

Nucleic Acid Delivery Methods

Delivery of nucleic acids into viable cells can be effected ex vivo, in situ, or in vivo by use of vectors, such as viral vectors (e.g., lentivirus, adenovirus, adeno-associated virus, or a retrovirus), or ex vivo by use of physical DNA transfer methods (e.g., liposomes or chemical treatments). Non-limiting techniques suitable for the transfer of nucleic acid into mammalian cells in vitro include the use of liposomes, electroporation, microinjection, cell fusion, DEAE-dextran, and the calcium phosphate precipitation method (See, for example, Anderson, *Nature,* 1998) supplement to 392 (6679):25( ). Introduction of a nucleic acid or a gene encoding a polypeptide of the invention can also be accomplished with extrachromosomal substrates (transient expression) or artificial chromosomes (stable expression). Cells can also be cultured ex vivo in the presence of therapeutic compositions of the present invention in order to proliferate or to produce a desired effect on or activity in such cells. Treated cells can then be introduced in vivo for therapeutic purposes.

Nucleic acids can be inserted into vectors and used as gene therapy vectors. A number of viruses have been used as gene transfer vectors, including papovaviruses, e.g., SV40 (Madzak et al., (1992) *J Gen Virol.* 73(Pt 6):1533-6), adenovirus (Berkner (1992) *Curr Top Microbiol Immunol.* 158: 39-66; Berkner (1988) *Biotechniques,* 6(7):616-29; Gorziglia and Kapikian (1992) *J Virol.* 66(7):4407-12; Quantin et al., (1992) *Proc Natl Acad Sci USA.* 89(7):2581-4; Rosenfeld et al., (1992) *Cell.* 68(1):143-55; Wilkinson et al., (1992) *Nucleic Acids Res.* 20(9):2233-9; Stratford-Perricaudet et al., (1990) *Hum Gene Ther.* 1(3):241-56), vaccinia virus (Moss (1992) *Curr Opin Biotechnol.* 3(5):518-22), adeno-associated virus (Muzyczka, (1992) *Curr Top Microbiol Immunol.* 158:97-129; Ohi et al., (1990) *Gene.* 89(2): 279-82), herpesviruses including HSV and EBV (Margolskee (1992) *Curr Top Microbiol Immunol.* 158:67-95;

Johnson et al., (1992) *Brain Res Mol Brain Res.* 12(1-3): 95-102; Fink et al., (1992) *Hum Gene Ther.* 3(1):11-9; Breakefield and Geller (1987) *Mol Neurobiol.* 1(4):339-71; Freese et al., (1990) *Biochem Pharmacol.* 40(10):2189-99), and retroviruses of avian (Bandyopadhyay and Temin (1984) *Mol Cell Biol.* 4(4):749-54; Petropoulos et al., (1992) *J Virol.* 66(6):3391-7), murine (Miller et al. (1992) *Mol Cell Biol.* 12(7):3262-72; Miller et al., (1985) *J Virol.* 55(3):521-6; Sorge et al., (1984) *Mol Cell Biol.* 4(9):1730-7; Mann and Baltimore (1985) *J Virol.* 54(2):401-7; Miller et al., (1988) *J Virol.* 62(11):4337-45), and human origin (Shimada et al., (1991) *J Clin Invest.* 88(3):1043-7; Helseth et al., (1990) *J Virol.* 64(12):6314-8; Page et al., (1990) *J Virol.* 64(11): 5270-6; Buchschacher and Panganiban (1992) *J Virol.* 66(5): 2731-9).

Non-limiting examples of in vivo gene transfer techniques include transfection with viral (e.g., retroviral) vectors (see U.S. Pat. No. 5,252,479, which is incorporated by reference in its entirety) and viral coat protein-liposome mediated transfection (Dzau et al., (1993) *Trends in Biotechnology* 11:205-210), incorporated entirely by reference). For example, naked DNA vaccines are generally known in the art; see Brower, (1998) *Nature Biotechnology,* 16:1304-1305, which is incorporated by reference in its entirety. Gene therapy vectors can be delivered to a subject by, for example, intravenous injection, local administration (see, e.g., U.S. Pat. No. 5,328,470) or by stereotactic injection (see, e.g., Chen, et al., (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

For reviews of nucleic acid delivery protocols and methods see Anderson et al. (1992) *Science* 256:808-813; U.S. Pat. Nos. 5,252,479, 5,747,469, 6,017,524, 6,143,290, 6,410,010 6,511,847; and U.S. Application Publication No. 2002/0077313, which are all hereby incorporated by reference in their entireties. For additional reviews, see Friedmann (1989) *Science,* 244:1275-1281; Verma, *Scientific American:* 68-84 (1990); Miller (1992) *Nature,* 357: 455-460; Kikuchi et al. (2008) *J Dermatol Sci.* 50(2):87-98; Isaka et al. (2007) *Expert Opin Drug Deliv.* 4(5):561-71; Jager et al. (2007) *Curr Gene Ther.* 7(4):272-83; Waehler et al. (2007) *Nat Rev Genet.* 8(8):573-87; Jensen et al. (2007) *Ann Med.* 39(2):108-15; Herweijer et al. (2007) *Gene Ther.* 14(2):99-107; Eliyahu et al. (2005) *Molecules* 10(1):34-64; and Altaras et al. (2005) *Adv Biochem Eng Biotechnol.* 99:193-260, all of which are hereby incorporated by reference in their entireties.

An EGFR fusion nucleic acid can also be delivered in a controlled release system. For example, the EGFR fusion molecule can be administered using intravenous infusion, an implantable osmotic pump, a transdermal patch, liposomes, or other modes of administration. In one embodiment, a pump can be used (see Sefton (1987) *Biomed. Eng.* 14:201; Buchwald et al. (1980) *Surgery* 88:507; Saudek et al. (1989) *N. Engl. J. Med.* 321:574). In another embodiment, polymeric materials can be used (see *Medical Applications of Controlled Release,* Langer and Wise (eds.), CRC Pres., Boca Raton, Fla. (1974); *Controlled Drug Bioavailability, Drug Product Design and Performance,* Smolen and Ball (eds.), Wiley, New York (1984); Ranger and Peppas, (1983) *J. Macromol. Sci. Rev. Macromol. Chem.* 23:61; see also Levy et al. (1985) *Science* 228:190; During et al. (1989) *Ann. Neurol.* 25:351; Howard et al. (1989) *J. Neurosurg.* 71:105). In yet another embodiment, a controlled release system can be placed in proximity of the therapeutic target thus requiring only a fraction of the systemic dose (see, e.g., Goodson, in *Medical Applications of Controlled Release,* supra, vol. 2, pp. 115-138 (1984)). Other controlled release systems are discussed in the review by Langer (*Science* (1990) 249:1527-1533).

Pharmaceutical Compositions and Administration for Therapy

An inhibitor of the invention can be incorporated into pharmaceutical compositions suitable for administration, for example the inhibitor and a pharmaceutically acceptable carrier AN EGFR fusion molecule or inhibitor of the invention can be administered to the subject once (e.g., as a single injection or deposition). Alternatively, an EGFR fusion molecule or inhibitor can be administered once or twice daily to a subject in need thereof for a period of from about two to about twenty-eight days, or from about seven to about ten days. AN EGFR fusion molecule or inhibitor can also be administered once or twice daily to a subject for a period of 1, 2, 3, 4, 5, 6, 7, 8, 9, 10, 11, 12 times per year, or a combination thereof. Furthermore, an EGFR fusion molecule or inhibitor of the invention can be co-administrated with another therapeutic. Where a dosage regimen comprises multiple administrations, the effective amount of the EGFR fusion molecule or inhibitor administered to the subject can comprise the total amount of gene product administered over the entire dosage regimen.

AN EGFR fusion molecule or inhibitor can be administered to a subject by any means suitable for delivering the EGFR fusion molecule or inhibitor to cells of the subject, such as cancer cells, e.g., glioblastoma multiforme, breast cancer, lung cancer, prostate cancer, or colorectal carcinoma. For example, an EGFR fusion molecule or inhibitor can be administered by methods suitable to transfect cells. Transfection methods for eukaryotic cells are well known in the art, and include direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

The compositions of this invention can be formulated and administered to reduce the symptoms associated with a gene fusion-associated cancer, e.g., glioblastoma multiforme, breast cancer, lung cancer, prostate cancer, or colorectal carcinoma, by any means that produces contact of the active ingredient with the agent's site of action in the body of a subject, such as a human or animal (e.g., a dog, cat, or horse). They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

A therapeutically effective dose of EGFR fusion molecule or inhibitor can depend upon a number of factors known to those or ordinary skill in the art. The dose(s) of the EGFR fusion molecule inhibitor can vary, for example, depending upon the identity, size, and condition of the subject or sample being treated, further depending upon the route by which the composition is to be administered, if applicable, and the effect which the practitioner desires the an EGFR fusion molecule inhibitor to have upon the nucleic acid or polypeptide of the invention. These amounts can be readily determined by a skilled artisan. Any of the therapeutic applications described herein can be applied to any subject in need of such therapy, including, for example, a mammal such as a dog, a cat, a cow, a horse, a rabbit, a monkey, a pig, a sheep, a goat, or a human.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remington's Pharmaceutical Sciences*, Meade Publishing Co., Easton, Pa. (20$^{th}$ Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

A pharmaceutical composition containing EGFR fusion molecule inhibitor can be administered in conjunction with a pharmaceutically acceptable carrier, for any of the therapeutic effects discussed herein. Such pharmaceutical compositions can comprise, for example antibodies directed to an EGFR fusion molecule, or a variant thereof, or antagonists of an EGFR fusion molecule. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones.

Sterile injectable solutions can be prepared by incorporating the EGFR fusion molecule inhibitor (e.g., a polypeptide or antibody) in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

In some embodiments, the EGFR fusion molecule inhibitor can be applied via transdermal delivery systems, which slowly releases the active compound for percutaneous absorption. Permeation enhancers can be used to facilitate transdermal penetration of the active factors in the conditioned media. Transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

"Subcutaneous" administration can refer to administration just beneath the skin (i.e., beneath the dermis). Generally, the subcutaneous tissue is a layer of fat and connective tissue that houses larger blood vessels and nerves. The size of this layer varies throughout the body and from person to person. The interface between the subcutaneous and muscle layers can be encompassed by subcutaneous administration. This mode of administration can be feasible where the subcutaneous layer is sufficiently thin so that the factors present in the compositions can migrate or diffuse from the locus of administration. Thus, where intradermal administration is utilized, the bolus of composition administered is localized proximate to the subcutaneous layer.

Administration of the cell aggregates (such as DP or DS aggregates) is not restricted to a single route, but can encompass administration by multiple routes. For instance, exemplary administrations by multiple routes include, among others, a combination of intradermal and intramuscular administration, or intradermal and subcutaneous administration. Multiple administrations can be sequential or concurrent. Other modes of application by multiple routes will be apparent to the skilled artisan.

In other embodiments, this implantation method will be a one-time treatment for some subjects. In further embodiments of the invention, multiple cell therapy implantations will be required. In some embodiments, the cells used for implantation will generally be subject-specific genetically engineered cells. In another embodiment, cells obtained from a different species or another individual of the same species can be used. Thus, using such cells can require administering an immunosuppressant to prevent rejection of the implanted cells. Such methods have also been described in U.S. Pat. No. 7,419,661 and PCT application publication WO 2001/32840, and are hereby incorporated by reference.

A pharmaceutical composition of the invention is formulated to be compatible with its intended route of administration. Examples of routes of administration include parenteral, e.g., intravenous, intradermal, subcutaneous, oral (e.g., inhalation or ingestion), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the inhibitor (e.g., a polypeptide or antibody or small molecule) of the invention in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier and subsequently swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the effective amount of the administered EGFR fusion molecule inhibitor is at least about 0.0001 µg/kg body weight, at least about 0.00025 µg/kg body weight, at least about 0.0005 µg/kg body weight, at least about 0.00075 µg/kg body weight, at least about 0.001 µg/kg body weight, at least about 0.0025 µg/kg body weight, at least about 0.005 µg/kg body weight, at least about 0.0075 µg/kg body weight, at least about 0.01 µg/kg body weight, at least about 0.025 µg/kg body weight, at least about 0.05 µg/kg body weight, at least about 0.075 µg/kg body weight, at least about 0.1 µg/kg body weight, at least about 0.25 µg/kg body weight, at least about 0.5 µg/kg body weight, at least about 0.75 µg/kg body weight, at least about 1 µg/kg body weight, at least about 5 µg/kg body weight, at least about 10 µg/kg body weight, at least about 25 µg/kg body weight, at least about 50 µg/kg body weight, at least about 75 µg/kg body weight, at least about 100 µg/kg body weight, at least about 150 µg/kg body weight, at least about 200 µg/kg body weight, at least about 250 µg/kg body weight, at least about 300 µg/kg body weight, at least about 350 µg/kg body weight, at least about 400 µg/kg body weight, at least about 450 µg/kg body weight, at least about 500 µg/kg body weight, at least about 550 µg/kg body weight, at least about 600 µg/kg body weight, at least about 650 µg/kg body weight, at least about 700 µg/kg body weight, at least about 750 µg/kg body weight, at least about 800 µg/kg body weight, at least about 850 µg/kg body weight, at least about 900 µg/kg body weight, at least about 950 µg/kg body weight, at least about 1000 µg/kg body weight, at least about 2000 µg/kg body weight, at least about 3000 µg/kg body weight, at least about 4000 µg/kg body weight, at least about 5000 µg/kg body weight, at least about 6000 µg/kg body weight, at least about 7000 µg/kg body weight, at least about 8000 µg/kg body weight, at least about 9500 µg/kg body weight, or at least about 10,000 µg/kg body weight.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: The Integrated Landscape of Driver Genomic Alterations in Glioblastoma To address the challenge of driver mutations in glioblastoma (GBM) and uncover new driver genes in human GBM, a computational platform was developed that integrates the analysis of copy number variations and somatic mutations from a whole-exome dataset. The full spectrum of in-frame gene fusions was unveiled from a large transcriptome dataset of glioblastoma. The analyses revealed focal copy number variations and mutations in all the genes previously implicated in glioblastoma pathogenesis. Recurrent copy number variations and somatic mutations were detected in 18 genes not yet implicated in glioblastoma. For each of the new genes, the occurrence of focal and recurrent copy number changes in addition to somatic mutations underscores the relevance for glioblastoma pathogenesis. Without being bound by theory, mutations in LZTR-1, a Keltch-BTB-BACK-BTB-BACK adaptor of Cul3-containing E3 ligase complexes impacted ubiquitination of LZTR-1 substrates. Loss-of-function mutations of CTNND2 (coding for δ-catenin) targeted a neural-specific gene and were associated with the transformation of glioma cells along the mesenchymal lineage, a hallmark of aggressive glioblastoma. Reconstitution of δ-catenin in mesenchymal glioma cells reprogrammed them towards a neuronal cell fate. Recurrent translocations were also identified that fuse in-frame the coding sequence of EGFR to several partners in 7.6% of tumors, with EGFR-Septin-14 scoring as the most frequent functional gene fusion in human glioblastoma. EGFR fusions enhance proliferation and motility of glioma cells and confer sensitivity to EGFR inhibition in glioblastoma xenografts. These results provide important insights into the pathogenesis of glioblastoma and highlight new targets for therapeutic intervention.

Glioblastoma (GBM) is the most common primary intrinsic malignant brain tumor affecting ~10,000 new patients each year with a median survival rate of only 12-15 months[1,2]. Identifying and understanding the functional significance of the genetic alterations that drive initiation and progression of GBM is crucial to develop more effective therapies. Previous efforts in GBM genome characterization included array-based profiling of copy number changes, methylation and gene expression and targeted sequencing of candidate genes[3-6]. These studies identified somatic changes in well-known GBM genes (EGFR, PTEN, IDH1, TP53, NF1, etc.) and nominated putative cancer genes with somatic mutations, but the functional consequences of most alterations is unknown. The lack of strict correlation between somatic alterations and functionality in GBM is manifested by regions of large copy number variations (CNVs), in which the relevant gene(s) are masked within genomic domains encompassing many other genes. Furthermore, although the potential of next-generation sequencing of the whole coding exome is widely recognized for the nomination of new cancer genes, the elevated somatic mutation rate of GBM is a significant challenge for statistical approaches aimed to distinguish genes harboring driver from those with passenger mutations. A statistical approach was used to nominate driver genes in GBM from the integration of whole-exome sequencing data calling for somatic mutations with a CNVs analysis that prioritizes focality and magnitude of the genetic alterations.

Chromosomal rearrangements resulting in recurrent and oncogenic gene fusions are hallmarks of hematological malignancies and recently they have also been uncovered in solid tumors (breast, prostate, lung and colorectal carcinoma)[7,8]. Recently, a small subset of GBM harbor FGFR-TACC gene fusions were provided indicating that the patients with FGFR-TACC-positive tumors would benefit from targeted EGFR kinase inhibition[9]. It remains unknown whether gene fusions involving other RTK-coding genes exist in GBM to create different oncogene addicting states. A large RNA-sequencing dataset of primary GBM and glioma stem cells (GSCs) was analyzed and the global landscape of in-frame gene fusions in human GBM was reported.

Nomination of Candidate GBM Genes

Focal CNVs and point mutations provide exquisite information on candidate driver genes by pinpointing their exact location. Without being bound by theory, the integration of somatic point mutations and focal CNV information in a single framework will nominate candidate genes implicated in GBM. MutComFocal is an algorithm designed for this purpose, in which driver genes are ranked by an integrated recurrence, focality and mutation score (see Methods). Overall, this strategy was applied to a cohort of 139 GBM and matched normal DNA analyzed by whole exome sequencing to identify somatic mutations and 469 GBM were analyzed by the Affymetrix SNP6.0 platform to identify CNVs.

Figure 6:
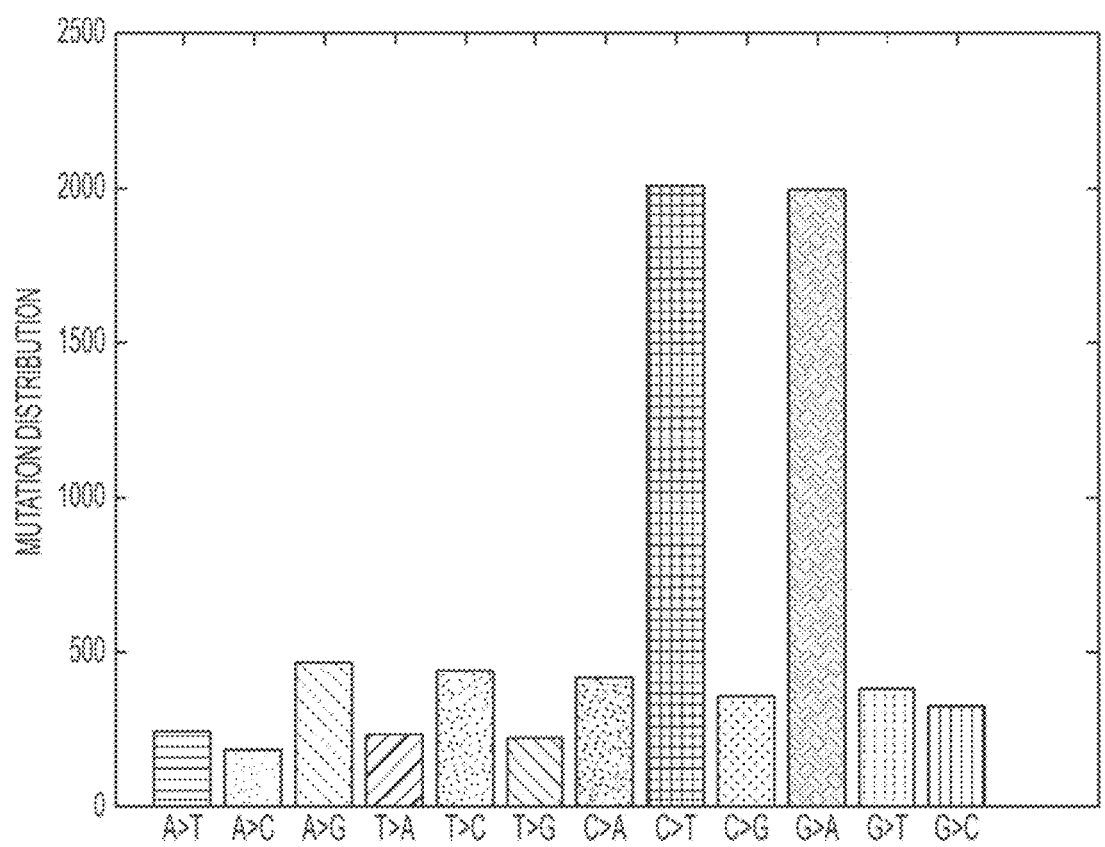
FIG. 6 shows the distribution of substitutions from whole exome data.
Figure 7:
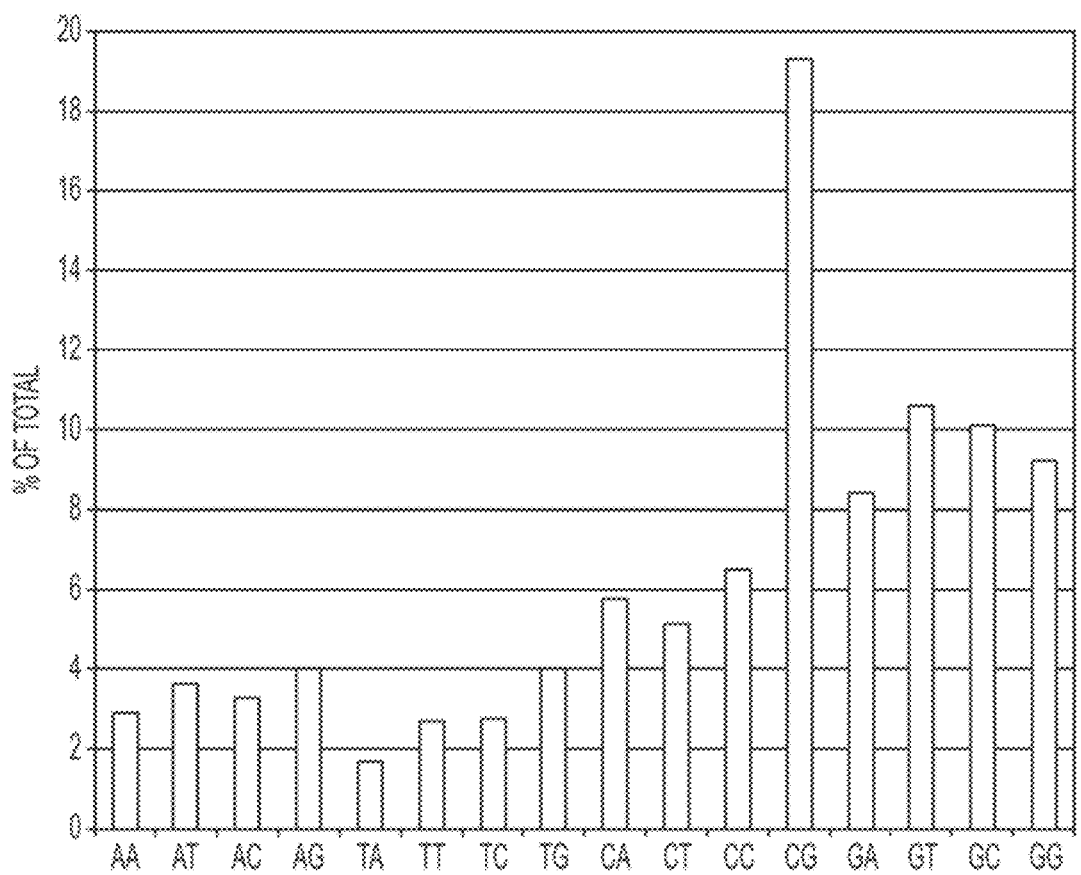
FIG. 7. shows dinucleotide distribution in mutated sites.
Figure 9:
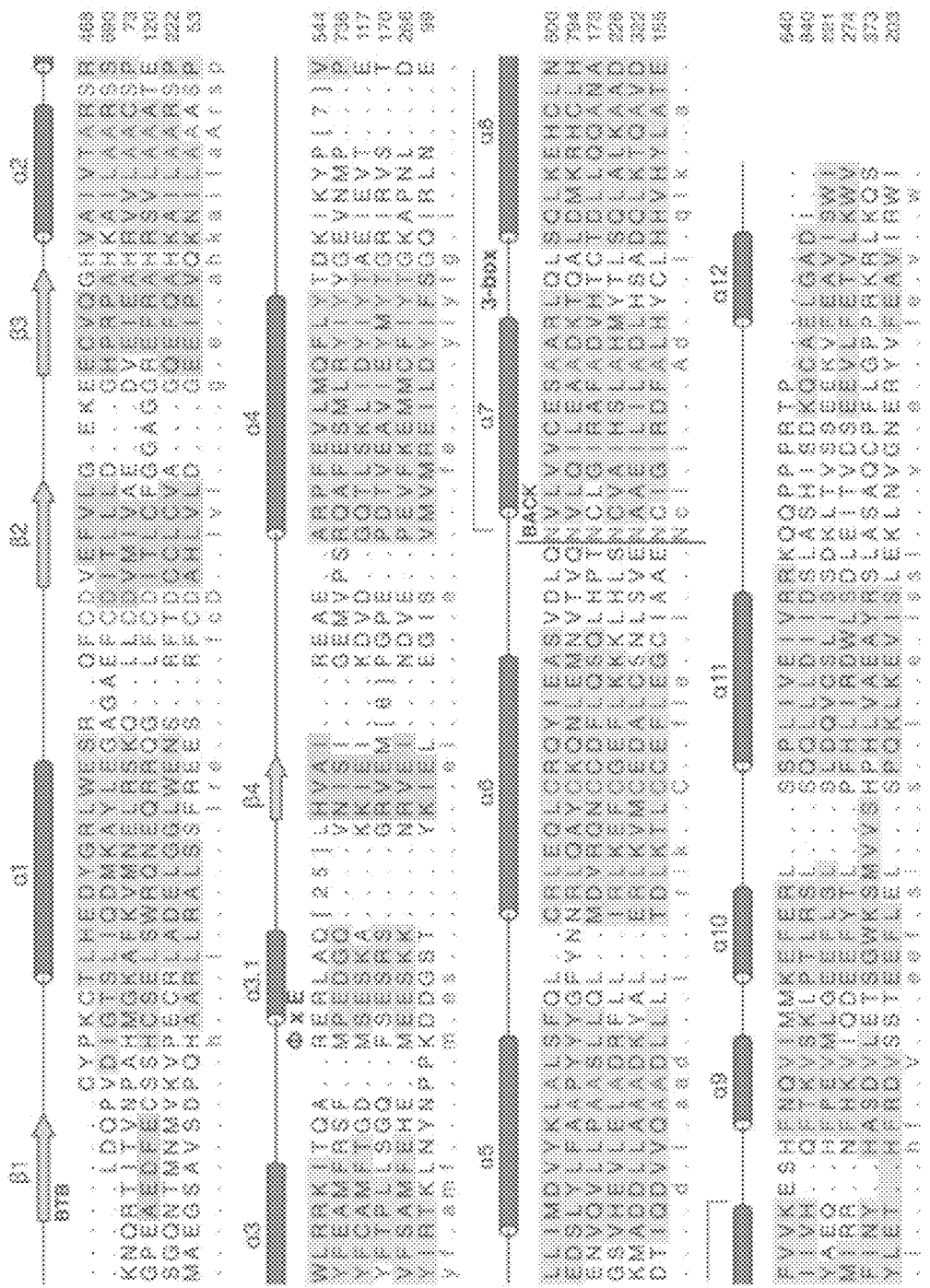
FIG. 9. Sequence alignment of BTB-BACK domains. The two BTB-BACK domains of LZTR-1 are included along with the predicted secondary structure from HHpred[6]. The 3-box is the Cul3 binding element within the BACK domain. The secondary structure of KLHL3 (PDB ID 4HXI), KLHL11 (PDB ID 4AP2) and Gigaxonin (PDB ID 3HVE) are based on the crystal structures. The secondary structure of SPOP is based on a crystal structure for the BTB and 3-box region (PDB ID 3HTM) and HHpred predictions from the remainder of the BACK domain. Only the N-terminal half of the BACK domain from KLHL3, KLHL11 and Gigaxonin is included, as SPOP and LZTR-1 contain truncated versions of the BACK domain. Figure discloses SEQ ID NOS 8483-8488, respectively, in order of appearance.

The whole-exome analysis identified a mean of 43 protein-changing somatic mutations per tumor sample. The distribution of substitutions shows a higher rate of transitions vs tranversions (67%), with a strong preference for C→T and G→A (55%) (FIG. 6). As seen in other tumor types[10], 19.2% of the mutations occurred in a CpG dinucleotide context (FIG. 7). Among somatic small nucleotide variants, the most frequently mutated genes have well-established roles in cancer, including GBM (TP53, EGFR, PTEN, and IDH1). In addition to known cancer genes, whole-exome sequencing identified several potentially new candidate driver genes mutated in ~5% of tumor samples. To uncover the most likely driver genes of GBM initiation and/or progression, the mutation results were integrated with common focal genomic alterations, detected using an algorithm applied to high-density SNP arrays to generate MutComFocal scores. This analysis stratified somatically mutated genes into three groups: recurrently mutated genes without significant copy number alterations (Mut), mutated genes in regions of focal and recurrent amplifications (Amp-Mut) and mutated genes in regions of focal and recurrent deletions (Del-Mut). Employing this framework, a list of 67 genes was generated that score at the top of each of the three categories and that included nearly all the genes previously implicated in GBM. These genes, which are labeled in green in FIG. 1 include IDH1 (Mut, FIG. 1a), PIK3C2B, MDM4, MYCN, PIK3CA, PDGFRA, KIT, EGFR, and BRAF (Amp-Mut, FIG. 1b) and PIK3R1, PTEN, RB1, TP53, NF1 and ATRX (Del-Mut, FIG. 1c). Interestingly, the analysis also selected 52 new candidate driver genes previously unreported in GBM. Based upon their role in development and homeostasis of the CNS and their potential function in oncogenesis and tumor progression, 24 genes were selected for re-sequencing in an independent dataset of 35 GBM and matched normal controls. Eighteen genes were found somatically mutated by Sanger sequencing in the independent panel and are labeled in red in FIG. 1. Each of the validated new GBM genes is targeted by somatic mutations and CNVs in a cumulative fraction comprised between 2.9% and 45.7% of GBM (FIG. 9).

Figure 1B:
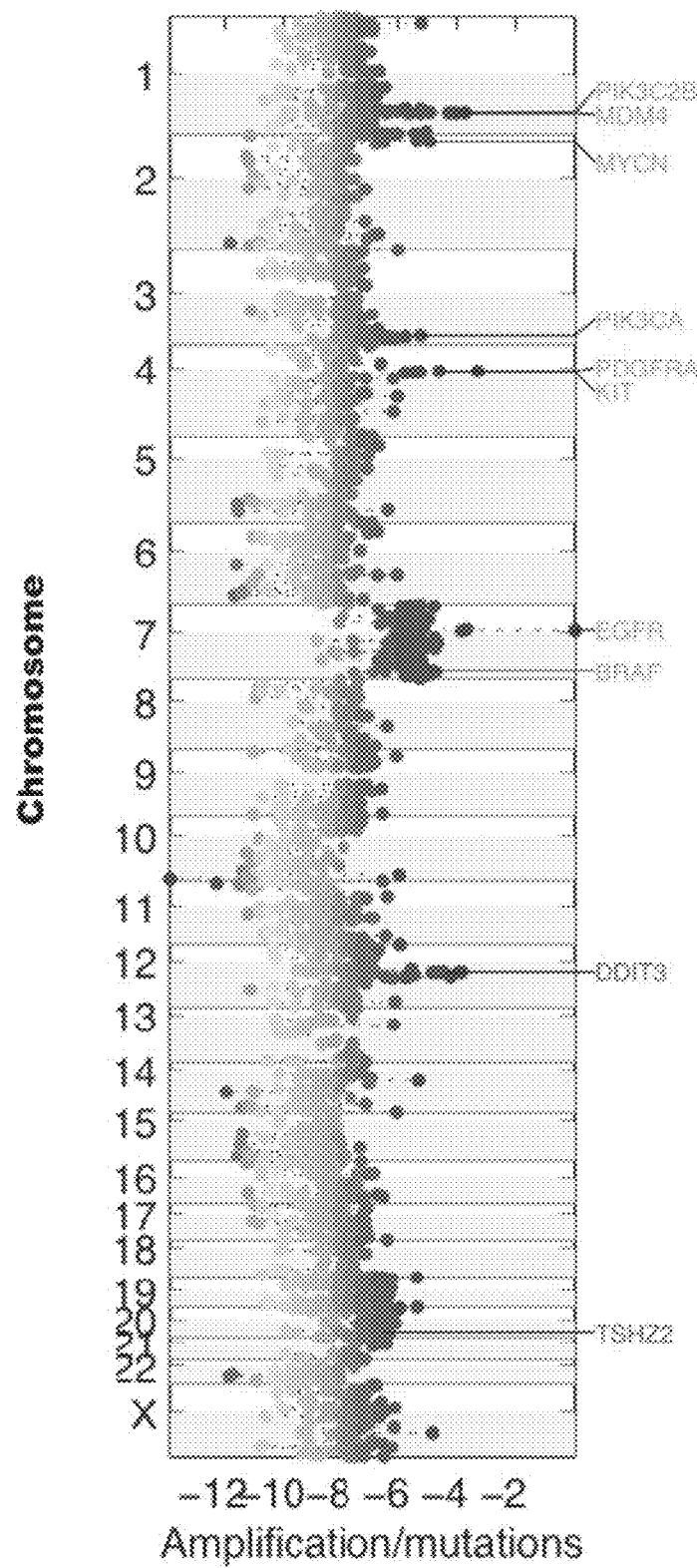
FIG. 1B is a chromosome view of validated GBM genes scoring at the top of each of the three categories by Mut-ComFocal. The plot shows mutated genes in regions of focal and recurrent amplifications (Amp-Mut, Amplification/mutation scores). Previously known GBM genes are indicated in green (light grey in black and white image), new and independently validated GBM genes are indicated in red (dark grey in black and white image).

Among the commonly mutated and focally deleted genes that exhibited top MutComFocal scores and were validated in the independent GBM dataset, BCOR, LRP family members, HERC2, LZTR-1 and CTNND2. BCOR, a chromosome X-linked gene, encodes for a component of the nuclear co-repressor complex that is essential for normal development of the neuroectoderm and stem cell functions[11-13]. BCOR mutations have recently been described in retinoblastoma and medulloblastoma, thus indicating that loss-of-function mutations in BCOR are common genetic events in neuroectodermal tumors[14,15]. LRP1B is a member of the LDL receptor family and is among the most frequently mutated genes in human cancer (FIG. 1c)[16]. Interestingly, two other LDL receptor family members (LRP2 and LRP1) are mutated in 4.4% and 2.9% of tumors, respectively (FIG. 1a). The LRP proteins are highly expressed in the neuroepithelium and are essential for morphogenesis of the forebrain in mouse and humans[17,18]. The tumor suppressor function of LRP proteins in GBM may be linked to their ability to promote chemosensitivity and control signaling through the Sonic hedgehog pathway, which is responsible for maintenance of cancer initiating cells in GBM[19-21]. The gene coding for the Hect ubiquitin ligase Herc2 is localized on chromosome 15q13 and is deleted and mutated in 15.1% and 2.2% of GBM cases, respectively. This gene has been implicated in severe neurodevelopmental syndromes. Moreover, protein substrates of Herc2 are crucial factors in genome stability and DNA damage-repair, two cell functions frequently disrupted in cancer[22,23].

Loss-of-Function Genetic Alterations Target the LZTR-1 and CTNND2 Genes in GBM

Figure 1C:
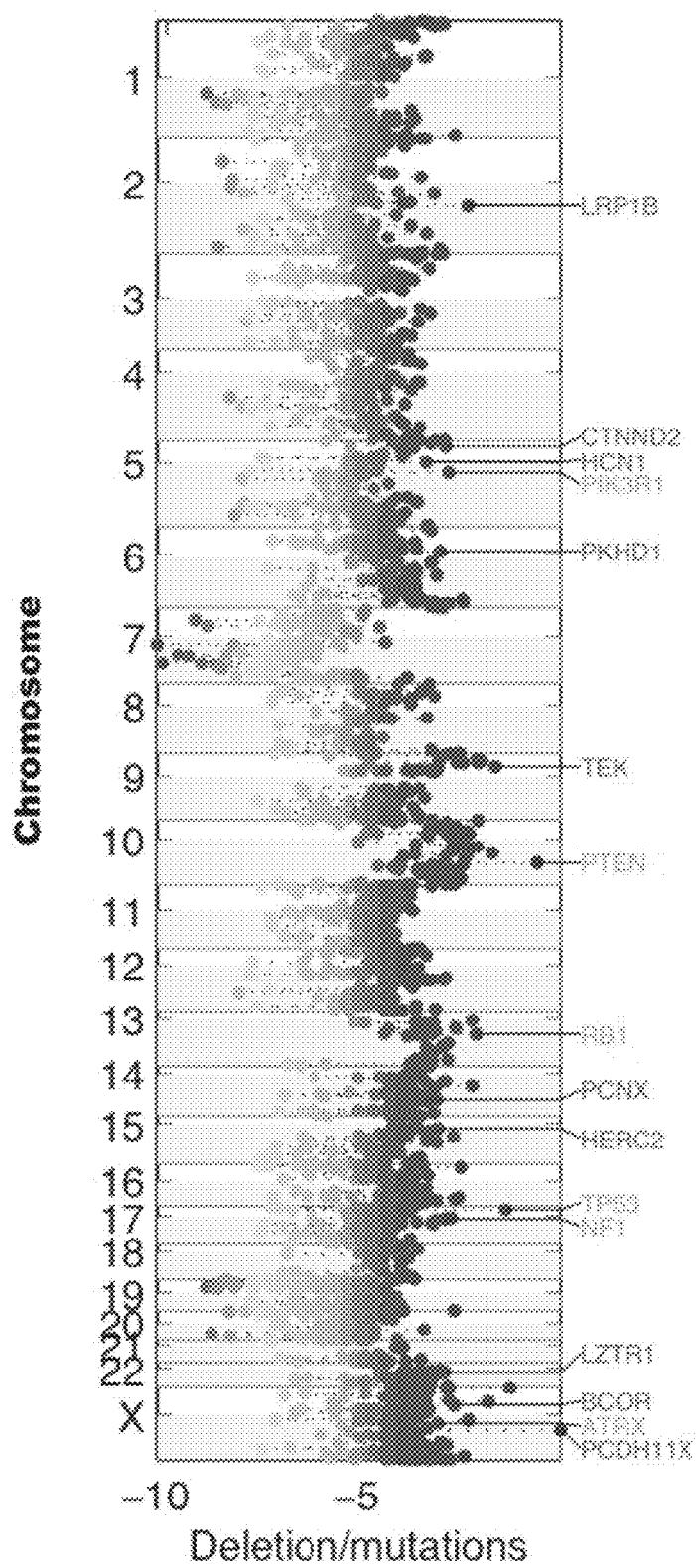
FIG. 1C is a chromosome view of validated GBM genes scoring at the top of each of the three categories by Mut-ComFocal. The plot shows mutated genes in regions of focal and recurrent deletions (Del-Mut, Deletion/mutation scores). Previously known GBM genes are indicated in green (light grey in black and white image), new and independently validated GBM genes are indicated in red (dark grey in black and white image).
Figure 8:
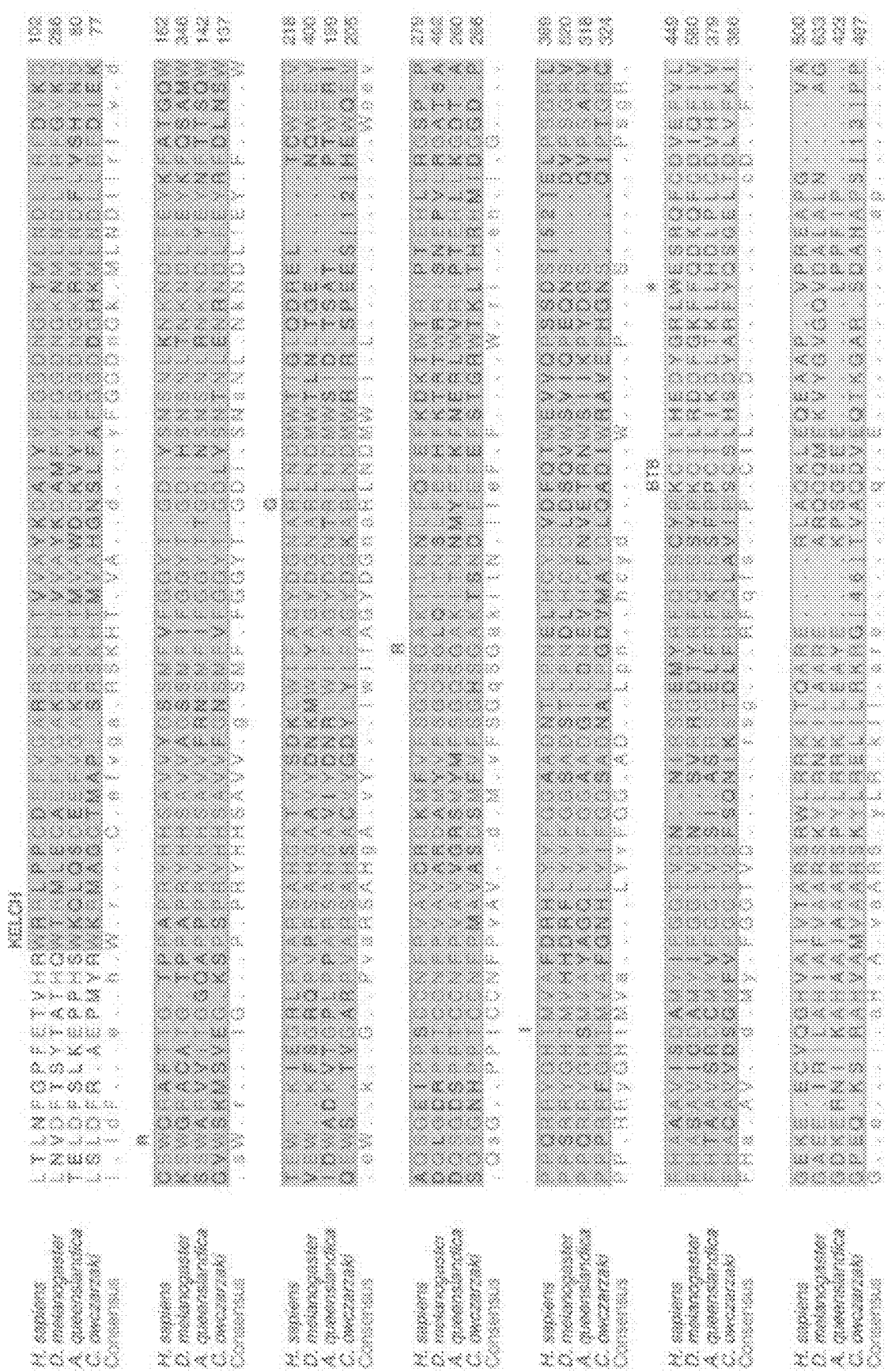
FIG. 8. Sequence alignment of selected LZTR-1 orthologs. Mutations detected in GBM are indicated in red above of the aligned sequences. The LZTR-1 gene is present in most metazoans, including the sponge *Amphimedon queenslandica*, which is generally recognized as the most ancient surviving metazoan lineage[17]. LZTR-1 is also present in some near-metazoan unicellular protists, including *Capsaspora owczarzaki* (included in the Figure) and the choanoflagellates *Salpingoeca rosetta* and *Monosiga brevicollis*. These opisthokonts are key organisms for the study of the evolution of multicellularity, differentiation and cell-cell communication in animals and help in our understanding of the role of molecular pathways in cancer[18]. LZTR-1 has a characteristic Kelch-BTB-BACK-BTB-BACK domain architecture, and unlike the BTB-BACK-Kelch proteins[8], there has been little, if any, duplication of the LZTR-1 gene since its appearance. Despite its name, LZTR-1 does not contain a leucine zipper region. Figure discloses SEQ ID NOS 8479-8482, respectively, in order of appearance.
Figure 8:
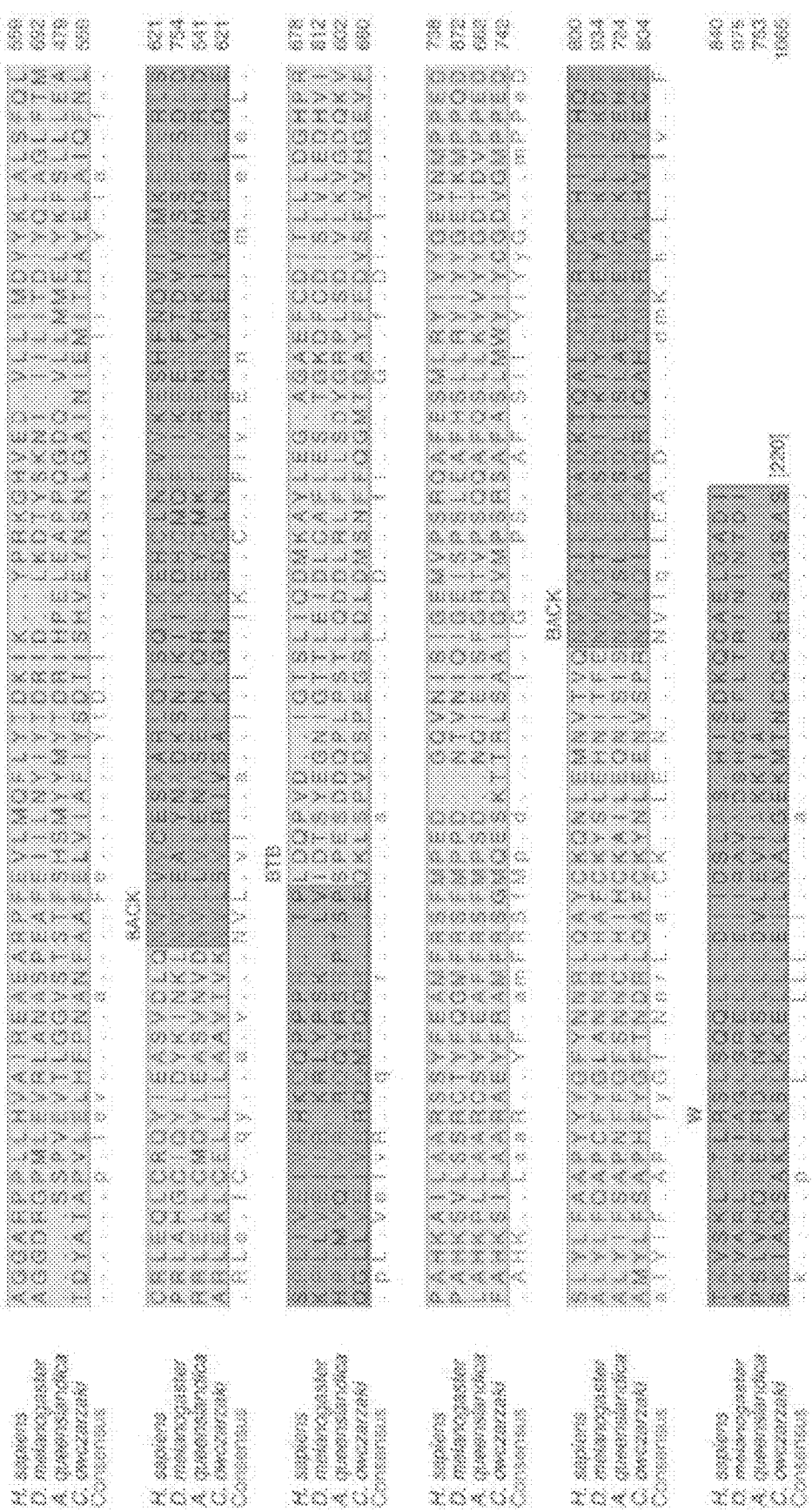

A gene that received one of the highest Del-Mut score by MutComFocal is LZTR-1 (FIG. 1c). The LZTR-1 coding region had non-synonymous mutations in 4.4% and the LZTR-1 locus (human chromosome 22q11) was deleted in 22.4% of GBM. LZTR-1, which is normally expressed in the human brain, codes for a protein with a characteristic Kelch-BTB-BACK-BTB-BACK domain architecture (FIGS. 8, 9). The LZTR-1 gene is highly conserved in the metazoans and was initially proposed to function as a transcriptional regulator, but follow-up studies have excluded a transcriptional role for this protein[24]. Most proteins with BTB-BACK domains are substrate adaptors in Cullin3 (Cul3) ubiquitin ligase complexes, in which the BTB-BACK region binds to the N-terminal domain of Cul3, while a ligand binding domain, often a Kelch 6-bladed β-propeller motif, binds to substrates targeted for ubiquitination[25]. To ask whether LZTR-1 directly binds Cul3, co-immunoprecipitation experiments were performed. FIG. 2a shows that Cul3 immunoprecipitates contain LZTR-1, thus indicating that LZTR-1 is an adaptor in Cul3 ubiquitin ligase complexes.

To address the potential function of LZTR-1 mutants, a homology model of LZTR-1 was built based in part on the crystal structures of the MATH-BTB-BACK protein SPOP[26], the BTB-BACK-Kelch proteins KLHL3 and KLHL11[27], and the Kelch domain of Keap1[28] (FIG. 2b). Without being bound by theory, the second BTB-BACK region of LZTR-1 binds Cul3 because of the presence of a φ-X-E motif in this BTB domain, followed by a 3-Box/BACK region (FIG. 9)[26]. However, the preceding BTB-BACK region also participates in Cul3 binding. Four of the six LZTR-1 mutations identified in GBM are located within the Kelch domain and target highly conserved amino acids (FIG. 2b, c, FIG. 8). Interestingly, the concentration of LZTR-1 mutations in the Kelch domain reflects a similar pattern of mutations in the Kelch-coding region of the KLHL3 gene, recently identified in families with hypertension and electrolytic abnormalities[29,30]. The R198G and G248R mutations localize to the b-c loop of the Kelch domain, in a region predicted to provide the substrate-binding surface of the domain[28]. The W105R mutation targets a highly conserved anchor residue in the Kelch repeats and the T288I mutation disrupts a buried residue that is conserved in LZTR-1 (FIG. 2b, FIG. 8). Both of these mutations are expected to perturb the folding of the Kelch domain. The remaining two mutations, located in the BTB-BACK domains are predicted to affect the interaction with Cul3 either by removing the entire BTB-BACK-BTB-BACK region (W437STOP) or by disrupting the folding of the last helical hairpin in the BTB-BACK domain (R810W, FIG. 2b). The pattern of mutations of LZTR-1 in GBM indicates that they impair binding either to specific substrates or to Cul3.

Figure 10A:
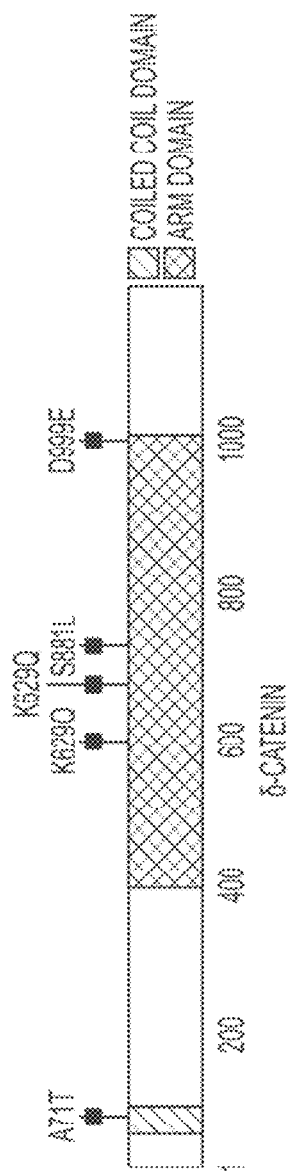
FIG. 10A. Pattern of somatic mutations, CNVs and expression of CTNND2 in GBM. Schematic representation of identified somatic mutations in CTNND2 shown in the context of the known domain structure of the protein. Numbers refer to amino acid residues of the δ-catenin protein.

Among the top ranking genes in MutComFocal, CTNND2 is the gene expressed at the highest levels in the normal brain. CTNND2 codes for □-catenin, a member of the p120 subfamily of catenins that is expressed almost exclusively in the nervous system where it is crucial for neurite elongation, dendritic morphogenesis and synaptic plasticity[31-33]. Germ-line hemizygous loss of CTNND2 severely impairs cognitive function and underlies some forms of mental retardation[34,35]. CTNND2 shows a pronounced clustering of mutations in GBM. The observed spectrum of mutations includes four mutations located in the armadillo-coding domain and one in the region coding for the N-terminal coiled-coil domain (FIG. 10a). These regions are the two most relevant functional domains of δ-catenin and each of the mutations targets highly conserved residues with probably (K629Q, A776T, S881L, D999E) and possibly (A71T) damaging consequences[36]. Together with focal genomic losses of CTNND2 (FIG. 10b), the mutation pattern indicates that CTNND2 is a tumor suppressor gene in GBM.

Figure 3A:
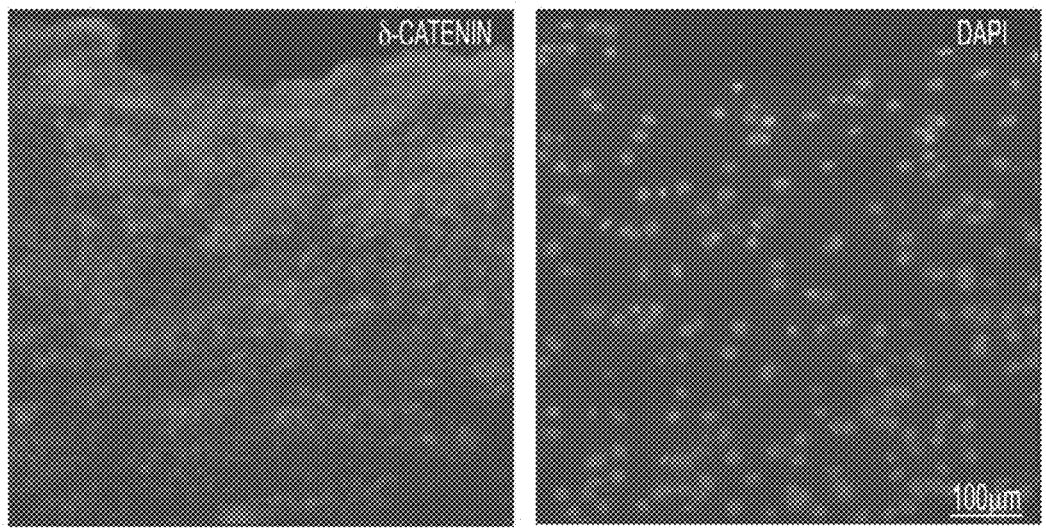
FIGS. 3A-B. Loss of C●●●D● drives mesenchymal transformation of GBM. 3a, Immunofluorescence staining of human brain cortex using δ-catenin antibody (red, left panel); Nuclei are counterstained with Dapi (blue, right panel). 3b, Immunofluorescence staining of human primary GBM included in tissue microarrays (TMA) using δ-catenin antibody (red); Nuclei are counterstained with Dapi (blue). A representative δ-catenin-positive and negative tumor is shown in the left and right panel, respectively.
Figure 3B:
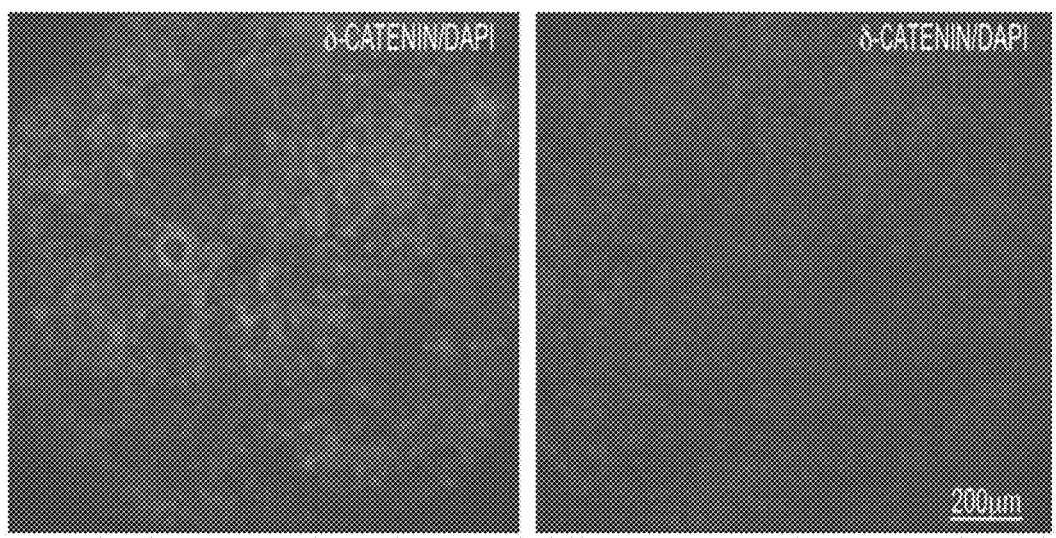
Figure 3C:
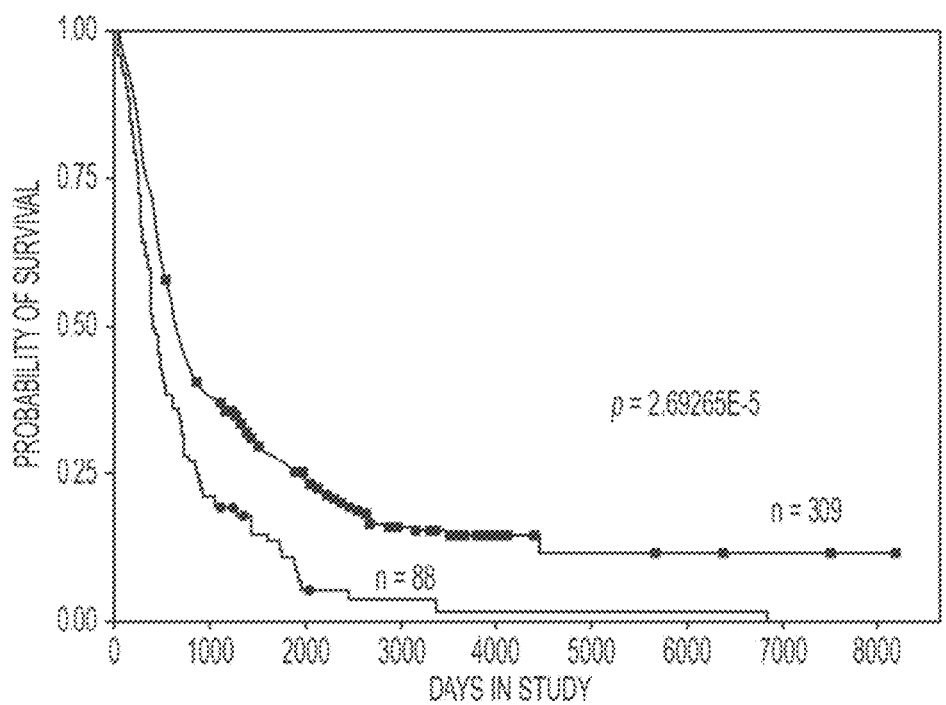
FIGS. 3C-D. Loss of C●●●D● drives mesenchymal transformation of GBM. 3c, Kaplan-Meier analysis for glioma patients with low CTNND2 mRNA expression (≤2-fold, red line) compared with the rest of glioma (blue line). 3d, Kaplan-Meier analysis for glioma patients with low CTNND2 mRNA expression (≤2-fold) and decreased CTNND2 gene copy number (≤1) (red line) compared with the rest of glioma (blue line).
Figure 3D:
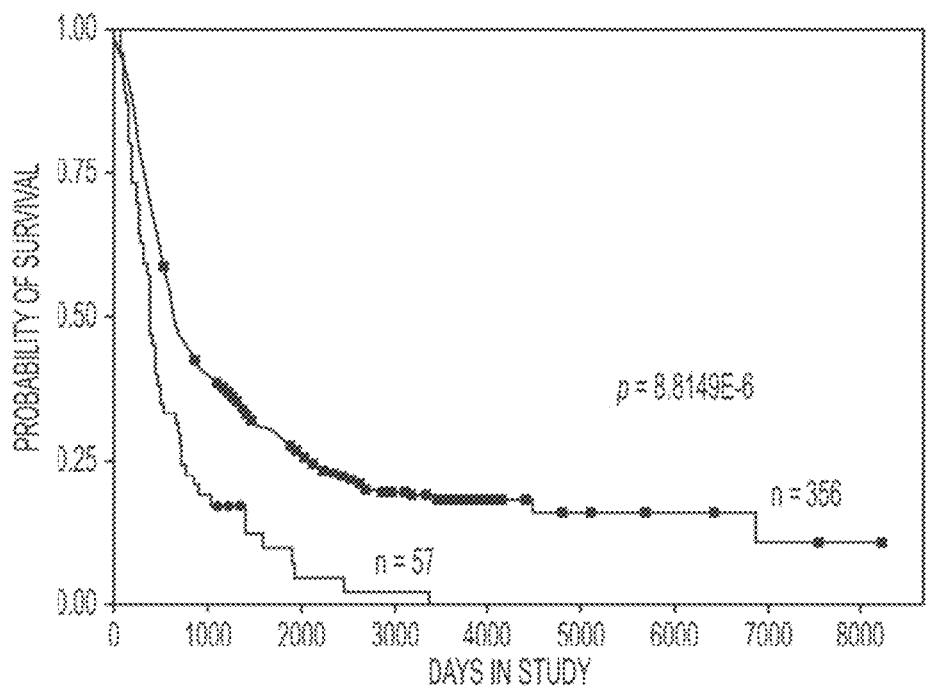
Figure 3E:
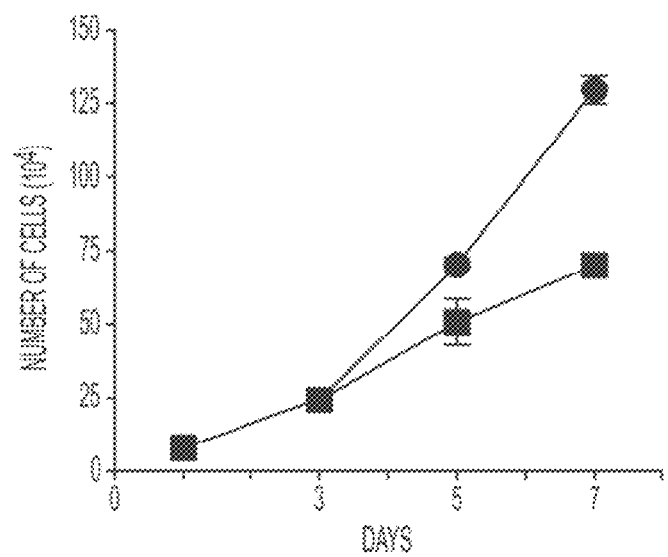
FIGS. 3E-F. Loss of C●●●D● drives mesenchymal transformation of GBM. 3e, Growth rate of U87 glioma cells transduced with a lentivirus expressing δ-catenin (squares) or the empty vector (circles, average of triplicate cultures). 3f, Expression of mesenchymal genes in glioma cells expressing δ-catenin or the empty vector (averages of triplicate quantitative RT-PCR). All error bars are SD. *, p≤0.005; **, p≤0.001.
Figure 3F:
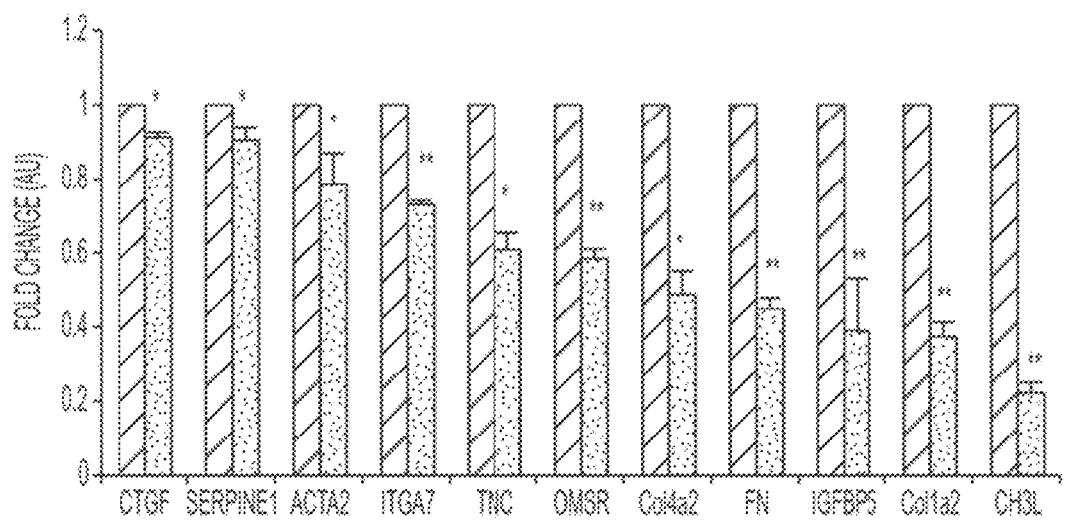
Figure 3G:
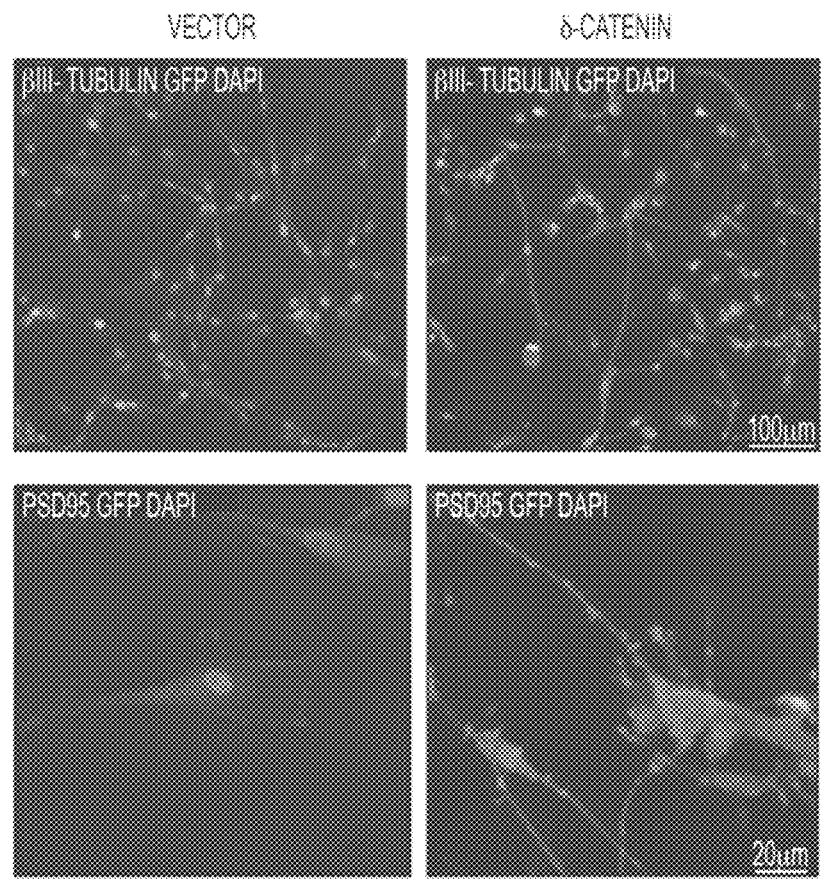
FIGS. 3G-H. Loss of C●●●D● drives mesenchymal transformation of GBM. 3g, Immunofluorescence staining for βIII-tubulin (upper panels) and PSD95 (lower panels) in glioma cells expressing δ-catenin or the empty vector. 3h, Western blot using the indicated antibodies in glioma cells expressing δ-catenin or the empty vector. Vinculin is shown as control for loading.
Figure 3H:
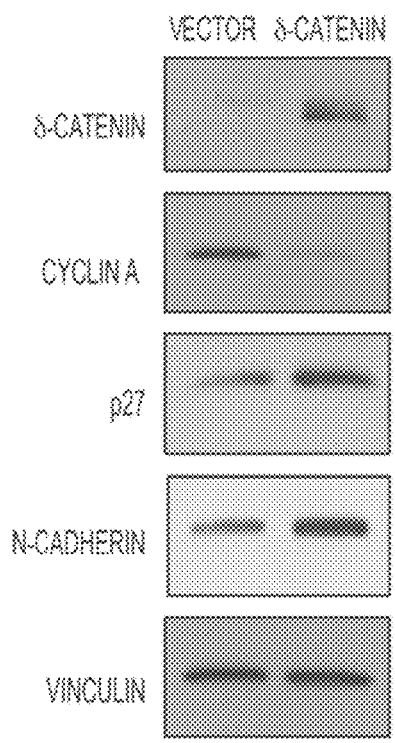
Figure 10B:
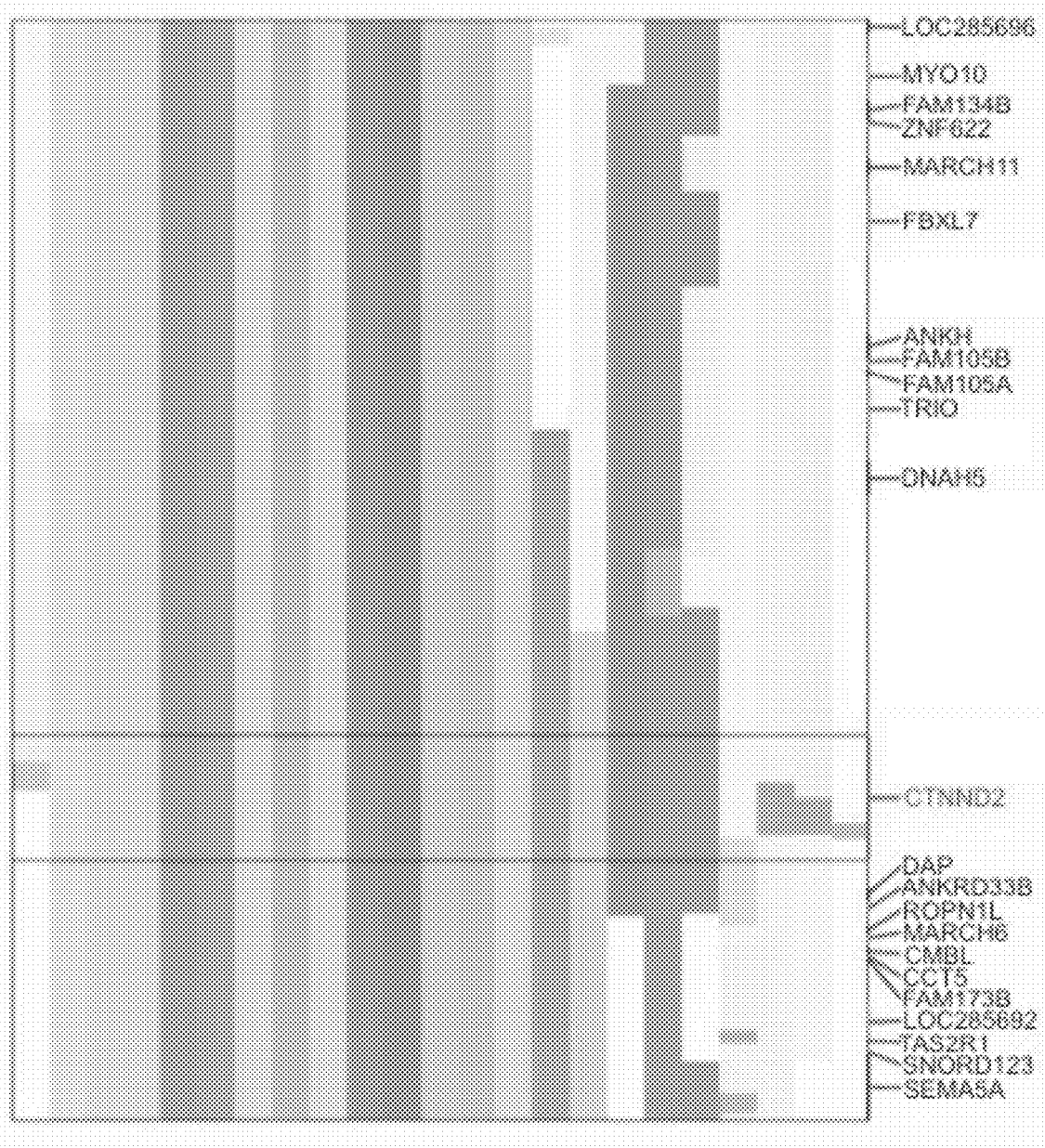
FIG. 10B. Pattern of somatic mutations, CNVs and expression of CTNND2 in GBM. Somatic deletions of CTNND2. Samples are sorted according to the focality of CTNND2 deletion. In the red-blue scale, white corresponds to normal (diploid) copy number, blue is deletion and red is gain.
Figure 10C:
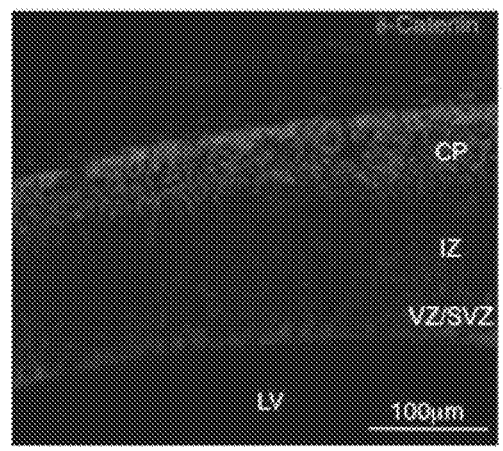
FIG. 10C. Pattern of somatic mutations, CNVs and expression of CTNND2 in GBM. Pattern of expression of δ-catenin in the developing mouse brain (embryonic day 14.5), as determined by immunostaining. The highest levels of δ-catenin are detected in the cortical plate (CP) that contains differentiating neurons. IZ, intermediate zone; VZ/SVZ ventricular zone/subventricular zone; LV, lateral ventricle.
Figure 10D:
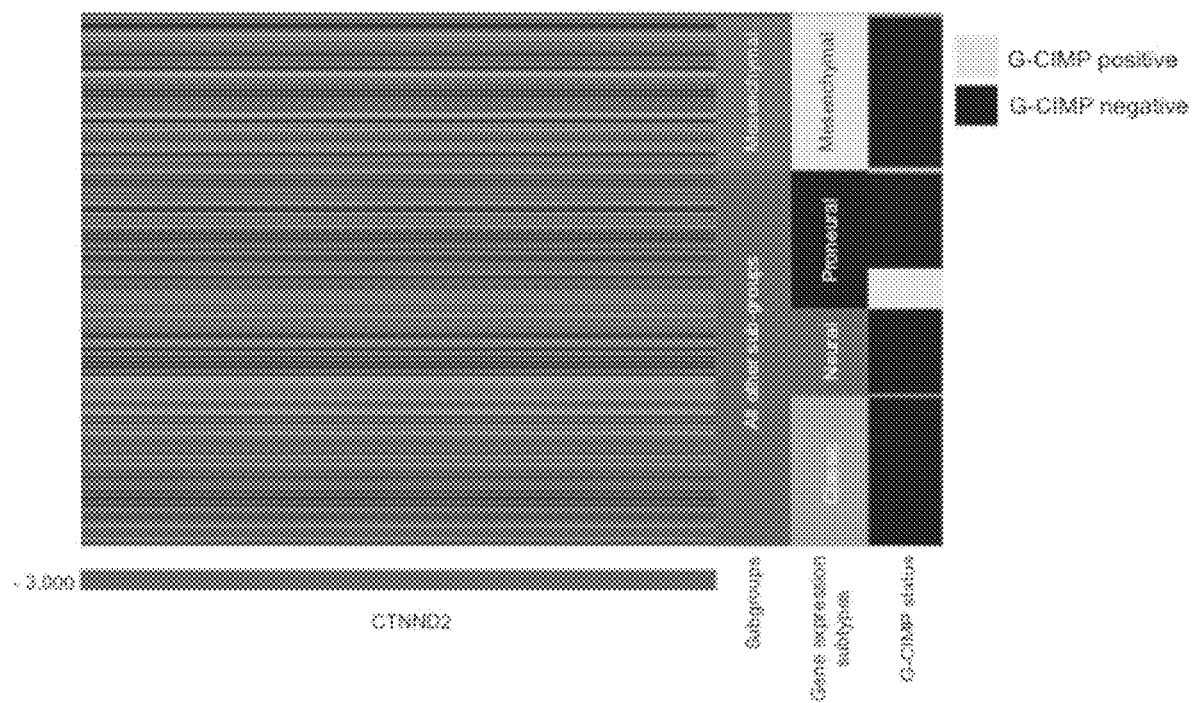
FIG. 10D. Pattern of somatic mutations, CNVs and expression of CTNND2 in GBM. CTNND2 mRNA expression analysis from Atlas-TCGA samples shows that CTNND2 is significantly down-regulated in the mesenchymal subgroup. In the green-red scale, black is the median, green is down-regulation and red is up-regulation.

It was asked whether the expression of CTNND2 is down-regulated during oncogenic transformation in the CNS. Immunostaining experiments showed that δ-catenin is strongly expressed in the normal human and mouse brain with the highest expression in neurons (FIG. 3a, FIG. 10c). Conversely, the immunostaining analysis of 69 GBM revealed negligible or absent expression of δ-catenin in 21 cases (FIG. 3b). Oncogenic transformation in the CNS frequently results in loss of the default proneural cell fate in favor of an aberrant mesenchymal phenotype, which is associated with a very aggressive clinical outcome[37]. The analysis of gene expression profiles of 498 GBM from the ATLAS-TCGA collection showed that low expression of CTNND2 is strongly enriched in tumors identified by a mesenchymal gene expression signature (T-test p-value=2.4 10$^{-12}$, FIG. 10d). Tumors with low CTNND2 expression were also characterized by poor clinical outcome and, among them tumors with copy number losses of the CTNND2 gene displayed the worst prognosis (FIG. 3c, d). Mesenchymal transformation of GBM, which is detected in the vast majority of established glioma cell lines, is associated with an apparently irreversible loss of the proneural cell fate and neuronal markers[37]. Expression of δ-catenin in the U87 human glioma cell line reduced cell proliferation (FIG. 3e), decreased the expression of mesenchymal markers (FIG. 3f) and induced neuronal differentiation as shown by elongation of β3-tubulin-positive neurites and development of branched dendritic processes that stained positive for the post-synaptic marker PSD95 (FIG. 3g). Accordingly, δ-catenin decreased expression of cyclin A, a S-phase cyclin and up-regulated the Cdk inhibitor p27$^{Kip1}$ and the neuronal-specific gene N-cadherin (FIG. 3h). Thus, restoring the normal expression of δ-catenin reprograms mesenchymal glioma cells towards the proneural lineage.

Recurrent EGFR Fusions in GBM

To identify gene fusions in GBM, RNA-seq data was analyzed from a total of 185 GBM samples (161 primary GBM plus 24 short-term cultures of glioma stem-like cells (GSCs) freshly isolated from patients carrying primary GBM). The analysis of the RNA-seq dataset led to the discovery of 92 candidate rearrangements that give rise to in-frame fusion transcripts (FIG. 27). Beside the previously reported FGFR3-TACC3 fusions events, the most frequent recurrent in-frame fusions involved EGFR in 7.6% of samples (14/185, 3.8%-11.3% CI). Nine of the 14 EGFR fusions included the recurrent partners SEPT14 (6/185, 3.2%) and PSPH (3/185, 1.6%) as the 3' gene segment in the fusion. Two in-frame highly expressed fusions were also found involving the neurotrophic tyrosine kinase receptor 1 gene (NTRK1) as 3' gene with two different 5' partners (NFASC-NTRK1 and BCAN-NTRK1). Fusions with a similar structure involving NTRK1 are commonly found in papillary thyroid carcinomas[38]. Using EXomeFuse, an algorithm for the reconstruction of genomic fusions from whole-exome data, EGFR-SEPT14 and NRTK1 fusions are the result of recurrent chromosomal translocations and reconstructed the corresponding genomic breakpoints (FIG. 27).

Figure 4A:
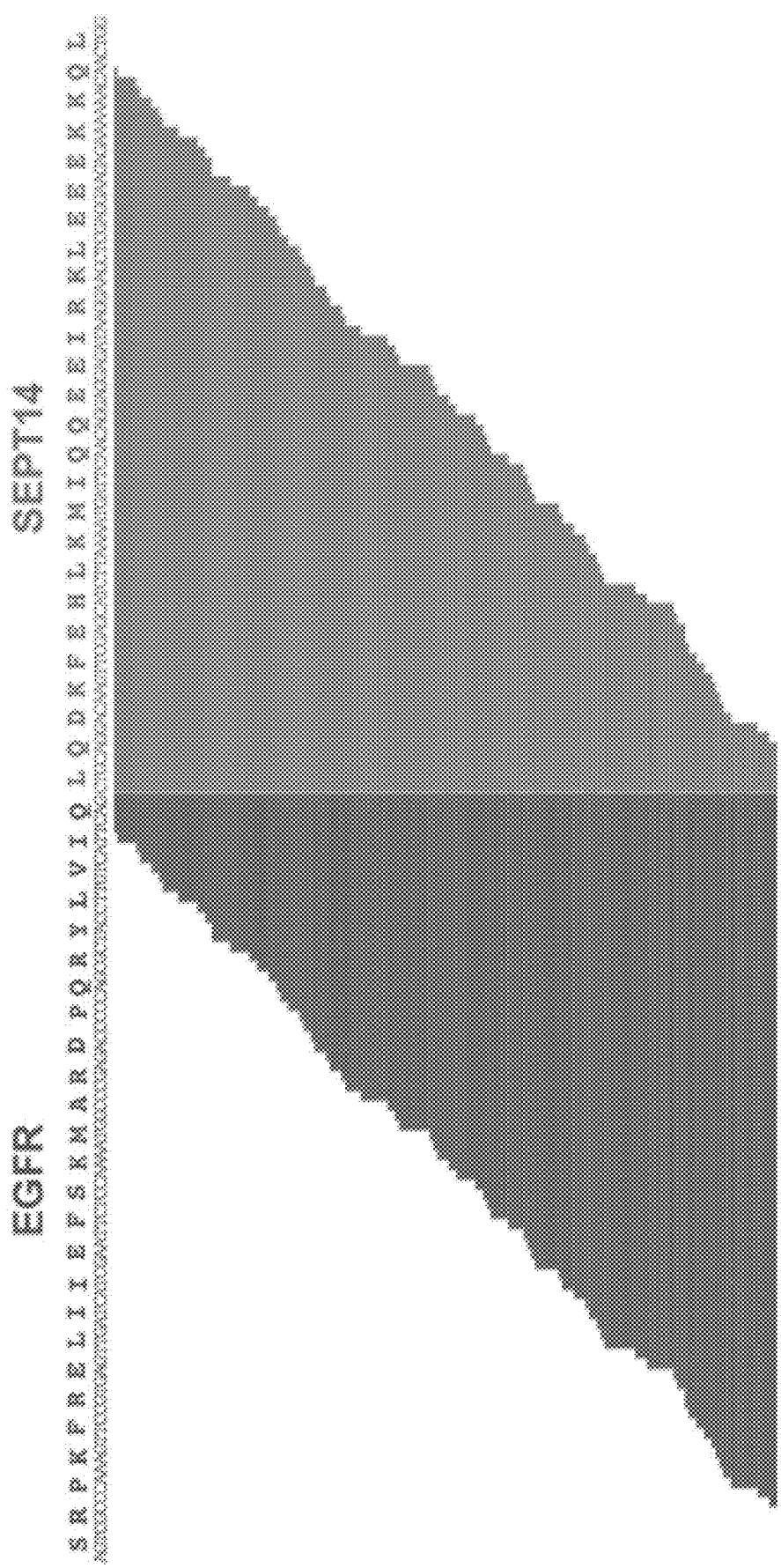
FIG. 4A. EGFR-SEPT14 gene fusion identified by whole transcriptome sequencing. Split reads are shown aligning on the breakpoint. The predicted reading frame at the breakpoint is shown at the top with EGFR sequences in blue and SEPT14 in red. The amino acid sequence (TOP) is SEQ ID NO: 1; the nucleotide sequence (bottom) is SEQ ID NO: 2.
Figure 11A:
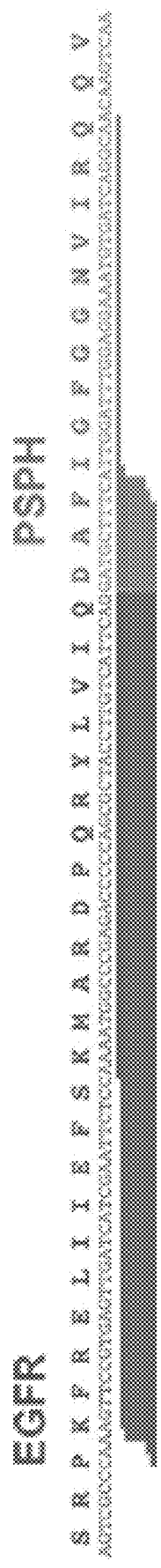
FIG. 11A. EGFR-PSPH gene fusion identified by whole transcriptome sequencing. Split reads are shown aligning on the breakpoint. The predicted reading frame at the breakpoint is shown at the top with EGFR sequences in blue (grey in black and white image; encompassing "SRR . . . VIQ" amino acids and "AGT . . . CAG" nucleotides) and PSPH in red (light grey in black and white image; encompassing "DAF . . . QQV" amino acids and "GAT . . . CAA" nucleotides). The amino acid sequence (TOP) is SEQ ID NO: 7; the nucleotide sequence (bottom) is SEQ ID NO: 8.
Figure 11B:
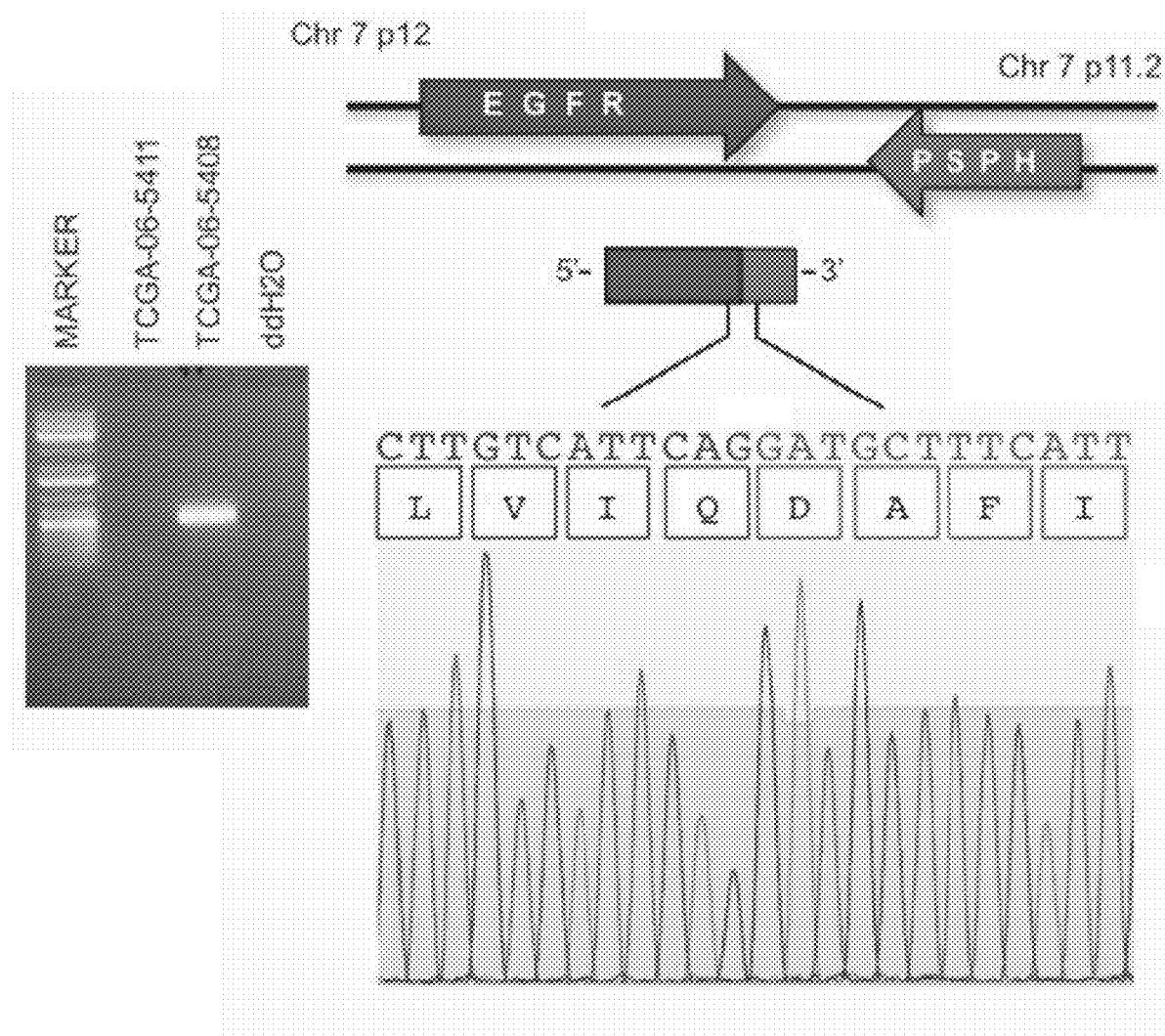
FIG. 11B. EGFR-PSPH gene fusion identified by whole transcriptome sequencing. (left panel), EGFR-PSPH specific PCR from cDNA derived from GBMs. Marker, 1 kb ladder. (right panel), Sanger sequencing chromatogram showing the reading frame (SEQ ID NO: 10) at the breakpoint and putative translation of the fusion protein (SEQ ID NO: 9) in the positive sample.
Figure 12A:
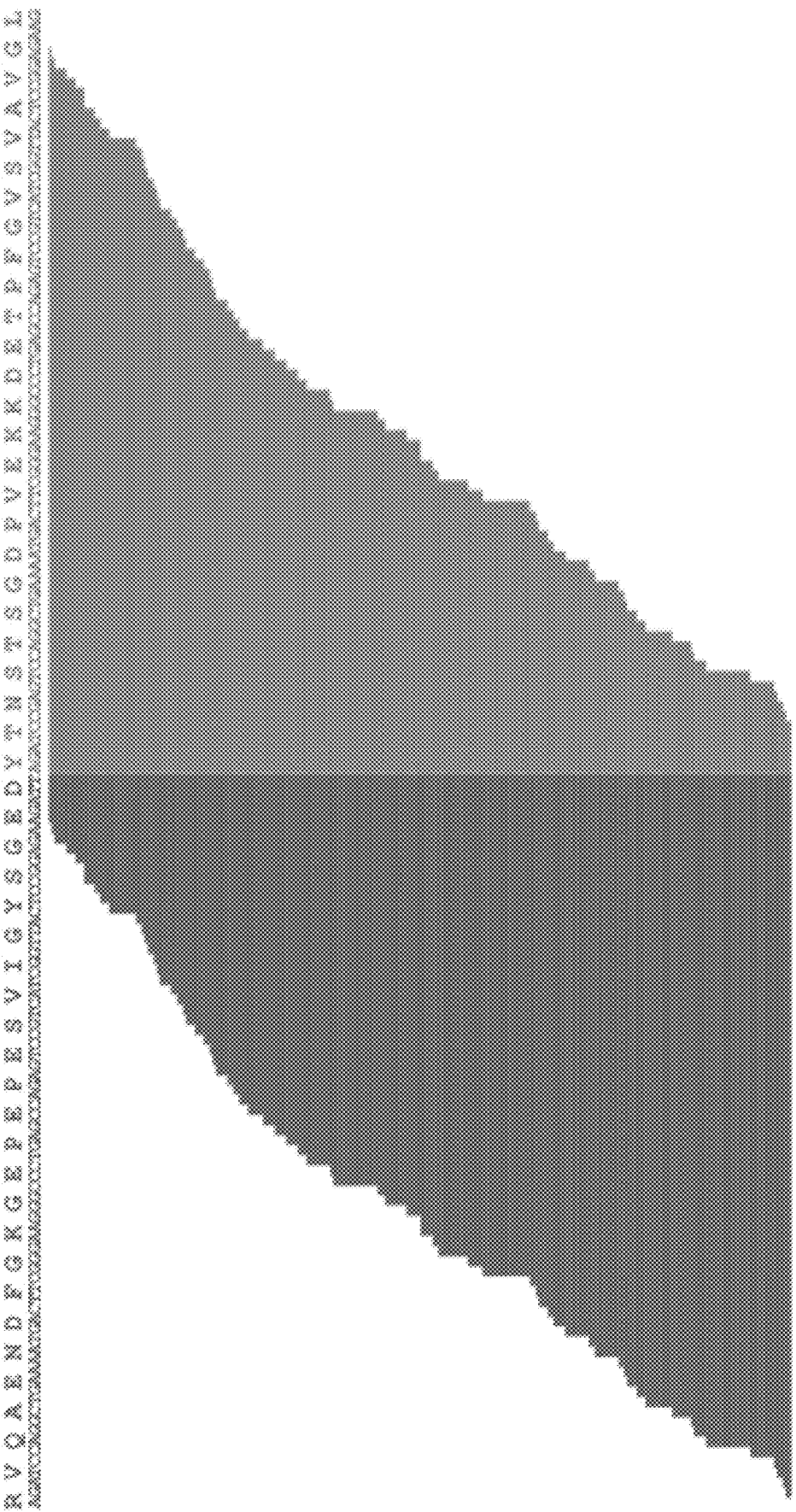
FIG. 12A. NFASC-NTRK1 gene fusion identified by whole transcriptome sequencing. Split reads are shown aligning on the breakpoint. The predicted reading frame at the breakpoint is shown at the top with NFASC sequences in blue (grey in black and white image; encompassing "RVQ . . . GED" amino acids and "AGA . . . ATT" nucleotides) and NTRK1 in red (light grey in black and white image; encompassing "YTN . . . VGL" amino acids and "AGA . . . AAG" nucleotides). Figure discloses SEQ ID NOS 8489-8490, respectively, in order of appearance.
Figure 12B:
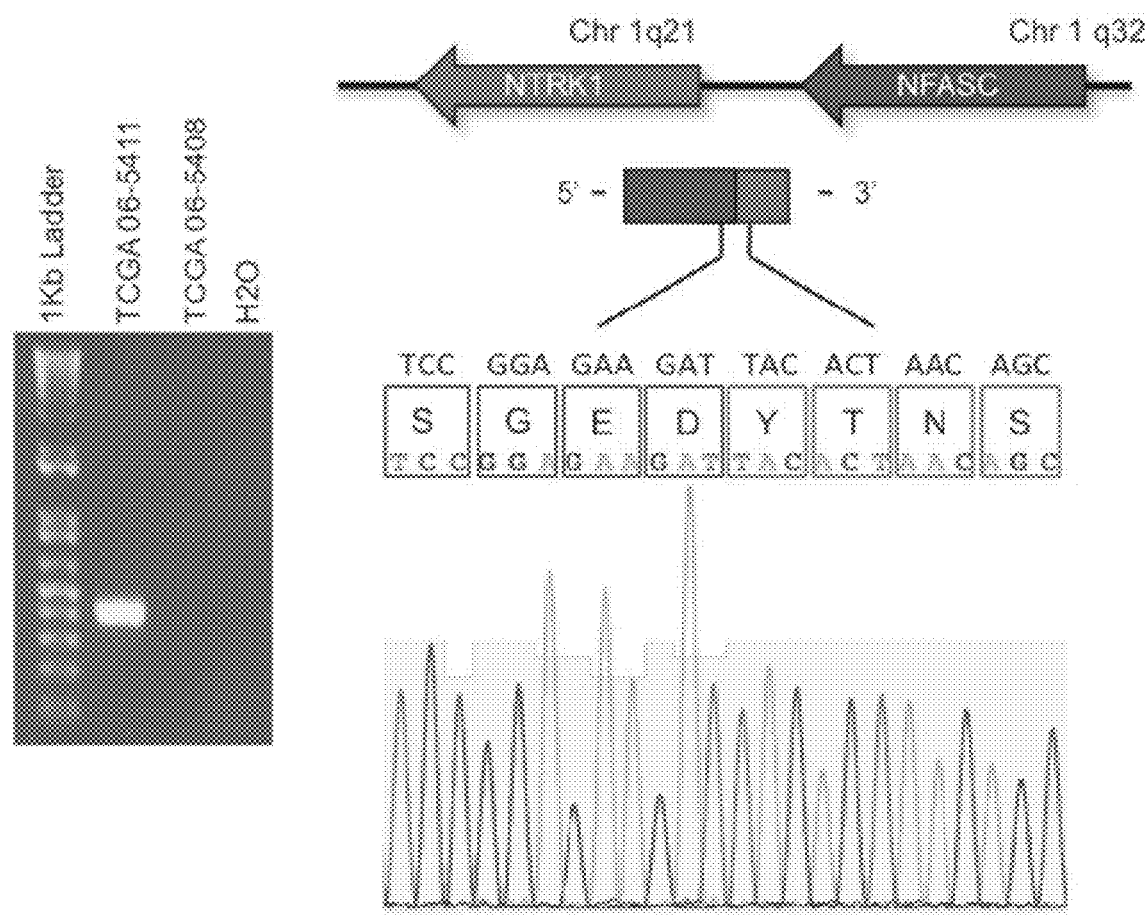
FIG. 12B. NFASC-NTRK1 gene fusion identified by whole transcriptome sequencing. (left panel), NFASC-NTRK1 specific PCR from cDNA derived from GBMs. Marker, 1 kb ladder. (right panel), Sanger sequencing chromatogram showing the reading frame (SEQ ID NO: 8491) at the breakpoint and putative translation of the fusion protein (SEQ ID NO: 8492) in the positive sample.
Figure 12D:
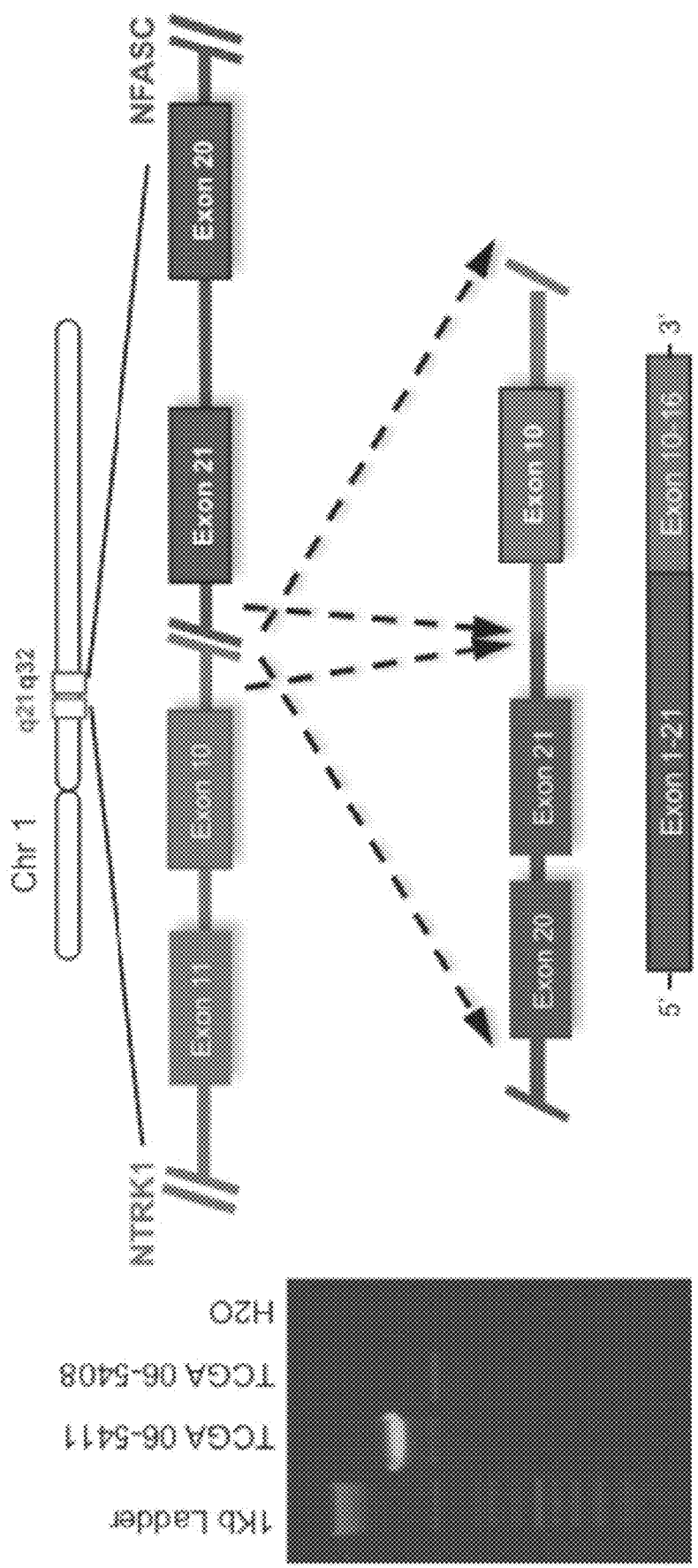
FIG. 12D. NFASC-NTRK1 gene fusion identified by whole transcriptome sequencing. Genomic fusion of NFASC intron 9 with intron 21 of NTRK1. In the fuse mRNA exon 21 of NFASC is spliced 5' to exon 10 of NTRK1. Solid arrows indicate the position of the fusion genome primers that generate a fusion specific PCR product in the GBM sample TCGA-06-5411.
Figure 13:
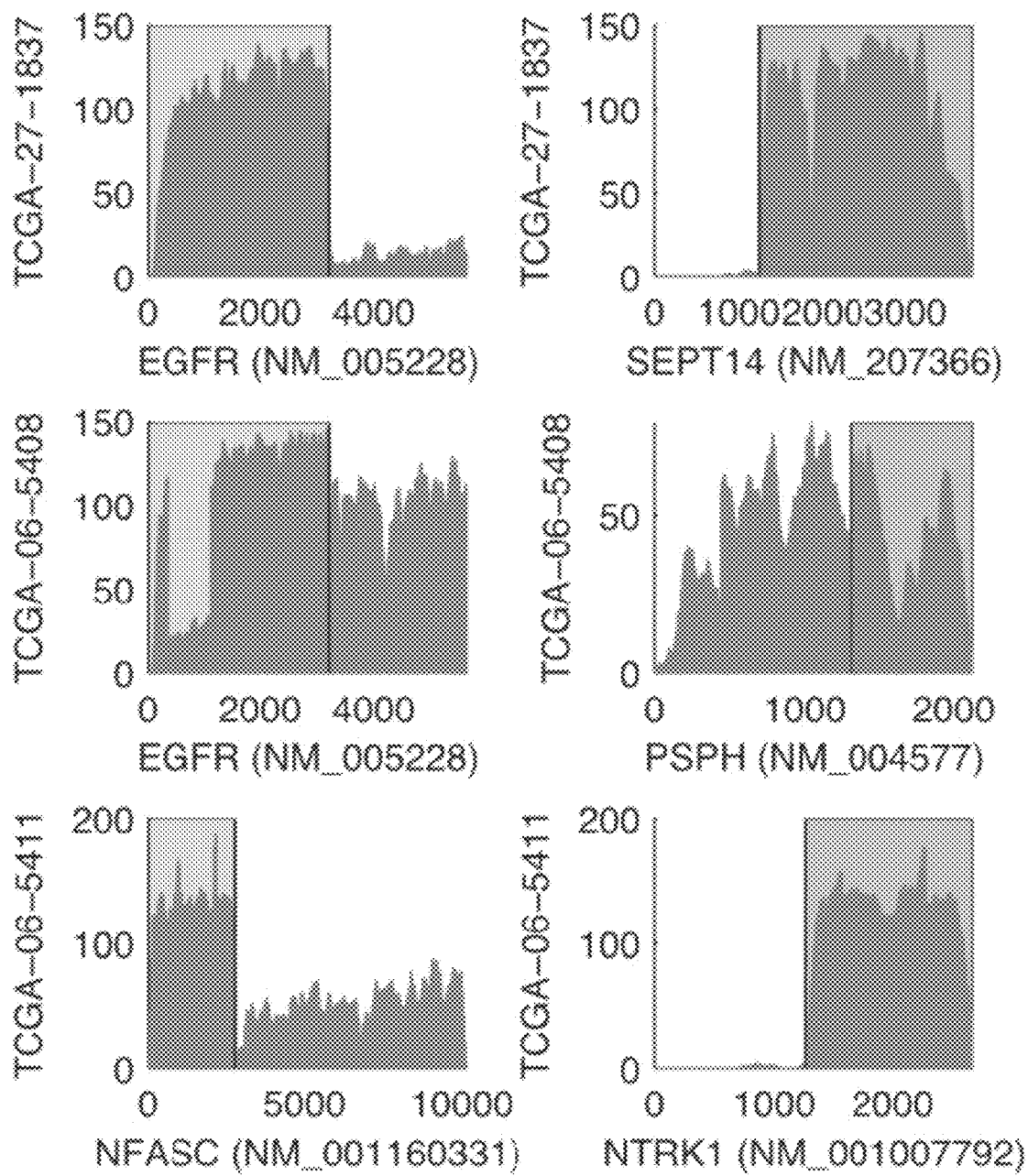
FIG. 13 shows the expression measured by read depth from RNA-seq data. Note the very high level of expression in the regions of the genes implicated in the fusion events.
Figure 14A:
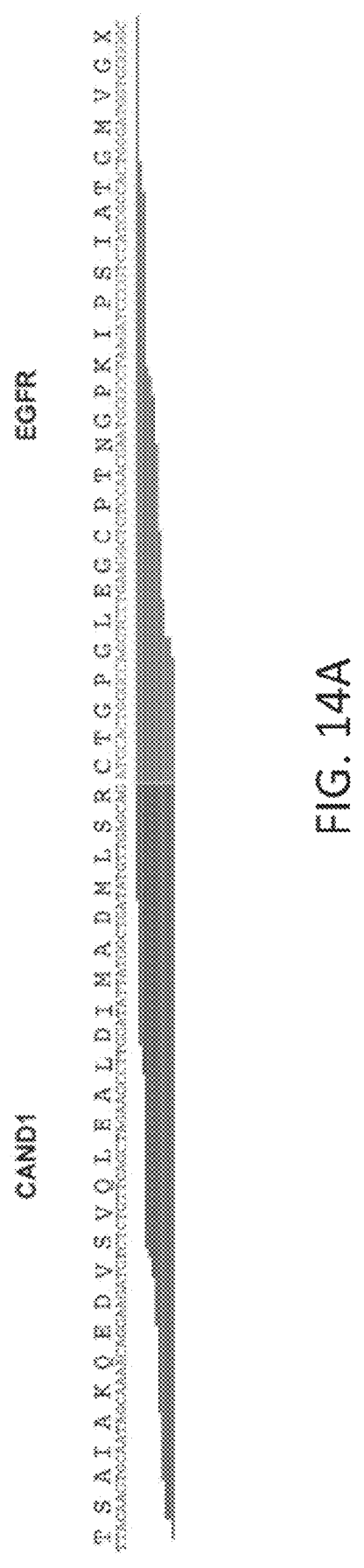
Figure 14B:
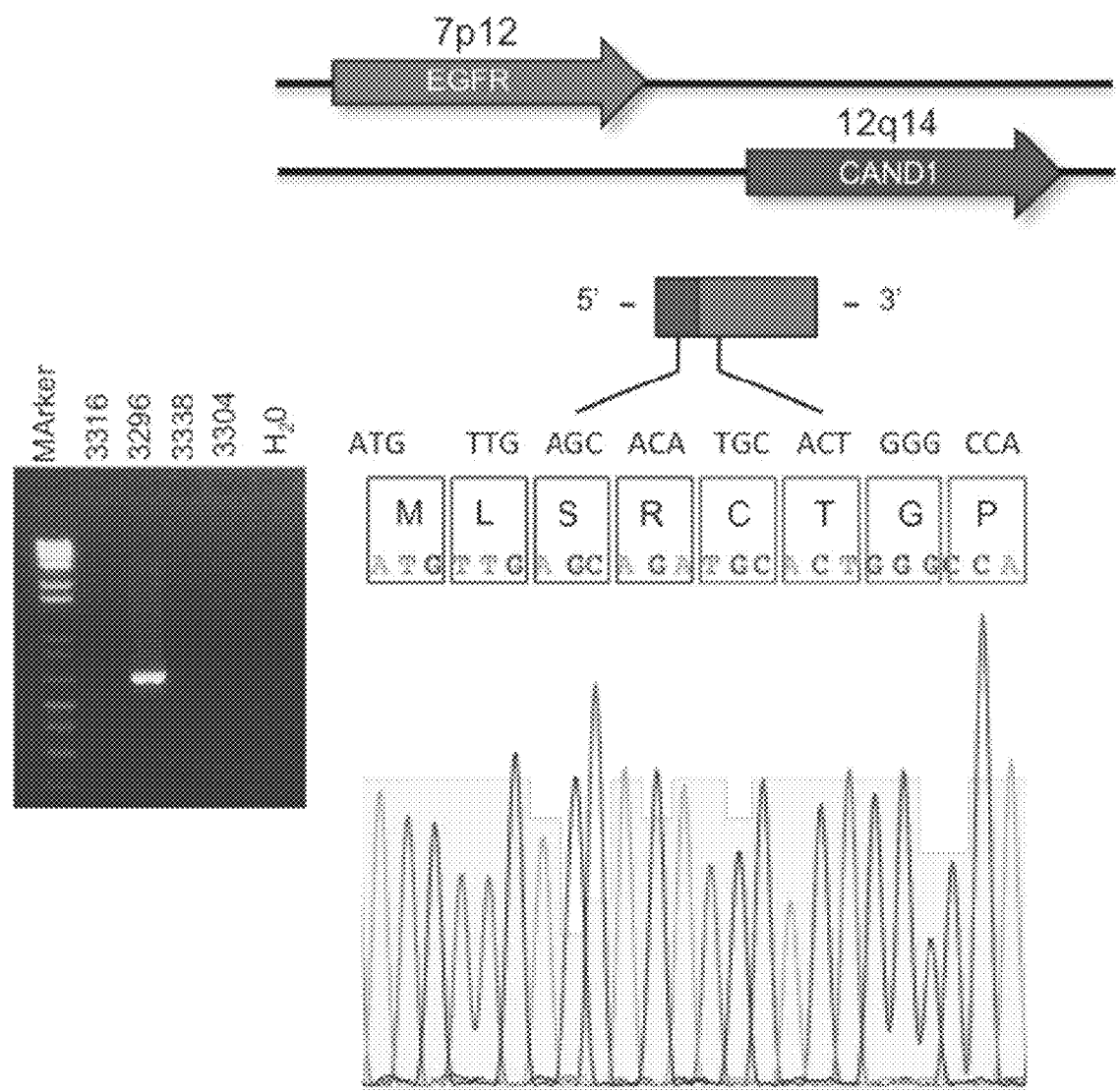
FIG. 14B. CAND1-EGFR gene fusion identified by whole transcriptome sequencing. (left panel), CAND1-EGFR specific PCR from cDNA derived from GBMs. Marker, 1 kb ladder. (right panel), Sanger sequencing chromatogram showing the reading frame at the breakpoint (SEQ ID NO: 15) and putative translation of the fusion protein (SEQ ID NO: 16) in the positive sample (boxed sequences). Figure also discloses SEQ ID NO: 8494.
Figure 14D:
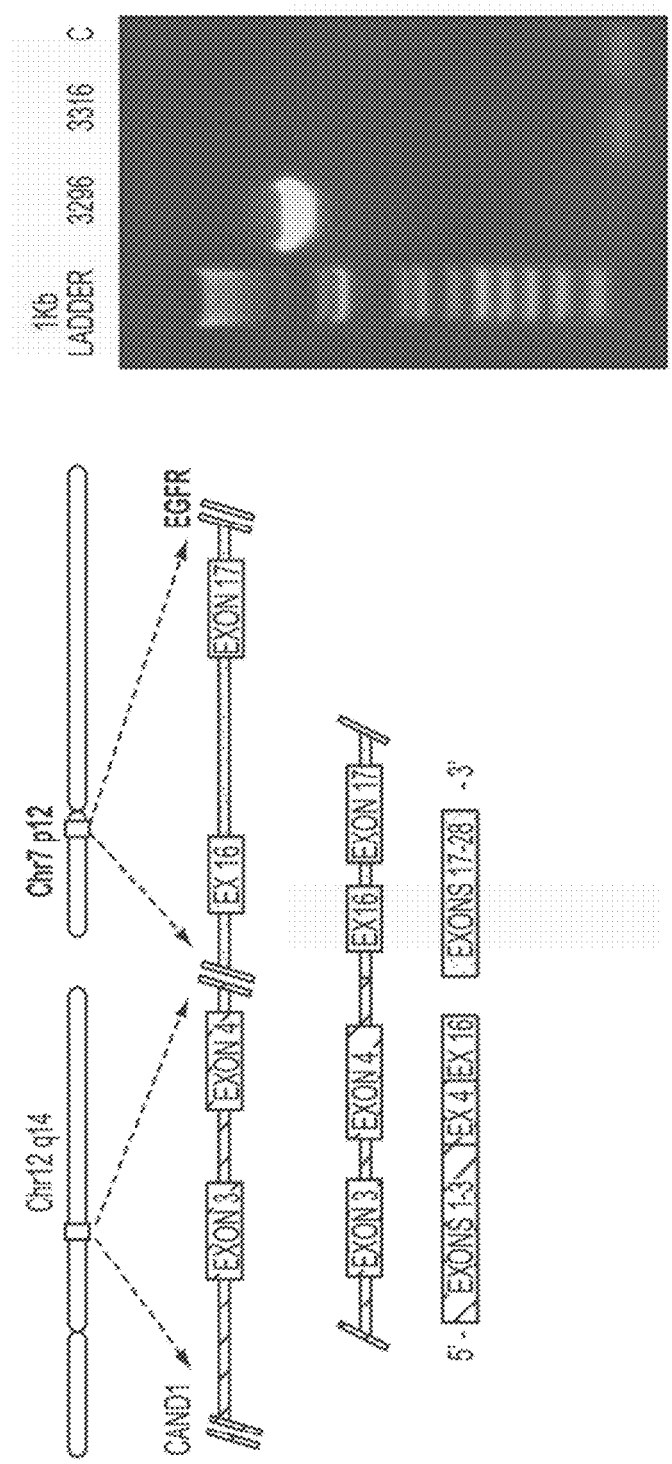
FIG. 14D. CAND1-EGFR gene fusion identified by whole transcriptome sequencing. Genomic fusion of CAND1 intron 4 with intron 15 of EGFR. In the fuse mRNA exon 4 of CAND1 is spliced 5' to exon 16 of EGFR.

By sequencing the PCR products spanning the fusion breakpoint, each of the three types of recurrent in-frame fusion predictions (EGFR-SEPT14, EGFR-PSPH and NRTK1 fusions, FIG. 4, FIG. 11, and FIG. 12) were validated. In FIG. 4a, b the prediction and cDNA sequence validation are shown, respectively, for one of the tumors harboring an EGFR-SEPT14 fusion (TCGA-27-1837). The amplified cDNA contained an open reading frame for a protein of 1,041 amino acids resulting from the fusion of an EGFR amino-terminal portion of residues 1-982 with a SEPT14 carboxy-terminal portion of residues 373-432 (FIG. 4c). Thus, the structure of the EGFR-Septin14 fusion proteins involves EGFR at the N-terminus, providing a receptor tyrosine kinase domain fused to a coiled-coil domain from Septin14. Exon-specific gene expression analysis from the RNA-seq coverage in TCGA-27-1837 demonstrated that the EGFR and SEPT14 exons implicated in the fusion are highly overexpressed compared with the mRNA sequences not included in the fusion event (FIG. 13). Using PCR, the genomic breakpoint coordinates were mapped to chromosome 7 (#55,268,937 for EGFR and #55,870,909 for SEPT14, genome build GRCh37/hg19) falling within EGFR exon 25 and SEPT14 intron 9, which gives rise to a transcript in which the 5' EGFR exon 24 is spliced to the 3' SEPT14 exon 10 (FIG. 4d). Interestingly, the fused EGFR-PSPH cDNA and predicted fusion protein in the GBM sample TCGA-06-5408 involves the same EGFR N-terminal region implicated in the EGFR-SEPT14 with PSPH providing a carboxy-terminal portion of 35 amino acids (FIG. 11). An example of a fusion in which the EGFR-TK region is the 3' partner is the CAND1-EGFR fusion in GSC-3316 (FIG. 14). Thus, either in the more frequent fusions in which EGFR is the 5' partner or in those with EGFR as the 3' gene, the region of the EGFR mRNA coding for the TK domain is invariably retained in each of the fusion transcripts (FIG. 27). RT-PCR and genomic PCR followed by Sanger sequencing from GBM TCGA-06-5411 were also used to successfully validate successfully the NFASC-NTRK1 fusions in which the predicted fusion protein includes the TK domain of the high-affinity NGF receptor (TrkA) fused downstream to the immunoglobulin-like region of the cell adhesion and ankyrin-binding region of neurofascin (FIG. 12).

To confirm that GBM harbor recurrent EGFR fusions and determine the frequency in an independent dataset, cDNA was screened from a panel of 248 GBMs and discovered 10 additional cases harboring EGFR-SEPT14 fusions (4%). Conversely, NFASC-NTRK1 fusions were not detected in this dataset. The frequency of EGFR-PSPH fusions was 2.2% (3/135).

Figure 5A:
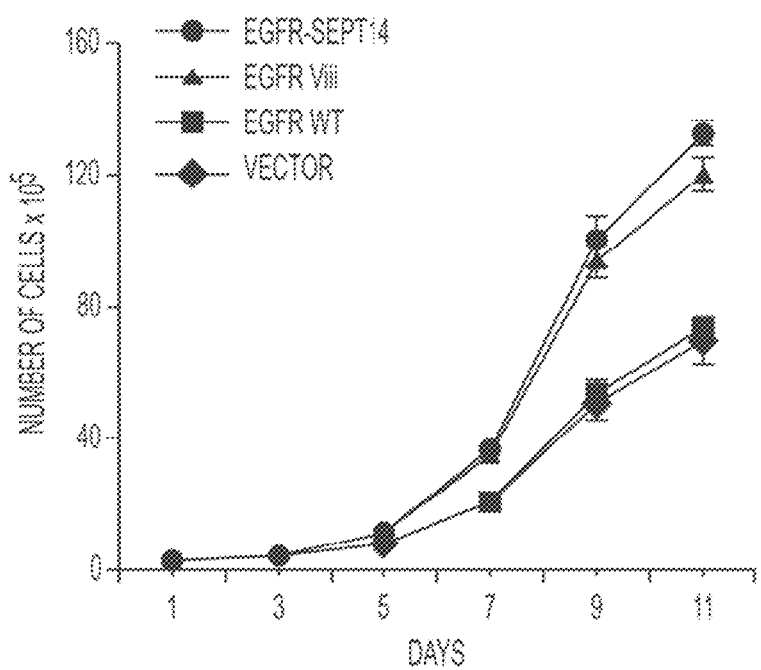
FIG. 5A. Expression of EGFR-SEPT14 fusion promotes an aggressive phenotype and inhibition of EGFR kinase delays GBM growth in vivo. Growth rate of SNB19 glioma cells transduced with a lentivirus expressing EGFR-SEPT14, EGFR Viii, EGFR WT or the empty vector (average of triplicate cultures).
Figure 5B:
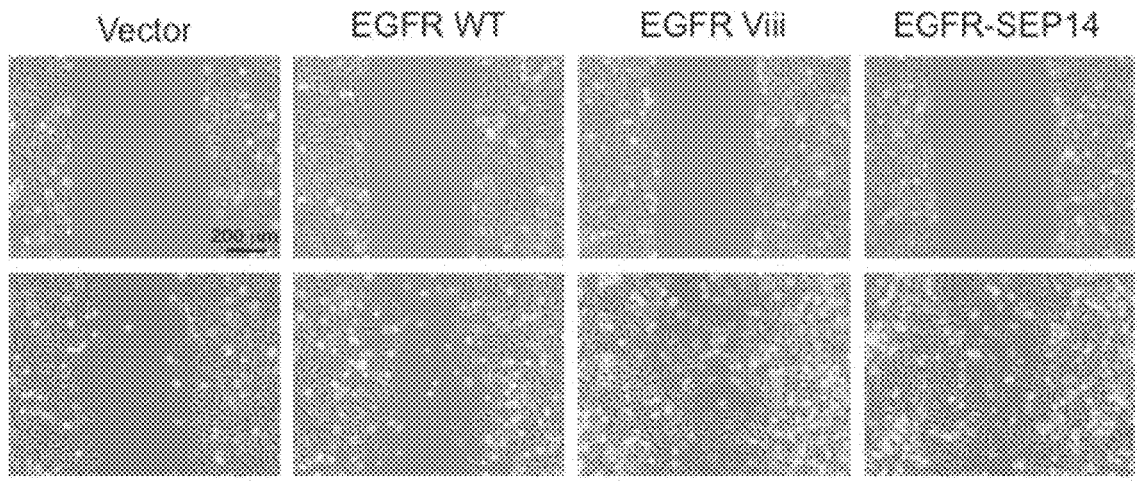
FIG. 5B. Expression of EGFR-SEPT14 fusion promotes an aggressive phenotype and inhibition of EGFR kinase delays GBM growth in vivo. Migration assay in SNB19 glioma cells transduced with a lentivirus expressing EGFR-SEPT14, EGFR Viii, EGFR WT or the empty vector.

The discovery of recurrent EGFR fusions in GBM is of particular interest. EGFR is activated in a significant fraction of primary GBM (~25%) by an in-frame deletion of exons 2-7 (EGFRvIII)[39]. To establish the functional relevance of EGFR fusions, it was determined whether the most frequent EGFR fusion in GBM (EGFR-SEPT14) provides an alternative mechanism of EGFR activation and confers sensitivity to EGFR inhibition. The EGFR-SEPT14 cDNA was cloned and prepared lentiviruses expressing EGFR-SEPT14, EGFRvIII or EGFR wild type. Transduction of the SNB19 glioma cell line (which lacks genomic alteration of EGFR) with the recombinant lentiviruses showed that cells expressing EGFR-SEPT14 or EGFRvIII proliferated at a rate that was 2-fold higher than control cells or cells expressing wild type EGFR (FIG. 5a). Furthermore, EGFR-SEPT14 and EGFRvIII markedly enhanced the ability of SNB19 cells to migrate in a wound assay (FIG. 5b, c). Finally it was investigated whether EGFR-SEPT14 fusions confer sensitivity to EGFR-TK activity in vivo. The analysis of a collection of 30 GBM xenografts directly established in the mouse from human GBM identified one xenograft model (D08-0537 MG) harboring the EGFR-SEPT14 fusion. The D08-0537 MG had been established from a heavily pre-treated GBM. Treatment of D08-0537 MG tumors with two EGFR inhibitors showed that each of the two drugs significantly delayed the rate of tumor growth (FIG. 5d). Interestingly, lapatinib, an irreversible EGFR inhibitor recently proposed to target EGFR alterations in GBM[40], displayed the strongest anti-tumor effects (FIG. 5d, e). Conversely, EGFR inhibitors were ineffective against the GBM xenograft D08-0714 MG, which lacks genomic alterations of the EGFR gene (FIG. 5d, e). Taken together, these data determine that the EGFR-SEPT14 fusion confers a proliferative and migratory phenotype to glioma cells and imparts sensitivity to EGFR inhibition to human glioma harboring the fusion gene.

DISCUSSION

A computational pipeline is described for the nomination of somatic cancer genes. This approach computes frequency, magnitude and focality of CNVs at any loci in the human genome with the somatic mutation rate for the genes residing at that genomic location. Thus, two of the genetic hallmarks of driver cancer genes (focality of copy number aberrations and point mutations) are integrated into a single score. The approach identifies marks of positive somatic selection in large unbiased cancer genome studies by efficiently removing the large burden of passenger mutations that characterize most human tumors and will be applicable to the dissection of the genomic landscape of other cancer types.

Besides recognizing nearly all the known genes reported to have functional relevance in GBM, our study discovered and validated somatic mutations in 18 new genes, which also harbor focal and recurrent CNVs in a significant fraction of GBM. For some of these genes, their importance extends beyond GBM, as underscored by cross-tumor relevance (e.g. BCOR), and protein family recurrence (e.g. LRP family members). For example, mutations of LZTR-1 have been reported in other tumors. In particular, mutations of the highly conserved residues in the Keltch domain (W105, G248, T288) and in the second BTB-BACK domain (R810) reported here are recurrent events in other tumor types[41].

Thus, understanding the nature of the substrates of LZTR-1-Cul3 ubiquitin ligase activity will provide important insights into the pathogenesis of multiple cancer types.

The identification of genetic and epigenetic loss-of-function alterations of the CTNND2 gene clustered in mesenchymal GBM provides a clue to the genetic events driving this aggressive GBM subtype. The important functions of δ-catenin for such crucial neuronal morphogenesis activities as the coordinated control of axonal and dendritic arborization indicates that full-blown mesenchymal transformation in the brain requires loss of the master regulators constraining cell determination in the CNS along the default neuronal lineage. The ability of δ-catenin to reprogram glioma cells that express mesenchymal genes towards a neuronal fate unravels an unexpected plasticity of mesenchymal GBM that might be exploited therapeutically.

In this study, the landscape of gene fusions is reported from a large dataset of GBM analyzed by RNA-Sequencing. In-frame gene fusions retaining the RTK-coding domain of EGFR emerged as the most frequent gene fusion events in GBM. In this tumor, EGFR is frequently targeted by focal amplifications and our finding underscores the strong recombinogenic probability of focally amplified genes, as recently reported for the myc locus in medulloblastoma[42]. Resembling intragenic rearrangements that generate the EGFRvIII allele, EGFR-SEPT14 fusions enhance the proliferative and migratory capacity of glioma cells. They also confer sensitivity to EGFR inhibition to human GBM grown as mouse xenografts. These findings highlight the relevance of gene fusions implicating RTK-coding genes in the pathogenesis of GBM[9]. They also provide a strong rationale for the inclusion of GBM patients harboring EGFR fusions in clinical trials based on EGFR inhibitors.

Methods 139 paired tumor-normal samples from TCGA were analyzed with the SAVI pipeline[43]. The SAVI algorithm estimates frequencies of variant alleles in sample as well as the difference in allele frequency between paired samples. The algorithm establishes posterior high credibility intervals for those frequencies and differences of frequencies, which can be used for genotyping the samples on the one hand, and detecting somatic mutations in the case of tumor/normal pairs of samples on the other. The algorithm allows for random sequencing errors and uses the Phred scores of the sequenced alleles as an estimate of their reliability. To integrate point mutation and 469 GBM CNV data (Affymetrix SNP6.0), MutComFocal (see below) was used. The MutComFocal algorithm assigns a driver score to each gene through three different strategies that give priority to lesions, samples, and genes in which there is less uncertainty regarding potential tumorigenic drivers. First, the focality component of the score is inversely proportional to the size of the genomic lesion to which a gene belongs and thus prioritizes more focal genomic lesions. Second, the recurrence component of the MutComFocal score is inversely proportional to the total number of genes altered in a sample, which prioritizes samples with a smaller number of altered genes. Finally, the mutation component of the score is inversely proportional to the total number of genes mutated in a sample, which achieves the two-fold goal of prioritizing mutated genes on one hand, and samples with a smaller number of mutations on the other.

161 RNA-Seq GBM tumor samples were also analyzed from TCGA plus 24 generated from our own dataset of GSCs. Nine of these samples previously reported in other studies were kept in the list to evaluate recurrence[9]. The samples were analyzed by means of the ChimeraScan algorithm in order to detect a list of gene fusion candidates[44]. Using the Pegasus annotation pipeline (http://sourceforge.net/projects/pegasus-fus/), the fusion transcript was reconstructed, the reading frame was annotated and protein domains were detected that are either conserved or lost in the new chimeric event. The genomic breakpoint of recurrent gene fusion RNA transcripts was also probed for using whole-exome sequencing data (EXome-Fuse algorithm)[9]. The Kaplan-Meier survival analysis for CTNND2 CNV and CTNND2 expression were obtained using the REMBRANDT glioma dataset.

SAVI (Statistical Algorithm for Variant Frequency Identification):

The frequency of alleles in a sample was estimated by the SAVI pipeline, which constructs an empirical Bayesian prior for those frequencies, using data from the whole sample, and obtains a posterior distribution and high credibility intervals for each allele[S1]. The prior and posterior are distributed over a discrete set of frequencies with a precision of 1% and are connected by a modified binomial likelihood, which allows for some error rate. More precisely, a prior distribution p(f) of the frequency f and a prior for the error e uniform on the interval [0, E] was assumed for a fixed $0 \leq E \leq 1$. The sequencing data at a particular allele is a random experiment producing a string of m (the total depth at the allele) bits with n "1"s (the variant depth at the allele). Assuming a binomial likelihood of the data and allowing for bits being misread due to random errors, the posterior probability P(f) of the frequency f is $$P(f) = \frac{p(f)}{C} \cdot \frac{1}{b-a} \int_f^{f+E-2Ef} x^n (1-x)^{m-n} dx$$

where C is a normalization constant. For a particular allele, the value of E is determined by the quality of the nucleotides sequenced at that position as specified by their Phred scores. The SAVI pipeline takes as input the reads produced by the sequencing technology, filters out low quality reads and maps the rest onto a human reference genome. After mapping, a Bayesian prior for the distribution of allele frequencies for each sample is constructed by an iterative posterior update procedure, starting with a uniform prior. To genotype the sample, the posterior high credibility intervals were used for the frequency of the alleles at each genomic location. Alternatively, combining the Bayesian priors from different samples, posterior high credibility intervals were obtained for the difference between the samples of the frequencies of each allele. Finally, the statistically significant differences between the tumor and normal samples are reported as somatic variants. To estimate the positive prediction value of SAVI in the TCGA GBM samples, 41 mutations were selected for independent validation by Sanger sequencing. 39 of the 41 mutations were confirmed using Sanger sequencing, resulting in 0.95 (95% CI 0.83-0.99) validation rate.

Candidate genes were ranked by the number of somatic non-synonymous mutations. A robust fit of the ratio of non-synonymous to synonymous ratio was generated with a bisquare weighting function. Excess of non-synonymous alterations was estimated using a Poisson distribution with mean equal to the product of the ratio from the robust fit and the number of synonymous mutations. Genes in highly polymorphic genomic regions were filtered out based on an independent cohort of normal samples. The list of these regions includes families of genes known to generate false positives in somatic predictions (e.g. HLA, KRT and OR).

MutComFocal.

Key cancer genes are often found amplified or deleted in chromosomal regions containing many other genes. Point mutations and gene fusions, on the other hand, provide more specific information about which genes may be implicated in the oncogenic process. MutComFocal, a Bayesian approach aiming to identify driver genes by integrating CNV and point mutation data was developed.

For a particular sample, let $(c_1,N_1), \ldots, (c_k,N_k)$ describe the amplification lesions in that sample so that $N_i$ is the number of genes in the i-th lesion and $c_i$ is its copy number change from normal. For a gene belonging to the i-th lesion the amplification recurrence sample score is defined as $c_i/(\Sigma_j c_j \cdot N_j)$ and its amplification focality sample score is defined as $(c_i/\Sigma_j c_j)\cdot(1/N_i)$. To obtain the amplification recurrence and focality scores for a particular gene, the corresponding sample scores were summed over all samples and normalize the result so that each score sums to 1. The deletion and recurrence scores are defined in a similar manner. The mutation score is analogous to a recurrence score in which it was assumed that mutated genes belong to lesions with only one gene.

The amplification/mutation score is defined as the product of the two amplification scores and the mutation score while deletion/mutation score is defined as the product of the two deletion scores and the mutation score. The amplification/mutation and deletion/mutation scores are normalized to 1 and for each score, genes are divided into tiers iteratively, so that the top $2^H$ remaining genes are included in the next tier, where H is the entropy of the scores of the remaining genes normalized to 1. Based on their tier across the different types of scores, genes are assigned to being either deleted/mutated or amplified/mutated and genes in the top tiers are grouped into contiguous regions. The top genes in each region are considered manually and selected for further functional validation.

The recurrence and focality scores can be interpreted as the posterior probabilities that a gene is driving the selection of the disease, under two different priors for this: one global and one local in nature. The recurrence score is higher if a gene participates in many samples that do not have too many altered genes, while the focality score is higher if the gene participates in many focal lesions. Besides lending strong support to the inference of a gene as a potential driver, the directionality of the copy number alteration (amplification or deletion) informs us of the likely behavior of the candidate gene as an oncogene or tumor suppressor, respectively.

The genes displayed in FIG. 1 are selected based on the MutComFocal ranking (top 250 genes), the size of minimal region (less than 10 genes) and frequency of mutations (more than 2% for deletion/mutations and at least 1% in amplification/mutations).

RNA-Seq Bioinformatics Analysis.

161 RNA-Seq GBM tumor samples were analyzed from The Cancer Genome Atlas (TCGA), a public repository containing large-scale genome-sequencing of different cancers, plus 24 patients-derived GSCs. Nine of the GSCs samples reported in previous studies were kept in the list to evaluate recurrence[52]. The samples were analyzed by means of the ChimeraScan[53] algorithm in order to detect a list of gene fusion candidates. Briefly, ChimeraScan detects those reads that discordantly align to different transcripts of the same reference (split inserts). These reads provide an initial set of putative fusion candidates. Finally, the algorithm realigns the initially unmapped reads to the putative fusion candidates and detects those reads that align across the junction boundary (split reads). These reads provide the genomic coordinates of the breakpoint.

RNA-Seq analysis detected a total of 39,329 putative gene fusion events. In order to focus the experimental analysis on biologically relevant fused transcripts, Pegasus annotation pipeline (http://sourceforge.net/projects/pegasus-fus/) were applied. For each putative fusion, Pegasus reconstructs the entire fusion sequence on the base of genomic fusion breakpoint coordinates and gene annotations. Pegasus also annotates the reading frame of the resulting fusion sequences as either in-frame or frame-shift. Moreover, Pegasus detects the protein domains that are either conserved or lost in the new chimeric event by predicting the amino acid sequence and automatically querying the UniProt web service. On the basis of the Pegasus annotation report, relevant gene fusions were selected for further experimental validation according to the reading frame and the conserved/lost domains. The selected list (FIG. 27) was based on in-frame events expressed by ten or more reads and at least one read spanning the breaking point. To filter out candidate transplicing events, events with putative breakpoints at a distance of at least 25 kb were focused.

EXome-Fuse: Identification of Genetic Rearrangements using Whole-Exome Data.

Although whole-exome sequencing data contains low intronic coverage that reduces the sensitivity for fusion discovery, it is readily available through the TCGA database. To characterize the genomic breakpoint of the chromosomal rearrangement, EXome-Fuse was designed: a gene fusion discovery pipeline particularly designed to analyze whole-exome data. For the samples harboring EGFR-SEPT14, EGFR-PSPH, NFASC-NTRK1, and BCAN-NTRK1 fusions in RNA, EXome-Fuse was applied to the corresponding whole-exome sequencing data deposited in TCGA. This algorithm can be divided into three stages: split insert identification, split read identification, and virtual reference alignment. Mapping against the human genome reference hg18 with BWA, all split inserts were first identified to compile a preliminary list of fusion candidates. This list was cut of any false positives produced from paralogous gene pairs using the Duplicated Genes Database and the EnsemblCompara GeneTrees[4]. Pseudogenes in the candidate list were annotated using the list from HUGO Gene Nomenclature Committee (HGNC) database[55] and given lower priority. Candidates were also filtered out between homologous genes, as well as those with homologous or low-complexity regions around the breakpoint. For the remaining fusion candidates, any supporting split reads and their mates were probed using BLAST with a word size of 16, identity cutoff of 90%, and an expectation cutoff of $10^{-4}$. Finally, a virtual reference was created for each fusion transcript and all reads were re-align to calculate a final tally of split inserts and split reads such that all aligning read pairs maintain F-R directionality.

Targeted Exon Sequencing

All protein-coding exons for the 24 genes of interest were sequenced using genomic DNA extracted from frozen tumors and matched blood. 500 ng of DNA from each sample were sheared to an average of 150 bp in a Covaris instrument for 360 seconds (Duty cycle—10%; intensity—5; cycles/Burst—200). Barcoded libraries were prepared using the Kapa High-Throughput Library Preparation Kit Standard (Kapa Biosystems). Libraries were amplified using the KAPA HiFi Library Amplification kit (Kapa Biosystems) (8 cycles). Libraries were quantified using Qubit Fluorimetric Quantitation (Invitrogen) and the quality and size assessed using an Agilent Bioanalyzer. An equimolar pool of the 4 barcoded libraries (300 ng each) was created and 1,200 ng was input to exon capture using one reaction tube of the custom Nimblegen SeqCap EZ (Roche) with custom probes target the coding exons of the 38 genes. Capture by hybridization was performed according to the manufacturer's protocols with the following modifications: 1 nmol of a pool of blocker oligonucleotides (complementary to the barcoded adapters), and (B) post-capture PCR amplification was done using the KAPA HiFi Library Amplification kit instead of the Phusion High-Fidelity PCR Master Mix with HF Buffer Kit, in a 60 µl volume, since the Kapa HiFi kit greatly reduced or eliminated the bias against GC-rich regions. The pooled capture library was quantified by Qubit (Invitrogen) and Bioanalyzer (Agilent) and sequenced in on an Illumina MiSeq sequencer using the 2×150 paired-end cycle protocol. Reads were aligned to the hg19 build of the human genome using BWA with duplicate removal using samtools as implemented by Illumina MiSeq Reporter. Variant detection was performed using GATK UnifiedGenotyper. Somatic mutations were identified for paired samples using SomaticSniper and filtered for frequency of less than 3% in normal and over 3% in tumor samples. Variants were annotated with Charity annotator to identify protein-coding changes and cross-referenced against known dbSNP, 1000 Genomes, and COSMIC mutations. Sanger sequencing was used to confirm each mutation from normal and tumor DNA.

Modeling of LZTR-1

Structural templates for the Kelch and BTB-BACK regions of human LZTR-1 were identified with HHpred[S6]. An initial 3D model was generated with the I-TASSER server[S7]. The Cul3 N-terminal domain was docked onto the model by superposing the KLHL3$^{BTB-BACK}$/Cul3$^{NTD}$ crystal structure (PDB ID 4HXI, Xi and Privé PLOS ONE 2013) onto the second LZTR-1 BTB-BACK domain. The model does not include higher quaternary structure, although many BTB domains, and many Kelch domains, are known to self-associate[S8]. The short linkage between the end of the first BACK domain and the beginning of the second BTB domain would appear to preclude an intrachain BTB-BTB pseudo-homodimer; without being bound by theory, LZTR-1 self-associates and forms higher order assemblies. Both BACK domains are the shorter, atypical form of the domain and consist of 2 helical hairpin motifs, as in SPOP[S9, S10] and not the 4-hairpin motif seen most BTB-BACK-Kelch proteins[S10, S11]. The model from the Kelch domain predicts an unusual 1+3 velcro arrangement[S12], with the N-terminal region contributing strand d of blade 1 and the C-terminal region contributing strands a,b,c of the same blade, although an alternative 2+2 velcro model cannot be ruled out.

Cell Culture

SNB19 and U87 cells were cultured in DMEM supplemented with 10% Fetal Bovine Serum. Growth rate was determined by plating cells in six-well plates post 3 days after infection with the lentivirus indicated in Figure Legends. The number of viable cells was determined by trypan blue exclusion in triplicate cultures obtained from triplicate independent infections. Migration was evaluated by Confluent cells were scratched with a pipette tip and cultured in 0.25% FBS. After 16 h, images were taken using the Olympus IX70 connected to a digital camera. Images were processed using the ImageJ64 software. The area of the cell-free wound was assessed in triplicate samples. Experiments were repeated twice.

Immunofluorescence and Western Blot immunofluorescence staining on brain tumor tissue microarrays were performed as previously described[S17]. Immunofluorescence microscopy was performed on cells fixed with 4% para-formaldehyde (PFA) in phosphate buffer. Cells were permeabilized using 0.2% Triton X 100. Antibodies and concentrations used in immunofluorescence staining are:

| B-III Tubulin | Mouse | 1:400 | Promega |
| Catenin D2 | Guinea Pig | 1:500 | Acris |
| Fibronectin | Mouse | 1:1,000 | BD-Pharmingen |
| PSD-95 | Rabbit | 1:500 | Invitrogen |

Secondary antibodies conjugated to Alexa Fluor 594 (Molecular Probes) were used. DNA was stained by DAPI (Sigma). Fluorescence microscopy was performed on a Nikon A1R MP microscope.

Western blot analysis of U87 cells transduced with pLOC-GFP or pLOC CTNND2 was performed using the following antibodies:

| Anti-Vinculin | Mouse | 1:400 | SIGMA |
| Anti-N-Cadherin | Mouse | 1:200 | BD-Pharmingen |
| Cyclin A | Rabbit | 1:500 | Santa Cruz |
| P27 | Mouse | 1:250 | BD Transduction |

Cloning and Lentiviral Production

The lentiviral expression vector, pLOC-GFP and pLOC-LZTR1 were purchased from Open Biosystems. The full length EGFR-SEPT14 cDNA was amplified from tumor sample TCGA-27-1837. Primers used were: EGFR FW: 5'-agcgATGCGACCCTCCGGGA-3' (SEQ ID NO: 30) and SEPT14 REV: 5'-TCTTACGATGTTTGTCTTTCTTTGT (SEQ ID NO: 31); EGFR wild type, EGFR Viii and EGFR-SEPT14 cDNAs were cloned into pLoc and lentiviral particles were produced using published protocols[S13-S15].

Genomic and mRNA RT-PCR

Total RNA was extracted from cells by using RNeasy Mini Kit (QIAGEN), following the manufacturer instructions. 500 ng of total RNA was retro-transcribed by using the Superscript III kit (Invitrogen), following the manufacturer instructions. The cDNAs obtained after the retro-transcription was used as templates for qPCR as described[S13, S15]. The reaction was performed with a Roche480 thermal cycler, using the Absolute Blue QPCR SYBR Green Mix from Thermo Scientific. The relative amount of specific mRNA was normalized to GAPDH. Results are presented as the mean±SD of triplicate amplifications. The validation of fusion transcripts was performed using both genomic and RT-PCR with forward and reverse primer combinations designed within the margins of the paired-end read sequences detected by RNA-seq. Expressed fusion transcript variants were subjected to direct sequencing to confirm sequence and translation frame. Primers used for the screening of gene fusions are:

hEGFR-RT-FW1:
(SEQ ID NO: 32)
5'-GGGTGACTGTTTGGGAGTTGATG-3';

hSEP14-RT-REV1:
(SEQ ID NO: 33)
5'-TGTTTGTCTTTCTTTGTATCGGTGC-3';

```
-continued
hEGFR-RT-FW1:
                                       (SEQ ID NO: 34)
5'-GTGATGTCTGGAGCTACGGG-3';

hPSPH-RT-REV1:
                                       (SEQ ID NO: 35)
5'-TGCCTGATCACATTTCCTCCA-3';

hNFASC-RT-FW1:
                                       (SEQ ID NO: 36)
5'-AGTTCCGTGTCATTGCCATCAAC-3';

hNTRK1-RT-REV1:
                                       (SEQ ID NO: 37)
5'-TGTTTCGTCCTTCTTCTCCACCG-3';

hCAND1-RT-FW1:
                                       (SEQ ID NO: 38)
5'-GGAAAAAATGACATCCAGCGAC-3';

hEGFR-RT-REV1:
                                       (SEQ ID NO: 39)
5'-TGGGTGTAAGAGGCTCCACAAG-3'.

Primers used for genomic detection of gene
fusions are:
genomic EGFR-FW1:
                                       (SEQ ID NO: 40)
5'-GGATGATAGACGCAGATAGTCGCC-3';

genomic SEPT14-REV1:
                                       (SEQ ID NO: 41)
5'-TCCAGTTGTTTTTCTCTTCCTCG-3';

genomic NFASC-FW1:
                                       (SEQ ID NO: 42)
5'-AAGGGAGAGGGGACCAGAAAGAAC-3';

genomic NTRK1-REV1:
                                       (SEQ ID NO: 43)
5'-GAAAGGAAGAGGCAGGCAAAGAC-3';

genomic CAND1-FW1:
                                       (SEQ ID NO: 44)
5'-GCAATAGCAAAACAGGAAGATGTC-3';

genomic EGFR-REV1:
                                       (SEQ ID NO: 45)
5'-GAACACTTACCCATTCGTTGG-3'.
```

Subcutaneous Xenografts and Drug Treatment

Female athymic mice (nu/nu genotype, Balb/c background, 6 to 8 weeks old) were used for all antitumor studies. Patient-derived adult human glioblastoma xenografts were maintained. Xenografts were excised from host mice under sterile conditions, homogenized with the use of a tissue press/modified tissue cytosieve (Biowhitter Inc, Walkersville, Md.) and tumor homogenate was loaded into a repeating Hamilton syringe (Hamilton, Co., Reno, Nev.) dispenser. Cells were injected sub-cutaneously into the right flank of the athymic mouse at an inoculation volume of 50 µl with a 19-gauge needle$^{S16}$. Subcutaneous tumors were measured twice weekly with hand-held vernier calipers (Scientific Products, McGraw, Ill.). Tumor volumes, V were calculated with the following formula: $[(width)^2 \times (length)]/2 = V$ (mm$^3$). For the sub-cutaneously tumor studies, groups of mice randomly selected by tumor volume were treated with EGFR kinase inhibitors when the median tumor volumes were on average 150 mm$^3$ and were compared with control animals receiving vehicle (saline). Erlotinib was administered at 100 mg/Kg orally daily for 10 days. Lapatinib was administered at 75 mg/Kg orally twice per day for 20 days. Response to treatment was assessed by delay in tumor growth and tumor regression. Growth delay, expressed as T-C, is defined as the difference in days between the median time required for tumors in treated and control animals to reach a volume five times greater than that measured at the start of the treatment. Tumor regression is defined as a decrease in tumor volume over two successive measurements. Statistical analysis was performed using a SAS statistical analysis program, the Wilcoxon rank order test for growth delay, and Fisher's exact test for tumor regression as previously described.

REFERENCES

1 Porter, K. R., McCarthy, B. J., Freels, S., Kim, Y. & Davis, F. G. Prevalence estimates for primary brain tumors in the United States by age, gender, behavior, and histology. *Neuro-oncology* 12, 520-527, doi:10.1093/neuonc/nop066 (2010).

2 Stupp, R. et al. Radiotherapy plus concomitant and adjuvant temozolomide for glioblastoma. *The New England journal of medicine* 352, 987-996, doi:10.1056/NEJMoa043330 (2005).

3 Cancer Genome Atlas Research, N. Comprehensive genomic characterization defines human glioblastoma genes and core pathways. *Nature* 455, 1061-1068, doi:10.1038/nature07385 (2008).

4 Noushmehr, H. et al. Identification of a CpG island methylator phenotype that defines a distinct subgroup of glioma. *Cancer Cell* 17, 510-522, doi:10.1016/j.ccr.2010.03.017 (2010).

5 Parsons, D. W. et al. An integrated genomic analysis of human glioblastoma multiforme. *Science* 321, 1807-1812, doi:10.1126/science.1164382 (2008).

6 Verhaak, R. G. et al. Integrated genomic analysis identifies clinically relevant subtypes of glioblastoma characterized by abnormalities in PDGFRA, IDH1, EGFR, and NF1. *Cancer Cell* 17, 98-110, doi:10.1016/j.ccr.2009.12.020 (2010).

7 Bass, A. J. et al. Genomic sequencing of colorectal adenocarcinomas identifies a recurrent VTI1A-TCF7L2 fusion. *Nat Genet* 43, 964-968, doi:10.1038/ng.936 (2011).

8 Chinnaiyan, A. M. & Palanisamy, N. Chromosomal aberrations in solid tumors. *Prog Mol Biol Transl Sci* 95, 55-94, doi:10.1016/B978-0-12-385071-3.00004-6 (2010).

9 Singh, D. et al. Transforming fusions of FGFR and TACC genes in human glioblastoma. *Science* 337, 1231-1235, doi:10.1126/science.1220834 (2012).

10 Rubin, A. F. & Green, P. Mutation patterns in cancer genomes. *Proc Natl Acad Sci USA* 106, 21766-21770, doi:10.1073/pnas.0912499106 (2009).

11 Fan, Z. et al. BCOR regulates mesenchymal stem cell function by epigenetic mechanisms. *Nat Cell Biol* 11, 1002-1009, doi:10.1038/ncb1913 (2009).

12 Wamstad, J. A. & Bardwell, V. J. Characterization of Bcor expression in mouse development. *Gene Expr Patterns* 7, 550-557, doi:10.1016/j.modgep.2007.01.006 (2007).

13 Wamstad, J. A., Corcoran, C. M., Keating, A. M. & Bardwell, V. J. Role of the transcriptional corepressor Bcor in embryonic stem cell differentiation and early embryonic development. *PLoS One* 3, e2814, doi:10.1371/journal.pone.0002814 (2008).

14 Pugh, T. J. et al. Medulloblastoma exome sequencing uncovers subtype-specific somatic mutations. *Nature* 488, 106-110, doi:10.1038/nature11329 (2012).

15 Zhang, J. et al. A novel retinoblastoma therapy from genomic and epigenetic analyses. *Nature* 481, 329-334, doi:10.1038/nature10733 (2012).

16 Beroukhim, R. et al. The landscape of somatic copy-number alteration across human cancers. *Nature* 463, 899-905, doi:10.1038/nature08822 (2010).

17 Kantarci, S. et al. Mutations in LRP2, which encodes the multiligand receptor megalin, cause Donnai-Barrow and facio-oculo-acoustico-renal syndromes. *Nat Genet* 39, 957-959, doi:10.1038/ng2063 (2007).

18 Willnow, T. E. et al. Defective forebrain development in mice lacking gp330/megalin. *Proc Natl Acad Sci USA* 93, 8460-8464 (1996).

19 Christ, A. et al. LRP2 is an auxiliary SHH receptor required to condition the forebrain ventral midline for inductive signals. *Dev Cell* 22, 268-278, doi:10.1016/j.devcel.2011.11.023 (2012).

20 Cowin, P. A. et al. LRP1B deletion in high-grade serous ovarian cancers is associated with acquired chemotherapy resistance to liposomal doxorubicin. *Cancer Res* 72, 4060-4073, doi:10.1158/0008-5472.CAN-12-0203 (2012).

21 Lima, F. R. et al. Glioblastoma: therapeutic challenges, what lies ahead. *Biochim Biophys Acta* 1826, 338-349, doi:10.1016/j.bbcan.2012.05.004 (2012).

22 Bekker-Jensen, S. et al. HERC2 coordinates ubiquitin-dependent assembly of DNA repair factors on damaged chromosomes. *Nat Cell Biol* 12, 80-86; sup pp 81-12, doi:10.1038/ncb2008 (2010).

23 Harlalka, G. V. et al. Mutation of HERC2 causes developmental delay with Angelman-like features. *J Med Genet* 50, 65-73, doi:10.1136/jmedgenet-2012-101367 (2013).

24 Nacak, T. G., Leptien, K., Fellner, D., Augustin, H. G. & Kroll, J. The BTB-kelch protein LZTR-1 is a novel Golgi protein that is degraded upon induction of apoptosis. *J Biol Chem* 281, 5065-5071, doi:10.1074/jbc.M509073200 (2006).

25 Stogios, P. J., Downs, G. S., Jauhal, J. J., Nandra, S. K. & Prive, G. G. Sequence and structural analysis of BTB domain proteins. *Genome Biol* 6, R82, doi:10.1186/gb-2005-6-10-r82 (2005).

26 Errington, W. J. et al. Adaptor protein self-assembly drives the control of a cullin-RING ubiquitin ligase. *Structure* 20, 1141-1153, doi:10.1016/j.str.2012.04.009 (2012).

27 Canning, P. et al. Structural basis for Cul3 assembly with the BTB-Kelch family of E3 ubiquitin ligases. *J Biol Chem, doi:*10.1074/jbc.M112.437996 (2013).

28 Lo, S. C., Li, X., Henzl, M. T., Beamer, L. J. & Hannink, M. Structure of the Keap1:Nrf2 interface provides mechanistic insight into Nrf2 signaling. *EMBO J* 25, 3605-3617, doi:10.1038/sj.emboj.7601243 (2006).

29 Boyden, L. M. et al. Mutations in kelch-like 3 and cullin 3 cause hypertension and electrolyte abnormalities. *Nature* 482, 98-102, doi:10.1038/nature10814 (2012).

30 Louis-Dit-Picard, H. et al. KLHL3 mutations cause familial hyperkalemic hypertension by impairing ion transport in the distal nephron. *Nat Genet* 44, 456-460, S451-453, doi:10.1038/ng.2218 (2012).

31 Abu-Elneel, K. et al. A delta-catenin signaling pathway leading to dendritic protrusions. *J Biol Chem* 283, 32781-32791, doi:10.1074/jbc.M804688200 (2008).

32 Arikkath, J. et al. Delta-catenin regulates spine and synapse morphogenesis and function in hippocampal neurons during development. *J Neurosci* 29, 5435-5442, doi:10.1523/JNEUROSCI.0835-09.2009 (2009).

33 Kosik, K. S., Donahue, C. P., Israely, I., Liu, X. & Ochiishi, T. Delta-catenin at the synaptic-adherens junction. *Trends Cell Biol* 15, 172-178, doi:10.1016/j.tcb.2005.01.004 (2005).

34 Israely, I. et al. Deletion of the neuron-specific protein delta-catenin leads to severe cognitive and synaptic dysfunction. *Curr Biol* 14, 1657-1663, doi:10.1016/j.cub.2004.08.065 (2004).

35 Jun, G. et al. delta-Catenin is genetically and biologically associated with cortical cataract and future Alzheimer-related structural and functional brain changes. *PLoS One* 7, e43728, doi:10.1371/journal.pone.0043728 (2012).

36 Hicks, S., Wheeler, D. A., Plon, S. E. & Kimmel, M. Prediction of missense mutation functionality depends on both the algorithm and sequence alignment employed. *Hum Mutat* 32, 661-668, doi:10.1002/humu.21490 (2011).

37 Phillips, H. S. et al. Molecular subclasses of high-grade glioma predict prognosis, delineate a pattern of disease progression, and resemble stages in neurogenesis. *Cancer Cell* 9, 157-173, doi:10.1016/j.ccr.2006.02.019 (2006).

38 Pierotti, M. A. & Greco, A. Oncogenic rearrangements of the NTRK1/NGF receptor. *Cancer Lett* 232, 90-98, doi: 10.1016/j.canlet.2005.07.043 (2006).

39 Dunn, G. P. et al. Emerging insights into the molecular and cellular basis of glioblastoma. *Genes Dev* 26, 756-784, doi:10.1101/gad.187922.112 (2012).

40 Vivanco, I. et al. Differential sensitivity of glioma-versus lung cancer-specific EGFR mutations to EGFR kinase inhibitors. *Cancer Discov* 2, 458-471, doi:10.1158/2159-8290.CD-11-0284 (2012).

41 Forbes, S. A. et al. COSMIC (the Catalogue of Somatic Mutations in Cancer): a resource to investigate acquired mutations in human cancer. *Nucleic Acids Res* 38, D652-657, doi:10.1093/nar/gkp995 (2010).

42 Northcott, P. A. et al. Subgroup-specific structural variation across 1,000 medulloblastoma genomes. *Nature* 488, 49-56, doi:10.1038/nature11327 (2012).

43 Tiacci, E. et al. BRAF mutations in hairy-cell leukemia. *The New England journal of medicine* 364, 2305-2315, doi:10.1056/NEJMoa1014209 (2011).

44 Iyer, M. K., Chinnaiyan, A. M. & Maher, C. A. ChimeraScan: a tool for identifying chimeric transcription in sequencing data. *Bioinformatics* 27, 2903-2904, doi: 10.1093/bioinformatics/btr467 (2011).

S1 Tiacci, E. et al. BRAF mutations in hairy-cell leukemia. *The New England journal of medicine* 364, 2305-2315, doi:10.1056/NEJMoa1014209 (2011).

S2 Singh, D. et al. Transforming fusions of FGFR and TACC genes in human glioblastoma. *Science* 337, 1231-1235, doi:10.1126/science.1220834 (2012).

S3 Iyer, M. K., Chinnaiyan, A. M. & Maher, C. A. ChimeraScan: a tool for identifying chimeric transcription in sequencing data. *Bioinformatics* 27, 2903-2904, doi: 10.1093/bioinformatics/btr467 (2011).

S4 Vilella, A. J. et al. EnsemblCompara GeneTrees: Complete, duplication-aware phylogenetic trees in vertebrates. *Genome Res* 19, 327-335, doi:10.1101/gr.073585.107 (2009).

S5 Seal, R. L., Gordon, S. M., Lush, M. J., Wright, M. W. & Bruford, E. A. genenames.org: the HGNC resources in 2011. *Nucleic Acids Res* 39, D514-519, doi:10.1093/nar/gkq892 (2011).

S6 Soding, J. Protein homology detection by HMM-HMM comparison. *Bioinformatics* 21, 951-960, doi:10.1093/bioinformatics/bti125 (2005).

S7 Roy, A., Kucukural, A. & Zhang, Y. I-TASSER: a unified platform for automated protein structure and function prediction. *Nat Protoc* 5, 725-738, doi:10.1038/nprot.2010.5 (2010).

S8 Stogios, P. J., Downs, G. S., Jauhal, J. J., Nandra, S. K. & Prive, G. G. Sequence and structural analysis of BTB domain proteins. *Genome Biol* 6, R82, doi:10.1186/gb-2005-6-10-r82 (2005).

S9 Errington, W. J. et al. Adaptor protein self-assembly drives the control of a cullin-RING ubiquitin ligase. *Structure* 20, 1141-1153, doi:10.1016/j.str.2012.04.009 (2012).

S10 Zhuang, M. et al. Structures of SPOP-substrate complexes: insights into molecular architectures of BTB-Cul3 ubiquitin ligases. *Mol Cell* 36, 39-50, doi:10.1016/j.molcel.2009.09.022 (2009).

S11 Canning, P. et al. Structural basis for Cul3 assembly with the BTB-Kelch family of E3 ubiquitin ligases. *J Biol Chem*, doi:10.1074/jbc.M112.437996 (2013).

S12 Fulop, V. & Jones, D. T. Beta propellers: structural rigidity and functional diversity. *Curr Opin Struct Biol* 9, 715-721 (1999).

S13 Carro, M. S. et al. The transcriptional network for mesenchymal transformation of brain tumours. *Nature* 463, 318-325, doi:10.1038/nature08712 (2010).

S14 Niola, F. et al. Mesenchymal high-grade glioma is maintained by the ID-RAP1 axis. *J Clin Invest* 123, 405-417, doi:10.1172/JCI63811 (2013).

S15 Zhao, X. et al. The N-Myc-DLL3 cascade is suppressed by the ubiquitin ligase Huwe1 to inhibit proliferation and promote neurogenesis in the developing brain. *Dev Cell* 17, 210-221, doi:10.1016/j.devcel.2009.07.009 (2009).

S16 Friedman, H. S. et al. Experimental chemotherapy of human medulloblastoma cell lines and transplantable xenografts with bifunctional alkylating agents. *Cancer Res* 48, 4189-4195 (1988).

S17 Srivastava, M. et al. The *Amphimedon queenslandica* genome and the evolution of animal complexity. *Nature* 466, 720-726, doi:10.1038/nature09201 (2010).

S18 Sebe-Pedros, A., Roger, A. J., Lang, F. B., King, N. & Ruiz-Trillo, I. Ancient origin of the integrin-mediated adhesion and signaling machinery. *Proc Natl Acad Sci USA* 107, 10142-10147, doi:10.1073/pnas.1002257107 (2010).

Example 2—Genomic Alterations in Glioblastoma

Glioblastoma remains one of the most challenging forms of cancer to treat. This example discusses a computational platform that integrates the analysis of copy number variations and somatic mutations and unravels the landscape of in frame gene fusions in glioblastoma. Mutations were found with loss of heterozygosity of LZTR-1, an adaptor of Cul3-containing E3 ligase complexes. Mutations and deletions disrupt LZTR-1 function, which restrains self-renewal and growth of glioma spheres retaining stem cell features. Loss-of-function mutations of CTNND2 target a neural-specific gene and are associated with transformation of glioma cells along the very aggressive mesenchymal phenotype. Recurrent translocations are reported that fuse the coding sequence of EGFR to several partners, with EGFR-SEPT14 as the most frequent functional gene fusion in human glioblastoma. EGFR-SEPT14 fusions activate Stat3 signaling and confer mitogen independency and sensitivity to EGFR inhibition. These results provide important insights into the pathogenesis of glioblastoma and highlight new targets for therapeutic intervention.

Glioblastoma (GBM) is the most common primary intrinsic malignant brain tumor affecting ~10,000 new patients each year with a median survival rate of 12-15 months[1,2]. Identifying and understanding the functional significance of genetic alterations that drive initiation and progression of GBM is crucial to develop effective therapies. Previous efforts in GBM genome characterization identified somatic changes in well-known GBM genes (EGFR, PTEN, IDH1, TP53, NF1, etc.) and nominated putative cancer genes with somatic mutations, but the functional consequence of most alterations is unknown[3-6]. Furthermore, the abundance of passenger mutations and large regions of copy number variations (CNVs) complicates the definition of the landscape of driver mutations in glioblastoma. To address this challenge, a statistical approach was used to nominate driver genes in GBM by integrating somatic mutations identified by whole-exome sequencing with a CNVs analysis that prioritizes focality and magnitude of the genetic alterations.

Recurrent and oncogenic gene fusions are hallmarks of hematological malignancies and have also been uncovered in solid tumors[7,8]. Recently, a small subset of GBM harbor FGFR-TACC gene fusions was reported indicating that the patients with FGFR-TACC-positive tumors would benefit from targeted FGFR kinase inhibition[9]. It remains unknown whether gene fusions involving other RTK-coding genes exist and produce oncogene addiction in GBM. Here, a large RNA-sequencing dataset of primary GBM and Glioma Sphere Cultures (GSCs) is investigated and the global landscape of in frame gene fusions in human GBM are reported.

Nomination of Candidate GBM Genes

Without being bound by theory, integration of somatic point mutations and focal CNVs will uncover candidate driver GBM genes. MutComFocal is an algorithm designed to rank genes by an integrated recurrence, focality and mutation score (see Methods). This strategy was applied to 139 GBM and matched normal DNA analyzed by whole-exome sequencing to identify somatic mutations and 469 GBM analyzed by the Affymetrix SNP6.0 platform to identify CNVs.

The whole-exome analysis revealed a mean of 43 non-synonymous somatic mutations per tumor sample. The distribution of substitutions shows a higher rate of transitions versus tranversions (67%), with a strong preference for C→T and G→A (55%) (FIG. 6). As seen in other tumor types[10], 19.2% of the mutations occurred in a CpG dinucleotide context (FIG. 7). Among somatic small nucleotide variants, the most frequently mutated genes have roles in cancer, including GBM (TP53, EGFR, PTEN, and IDH1). In addition to known cancer genes, new candidate driver genes were mutated in ~5% of tumor samples. By integrating mutational and common focal genomic lesions, MutComFocal stratified somatically mutated genes into three groups: recurrently mutated genes without significant copy number alterations (Mut), in regions of focal and recurrent amplifications (Amp-Mut) and in regions of focal and recurrent deletions (Del-Mut).

Figure 2C:
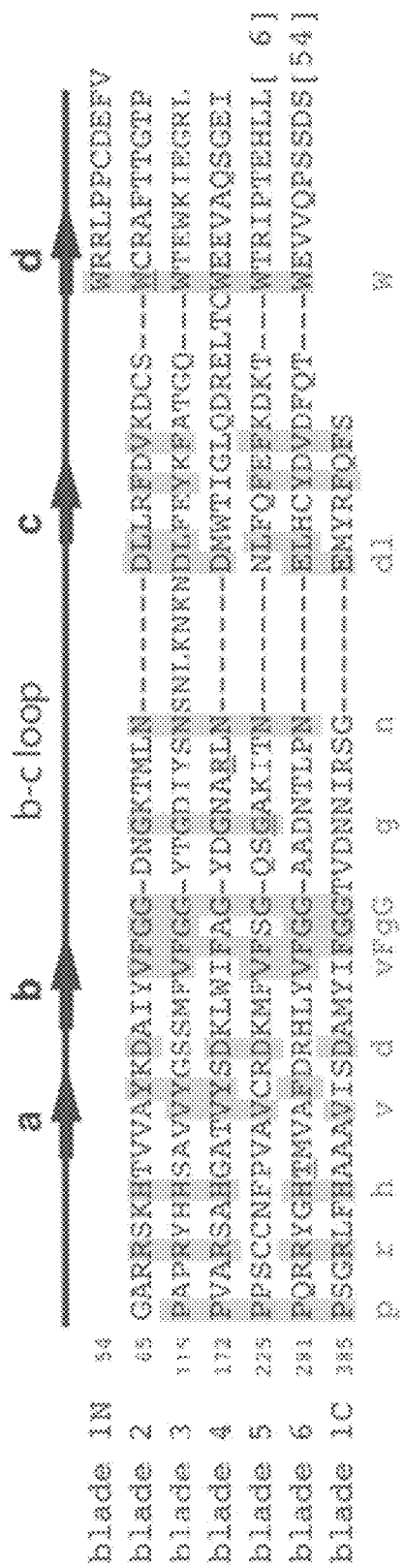
FIG. 2C. Sequence alignment of the six blades from the Kelch β-propeller domain. Each blade contains four core β-strands, labeled a, b, c, d. Conserved residues are highlighted in gray and residues mutated in GBM are shown in red. Insertions at the end of blades 5 and 6 are indicated in brackets. Figure discloses SEQ ID NO: 8478.

A list of 67 genes were generated that score at the top of each of the three categories and included nearly all the genes previously implicated in GBM. Among these genes, (labeled in light grey in FIG. 1) are IDH1 (Mut, FIG. 1a), PIK3C2B, MDM4, MYCN, PIK3CA, PDGFRA, KIT, EGFR, and BRAF (Amp-Mut, FIG. 1b) and PIK3R1, PTEN, RB1, TP53, NF1 and ATRX (Del-Mut, FIG. 1c). The analysis also selected 52 new candidate driver genes previously unreported in GBM. Based upon their role in CNS development and homeostasis as well as their potential function in gliomagenesis, 24 genes were selected for re-sequencing in an independent dataset of 83 GBM and matched normal controls. Eighteen genes were found somatically mutated by Sanger sequencing in the independent panel (labeled in dark grey in FIG. 1). Each validated new GBM gene is targeted by somatic mutations and CNVs in a cumulative fraction comprised between 2.9% and 45.7% of GBM. Furthermore, mutations of the 18 new GBM genes occur mostly in tumors with global mutation rates similar to the mean of 43 mutations per tumor and well within the 95% confidence interval, indicating that mutations of the 18 new genes do not cluster in hypermutated tumors (FIG. 2C and FIG. 9).

Among the commonly mutated and focally deleted genes exhibiting top MutComFocal scores and validated in the independent GBM dataset, BCOR, LRP family members, HERC2, LZTR-1 and CTNND2. BCOR, an X-linked gene, encodes for a component of the nuclear co-repressor complex that is essential for normal development of neuroectoderm and stem cell functions[11-13]. BCOR mutations have recently been described in retinoblastoma and medulloblastoma[14,15]. LRP1B, a member of the LDL receptor family, is among the most frequently mutated genes in human cancer (FIG. 1c)[16]. Interestingly, two other LDL receptor family members (LRP2 and LRP1) are mutated in 4.4% and 2.9% of tumors, respectively (FIG. 1a). The LRP proteins are highly expressed in the neuroepithelium and are essential for forebrain morphogenesis in mouse and humans[17,18]. The tumor suppressor function of LRP proteins in GBM may relate to the ability to promote chemosensitivity and control in the Sonic hedgehog signaling pathway, which is implicated in cancer initiating cells in GBM[19-21]. Localized on chromosome 15q13, the Hect ubiquitin ligase Herc2 gene is deleted and mutated in 15.1% and 2.2% of GBM cases, respectively. Herc2 has been implicated in severe neurodevelopmental syndromes and Herc2 substrates regulate genome stability and DNA damage-repair[22,23].

LZTR-1 Mutations Inactivate a Cullin-3 Adaptor to Drive Self-Renewal and Growth of Glioma Spheres A gene that received one of the highest Del-Mut score by MutComFocal is LZTR-1 (FIG. 1c). The LZTR-1 coding region had non-synonymous mutations in 4.4%, and the LZTR-1 locus (human chromosome 22q11) was deleted in 22.4% of GBM. Among the 18 new GBM genes, LZTR-1 had the highest co-occurrence score of mutations and deletions (Fisher's exact test, p=0.0007). It also scored at the top of the list of genes whose CNVs are statistically correlated with expression (Pearson correlation between LZTR-1 CNVs and expression is 0.36, p-value <$10^{-6}$ by Student's t-distribution). Finally, LZTR-1 emerged as the gene with the highest correlation for monoallelic expression of mutant alleles in tumors harboring LZTR-1 deletions (p-value=0.0007). Taken together, these findings indicate that LZTR-1 is concurrently targeted in GBM by mutations and copy number loss, fulfilling the two-hits model for tumor suppressor inactivation in cancer.

Figure 15:
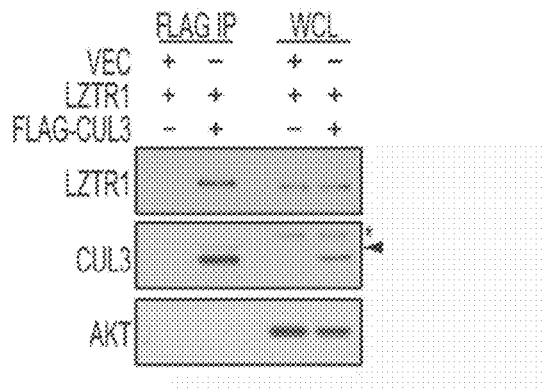
FIG. 15 is a photographic image of a blot showing the interaction with Cul3 and protein stability of wild type and mutant LZTR-1. Lysates from SF188 glioma cells transfected with vectors expressing Myc-LZTR-1 and Flag-Cul3 or the empty vector were immunoprecipitated with Flag antibody and assayed by western blot with the indicated antibodies. *, non specific band; arrowhead indicates nedylated Cul3.

LZTR-1 codes for a protein with a characteristic Kelch-BTB-BACK-BTB-BACK domain architecture (FIGS. 2C, 8, 9) and is expressed in normal brain. The LZTR-1 gene is highly conserved in metazoans. Although it was initially proposed that LZTR-1 functions as a transcriptional regulator, this role was not confirmed in follow-up studies[24]. Most proteins with BTB-BACK domains are substrate adaptors in Cullin-3 (Cul3) ubiquitin ligase complexes, in which the BTB-BACK region binds to the N-terminal domain of Cul3, while a ligand binding domain, often a Kelch 6-bladed β-propeller motif, binds to substrates targeted for ubiquitylation[25]. To ask whether LZTR-1 directly binds Cul3, co-immunoprecipitation experiments were performed in human glioma cells. FIG. 15 shows that Cul3 immunoprecipitates contain LZTR-1, indicating that LZTR-1 is an adaptor in Cul3 ubiquitin ligase complexes.

To address the function of LZTR-1 mutants, a homology model of LZTR-1 was built based partly on the crystal structures of the MATH-BTB-BACK protein SPOP[26], the BTB-BACK-Kelch proteins KLHL3[27] and KLHL11[28], and the Kelch domain of Keap1[29] (FIG. 2b). Without being bound by theory, the second BTB-BACK region of LZTR-1 binds Cul3 because of a φ-X-E motif in this BTB domain, followed by a 3-Box/BACK region (FIG. 9)[26]. However, the preceding BTB-BACK region can also participate in Cul3 binding. Five of seven LZTR-1 mutations identified in GBM are located within the Kelch domain and target highly conserved amino acids (FIG. 2b, FIG. 2C, FIG. 8). Interestingly, the concentration of LZTR-1 mutations in the Kelch domain reflects a similar pattern of mutations in the Kelch-coding region of KLHL3, recently identified in families with hypertension and electrolytic abnormalities[30,31].

The R198G and G248R mutations localize to the b-c loop of the Kelch domain, in a region predicted to provide the substrate-binding surface[29]. The W105R mutation targets a highly conserved anchor residue in the Kelch repeats and the T288I mutation disrupts a buried residue conserved in LZTR-1 (FIG. 2b, FIG. 2C, FIG. 8). Both mutations are expected to perturb folding of the Kelch domain. The E353STOP mutation is expected to produce a misfolded Kelch domain besides removing the C-terminal BTB-BACK regions. Located in the BTB-BACK domains, the remaining two mutations either truncate the entire BTB-BACK-BTB-BACK region (W437STOP) or are predicted to disrupt the folding of the last helical hairpin in the BTB-BACK domain (R810W, FIG. 2b).

Figure 16A:
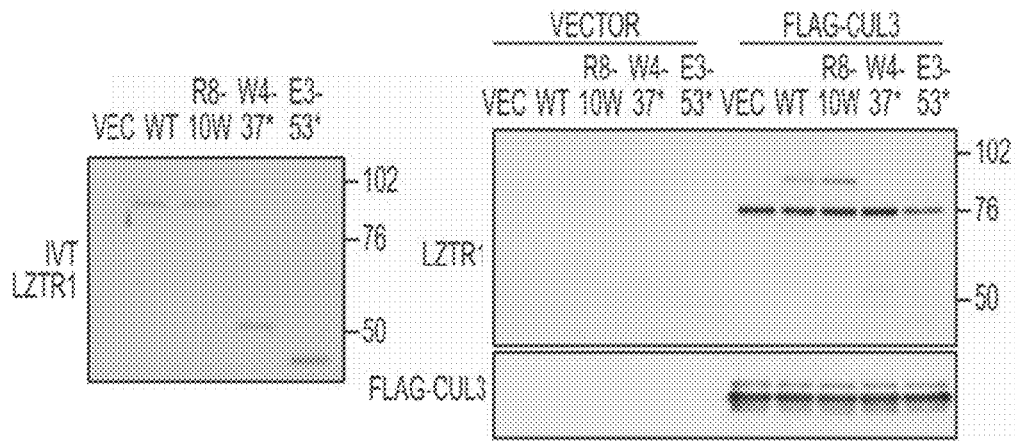
FIG. 16A are a photographic images of a blot showing the interaction with Cul3 and protein stability of wild type and mutant LZTR-1. In vitro analysis of the interaction between Cul3 and LZTR-1 wild type and GBM related mutants. Left panel, In vitro translated Myc-LZTR-1 input. Right panel, In vitro translated Myc-LZTR-1 was mixed with Flag-Cul3 immunoprecipitated from transfected HEK-293T cells. Bound proteins were analyzed by western blot using the indicated antibodies.
Figure 16B:
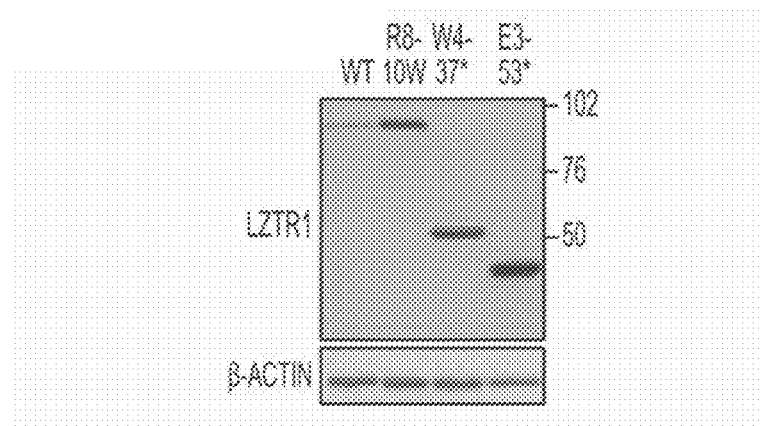
FIG. 16B is a photographic image of a blot showing the interaction with Cul3 and protein stability of wild type and mutant LZTR-1. Steady state protein levels of wild type LZTR-1 and GBM-related mutants.
Figure 16C:
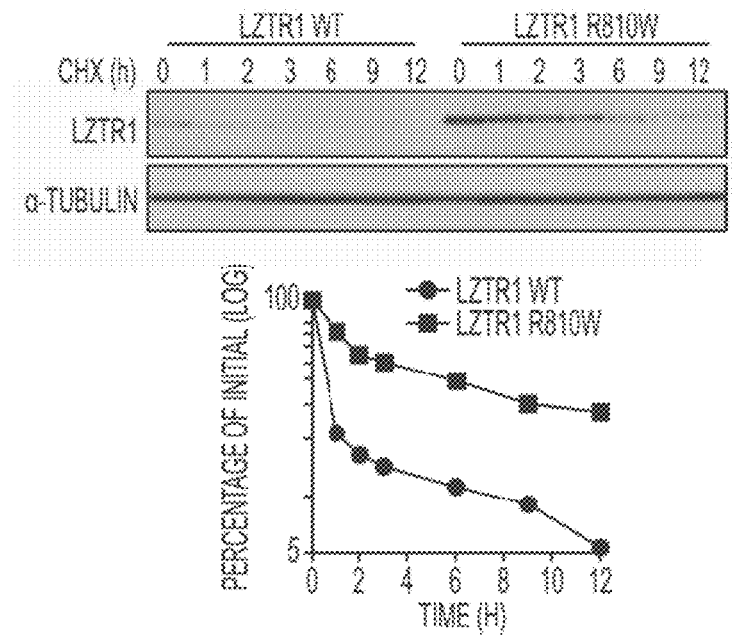
FIG. 16C is a photographic image of a blot (top) and a graph (bottom) Top panel, Cells transfected with LZTR-1 wild type or the R810W mutant were treated with cyclohexamide for the indicated time. Bottom panel, Quantification of LZTR-1 wild type and LZTR-1-R810W protein from the experiment in the left panel.
Figure 16D:
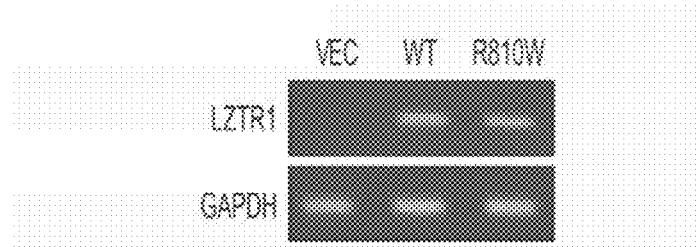
FIG. 16D is a photographic image of a blot showing the interaction with Cul3 and protein stability of wild type and mutant LZTR-1. Semi-quantitative RT-PCR evaluation of LZTR-1 wild type and LZTR-1-R810W RNA expression in cells transfected as in FIG. 16C.

To ask whether the mutations predicted to affect the BTB-BACK domains perturb the interaction with Cul3, in vitro translated wild type, E353STOP, W437STOP and R810W LZTR-1 Myc-tagged proteins were prepared and their ability to bind to Flag-Cul3 purified from mammalian cells was tested. Wild type LZTR-1 bound Flag-Cul3, but the E353STOP and W437STOP mutants lost this property. However, the R810W mutant retained Cul3 binding in this assay (FIG. 16A). Besides promoting ubiquitin-mediated degradation of substrates, Cullin adaptors are short-lived proteins that undergo auto-ubiquitylation and destruction by the same Cullin complexes that direct substrate ubiquitylation[32-34]. Thus, impaired ubiquitin ligase activity of the LZTR-1-Cul3 complex should result in accumulation of mutant LZTR-1 proteins. Each of the three LZTR-1 mutants predicted to compromise integrity of the BTB-BACK domains accumulated at higher levels than wild-type LZTR-1 in transient transfection assays (FIG. 16B). The steady state and half-life of the LZTR-1 R810W mutant protein were markedly increased, in the absence of changes of the mutant mRNA (FIG. 16C-D). Thus, as for the two truncated mutants, the R810W mutation compromised protein degradation.

Figure 17A:
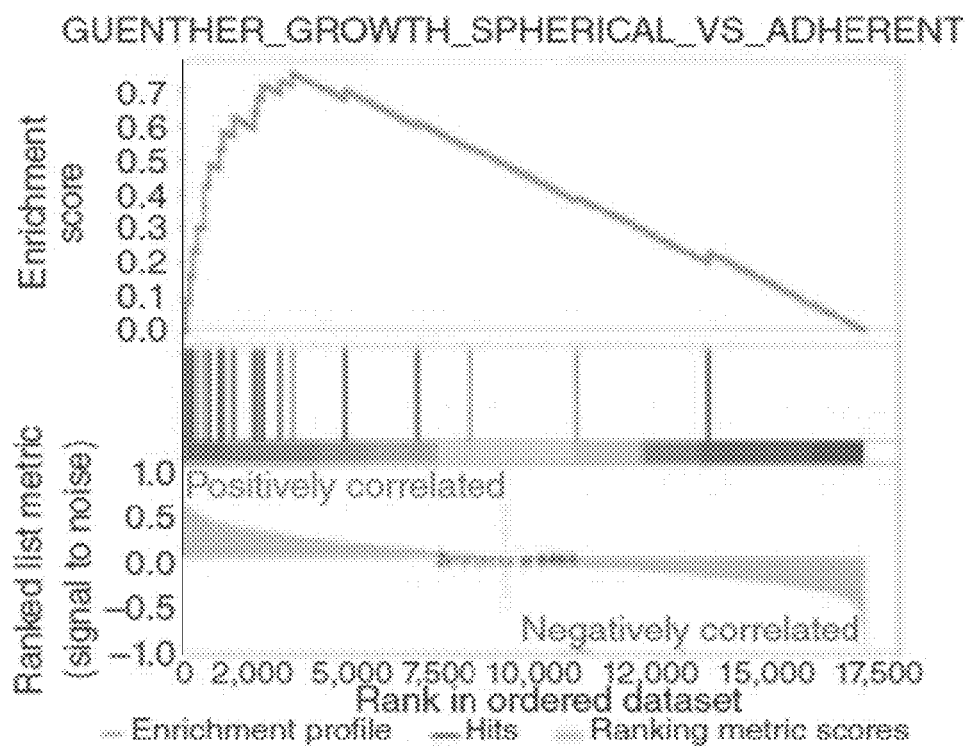
FIG. 17A is a graph showing functional analysis of LZTR-1 wild type and GBM associated mutants in GBM-derived cells. GSEA shows up-regulation of genes associated with the phenotype of "spherical cultures" of glioma cells in primary human GBM carrying mutations in the LZTR-1 gene [Enrichment Score (ES)=0.754; P (family-wise error rate, FWER)=0.000 q (false discovery rate, FDR)=0.000].
Figure 17B:
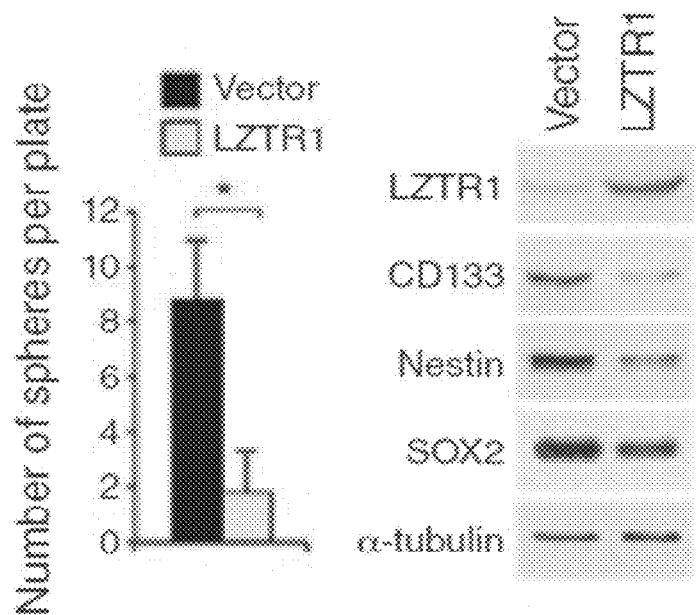
FIG. 17B is a graph showing functional analysis of LZTR-1 wild type and GBM associated mutants in GBM-derived cells. Sphere forming assay (left panel) and western blot analysis (right panel) of GBM-derived glioma spheres (#48) expressing vector or LZTR-1. Data are Mean±SD of triplicate samples (p=0.0036). Error bars are SD.
Figure 17C:
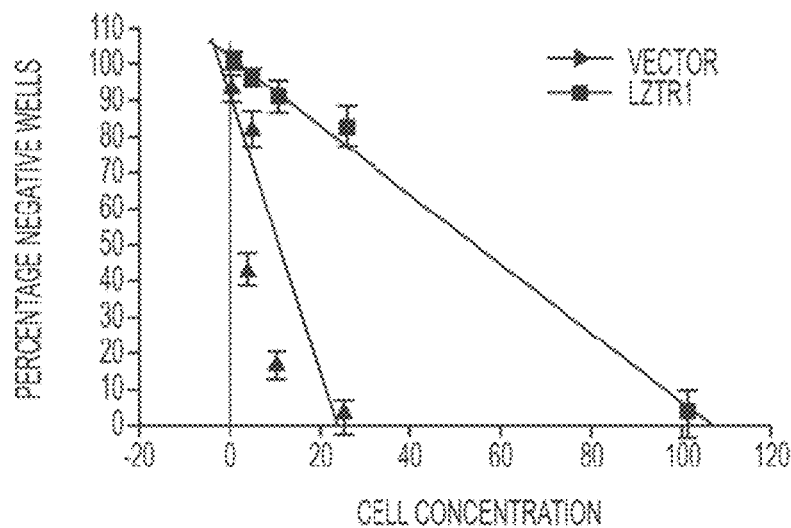
FIG. 17C is a linear regression plot of in vitro limiting dilution assay using GBM-derived glioma spheres #46 expressing vector or LZTR-1. The frequency of sphere forming cells was 8.49±1.04 and 1.44±0.05% in vector and LZTR-1 expressing cells, respectively (p=0.00795). Each data point represents the average of triplicates. Error bars are SD.
Figure 17D:
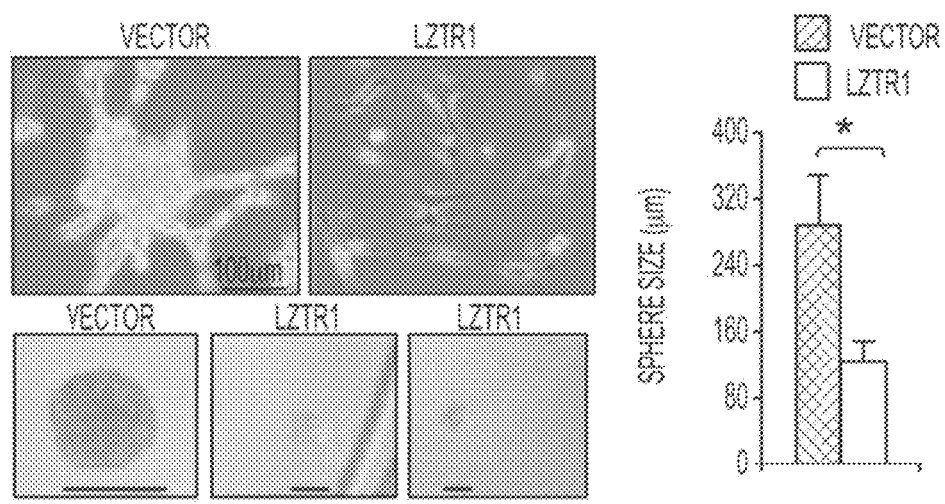
FIG. 17D is a graph and photographic microscopy images showing functional analysis of LZTR-1 wild type and GBM associated mutants in GBM-derived cells. Left upper panels, Bright field microphotographs of GBM-derived line 46 cells six days after transduction with vector or LZTR-1 expressing lentivirus. Left lower panels, Bright field microphotographs of spheres from GBM-derived glioma cells #46 expressing lentivirus expressing vector or LZTR-1 from experiment in FIG. 17C. Right panel, The size of tumor spheres from cultures in c was determined by microscopy review after 14 days of culture. n=60 spheres from triplicates for each condition. Data are Mean±SD (p<0.0001). Error bars are SD.
Figure 17E:
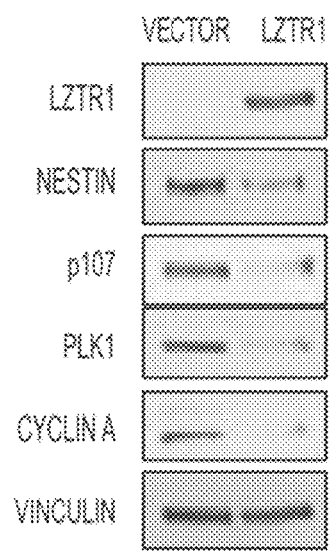
FIG. 17E is a photographic image of a western blot analysis of GBM-derived cells #84 expressing vector or LZTR-1.
Figure 17F:
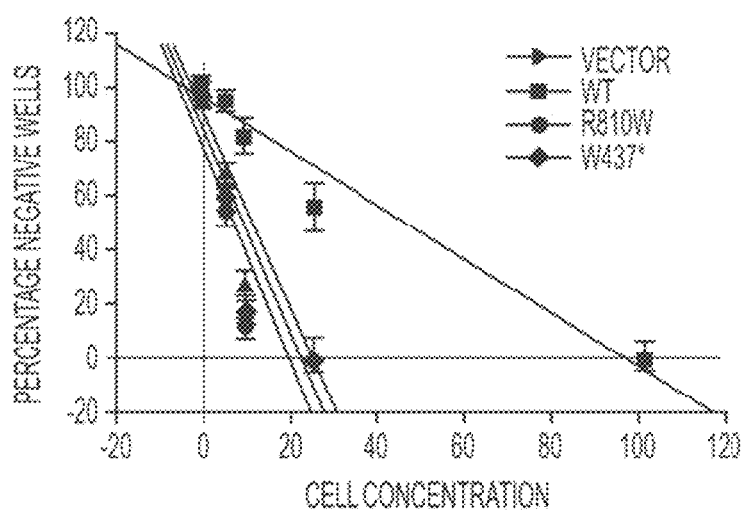
FIG. 17F is a linear regression plot of in vitro limiting dilution assay using GBM-derived line 84 expressing vector, LZTR-1, LZTR-1-R810W or LZTR-1-W437STOP. The frequency of sphere forming cells was 7.2±0.92 for vector, 1.48±0.09 for LZTR-1 wild type (p=0.0096); 7.82±0.99 for LZTR-1-R810W (p=0.2489); and 6.74±1.07 for LZTR-1-W437STOP (p=0.2269). Error bars are SD.

Next, the biological consequences of LZTR-1 inactivation in human GBM. Differential gene expression pattern of GBM harboring mutations was examined and deletions of LZTR-1 or normal LZTR-1 revealed that tumors with genetic inactivation of LZTR-1 were enriched for genes associated with glioma sphere growth and proliferation[35] (FIG. 17A). Introduction of LZTR-1 in three independent GBM-derived sphere cultures resulted in strong inhibition of glioma sphere formation and expression of glioma stem cell markers (FIG. 17B-E). LZTR-1 also decreased the size of tumor spheres, induced a flat and adherent phenotype and reduced proteins associated with cell cycle progression (cyclin A, PLK1, p107, FIG. 17D-E). Interestingly, both R810W and W437STOP LZTR-1 mutations abolished LZTR-1 ability to impair glioma sphere formation (FIG. 17F). The above experiments indicate that LZTR-1 inactivation in human GBM drives self-renewal and growth of glioma spheres.

Inactivation of CTNND2 Induces Mesenchymal Transformation in Glioblastoma

Among the top ranking genes in MutComFocal, CTNND2 is expressed at the highest levels in normal brain. CTNND2 codes for δ-catenin, a member of the p120 subfamily of catenins expressed almost exclusively in the nervous system where it is crucial for neurite elongation, dendritic morphogenesis and synaptic plasticity[36-38]. Germline hemizygous loss of CTNND2 impairs cognitive functions and underlies some forms of mental retardation[39,40]. CTNND2 shows pronounced clustering of mutations in GBM. The observed spectrum of mutations includes four mutations in the armadillo-coding domain and one in the region coding for the N-terminal coiled-coil domain (FIG. 10A), the two most relevant functional domains of δ-catenin. Each mutation targets highly conserved residues with probably (K629Q, A776T, S881L, D999E) and possibly (A71T) damaging consequences[41]. GBM harbors focal genomic losses of CTNND2, and deletions correlate with loss of CTNND2 expression (FIG. 10B).

Figure 18A:
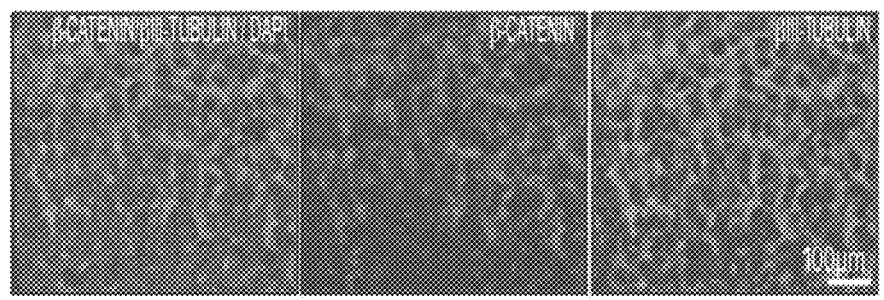
FIGS. 18A-B are photographic microscopy images showing expression of δ-catenin in neurons and δ-catenin driven loss of mesenchymal marker in GBM.
Figure 18B:
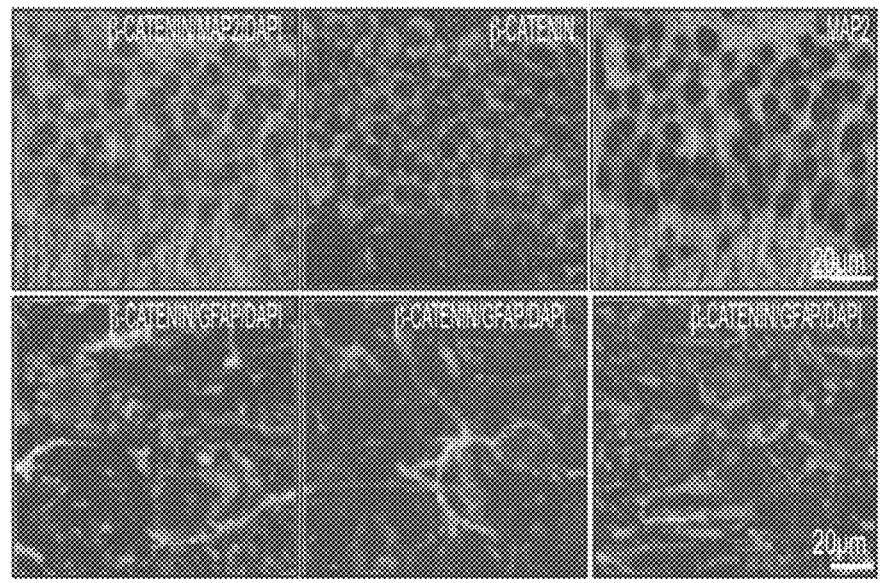
Figure 22A:
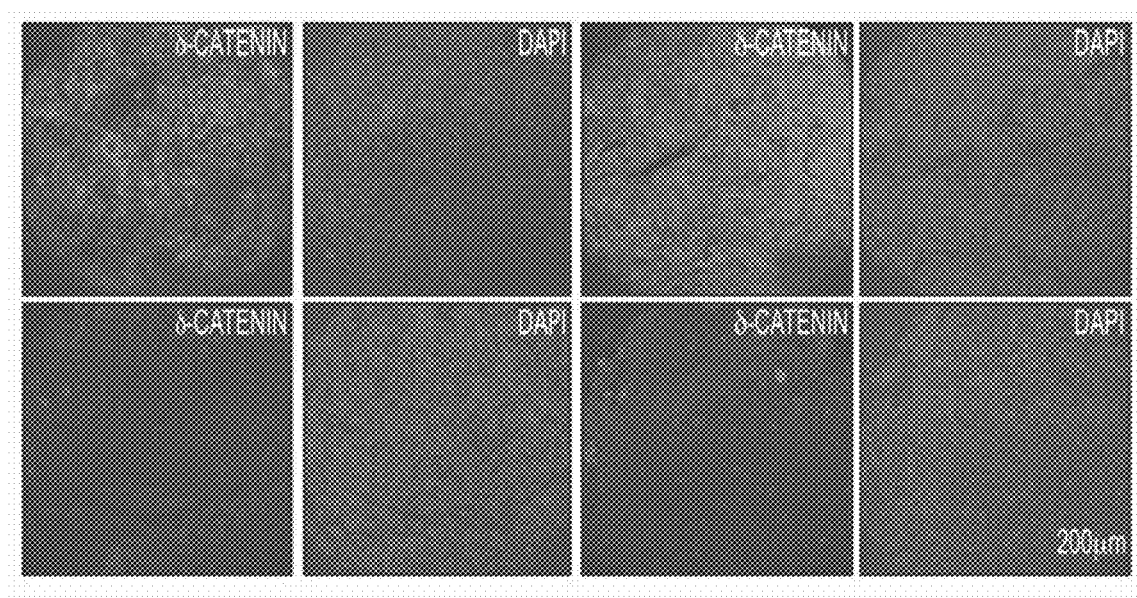
FIGS. 22A-B show pattern of somatic mutations, CNVs and expression of CTNND2 in GBM.
Figure 22B:
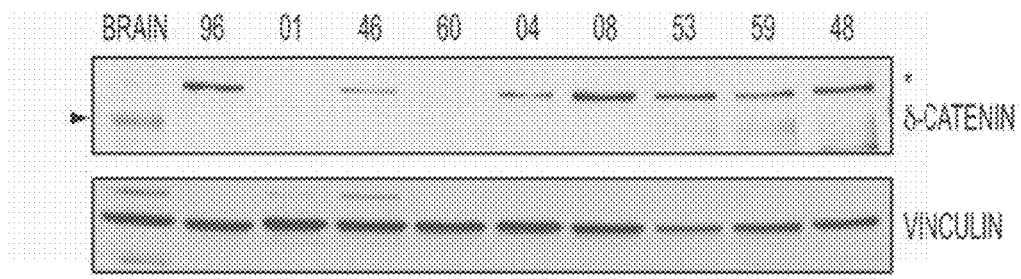

Immunostaining experiments showed that δ-catenin is strongly expressed in normal brain, particularly in neurons, as demonstrated by co-staining with the neuronal markers β3-tubulin and MAP2 but not the astrocytic marker GFAP (FIG. 18A-B). Conversely, immunostaining of 69 GBM and western blot of 9 glioma sphere cultures revealed negligible or absent expression of δ-catenin in 21 tumors and in most glioma sphere cultures (FIG. 22). Oncogenic transformation in the CNS frequently disrupts the default proneural cell fate and induces an aberrant mesenchymal phenotype associated with aggressive clinical outcome[42]. Gene expression analysis of 498 GBM from ATLAS-TCGA showed that low CTNND2 expression is strongly enriched in tumors exhibiting the mesenchymal gene expression signature (t-test p-value=2.4 $10^{-12}$, FIG. 10D). Tumors with reduced CTNND2 were characterized by poor clinical outcome and, among them, tumors with CTNND2 copy number loss displayed the worst prognosis (FIG. 3C-D). Patients with low CTNND2 expression showed the worst clinical outcome in mesenchymal GBM, though non-mesenchymal tumors also demonstrated poor prognosis, albeit with reduced strength (FIG. 3D).

Figure 18C:
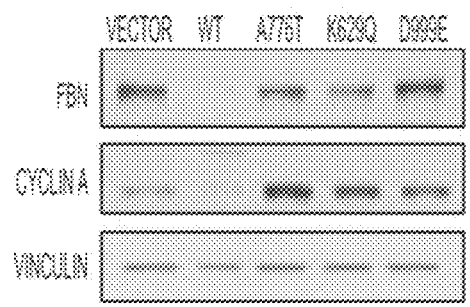
FIG. 18C is a photographic image of a western blot using the indicated antibodies for U87 cells expressing δ-catenin wild type, glioma-associated δ-catenin mutants or the empty vector. FBN, fibronectin. Vinculin is shown as control for loading.
Figure 23A:
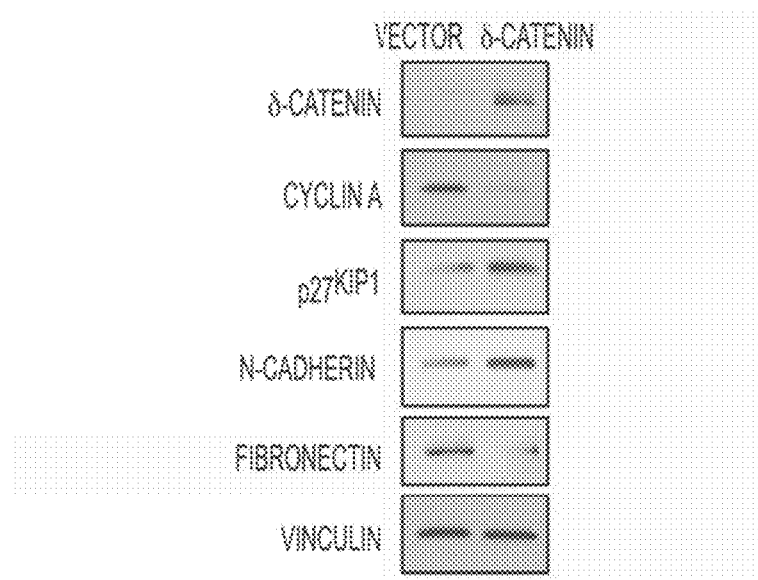
FIGS. 23A-B show the effects of expression of δ-catenin in glioma cells.
Figure 23B:
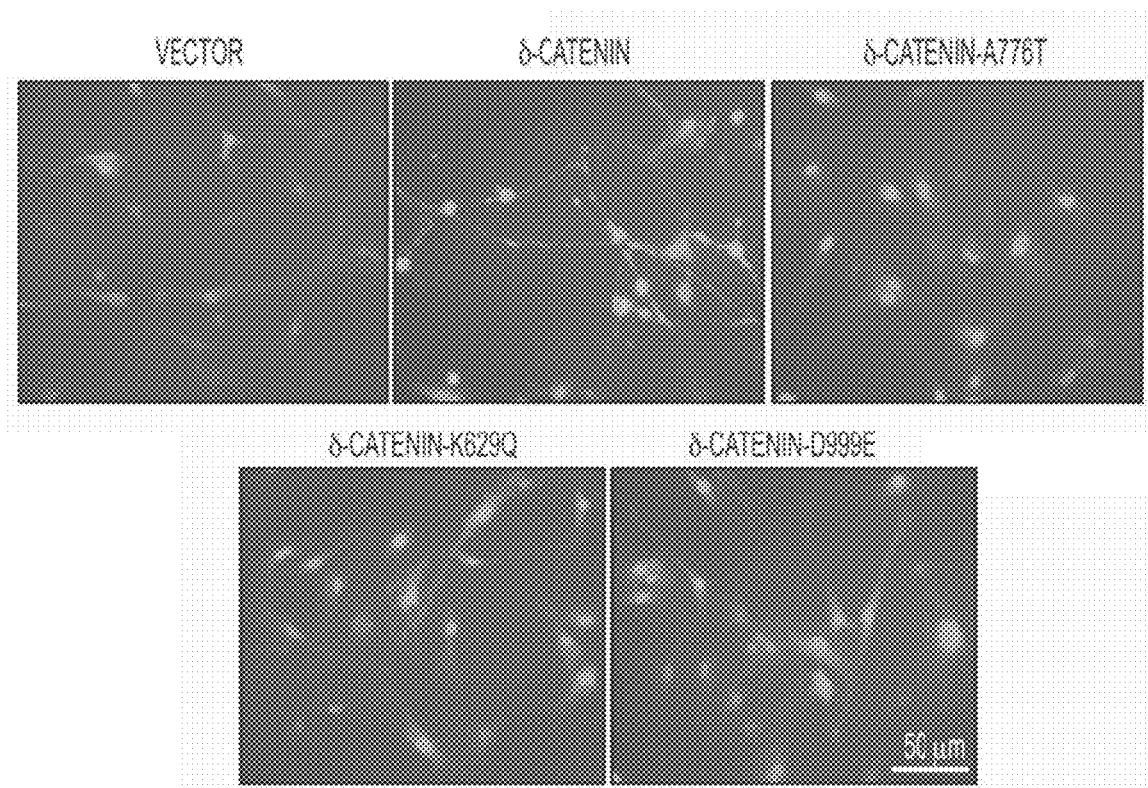
Figure 23C:
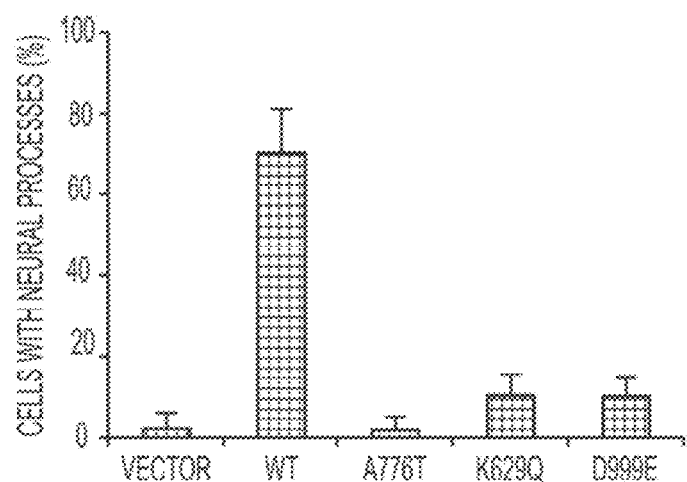
FIG. 23C is a bar graph that shows the effects of expression of δ-catenin in glioma cells. The number of cells displaying neural processes was scored. At least 200 cells/sample were analyzed.

Mesenchymal transformation of GBM is associated with irreversible loss of proneural cell fate and neuronal markers[42] and is detected in most established glioma cell lines. Expression of δcatenin in the U87 human glioma cell line reduced cell proliferation (FIG. 3E), elevated expression of neuronal proteins βIII-tubulin, PSD95 (a post-synaptic marker) and N-cadherin (FIG. 3G, FIG. 23A) and decreased mRNA and protein levels of mesenchymal markers (FIG. 3F, FIG. 18C, FIG. 23A). These effects were associated with morphologic changes characterized by neurite extension and development of branched dendritic processes (FIG. 3F, FIG. 23B-23C). Conversely, expression of the A776T, K629Q and D999E mutants of CTNND2 failed to induce neuronal features and down-regulate the mesenchymal marker fibronectin (FBN, FIG. 18C, FIG. 23B-23C). Consistent with δ-catenin inhibition of cell proliferation in glioma cells, only wild type δ-catenin decreased cyclin A, a S-phase cyclin (FIG. 18C).

Figure 19A:
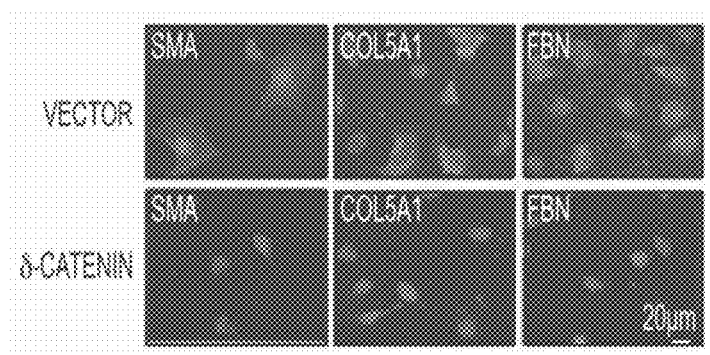
FIGS. 19A-B show a functional analysis of δ-catenin in mesenchymal GBM.
Figure 19B:
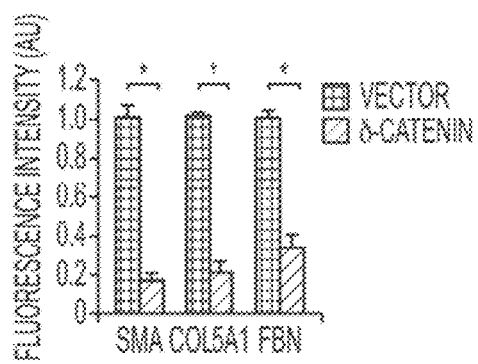
Figure 19C:
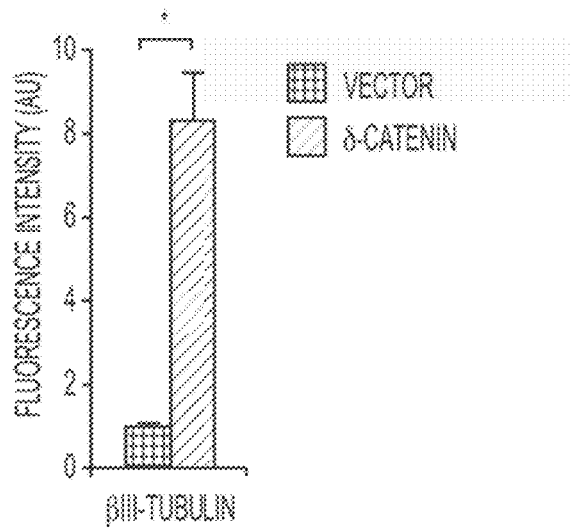
FIG. 19C is a bar graph showing the quantification of fluorescence intensity for βIII-tubulin in cells #48 infected with lentiviruses expressing CTNND2 or the empty vector.
Figure 19D:
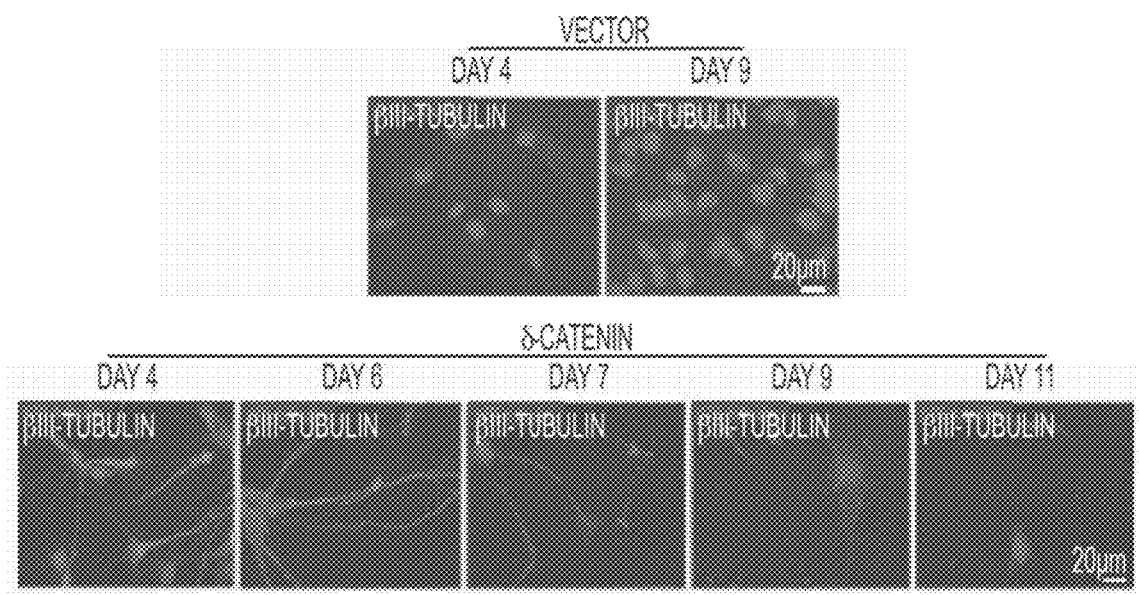
FIG. 19D are photographic microscopy images showing time course analysis of βIII-tubulin expression in glioma spheres #48 transduced with lentiviruses expressing CTNND2 or the empty vector. Note the loss from the advanced culture of βIII-Tubulin expressing cells.
Figure 19E:
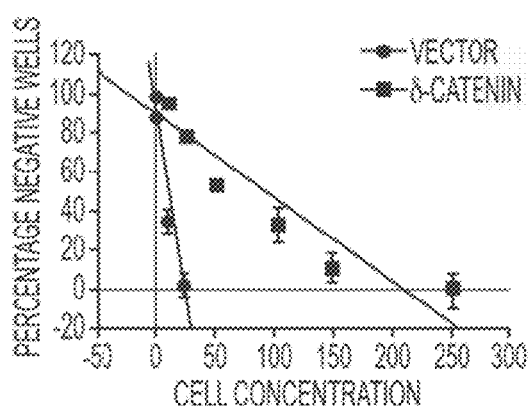
FIGS. 19E-F are graphs.
Figure 19F:
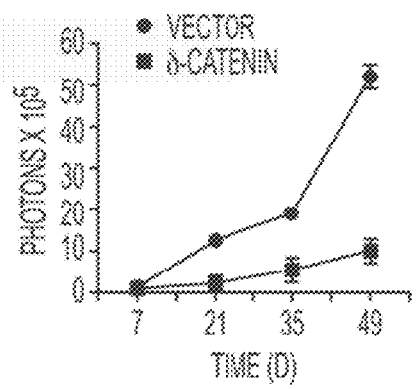
Figure 23D:
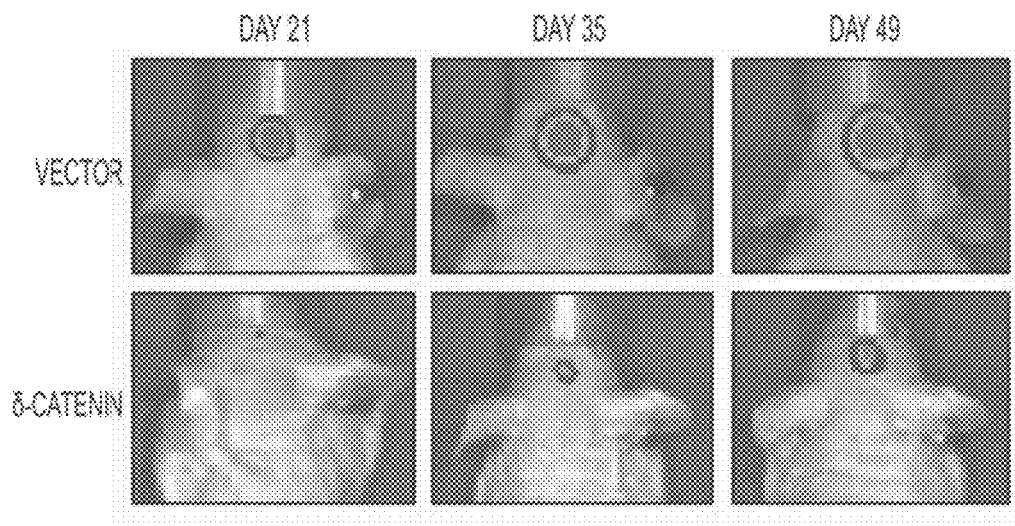
FIG. 23D are photographs of longitudinal bioluminescence imaging for one representative mouse injected intracranially with glioma sphere cells #48 transduced with lentivirus expressing CTNND2 (lower panels) or the empty vector (upper panels).

Next, the effect of expressing δ-catenin in GBM-derived sphere culture #48 that lacks the endogenous δ-catenin protein (FIG. 22B) and expresses high levels of mesenchymal markers was analyzed[43]. Introduction of δ-catenin in sphere culture #48 strongly reduced mesenchymal proteins smooth muscle actin (SMA), collagen-5A1 (Col5A1) and FBN, as measured by quantitative immunofluorescence (FIGS. 19A-B). It also induced βIII-tubulin more than eight-fold (FIGS. 19C-D). Time course analysis showed the highest degree of βIII-tubulin-positive neurite extension at 4-6 days post-transduction followed by progressive depletion of neuronal-like cells from culture (FIG. 19D). Finally, whether δ-catenin impacts self-renewal and growth of glioma spheres in vitro and their ability to grow as tumor masses in vivo were examined. In a limiting dilution assay, δ-catenin inhibited glioma sphere formation more than 8-fold (FIG. 19E). To determine the effect of δ-catenin on brain tumorigenesis in vivo, #48 glioma sphere cultures were generated expressing luciferase and bioluminescence imaging was conducted at different times after stereotactic transduction of control and δ-catenin-expressing cells in the mouse brain. When compared to controls, a 5-fold inhibition of tumor growth by δ-catenin at each time point analyzed (FIG. 19F, FIG. 23D). These results identify CTNND2 inactivation as a key genetic alteration driving the aggressive mesenchymal phenotype of GBM.

Recurrent EGFR Fusions in GBM

Figure 24:
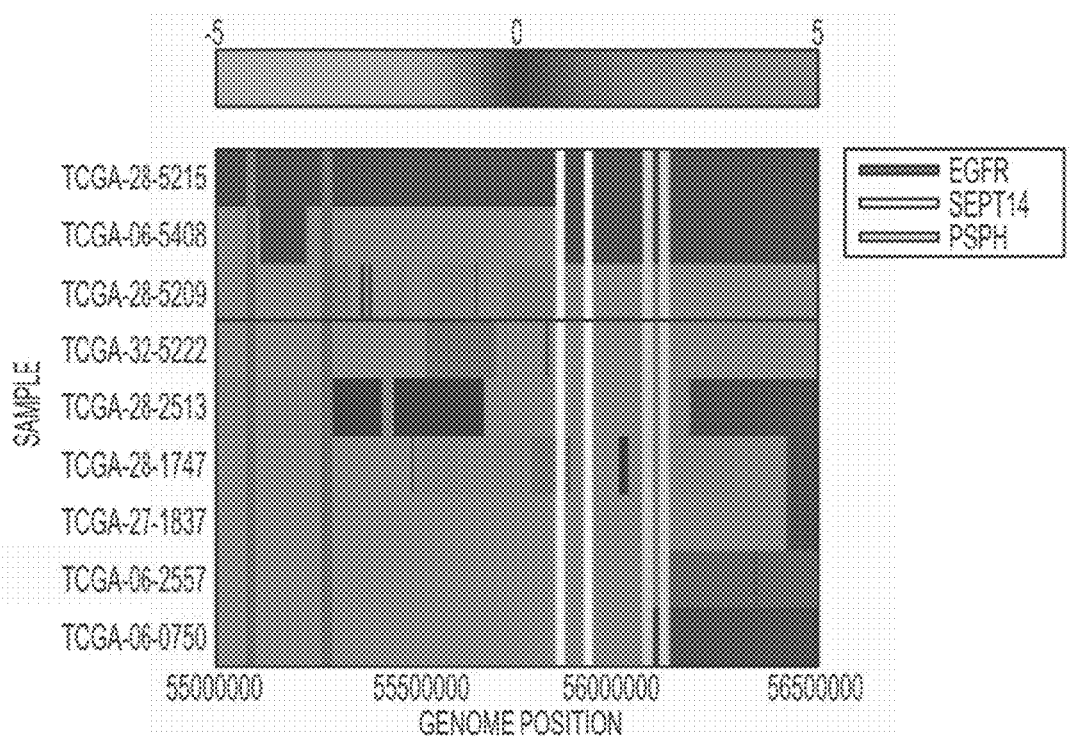
FIG. 24 is a heat map showing amplification surrounding the genomic neighborhood of EGFR, SEPT14, and PSPH among samples harboring EGFR fusions. Copy number was plotted log 2 ratio across the genomic region of chr7: 55000000-56500000 for samples with EGFR-PSPH (top three rows) and EGFR-SEPT14 (bottom six rows). Genomic coordinates are also plotted for EGFR (blue; dark grey in black and white image), SEPT14 (yellow; light grey in black and white image), and PSPH (cyan; grey in black and white image).

To identify gene fusions in GBM, RNA-seq data was analyzed from a total of 185 GBM samples (161 primary GBM plus 24 short-term glioma sphere cultures freshly isolated from patients carrying primary GBM). The analysis of RNA-seq led to the discovery of 92 candidate rearrangements giving rise to in-frame fusion transcripts (FIG. 27). Besides previously reported FGFR3-TACC3 fusions events, the most frequent recurrent in-frame fusions involved EGFR in 7.6% of samples (14/185, 3.8%-11.3% CI). Nine of 14 EGFR fusions included recurrent partners SEPT14 (6/185, 3.2%) and PSPH (3/185, 1.6%) as the 3' gene segment in the fusion. All EGFR-SEPT14 and two of three EGFR-PSPH gene fusions occurred within amplified regions of the fusion genes (FIG. 24).

The quantitative analysis of expressed reads spanning the fusion breakpoint versus reads spanning EGFR exons not implicated in the fusion transcripts revealed that EGFR fusion genes were expressed at higher levels in five of nine tumors (FIG. 30). Two in-frame highly expressed fusions involving the neurotrophic tyrosine kinase receptor 1 gene (NTRK1) as the 3' gene with two different 5' partners (NFASC-NTRK1 and BCAN-NTRK1). Fusions involving NTRK1 are common in papillary thyroid carcinomas[44]. Using EXomeFuse, an algorithm that reconstructs genomic fusions from whole-exome data, EGFR-SEPT14 and NRTK1 fusions result from recurrent chromosomal translocations and the corresponding genomic breakpoints were reconstructed (FIG. 31).

Figure 4B:
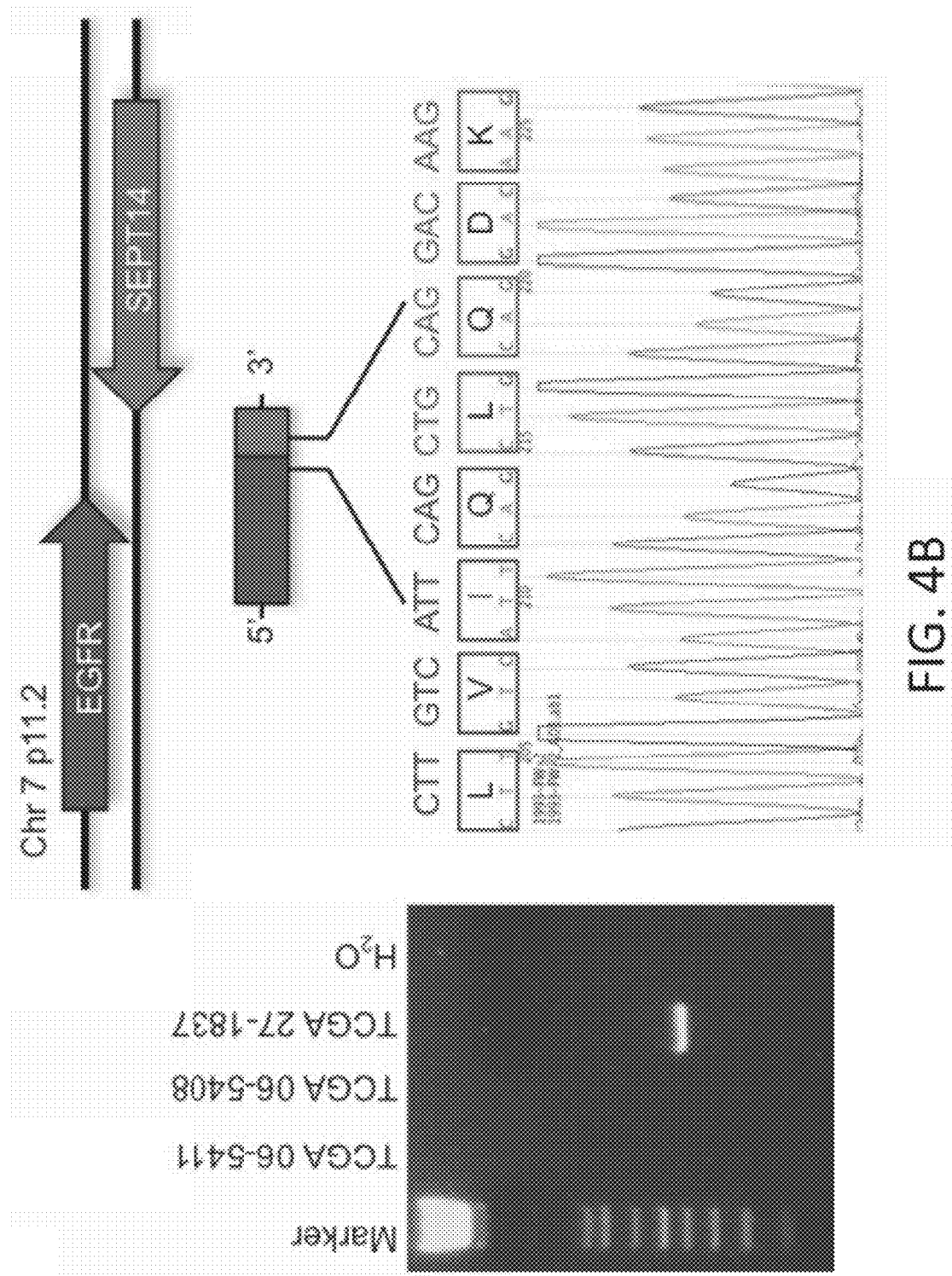
FIG. 4B. EGFR-SEPT14 gene fusion identified by whole transcriptome sequencing. (left panel), EGFR-SEPT14-specific PCR from cDNA derived from GBMs. Marker, 1 kb ladder. (right panel), Sanger sequencing chromatogram showing the reading frame at the breakpoint (SEQ ID NO: 4) and putative translation of the fusion protein (SEQ ID NO: 3) in the positive sample.
Figure 4D:
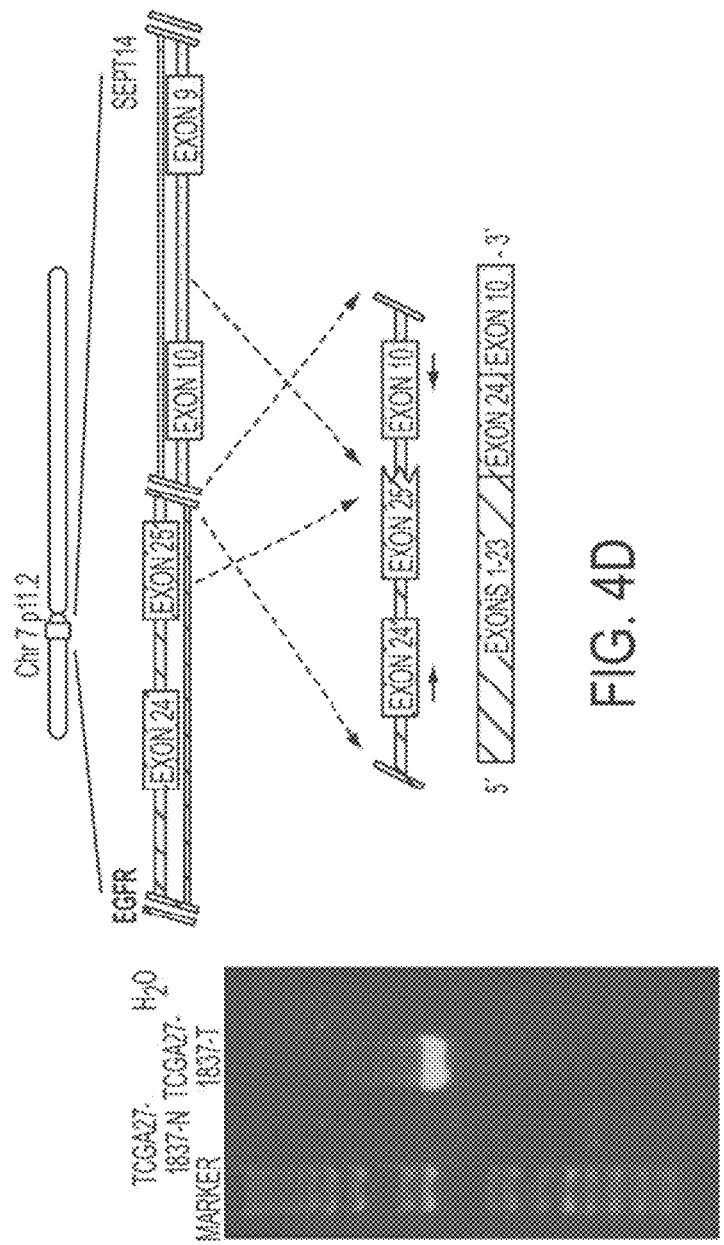
FIG. 4D. EGFR-SEPT14 gene fusion identified by whole transcriptome sequencing. Genomic fusion of EGFR exon 25 with intron 9 of SEPT14. In the fuse mRNA exon 24 of EGFR is spliced 5' to exon 10 of SEPT14. Solid arrows indicate the position of the fusion genome primers that generate a fusion specific PCR product in the GBM sample TCGA-27-1837.

The sequence of the PCR products spanning the fusion breakpoint validated all three types of recurrent in frame fusion predictions (EGFR-SEPT14, EGFR-PSPH and NRTK1 fusions, FIGS. 4, 11, 12). In FIGS. 4A-B, the prediction and cDNA sequence validation is shown respectively, for one tumor harboring an EGFR-SEPT14 fusion (TCGA-27-1837). The amplified cDNA contained an open reading frame for a 1,041 amino-acid protein resulting from the fusion of EGFR residues 1-982 with SEPT14 residues 373-432 (FIG. 4C). Thus, the structure of EGFR-Septin14 fusions involves EGFR at the N-terminus, providing a receptor tyrosine kinase domain fused to a coiled-coil domain from Septin14. Exon-specific RNA-seq expression in TCGA-27-1837 demonstrated that EGFR and SEPT14 exons implicated in the fusion are highly expressed compared with mRNA sequences not included in the fusion event (FIG. 13).

Using PCR, the genomic breakpoint was mapped to chromosome 7 (#55,268,937 for EGFR and #55,870,909 for SEPT14, genome build GRCh37/hg19) within EGFR exon 25 and SEPT14 intron 9, creating a transcript in which the 5' EGFR exon 24 is spliced to the 3' SEPT14 exon 10 (FIG. 4D). Interestingly, the fused EGFR-PSPH cDNA and predicted fusion protein in sample TCGA-06-5408 involves the same EGFR N-terminal region implicated in the EGFR-SEPT14 with PSPH providing a carboxy-terminal portion of 35 amino acids (FIG. 11). An example of a fusion in which the EGFR-TK region is the 3' partner is the CAND1-EGFR fusion in the glioma sphere culture #16 (FIG. 14). Each fusion transcript includes the region of the EGFR mRNA coding for the TK domain (FIG. 27). RT-PCR and genomic PCR followed by Sanger sequencing of GBM TCGA-06-5411 validated the NFASC-NTRK1 fusions in which the predicted fusion protein includes the TK domain of the high-affinity NGF receptor (TrkA) fused downstream to the immunoglobulin-like region of the cell adhesion and ankyrin-binding region of neurofascin (FIG. 12).

To confirm that GBM harbors recurrent EGFR fusions and determine the frequency in an independent dataset, cDNA was screened from a panel of 248 GBMs and discovered 10 additional cases with EGFR-SEPT14 fusions (4%). Conversely, NFASC-NTRK1 fusions were not detected in this dataset. A 2.2% (3/135) frequency of EGFR-PSPH fusions was determined.

The discovery of recurrent EGFR fusions in GBM is of particular interest. EGFR is activated in a significant fraction of primary GBM (~25%) by an in-frame deletion of exons 2-7 (EGFRvIII)[45]. However, seven of nine tumors harboring EGFR-SEPT14 and EGFR-PSPH gene fusions lacked the EGFRvIII rearrangement (FIG. 32). It was determined whether the most frequent EGFR fusion in GBM (EGFR-SEPT14) provides an alternative mechanism of EGFR activation and confers sensitivity to EGFR inhibition. First, whether EGFR gene fusions cluster into any gene expression subtype of GBM (proneural, neural, classical, mesenchymal) was investigated. Although no individual subtype displayed a statistically significant enrichment of EGFR fusions, 8 of 9 GBM harboring EGFR-SEPT14 or EGFR-PSPH belonged to the classical or mesenchymal subtype (Fisher's P value=0.05 for classical/mesenchymal enrichment, FIG. 33).

Figure 5C:
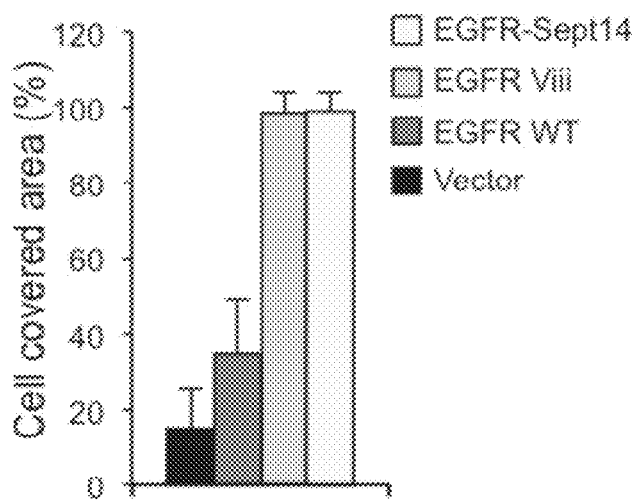
FIG. 5C. Expression of EGFR-SEPT14 fusion promotes an aggressive phenotype and inhibition of EGFR kinase delays GBM growth in vivo. Quantification of the cell covered area for the experiments shown in b (average of triplicate cultures). All error bars are SD.
Figures 20A, 20B, 20C:
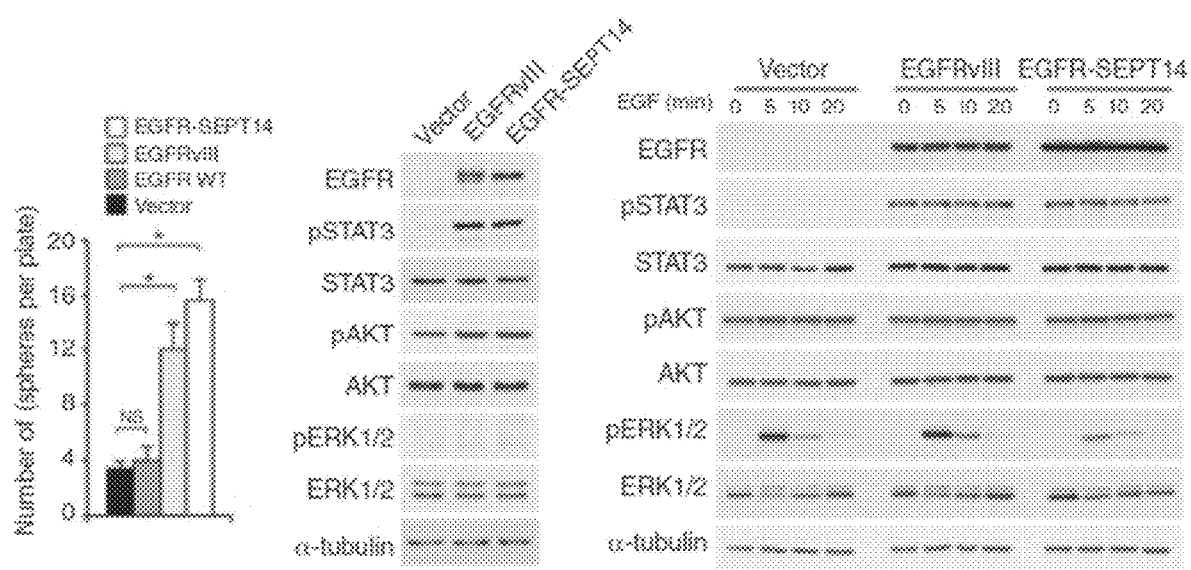
FIGS. 20A-E show the functional analysis of EGFR-SEPT14 fusion and effect of inhibition of EGFR kinase on glioma growth.
Figures 20D, 20E:
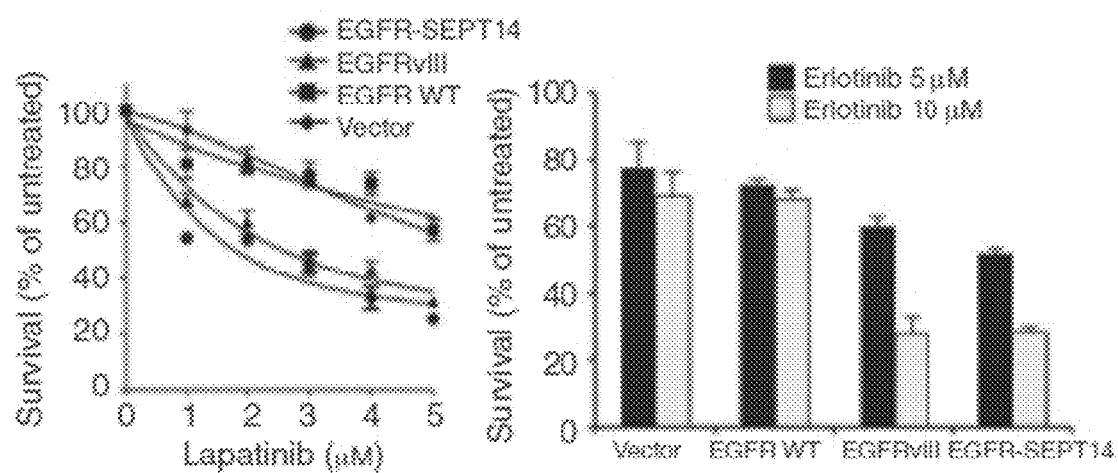
Figure 21:
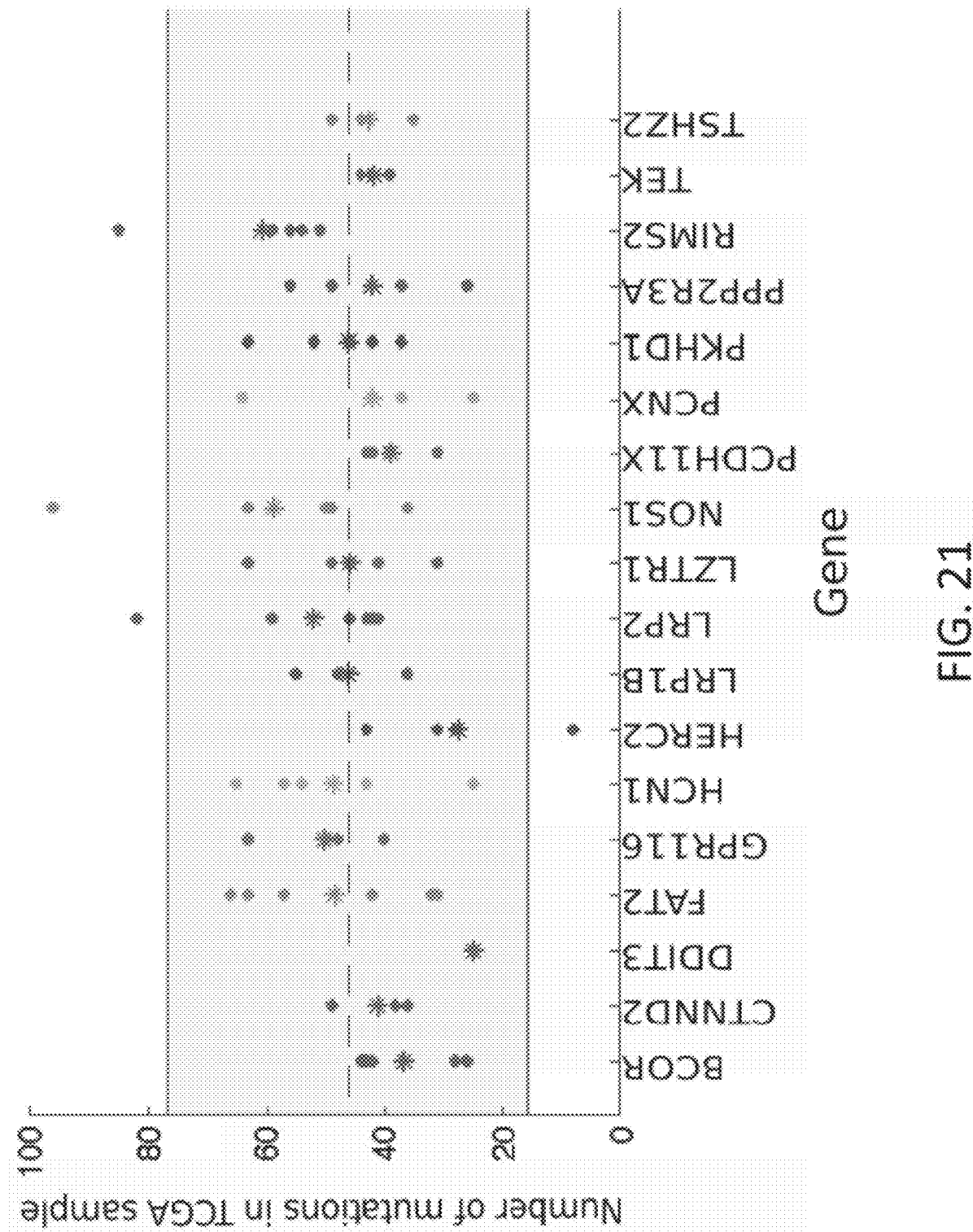
FIG. 21 is a plot showing the number of mutations in TCGA samples harboring MutComFocal gene candidates. For a given gene G, the number of mutations M8 was plotted in samples harboring G as solid circles. The mean of M8 is also plotted as asterisks. Given the mean, μ and standard deviation 6 of the number of mutations in all TCGA samples, the 95% confidence interval of a sample being hyper-mutated (11±1.96*a) was plotted and shown that for all G, the mean of M8 falls well within the 95% confidence interval, demonstrating that MutComFocal genes do not tend to occur in hypermutated samples.
Figure 25:
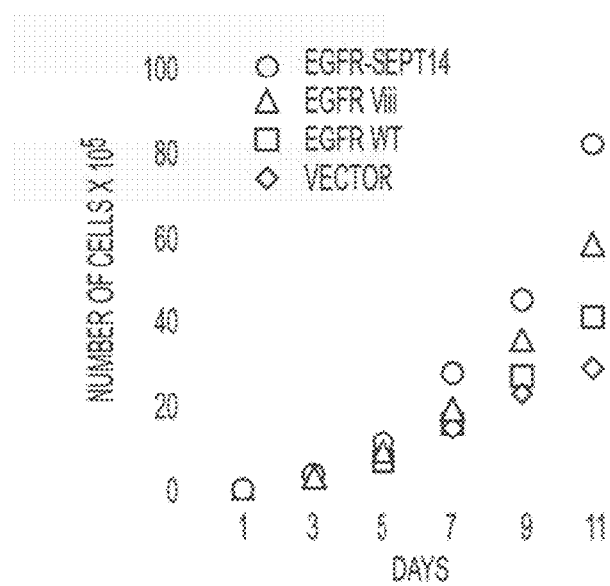
FIG. 25 is a plot showing the expression of EGFR-SEPT14 fusion promotes an aggressive phenotype and inhibition of EGFR kinase delays GBM growth in vivo. Growth rate of U87 glioma cells transduced with a lentivirus expressing EGFR-SEPT14, EGFR Viii, EGFR WT or the empty vector (average of triplicate cultures).
Figure 26:
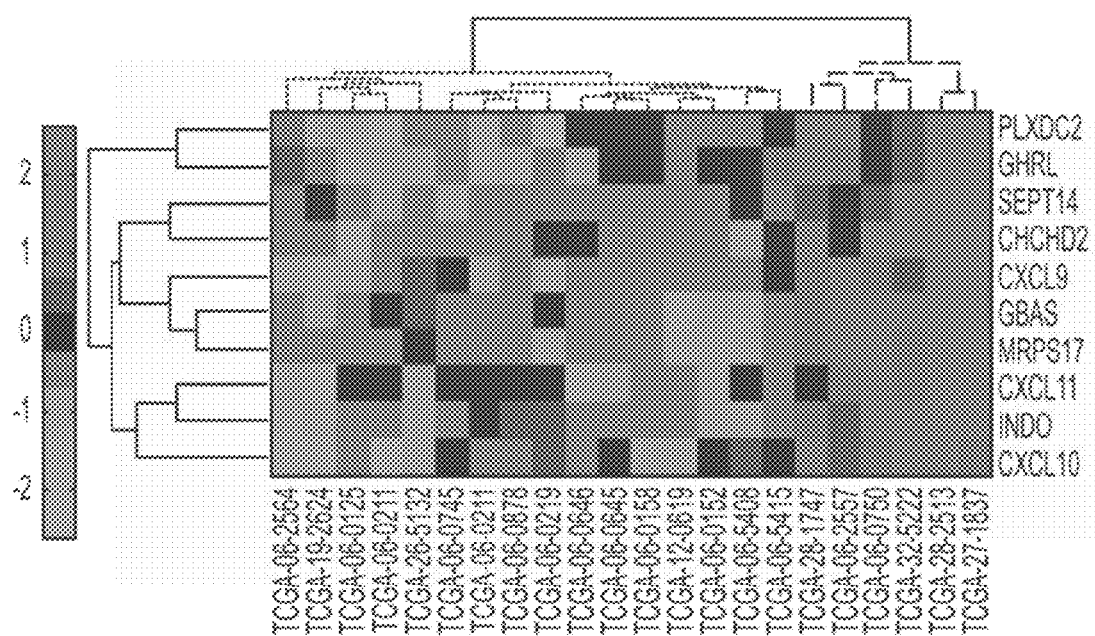
FIG. 26 is a map showing differential expression of GBM tumor samples harboring EGFR-SEPT14 fusions and EGFRvIII rearrangements. After filtering for statistical significance for differential expression, ten genes remained that characterized the EGFR-SEPT14 phenotype from the EGFRvIII phenotype. Log 2 expression was plotted as a heat map. Samples were hierarchically clustered by Euclidean distance using average linkage. This clustering demonstrates clear separation between EGFR-SEPT14 samples (red; dark grey in black and white image; corresponding to top half of intensity bar of left hand side) and EGFRvIII samples (green; light grey in black and white image; corresponding to bottom half of intensity bar of left hand side), confirming the unique molecular signature of the EGFR-SEPT14 gene fusion.

Next, the effects of ectopic EGFR-SEPT14, EGFRvIII or EGFR wild type on glioma cells were investigated. Lentiviral transduction of #48 human glioma sphere culture (which lacks genomic alteration of EGFR) showed that cells expressing EGFR-SEPT14 or EGFRvIII but not those expressing wild type EGFR or vector retained growth and self-renewal in the absence of EGF and bFGF (FIG. 20A). Accordingly, established glioma cell lines expressing EGFR-SEPT14 or EGFRvIII proliferated at higher rate than control cells or cells expressing wild type EGFR (FIG. 5A, FIG. 25). Furthermore, EGFR-SEPT14 and EGFRvIII markedly enhanced migration of glioma cells in a wound assay (FIG. 5B-C). The above findings indicate that EGFR-SEPT14 might constitutively activate signaling events downstream of EGFR. When analyzed in the presence and absence of mitogens, the expression of EGFR-SEPT14 (or EGFRvIII) in glioma sphere cultures #48 triggered constitutive activation of phospho-STAT3 but had no effects on phospho-ERK and phospho-AKT (FIG. 20B-C). This is consistent with enrichment of STAT3-target genes in primary human GBM harboring EGFR-SEPT14 fusions compared with tumors carrying wild type EGFR (FIG. 20D). Differential gene expression analysis identified a set of 9 genes up-regulated in EGFR-SEPT14 tumors compared with EGFRvIII-positive GBM (FIG. 26). These genes broadly relate to inflammatory/immune response, and some code for chemokines (CXCL9, 10, 11) that have been associated with aggressive glioma phenotypes[46].

Finally, it was investigated whether EGFR-SEPT14 fusions confer sensitivity to inhibition of EGFR-TK. Treatment of #48 expressing EGFR-SEPT14, EGFRvIII, wild type EGFR or vector control with lapatinib, an irreversible EGFR inhibitor recently proposed to target EGFR alterations in GBM[47], revealed that EGFR-Sept14 and EGFRvIII but not wild-type EGFR sensitized glioma cells to pharmaceutical EGFR inhibition (FIG. 20E). Similar effects were obtained following treatment of #48-derivatives with erlotinib, another inhibitor of EGFR-TK (FIG. 5D).

Figure 5E:
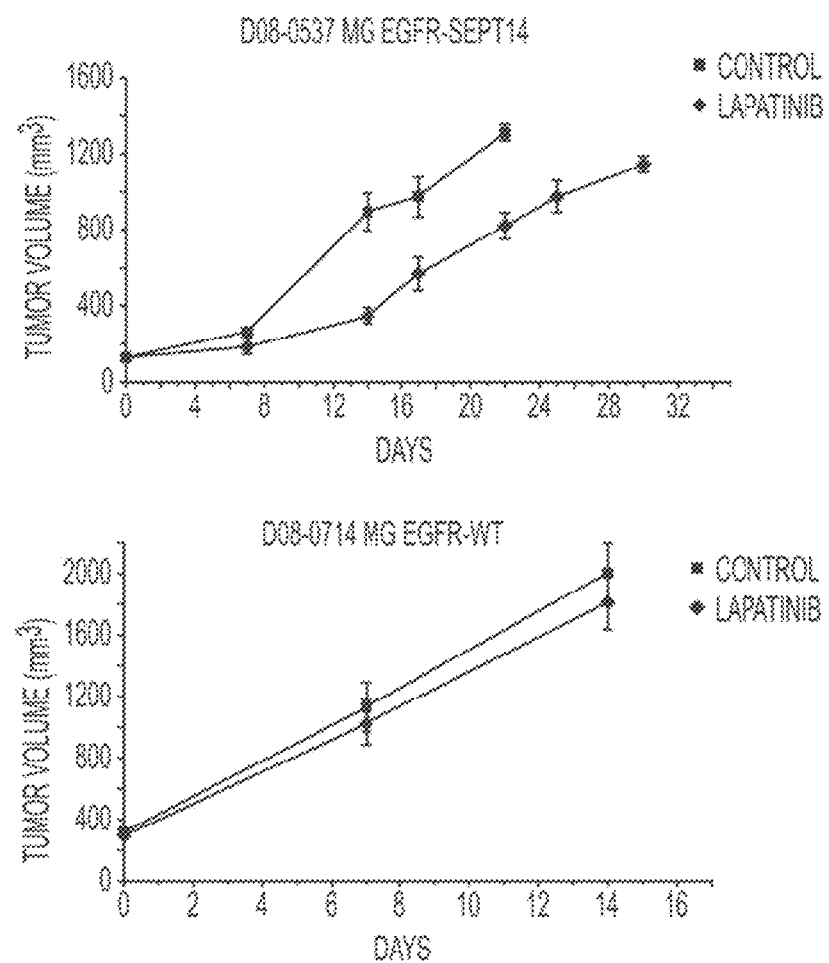
FIG. 5E. Expression of EGFR-SEPT14 fusion promotes an aggressive phenotype and inhibition of EGFR kinase delays GBM growth in vivo. Kinetics of tumor growth for the same xenografts treated with Lapatinib or vehicle (control). All error bars are SD.

To ask whether sensitivity to EGFR-TK inhibition is retained in human glioma cells naturally harboring EGFR-SEPT14 in vivo, an EGFR-SEPT14-positive GBM xenograft (D08-0537 MG) established from a heavily pretreated patient was used. Treatment of D08-0537 MG tumors with lapatinib or erlotinib showed that both drugs significantly delayed tumor growth, with lapatinib displaying the strongest anti-tumor effects. Conversely, EGFR inhibitors were ineffective against GBM xenograft D08-0714 MG, which lacks EGFR genomic alterations (FIG. 5E). Taken together, these data determine that EGFR-SEPT14 fusions confer mitogen-independent growth, constitutively activate STAT3 signaling and impart sensitivity to EGFR kinase inhibition to glioma cells harboring the fusion gene.

Discussion

A computational pipeline was described that computes frequency, magnitude and focality of CNVs at any loci in the human genome with the somatic mutation rate for genes residing at that genomic location, thus integrating into a single score two genetic hallmarks of driver cancer genes (focality of CNVs and point mutations). Besides recognizing nearly all genes known to have functional relevance in GBM, this study discovered and validated somatic mutations in 18 new genes, which also harbor focal and recurrent CNVs in a significant fraction of GBM. The importance of some of these genes extends beyond GBM, as underscored by cross-tumor relevance (e.g. BCOR), and protein family recurrence (e.g. LRP family members).

Also, the LZTR-1 mutations targeting highly conserved residues in the Kelch domain (W105, G248, T288) and in the second BTB-BACK domain (R810) are recurrent events in other tumor types[48]. Thus, understanding the nature of substrates of LZTR-1-Cul3 ubiquitin ligase activity will provide important insights into the pathogenesis of multiple cancer types. The importance of LZTR-1 genetic alterations in GBM is underscored by concurrent targeting of LZTR-1 by mutations and deletions that supports a two-hits mechanism of tumor suppressor gene inactivation as well as the impact of mutations targeting the BTB-BACK domains on Cul3 binding and/or protein stability, and their ability to release glioma cells from the restraining activity of the wild-type protein on self-renewal.

The finding that loss-of-function of CTNND2 cluster in mesenchymal GBM provides a clue to the genetic events driving this aggressive GBM subtype. The function of δ-catenin for crucial neuronal morphogenesis indicates that full-blown mesenchymal transformation in the brain requires loss of master regulators constraining cell determination along the neuronal lineage. Introduction of δ-catenin in human glioma spheres collapsed the mesenchymal phenotype and inhibited sphere formation and tumor growth. Thus, the ability of δ-catenin to reprogram glioma cells expressing mesenchymal genes towards a neuronal fate unravels an unexpected plasticity of mesenchymal GBM that might be exploited therapeutically.

In this study, the landscape of gene fusions from a large dataset of GBM analyzed by RNA-Sequencing is also reported. In-frame gene fusions retaining the RTK-coding domain of EGFR emerged as the most frequent gene fusion in GBM. In this tumor, EGFR is frequently targeted by focal amplifications and our finding underscores the strong recombinogenic probability of focally amplified genes, as recently reported for the myc locus in medulloblastoma[49]. Resembling intragenic rearrangements that generate the EGFRvIII allele, EGFR-SEPT14 fusions impart to glioma cells the ability to self-renew and grow in the absence of mitogens, constitutively activate STAT3 signaling, and confer sensitivity to EGFR inhibition. These findings highlight the relevance of fusions implicating RTK-coding genes in the pathogenesis of GBM[9]. They also provide a strong rationale for the inclusion of GBM patients harboring EGFR fusions in clinical trials based on EGFR inhibitors.

Methods

SAVI (Statistical Algorithm for Variant Frequency Identification).

The frequencies of variant alleles were estimated in 139 paired tumor and normal whole-exome samples from TCGA using the SAVI pipelines[50]. The algorithm estimates the frequency of variant alleles by constructing an empirical Bayesian prior for those frequencies, using data from the whole sample, and obtains a posterior distribution and high credibility intervals for each allele[50]. The prior and posterior are distributed over a discrete set of frequencies with a precision of 1% and are connected by a modified binomial likelihood, which allows for some error rate. More precisely, a prior distribution p(f) of the frequency f and a prior for the error e uniform on the interval [0,E] for a fixed $0 \leq E \leq 1$ is assumed. The sequencing data at a particular allele is a random experiment producing a string of m (the total depth at the allele) bits with n '1's (the variant depth at the allele). Assuming a binomial likelihood of the data and allowing for bits being misread because of random errors, the posterior probability P(f) of the frequency f is $$P(f) = \frac{p(f)}{C} \times \frac{1}{b-a} \int_f^{f+E-2Ef} x^n (1-x)^{m-n} dx$$

where C is a normalization constant. For a particular allele, the value of E is determined by the quality of the nucleotides sequenced at that position as specified by their Phred scores. The SAVI pipeline takes as input the reads produced by the sequencing technology, filters out low-quality reads and maps the rest onto a human reference genome. After mapping, a Bayesian prior for the distribution of allele frequencies for each sample is constructed by an iterative posterior update procedure starting with a uniform prior. To genotype the sample, the posterior high-credibility intervals were used for the frequency of the alleles at each genomic location. Alternatively, combining the Bayesian priors from different samples, posterior high-credibility intervals were obtained for the difference between the samples of the frequencies of each allele. Finally, the statistically significant differences between the tumor and normal samples are reported as somatic variants. To estimate the positive prediction value of SAVI in the TCGA GBM samples, 41 mutations were selected for independent validation by Sanger sequencing. 39 of the 41 mutations using Sanger sequencing were confirmed, resulting in a 0.95 (95% CI 0.83-0.99) validation rate.

Candidate genes were ranked by the number of somatic nonsynonymous mutations. A robust fit of the ratio of nonsynonymous to synonymous mutations was generated with a bisquare weighting function. The excess of nonsynonymous alterations was estimated using a Poisson distribution with a mean equal to the product of the ratio from the robust fit and the number of synonymous mutations. Genes in highly polymorphic genomic regions were filtered out based on an independent cohort of normal samples. The list of these regions includes families of genes known to generate false positives in somatic predictions (for example, the HLA, KRT and OR gene families).

MutComFocal.

Key cancer genes are often amplified or deleted in chromosomal regions containing many other genes. Point mutations and gene fusions, conversely, provide more specific information about which genes may be implicated in the oncogenic process. MutComFocal was developed, a Bayesian approach that assigns a driver score to each gene by integrating point mutations and CNV data from 469 GBMs (Affymetrix SNP6.0). In general, MutComFocal uses three different strategies. First, the focality component of the score is inversely proportional to the size of the genomic lesion to which a gene belongs and thus prioritizes more focal genomic lesions. Second, the recurrence component of the MutComFocal score is inversely proportional to the total number of genes altered in a sample, which prioritizes samples with a smaller number of altered genes. Third, the mutation component of the score is inversely proportional to the total number of genes mutated in a sample, which achieves the twofold goal of prioritizing mutated genes on one hand and prioritizing samples with a smaller number of mutations on the other.

More specifically, for a particular sample, let $(c_1, N_1), \ldots, (c_k, N_k)$ describe the amplification lesions in that sample so that $N_i$ is the number of genes in the ith lesion and $c_i$ is its copy number change from normal. For a gene belonging to the ith lesion, the amplification recurrence sample score is defined as $(c_1, N_1), \ldots, (c_k, N_k)$, and its amplification focality sample score is defined as $(c_i/\Sigma_j c_j) \times (1/N_i)$. To obtain the amplification recurrence and focality scores for a particular gene, the corresponding sample scores were summed over all the samples and the result was normalized so that each score sums to 1. The deletion and recurrence scores are defined in a similar manner. The mutation score is analogous to a recurrence score in which it is assumed that mutated genes belong to lesions with only one gene.

The amplification/mutation score is defined as the product of the two amplification scores and the mutation score, whereas the deletion/mutation score is defined as the product of the two deletion scores and the mutation score. The amplification/mutation and deletion/mutation scores are normalized to 1, and for each score, genes are divided into tiers iteratively so that the top $2^H$ remaining genes are included in the next tier, where H is the entropy of the scores of the remaining genes normalized to 1. On the basis of their tier across the different types of scores, genes are assigned to being either deleted/mutated or amplified/mutated, and genes in the top tiers are grouped into contiguous regions. The top genes in each region are considered manually and selected for further functional validation.

The recurrence and focality scores can be interpreted as the posterior probabilities that a gene is driving the selection of the disease under two different priors, one global and one local in nature. The recurrence score is higher if a gene participates in many samples that do not have too many altered genes, whereas the focality score is higher if the gene participates in many focal lesions. Besides lending strong support to the inference of a gene as a potential driver, the directionality of the copy number alteration (amplification or deletion) informs the probable behavior of the candidate gene as an oncogene or tumor suppressor, respectively.

The genes displayed in FIG. 1 were selected on the basis of the MutComFocal ranking (top 250 genes), the size of the minimal region (less than 10 genes) and the frequency of mutations (more than 2% for deletion/mutations and at least 1% for amplification/mutations).

RNA-Seq Bioinformatics Analysis.

161 RNA-seq GBM tumor samples were analyzed from TCGA, a public repository containing large-scale genome sequencing of different cancers, plus 24 patient-derived GSCs. Nine GSC samples reported in previous studies were kept in our analysis to evaluate recurrence[9]. The samples were analyzed using the ChimeraScan[51] algorithm to detect a list of gene fusion candidates. Briefly, ChimeraScan detects those reads that discordantly align to different transcripts of the same reference (split inserts). These reads provide an initial set of putative fusion candidates. The algorithm then realigns the initially unmapped reads to the putative fusion candidates and detects those reads that align across the junction boundary (split reads). These reads provide the genomic coordinates of the breakpoint.

RNA-seq analysis detected a total of 39,329 putative gene fusion events. To focus the experimental analysis on biologically relevant fused transcripts, the Pegasus annotation pipeline (http://sourceforge.net/projects/pegasus-fus/) was applied. For each putative fusion, Pegasus reconstructs the entire fusion sequence on the basis of the genomic fusion breakpoint coordinates and gene annotations. Pegasus also annotates the reading frame of the resulting fusion sequences as either in frame or a frame shift. Moreover, Pegasus detects the protein domains that are either conserved or lost in the new chimeric event by predicting the amino acid sequence and automatically querying the UniProt web service. On the basis of the Pegasus annotation report, relevant gene fusions were selected for further experimental validation according to the reading frame and the conserved and lost domains. The selected list was based on in-frame events expressed by ten or more reads, with at least one read spanning the breaking point. To filter out candidate trans-splicing events, events with putative breakpoints at a distance of at least 25 kb were pursued.

Identification of Genetic Rearrangements Using Whole-Exome Data.

Although whole-exome sequencing data contain low intronic coverage that reduces the sensitivity for fusion discovery, they are readily available through the TCGA database. To characterize the genomic breakpoint of the chromosomal rearrangement, EXome-Fuse, a new gene fusion discovery pipeline that is designed particularly to analyze whole-exome data, was designed. For the samples harboring EGFR-SEPT14, EGFR-PSPH, NFASC-NTRK1 and BCAN-NTRK1 fusions in RNA, EXome-Fuse was applied to the corresponding whole-exome sequencing data deposited in TCGA. This algorithm can be divided into three stages: split-insert identification, split-read identification and virtual reference alignment. Mapping against the human genome reference hg18 with BWA, all split inserts are first identified to compile a preliminary list of fusion candidates. This list was pruned of any false positives produced from paralogous gene pairs using the Duplicated Genes Database and the EnsemblCompara GeneTrees[52]. Pseudogenes in the candidate list were annotated using the list from the HUGO Gene Nomenclature Committee (HGNC) database[53] and were given lower priority. Candidates were also filtered out between homologous genes, as well as those with homologous or low-complexity regions around the breakpoint. For the remaining fusion candidates, any supporting split reads were probed for and their mates using BLAST with a word size of 16, identity cutoff of 90% and an expectation cutoff of $10^{-4}$. A virtual reference was created for each fusion transcript and all reads were realigned to calculate a final tally of split inserts and split reads such that all aligning read pairs maintain forward-reverse directionality.

Targeted Exon Sequencing.

All protein-coding exons for the 24 genes of interest were sequenced using genomic DNA extracted from frozen tumors and matched blood. Five-hundred nanograms of DNA from each sample were sheared to an average size of 150 bp in a Covaris instrument for 360 s (duty cycle, 10%; intensity, 5; cycles per burst, 200). Bar-coded libraries were prepared using the Kapa High-Throughput Library Preparation Kit Standard (Kapa Biosystems). Libraries were amplified using the KAPA HiFi Library Amplification kit (Kapa Biosystems) (eight cycles). Libraries were quantified using Qubit Fluorimetric Quantitation (Invitrogen), and the quality and size was assessed using an Agilent Bioanalyzer. An equimolar pool of the four bar-coded libraries (300 ng each) was created, and 1,200 ng was input to exon capture using one reaction tube of the custom Nimblegen SeqCap EZ (Roche) with custom probes targeting the coding exons of the 38 genes. Capture by hybridization was performed according to the manufacturer's protocols with the following modifications: 1 nmol of a pool of blocker oligonucleotides (complementary to the bar-coded adapters) was used, and post-capture PCR amplification was done using the KAPA HiFi Library Amplification kit, instead of the Phusion High-Fidelity PCR Master Mix with HF Buffer Kit, in a 60 µl volume, as the Kapa HiFi kit greatly reduced or eliminated the bias against GC-rich regions.

The pooled capture library was quantified by Qubit (Invitrogen) and Bioanalyzer (Agilent) and sequenced in on an Illumina MiSeq sequencer using the 2×150 paired-end cycle protocol. Reads were aligned to the hg19 build of the human genome using BWA with duplicate removal using SAMtools as implemented by Illumina MiSeq Reporter. Variant detection was performed using GATK UnifiedGenotyper. Somatic mutations were identified for paired samples using SomaticSniper and filtered for frequency of less than 3% in normal samples and over 3% in tumor samples. Variants were annotated with the Charity annotator to identify protein-coding changes and cross referenced against known dbSNP, 1000 Genomes and COSMIC variants. Sanger sequencing was used to confirm each mutation from normal and tumor DNA.

Enrichment of Amplified and Deleted Genes for Single-Nucleotide Variants (SNVs).

Although MutComFocal combines SNV and CNV data to identify genes driving oncogenesis, it does not explicitly determine whether amplified or deleted genes are enriched for SNVs within the same sample. Deletions and SNVs of a gene within the same sample might indicate a two-hit model of a tumor suppressor. Alternatively, amplifications and gain-of-function mutations of an oncogene within the sample might further promote oncogenesis. For each MutComFocal candidate gene, the number of TCGA samples was determined with both amplification and SNVs, amplification alone, SNVs alone or neither. The corresponding Fisher's P value was calculated. A similar analysis for deletions was performed.

Correlation Between Copy Number and Expression.

One method of assessing the functional relevance of an amplified or deleted gene is to assess the effect of gene dosage. For each gene nominated by MutComFocal, the Pearson's correlation coefficient was calculated between copy number and expression. The corresponding P values were computed using paired Student's t test.

Allele-Specific Expression of SNVs.

For a given gene nominated by MutComFocal, RNA sequencing can determine whether the mutant or wild-type allele is expressed. Toward this end, VCFtools54 was applied to the TCGA BAM RNA-seq files produced by TopHat, which produces the depth of reads calling the reference (R) and variant (V) allele. A measure of relative expression of the variant allele is then V/(V+R). For each mutation, the binomial P value of observing more than V out of V+R reads was calculated, assuming that it is equally probable for a read to call the variant or reference. The binomial P values of each mutation were then pooled using the Stouffer's Z-score method to calculate the combined P value per gene.

Ruling Out Passenger Mutations in Hypermutated Samples.

To rule out the possibility that MutComFocal candidates tend to be passenger mutations in hypermutated samples, the number of mutations was compared in samples harboring a MutComFocal mutation to the distribution N of the number of mutations in each TCGA sample. Because the number of TCGA samples was well above 30, N was assumed to be well approximated by the normal distribution and calculated the mean, $\mu$, and s.d., $\sigma$. For each MutComFocal mutation, the Z-test was performed and all mutations failed statistical significance after correction by the Benjamini-Hochberg method.

Determining the Presence of EGFRvIII Transcripts.

To determine the prevalence of EGFRvIII transcripts, an in-house script was created to calculate the number of split inserts and split reads supporting the junction between EGFR exons 1 and 8. The EGFRvIII isoform was considered to be expressed if there were more than five split reads or five split inserts in a sample.

Calculating the Relative Expression of EGFR Fusions Compared to Wild-Type EGFR.

To determine the functional relevance of EGFR-SEPT14 and EGFR-PSPH fusions, the relative expression was determined between the fusion and wild-type transcripts within each sample on the basis of BAM files mapped by TopHat and provided by TCGA. As a proxy for expression of the transcript, the depth of reads covering either a mutant or wild-type junction was calculated. In particular, the depth of reads covering the fusion breakpoint of EGFR-SEPT14 or EGFR-PSPH was considered to estimate the expression of the fusion transcript. Because all EGFR fusions stereotypically involved exon 24 joined to either SEPT14 or PSPH, the depth of reads covering the junctions between EGFR exons 25-26, 26-27 and 27-28 to be a specific gauge of wild-type EGFR expression was assessed.

Enrichment of the Classical and Mesenchymal Subtype Among Samples with EGFR Fusions.

To assess whether samples with EGFR fusions tended to occur in a particular GBM subtype, each TCGA GBM sample was first classified by expression according to the methods of Verhaak et al.[6]. The number of classical, mesenchymal, proneural and neural samples was then tallied with and without EGFR gene fusions. The combined class of classical and mesenchymal phenotype was enriched for EGFR fusions according to the Fisher's exact test.

Copy Number Variation in EGFR Fusions.

Gene fusions often arise from genomic instability. Motivated by this observation, segmented SNP array data was downloaded from TCGA and calculated the log 2 ratio between the tumor and normal copy numbers. This was plotted along the chromosomal neighborhood of EGFR, SEPT14 and PSPH (chr7:55,000,000-56,500,000).

GSEA.

To determine the biological impact of LZTR1 mutations, GSEA[55] was used, which is an analytical tool that harnesses expression data to nominate gene sets enriched for a particular phenotype. Having identified TCGA samples with LZTR1 SNVs, GSEA was applied to the TCGA expression data. Samples were first compared with LZTR1 SNVs against those with wild-type LZTR1 (excluding LZTR1 deletions). To assess statistical significance, the data set was randomized by permuting gene sets 500 times and considered only gene sets with an FDR q<0.05.

Differential Expression Between Samples with EGFR-SEPT14 and EGFRvIII.

In-house differential expression analysis was also performed to determine a distinct molecular signature distinguishing the EGFR-SEPT14 and EGFRvIII phenotypes. Toward this end, a t test was performed comparing the expression of the two groups of samples for each gene. Correcting using the Benjamini-Hochberg method, only genes with FDR<0.05 were considered. In addition, genes were excluded with a variance less than the tenth percentile or absolute value lower than two across all samples. These filters left a predictive set of ten genes. Hierarchical clustering was then performed on the expression of these ten genes using Euclidean distance and average linkage.

Modeling of LZTR1.

Structural templates for the kelch and BTB-BACK regions of human LZTR1 were identified with HHpred[56]. An initial three-dimensional model was generated with the I-TASSER server[57]. The CUL3 N-terminal domain was docked onto the model by superposing the KLHL3$^{BTB-BACK}$/CUL3$^{NTD}$ crystal structure[27] onto the second LZTR1 BTB-BACK domain. The model does not include higher quaternary structure, although many BTB domains, and many kelch domains, are known to self associate[25]. The short linkage between the end of the first BACK domain and the beginning of the second BTB domain would seem to preclude an intrachain BTB-BTB pseudo-homodimer, and without being bond by theory, LZTR1 should self associate and form higher-order assemblies. Both BACK domains are the shorter, atypical form of the domain and consist of two helical hairpin motifs, as in SPOP[26, 58], and not the four-hairpin motif seen in most BTB-BACK-kelch proteins[28, 58]. The model from the kelch domain predicts an unusual 1+3 velcro arrangement[59], with the N-terminal region contributing strand d of blade 1 and the C-terminal region contributing strands a, b and c of the same blade, although an alternative 2+2 velcro model cannot be ruled out.

Cell Culture.

U87 cells were obtained from ATCC. SNB19, U87 and HEK-293T cells were cultured in DMEM supplemented with 10% fetal bovine serum (FBS). Growth rates were determined by plating cells in six-well plates at 3 d after infection with the lentivirus indicated in the figure legends. The number of viable cells was determined by Trypan blue exclusion in triplicate cultures obtained from triplicate independent infections. For the wound assay testing migration, confluent cells were scratched with a pipette tip and cultured in 0.25% FBS. After 16 h, images were taken using the Olympus IX70 connected to a digital camera. Images were processed using the ImageJ64 software. The area of the cell-free wound was assessed in triplicate samples. Experiments were repeated twice.

GBM-derived primary cultures were grown in DMEM: F12 medium containing N2 and B27 supplements and human recombinant FGF-2 and EGF (50 ng/ml each; Peprotech). For sphere formation, cells were infected with lentiviral particles. Four days later, single cells were plated at density of 1 cells per well in triplicate in low-attachment 96-well plates. The number and the size of spheres were scored after 10-14 d. Limiting dilution assays were performed as described previously[60]. Spheres were dissociated into single cells and plated in low-attachment 96-well plates in 0.2 ml of medium containing growth factors (EGF and FGF-2), except for the EGFR-transduced cells, which were cultured in the absence of EGF. Cultures were left undisturbed for 10 d, and then the percentage of wells not containing spheres for each cell dilution was calculated and plotted against the number of cells per well. Linear regression lines were plotted, and the number of cells required to generate at least one sphere in every well (the stem cell frequency) was calculated. The experiment was repeated twice. Treatment of GBM primary cultures with erlotinib or lapatinib was performed in cells transduced with the pLOC vector, wild-type pLOC-EGFR, EGFRvIII or EGFR-SEPT14 and selected with blasticidin for 5 d. Cells were seeded on 6-cm dishes in the absence of EGF and treated with the indicated drugs at the indicated doses for 48 h. Each treatment group was seeded in triplicate. Absolute viable cell counts were determined by Trypan blue exclusion and counted on a hemocytometer. EGF stimulation of EGFR-transduced primary glioma cells was performed in cells deprived of growth factors for 48 h. Cells were collected at the indicated times and processed for protein blot analysis.

Immunofluorescence.

Immunofluorescence staining on normal mouse and human brain and brain tumor tissue microarrays were performed as previously described[43, 61, 62]. Immunofluorescence microscopy was performed on cells fixed with 4% paraformaldehyde in phosphate buffer. Cells were permeabilized using 0.2% Triton X-100. The antibodies and concentrations used in the immunofluorescence staining are detailed in FIG. 34.

Secondary antibodies conjugated to Alexa Fluor 594 (1:300, A11037, Molecular Probes) or Alexa 488 (1:500, A11008, Molecular Probes) were used. DNA was stained with DAPI (Sigma). Fluorescence microscopy was performed on a Nikon A1R MP microscope. Quantification of the fluorescence intensity staining in primary or established glioma cells was performed using NIH ImageJ software (see URLs). A histogram of the intensity of fluorescence of each point of a representative field for each condition was generated. The fluorescence intensity of ten fields from three independent experiments was scored, standardized to the number of cells in the field and divided by the intensity of the vector.

Protein Blotting, Immunoprecipitation and In Vitro Binding.

Protein blot analysis and immunoprecipitation were performed using the antibodies detailed in FIG. 35. For the in vitro binding between CUL3 and LZTR1, wild-type and mutant LZTR1 were translated in vitro using the TNT Quick Coupled Transcription/Translation System (Promega). Flag-CUL3 was immunoprecipitated from transfected HEK-293T cells with Flag-M2 beads (Sigma) using RIPA buffer (50 mM Tris-HCl, pH 7.5, 150 mM NaCl, 1% NP-40, 0.5% sodium deoxycholate (DOC), 0.1% SDS, 1 mM phenylmethylsulfonyl fluoride (PMSF), 10 mM NaF, 0.5 M $Na_3OV_4$ (sodium orthovanadate) and Complete Protease Inhibitor Cocktail, Roche). Binding was performed in 200 mM NaCl plus 0.5% NP-40 for 2 h at 4° C. Immunocomplexes were analyzed by SDS-PAGE and immunoblot.

Cloning and Lentiviral Production.

The lentiviral expression vectors pLOC-GFP and pLOC-CTNND2 were purchased from Open Biosystems. Full-length EGFR-SEPT14 cDNA was amplified from tumor sample TCGA-27-1837. Wild-type EGFR, EGFRvIII and EGFR-SEPT14 cDNAs were cloned into the pLOC vector. pCDNA-MYC-Hist-LZTR1 was a kind gift[24]. pCDNA-Flag-CUL3 was a gift. Wild-type and mutant cDNAs for LZTR1 and CTNND2 obtained by site-directed mutagenesis (QuikChange II, Agilent) were cloned into the pLOC vector. Lentiviral particles were produced using published protocols[43, 61, 62, 63, 64].

Genomic PCR and RT-PCR.

Total RNA was extracted from cells using an RNeasy Mini Kit (QIAGEN) following the manufacturer's instructions. Five-hundred nanograms of total RNA was retrotranscribed using the Superscript III kit (Invitrogen) following the manufacturer's instructions. The cDNAs obtained after the retrotranscription were used as templates for quantitative PCR as described[43, 64]. The reaction was performed with a Roche480 thermal cycler using the Absolute Blue QPCR SYBR Green Mix from Thermo Scientific. The relative amount of specific mRNA was normalized to GAPDH. Results are presented as the mean±s. d. of triplicate amplifications. The validation of fusion transcripts was performed using both genomic PCR and RT-PCR with forward and reverse primer combinations designed within the margins of the paired-end read sequences detected by RNA-seq. Expressed fusion transcript variants were subjected to direct sequencing to confirm the sequence and translation frame. The primers used for the screening of gene fusions are detailed in FIG. 36. The primers used for genomic detection of gene fusions are listed in FIG. 37. Semiquantitative RT-PCR to detect exogenous wild-type MYC-LZTR1 and mutant p.Arg801Trp LZTR1 was performed using the primers listed in FIG. 38.

Subcutaneous Xenografts and Drug Treatment.

Female athymic mice (nu/nu genotype, BALB/c background, 6-8 weeks old) were used for all antitumor studies. Patient-derived adult human glioblastoma xenografts were maintained. Xenografts were excised from host mice under sterile conditions and homogenized with the use of a tissue press and modified tissue cytosieve (Biowhitter Inc.), and tumor homogenate was loaded into a repeating Hamilton syringe (Hamilton, Co.) dispenser. Cells were injected subcutaneously into the right flank of the athymic mouse at an inoculation volume of 50 ml with a 19-gauge needle[65].

Subcutaneous tumors were measured twice weekly with hand-held vernier calipers (Scientific Products). Tumor volumes (V) were calculated with the following formula: $((width)^2 \times (length))/2 = V$ (mm$^3$). For the subcutaneous tumor studies, groups of mice randomly selected by tumor volume were treated with EGFR kinase inhibitors when the median tumor volumes were an average of 150 mm$^3$ and were compared with control animals receiving vehicle (saline).

Erlotinib was administered at 100 mg per kg body weight orally once per day for 10 d. Lapatinib was administered at 75 mg per kg body weight orally twice per day for 20 d. Response to treatment was assessed by a delay in tumor growth and tumor regression.

Growth delay, expressed as a T-C value, is defined as the difference in days between the median time required for tumors in treated and control animals to reach a volume five times greater than that measured at the start of the treatment. Tumor regression is defined as a decrease in tumor volume over two successive measurements. Statistical analysis was performed using a SAS statistical analysis program, the Wilcoxon rank-order test for growth delay and Fisher's exact test for tumor regression.

Intracranial Injection.

GBM-derived primary cells were first infected with a lentivirus expressing luciferase and subsequently transduced with the pLOC vector or pLOC-CTNND2 lentiviral particles. Intracranial injection was performed in 9-week-old male nu/nu mice (Charles River Laboratories). Briefly, $5 \leq 10^5$ cells were resuspended in 2.5 µl of PBS and injected into the caudate putamen using a stereotaxic frame (coordinates relative to the bregma: 0.6 mm anterior; 1.65 mm medium-lateral; 3 mm depth-ventral). Tumor growth was monitored using the IVIS Imaging system. Briefly, mice were anesthetized with 3% isoflurane before intraperitoneal injection of 100 mg per kg body weight n-luciferin (Xenogen). Ten minutes after injection of n-luciferin, images were acquired for 1 min with the Xenogen IVIS system (Xenogen) using Living Image acquisition and analysis software (Xenogen). The bioluminescent signal was expressed in photons per second and displayed as a pseudo-color image representing the spatial distribution of photon counts.

URLs.

DNA and RNA sequencing and copy number variant data in The Cancer Genome Atlas (TCGA), http://cancergenome.nih.gov; glioma patient survival data from the Repository for Molecular Brain Neoplasia Data (REMBRANDT), https://caintegrator.nci.nih.gov/rembrandt/; sequence data deposition in database of Genotypes and Phenotypes (dbGaP), http://www.ncbi.nlm.nih.gov/gap; gene fusion annotation software package Pegasus, http://sourceforge.net/projects/pegasus-fus/.

Data Access.

RNA sequencing of twenty-four human GBM sphere cultures in this study were deposited under the dbGaP study accession phs000505.v2.p1. RNA and DNA sequencing of TCGA GBM samples was also analyzed from the dbGaP study accession phs000178.v1.p1.

References for Example 2

1 Porter, K. R., McCarthy, B. J., Freels, S., Kim, Y. & Davis, F. G. Prevalence estimates for primary brain tumors in the United States by age, gender, behavior, and histology. *Neuro-oncology* 12, 520-527, doi:10.1093/neuonc/nop066 (2010).

2 Stupp, R. et al. Radiotherapy plus concomitant and adjuvant temozolomide for glioblastoma. *The New England journal of medicine* 352, 987-996, doi:10.1056/NEJMoa043330 (2005).

3 Cancer Genome Atlas Research, N. Comprehensive genomic characterization defines human glioblastoma genes and core pathways. *Nature* 455, 1061-1068, doi:10.1038/nature07385 (2008).

4 Noushmehr, H. et al. Identification of a CpG island methylator phenotype that defines a distinct subgroup of glioma. *Cancer Cell* 17, 510-522, doi:10.1016/j.ccr.2010.03.017 (2010).

5 Parsons, D. W. et al. An integrated genomic analysis of human glioblastoma multiforme. *Science* 321, 1807-1812, doi:10.1126/science.1164382 (2008).

6 Verhaak, R. G. et al. Integrated genomic analysis identifies clinically relevant subtypes of glioblastoma characterized by abnormalities in PDGFRA, IDH1, EGFR, and NF1. *Cancer Cell* 17, 98-110, doi:10.1016/j.ccr.2009.12.020 (2010).

7 Bass, A. J. et al. Genomic sequencing of colorectal adenocarcinomas identifies a recurrent VTI1A-TCF7L2 fusion. *Nat Genet* 43, 964-968, doi:10.1038/ng.936 (2011).

8 Chinnaiyan, A. M. & Palanisamy, N. Chromosomal aberrations in solid tumors. *Prog Mol Biol Transl Sci* 95, 55-94, doi:10.1016/B978-0-12-385071-3.00004-6 (2010).

9 Singh, D. et al. Transforming fusions of FGFR and TACC genes in human glioblastoma. *Science* 337, 1231-1235, doi:10.1126/science.1220834 (2012).

10 Rubin, A. F. & Green, P. Mutation patterns in cancer genomes. *Proc Natl Acad Sci USA* 106, 21766-21770, doi:10.1073/pnas.0912499106 (2009).

11 Fan, Z. et al. BCOR regulates mesenchymal stem cell function by epigenetic mechanisms. *Nat Cell Biol* 11, 1002-1009, doi:10.1038/ncb1913 (2009).

12 Wamstad, J. A. & Bardwell, V. J. Characterization of Bcor expression in mouse development. *Gene Expr Patterns* 7, 550-557, doi:10.1016/j.modgep.2007.01.006 (2007).

13 Wamstad, J. A., Corcoran, C. M., Keating, A. M. & Bardwell, V. J. Role of the transcriptional corepressor Bcor in embryonic stem cell differentiation and early embryonic development. *PLoS One* 3, e2814, doi:10.1371/journal.pone.0002814 (2008).

14 Pugh, T. J. et al. Medulloblastoma exome sequencing uncovers subtype-specific somatic mutations. *Nature* 488, 106-110, doi:10.1038/nature11329 (2012).

15 Zhang, J. et al. A novel retinoblastoma therapy from genomic and epigenetic analyses. *Nature* 481, 329-334, doi:10.1038/nature10733 (2012).

16 Beroukhim, R. et al. The landscape of somatic copy-number alteration across human cancers. *Nature* 463, 899-905, doi:10.1038/nature08822 (2010).

17 Kantarci, S. et al. Mutations in LRP2, which encodes the multiligand receptor megalin, cause Donnai-Barrow and facio-oculo-acoustico-renal syndromes. *Nat Genet* 39, 957-959, doi:10.1038/ng2063 (2007).

18 Willnow, T. E. et al. Defective forebrain development in mice lacking gp330/megalin. *Proc Natl Acad Sci USA* 93, 8460-8464 (1996).

19 Christ, A. et al. LRP2 is an auxiliary SHH receptor required to condition the forebrain ventral midline for inductive signals. *Dev Cell* 22, 268-278, doi:10.1016/j.devcel.2011.11.023 (2012).

20 Cowin, P. A. et al. LRP1B deletion in high-grade serous ovarian cancers is associated with acquired chemotherapy resistance to liposomal doxorubicin. *Cancer Res* 72, 4060-4073, doi:10.1158/0008-5472.CAN-12-0203 (2012).

21 Lima, F. R. et al. Glioblastoma: therapeutic challenges, what lies ahead. *Biochim Biophys Acta* 1826, 338-349, doi:10.1016/j.bbcan.2012.05.004 (2012).

22 Bekker-Jensen, S. et al. HERC2 coordinates ubiquitin-dependent assembly of DNA repair factors on damaged chromosomes. *Nat Cell Biol* 12, 80-86; sup pp 81-12, doi:10.1038/ncb2008 (2010).

23 Harlalka, G. V. et al. Mutation of HERC2 causes developmental delay with Angelman-like features. *J Med Genet* 50, 65-73, doi:10.1136/jmedgenet-2012-101367 (2013).

24 Nacak, T. G., Leptien, K., Fellner, D., Augustin, H. G. & Kroll, J. The BTB-kelch protein LZTR-1 is a novel Golgi protein that is degraded upon induction of apoptosis. *J Biol Chem* 281, 5065-5071, doi:10.1074/jbc.M509073200 (2006).

25 Stogios, P. J., Downs, G. S., Jauhal, J. J., Nandra, S. K. & Prive, G. G. Sequence and structural analysis of BTB domain proteins. *Genome Biol* 6, R82, doi:10.1186/gb-2005-6-10-r82 (2005).

26 Errington, W. J. et al. Adaptor protein self-assembly drives the control of a cullin-RING ubiquitin ligase. *Structure* 20, 1141-1153, doi:10.1016/j.str.2012.04.009 (2012).

27 Ji, A. X. & Prive, G. G. Crystal structure of KLHL3 in complex with Cullin3. *PLoS One* 8, e60445, doi:10.1371/journal.pone.0060445 (2013).

28 Canning, P. et al. Structural basis for Cul3 assembly with the BTB-Kelch family of E3 ubiquitin ligases. *J Biol Chem*, doi:10.1074/jbc.M112.437996 (2013).

29 Lo, S. C., Li, X., Henzl, M. T., Beamer, L. J. & Hannink, M. Structure of the Keap1:Nrf2 interface provides mechanistic insight into Nrf2 signaling. *EMBO J* 25, 3605-3617, doi:10.1038/sj.emboj.7601243 (2006).

30 Boyden, L. M. et al. Mutations in kelch-like 3 and cullin 3 cause hypertension and electrolyte abnormalities. *Nature* 482, 98-102, doi:10.1038/nature10814 (2012).

31 Louis-Dit-Picard, H. et al. KLHL3 mutations cause familial hyperkalemic hypertension by impairing ion transport in the distal nephron. *Nat Genet* 44, 456-460, S451-453, doi:10.1038/ng.2218 (2012).

32 Emanuele, M. J. et al. Global identification of modular cullin-RING ligase substrates. *Cell* 147, 459-474, doi:10.1016/j.cell.2011.09.019 (2011).

33 Galan, J. M. & Peter, M. Ubiquitin-dependent degradation of multiple F-box proteins by an autocatalytic mechanism. *Proc Natl Acad Sci USA* 96, 9124-9129 (1999).

34 Zhang, D. D. et al. Ubiquitination of Keap1, a BTB-Kelch substrate adaptor protein for Cul3, targets Keap1 for degradation by a proteasome-independent pathway. *J Biol Chem* 280, 30091-30099, doi:10.1074/jbc.M501279200 (2005).

35 Gunther, H. S. et al. Glioblastoma-derived stem cell-enriched cultures form distinct subgroups according to molecular and phenotypic criteria. *Oncogene* 27, 2897-2909, doi:10.1038/sj.onc.1210949 (2008).

36 Abu-Elneel, K. et al. A delta-catenin signaling pathway leading to dendritic protrusions. *J Biol Chem* 283, 32781-32791, doi:10.1074/jbc.M804688200 (2008).

37 Arikkath, J. et al. Delta-catenin regulates spine and synapse morphogenesis and function in hippocampal neurons during development. *J Neurosci* 29, 5435-5442, doi:10.1523/JNEUROSCI.0835-09.2009 (2009).

38 Kosik, K. S., Donahue, C. P., Israely, I., Liu, X. & Ochiishi, T. Delta-catenin at the synaptic-adherens junction. *Trends Cell Biol* 15, 172-178, doi:10.1016/j.tcb.2005.01.004 (2005).

39 Israely, I. et al. Deletion of the neuron-specific protein delta-catenin leads to severe cognitive and synaptic dysfunction. *Curr Biol* 14, 1657-1663, doi:10.1016/j.cub.2004.08.065 (2004).

40 Jun, G. et al. delta-Catenin is genetically and biologically associated with cortical cataract and future Alzheimer-related structural and functional brain changes. *PLoS One* 7, e43728, doi:10.1371/journal.pone.0043728 (2012).

41 Hicks, S., Wheeler, D. A., Plon, S. E. & Kimmel, M. Prediction of missense mutation functionality depends on both the algorithm and sequence alignment employed. *Hum Mutat* 32, 661-668, doi:10.1002/humu.21490 (2011).

42 Phillips, H. S. et al. Molecular subclasses of high-grade glioma predict prognosis, delineate a pattern of disease progression, and resemble stages in neurogenesis. *Cancer Cell* 9, 157-173, doi:10.1016/j.ccr.2006.02.019 (2006).

43 Carro, M. S. et al. The transcriptional network for mesenchymal transformation of brain tumours. *Nature* 463, 318-325, doi:10.1038/nature08712 (2010).

44 Pierotti, M. A. & Greco, A. Oncogenic rearrangements of the NTRK1/NGF receptor. *Cancer Lett* 232, 90-98, doi:10.1016/j.canlet.2005.07.043 (2006).

45 Dunn, G. P. et al. Emerging insights into the molecular and cellular basis of glioblastoma. *Genes Dev* 26, 756-784, doi:10.1101/gad.187922.112 (2012).

46 Liu, C. et al. Chemokine receptor CXCR3 promotes growth of glioma. *Carcinogenesis* 32, 129-137, doi:10.1093/carcin/bgq224 (2011).

47 Vivanco, I. et al. Differential sensitivity of glioma-versus lung cancer-specific EGFR mutations to EGFR kinase inhibitors. *Cancer Discov* 2, 458-471, doi:10.1158/2159-8290.CD-11-0284 (2012).

48 Forbes, S. A. et al. COSMIC (the Catalogue of Somatic Mutations in Cancer): a resource to investigate acquired mutations in human cancer. *Nucleic Acids Res* 38, D652-657, doi:10.1093/nar/gkp995 (2010).

49 Northcott, P. A. et al. Subgroup-specific structural variation across 1,000 medulloblastoma genomes. *Nature* 488, 49-56, doi:10.1038/nature11327 (2012).

Srivastava, M. et al. The *Amphimedon queenslandica* genome and the evolution of animal complexity. Nature 466, 720-726 (2010).

Stogios et al. Sequence and structural analysis of BTB domain proteins. Genome Biol. 6(10):R82 (2005).

Soding, J. Protein homology detection by HMM-HMM comparison. Bioinformatics. 21(7):951-60 (2005).

ANNOTATIONS TO FIGURES

Annotation information in each column is described below for FIG. 27:
sample: Name of TCGA or private sample.
chrom5p: 5' chromosome
start5p: 5' genomic start coordinate
end5p: 5' genomic end coordinate
chrom3p: 3' chromosome
start3p: 3' genomic start coordinate
end3p: 3' genomic end coordinate
strand5p: 5' strand
strand3p: 3' strand genes5p: 5' gene
genes3p: 3' gene
total_frags (split inserts+split reads): Total number of split inserts and split reads
spanning_frags (split reads): Number of split reads
GeneBreakpoint5p: The genomic coordinate of the breakpoint in the 5' gene
GeneBreakpoint3p: The genomic coordinate of the breakpoint in the 3' gene
FrameType: Reading frame of gene fusions. Values include in-frame, frameshift, or null (no transcript information was found in the Ensembl *Homo_sapiens*.GRCh37.60.gtf file).
FusedSequence: Reconstructed sequence of the fusion RNA transcript
ProteinStart5p: The start coordinate of the 5' protein segment
ProteinStop5p: The stop coordinate (breakpoint) of the 5' protein segment
ProteinStart3p: The start coordinate (breakpoint) of the 3' protein segment
ProteinStop3p: The stop coordinate of the 3' protein segment
ProteinSequence: Reconstructed sequence of the fusion protein
ExonBreak5p: The last exon of the 5' gene before the breakpoint
ExonBreak3p: The first exon of the 3' gene after the breakpoint Annotation information in each column is described below for FIG. 28:
sample: Name of TCGA sample
split reads: Total number of split reads
gene5p: 5' gene
chr5p: 5' chromosome
sense5p: 5' sense
start5p: 5' genomic start coordinate
end5p: 5' genomic end coordinate
breakpoint5p: 5' genomic coordinate of breakpoint
exonBeforeBreakpoint5p: Exon number of 5' gene before the breakpoint
gene3p: 3' gene
chr3p: 3' chromosome
sense3p: 3' sense
start3p: 3' genomic start coordinate
end3p: 3' genomic end coordinate
breakpoint3p: 3' genomic coordinate of breakpoint
exonAfterBreakpoint3p: Exon number of 3' gene after the breakpoint
split inserts: Total number of split inserts
posA5p: Coordinate of split insert read closest to 5' end in 5' gene
posB5p: Coordinate of split insert read closest to 3' end in 5' gene
readDir5p: Read direction of split insert reads in 5' gene
posA3p: Coordinate of split insert read closest to 5' end in 3' gene
posB3p: Coordinate of split insert read closest to 3' end in 3' gene
readDir3p: Read direction of split insert reads in 3' gene Annotation information in each column is described below for FIG. 31:
sample: Name of TCGA sample
split reads: Total number of split reads
gene5p: 5' gene
chr5p: 5' chromosome
sense5p: 5' sense
start5p: 5' genomic start coordinate
end5p: 5' genomic end coordinate
breakpoint5p: 5' genomic coordinate of breakpoint
exonBeforeBreakpoint5p: Exon number of 5' gene before the breakpoint
gene3p: 3' gene
chr3p: 3' chromosome
sense3p: 3' sense
start3p: 3' genomic start coordinate
end3p: 3' genomic end coordinate
breakpoint3p: 3' genomic coordinate of breakpoint
exonAfterBreakpoint3p: Exon number of 3' gene after the breakpoint
split inserts: Total number of split inserts
posA5p: Coordinate of split insert read closest to 5' end in 5' gene
posB5p: Coordinate of split insert read closest to 3' end in 5' gene
readDir5p: Read direction of split insert reads in 5' gene
posA3p: Coordinate of split insert read closest to 5' end in 3' gene
posB3p: Coordinate of split insert read closest to 3' end in 3' gene
readDir3p: Read direction of split insert reads in 3' gene.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11505788B2). An electronic copy of the "Sequence Listing" will also be available from the USPTO upon request and payment of the fee set forth in 37 CFR 1.19(b)(3).

What is claimed is:

1. A purified EGFR-Septin-14 (EGFR-SEPT14) fusion protein comprising an EGFR portion fused to a Septin-14 portion, wherein the EGFR portion comprises the tyrosine kinase domain of EGFR and wherein the Septin-14 portion comprises a coiled-coil domain of a Septin-14 protein, wherein the EGFR-SEPT14 fusion protein comprises SEQ ID NO: 1.

2. The purified EGFR-SEPT14 fusion protein of claim 1, wherein the fusion protein comprises SEQ ID NO: 5.

3. The purified EGFR-SEPT14 fusion protein of claim 1, wherein the EGFR portion comprises amino acids:

CTGPGLEGCPTNGPKIPSIATGMVGALLLLLVVALGIGLFMRRRHIVRK

RTLRRLLQERELVEPLTPSGEAPNQALLRILKETEFKKIKVLGSGAFGT

VYKGLWIPEGEKVKIPVAIKELREATSPKANKEILDEAYVMASVDNPHV

CRLLGICLTSTVQLITQLMPFGCLLDYVREHKDNIGSQYLLNWCVQIAK

GMNYLEDRRLVHRDLAARNVLVKTPQHVKITDFGLAKLLGAEEKEYHAE

GGKVPIKWMALESILHRIYTHQSDVWSYGVTVWELMTFGSKPYDGIPAS

EISSILEKGERLPQPPICTIDVYMIMVKCWMIDADSRPKFRELIIEFSK

MARDPQRYLVIQ (amino acids 628-982 of SEQ ID NO: 5);

and wherein the Septin-14 portion comprises amino acids:

LQDKFEHLKNIIQQEEIRKLEEEKKQLEGEIIDFYKNIKAASEALQTQL

STDTKKDKHRKK (amino acids 983-1041 of SEQ ID NO: 5).

4. The purified EGFR-SEPT14 fusion protein of claim 1, wherein the Septin-14 portion comprises amino acids:

LQDKFEHLKNIIQQEEIRKLEEEKKQLEGEIIDFYKNIKAASEALQTQL

STDTKKDKHRKK (amino acids 983-1041 of SEQ ID NO: 5).

5. The purified EGFR-SEPT14 fusion protein of claim 1, wherein the EGFR portion comprises amino acids:

CTGPGLEGCPTNGPKIPSIATGMVGALLLLLVVALGIGLFMRRRHIVRK

RTLRRLLQERELVEPLTPSGEAPNQALLRILKETEFKKIKVLGSGAFGT

VYKGLWIPEGEKVKIPVAIKELREATSPKANKEILDEAYVMASVDNPHV

CRLLGICLTSTVQLITQLMPFGCLLDYVREHKDNIGSQYLLNWCVQIAK

GMNYLEDRRLVHRDLAARNVLVKTPQHVKITDFGLAKLLGAEEKEYHAE

GGKVPIKWMALESILHRIYTHQSDVWSYGVTVWELMTFGSKPYDGIPAS

EISSILEKGERLPQPPICTIDVYMIMVKCWMIDADSRPKFRELIIEFSK

MARDPQRYLVIQ (amino acids 628-982 of SEQ ID NO: 5).

6. The purified EGFR-SEPT14 fusion protein of claim 1, wherein the EGFR portion comprises amino acids:

MRPSGTAGAALLALLAALCPASRALEEKKVCQGTSNKLTQLGTFEDHFL

SLQRMFNNCEVVLGNLEITYVQRNYDLSFLKTIQEVAGYVLIALNTVER

IPLENLQIIRGNMYYENSYALAVLSNYDANKTGLKELPMRNLQEILHGA

VRFSNNPALCNVESIQWRDIVSSDFLSNMSMDFQNHLGSCQKCDPSCPN

GSCWGAGEENCQKLTKIICAQQCSGRCRGKSPSDCCHNQCAAGCTGPRE

SDCLVCRKFRDEATCKDTCPPLMLYNPTTYQMDVNPEGKYSFGATCVKK

CPRNYVVTDHGSCVRACGADSYEMEEDGVRKCKKCEGPCRKVCNGIGIG

EFKDSLSINATNIKHFKNCTSISGDLHILPVAFRGDSFTHTPPLDPQEL

DILKTVKEITGFLLIQAWPENRTDLHAFENLEIIRGRTKQHGQFSLAVV

SLNITSLGLRSLKEISDGDVIISGNKNLCYANTINWKKLFGTSGQKTKI

ISNRGENSCKATGQVCHALCSPEGCWGPEPRDCVSCRNVSRGRECVDKC

NLLEGEPREFVENSECIQCHPECLPQAMNITCTGRGPDNCIQCAHYIDG

PHCVKTCPAGVMGENNTLVWKYADAGHVCHLCHPNCTYGCTGPGLEGCP

TNGPKIPSIATGMVGALLLLLVVALGIGLFMRRRHIVRKRTLRRLLQER

ELVEPLTPSGEAPNQALLRILKETEFKKIKVLGSGAFGTVYKGLWIPEG

EKVKIPVAIKELREATSPKANKEILDEAYVMASVDNPHVCRLLGICLTS

TVQLITQLMPFGCLLDYVREHKDNIGSQYLLNWCVQIAKGMNYLEDRRL

VHRDLAARNVLVKTPQHVKITDFGLAKLLGAEEKEYHAEGGKVPIKWMA

LESILHRIYTHQSDVWSYGVTVWELMTFGSKPYDGIPASEISSILEKGE

RLPQPPICTIDVYMIMVKCWMIDADSRPKFRELIIEFSKMARDPQRYLV

IQ (amino acids 1-982 of SEQ ID NO: 5).

7. The purified EGFR-SEPT14 fusion protein of claim 1, wherein the EGFR portion consists of amino acids:

MRPSGTAGAALLALLAALCPASRALEEKKVCQGTSNKLTQLGTFEDHFL

SLQRMFNNCEVVLGNLEITYVQRNYDLSFLKTIQEVAGYVLIALNTVER

IPLENLQIIRGNMYYENSYALAVLSNYDANKTGLKELPMRNLQEILHGA

VRFSNNPALCNVESIQWRDIVSSDFLSNMSMDFQNHLGSCQKCDPSCPN

GSCWGAGEENCQKLTKIICAQQCSGRCRGKSPSDCCHNQCAAGCTGPRE

SDCLVCRKFRDEATCKDTCPPLMLYNPTTYQMDVNPEGKYSFGATCVKK

CPRNYVVTDHGSCVRACGADSYEMEEDGVRKCKKCEGPCRKVCNGIGIG

EFKDSLSINATNIKHFKNCTSISGDLHILPVAFRGDSFTHTPPLDPQEL

DILKTVKEITGFLLIQAWPENRTDLHAFENLEIIRGRTKQHGQFSLAVV

SLNITSLGLRSLKEISDGDVIISGNKNLCYANTINWKKLFGTSGQKTKI

ISNRGENSCKATGQVCHALCSPEGCWGPEPRDCVSCRNVSRGRECVDKC

NLLEGEPREFVENSECIQCHPECLPQAMNITCTGRGPDNCIQCAHYIDG

PHCVKTCPAGVMGENNTLVWKYADAGHVCHLCHPNCTYGCTGPGLEGCP

TNGPKIPSIATGMVGALLLLLVVALGIGLFMRRRHIVRKRTLRRLLQER

ELVEPLTPSGEAPNQALLRILKETEFKKIKVLGSGAFGTVYKGLWIPEG

EKVKIPVAIKELREATSPKANKEILDEAYVMASVDNPHVCRLLGICLTS

TVQLITQLMPFGCLLDYVREHKDNIGSQYLLNWCVQIAKGMNYLEDRRL

VHRDLAARNVLVKTPQHVKITDFGLAKLLGAEEKEYHAEGGKVPIKWMA

LESILHRIYTHQSDVWSYGVTVWELMTFGSKPYDGIPASEISSILEKGE

RLPQPPICTIDVYMIMVKCWMIDADSRPKFRELIIEFSKMARDPQRYLV

IQ (amino acids 1-982 of SEQ ID NO: 5)

8. The purified EGFR-SEPT14 fusion protein of claim 1, wherein the Septin-14 portion consists of amino acids:

```
LQDKFEHLKNIIQQEEIRKLEEEKKQLEGEIIDFYKNIKAASEALQTQL
STDTKKDKHRKK (amino acids 983-1041 of SEQ ID NO: 5).
```

9. The purified EGFR-SEPT14 fusion protein of claim 1, wherein the fusion protein consists of SEQ ID NO: 5.

* * * * *

UNITED STATES PATENT AND TRADEMARK OFFICE
CERTIFICATE OF CORRECTION

PATENT NO. : 11,505,788 B2
APPLICATION NO. : 16/246167
DATED : November 22, 2022
INVENTOR(S) : Antonio Iavarone et al.

It is certified that error appears in the above-identified patent and that said Letters Patent is hereby corrected as shown below:

In the Claims

Please correct Claim 3, Column 84, Line 60-Column 85, Lines 1-20, to read as:
3. The purified EGFR-SEPT14 fusion protein of claim 1, wherein the EGFR portion comprises amino acids:
CTGPGLEGCPTNGPKIPSIATGMVGALLLLLVVALGIGLFMRRRHIVRKRTLRRLLQERELVEPLTPSGEAPNQALLRILKETEFKKIKVLGSGAFGTVYKGLWIPEGEKVKIPVAIKELREATSPKANKEILDEAYVMASVDNPHVCRLLGICLTSTVQLITQLMPFGCLLDYVREHKDNIGSQYLLNWCVQIAKGMNYLEDRRLVHRDLAARNVLVKTPQHVKITDFGLAKLLGAEEKEYHAEGGKVPIKWMALESILHRIYTHQSDVWSYGVTVWELMTFGSKPYDGIPASEISSILEKGERLPQPPICTIDVYMIMVKCWMIDADSRPKFRELIIEFSKMARDPQRYLVIQ (amino acids 628-982 of SEQ ID NO: 5);

and wherein the Septin-14 portion comprises amino acids:
LQDKFEHLKMIQQEEIRKLEEEKKQLEGEIIDFYKMKAASEALQTQLSTDTKKDKHRKK (amino acids 983-1041 of SEQ ID NO: 5).

Please correct Claim 4, Column 85, Line 51, to read as:
4. The purified EGFR-SEPT14 fusion protein of claim 1, wherein the Septin-14 portion comprises amino acids:
LQDKFEHLKMIQQEEIRKLEEEKKQLEGEIIDFYKMKAASEALQTQLSTDTKKDKHRKK (amino acids 983-1041 of SEQ ID NO: 5).

Please correct Claim 8, Column 87, Line 1, to read as:
8. The purified EGFR-SEPT14 fusion protein of claim 1, wherein the Septin-14 portion consists of amino acids:
LQDKFEHLKMIQQEEIRKLEEEKKQLEGEIIDFYKMKAASEALQTQLSTDTKKDKHRKK (amino acids 983-1041 of SEQ ID NO: 5).

Signed and Sealed this
Thirtieth Day of July, 2024

Katherine Kelly Vidal
*Director of the United States Patent and Trademark Office*